(12) United States Patent
Franano et al.

(10) Patent No.: US 12,303,135 B2
(45) Date of Patent: May 20, 2025

(54) MEDICAL DEVICES COMPRISING DETACHABLE BALLOONS AND METHODS OF MANUFACTURING AND USE

(71) Applicant: METACTIVE MEDICAL, INC., Olathe, KS (US)

(72) Inventors: F. Nicholas Franano, Olathe, KS (US); Howard M. Loree, II, Olathe, KS (US); J. Scott Richardson, Olathe, KS (US); Kieran Murphy, Toronto (CA)

( * ) Notice: Subject to any disclaimer, the term of this patent is extended or adjusted under 35 U.S.C. 154(b) by 1298 days.

(21) Appl. No.: 16/765,465

(22) PCT Filed: May 17, 2018

(86) PCT No.: PCT/US2018/033251
§ 371 (c)(1),
(2) Date: May 19, 2020

(87) PCT Pub. No.: WO2018/176064
PCT Pub. Date: Sep. 27, 2018

(65) Prior Publication Data
US 2021/0386429 A1    Dec. 16, 2021

Related U.S. Application Data

(60) Provisional application No. 62/629,532, filed on Feb. 12, 2018, provisional application No. 62/623,287, (Continued)

(51) Int. Cl.
*A61B 17/12* (2006.01)
*A61B 17/00* (2006.01)
(Continued)

(52) U.S. Cl.
CPC .. *A61B 17/12136* (2013.01); *A61B 17/12036* (2013.01); *A61B 17/12113* (2013.01);
(Continued)

(58) Field of Classification Search
CPC ........ A61B 17/12136; A61B 17/12172; A61B 17/1214; A61B 17/12113;
(Continued)

(56) References Cited

U.S. PATENT DOCUMENTS

| 3,794,268 A | 2/1974 | McNeill |
| 3,938,530 A | 2/1976 | Santomieri |

(Continued)

FOREIGN PATENT DOCUMENTS

| CN | 1342056 A | 3/2002 |
| CN | 1813638 A | 8/2006 |

(Continued)

OTHER PUBLICATIONS

Office Action for Japanese Application No. 2022-164824, issued on Jul. 25, 2023, 08 Pages (3 Pages of Official Copy and 5 Pages of English Translation).

(Continued)

*Primary Examiner* — Katherine H Schwiker
*Assistant Examiner* — Lauren Dubose
(74) *Attorney, Agent, or Firm* — Polsinelli PC

(57) ABSTRACT

The present disclosure relates to medical devices comprising detachable balloons and catheter assemblies, wherein the detachable balloons are polymer balloons, metal balloons, polymer-coated metal balloons, and metalized polymer balloons. Various means of attachment and detachment of the balloons to the catheter assemblies are described. Kits and uses of systems having one or more medical devices, detachable balloons, and elongated or expandable bodies are also disclosed.

34 Claims, 169 Drawing Sheets

Related U.S. Application Data filed on Jan. 29, 2018, provisional application No. 62/553,705, filed on Sep. 1, 2017.

(51) Int. Cl.
*A61B 17/22* (2006.01)
*A61B 17/34* (2006.01)
*A61L 29/02* (2006.01)

(52) U.S. Cl.
CPC .... *A61B 17/12181* (2013.01); *A61B 17/3415* (2013.01); *A61L 29/02* (2013.01); *A61B 2017/00632* (2013.01); *A61B 2017/12068* (2013.01); *A61B 2017/22038* (2013.01); *A61B 2017/3486* (2013.01)

(58) Field of Classification Search
CPC ........ A61B 17/12022; A61B 17/12181; A61B 17/12186; A61B 17/12145; A61B 17/12031; A61B 17/0057; A61B 17/12131; A61B 17/12195; A61B 17/12036; A61B 17/3415; A61B 17/12109; A61B 2017/00632; A61B 2017/3486; A61B 2017/12054; A61B 2017/00526; A61B 2017/12068; A61B 2017/12081; A61B 2017/00575; A61B 2017/22038; A61B 2017/12063; A61B 2018/00416; A61M 2025/1054; A61M 2025/1075; A61M 2025/1004; A61M 25/10; A61M 25/1029; A61L 29/02; A61F 2/2442

See application file for complete search history.

(56) References Cited

U.S. PATENT DOCUMENTS

| | | |
|---|---|---|
| 4,311,133 A | 1/1982 | Robinson |
| 4,311,146 A | 1/1982 | Wonder |
| 4,341,218 A | 7/1982 | U |
| 4,364,392 A | 12/1982 | Strother et al. |
| 4,395,806 A | 8/1983 | Wonder et al. |
| 4,402,319 A | 9/1983 | Handa et al. |
| 4,416,028 A | 11/1983 | Eriksson et al. |
| 4,471,779 A | 9/1984 | Antoshkiw et al. |
| 4,517,979 A | 5/1985 | Pecenka |
| 4,527,549 A | 7/1985 | Gabbay |
| 4,569,332 A | 2/1986 | Schiff et al. |
| 4,638,803 A | 1/1987 | Rand |
| 4,685,446 A | 8/1987 | Choy |
| 4,770,067 A | 9/1988 | Liu et al. |
| 4,819,637 A | 4/1989 | Dormandy, Jr. et al. |
| 5,002,556 A * | 3/1991 | Ishida .............. A61B 17/12136 604/103.1 |
| 5,041,090 A | 8/1991 | Scheglov et al. |
| 5,167,627 A | 12/1992 | Clegg et al. |
| 5,181,921 A | 1/1993 | Makita et al. |
| 5,222,970 A | 6/1993 | Reeves |
| 5,250,059 A | 10/1993 | Andreas et al. |
| 5,282,847 A | 2/1994 | Trescony et al. |
| 5,327,885 A | 7/1994 | Griffith |
| 5,344,401 A | 9/1994 | Radisch et al. |
| 5,354,295 A | 10/1994 | Guglielmi et al. |
| 5,370,691 A | 12/1994 | Samson |
| 5,382,261 A | 1/1995 | Palmaz |
| 5,522,836 A | 6/1996 | Palermo |
| 5,527,337 A | 6/1996 | Stack et al. |
| 5,609,606 A | 3/1997 | O'Boyle |
| 5,769,817 A | 6/1998 | Burgmeier |
| 5,833,671 A | 11/1998 | Macoviak et al. |
| 5,902,308 A | 5/1999 | Murphy |
| 5,951,599 A | 9/1999 | McCrory |
| 5,980,530 A | 11/1999 | Willard et al. |
| 6,022,359 A | 2/2000 | Frantzen |
| 6,063,070 A | 5/2000 | Eder |
| 6,096,021 A | 8/2000 | Helm et al. |
| 6,146,372 A | 11/2000 | Leschinsky et al. |
| 6,156,005 A | 12/2000 | Theron |
| 6,186,978 B1 | 2/2001 | Samson et al. |
| 6,187,034 B1 | 2/2001 | Frantzen |
| 6,293,960 B1 * | 9/2001 | Ken ................ A61B 17/12136 606/195 |
| 6,293,968 B1 | 9/2001 | Taheri |
| 6,312,405 B1 | 11/2001 | Meyer et al. |
| 6,344,041 B1 | 2/2002 | Kupiecki et al. |
| 6,346,117 B1 | 2/2002 | Greenhalgh |
| 6,375,668 B1 | 4/2002 | Gifford et al. |
| 6,390,969 B1 | 5/2002 | Bolling et al. |
| 6,395,008 B1 | 5/2002 | Ellis et al. |
| 6,409,754 B1 | 6/2002 | Smith et al. |
| 6,425,893 B1 | 7/2002 | Guglielmi |
| 6,454,780 B1 | 9/2002 | Wallace |
| 6,463,317 B1 | 10/2002 | Kucharczyk et al. |
| 6,676,667 B2 | 1/2004 | Mareiro et al. |
| 6,706,064 B1 | 3/2004 | Anson |
| 6,733,513 B2 | 5/2004 | Boyle et al. |
| 6,976,950 B2 | 12/2005 | Connors et al. |
| 6,976,951 B2 | 12/2005 | Connors et al. |
| 7,252,677 B2 | 8/2007 | Burwell et al. |
| 7,329,236 B2 | 2/2008 | Kesten et al. |
| 7,410,482 B2 | 8/2008 | Murphy et al. |
| 7,527,622 B2 | 5/2009 | Lane et al. |
| 7,632,291 B2 | 12/2009 | Stephens et al. |
| 7,632,301 B2 | 12/2009 | Alt |
| 7,713,297 B2 | 5/2010 | Alt |
| 7,955,246 B2 | 6/2011 | Lubock et al. |
| 8,007,674 B2 | 8/2011 | Johnson |
| 8,016,853 B2 | 9/2011 | Griffen et al. |
| 8,333,798 B2 | 12/2012 | Gandhi et al. |
| 8,372,114 B2 | 2/2013 | Hines |
| 8,574,146 B2 | 11/2013 | Gillespie, Jr. et al. |
| 8,668,717 B2 | 3/2014 | Hines |
| 9,283,100 B2 | 3/2016 | Wang et al. |
| 9,572,697 B2 | 2/2017 | Franano et al. |
| 9,572,698 B2 | 2/2017 | Franano et al. |
| 10,285,711 B2 | 5/2019 | Griffin |
| 10,537,451 B2 | 1/2020 | Franano et al. |
| 10,543,115 B2 | 1/2020 | Franano et al. |
| 2002/0016624 A1 | 2/2002 | Patterson et al. |
| 2002/0026210 A1 | 2/2002 | Abdel-Gawwad |
| 2002/0029035 A1 | 3/2002 | Lee et al. |
| 2002/0052638 A1 | 5/2002 | Zadno-Azizi |
| 2002/0052639 A1 | 5/2002 | Fischell et al. |
| 2002/0082638 A1 | 6/2002 | Porter et al. |
| 2002/0143383 A1 | 10/2002 | Parodi |
| 2002/0165572 A1 | 11/2002 | Saadat |
| 2002/0169473 A1 | 11/2002 | Sepetka et al. |
| 2003/0028210 A1 | 2/2003 | Boyle et al. |
| 2003/0074039 A1 | 4/2003 | Puskas |
| 2003/0083732 A1 | 5/2003 | Stinson |
| 2003/0135265 A1 | 7/2003 | Stinson |
| 2003/0171739 A1 | 9/2003 | Murphy et al. |
| 2003/0187492 A1 | 10/2003 | McHale |
| 2003/0212419 A1 | 11/2003 | West |
| 2003/0220666 A1 | 11/2003 | Mirigian et al. |
| 2003/0229366 A1 | 12/2003 | Reggie et al. |
| 2003/0236494 A1 | 12/2003 | Seward |
| 2004/0019322 A1 | 1/2004 | Hoffmann |
| 2004/0093014 A1 | 5/2004 | Ho et al. |
| 2004/0138733 A1 | 7/2004 | Weber et al. |
| 2004/0193177 A1 | 9/2004 | Houghton et al. |
| 2004/0220610 A1 | 11/2004 | Kreidler et al. |
| 2004/0236278 A1 | 11/2004 | Herweck et al. |
| 2004/0243119 A1 | 12/2004 | Lane et al. |
| 2004/0254625 A1 | 12/2004 | Stephens et al. |
| 2005/0033408 A1 | 2/2005 | Jones et al. |
| 2005/0038470 A1 * | 2/2005 | van der Burg ..... A61B 17/0057 606/213 |
| 2005/0090888 A1 | 4/2005 | Hines et al. |
| 2005/0136090 A1 | 6/2005 | Falotico et al. |
| 2005/0171593 A1 | 8/2005 | Whirley et al. |
| 2006/0015169 A1 | 1/2006 | Letort |
| 2006/0079923 A1 | 4/2006 | Chhabra et al. |

(56) References Cited

U.S. PATENT DOCUMENTS

| | | |
|---|---|---|
| 2006/0085070 A1 | 4/2006 | Kim |
| 2006/0135947 A1 | 6/2006 | Soltesz et al. |
| 2006/0155296 A1 | 7/2006 | Richter |
| 2006/0155364 A1 | 7/2006 | Holloway et al. |
| 2006/0155367 A1 | 7/2006 | Hines |
| 2006/0200191 A1 | 9/2006 | Zadno-Azizi |
| 2006/0206199 A1 | 9/2006 | Churchwell et al. |
| 2006/0224229 A1 | 10/2006 | Goto |
| 2007/0032854 A1 | 2/2007 | Schmid et al. |
| 2007/0067009 A1 | 3/2007 | Gandhi et al. |
| 2007/0112370 A1 | 5/2007 | Andrews et al. |
| 2007/0129746 A1 | 6/2007 | Mische |
| 2007/0142772 A1* | 6/2007 | Deshmukh ............ A61L 29/06 604/103.06 |
| 2007/0150041 A1 | 6/2007 | Evans et al. |
| 2007/0239191 A1 | 10/2007 | Ramzipoor |
| 2007/0244431 A1 | 10/2007 | Limon |
| 2007/0265656 A1 | 11/2007 | Amplatz et al. |
| 2007/0267780 A1 | 11/2007 | Schewe et al. |
| 2007/0288083 A1 | 12/2007 | Hines |
| 2007/0299422 A1 | 12/2007 | Inganas et al. |
| 2007/0299460 A9 | 12/2007 | Boucher et al. |
| 2008/0140177 A1 | 6/2008 | Hines |
| 2008/0188825 A1 | 8/2008 | Atanasoska et al. |
| 2008/0188923 A1 | 8/2008 | Chu |
| 2008/0195112 A1 | 8/2008 | Liu et al. |
| 2008/0281350 A1 | 11/2008 | Sepetka et al. |
| 2008/0294205 A1 | 11/2008 | Greenhalgh et al. |
| 2009/0062726 A1 | 3/2009 | Ford et al. |
| 2009/0088829 A1 | 4/2009 | Wang et al. |
| 2009/0287291 A1 | 11/2009 | Becking et al. |
| 2009/0287297 A1 | 11/2009 | Cox |
| 2009/0297582 A1 | 12/2009 | Meyer et al. |
| 2009/0299327 A1 | 12/2009 | Tilson et al. |
| 2010/0096320 A1 | 4/2010 | Opperman |
| 2010/0114299 A1 | 5/2010 | Ben Muvhar et al. |
| 2010/0160949 A1 | 6/2010 | Takuma |
| 2010/0174353 A1 | 7/2010 | Kantor |
| 2010/0198336 A1 | 8/2010 | Weber et al. |
| 2010/0222803 A1 | 9/2010 | Seifert et al. |
| 2010/0241178 A1 | 9/2010 | Tilson et al. |
| 2010/0268260 A1 | 10/2010 | Riina et al. |
| 2010/0312179 A1 | 12/2010 | Nikolchev et al. |
| 2010/0324649 A1 | 12/2010 | Mattsson et al. |
| 2011/0022149 A1 | 1/2011 | Cox et al. |
| 2011/0046658 A1 | 2/2011 | Connor et al. |
| 2011/0190776 A1 | 8/2011 | Palmaz |
| 2011/0213403 A1 | 9/2011 | Aboytes |
| 2011/0264185 A1 | 10/2011 | Haslinger |
| 2011/0270383 A1 | 11/2011 | Jow et al. |
| 2012/0009325 A1 | 1/2012 | Storment |
| 2012/0283768 A1 | 11/2012 | Cox et al. |
| 2012/0296407 A1 | 11/2012 | Caselnova |
| 2012/0330348 A1 | 12/2012 | Strauss et al. |
| 2013/0046326 A1 | 2/2013 | Jones et al. |
| 2013/0317409 A1 | 11/2013 | Cully et al. |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0081314 A1 | 3/2014 | Zaver et al. |
| 2014/0135812 A1 | 5/2014 | Divino et al. |
| 2014/0163601 A1 | 6/2014 | Stamberg |
| 2014/0236127 A1* | 8/2014 | Lee ................... A61B 17/1214 606/191 |
| 2014/0364895 A1 | 12/2014 | Hines |
| 2015/0005804 A1 | 1/2015 | Franano et al. |
| 2015/0133994 A1 | 5/2015 | Amplatz et al. |
| 2016/0030050 A1 | 2/2016 | Franano et al. |
| 2016/0206321 A1 | 7/2016 | Connor |
| 2017/0156734 A1 | 6/2017 | Griffin |
| 2017/0245864 A1* | 8/2017 | Franano ............ A61B 17/1214 |
| 2017/0258612 A1 | 9/2017 | Franano et al. |
| 2017/0258613 A1 | 9/2017 | Franano et al. |
| 2020/0155333 A1 | 5/2020 | Franano et al. |
| 2020/0163784 A1 | 5/2020 | Franano et al. |

FOREIGN PATENT DOCUMENTS

| | | |
|---|---|---|
| CN | 101843949 A | 9/2010 |
| CN | 101945624 A | 1/2011 |
| CN | 102770091 A | 11/2012 |
| CN | 103476349 A | 12/2013 |
| DE | 10302241 A1 | 8/2004 |
| EP | 0101012 A2 | 2/1984 |
| EP | 0449786 A1 | 10/1991 |
| EP | 0915685 B1 | 9/2004 |
| EP | 0793457 B2 | 4/2006 |
| EP | 1982655 A1 | 10/2008 |
| EP | 2055343 A2 | 5/2009 |
| EP | 2777542 A2 | 9/2014 |
| FR | 2201908 A1 | 5/1974 |
| FR | 2580504 A1 | 10/1986 |
| JP | 2001518320 A | 10/2001 |
| JP | 2002513612 A | 5/2002 |
| JP | 2004215797 A | 8/2004 |
| JP | 2007236472 A | 9/2007 |
| JP | 2009527316 A | 7/2009 |
| JP | 2012512718 A | 6/2012 |
| JP | 2014523274 A | 9/2014 |
| WO | 1989001765 A1 | 3/1989 |
| WO | 9317731 A1 | 9/1993 |
| WO | 9717911 A1 | 5/1997 |
| WO | 1997026939 A1 | 7/1997 |
| WO | 9903404 A1 | 1/1999 |
| WO | 9905977 A1 | 2/1999 |
| WO | 9907294 A1 | 2/1999 |
| WO | 9960932 A1 | 12/1999 |
| WO | 0027292 A1 | 5/2000 |
| WO | 0152752 A1 | 7/2001 |
| WO | 0238038 A2 | 5/2002 |
| WO | 02051320 A2 | 7/2002 |
| WO | 2002064204 A1 | 8/2002 |
| WO | 02080782 A1 | 10/2002 |
| WO | 02087449 A1 | 11/2002 |
| WO | 03011363 A2 | 2/2003 |
| WO | 03061528 A1 | 7/2003 |
| WO | 2004030518 A2 | 4/2004 |
| WO | 2004091712 A2 | 10/2004 |
| WO | 2004112656 A2 | 12/2004 |
| WO | 2006074410 A2 | 7/2006 |
| WO | 2007006139 A1 | 1/2007 |
| WO | 2007092103 A2 | 8/2007 |
| WO | 2008063455 A1 | 5/2008 |
| WO | 2009027530 A1 | 3/2009 |
| WO | 2009045764 A1 | 4/2009 |
| WO | 2009134337 A1 | 11/2009 |
| WO | 2009135166 A2 | 11/2009 |
| WO | 2010028310 A2 | 3/2010 |
| WO | 2012099704 A2 | 7/2012 |
| WO | 2012099909 A2 | 7/2012 |
| WO | 2012099910 A2 | 7/2012 |
| WO | 2012166804 A1 | 12/2012 |
| WO | 2013109309 A1 | 7/2013 |
| WO | 2014146001 A2 | 9/2014 |
| WO | 2016044647 A2 | 3/2016 |
| WO | 2016161344 A1 | 10/2016 |
| WO | 2018169854 A1 | 9/2018 |

OTHER PUBLICATIONS

Office Action for Indian Application No. 201937043217, issued Jul. 14, 2023 (10 Pages).

* cited by examiner

| Body Diameter (Nominal, D1, mm) | Detachable Balloon Overall Dimensions ||||||||||
|---|---|---|---|---|---|---|---|---|---|---|
| | Body Length (L1, mm) ||| Total Body + Cone Length (L2, mm) ||| Proximal Cone Length (L3, mm) |||
| | Nominal | Minimum | Maximum | Nominal | Minimum | Maximum | Nominal | Minimum | Maximum |
| 2.5 | 2.5 | 2.0 | 3.0 | 5.0 | 3.4 | 7.2 | 1.2 | 0.7 | 2.1 |
| 3 | 3.0 | 2.0 | 4.0 | 6.0 | 3.7 | 9.1 | 1.5 | 0.9 | 2.5 |
| 4 | 4.0 | 3.0 | 5.0 | 8.0 | 5.3 | 11.8 | 2.0 | 1.1 | 3.4 |
| 5 | 5.0 | 4.0 | 6.0 | 10.0 | 6.9 | 14.5 | 2.5 | 1.4 | 4.3 |
| 6 | 6.0 | 5.0 | 7.0 | 12.0 | 8.4 | 17.3 | 3.0 | 1.7 | 5.1 |
| 8 | 6.0 | 5.0 | 7.0 | 14.0 | 9.6 | 20.7 | 4.0 | 2.3 | 6.9 |
| 10 | 6.0 | 5.0 | 7.0 | 16.0 | 10.7 | 24.2 | 5.0 | 2.9 | 8.6 |
| 12 | 8.0 | 7.0 | 9.0 | 20.0 | 13.9 | 29.7 | 6.0 | 3.4 | 10.3 |
| 14 | 8.0 | 7.0 | 9.0 | 22.0 | 15.1 | 33.1 | 7.0 | 4.0 | 12.1 |
| 16 | 10.0 | 8.0 | 12.0 | 25.9 | 17.2 | 39.6 | 8.0 | 4.6 | 13.8 |
| 18 | 10.0 | 8.0 | 12.0 | 27.9 | 18.4 | 43.1 | 9.0 | 5.2 | 15.5 |
| 20 | 10.0 | 8.0 | 12.0 | 29.9 | 19.5 | 46.5 | 10.0 | 5.8 | 17.2 |
| 24 | 12.0 | 10.0 | 14.0 | 35.9 | 23.8 | 55.4 | 12.0 | 6.9 | 20.7 |

FIG. 2A

| Detachable Balloon Overall Dimensions (Cont.) ||||||||||
|---|---|---|---|---|---|---|---|---|---|
| Body Diameter (Nominal, D1, mm) | Distal Cone Length (L4, mm) ||| Proximal Neck Length (L5, mm) ||| Distal Neck Length (L6, mm) |||
| | Nominal | Minimum | Maximum | Nominal | Minimum | Maximum | Nominal | Minimum | Maximum |
| 2.5 | 1.2 | 0.7 | 2.1 | 1.0 | 0.5 | 2.0 | 1.0 | 0.5 | 2.0 |
| 3 | 1.5 | 0.9 | 2.5 | 1.0 | 0.5 | 2.0 | 1.0 | 0.5 | 2.0 |
| 4 | 2.0 | 1.1 | 3.4 | 1.0 | 0.5 | 2.0 | 1.0 | 0.5 | 2.0 |
| 5 | 2.5 | 1.4 | 4.3 | 1.0 | 0.5 | 2.0 | 1.0 | 0.5 | 2.0 |
| 6 | 3.0 | 1.7 | 5.1 | 1.0 | 0.5 | 2.0 | 1.0 | 0.5 | 2.0 |
| 8 | 4.0 | 2.3 | 6.9 | 1.0 | 0.5 | 2.0 | 1.0 | 0.5 | 2.0 |
| 10 | 5.0 | 2.9 | 8.6 | 1.0 | 0.5 | 2.0 | 1.0 | 0.5 | 2.0 |
| 12 | 6.0 | 3.5 | 10.3 | 1.0 | 0.5 | 2.0 | 1.0 | 0.5 | 2.0 |
| 14 | 7.0 | 4.0 | 12.1 | 1.0 | 0.5 | 2.0 | 1.0 | 0.5 | 2.0 |
| 16 | 8.0 | 4.6 | 13.8 | 1.0 | 0.5 | 2.0 | 1.0 | 0.5 | 2.0 |
| 18 | 9.0 | 5.2 | 15.5 | 1.0 | 0.5 | 2.0 | 1.0 | 0.5 | 2.0 |
| 20 | 10.0 | 5.8 | 17.3 | 1.0 | 0.5 | 2.0 | 1.0 | 0.5 | 2.0 |
| 24 | 12.0 | 6.9 | 20.7 | 1.0 | 0.5 | 2.0 | 1.0 | 0.5 | 2.0 |

FIG. 2B

| Body Diameter (Nominal, D1, mm) | Detachable Balloon Overall Dimensions (Cont.) | | | | | | | | |
|---|---|---|---|---|---|---|---|---|---|
| | Total Body + Cone + Neck Length (L7, mm) | | | Proximal Neck OD (D2, in) | | | Distal Neck OD (D3, in) | | |
| | Nominal | Minimum | Maximum | Nominal | Minimum | Maximum | Nominal | Minimum | Maximum |
| 2.5 | 7.0 | 4.4 | 11.2 | 0.0550 | 0.052 | 0.082 | 0.036 | 0.033 | 0.063 |
| 3 | 8.0 | 4.7 | 13.1 | 0.0550 | 0.052 | 0.082 | 0.036 | 0.033 | 0.063 |
| 4 | 10.0 | 6.3 | 15.8 | 0.0550 | 0.052 | 0.082 | 0.036 | 0.033 | 0.063 |
| 5 | 12.0 | 7.9 | 18.5 | 0.0550 | 0.052 | 0.082 | 0.036 | 0.033 | 0.063 |
| 6 | 14.0 | 9.4 | 21.3 | 0.0550 | 0.052 | 0.082 | 0.036 | 0.033 | 0.063 |
| 8 | 16.0 | 10.6 | 24.7 | 0.0590 | 0.052 | 0.082 | 0.040 | 0.033 | 0.063 |
| 10 | 18.0 | 11.7 | 28.2 | 0.0590 | 0.052 | 0.082 | 0.040 | 0.033 | 0.063 |
| 12 | 22.0 | 14.9 | 33.7 | 0.0590 | 0.052 | 0.082 | 0.040 | 0.033 | 0.063 |
| 14 | 24.0 | 16.1 | 37.1 | 0.0790 | 0.052 | 0.082 | 0.060 | 0.033 | 0.063 |
| 16 | 27.9 | 18.2 | 43.6 | 0.0790 | 0.052 | 0.082 | 0.060 | 0.033 | 0.063 |
| 18 | 29.9 | 19.4 | 47.1 | 0.0790 | 0.052 | 0.082 | 0.060 | 0.033 | 0.063 |
| 20 | 31.9 | 20.5 | 50.5 | 0.0790 | 0.052 | 0.082 | 0.060 | 0.033 | 0.063 |
| 24 | 37.9 | 24.8 | 59.4 | 0.0790 | 0.052 | 0.082 | 0.060 | 0.033 | 0.063 |

FIG. 2C

| Detachable Balloon Overall Dimensions (Cont.) | | | | | | |
|---|---|---|---|---|---|---|
| Body Diameter (Nominal, D1, mm) | Proximal Cone Angle (A1, deg) | | | Distal Cone Angle (A2, deg) | | |
| | Nominal | Minimum | Maximum | Nominal | Minimum | Maximum |
| 2.5 | 45 | 30 | 60 | 45 | 30 | 60 |
| 3 | 45 | 30 | 60 | 45 | 30 | 60 |
| 4 | 45 | 30 | 60 | 45 | 30 | 60 |
| 5 | 45 | 30 | 60 | 45 | 30 | 60 |
| 6 | 45 | 30 | 60 | 45 | 30 | 60 |
| 8 | 45 | 30 | 60 | 45 | 30 | 60 |
| 10 | 45 | 30 | 60 | 45 | 30 | 60 |
| 12 | 45 | 30 | 60 | 45 | 30 | 60 |
| 14 | 45 | 30 | 60 | 45 | 30 | 60 |
| 16 | 45 | 30 | 60 | 45 | 30 | 60 |
| 18 | 45 | 30 | 60 | 45 | 30 | 60 |
| 20 | 45 | 30 | 60 | 45 | 30 | 60 |
| 24 | 45 | 30 | 60 | 45 | 30 | 60 |

FIG. 2D

| Body Diameter (Nominal, D1, mm) | Detachable Balloon Overall Dimensions ||||||||||||
|---|---|---|---|---|---|---|---|---|---|---|---|
| | Body Length (L1, mm) ||| Total Body + Cone Length (L2, mm) ||| Total Body + Cone + Neck Length (L3, mm) |||
| | Nominal | Minimum | Maximum | Nominal | Minimum | Maximum | Nominal | Minimum | Maximum |
| 3  | 0.2 | 0.2 | 0.4 | 1.5  | 1.4 | 2.1  | 3.5  | 2.4  | 6.1  |
| 4  | 0.2 | 0.2 | 0.9 | 2.0  | 1.8 | 2.8  | 4.0  | 2.8  | 6.8  |
| 5  | 0.2 | 0.2 | 1.1 | 2.5  | 2.3 | 3.6  | 4.5  | 3.3  | 7.6  |
| 6  | 0.4 | 0.4 | 1.1 | 3.0  | 2.7 | 4.3  | 5.0  | 3.7  | 8.3  |
| 7  | 0.4 | 0.4 | 0.8 | 3.5  | 3.2 | 5.0  | 5.5  | 4.2  | 9.0  |
| 8  | 0.5 | 0.5 | 1.2 | 4.0  | 3.6 | 5.3  | 6.0  | 4.6  | 9.3  |
| 9  | 1.0 | 0.9 | 1.1 | 4.5  | 4.1 | 5.6  | 6.5  | 5.1  | 9.6  |
| 10 | 1.1 | 1.0 | 1.9 | 5.0  | 4.5 | 6.0  | 7.0  | 5.5  | 10.0 |
| 12 | 1.3 | 1.2 | 2.3 | 6.0  | 5.4 | 7.8  | 8.0  | 6.4  | 11.8 |
| 14 | 1.5 | 1.4 | 2.7 | 7.0  | 6.3 | 9.1  | 9.0  | 7.3  | 13.1 |
| 16 | 1.8 | 1.6 | 3.0 | 8.0  | 7.2 | 10.4 | 10.0 | 8.2  | 14.4 |
| 18 | 2.0 | 1.8 | 3.4 | 9.0  | 8.1 | 11.7 | 11.0 | 9.1  | 15.7 |
| 20 | 2.2 | 2.0 | 3.8 | 10.0 | 9.0 | 13.0 | 12.0 | 10.0 | 17.0 |

FIG. 4A

| Body Diameter (Nominal, D1, mm) | Detachable Balloon Overall Dimensions (Cont.) | | | | | | | | |
|---|---|---|---|---|---|---|---|---|---|
| | Proximal Neck Length (L4, mm) | | | Distal Neck Length (L5, mm) | | | Proximal Cone Length (L6, mm) | | |
| | Nominal | Minimum | Maximum | Nominal | Minimum | Maximum | Nominal | Minimum | Maximum |
| 3 | 1.0 | 0.5 | 2.0 | 1.0 | 0.5 | 2.0 | 0.7 | 0.6 | 0.9 |
| 4 | 1.0 | 0.5 | 2.0 | 1.0 | 0.5 | 2.0 | 0.9 | 0.8 | 1.0 |
| 5 | 1.0 | 0.5 | 2.0 | 1.0 | 0.5 | 2.0 | 1.2 | 1.0 | 1.2 |
| 6 | 1.0 | 0.5 | 2.0 | 1.0 | 0.5 | 2.0 | 1.3 | 1.2 | 1.6 |
| 7 | 1.0 | 0.5 | 2.0 | 1.0 | 0.5 | 2.0 | 1.6 | 1.4 | 2.1 |
| 8 | 1.0 | 0.5 | 2.0 | 1.0 | 0.5 | 2.0 | 1.7 | 1.6 | 2.1 |
| 9 | 1.0 | 0.5 | 2.0 | 1.0 | 0.5 | 2.0 | 1.8 | 1.6 | 2.2 |
| 10 | 1.0 | 0.5 | 2.0 | 1.0 | 0.5 | 2.0 | 1.9 | 1.8 | 2.1 |
| 12 | 1.0 | 0.5 | 2.0 | 1.0 | 0.5 | 2.0 | 2.3 | 2.1 | 2.8 |
| 14 | 1.0 | 0.5 | 2.0 | 1.0 | 0.5 | 2.0 | 2.7 | 2.5 | 3.2 |
| 16 | 1.0 | 0.5 | 2.0 | 1.0 | 0.5 | 2.0 | 3.1 | 2.8 | 3.7 |
| 18 | 1.0 | 0.5 | 2.0 | 1.0 | 0.5 | 2.0 | 3.5 | 3.2 | 4.1 |
| 20 | 1.0 | 0.5 | 2.0 | 1.0 | 0.5 | 2.0 | 3.9 | 3.5 | 4.6 |

FIG. 4B

| Body Diameter (Nominal, D1, mm) | Detachable Balloon Overall Dimensions (Cont.) ||||||||||
|---|---|---|---|---|---|---|---|---|---|
| | Distal Cone Length (L7, mm) ||| Proximal Neck OD (D2, in) ||| Distal Neck OD (D3, in) |||
| | Nominal | Minimum | Maximum | Nominal | Minimum | Maximum | Nominal | Minimum | Maximum |
| 3 | 0.7 | 0.6 | 0.9 | 0.055 | 0.052 | 0.082 | 0.036 | 0.033 | 0.063 |
| 4 | 0.9 | 0.8 | 1.0 | 0.055 | 0.052 | 0.082 | 0.036 | 0.033 | 0.063 |
| 5 | 1.2 | 1.0 | 1.2 | 0.055 | 0.052 | 0.082 | 0.036 | 0.033 | 0.063 |
| 6 | 1.3 | 1.2 | 1.6 | 0.055 | 0.052 | 0.082 | 0.036 | 0.033 | 0.063 |
| 7 | 1.6 | 1.4 | 2.1 | 0.055 | 0.052 | 0.082 | 0.036 | 0.033 | 0.063 |
| 8 | 1.7 | 1.6 | 2.1 | 0.055 | 0.052 | 0.082 | 0.036 | 0.033 | 0.063 |
| 9 | 1.8 | 1.6 | 2.2 | 0.055 | 0.052 | 0.082 | 0.036 | 0.033 | 0.063 |
| 10 | 1.9 | 1.8 | 2.1 | 0.055 | 0.052 | 0.082 | 0.036 | 0.033 | 0.063 |
| 12 | 2.3 | 2.1 | 2.8 | 0.059 | 0.052 | 0.082 | 0.040 | 0.033 | 0.063 |
| 14 | 2.7 | 2.5 | 3.2 | 0.059 | 0.052 | 0.082 | 0.040 | 0.033 | 0.063 |
| 16 | 3.1 | 2.8 | 3.7 | 0.059 | 0.052 | 0.082 | 0.040 | 0.033 | 0.063 |
| 18 | 3.5 | 3.2 | 4.1 | 0.079 | 0.052 | 0.082 | 0.060 | 0.033 | 0.063 |
| 20 | 3.9 | 3.5 | 4.6 | 0.079 | 0.052 | 0.082 | 0.060 | 0.033 | 0.063 |

FIG. 4C

| Detachable Balloon Proximal Dimensions | | | | | | | |
|---|---|---|---|---|---|---|---|
| Body Diameter (Nominal, D1, mm) | Proximal Neck ID (D4, in) | | | Body Wall Thickness (T1, in) | | | |
| | Nominal | Minimum | Maximum | Nominal | Minimum | Maximum | |
| 2.5 | 0.052 | 0.049 | 0.079 | 0.0005 | 0.0003 | 0.0006 | |
| 3 | 0.052 | 0.049 | 0.079 | 0.0005 | 0.0003 | 0.0006 | |
| 4 | 0.052 | 0.049 | 0.079 | 0.0005 | 0.0003 | 0.0006 | |
| 5 | 0.052 | 0.049 | 0.079 | 0.0005 | 0.0003 | 0.0006 | |
| 6 | 0.052 | 0.049 | 0.079 | 0.0005 | 0.0003 | 0.0006 | |
| 8 | 0.056 | 0.049 | 0.079 | 0.0011 | 0.0008 | 0.0014 | |
| 10 | 0.056 | 0.049 | 0.079 | 0.0011 | 0.0008 | 0.0014 | |
| 12 | 0.056 | 0.049 | 0.079 | 0.0011 | 0.0008 | 0.0014 | |
| 14 | 0.056 | 0.049 | 0.079 | 0.0017 | 0.0015 | 0.0020 | |
| 16 | 0.076 | 0.049 | 0.079 | 0.0017 | 0.0015 | 0.0020 | |
| 18 | 0.076 | 0.049 | 0.079 | 0.0017 | 0.0015 | 0.0020 | |
| 20 | 0.076 | 0.049 | 0.079 | 0.0024 | 0.0022 | 0.0027 | |
| 24 | 0.076 | 0.049 | 0.079 | 0.0024 | 0.0022 | 0.0027 | |

FIG. 6A

| Detachable Balloon Proximal Dimensions (Cont.) |||||||||||
|---|---|---|---|---|---|---|---|---|---|---|
| Body Diameter (Nominal, D1, mm) | Proximal Neck Wall Thickness (T2, in) ||| Body to Cone Radius (R1, mm) ||| Cone to Proximal Neck Radius (R2, mm) |||
| | Nominal | Minimum | Maximum | Nominal | Minimum | Maximum | Nominal | Minimum | Maximum |
| 2.5 | 0.0005 | 0.0003 | 0.0006 | 0.5 | 0.25 | 1.0 | 0.5 | 0.25 | 1.0 |
| 3 | 0.0005 | 0.0003 | 0.0006 | 0.5 | 0.25 | 1.0 | 0.5 | 0.25 | 1.0 |
| 4 | 0.0005 | 0.0003 | 0.0006 | 1.0 | 0.5 | 2.0 | 1.0 | 0.5 | 2.0 |
| 5 | 0.0005 | 0.0003 | 0.0006 | 1.0 | 0.5 | 2.0 | 1.0 | 0.5 | 2.0 |
| 6 | 0.0005 | 0.0003 | 0.0006 | 1.0 | 0.5 | 2.0 | 1.0 | 0.5 | 2.0 |
| 8 | 0.0009 | 0.0006 | 0.0011 | 2.0 | 1.0 | 4.0 | 2.0 | 1.0 | 4.0 |
| 10 | 0.0009 | 0.0006 | 0.0011 | 2.0 | 1.0 | 4.0 | 2.0 | 1.0 | 4.0 |
| 12 | 0.0009 | 0.0006 | 0.0011 | 2.0 | 1.0 | 4.0 | 2.0 | 1.0 | 4.0 |
| 14 | 0.0014 | 0.0012 | 0.0016 | 2.0 | 1.0 | 4.0 | 2.0 | 1.0 | 4.0 |
| 16 | 0.0014 | 0.0012 | 0.0016 | 4.0 | 2.0 | 8.0 | 4.0 | 2.0 | 8.0 |
| 18 | 0.0014 | 0.0012 | 0.0016 | 4.0 | 2.0 | 8.0 | 4.0 | 2.0 | 8.0 |
| 20 | 0.0019 | 0.0017 | 0.0022 | 4.0 | 2.0 | 8.0 | 4.0 | 2.0 | 8.0 |
| 24 | 0.0019 | 0.0017 | 0.0022 | 4.0 | 2.0 | 8.0 | 4.0 | 2.0 | 8.0 |

FIG. 6B

| Detachable Balloon Proximal Dimensions | | | | | | |
|---|---|---|---|---|---|---|
| Body Diameter (Nominal, D1, mm) | Proximal Neck ID (D4, in) | | | Body Wall Thickness (TL, in) | | |
| | Nominal | Minimum | Maximum | Nominal | Minimum | Maximum |
| 3 | 0.052 | 0.049 | 0.079 | 0.0005 | 0.0003 | 0.0006 |
| 4 | 0.052 | 0.049 | 0.079 | 0.0005 | 0.0003 | 0.0006 |
| 5 | 0.052 | 0.049 | 0.079 | 0.0005 | 0.0003 | 0.0006 |
| 6 | 0.052 | 0.049 | 0.079 | 0.0005 | 0.0003 | 0.0006 |
| 7 | 0.052 | 0.049 | 0.079 | 0.0011 | 0.0008 | 0.0014 |
| 8 | 0.056 | 0.049 | 0.079 | 0.0011 | 0.0008 | 0.0014 |
| 9 | 0.056 | 0.049 | 0.079 | 0.0011 | 0.0008 | 0.0014 |
| 10 | 0.056 | 0.049 | 0.079 | 0.0011 | 0.0008 | 0.0014 |
| 12 | 0.056 | 0.049 | 0.079 | 0.0011 | 0.0008 | 0.0014 |
| 14 | 0.076 | 0.049 | 0.079 | 0.0017 | 0.0015 | 0.0020 |
| 16 | 0.076 | 0.049 | 0.079 | 0.0017 | 0.0015 | 0.0020 |
| 18 | 0.076 | 0.049 | 0.079 | 0.0017 | 0.0015 | 0.0020 |
| 20 | 0.076 | 0.049 | 0.079 | 0.0024 | 0.0022 | 0.0027 |

FIG. 6C

| Detachable Balloon Proximal Dimensions (Cont.) | | | | | | | | | | |
|---|---|---|---|---|---|---|---|---|---|---|
| Body Diameter (Nominal, D1, mm) | Proximal Neck Wall Thickness (T2, in) | | | Body to Cone Radius (R1, mm) | | | Cone to Proximal Neck Radius (R2, mm) | | |
| | Nominal | Minimum | Maximum | Nominal | Minimum | Maximum | Nominal | Minimum | Maximum |
| 3 | 0.0005 | 0.0003 | 0.0006 | 0.5 | 0.25 | 1.0 | 0.5 | 0.25 | 1.0 |
| 4 | 0.0005 | 0.0003 | 0.0006 | 1.0 | 0.50 | 2.0 | 1.0 | 0.50 | 2.0 |
| 5 | 0.0005 | 0.0003 | 0.0006 | 1.0 | 0.5 | 2.0 | 1.0 | 0.5 | 2.0 |
| 6 | 0.0005 | 0.0003 | 0.0006 | 1.0 | 0.5 | 2.0 | 1.0 | 0.5 | 2.0 |
| 7 | 0.0009 | 0.0006 | 0.0011 | 1.0 | 0.5 | 2.0 | 1.0 | 0.5 | 2.0 |
| 8 | 0.0009 | 0.0006 | 0.0011 | 2.0 | 1.0 | 4.0 | 2.0 | 1.0 | 4.0 |
| 9 | 0.0009 | 0.0006 | 0.0011 | 2.0 | 1.0 | 4.0 | 2.0 | 1.0 | 4.0 |
| 10 | 0.0009 | 0.0006 | 0.0011 | 2.0 | 1.0 | 4.0 | 2.0 | 1.0 | 4.0 |
| 12 | 0.0009 | 0.0006 | 0.0011 | 2.0 | 1.0 | 4.0 | 2.0 | 1.0 | 4.0 |
| 14 | 0.0014 | 0.0012 | 0.0016 | 2.0 | 1.0 | 4.0 | 2.0 | 1.0 | 4.0 |
| 16 | 0.0014 | 0.0012 | 0.0016 | 4.0 | 2.0 | 8.0 | 4.0 | 2.0 | 8.0 |
| 18 | 0.0014 | 0.0012 | 0.0016 | 4.0 | 2.0 | 8.0 | 4.0 | 2.0 | 8.0 |
| 20 | 0.0019 | 0.0017 | 0.0022 | 4.0 | 2.0 | 8.0 | 4.0 | 2.0 | 8.0 |

FIG. 6D (A) Guidewire 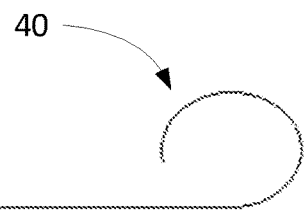
(B) Second Catheter
Guidewire Insertion
Coil Insertion ⟶
Contrast Injection
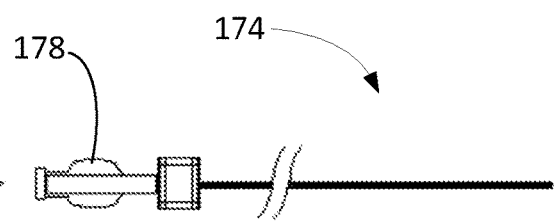
(C) First Catheter
Balloon Inflation ⟶
Second Catheter ⟶
Insertion
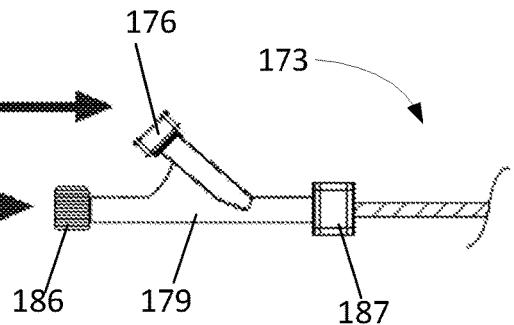
(D) Third Catheter
Contrast Injection ⟶
First Catheter and ⟶
Second Catheter Insertion
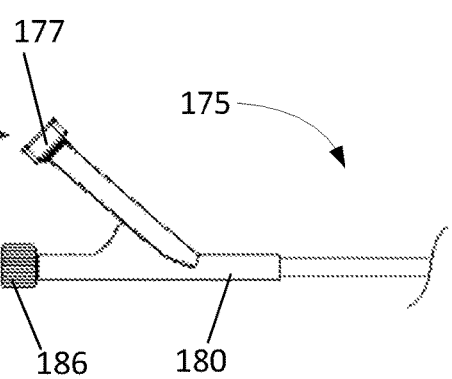
FIG. 13

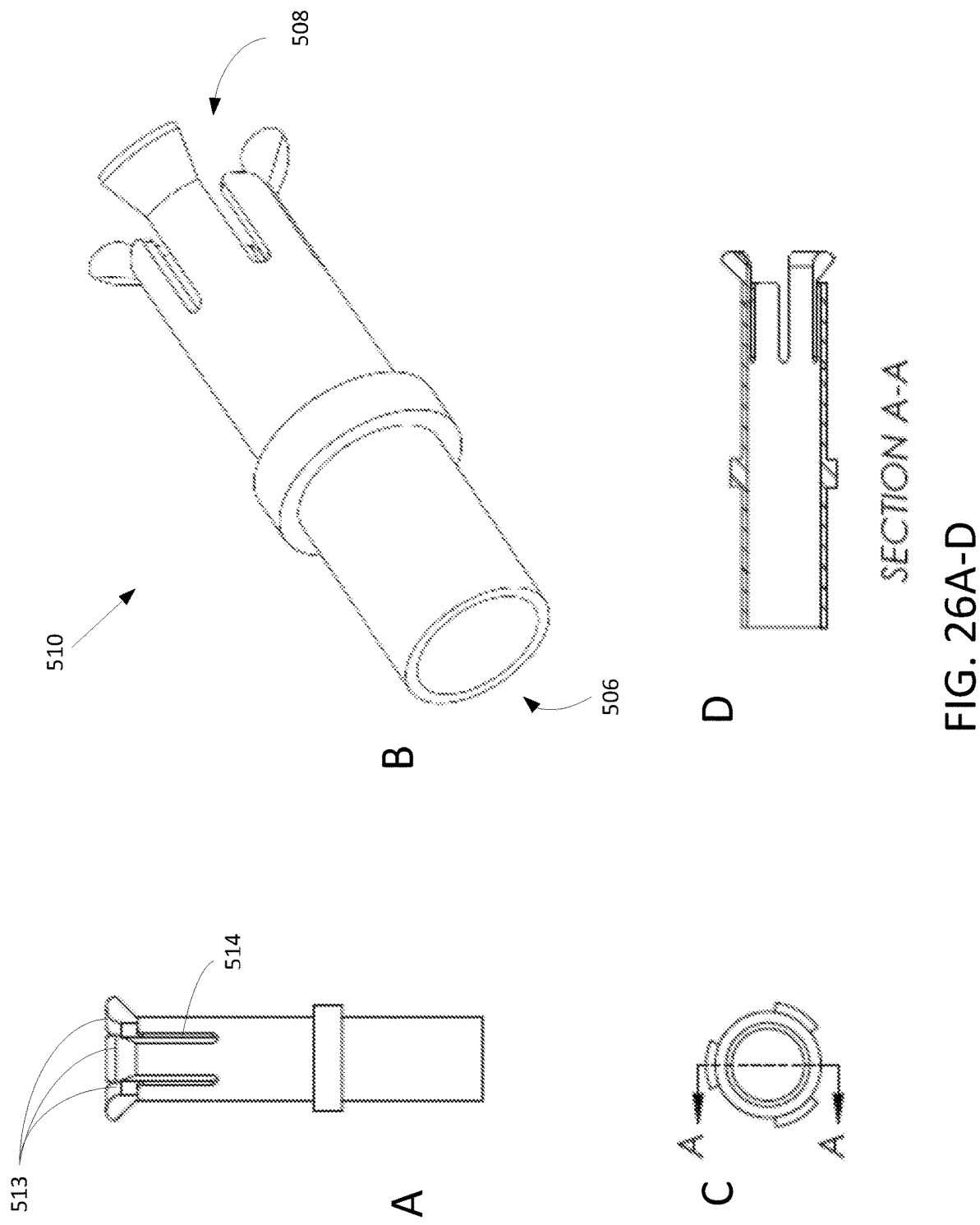
FIG. 26A-D

Section B

| Dimensions of Male Tubular Structure of Mechanical Latch | | | Allowable | | Preferred | |
|---|---|---|---|---|---|---|
| Dimension | Unit | Nominal | Minimum | Maximum | Minimum | Maximum |
| D1 | in | 0.045 | 0.025 | 0.065 | 0.040 | 0.050 |
| D2 | in | 0.038 | 0.018 | 0.058 | 0.033 | 0.043 |
| D3 | in | 0.067 | 0.047 | 0.087 | 0.062 | 0.072 |
| D4 | in | 0.057 | 0.037 | 0.077 | 0.052 | 0.062 |
| L1 | in | 0.157 | 0.119 | 0.177 | 0.152 | 0.162 |
| L2 | in | 0.040 | 0.020 | 0.060 | 0.035 | 0.045 |
| L3 | in | 0.052 | 0.059 | 0.012 | 0.062 | 0.042 |
| L4 | in | 0.05 | 0.030 | 0.070 | 0.045 | 0.055 |
| L5 | in | 0.0355 | 0.0205 | 0.0505 | 0.0315 | 0.0395 |
| L6 | in | 0.0145 | 0.0095 | 0.0195 | 0.0135 | 0.0155 |
| L7 | in | 0.015 | 0.010 | 0.035 | 0.010 | 0.020 |
| T1 | in | 0.0035 | 0.0025 | 0.0045 | 0.003 | 0.004 |
| T2 | in | 0.0035 | 0.0025 | 0.0045 | 0.003 | 0.004 |
| T3 | in | 0.0035 | 0.0025 | 0.0045 | 0.003 | 0.004 |
| T4 | in | 0.0035 | 0.0025 | 0.0045 | 0.003 | 0.004 |
| T5 | in | 0.0145 | 0.0095 | 0.0195 | 0.0135 | 0.0155 |
| A1 | deg | 135 | 130 | 140 | 133 | 137 |
| R1 | in | 0.005 | 0.003 | 0.007 | 0.004 | 0.006 |
| R2 | in | 0.008 | 0.006 | 0.010 | 0.007 | 0.009 |
| R3 | in | 0.003 | 0.001 | 0.005 | 0.002 | 0.004 |

FIG. 27

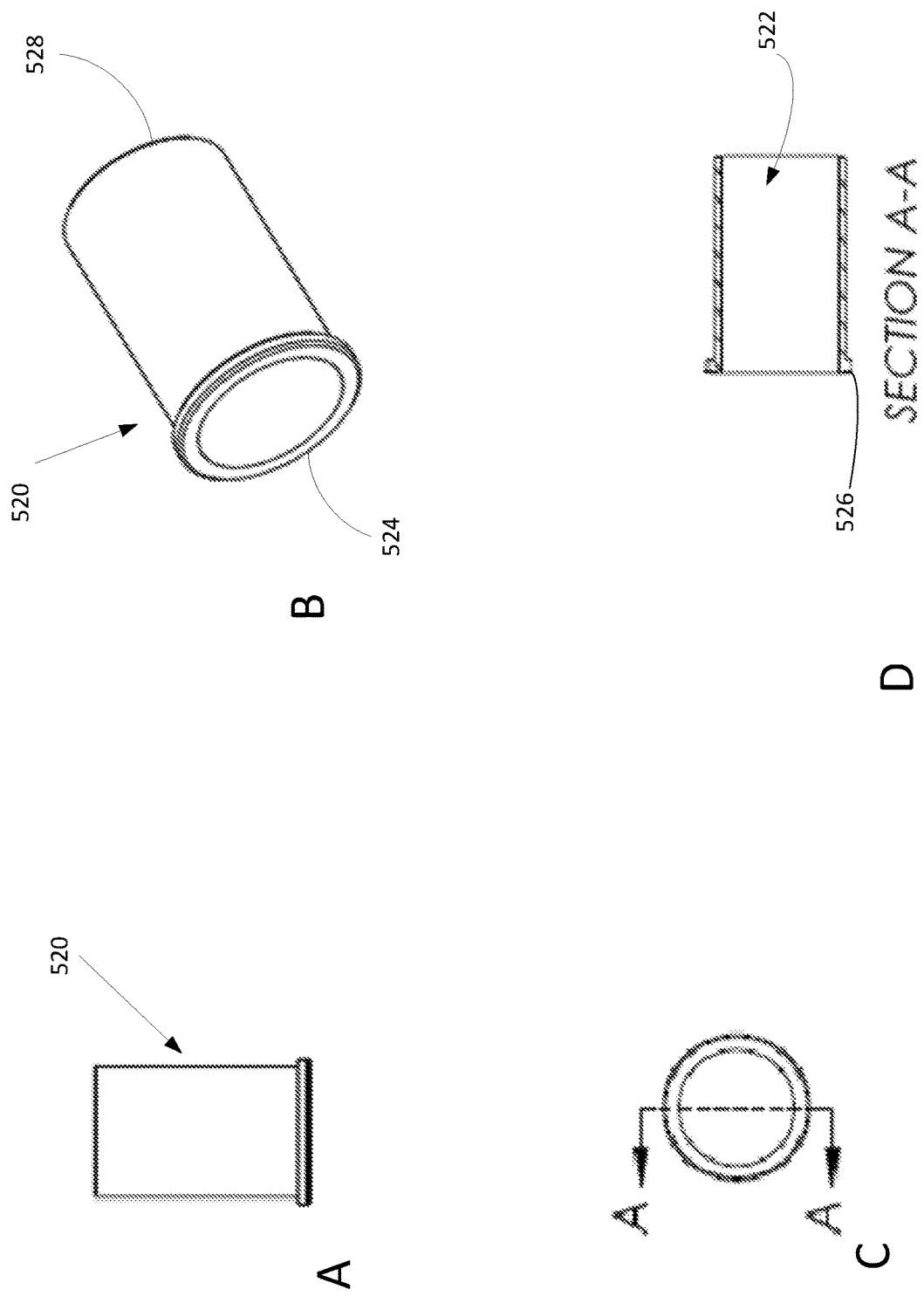
FIG. 28A-D

| Dimensions of Female Tubular Structure of Mechanical Latch |||||||
|---|---|---|---|---|---|---|
| Dimension | Unit | Nominal | Allowable || Preferred ||
| | | | Minimum | Maximum | Minimum | Maximum |
| D1 | in | 0.052 | 0.032 | 0.072 | 0.047 | 0.057 |
| D2 | in | 0.046 | 0.026 | 0.066 | 0.041 | 0.051 |
| D3 | in | 0.058 | 0.038 | 0.078 | 0.053 | 0.063 |
| L1 | in | 0.091 | 0.053 | 0.111 | 0.086 | 0.096 |
| L2 | in | 0.005 | 0.003 | 0.007 | 0.004 | 0.006 |
| L3 | in | 0.086 | 0.050 | 0.104 | 0.082 | 0.090 |
| T1 | in | 0.003 | 0.002 | 0.004 | 0.003 | 0.004 |
| R1 | in | 0.002 | 0.001 | 0.007 | 0.001 | 0.003 |
| R2 | in | 0.002 | 0.001 | 0.007 | 0.001 | 0.003 |

FIG. 29

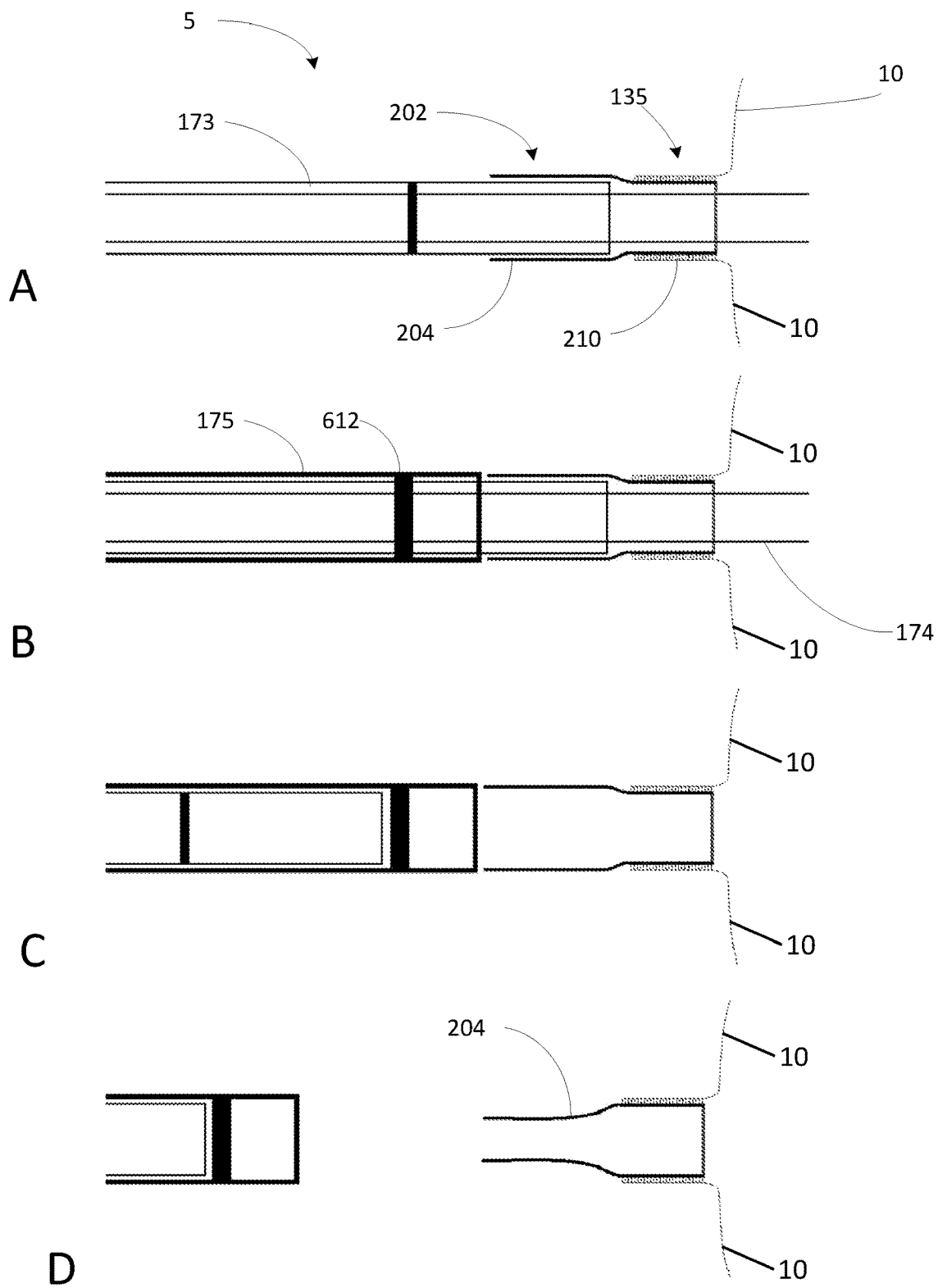
FIG. 30A-D

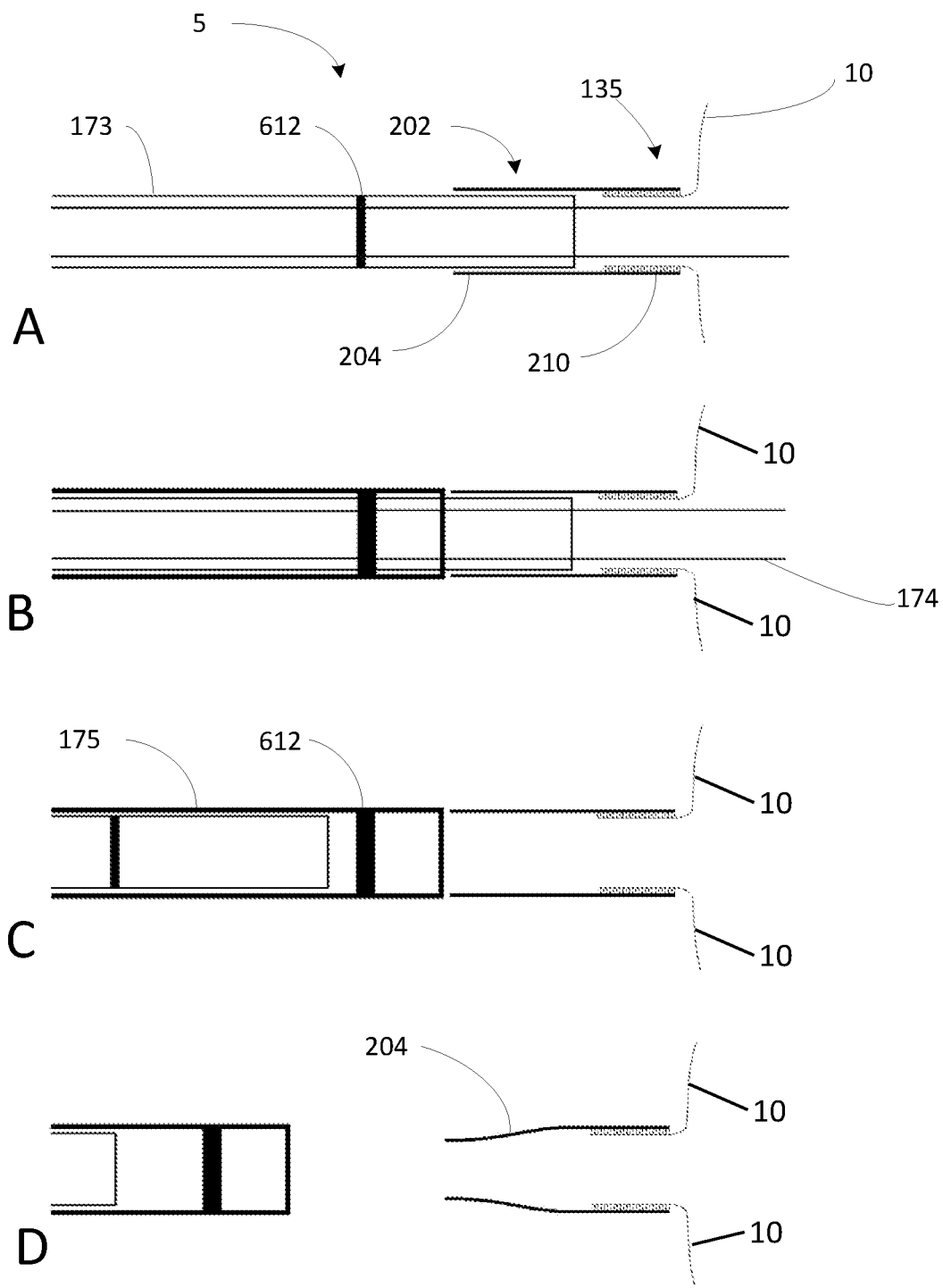
FIG. 31A-D

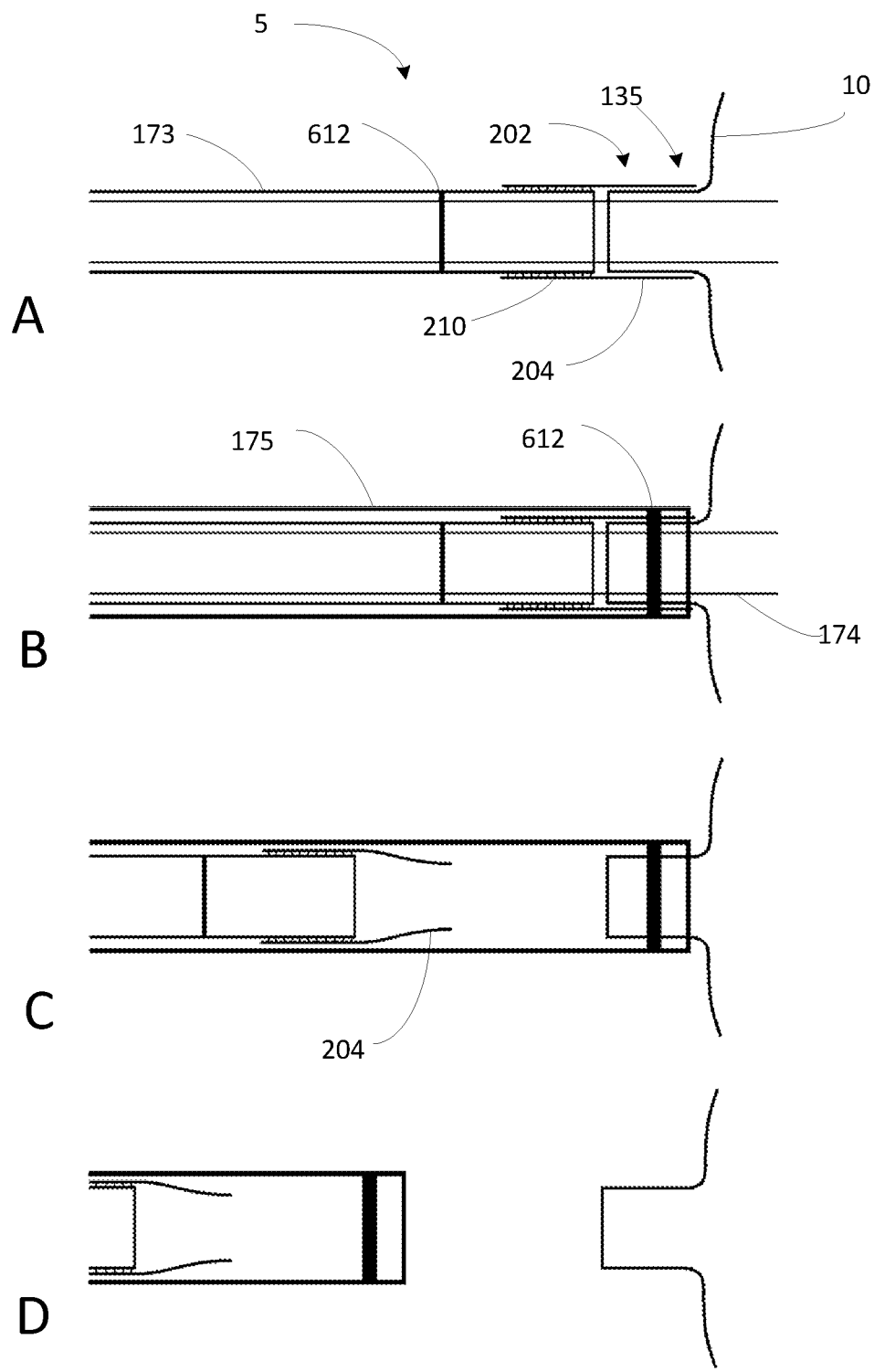
FIG. 32A-D

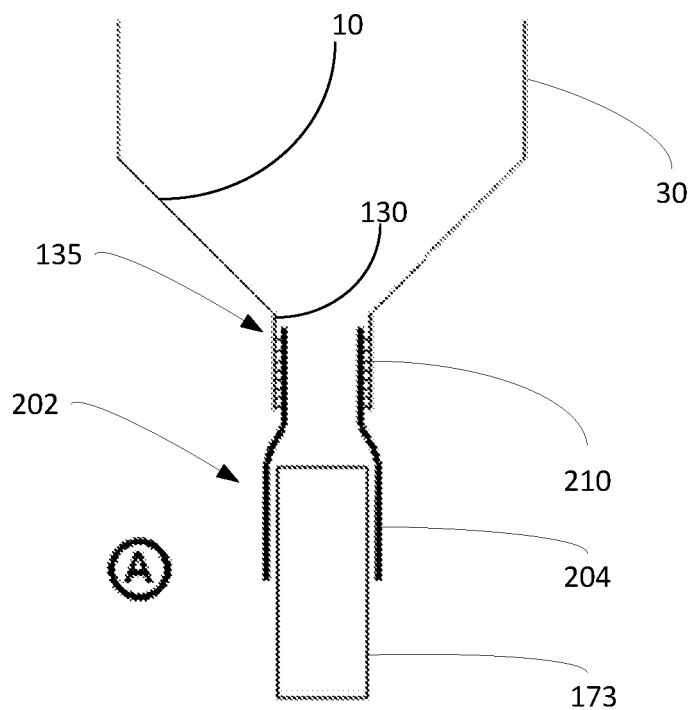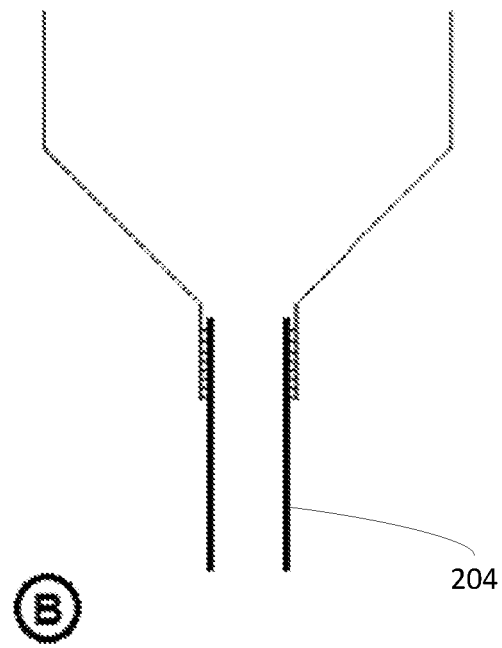
FIG. 33A-B

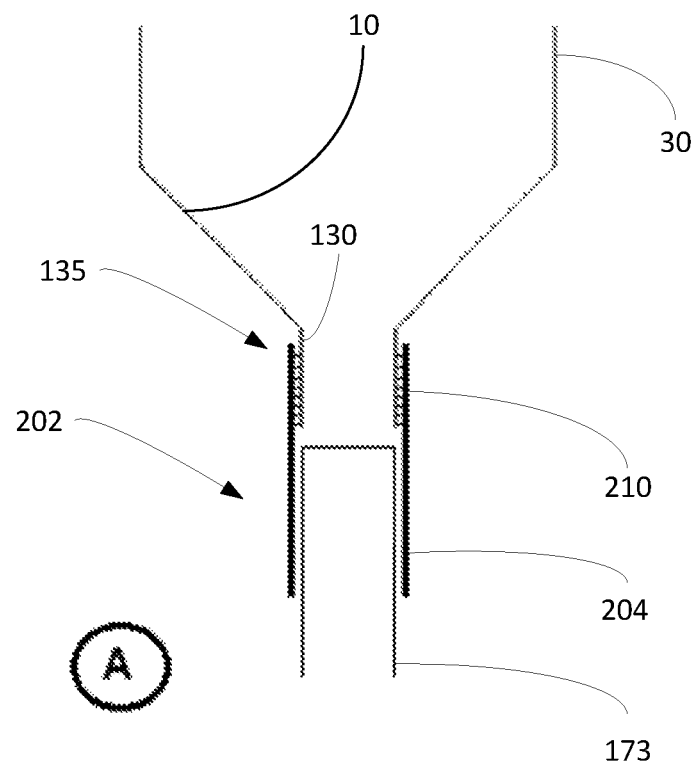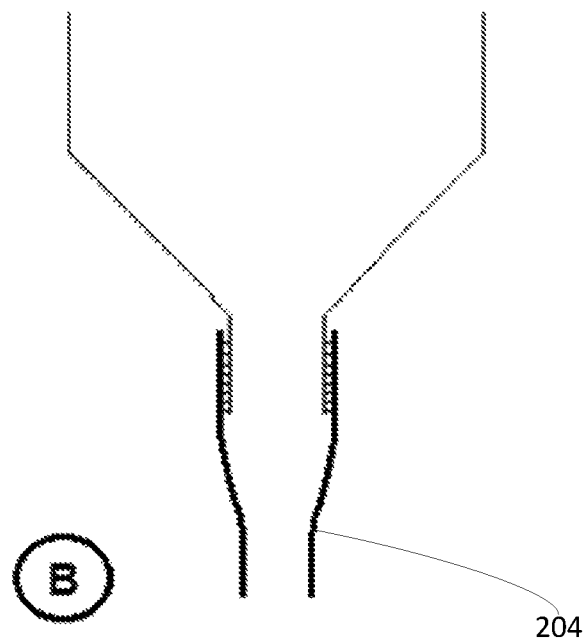
FIG. 34A-B

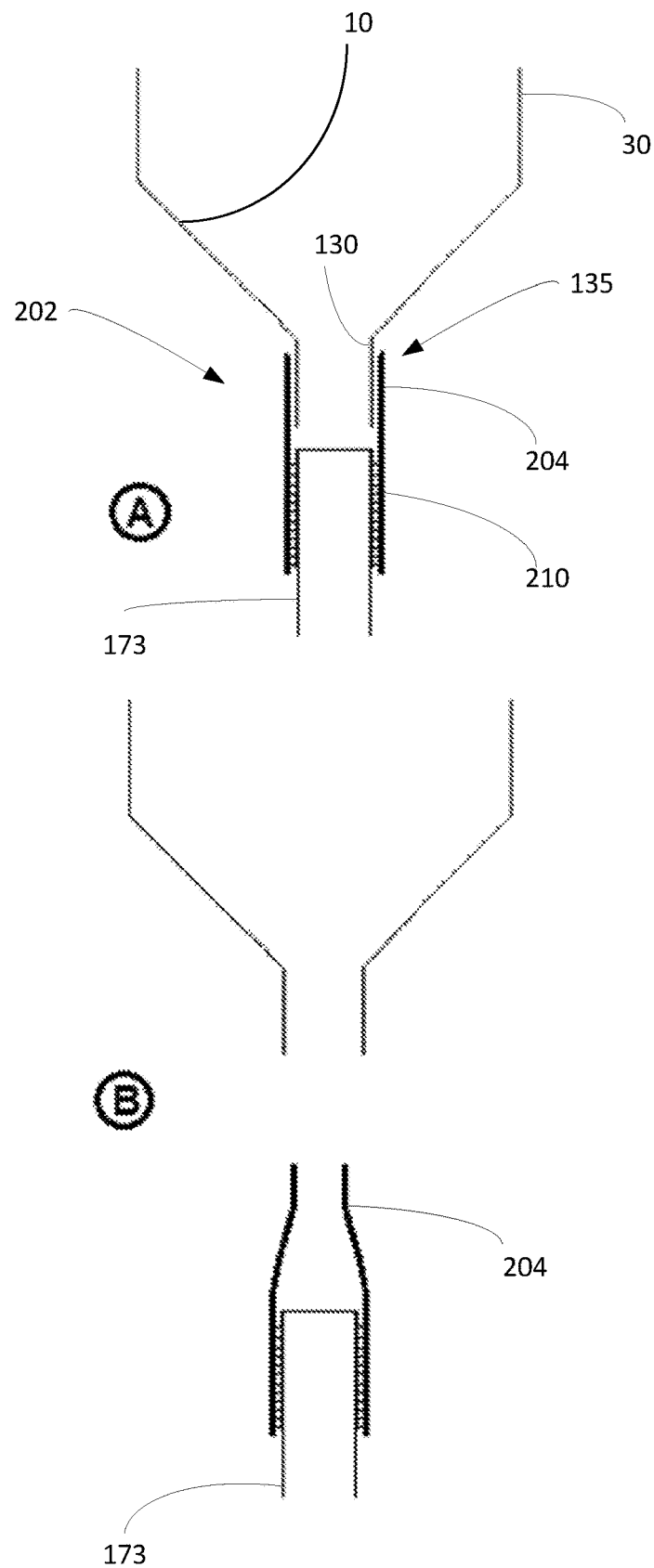
FIG. 35A-B

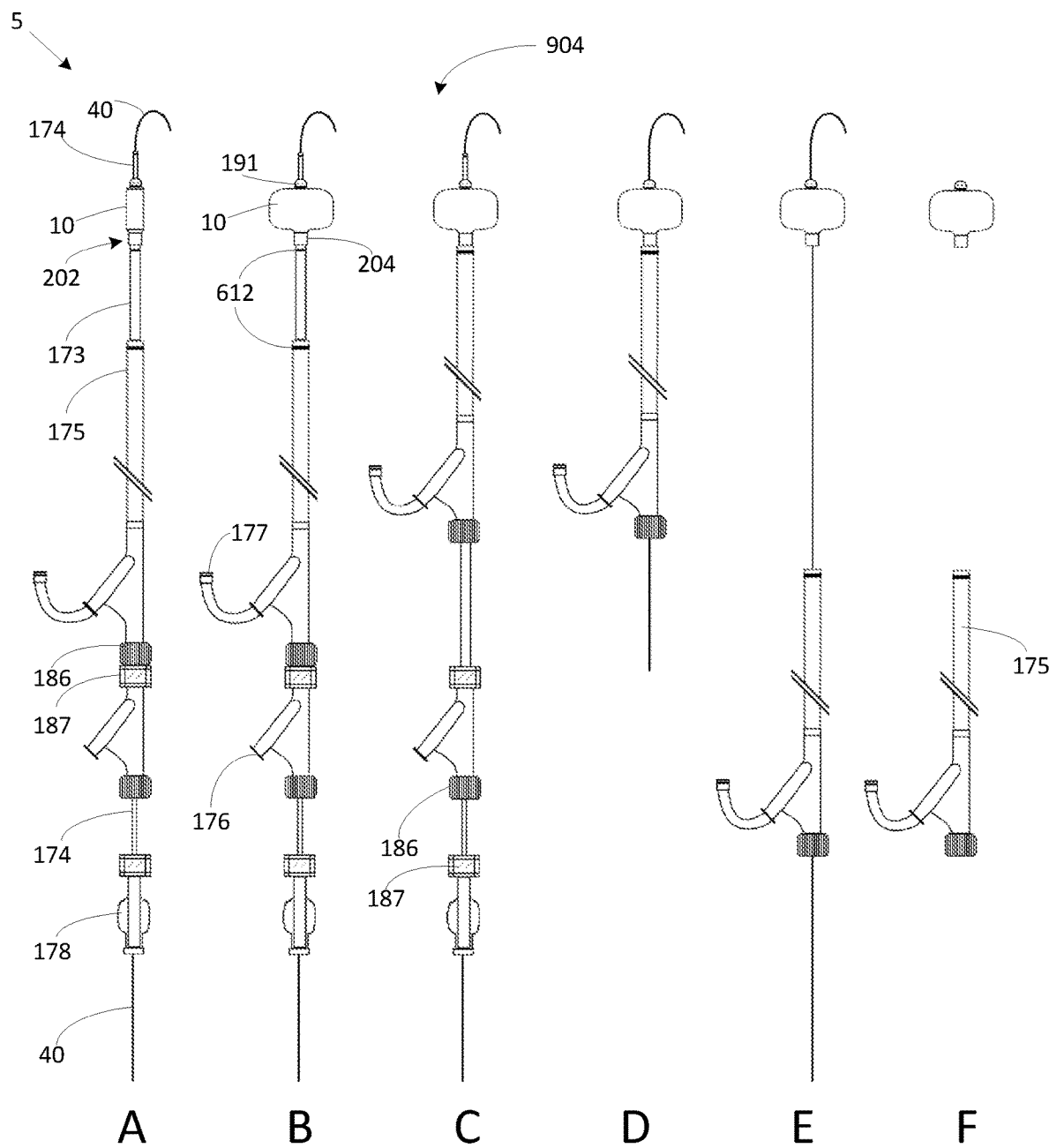
FIG. 36A-F

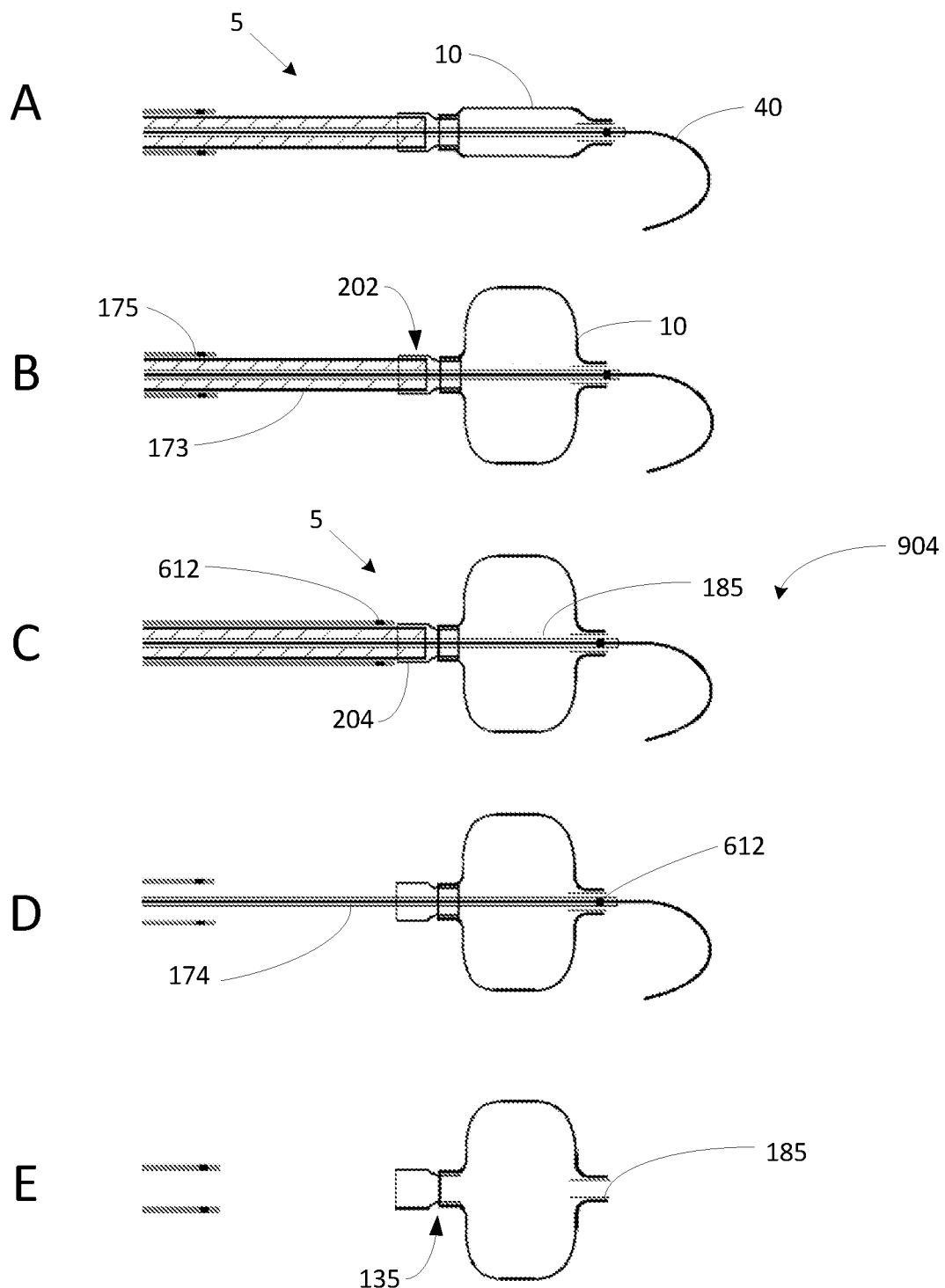
FIG. 37A-E

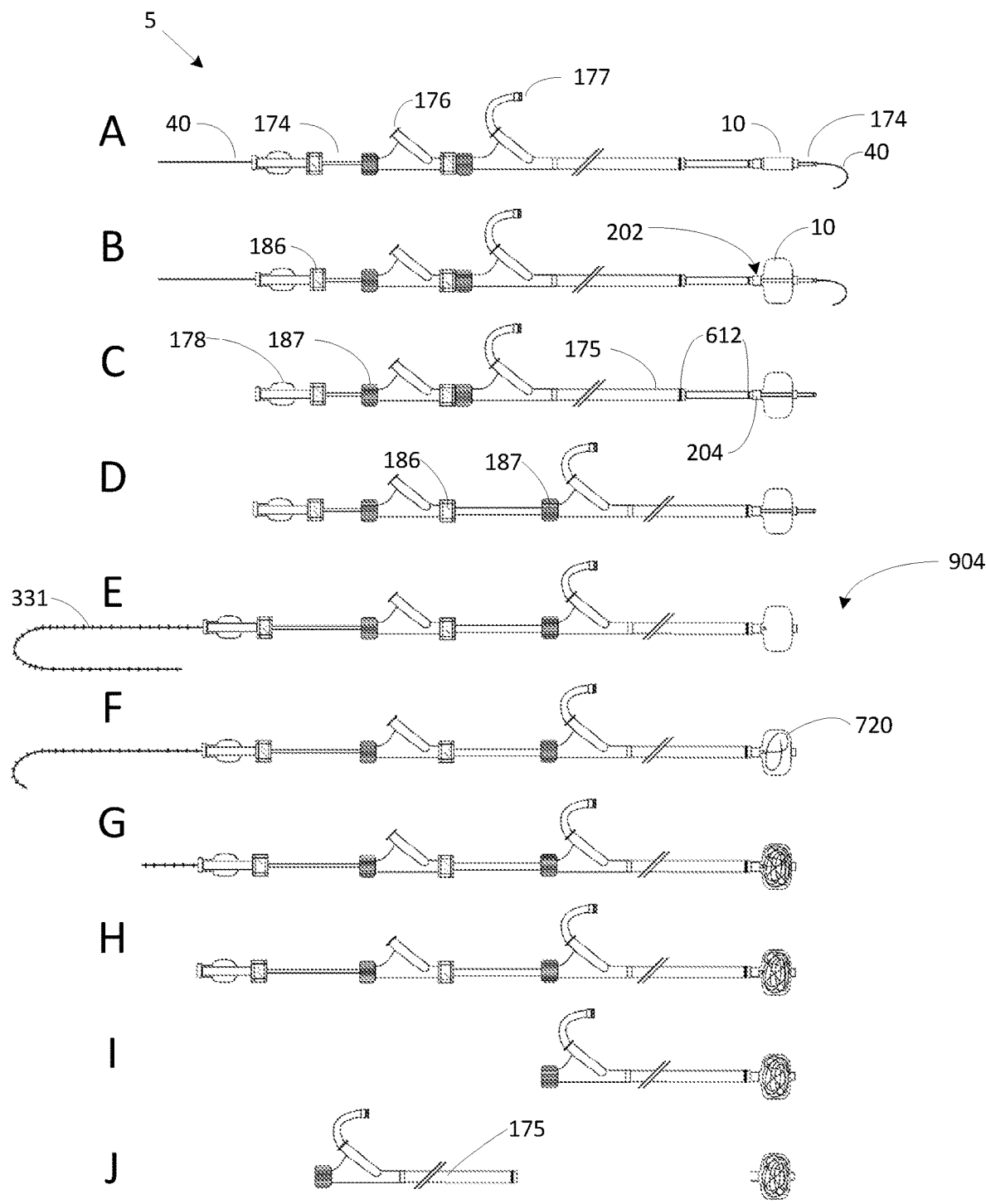
FIG. 38A-J

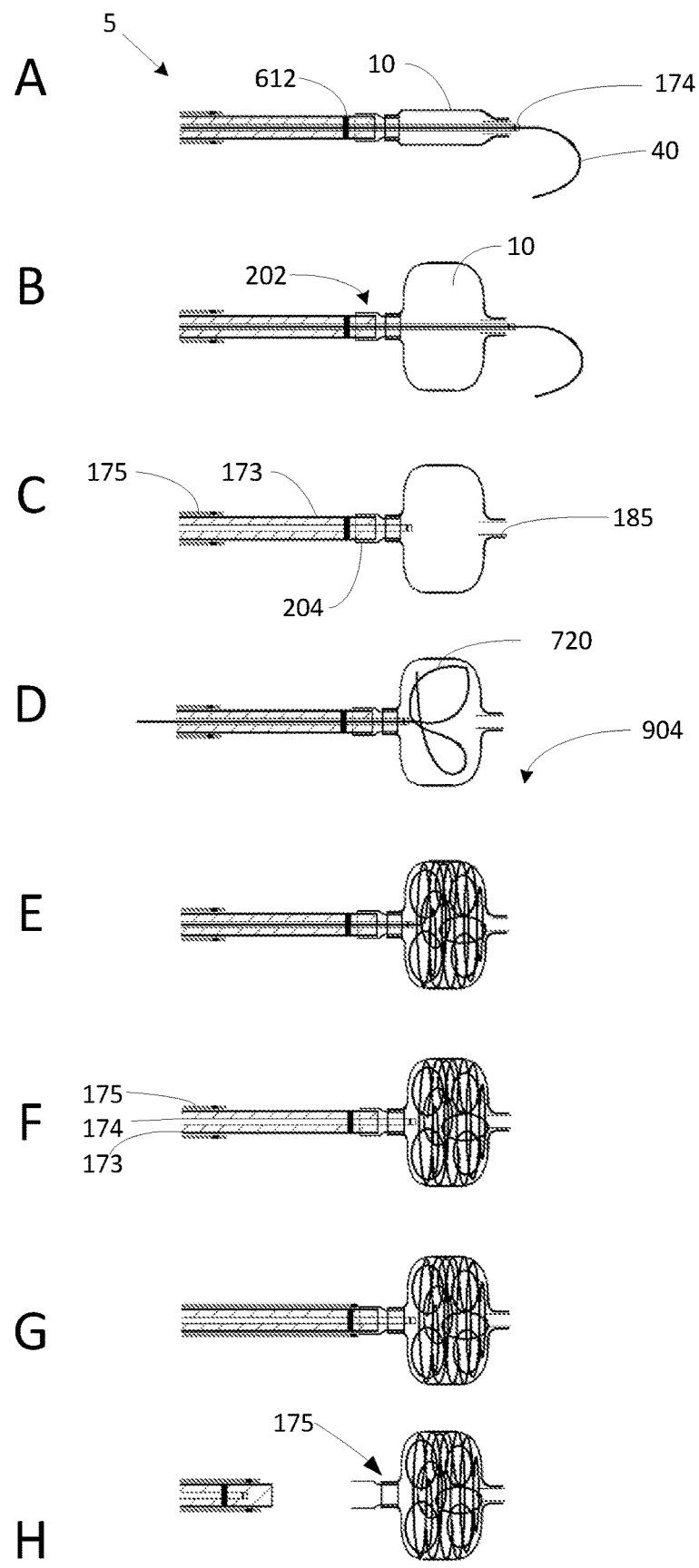
FIG. 39A-H

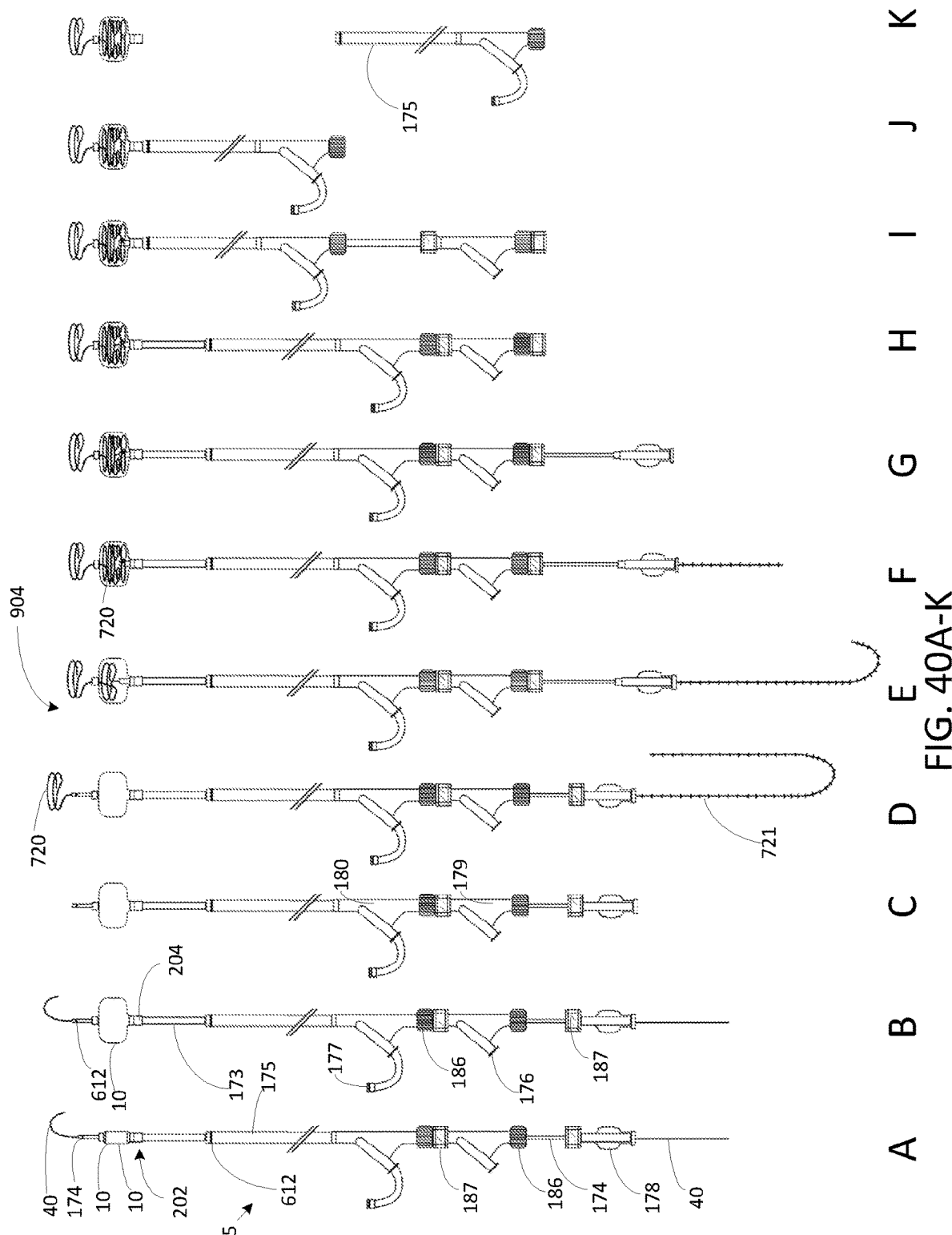
FIG. 40A-K

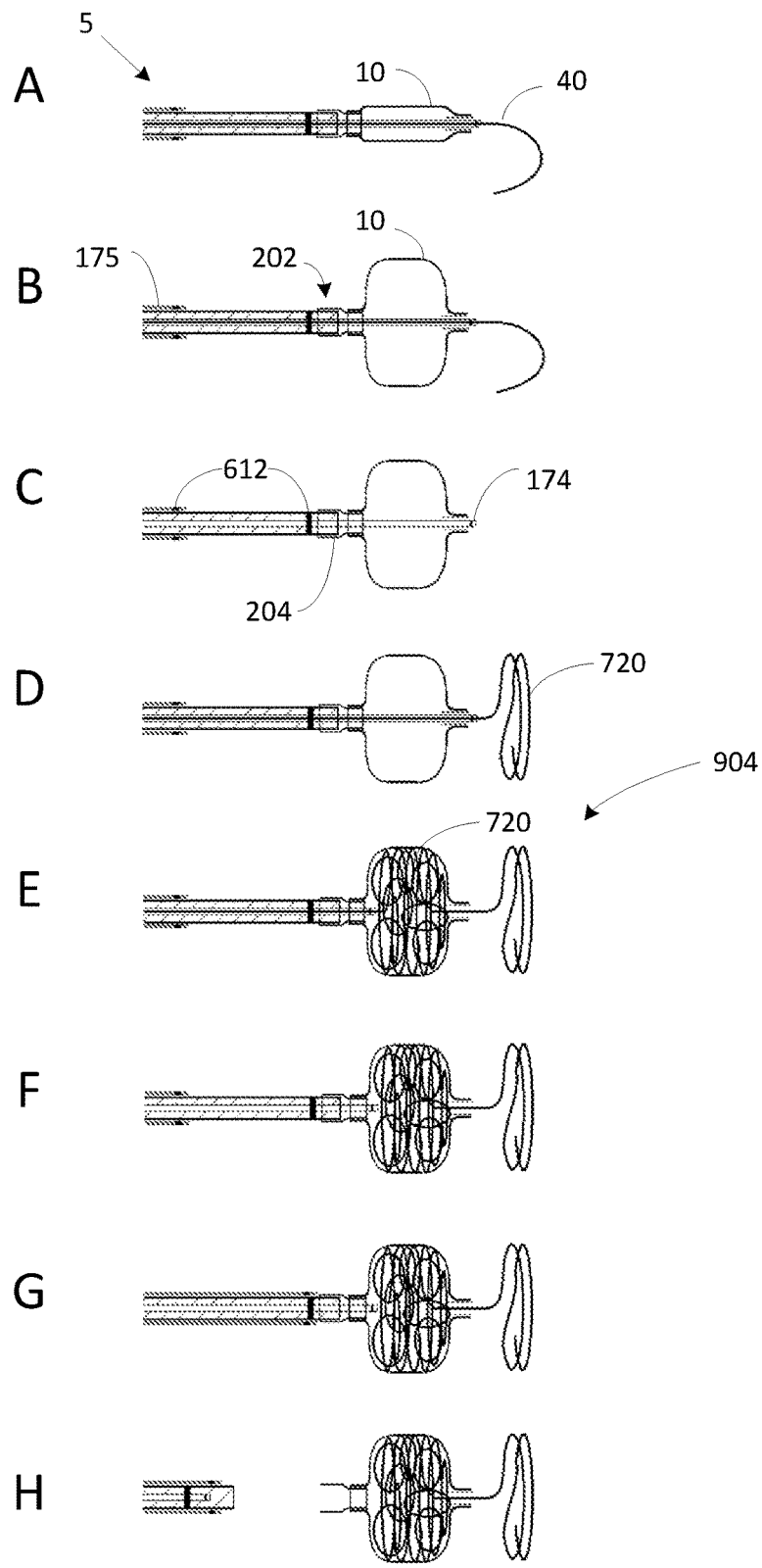
FIG. 41A-H

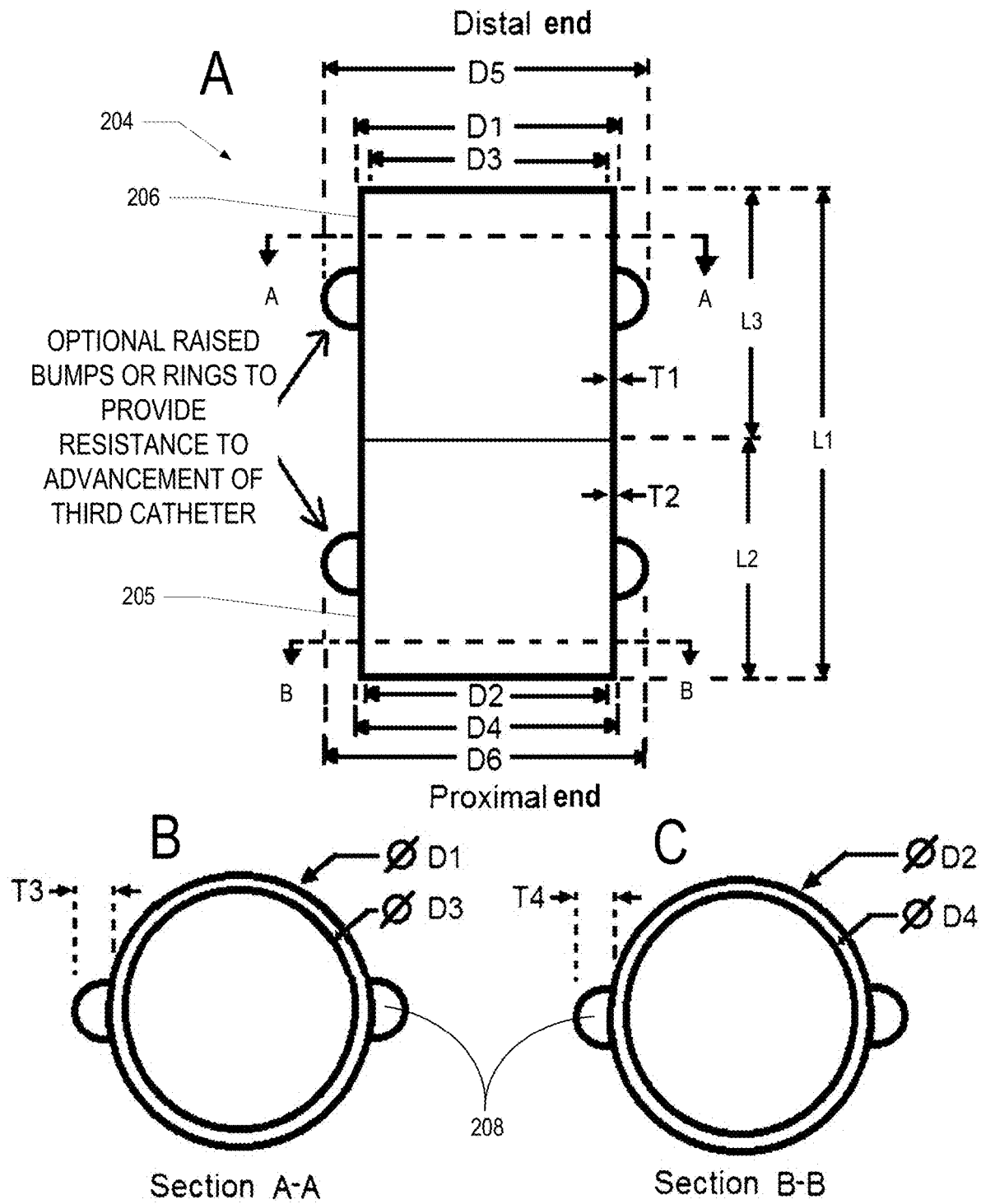
FIG. 42A-C

| Dimensions of Elastomeric Tubular Segment | | | | | | | |
|---|---|---|---|---|---|---|---|
| Dimension | Unit | Nominal | Allowable | | Preferred | |
| | | | Minimum | Maximum | Minimum | Maximum |
| D1 | in | 0.051 | 0.046 | 0.056 | 0.050 | 0.052 |
| D2 | in | 0.056 | 0.051 | 0.061 | 0.055 | 0.057 |
| D3 | in | 0.048 | 0.043 | 0.053 | 0.047 | 0.049 |
| D4 | in | 0.053 | 0.048 | 0.058 | 0.052 | 0.054 |
| D5 | in | 0.091 | 0.076 | 0.106 | 0.088 | 0.094 |
| D6 | in | 0.096 | 0.081 | 0.111 | 0.093 | 0.099 |
| L1 | in | 0.118 | 0.098 | 0.138 | 0.113 | 0.123 |
| L2 | in | 0.079 | 0.065 | 0.092 | 0.075 | 0.082 |
| L3 | in | 0.039 | 0.033 | 0.046 | 0.038 | 0.041 |
| T1 | in | 0.0015 | 0.001 | 0.004 | 0.001 | 0.0025 |
| T2 | in | 0.0015 | 0.001 | 0.004 | 0.001 | 0.0025 |
| T3 | in | 0.020 | 0.015 | 0.025 | 0.019 | 0.021 |
| T4 | in | 0.020 | 0.015 | 0.025 | 0.019 | 0.021 |

FIG. 43

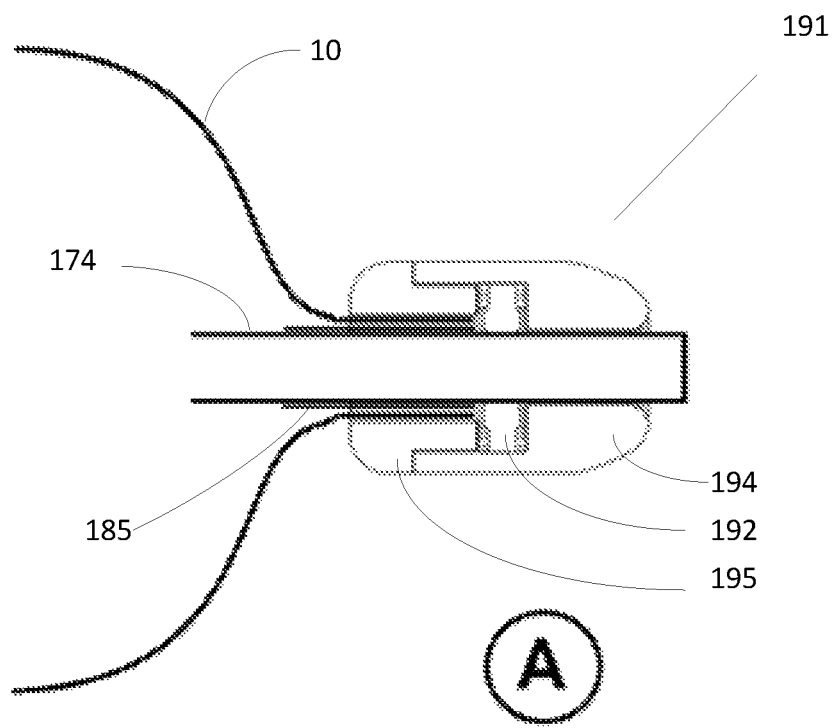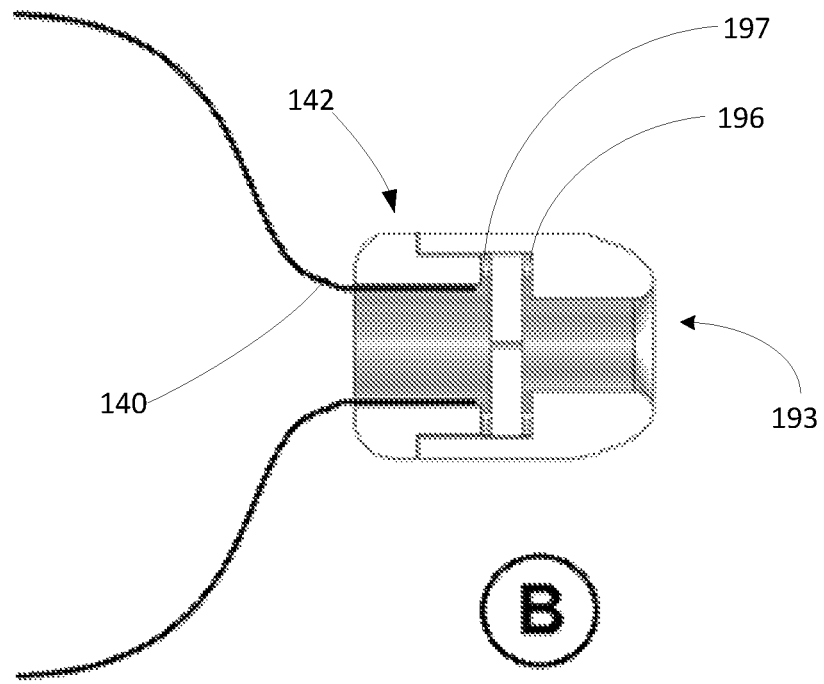
FIG. 44A-B

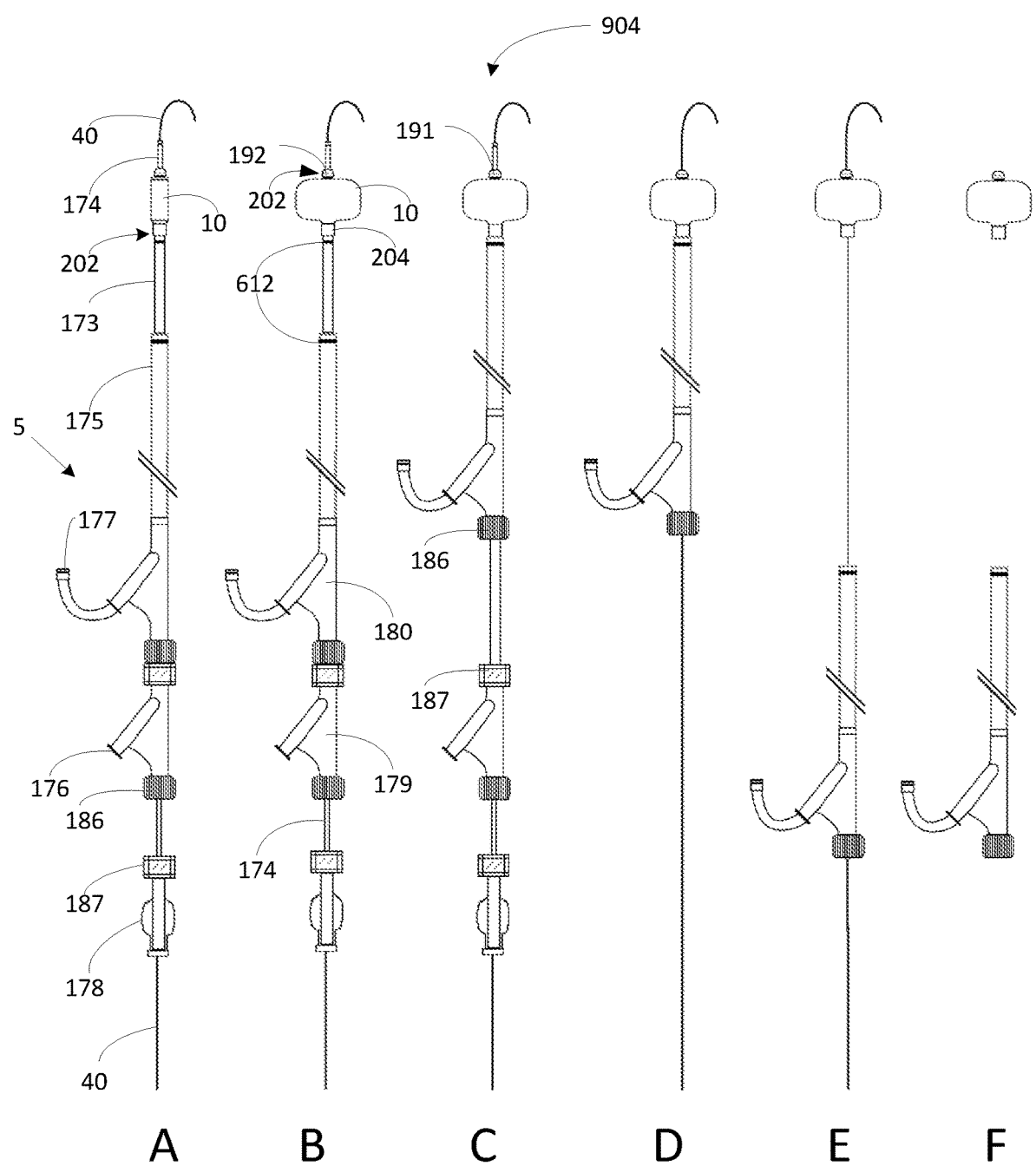
FIG. 45A-F

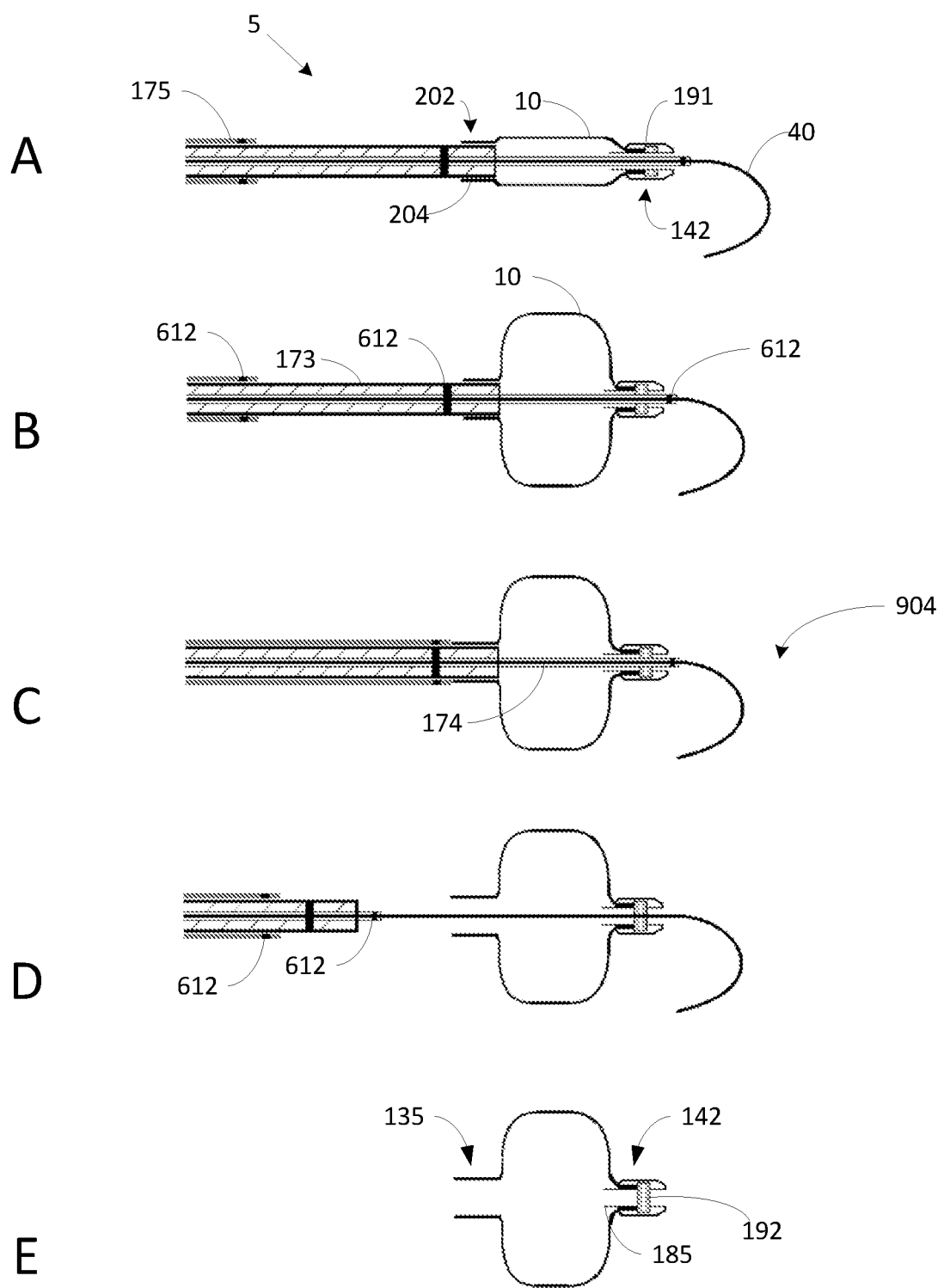
FIG. 46A-E

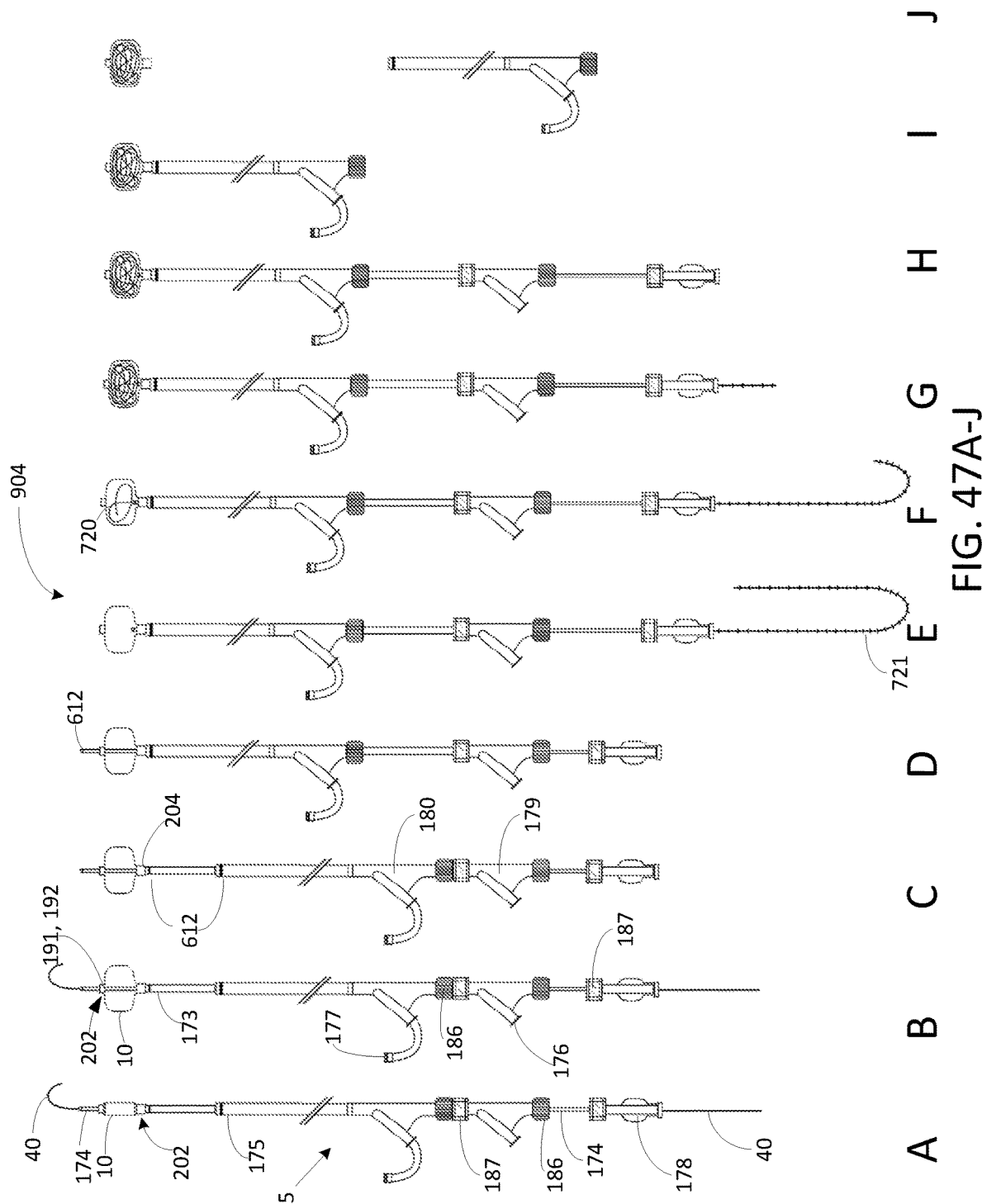
FIG. 47A-J

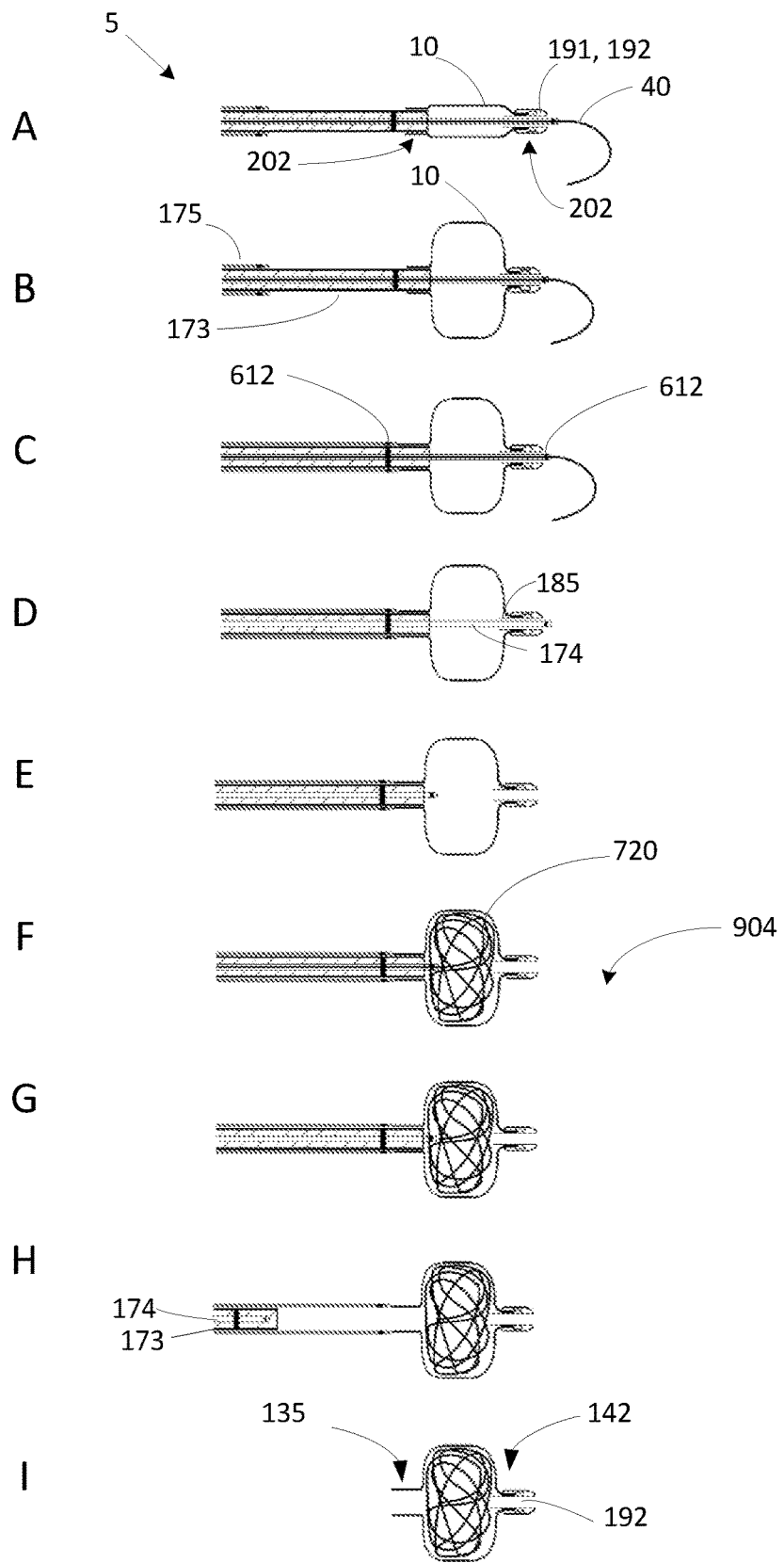
FIG. 48A-I

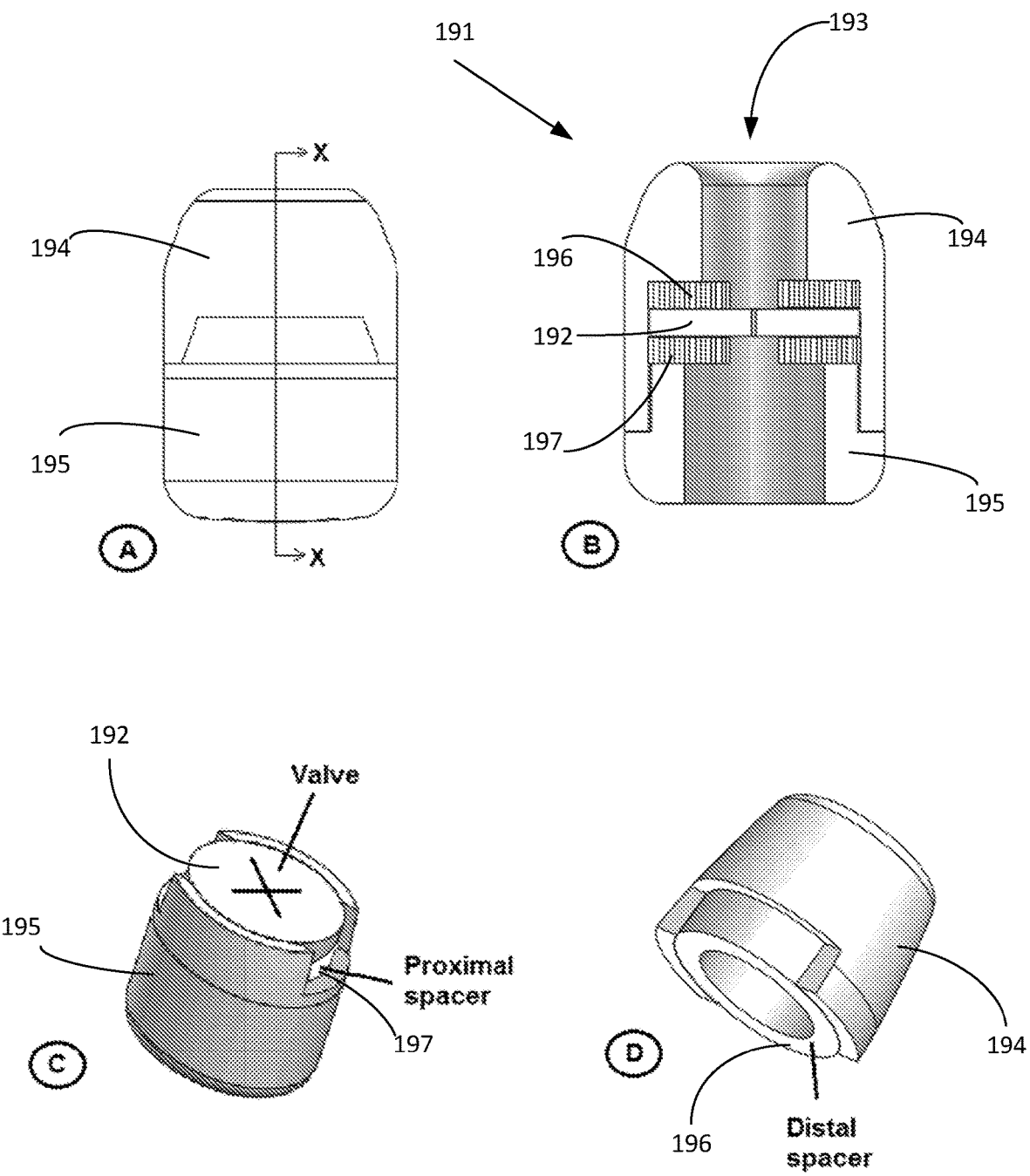
FIG. 49A-D

Dimensions of Distal Valve Components

| Dimension | Unit | Nominal | Allowable | | Preferred | |
|---|---|---|---|---|---|---|
| | | | Minimum | Maximum | Minimum | Maximum |
| D1 | in | 0.055 | 0.035 | 0.075 | 0.050 | 0.060 |
| D2 | in | 0.027 | 0.022 | 0.032 | 0.026 | 0.028 |
| D3 | in | 0.0175 | 0.0155 | 0.0195 | 0.0165 | 0.0185 |
| D4 | in | 0.027 | 0.022 | 0.032 | 0.026 | 0.028 |
| T1 | in | 0.026 | 0.020 | 0.049 | 0.022 | 0.038 |
| T2 | in | 0.006 | 0.004 | 0.012 | 0.005 | 0.010 |
| T3 | in | 0.013 | 0.011 | 0.020 | 0.012 | 0.017 |
| T4 | in | 0.006 | 0.004 | 0.012 | 0.005 | 0.010 |

Dimensions of Electrolytic Detachment System at Proximal Neck: Anode

| Dimension | Unit | Nominal | Allowable | | Preferred | |
|---|---|---|---|---|---|---|
| | | | Minimum | Maximum | Minimum | Maximum |
| D1 | in | 0.038 | 0.035 | 0.062 | 0.037 | 0.039 |
| D2 | in | 0.034 | 0.031 | 0.058 | 0.033 | 0.035 |
| D3 | in | 0.046 | 0.043 | 0.070 | 0.045 | 0.047 |
| D4 | in | 0.052 | 0.049 | 0.076 | 0.051 | 0.053 |
| L1 | in | 0.098 | 0.049 | 0.195 | 0.073 | 0.122 |
| L2 | in | 0.039 | 0.020 | 0.078 | 0.029 | 0.049 |
| L3 | in | 0.039 | 0.020 | 0.078 | 0.029 | 0.049 |
| L4 | in | 0.005 | 0.0025 | 0.010 | 0.004 | 0.006 |
| L5 | in | 0.020 | 0.010 | 0.039 | 0.015 | 0.024 |
| T1 | in | 0.005 | 0.003 | 0.007 | 0.004 | 0.006 |
| T2 | in | 0.0009 | 0.0007 | 0.0012 | 0.0008 | 0.0011 |
| T3 | in | 0.003 | 0.002 | 0.004 | 0.0025 | 0.0035 |
| T4 | in | 0.0005 | 0.0003 | 0.0022 | 0.00045 | 0.0010 |
| T5 | in | 0.0005 | 0.0003 | 0.0027 | 0.00045 | 0.0010 |
| T6 | in | 0.00005 | 0.0004 | 0.0007 | 0.0004 | 0.0006 |

FIG. 56

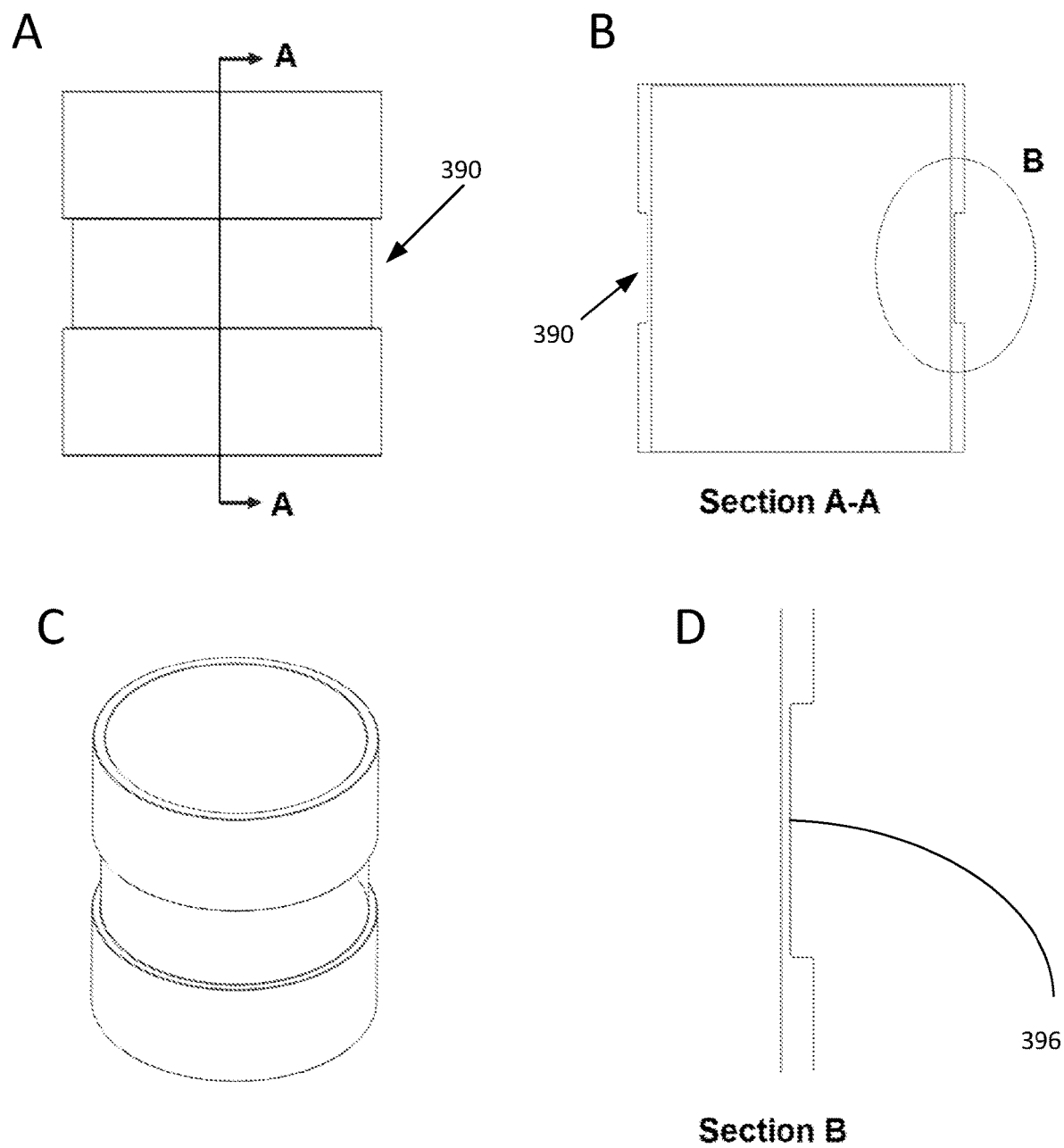
FIG. 57A-D

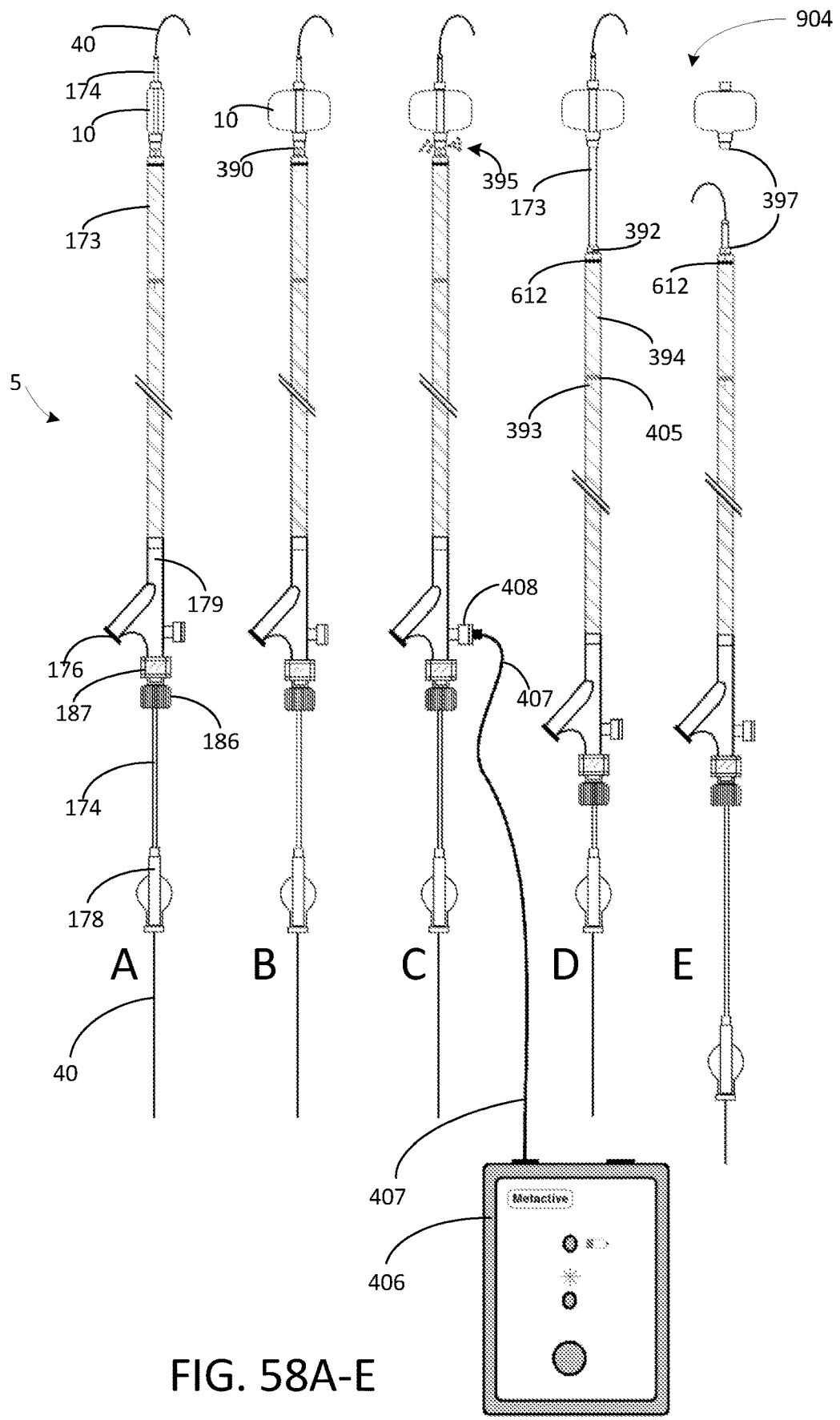
FIG. 58A-E

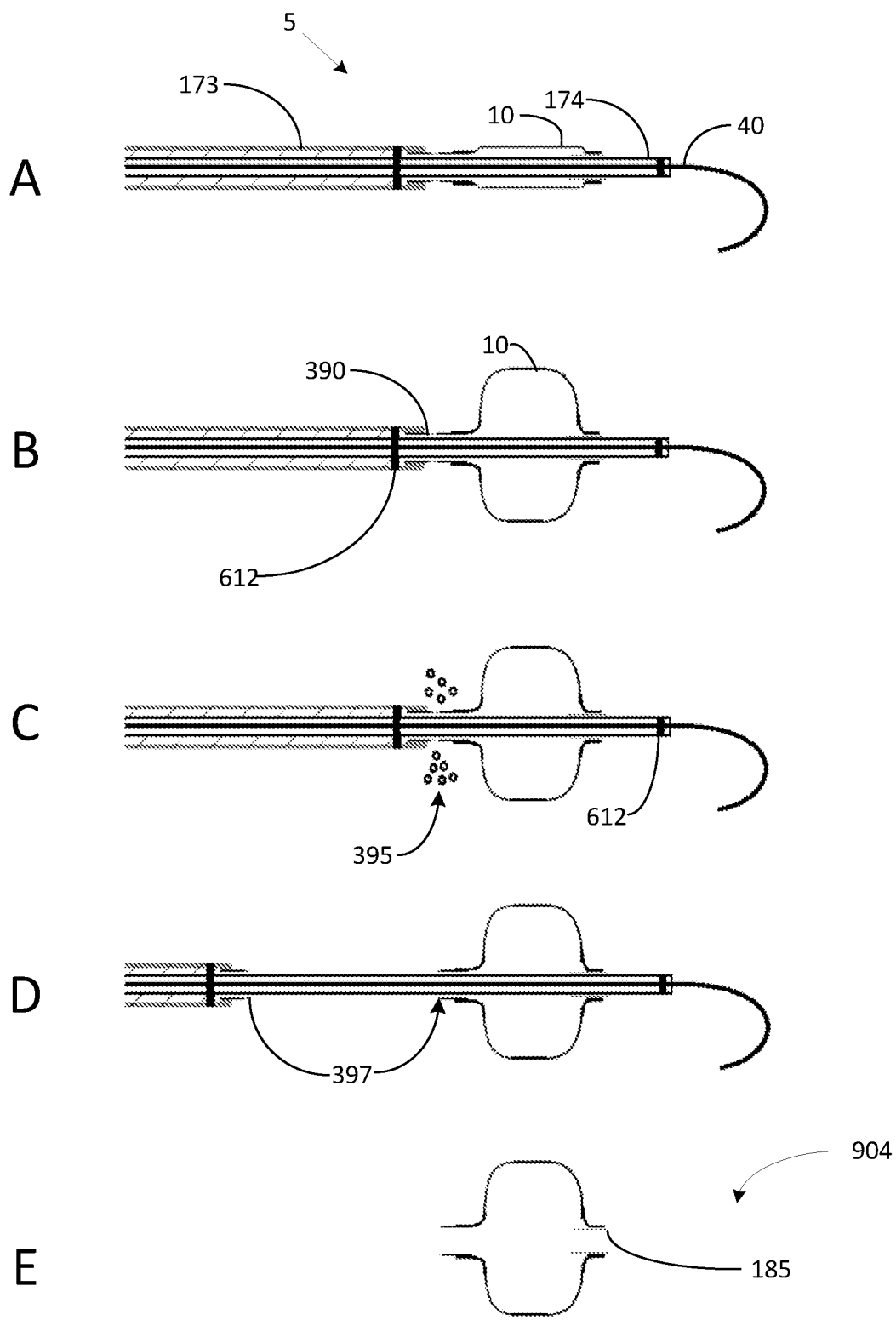
FIG. 59A-E

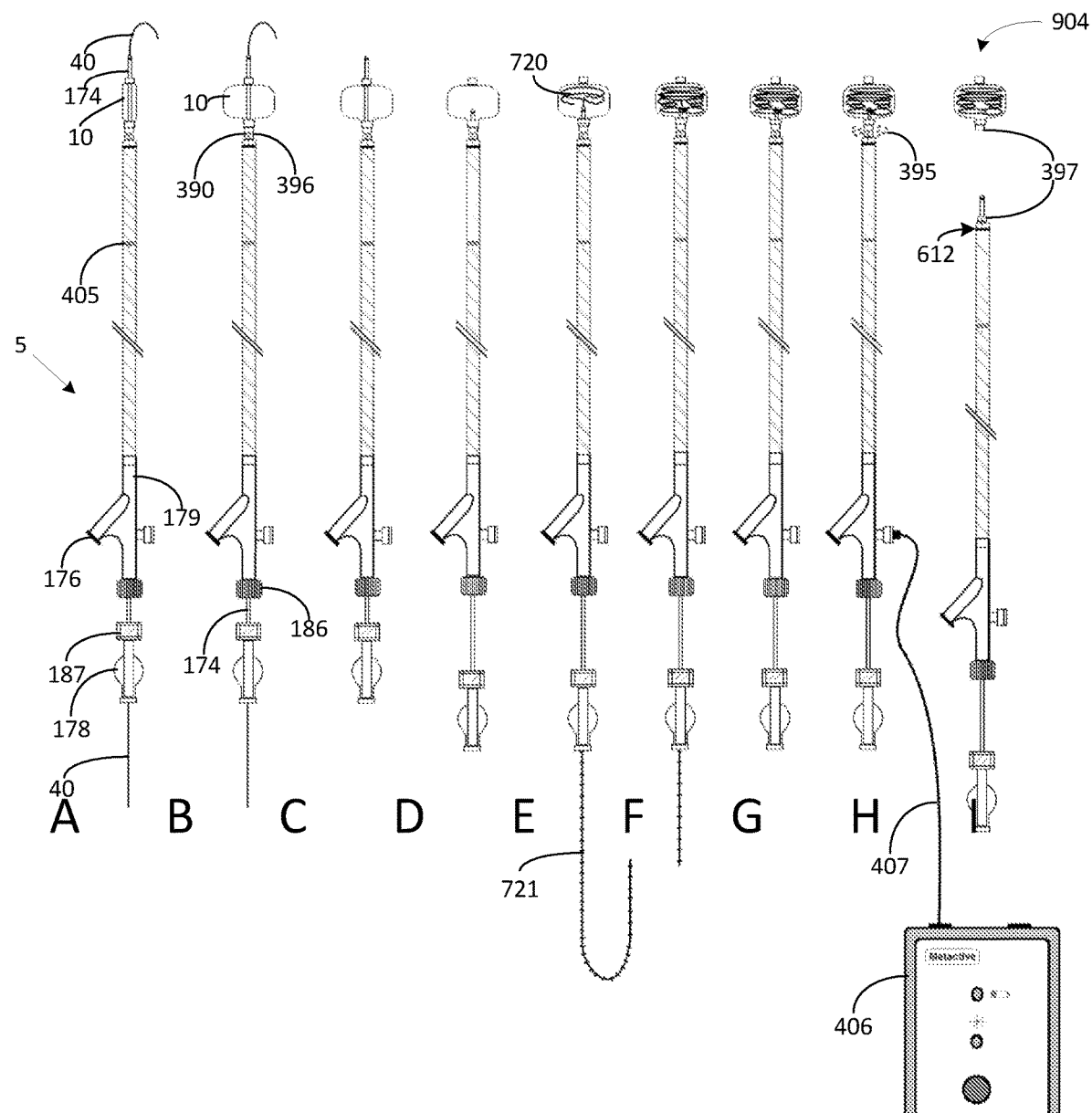
FIG. 60A-I

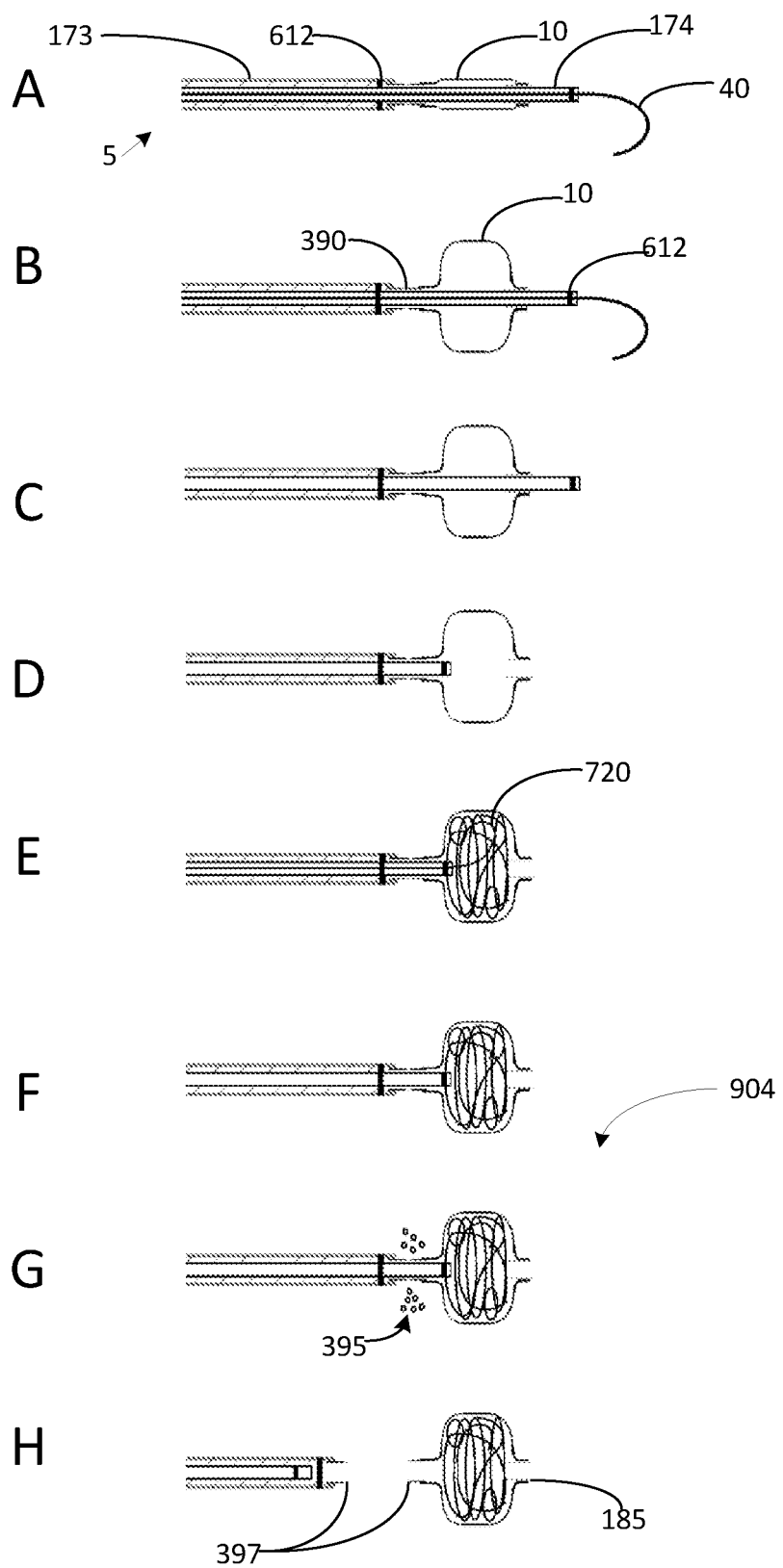
FIG. 61A-H

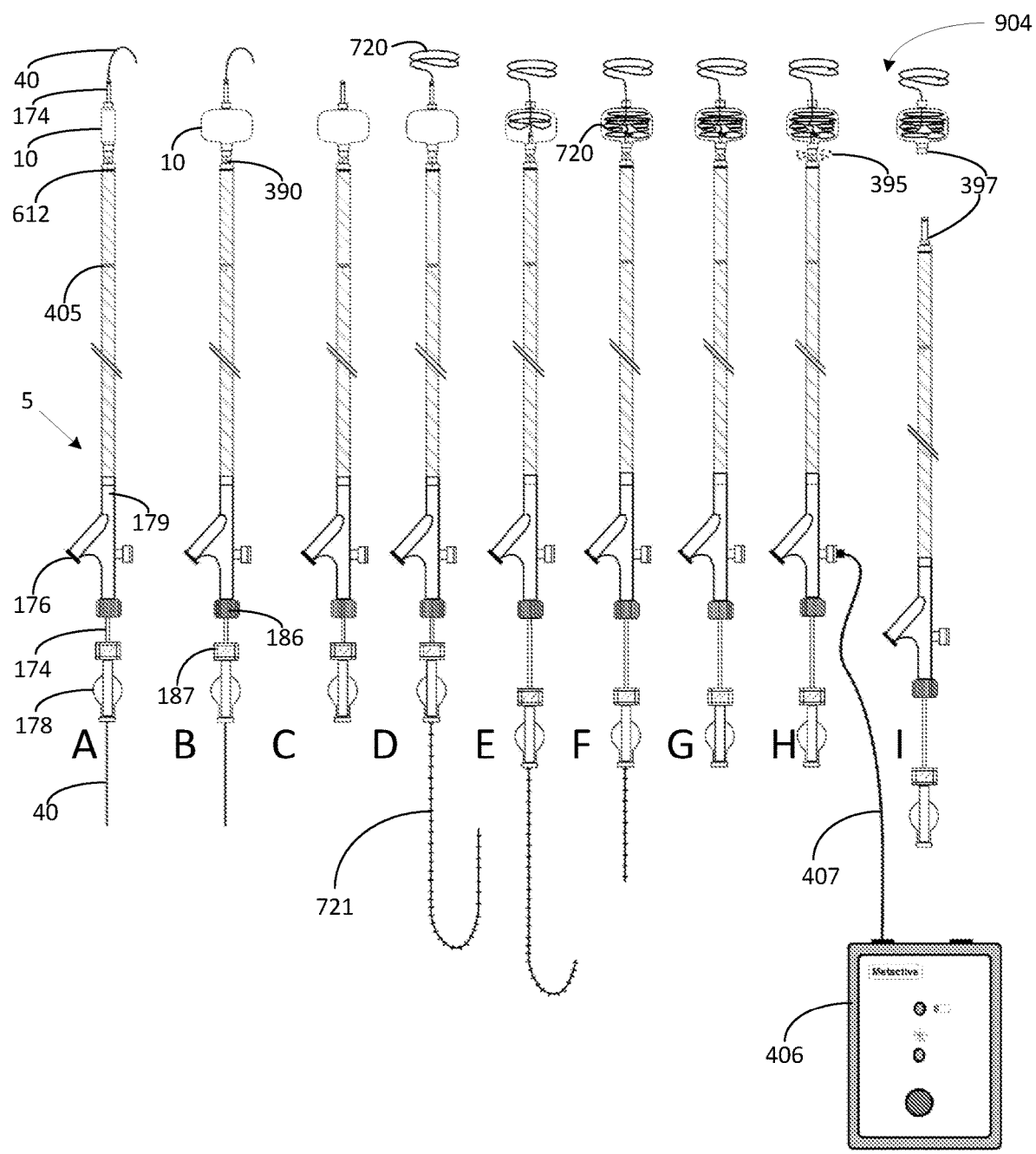
FIG. 62A-I

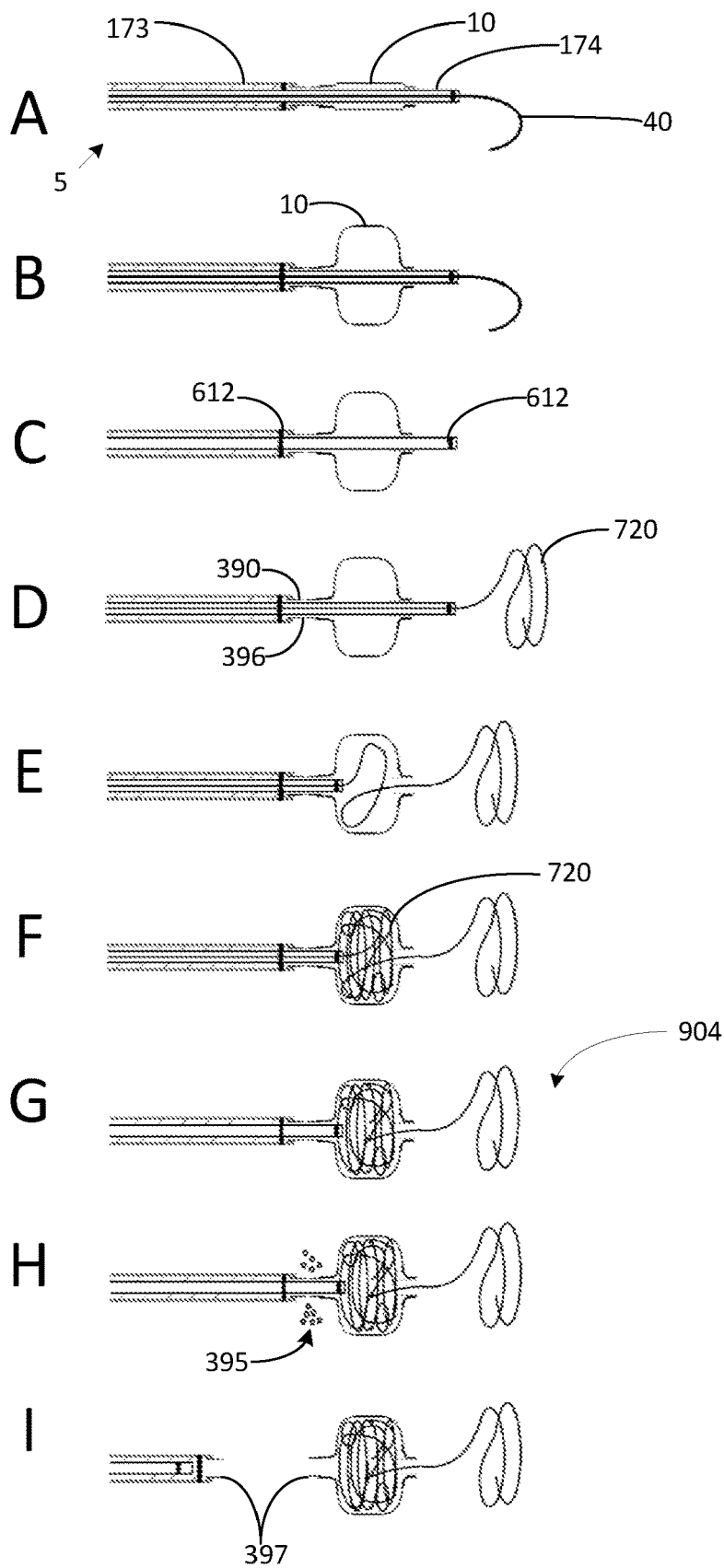
FIG. 63A-I

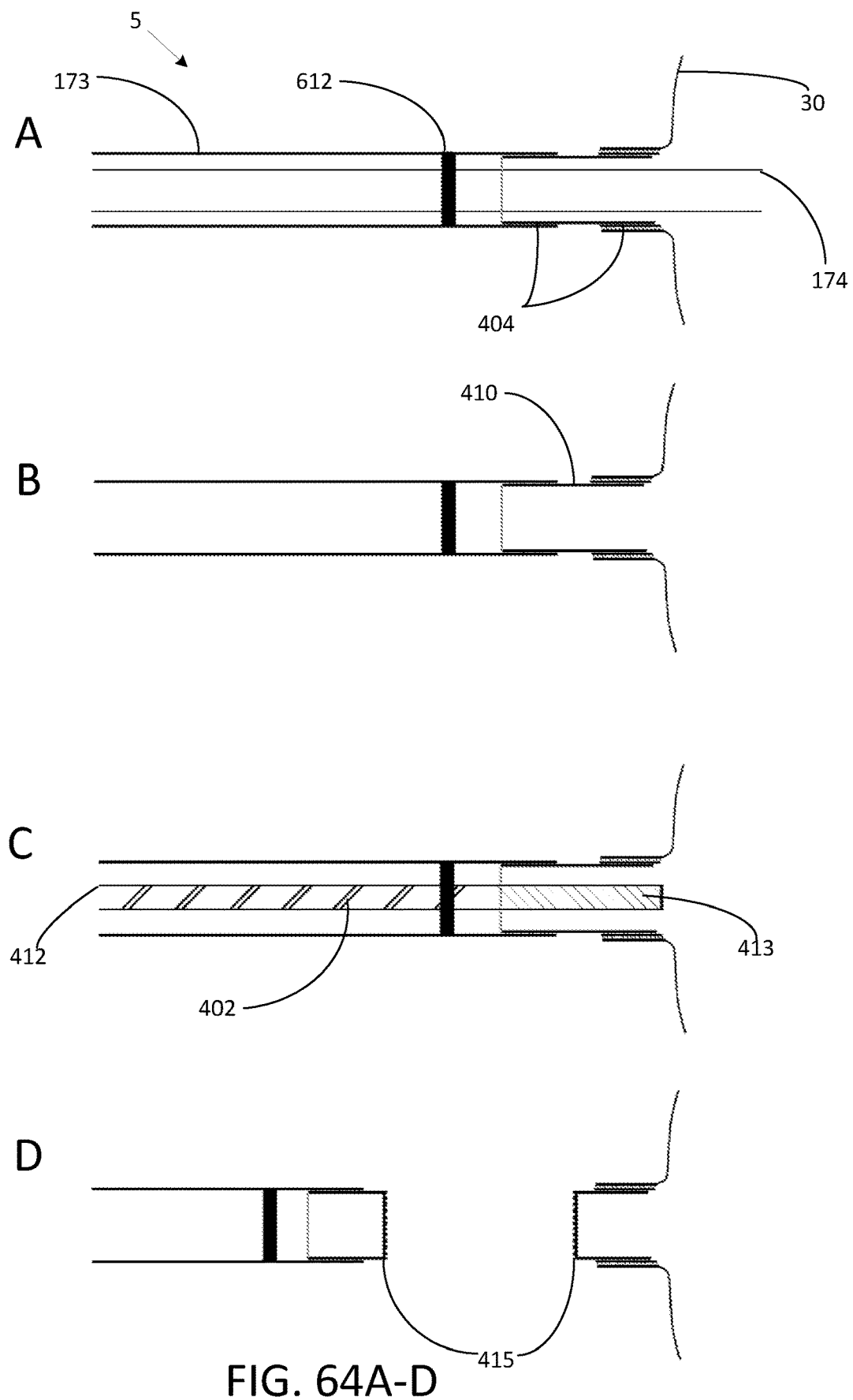
FIG. 64A-D

FIG. 65A-D
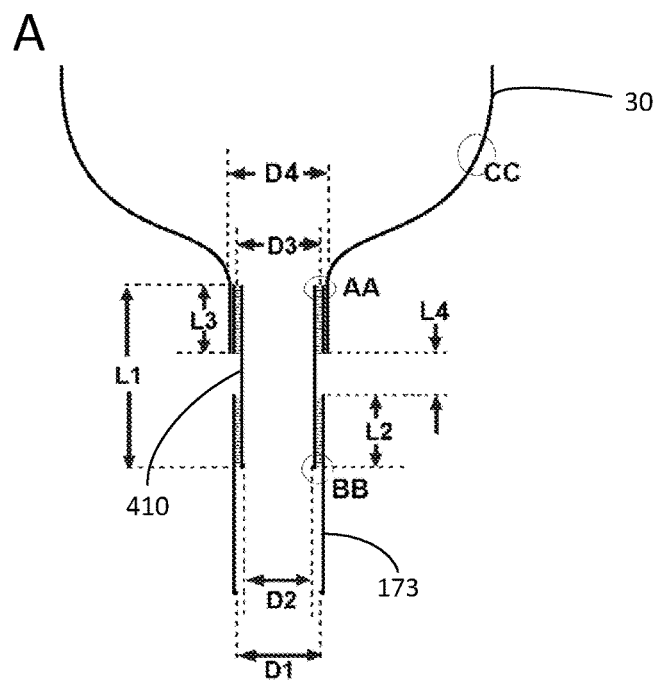
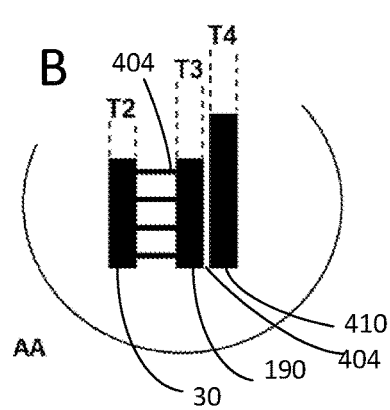
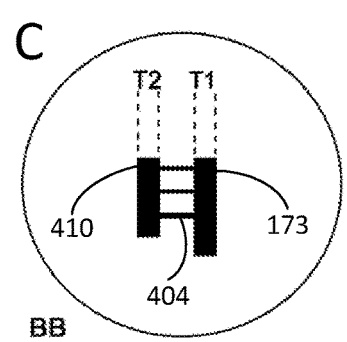
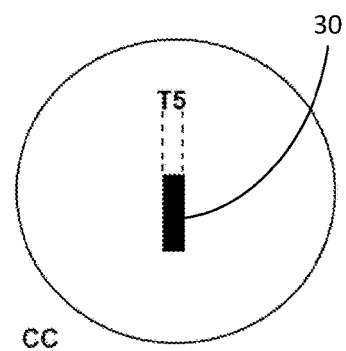

Dimensions of Electrothermal Detachment System at Proximal Neck: Heat Sensitive First Tubular Segment

| Dimension | Unit | Nominal | Allowable | | Preferred | |
|---|---|---|---|---|---|---|
| | | | Minimum | Maximum | Minimum | Maximum |
| D1 | in | 0.044 | 0.041 | 0.068 | 0.043 | 0.045 |
| D2 | in | 0.034 | 0.031 | 0.058 | 0.033 | 0.035 |
| D3 | in | 0.046 | 0.043 | 0.070 | 0.045 | 0.047 |
| D4 | in | 0.052 | 0.049 | 0.076 | 0.051 | 0.053 |
| L1 | in | 0.098 | 0.049 | 0.195 | 0.073 | 0.122 |
| L2 | in | 0.039 | 0.020 | 0.078 | 0.029 | 0.049 |
| L3 | in | 0.039 | 0.020 | 0.078 | 0.029 | 0.049 |
| L4 | in | 0.020 | 0.010 | 0.039 | 0.015 | 0.024 |
| T1 | in | 0.005 | 0.003 | 0.007 | 0.004 | 0.006 |
| T2 | in | 0.005 | 0.003 | 0.007 | 0.004 | 0.006 |
| T3 | in | 0.003 | 0.002 | 0.004 | 0.0025 | 0.0035 |
| T4 | in | 0.0005 | 0.0003 | 0.0022 | 0.00045 | 0.0010 |
| T5 | in | 0.0005 | 0.0003 | 0.0027 | 0.00045 | 0.0010 |

Dimensions of Electrothermal Detachment System at Proximal Neck: Heat Sensitive Distal End of First Catheter

| Dimension | Unit | Nominal | Allowable | | Preferred | |
|---|---|---|---|---|---|---|
| | | | Minimum | Maximum | Minimum | Maximum |
| D1 | in | 0.038 | 0.035 | 0.062 | 0.037 | 0.039 |
| D2 | in | 0.046 | 0.043 | 0.070 | 0.045 | 0.047 |
| D3 | in | 0.052 | 0.049 | 0.076 | 0.051 | 0.053 |
| L1 | in | 0.078 | 0.039 | 0.156 | 0.059 | 0.098 |
| L2 | in | 0.043 | 0.021 | 0.086 | 0.032 | 0.054 |
| L3 | in | 0.039 | 0.020 | 0.078 | 0.029 | 0.049 |
| T1 | in | 0.005 | 0.003 | 0.007 | 0.004 | 0.006 |
| T2 | in | 0.005 | 0.003 | 0.007 | 0.004 | 0.006 |
| T3 | in | 0.003 | 0.002 | 0.004 | 0.0025 | 0.0035 |
| T4 | in | 0.0005 | 0.0003 | 0.0022 | 0.00045 | 0.0010 |
| T5 | in | 0.0005 | 0.0003 | 0.0027 | 0.00045 | 0.0010 |

| Dimensions of Electrothermal Detachment System at Proximal Neck: Heat Sensitive Bond to First Catheter | | | | | | |
|---|---|---|---|---|---|---|
| | | | Allowable | | Preferred | |
| Dimension | Unit | Nominal | Minimum | Maximum | Minimum | Maximum |
| D1 | in | 0.038 | 0.035 | 0.062 | 0.037 | 0.039 |
| D2 | in | 0.046 | 0.043 | 0.070 | 0.045 | 0.047 |
| D3 | in | 0.052 | 0.049 | 0.076 | 0.051 | 0.053 |
| L1 | in | 0.043 | 0.021 | 0.086 | 0.032 | 0.054 |
| L2 | in | 0.039 | 0.020 | 0.078 | 0.029 | 0.049 |
| T1 | in | 0.005 | 0.003 | 0.007 | 0.004 | 0.006 |
| T2 | in | 0.003 | 0.002 | 0.004 | 0.0025 | 0.0035 |
| T3 | in | 0.0005 | 0.0003 | 0.0022 | 0.00045 | 0.0010 |
| T4 | in | 0.0005 | 0.0003 | 0.0027 | 0.00045 | 0.0010 |

| Dimensions of Pleated Balloon |||||||||
|---|---|---|---|---|---|---|---|---|
| Diameter (mm) || Wall Thickness (in) ||| Pleat # || Pleat Length (mm) ||
| Minimum | Maximum | Nominal | Minimum | Maximum | Minimum | Maximum | Minimum | Maximum |
| 2 | 6 | 0.0005 | 0.0003 | 0.0006 | 3 | 5 | 0.4 | 2.8 |
| 7 | 12 | 0.0011 | 0.0008 | 0.0014 | 3 | 5 | 2.0 | 5.9 |
| 13 | 18 | 0.0017 | 0.0015 | 0.0020 | 5 | 7 | 2.8 | 5.5 |
| 19 | 24 | 0.0024 | 0.0022 | 0.0027 | 5 | 7 | 4.2 | 7.4 |
| 25 | 30 | 0.0031 | 0.0028 | 0.0034 | 7 | 9 | 4.3 | 6.7 |
| 31 | 38 | 0.0033 | 0.0032 | 0.0035 | 7 | 9 | 5.4 | 8.5 |

FIG. 85

| Dimensions of 0.014" Second Catheter and Coil Delivery System |||||||
|---|---|---|---|---|---|---|
| Dimension | Unit | Nominal | Allowable || Preferred ||
| | | | Minimum | Maximum | Minimum | Maximum |
| D1 | in | 0.028 | 0.020 | 0.033 | 0.024 | 0.029 |
| D2 | in | 0.018 | 0.016 | 0.020 | 0.014 | 0.019 |
| D3 | in | 0.028 | 0.023 | 0.033 | 0.027 | 0.029 |
| D4 | in | 0.018 | 0.016 | 0.020 | 0.017 | 0.019 |
| D5 | in | 0.013 | 0.010 | 0.018 | 0.011 | 0.014 |
| D6 | in | 0.012 | 0.004 | 0.018 | 0.002 | 0.014 |
| D7 | in | 0.028 | 0.023 | 0.040 | 0.027 | 0.029 |
| D8 | in | 0.018 | 0.016 | 0.020 | 0.017 | 0.019 |
| L1 | cm | 130 | 80 | 405 | 125 | 135 |
| L2 | cm | 250 | 45 | 810 | 190 | 285 |
| L3 | cm | 75 | 10 | 400 | 25 | 100 |
| L4 | cm | 175 | 35 | 410 | 165 | 185 |
| L5 | cm | 100 | 30 | 405 | 90 | 110 |

FIG. 87

| Dimensions of 0.018" Second Catheter and Coil Delivery System |||||||
|---|---|---|---|---|---|---|
| Dimension | Unit | Nominal | Allowable || Preferred ||
| | | | Minimum | Maximum | Minimum | Maximum |
| D1 | in | 0.032 | 0.024 | 0.037 | 0.028 | 0.033 |
| D2 | in | 0.022 | 0.020 | 0.024 | 0.018 | 0.023 |
| D3 | in | 0.032 | 0.027 | 0.037 | 0.031 | 0.033 |
| D4 | in | 0.022 | 0.020 | 0.024 | 0.021 | 0.023 |
| D5 | in | 0.017 | 0.014 | 0.022 | 0.015 | 0.018 |
| D6 | in | 0.016 | 0.014 | 0.022 | 0.006 | 0.018 |
| D7 | in | 0.032 | 0.027 | 0.044 | 0.031 | 0.033 |
| D8 | in | 0.022 | 0.020 | 0.024 | 0.021 | 0.023 |
| L1 | cm | 130 | 80 | 405 | 125 | 135 |
| L2 | cm | 250 | 45 | 810 | 190 | 285 |
| L3 | cm | 75 | 10 | 400 | 25 | 100 |
| L4 | cm | 175 | 35 | 410 | 165 | 185 |
| L5 | cm | 100 | 30 | 405 | 90 | 110 |

FIG. 88

Dimensions of 0.035"/0.038" Second Catheter and Coil Delivery System

| Dimension | Unit | Nominal | Allowable | | Preferred | |
|---|---|---|---|---|---|---|
| | | | Minimum | Maximum | Minimum | Maximum |
| D1 | in | 0.062 | 0.054 | 0.064 | 0.058 | 0.063 |
| D2 | in | 0.042 | 0.037 | 0.044 | 0.038 | 0.043 |
| D3 | in | 0.062 | 0.057 | 0.064 | 0.061 | 0.063 |
| D4 | in | 0.042 | 0.037 | 0.044 | 0.041 | 0.043 |
| D5 | in | 0.037 | 0.031 | 0.042 | 0.035 | 0.038 |
| D6 | in | 0.036 | 0.031 | 0.042 | 0.026 | 0.038 |
| D7 | in | 0.062 | 0.057 | 0.064 | 0.061 | 0.063 |
| D8 | in | 0.042 | 0.037 | 0.044 | 0.041 | 0.043 |
| L1 | cm | 130 | 80 | 405 | 125 | 135 |
| L2 | cm | 250 | 45 | 810 | 190 | 285 |
| L3 | cm | 75 | 10 | 400 | 25 | 100 |
| L4 | cm | 175 | 35 | 410 | 165 | 185 |
| L5 | cm | 100 | 30 | 405 | 90 | 110 |

FIG. 89

| Length Dimensions of Second Catheter and Coil Delivery System ||||||||||
|---|---|---|---|---|---|---|---|---|---|
| Guidewire Shaft L1 (cm) || Coil & Pusher Wire L2 (cm) || Coil L3 (cm) || Pusher Wire L4 (cm) || Coil Sheath L5 (cm) ||
| Minimum | Maximum | Minimum | Maximum | Minimum | Maximum | Minimum | Maximum | Minimum | Maximum |
| 80 | 100 | 160 | 200 | 75 | 95 | 85 | 105 | 80 | 100 |
| 100 | 120 | 200 | 240 | 95 | 115 | 105 | 125 | 100 | 120 |
| 120 | 140 | 240 | 280 | 115 | 135 | 125 | 145 | 120 | 140 |
| 140 | 160 | 280 | 320 | 135 | 155 | 145 | 165 | 140 | 160 |
| 160 | 180 | 320 | 360 | 155 | 175 | 165 | 185 | 160 | 180 |
| 180 | 200 | 360 | 400 | 175 | 195 | 185 | 205 | 180 | 200 |
| 200 | 220 | 400 | 440 | 195 | 215 | 205 | 225 | 200 | 220 |
| 220 | 240 | 440 | 480 | 215 | 235 | 225 | 245 | 220 | 240 |
| 240 | 260 | 480 | 520 | 235 | 255 | 245 | 265 | 240 | 260 |
| 260 | 280 | 520 | 560 | 255 | 275 | 265 | 285 | 260 | 280 |
| 280 | 300 | 560 | 600 | 275 | 295 | 285 | 305 | 280 | 300 |
| 300 | 320 | 600 | 640 | 295 | 315 | 305 | 325 | 300 | 320 |
| 320 | 340 | 640 | 680 | 315 | 335 | 325 | 345 | 320 | 340 |
| 340 | 360 | 680 | 720 | 335 | 355 | 345 | 365 | 340 | 360 |
| 360 | 380 | 720 | 760 | 355 | 375 | 365 | 385 | 360 | 380 |

FIG. 90

| Diameter Dimensions of Second Catheter and Coil Delivery System |||||||||
|---|---|---|---|---|---|---|---|---|
| Guidewire (Nominal, in) | Guidewire Shaft Distal ID (D2, in) || Guidewire Shaft Proximal ID (D4, in) || Pusher Wire D5 (in) || Coil D6 (in) ||
| | Minimum | Maximum | Minimum | Maximum | Minimum | Maximum | Minimum | Maximum |
| 0.014 | 0.016 | 0.020 | 0.016 | 0.020 | 0.004 | 0.018 | 0.010 | 0.018 |
| 0.018 | 0.020 | 0.024 | 0.020 | 0.024 | 0.014 | 0.022 | 0.014 | 0.022 |
| 0.035/0.038 | 0.037 | 0.044 | 0.037 | 0.044 | 0.031 | 0.042 | 0.031 | 0.042 |

FIG. 91

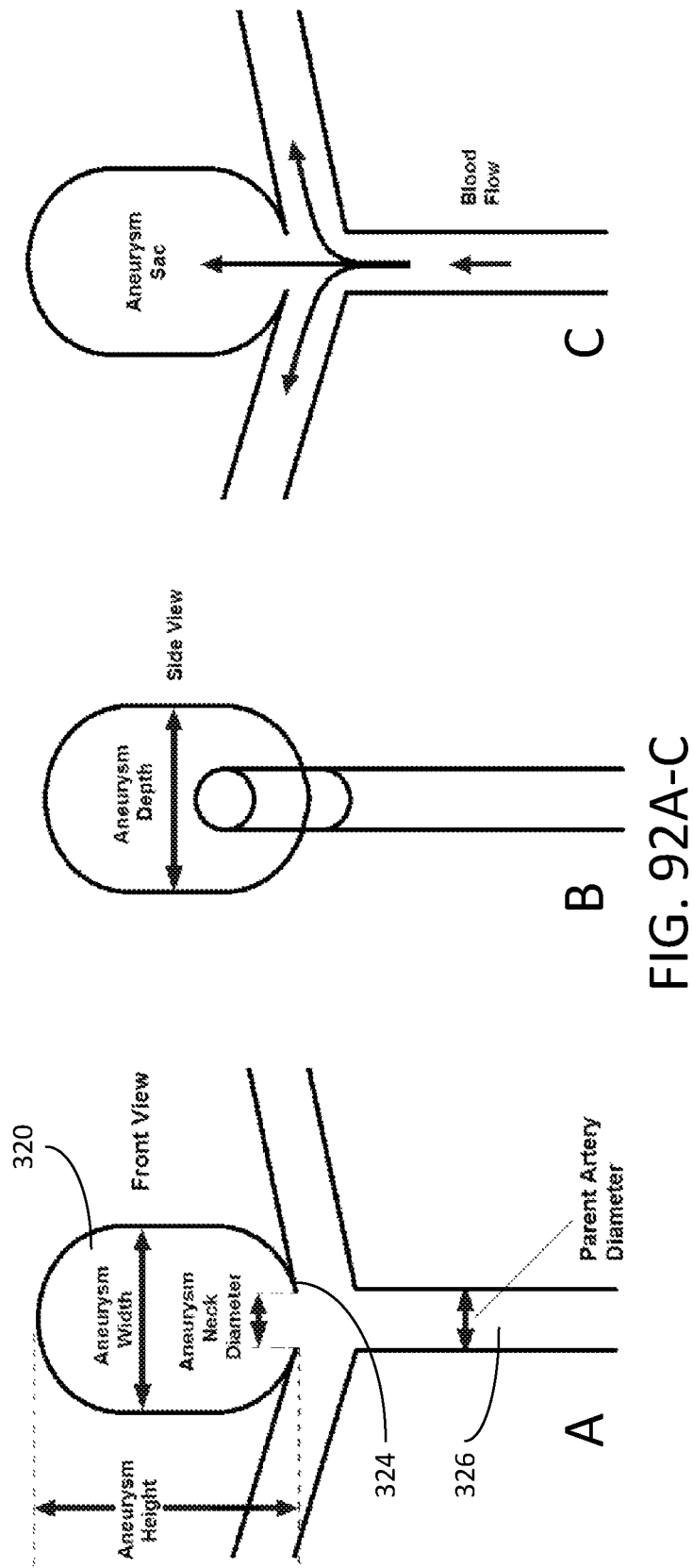
FIG. 92A-C

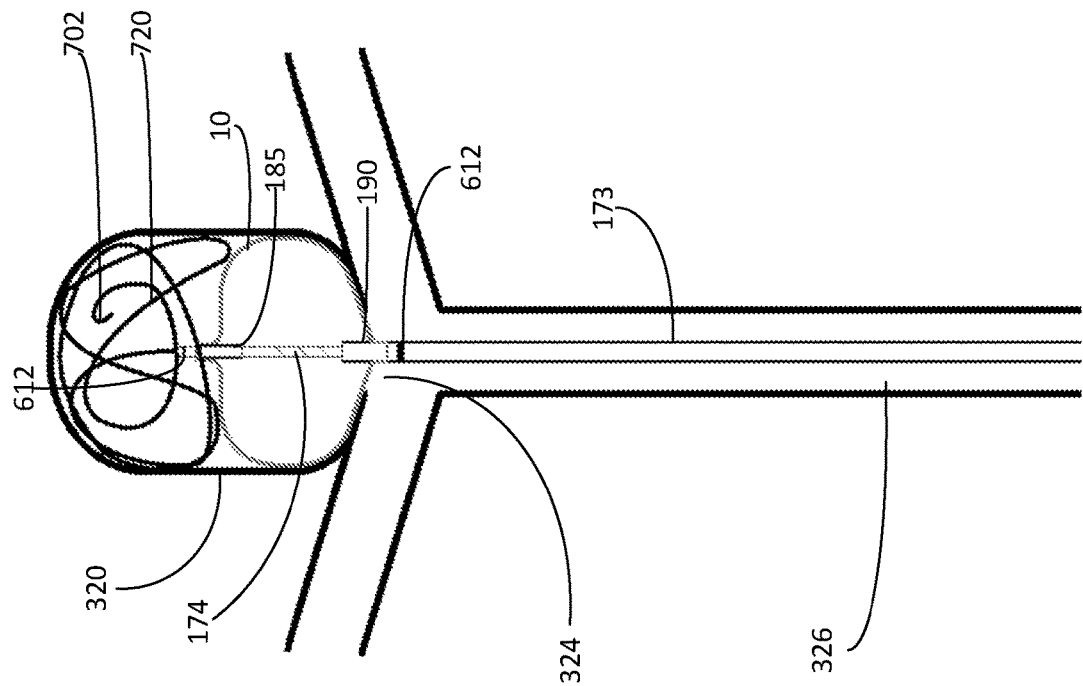
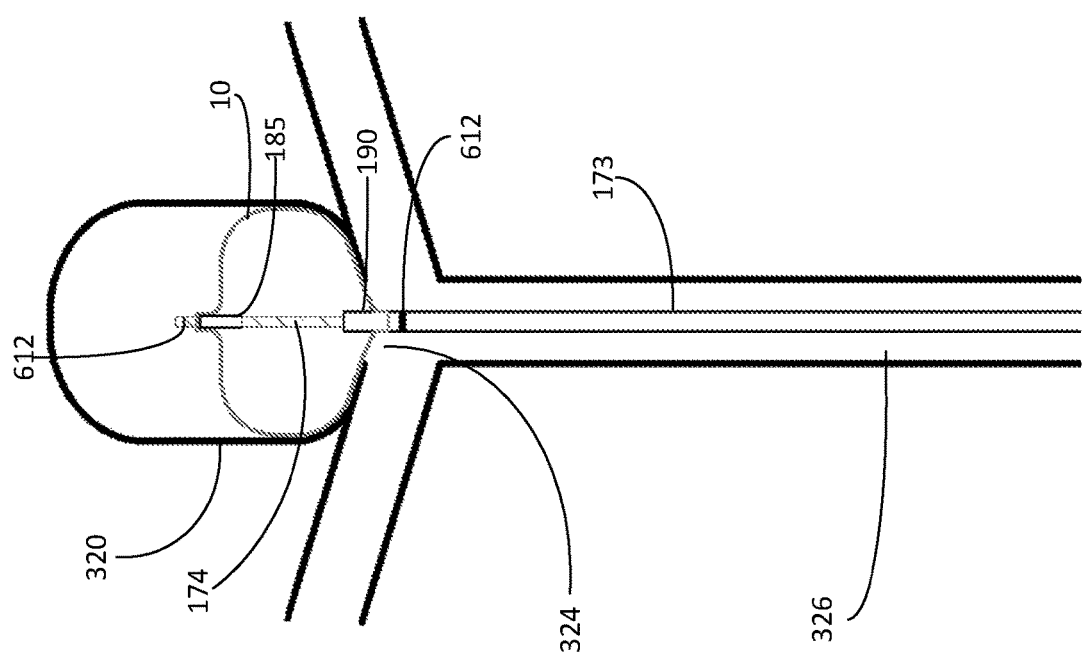
FIG. 93F
FIG. 93E

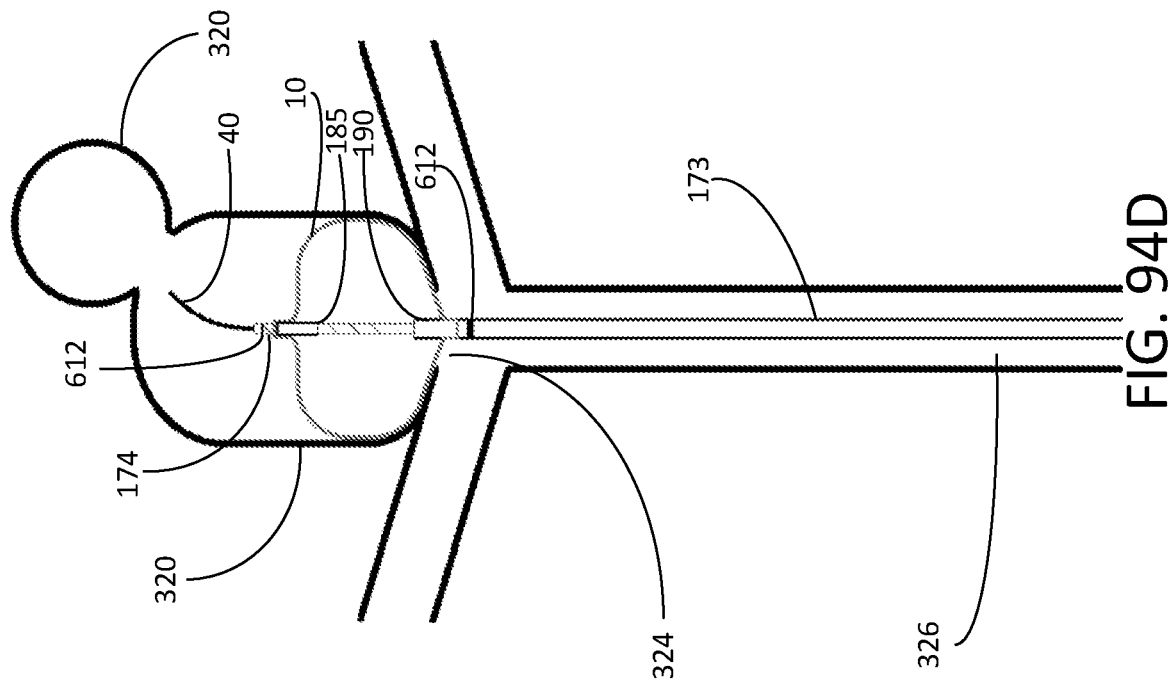
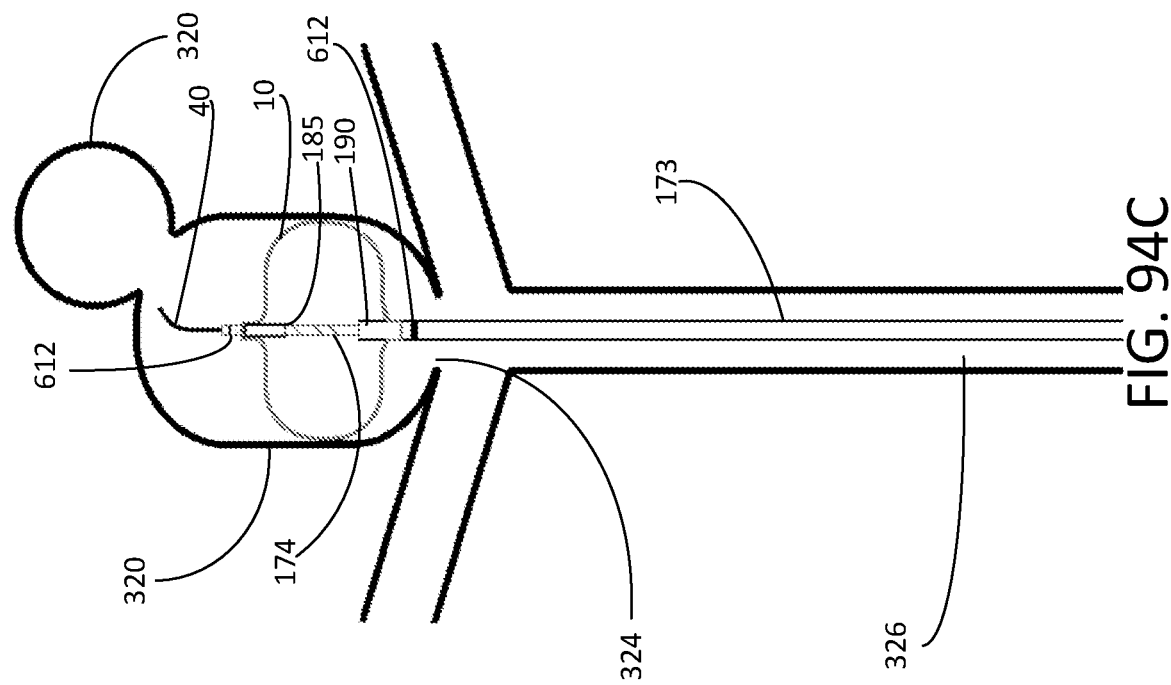

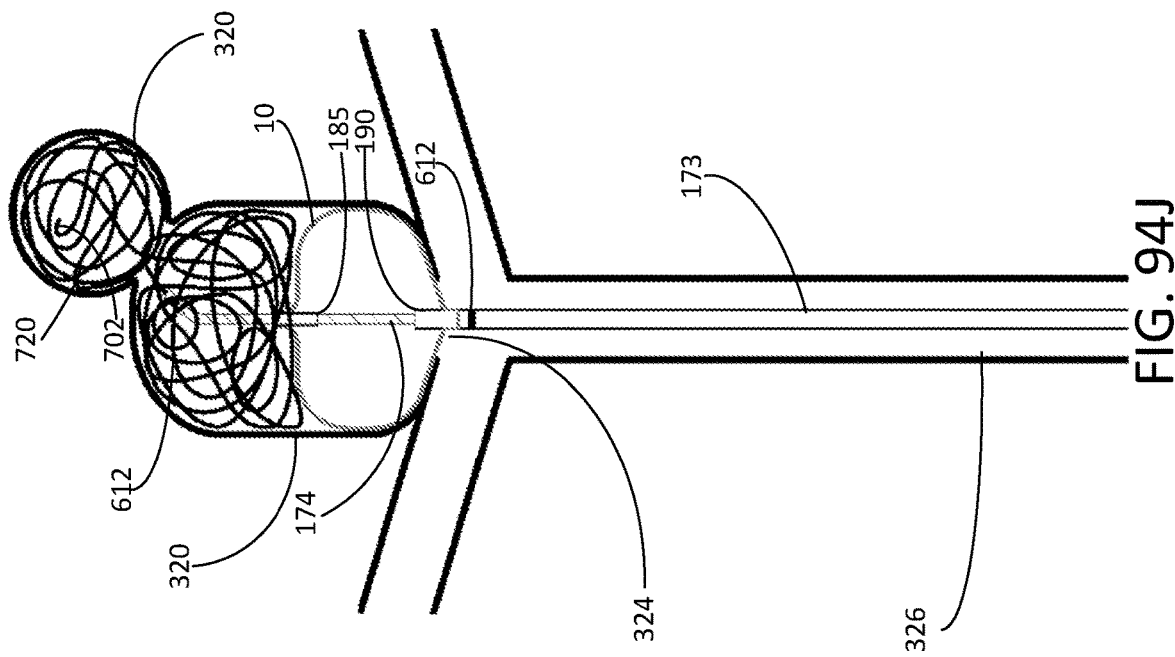
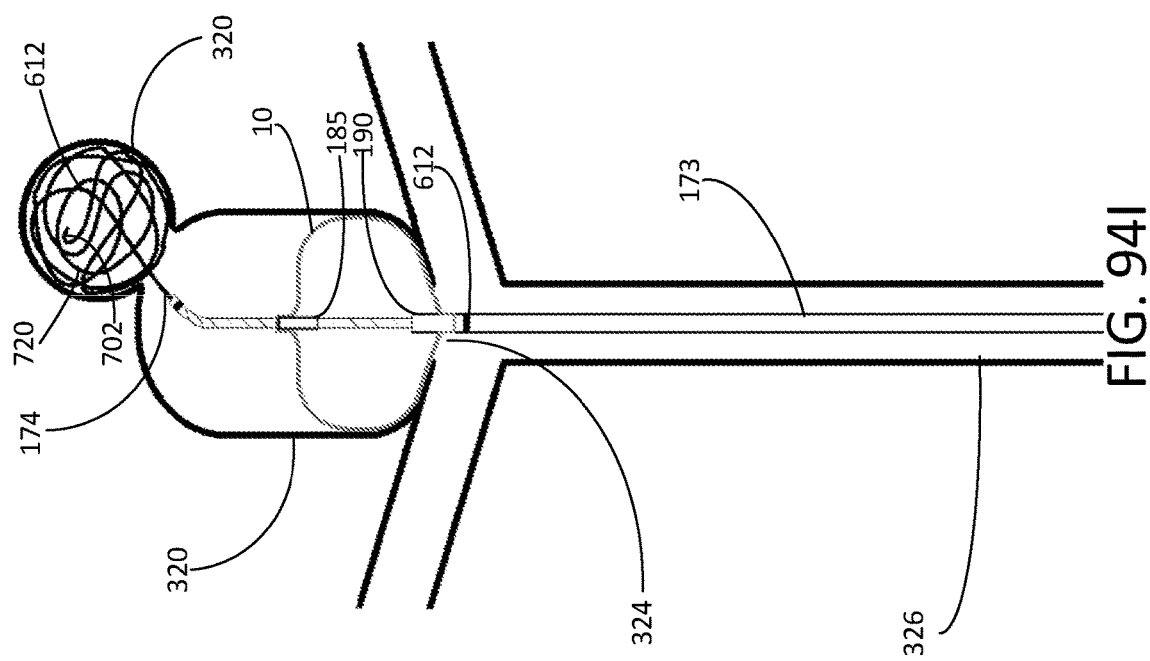

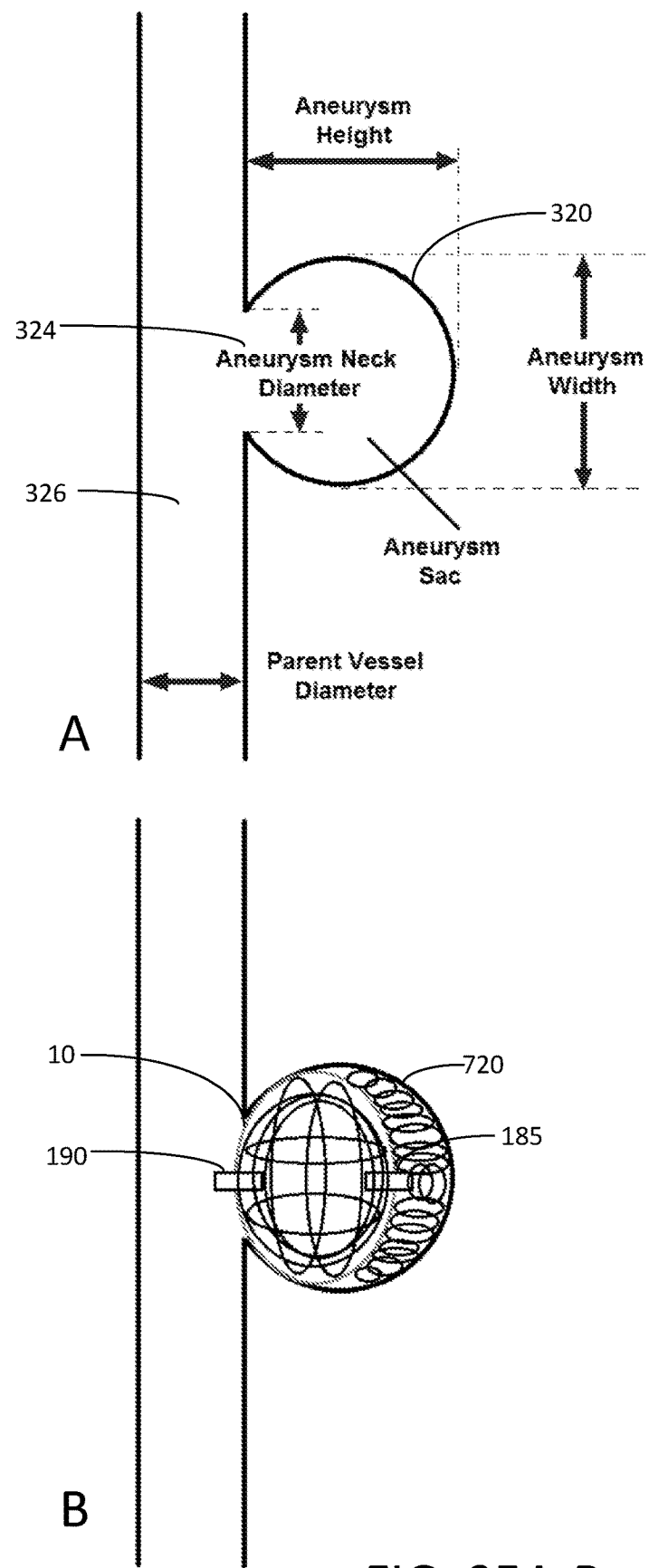
FIG. 95A-B

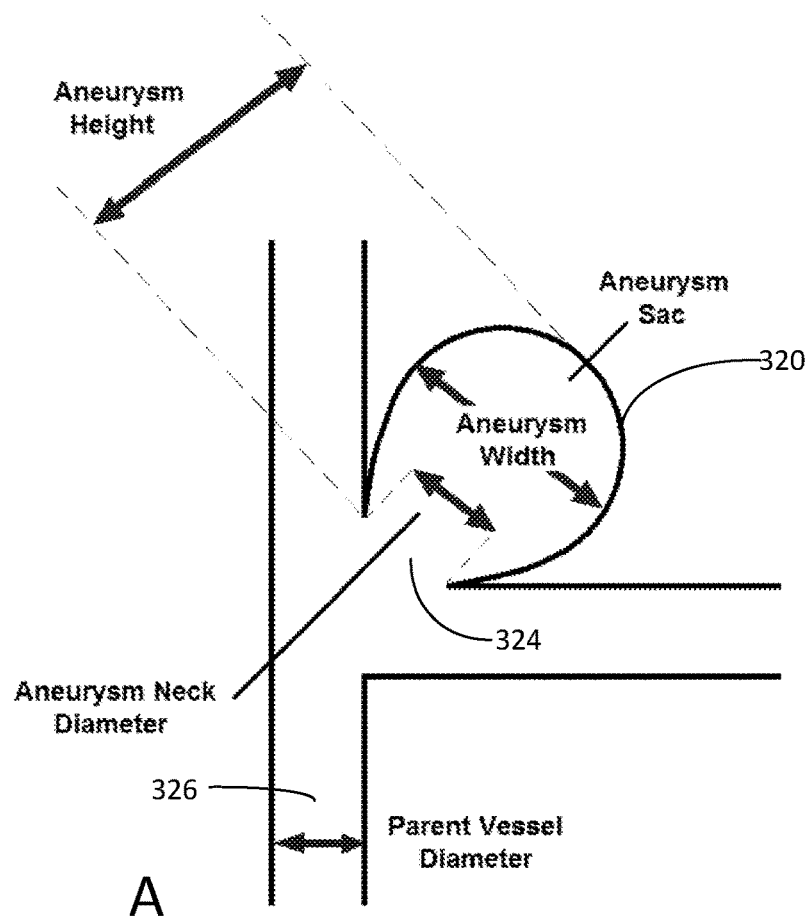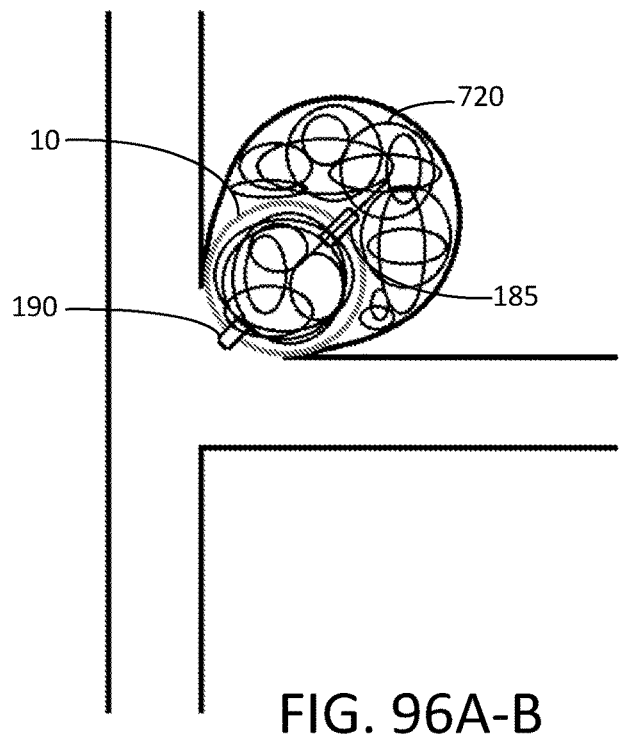
FIG. 96A-B

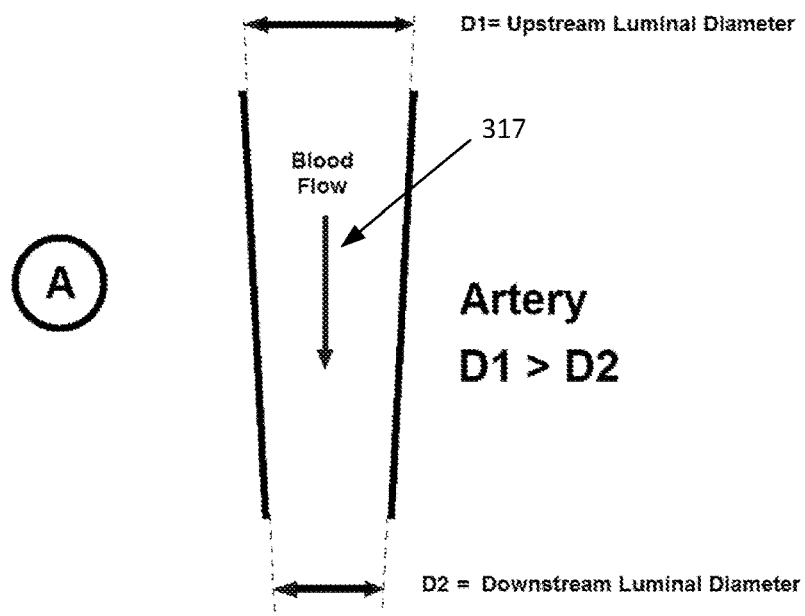
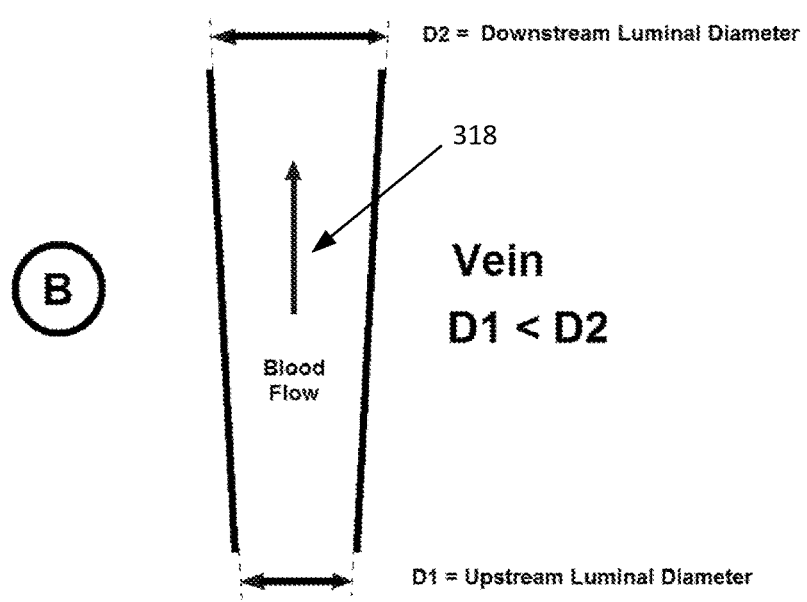
FIG. 97A-B

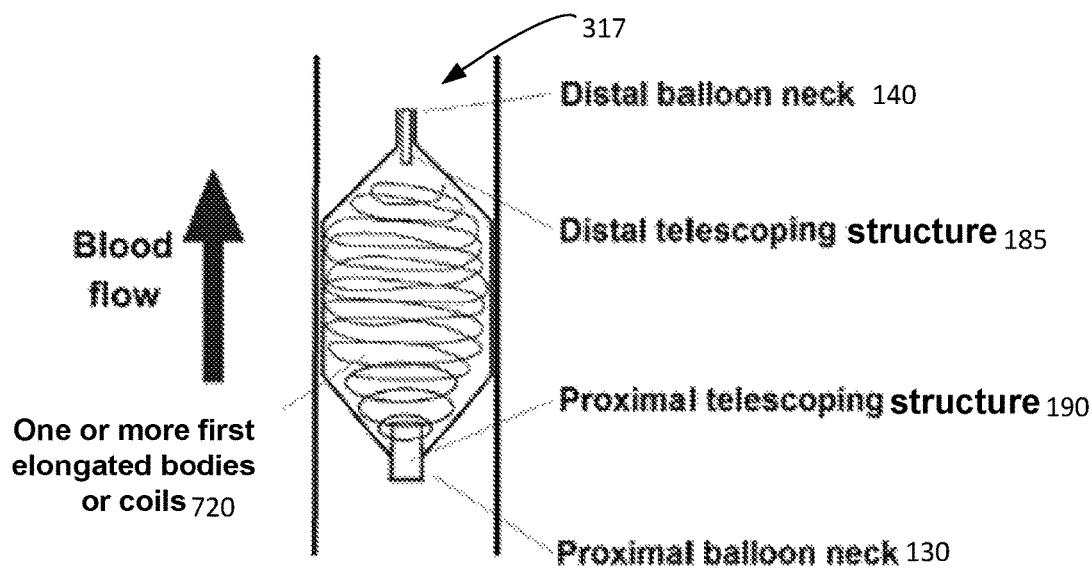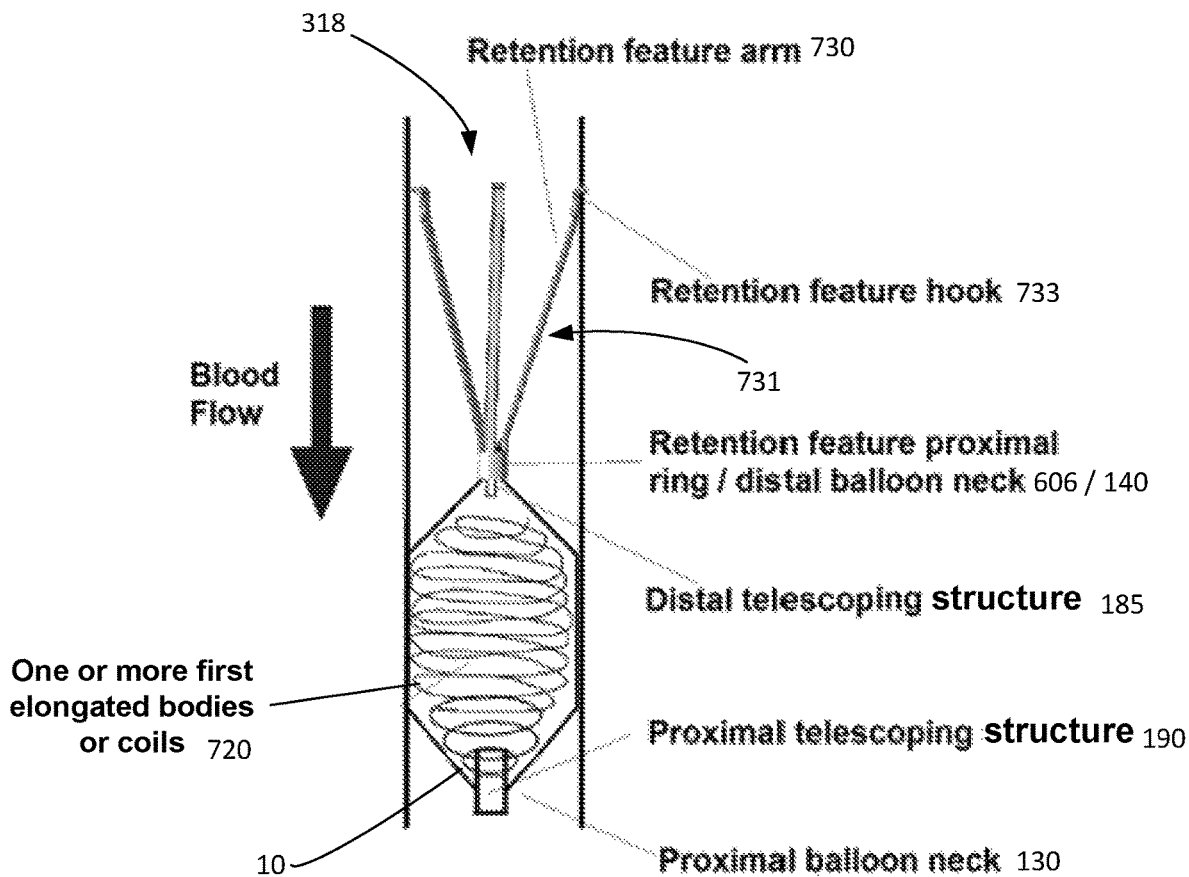
FIG. 98A-B

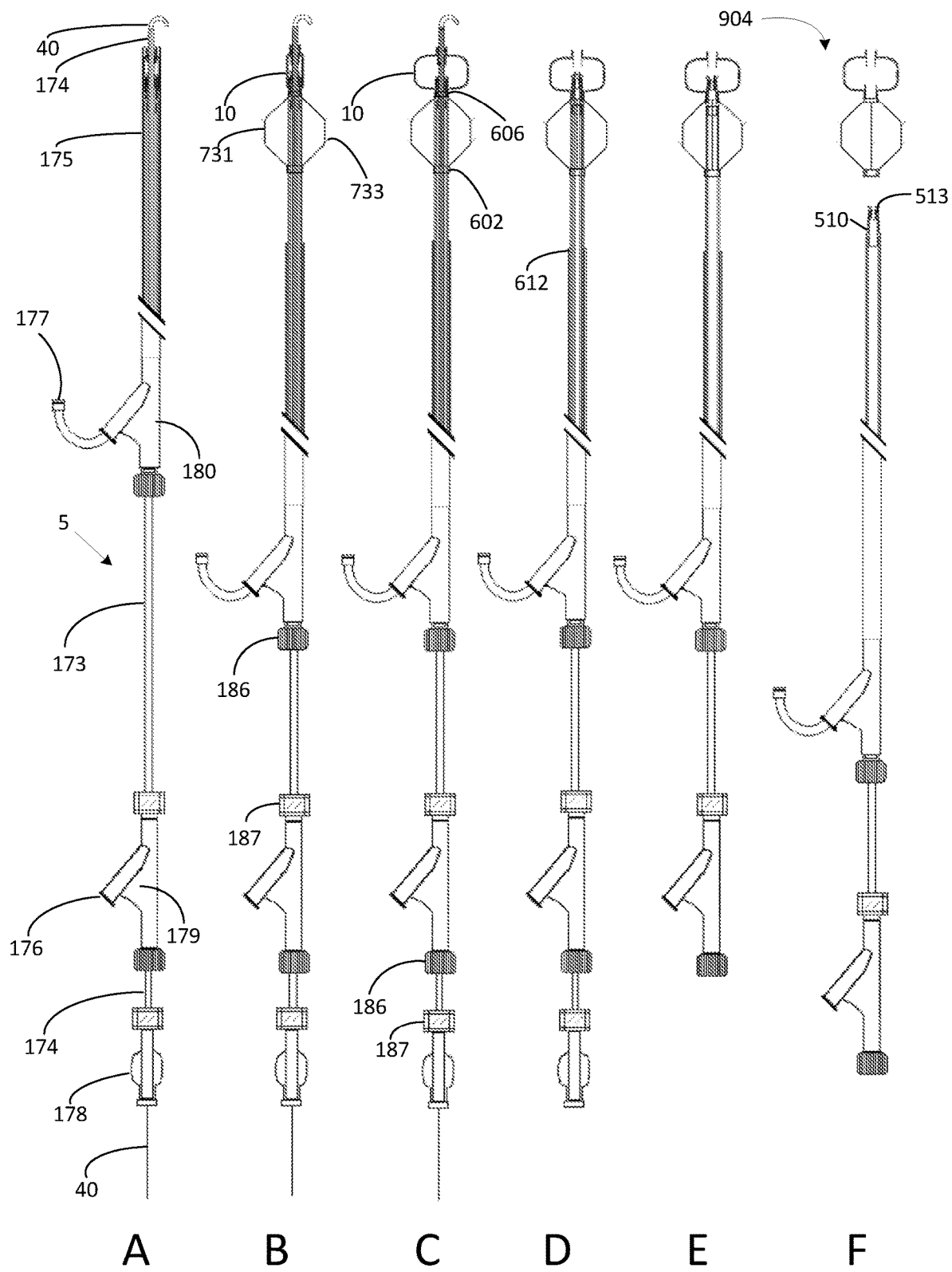
FIG. 101A-F

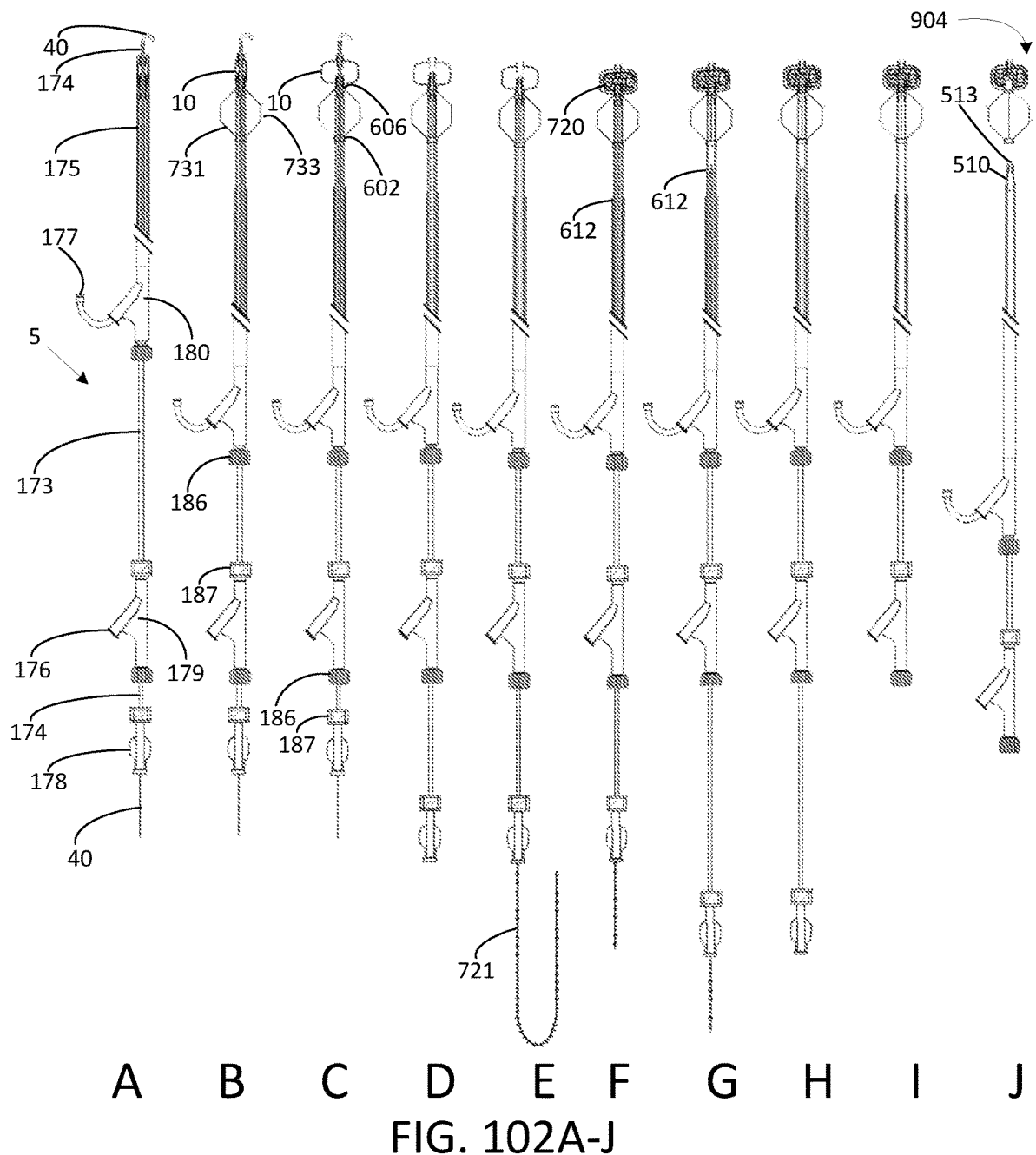
FIG. 102A-J

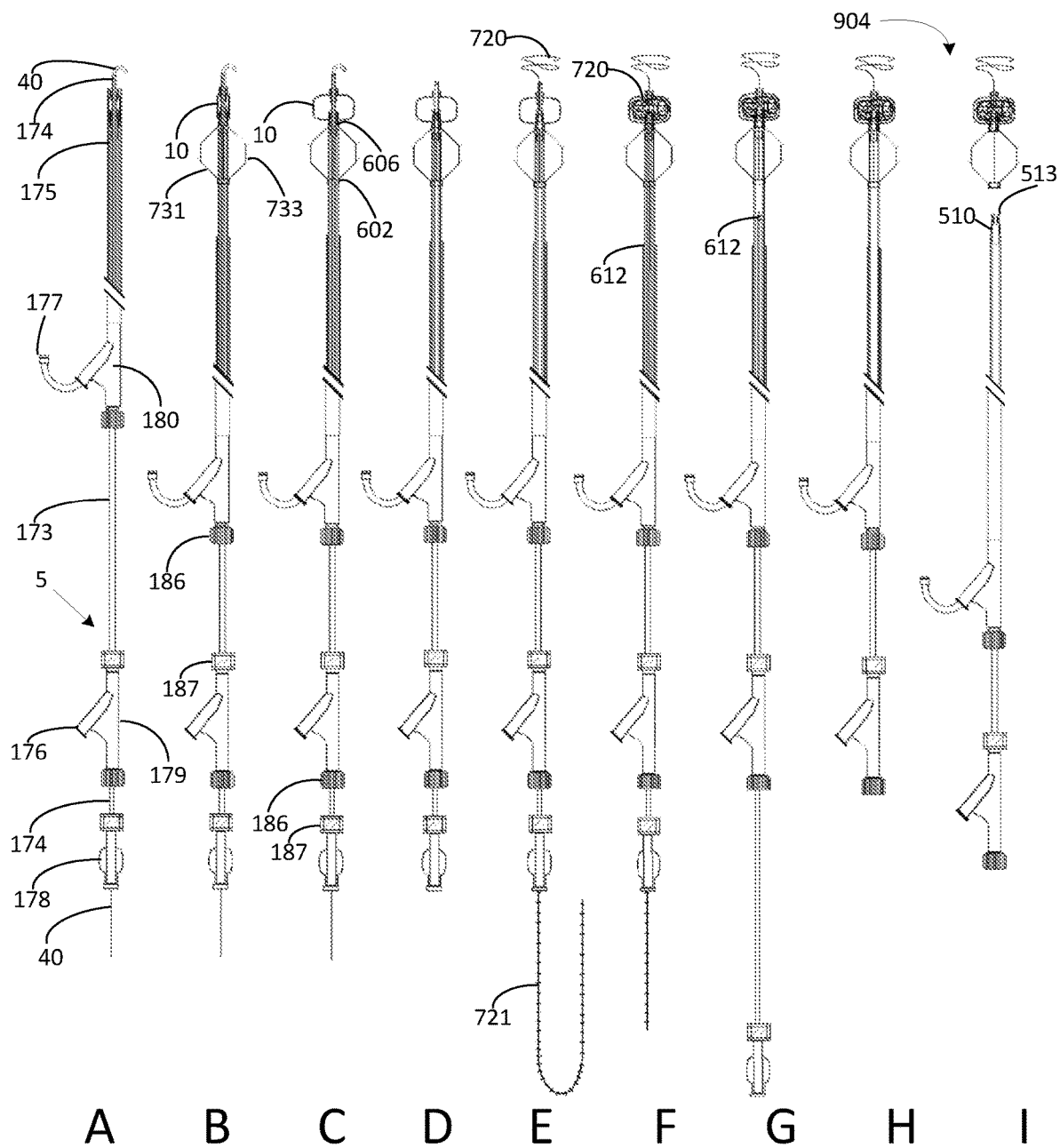
FIG. 103 A-I

Example 1: Treatment of Canine Terminal Bifurcation Aneurysm with Metal Balloon and Coils Example 6: Gold Metal Balloon Less Radiolucent Than Platinum Coils Example 10: Treatment of Canine Terminal Bifurcation Aneurysm with Coils Only Example 12A: Endothelialization of Canine Terminal Bifurcation Aneurysm Neck After Balloon and Coil Placement
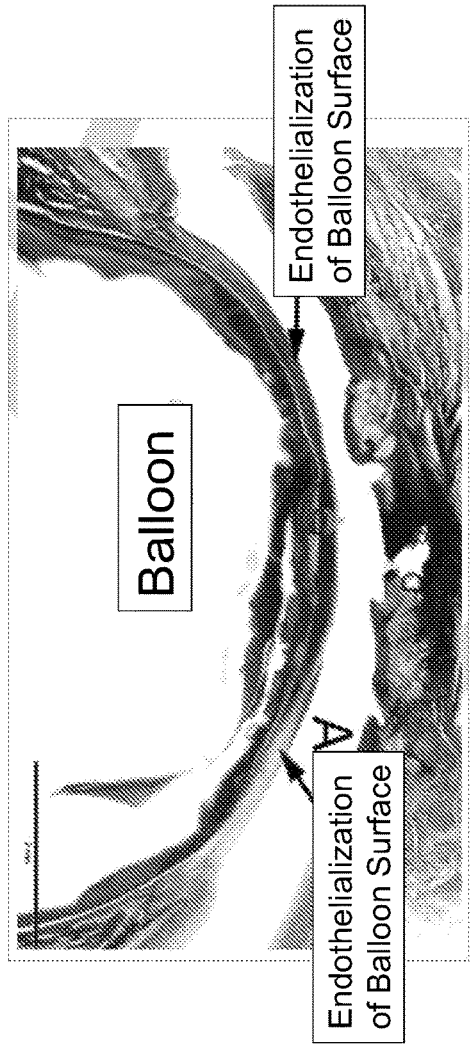
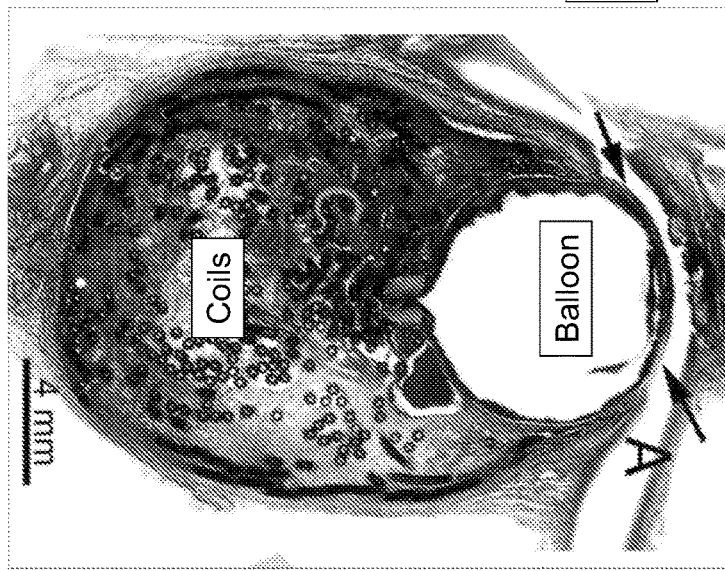
FIG. 115A Example 12B: Endothelialization of Canine Sidewall Aneurysm Neck After Balloon and Coil Placement Example 15: Effect of Treatment of Bleeding Canine Carotid Artery With Metal Balloon Example 16: Effect of Treatment of Bleeding Canine Carotid Artery With Amplatzer II Example 18: Treatment of Canine Axillary Artery With Metal Balloon - Continued Example 24: Placement of a Coil in Expanded Polymer and Metal Wire Balloon - Continued Example 24: Placement of a Coil in Expanded Polymer and Metal Wire Balloon – 1 Month Follow Up Example 26: Mechanical Latch Detachment on Bench

MEDICAL DEVICES COMPRISING DETACHABLE BALLOONS AND METHODS OF MANUFACTURING AND USE

CROSS-REFERENCE TO RELATED APPLICATIONS

The present disclosure claims priority to U.S. Provisional Patent Application No. 62/476,533, entitled "Expandable Body Devices and Methods of Manufacturing and Use," filed on Mar. 24, 2017; U.S. Provisional Patent Application No. 62/553,705, entitled "Metallized, Metal Plated, Partially Metallized, Partially Metal Plated, Wrapped Expandable Body Devices and Methods of Manufacturing and Use," filed on Sep. 1, 2017; U.S. Provisional Patent Application No. 62/623,287 entitled "Metal, Polymer, Metalized, Metal Plated, Partially Metalized, Partially Metal Plated, and Metal Wrapped Expandable Body Medical Devices and Methods of Manufacturing and Use," filed on Jan. 29, 2018; and U.S. Provisional Patent Application No. 62/629,532, entitled "Metal, Polymer, Metalized, Metal Plated, Partially Metalized, Partially Metal Plated, and Metal Wrapped Expandable Body Medical Devices and Methods of Manufacturing and Use," filed on Feb. 12, 2018; the entire contents of each is incorporated herein by reference in its entirety.

FIELD OF THE PRESENT DISCLOSURE

The present disclosure relates to a first medical device comprising a balloon and a catheter or catheter assembly, wherein the balloon can be delivered to a desired location in a human patient in a pleated and folded form, expanded, and detached from the catheter or catheter assembly in a manner that allows the expanded balloon to remain in the patient while the catheter or catheter assembly is removed from the patient, a "detachable balloon catheter". The present disclosure also describes a second medical device comprising elongated or expandable bodies configured for use with detachable balloon catheters, wherein all or a portion of an elongated or expandable body is used to help maintain the size, shape or position of the detached balloon of the detachable balloon catheter. Systems and kits comprising a detachable balloon catheter medical device and one or more elongated or expandable body medical devices are described. The use of detachable balloon catheter medical devices or systems comprising a detachable balloon catheter medical device and one or more elongated or expandable body medical devices to reduce the flow of blood or other biological fluids in saccular aneurysms, arteries, veins, left atrial appendages, paravalvular leaks, other blood-containing structures, biological conduits, and biological spaces is described. Kits comprising a detachable balloon catheter medical device and one or more elongated or expandable body medical devices, optionally along with other medical devices are also disclosed.

BACKGROUND OF THE PRESENT DISCLOSURE

The ability of a percutaneous medical device to reach a particular location in the body is dependent upon several factors. First, the device must be long enough to reach from the location where it is inserted (i.e. the insertion site) to the location where the treatment is desired (i.e. the treatment site). Second, the device should be flexible enough to navigate a tortuous path from the insertion site to the treatment site, a characteristic known as "trackability". For an embolic device, trackability involves the flexibility of the catheter or catheter assembly that is used to place the implant, as well as the flexibility of the implant itself. However, increasing the flexibility of the implants to improve the ability of a medical device to reach a particular location in the body may increase the risk that it could collapse or compact later, potentially leading to re-opening of the treated blood containing structure, biological conduit segment or biological space. Third, the device should have an outer diameter or "profile" that is low enough to pass easily through arteries, veins, or other biological conduits or spaces with small or irregular luminal diameters. Fourth, the device can generally be placed with greater ease and precision if it is delivered over a guidewire. However, adding a guidewire lumen to a medical device usually increases its outer diameter, which may offset some of the advantages of the "over-the-wire" approach.

An aneurysm is an excessive localized enlargement of an artery caused by a weakening of the artery wall. Aneurysms can rupture without warning, leading to internal bleeding. In the brain, bleeding from a ruptured aneurysm causes stroke and sometimes death. In the body outside the brain, bleeding from a ruptured aneurysm can cause hypotension and sometimes death. There are two main types of aneurysms, fusiform aneurysms and saccular aneurysms. A saccular aneurysm is a rounded or pouch-like aneurysm that is attached by a neck or stem to an artery or to a branching of an artery. Saccular aneurysms may occur throughout the body but are most commonly found in the arteries of the brain. A fusiform aneurysm is an outpouching of an arterial wall that is expanded in all directions, without a distinct neck or stem. Fusiform aneurysms are less common than saccular aneurysms and, because they seldom rupture, are often left untreated. The rate of spontaneous rupture of saccular aneurysm increases with increasing aneurysm size, and therefore large aneurysms that are found during a medical or surgical evaluation are usually treated. Ruptured saccular aneurysms are almost always treated, if possible. Saccular aneurysms can be treated by surgery, wherein a surgical clip is placed across the neck of the aneurysm to exclude it from blood flow, or preferentially with minimally invasive catheter-based procedures.

Minimally invasive, catheter-based, endovascular devices and treatment methods have been developed to occlude, embolize, seal, or reduce the flow of blood in saccular aneurysms. During one type of treatment, small metal wire segments ("coils") are placed into the aneurysm sac to occlude the aneurysm, or at a minimum to prevent further enlargement and rupture, a procedure known as "coiling." To treat an aneurysm with coils, a physician inserts a catheter into a lumen of the vascular system and maneuvers the catheter tip into the aneurysm sac. With the catheter tip in position, the physician pushes individual coils through the catheter into the lumen of the aneurysm. During and after the treatment, blood clot forms in and around the coils, resulting in embolic occlusion of the aneurysm. Over time, the blood clot matures into fibrous tissue, which covers the aneurysm neck and seals off the aneurysm sac from the parent artery. Although effective, coiling of saccular cerebral aneurysms has drawbacks. Coil placement is difficult to control, often resulting in coil protrusion into the parent vessel or coil migration to non-target locations, and sometimes results in occlusion of non-target vessels. In cases of coil migration, physicians may be compelled to attempt retrieval of the coils from the non-target location. Numerous coils are usually required during a treatment, resulting in high costs and long treatment times. Furthermore, coils only partially fill the aneurysm sac. Thrombus and scar tissue must accumulate to seal the aneurysm completely, a process that can take months to years and is often incomplete. Slow aneurysm sealing can reduce the effectiveness of coils in the treatment of acute aneurysm rupture with subarachnoid hemorrhage. Aneurysm sealing after coiling is often incomplete, subjecting the patient to a persistent risk of aneurysm rupture and leading to unacceptably high rates of retreatment. Even when the use of coils is initially effective, recanalization of the aneurysm may occur, resulting in a return of blood flow to the aneurysm and an increased risk of rupture. Incomplete filling of saccular aneurysms and inadequate aneurysm sealing with coils is especially common in the neck region of saccular aneurysms where coil density can be low and blood flow rates high. Coils are susceptible to compaction, further exposing the aneurysm neck and contributing to the high rate of aneurysm recurrence.

In some embodiments of a second medical device or first elongated body, a metal is chosen, and then a coil is created by undergoing a series of transformations from a primary (1°) to secondary (2°) to tertiary (3°) structure. The primary structure is the "stock" wire, which is fabricated in linear form with a diameter of any range. Most stock wires used for coil manufacturing range from 0.00175 to 0.003 inch. The stock wire diameter is the central factor in determining coil "stiffness." The stock wire is wound around a mandrel, also of varying diameter, to produce the secondary structure of the coil. The diameter of the secondary structure, in conjunction with the number of turns per unit of length around the mandrel, represents two additional factors that impact product stiffness. The secondary diameter dictates the historic coil grouping, in which coils deemed "10" coils are typically wound to approximately 0.010 inch and coils deemed "18" coils are typically wound to approximately 0.015 inch. However, many manufacturers now produce coils with secondary diameter between 0.010 and 0.015 inch, including 0.012-inch, and 0.014-inch coil lines. The secondary diameter dictate has important implications for both stiffness and packing attenuation. Finally, the secondary structure can be shaped into any number of tertiary configurations (helical, complex, spherical, etc.), which also are developed with a specific tertiary diameter and length, parameters that serve as a central factor in package labeling and coil selection during interventional procedures. For instance, coils are typically packaged as "3 mm×4 cm," where the millimeter measurement is that of the tertiary diameter and the centimeter measurement is that of the length. Just as the metals for coils are readily available, so too are the fabrication companies that are capable of shaping metals into an endless number of designs.

Biocompatibility of first elongated bodies and expandable bodies is very important. A biocompatible first elongated body and expandable body is one that is composed of primarily inert material that allows an effective treatment without the concern for a systemic host response. Metal alloys with a proved record for patient safety have been the main sources for first elongated body, expandable body, and coil production. Nitinol, platinum, nickel, iridium, and tungsten have been the primary metals used in construction and are usually developed as alloys to reach an optimal strength. Metal strength is determined experimentally and is referred to as the modulus of rigidity or shear modulus. The modulus of rigidity is the coefficient of elasticity for a shearing force, defined as the ratio of the shear stress to the shear strain. Modulus of rigidity can be experimentally determined from the slope of a stress-strain curve created during torsion tests conducted on a metal sample. A platinum (92%)/tungsten (8%) alloy has become the mainstay material for many current first elongated body and coil designs. Many metals in pure and alloy form are readily available in hundreds of permutations from distributors worldwide.

More recently, traditional tubular stents have been adapted to treat cerebral aneurysms. These stents are placed on delivery devices and positioned in the parent vessel adjacent to the aneurysm. The stents are then expanded in the parent vessel with the delivery device, followed by removal of the delivery device. The expanded metal stents divert flow away from the aneurysm sac and promote aneurysm thrombosis. Although often effective, these "flow diverting" stents have drawbacks. First, the stents may cover and divert blood flow away from important arterial branches adjacent to the aneurysm, sometimes resulting in ischemia and stroke. Second, the stents are a source of thrombus and intimal hyperplasia formation in the parent vessel, which can cause thromboembolism and narrowing in the parent vessel lumen that may lead to ischemia and stroke. Third, there is a need for long-term anticoagulation after flow diverting stent placement, which increases the risk of bleeding complications and stroke, and can be contraindicated in patients who have already experienced aneurysm rupture and subarachnoid hemorrhage.

More recently, vascular plugs made of braided or woven nitinol wire have been adapted to treat cerebral aneurysms. These devices are passed through the lumen of catheters and expand into the aneurysm sac when the catheter that guided their placement is retracted. The expanded devices then divert flow away from the aneurysm sac and promote aneurysm thrombosis. Although often effective, these "intrasaccular" devices have drawbacks. First, when in a compressed form, the devices are stiff and difficult to advance through the tortuous arteries of the cerebral circulation. Second, a large number of device sizes are needed to treat the many sizes and shapes of aneurysms. Notwithstanding the wide selection of sizes offered, the fit between the device and the aneurysm is sometimes sub-optimal which increases the risk of aneurysm persistence or recurrence. Third, intrasaccular devices are susceptible to compression and compaction which can re-open the aneurysm neck, also increasing the risk of aneurysm persistence or recurrence.

Previous attempts have been made to develop and use detachable balloons for the treatment of saccular aneurysms. Compliant, detachable polymer balloons joined to catheters are advanced into the aneurysm sac, inflated, and detached in an attempt to completely fill and occlude the aneurysm neck and sac. These devices and their associated methods of use have several drawbacks which led to their eventual abandonment in favor of other devices and methods. First, the balloons often did not completely occlude the aneurysm neck or completely fill the aneurysm sac, increasing the risk of aneurysm persistence or recurrence. Second, the balloons were typically made of compliant polymers such as latex and silicone that generally resist tissue incorporation. This reduced fixation of the devices to the aneurysm wall and increased the risk of balloon migration and embolization of downstream artery segments. Third, the balloons were elastic and used valves to preserve a high internal pressure after detachment that was needed to maintain their expanded size and shape. Unfortunately, there was a substantial rate of valve failure resulting in balloon deflation leading to aneurysm recanalization and balloon migration.

There remains an unmet clinical need for medical devices, catheter-based medical devices, systems, and methods for effectively and reliably occluding, embolizing, sealing, or reducing the flow of blood in saccular aneurysms, including cerebral aneurysms. Devices are needed which are low profile and highly flexible, easy to use, and can be quickly placed with a high degree of precision. Additionally, devices are needed which result in immediate and complete aneurysm neck and sac occlusion with just one or a few devices that have a reasonable cost, require a limited number of sizes and shapes to treat most aneurysms, and reduce the need for chronic anticoagulation. Finally, devices are needed which offer durable and permanent occlusion and sealing of saccular aneurysms with low rates of device collapse, compression, or compaction, and low rates of aneurysm persistence or recanalization.

In certain clinical situations, patients can benefit from the occlusion, embolization, or sealing of and reduction of blood flow in arteries or arterial segments. Clinical settings where endovascular arterial occlusion is beneficial include treating bleeding from injured vessels, reducing blood flow to tumors, and rerouting the path of blood in the vascular system to isolate vascular anomalies and malformations. Minimally invasive, catheter-based, endovascular treatments have therefore been developed to occlude arteries and arterial segments.

Medical devices for endovascular artery occlusion include coils that can be pushed through a catheter (i.e. "pushable coils") which are deposited in the lumen of the target arterial segment. There are benefits to using coils for arterial occlusion. The devices are flexible and highly elongated, making them easy to advance into small, distal, and tortuous vessels. They are also relatively inexpensive. However, as with their use in saccular aneurysms, they have disadvantages. Precise placement of coils in arteries is difficult and misplacement, migration, and non-target embolization are common. Because they present a porous barrier to blood flow, a large number of coils is often required for complete artery occlusion, leading to increased treatment time and cost. Finally, late recanalization or re-opening of treated artery segments is common with coiling.

Endovascular medical devices for arterial occlusion also include self-expanding vascular plugs that can also be pushed through a catheter and deposited in the lumen of the target arterial segment. There are benefits to using vascular plugs for arterial occlusion. The devices can be placed with greater accuracy than coils. Also, a single device is often all that is needed for arterial occlusion, reducing the complexity of the treatment. However, as with coils, there are drawbacks. The devices are often stiff, making them difficult to place in small, distal, and tortuous arteries. Like coils, vascular plugs present a porous barrier to the flow of blood, which can increase the time required for the devices to completely occlude an artery. They also frequently show late recanalization of treated arterial segments.

Previous attempts have been made to develop and use detachable balloon for the occlusion of arteries, wherein polymer balloons are inflated to fill the lumen of the target arterial segment and detached from a catheter. Compliant, detachable polymer balloons joined to catheters are advanced into the target arterial segment, inflated, and detached in an attempt to completely fill and occlude the arterial segment. There are two major benefits to using detachable balloon catheters for arterial occlusion. First, these devices have a low profile and are very flexible, enabling treatment of small, distal, and tortuous arteries. Second, after inflation, the expanded, compliant balloons generally conform well to irregularities in the surrounding vessel wall and often provide a good seal against the artery wall and good acute occlusion performance. However, these devices and their associated methods of use have several drawbacks and have been mostly abandoned in favor of other devices and methods. First, the devices are typically made of compliant polymers such as latex and silicone that generally resist tissue incorporation. This reduced fixation of the devices to the artery wall increases the risk of balloon migration. Second, the balloons are elastic and use valves to preserve a high internal pressure after detachment that is needed to maintain their expanded size and shape. Unfortunately, there is a substantial rate of valve failure resulting in balloon deflation, often leading to recanalization of the treated arterial segment and increasing the risk of balloon migration. Third, the polymers used to fabricate the balloons are biodegradable in vivo. The breakdown of the wall of the balloons increases the risk of balloon collapse and recanalization of the treated arterial segment.

There remains an unmet clinical need for medical devices, catheter-based medical devices, systems, and methods for effectively and reliably occluding, embolizing, sealing, or reducing the flow of blood in arteries and arterial segments. Devices are needed which are low profile and highly flexible, easy to use, and can be quickly placed with a high degree of precision. Additionally, devices are needed which result in immediate and complete arterial occlusion with just one or a few devices that have a reasonable cost and require a limited number of sizes and shapes to occlude most arteries. Finally, devices are needed which offer durable and permanent occlusion of arteries with low rates of device collapse, compression, compaction, and migration, and low rates of recanalization of the treated arterial segment.

The left atrial appendage (LAA) is a small, saccular protrusion of the muscular wall of the left atrium. The LAA is generally regarded as a vestigial structure, with no clear function. In normal hearts, the heart contracts with each heartbeat. During left atrial contraction, blood in the left atrium and LAA is expelled into the left ventricle. Electrical impulses control the timing of the beating of various chambers of the heart. When these impulses do not travel in an orderly fashion, fast and chaotic impulses can occur, reducing the coordination of atrial contraction and limiting the expulsion of blood from the left atrium and LAA, a condition known as atrial fibrillation which affects an estimated 2.7 million Americans. Blood flow is sluggish in the left atrium and LAA in patients with atrial fibrillation, increasing the risk of blood clot formation. When blood clots form in the LAA they can break free from the LAA wall and get pumped out of the heart. When these clots travel to the brain, they can cause an embolic stroke. Consequently, people with atrial fibrillation are 5 to 7 times more likely to have a stroke when compared to the general population. Patients with atrial fibrillation who are at risk of developing clots in the left atrium and LAA may take a blood thinner to reduce their stroke risk. Patients with a contraindication to taking a blood thinning medication or who don't want to take blood thinners chronically may be eligible for a procedure to seal off their LAA, which can reduce the risk of stroke and eliminate the need to take blood-thinning medication. Boston Scientific Corporation has developed the Watchman, a catheter-delivered device to occlude and seal the LAA. Although effective in reducing stroke in patients with atrial fibrillation, patients receiving the Watchman in a clinical trial had a higher rate of embolic stroke than expected. Also, physicians were unable to implant the Watchman in some patients who were assigned to get the device.

Some patients with atrial fibrillation can benefit from the embolization, occlusion, sealing, or reducing the flow of blood in their LAA. Clinical settings where LAA occlusion is beneficial include reducing the risk of embolic stroke in patients with atrial fibrillation in whom chronic anticoagulation is contraindicated. Medical devices and methods for minimally invasive, catheter-based, occlusion of the LAA have been developed. Currently available devices generally comprise a porous covering over a self-expanding metal cage with retention hooks. Although effective, these devices have drawbacks. The porous covering allows blood to seep into and out of the LAA, increasing the risk of thrombi forming on the device. Subsequent release and embolization of these thrombi can result in stroke. The cage support structures, when compressed, are rigid, making it more difficult to advance the devices into the LAA. When expanded, they are rigid and may not conform optimally to the highly variable shape of the LAA. Gaps between the device and the wall of the LAA can allow thrombus to escape from around the expanded device, which can also result in stroke. The outer diameter or profile of the delivery system and the compressed, fabric covered metal cage is large, requiring a large puncture through the inter-atrial septum to gain access to the left atrium from a venous access. The hole that is left behind in the inter-atrial septum after treatment can be slow to heal, resulting in a persistent left-to-right shunt of blood, which increases the work done by the heart. The hole also increases the risk of paradoxical emboli of clots from the right atrium that enter the left atrium and then reach the arterial circulation.

There remains an unmet clinical need for medical devices, catheter-based medical devices, systems, and methods for effectively and reliably occluding, embolizing, sealing, or reducing the flow of blood in the LAA. Devices are needed which are low profile and highly flexible, easy to use, and can be quickly placed with a high degree of precision. Additionally, devices are needed which offer immediate and complete occlusion of the LAA, present a solid, well washed surface to the left atrium that endothelializes quickly, and result in high rates of durable and permanent occlusion of the LAA.

In certain clinical situations, patients can benefit from the occlusion, embolization, sealing of and reduction of blood flow in veins or vein segments. Clinical settings where endovascular venous occlusion is beneficial include reducing bleeding from an injured vessel such as bleeding esophageal varices, occluding enlarged, painful veins such as pelvic varices, and rerouting the path of blood in the vascular system to isolate vascular anomalies and malformations. Minimally invasive, catheter-based, endovascular treatments have therefore been developed to occlude veins and venous segments.

Medical devices for endovascular vein occlusion include pushable coils that are delivered through a catheter and deposited in the lumen of the target venous segment. There are benefits to using coils for vein occlusion. The devices are flexible and highly elongated, making them easy to advance into small, distal, and tortuous vessels. They are also relatively inexpensive. However, as with their use in arteries, precise placement of coils in veins is difficult and misplacement, migration, and non-target embolization is common. Migration of devices is especially common in veins, as the diameter of veins increases from distal to proximal. When a coil is placed in a vein blood flow pushes the coil toward larger vessels, making it easier for a coil to come free and migrate a long distance. Often, coils that migrate in veins end up in critical structures such as the right atrium, right ventricle, or pulmonary arteries. Because they present a porous barrier to blood flow, a large number of coils is often required for complete vein occlusion, leading to increased treatment time and cost. Finally, late recanalization of treated vein segments is also common.

Endovascular medical devices for venous occlusion also include self-expanding vascular plugs that can also be pushed through a catheter and deposited in the lumen of the target venous segment. There are benefits to using vascular plugs for venous occlusion. The devices can be placed with greater accuracy than coils. Also, a single device is often all that is needed for vein occlusion, reducing the complexity of the treatment. However, as with coils, there are drawbacks. The devices are often stiff, making them difficult to place in small, distal, and tortuous veins. Like coils, vascular plugs present a porous barrier to the flow of blood, which can increase the time required for the devices to completely occlude a vein. They also frequently show late recanalization of treated venous segments. As with coils, migration is also common, and coils placed in veins often lodge in critical structures such as the right atrium, right ventricle, or pulmonary arteries.

Previous attempts have been made to develop and use detachable balloon for the occlusion of veins, wherein polymer balloons are inflated to fill the lumen of the target venous segment and detached from a catheter. Compliant, detachable polymer balloons joined to catheters are advanced into the target venous segment, inflated, and detached in an attempt to completely fill and occlude the venous segment. There are two major benefits to using detachable balloon catheters for venous occlusion. First, these devices have a low profile and are very flexible, enabling treatment of small, distal, and tortuous veins. Second, after inflation, the expanded, compliant balloons generally conform well to irregularities in the surrounding vessel wall and often provide a good seal against the vein wall and good acute occlusion performance. However, these devices and their associated methods of use have several drawbacks and have been mostly abandoned in favor of other devices and methods. First, the devices are typically made of compliant polymers such as latex and silicone that generally resist tissue incorporation. This reduced fixation of the devices to the vein wall increases the risk of balloon migration. Second, the balloons are elastic and use valves to preserve a high internal pressure after detachment that is needed to maintain their expanded size and shape. Unfortunately, there is a substantial rate of valve failure resulting in balloon deflation, often leading to recanalization or re-opening of the treated venous segment and increasing the risk of balloon migration. As with coils and vascular plugs, migration is common, and detachable balloons placed in veins often lodge in critical structures such as the right atrium, right ventricle, or pulmonary arteries. Third, the polymers used to fabricate the balloons are biodegradable in vivo. The breakdown of the wall of the balloons increases the risk of balloon collapse and recanalization or re-opening of the treated venous segment.

There remains an unmet clinical need for medical devices, catheter-based medical devices, systems, and methods for effectively and reliably occluding, embolizing, sealing, and reducing the flow of blood in veins and venous segments. Devices are needed which are low profile and highly flexible, easy to use, and can be quickly placed with a high degree of precision. Additionally, devices are needed which result in immediate and complete vein occlusion with just one or a few devices that have a reasonable cost, and require a limited number of sizes and shapes to occlude most veins. Finally, devices are needed which offer durable and permanent occlusion of veins with low rates of device collapse, compression, compaction or migration, and low rates of recanalization of the treated vein segment.

The valves in the heart can become obstructed and develop leaks, resulting in either a reduction in cardiac output, an increase in the cardiac workload, or both. These faulty valves can be repaired or replaced, either during a surgery or a minimally invasive procedure. After valve repair and replacement, a new leak may form in the region adjacent to the valve, which can reduce cardiac output and increase cardiac workload. These leaks can also lead to blood damage, including hemolysis of red blood cells, which can cause kidney damage and lead to anemia. Patients who develop these "paravalvular leaks" can benefit from occlusion of the leak path, which can improve cardiac output, reduce cardiac workload, and reduce blood damage. There are currently no medical devices specifically approved for the treatment of paravalvular leaks. Physicians sometimes use self-expanding vascular plugs that can be pushed through a catheter and deposited in the lumen of the paravalvular leak path in an attempt to occlude it. However, there are drawbacks with this approach. The devices are stiff, making them difficult to place. They also present a porous surface to the flow of blood resulting in a failure of some devices to fully occlude the leak path, which can be large and have a high rate of blood flow. The irregular, porous surface of the devices is susceptible to thrombus formation. Subsequent release and embolization of these thrombi can result in stroke. As with many porous devices, complete endothelialization of vascular plugs is likely to be slow and often incomplete, resulting in a persistent increase in the risk of thrombus formation and embolization of thrombi.

There remains an unmet clinical need for medical devices, catheter-based medical devices, systems, and methods for effectively and reliably occluding paravalvular leak paths. Devices needed which are low profile and highly flexible, easy to use, and can be quickly placed with a high degree of precision. Additionally, devices are needed which result in immediate and complete occlusion of the leak path, and have surfaces that are resistant to thrombus formation and endothelialize quickly. Finally, devices are needed which offer durable and permanent occlusion of the leak path with low rates of device collapse, compression, or compaction, and recanalization.

In certain clinical situations, patients can benefit from the occlusion, embolization, or sealing of and reduction of fluid or material flow in biological conduits. Clinical settings where endovascular conduit occlusion is beneficial include intentional blockage of fallopian tubes to prevent pregnancy. Minimally invasive, catheter-based, endovascular treatments have been developed to occlude biological conduits.

There remains an unmet clinical need for medical devices, catheter-based medical devices, systems, and methods for effectively and reliably occluding biological conduits. Devices are needed which are low profile and highly flexible, easy to use, and can be quickly placed with a high degree of precision. Additionally, devices are needed which result in immediate and complete conduit occlusion with just one or a few devices that have a reasonable cost, and require a limited number of sizes and shapes to occlude most conduits. Finally, devices are needed which offer durable and permanent occlusion of conduits with low rates of device collapse, compression, compaction or migration, and low rates of recanalization of the treated conduit segment. Examples of biological conduits includes arteries, veins, thoracic ducts, lymphatic ducts, pancreatic ducts, biliary ducts, fallopian tubes, bronchi, ureters, urethras, esophagus, duodenum, jejunum, ileum, colon, vas deferens, salivary ducts, parotid ducts, lactiferous ducts, Schlemm's canals, tear and nasolacrimal ducts, cerebral aqueducts, peripheral nerve sheaths, and any other tubular structure or channel in a human that conveys biological fluid and suspensions, solid or semi-solid biological materials, gas, or air. Examples of biological fluids, solid or semi-solid biological materials, gas, or air includes blood, lymph, cerebrospinal fluid, urine, bile, pancreatic juice, saliva, milk, tears, aqueous humor, eggs, semen, pulmonary secretions, food, water, feces, inspired air, or exhaled air.

There remains an unmet clinical need for medical devices, catheter-based medical devices, systems, and methods for effectively and reliably placing balloons, elongated bodies, and expandable bodies in biological spaces. Devices are needed which are low profile and highly flexible, easy to use, and can be quickly placed with a high degree of precision, and are resistant to collapse, compression, compaction or migration. As used herein, a biological space can mean a continuous area or expanse in a human patient, including a continuous area or expanse that is free, available, or unoccupied.

Additionally, there remains a need for a method of fabricating medical devices for treating, occluding, or sealing of saccular aneurysms (including cerebral aneurysms), arteries, veins, other hollow vascular or blood-containing structures, or biological conduits or spaces, wherein such medical devices incorporate detachable polymer balloons, detachable metal balloons, detachable polymer-coated metal balloons (including completely polymer-coated metal balloons and partially polymer-coated metal balloons) and detachable metalized polymer balloons (including completely metalized polymer balloons and partially metalized polymer balloons). There remains a need for fabricating detachable balloon medical devices that can be delivered through the lumen of an artery, vein, blood-containing structure, or biological conduit or space, wherein the balloon can be inflated to fill a void at the target location and then detached from the delivery device, catheter, or catheter assembly wherein the balloon remains in an expanded or partially expanded configuration without the need for a valve or other device to maintain the inflation pressure inside the balloon. There remains a further need for fabricating detachable balloon medical devices wherein the detachable balloon has acceptable biocompatibility, and optionally with a textured or micro textured surface to reduce the risk of balloon migration and to promote tissue incorporation into the balloon wall. There remains a need for fabricating metalized polymer balloons of such a medical device by applying metal to the surface of a polymer balloon by a mechanical process such wire wrapping; an electrochemical process such as electroplating, electroforming, or sputtering; or combinations thereof. There also remains a need for fabricating medical devices comprising elongated or expandable bodies that can be delivered through the lumen of the second catheter of (first) medical devices comprising a detachable balloon and used to fill a void at the target location, either in an aneurysm, artery, vein, LAA, paravalvular leak path, blood-containing structure, biological conduit, biological space, or in the central void or internal volume of the detachable balloon.

SUMMARY

The present disclosure relates to medical devices comprising a detachable balloon and a catheter or catheter assembly, and the use of these medical devices for occluding, embolizing, sealing, or reducing the flow of blood or other biological fluids in saccular aneurysms, arteries, veins, left atrial appendages (LAAs), paravalvular leaks, other blood containing structures, biological conduits, or biological spaces. The detachable balloon of the detachable balloon catheter may comprise a polymer balloon, metal balloon, polymer-coated metal balloon, or metalized polymer balloon. The present disclosure also relates to medical devices comprising elongated or expandable bodies, and their use with medical devices comprising a detachable balloon and a catheter or catheter assembly, wherein one or more elongated or expandable bodies, or a solidifying fluid, can be passed through a catheter of the medical device comprising a detachable balloon and a catheter or catheter assembly and a portion of the elongated or expandable body can be placed adjacent to the expanded balloon, inside the central void of the expanded balloon, or both adjacent to the expanded balloon and inside the central void of the expanded balloon to maintain the size, shape, and position of the expanded balloon.

The present disclosure relates to device components, devices, methods and systems for delivering and positioning various embodiments of the detachable balloon of the detachable balloon catheter, wherein the detachable balloons are dimensioned and configured to fill and/or seal at least a portion of the saccular aneurysm, artery, vein, LAA, paravalvular leak path, other blood-containing structure, biological conduit, or other biological space in which the detachable balloon remains in place in an expanded state. The present disclosure also relates to device components, devices, methods and systems for delivering and positioning various embodiments of the elongated bodies or expandable bodies after placement and expansion of the detachable balloon of the detachable balloon catheter. The elongated bodies or expandable bodies are dimensioned and configured to fill or seal at least a portion of a saccular aneurysm, artery, vein, LAA, paravalvular leak path, other blood-containing structure, biological conduit, other biological space, or the detachable balloon of the detachable balloon catheter, wherein the elongated bodies or expandable bodies remain in place in an elongated or expanded state. The present disclosure describes medical devices or device components of particular lengths to enable various described treatments. The present disclosure also describes devices or device components, including catheters, catheter assemblies, and detachable balloons, including detachable balloons comprising retention structures to enable various described treatments.

The present disclosure solves several long-standing limitations of other devices designed for these purposes. Elongated bodies, such as coils for vascular embolization, are highly flexible and trackable, and can be advanced through tortuous arteries and veins and into small and distal vessels, which allows for embolization of a wide range of blood-containing structures. However, when used alone, these vascular coil elongated bodies present a porous barrier to the flow of blood, often resulting in slow or incomplete embolization. Expandable bodies such as vascular plugs, when constrained for passage through catheters, are generally much stiffer than vascular coils but likewise present a porous surface to the flow of blood. The present disclosure describes highly flexible medical devices that place a balloon at a target location that presents a solid surface to the flow of blood or biological fluid, followed by the placement of one or more highly flexible elongated bodies or expandable bodies, which provides support to the balloon and helps it maintain its size and shape by resisting collapse, compression, and compaction of the balloon and, in certain instances, also helps maintain the position of the balloon to reduce the risk of balloon migration.

The present disclosure describes the use of a highly flexible catheter or catheter assembly (also called the "delivery catheter" or "first catheter") to deliver a highly flexible detachable balloon, and then using that same highly flexible catheter or catheter assembly to deliver a highly flexible elongated or expandable body such that an assembly of an expanded balloon and one or more elongated or expandable bodies is created in vivo that is highly resistant to collapse, compression, compaction, or migration. The present disclosure also describes medical devices wherein the component of the detachable balloon catheter that incorporates a guidewire lumen (also called the "guidewire catheter" or "second catheter") can be moved and used to direct the passage of elongated or expandable bodies to a variety of locations while the expanded balloon of the detachable balloon catheter remains fixed in position, enabling the second medical device to seal the detachable balloon, secure the location of the detachable balloon to reduce the risk of balloon migration, or maintain the expanded size and shape of the detachable balloon and reduce the risk of balloon collapse, compression, or compaction.

A detachable balloon catheter with a structure for guidewire insertion that can be moved independently of the detachable balloon and can also be used to deliver elongated or expandable bodies reduces the overall diameter or profile of the device, while improving device performance. A detachable balloon catheter with an assembly of at least two catheters, wherein one catheter is configured for guidewire insertion and can be moved independently of the detachable balloon and also used to deliver elongated or expandable bodies, and wherein another catheter is used to hold the detachable balloon to the catheter assembly also enables the use of a mechanical latch that can hold the detachable balloon to the catheter assembly. When the guidewire catheter is within the mechanical latch, the detachable balloon remains attached to delivery catheter. When the guidewire catheter is retracted from the mechanical latch, the detachable balloon can be separated from the delivery catheter.

The combination of these different elements produces a detachable balloon catheter that, when used with one or more elongated or expandable bodies creates a system that is low profile and highly flexible, provides immediate and complete occlusion of arteries, veins, and other blood-containing structures and other biological conduits, provides for simple, immediate mechanical detachment of the expanded, supported balloon from the catheter assembly, and results in a detachable, implantable balloon and coil assembly that is highly resistant to collapse, compression, compaction, or migration.

Polymer balloons may comprise a single, continuous layer of polymer, except for openings in the proximal and distal ends. Polymer balloons may further comprise one or more non-metallic coatings, including coatings on the external surface. The surfaces of the polymer balloons may be modified to improve biocompatibility, to accelerate endothelialization of blood-contacting surfaces, to roughen the surface texture to reduce the risk of balloon migration after placement in vivo, to smooth the surface texture to reduce adherence of biomolecules or cells and to reduce tissue injury after placement in vivo, or to increase the strength of the bonds that form between the balloon and the surrounding tissue after placement in vivo. Surface modifications may include plasma etching, surface roughening or smoothing, changes in surface chemistry, attachment of molecules or biomolecules, or various combinations of these methods.

Polymer balloons may comprise a proximal neck, a distal neck, or both a proximal and distal neck. Metal structures, including tubular structures or segments, may be joined to the proximal neck, forming a proximal neck assembly. These metal structures may comprise a radiopaque metal that is visible during fluoroscopy, may be a portion of an assembly for attaching a polymer balloon to a catheter or catheter assembly, may be a portion of an assembly for detaching a polymer balloon from a catheter or catheter assembly, may help a guide a catheter, including a second catheter of the first medical device, to pass through the central void or internal volume of the balloon, or may help reduce leakage from the first lumen of the first medical device during inflation of the balloon.

Metal structures, polymer structures, or metal and polymer structures, including tubular structures or segments, may be joined to the distal neck of polymer balloons, forming a proximal neck assembly. These metal, polymer, or metal and polymer structures may comprise a radiopaque metal that is visible during fluoroscopy, may be a portion of an assembly for attaching a polymer balloon to a catheter or catheter assembly, may be a portion of an assembly for detaching a polymer balloon from a catheter or catheter assembly, may help a guide a catheter, including a second catheter of the first medical device, to pass through the central void or internal volume of the balloon, or may help reduce leaking from the first lumen of the first medical device during inflation of the balloon. Metal structures, polymer structures, or metal and polymer structures, including tubular structures or segments, may be joined to the distal neck of polymer balloons, forming a distal neck assembly. These metal, polymer, or metal and polymer structures may comprise a radiopaque metal that is visible during fluoroscopy, may be a portion of an assembly for attaching a polymer balloon to a catheter or catheter assembly, may be a portion of an assembly for detaching a polymer balloon from a catheter or catheter assembly, may help a guide a catheter, including a second catheter of the first medical device, to pass through the central void or internal volume of the balloon, or may help reduce leakage from the first lumen of the first medical device during inflation of the balloon.

Metal balloons may comprise a single, continuous layer of metal, except for openings in the proximal and distal ends. The surface of the metal balloons may be modified to improve biocompatibility, to accelerate endothelialization of blood-contacting surfaces, to roughen the surface texture to reduce the risk of balloon migration after placement in vivo, to smooth the surface texture to reduce adherence of biomolecules or cells and to reduce tissue injury after placement in vivo, or to increase the strength of the bonds that form between the balloon and the surrounding tissue after placement in vivo. Surface modifications may include surface roughening or smoothing, changes in surface chemistry, attachment of molecules or biomolecules, or various combinations of these methods.

Metal balloons may comprise a proximal neck, a distal neck, or both a proximal and distal neck. Metal structures, polymer structures, or metal and polymer structures, including tubular structures or segments, may be joined to the proximal neck, forming a proximal neck assembly. These metal, polymer, or metal and polymer structures may comprise a radiopaque metal that is visible during fluoroscopy, may be a portion of an assembly for attaching a polymer balloon to a catheter or catheter assembly, may be a portion of an assembly for detaching a polymer balloon from a catheter or catheter assembly, may help a guide a catheter, including a second catheter of the first medical device, to pass through the central void or internal volume of the balloon, or may help reduce leakage from the first lumen of the first medical device during inflation of the balloon.

Metal structures, polymer structures, or metal and polymer structures, including tubular structures or segments, may be joined to the distal neck of metal balloons, forming a distal neck assembly. These metal, polymer, or metal and polymer structures may comprise a radiopaque metal that is visible during fluoroscopy, may be a portion of an assembly for attaching a polymer balloon to a catheter or catheter assembly, may be a portion of an assembly for detaching a polymer balloon from a catheter or catheter assembly, may help a guide a catheter, including a second catheter of the first medical device, to pass through the central void or internal volume of the balloon, or may help reduce leakage from the first lumen of the first medical device during inflation of the balloon.

Polymer-coated metal balloons may comprise a single, continuous layer of metal, except for openings in the proximal and distal ends, and one or more non-metallic coatings, and further comprise one or more polymer coatings or layers on the internal surface, external surface, or internal and external surfaces. The surfaces of the polymer-coated metal balloons may be modified to improve biocompatibility, to accelerate endothelialization of blood-contacting surfaces, to roughen the surface texture to reduce the risk of balloon migration after placement in vivo, to smooth the surface texture to reduce adherence of biomolecules or cells, or to reduce tissue injury after placement in vivo, or to increase the strength of the bonds that form between the balloon and the surrounding tissue after placement in vivo. Surface modifications may include plasma etching, surface roughening or smoothing, changes in surface chemistry, attachment of molecules or biomolecules, or various combinations of these methods.

Polymer-coated metal balloons may comprise a proximal neck, a distal neck, or both a proximal and distal neck. Metal structures, polymer structures, or metal and polymer structures, including tubular structures or segments, may be joined to the proximal neck, forming a proximal neck assembly. These metal, polymer, or metal and polymer structures may comprise a radiopaque metal that is visible during fluoroscopy, may be a portion of an assembly for attaching a polymer balloon to a catheter or catheter assembly, may be a portion of an assembly for detaching a polymer balloon from a catheter or catheter assembly, may help a guide a catheter, including a second catheter of the first medical device, to pass through the central void or internal volume of the balloon, or may help reduce leakage from the first lumen of the first medical device during inflation of the balloon.

Metal structures, polymer structures, or metal and polymer structures, including tubular structures or segments, may be joined to the distal neck of polymer-coated metal balloons, forming a distal neck assembly. These metal, polymer, or metal and polymer structures may comprise a radiopaque metal that is visible during fluoroscopy, may be a portion of an assembly for attaching a polymer balloon to a catheter or catheter assembly, may be a portion of an assembly for detaching a polymer balloon from a catheter or catheter assembly, may help a guide a catheter, including a second catheter of the first medical device, to pass through the central void or internal volume of the balloon, or may help reduce leakage from the first lumen of the first medical device during inflation of the balloon.

Metalized polymer balloons may comprise a single, continuous layer of polymer, except for openings in the proximal and distal ends. Metalized polymer balloons may further comprise one or more metallic structures, layers, or coatings, including non-continuous metallic structures, layers, or coatings as well as continuous metallic structures, layers, or coatings. Metal may be applied to polymer balloons by sputter coating, vapor deposition, electroplating or electroforming, by applying metal wire or mesh to the surface of a polymer balloon, or by various combinations of these methods. The metal wire or mesh may be applied in a ring, coil, braid, woven, or straight configuration, or combinations thereof. Metallic structures, layers, or coatings may be present on the external surface, the internal surface, or both the external and internal surfaces. The surface of the metalized polymer balloons may be modified to improve biocompatibility, to accelerate endothelialization of blood-contacting surfaces, to roughen the surface texture to reduce the risk of balloon migration after placement in vivo, or to increase the strength of the bonds that form between the balloon and the surrounding tissue after placement in vivo, among other things. Surface modifications may include plasma etching, surface roughening or smoothing, changes in the surface chemistry, attachment of molecules or biomolecules, or various combinations of these methods.

Metalized polymer balloons may comprise a proximal neck, a distal neck, or both a proximal and distal neck. Metal structures, polymer structures, or metal and polymer structures, including tubular structures or segments, may be joined to the proximal neck, forming a proximal neck assembly. These metal, polymer, or metal and polymer structures may comprise a radiopaque metal that is visible during fluoroscopy, may be a portion of an assembly for attaching a polymer balloon to a catheter or catheter assembly, may be a portion of an assembly for detaching a polymer balloon from a catheter or catheter assembly, may help a guide a catheter, including a second catheter of the first medical device, to pass through the central void or internal volume of the balloon, or may help reduce leakage from the first lumen of the first medical device during inflation of the balloon.

Metal structures, polymer structures, or metal and polymer structures, including tubular structures or segments, may be joined to the distal neck of metalized polymer balloons, forming a distal neck assembly. These metal, polymer, or metal and polymer structures may comprise a radiopaque metal that is visible during fluoroscopy, may be a portion of an assembly for attaching a polymer balloon to a catheter or catheter assembly, may be a portion of an assembly for detaching a polymer balloon from a catheter or catheter assembly, may help a guide a catheter, including a second catheter of the first medical device, to pass through the central void or internal volume of the balloon, or may help reduce leakage from the first lumen of the first medical device during inflation of the balloon.

The present disclosure presents devices, systems and methods to occlude, embolize, or reduce the flow of blood in saccular aneurysms wherein a detachable balloon is placed in the lumen of a saccular aneurysm and maintained there in an expanded configuration, and optionally one or more elongated or expandable bodies are placed adjacent to the expanded balloon, inside the central void of the expanded balloon, or both adjacent to the expanded balloon and inside the central void of the expanded balloon.

Detachable polymer balloons, metal balloons, polymer-coated metal balloons, and metalized balloons are described, wherein the balloons are made of low compliance polymer materials such as polyethylene terephthalate (PET) and metals such as gold that can be pleated and folded to achieve a low profile, are highly flexible, expand at low pressures, and promote rapid endothelialization on blood-contacting surfaces and rapid tissue incorporation and anchoring to the surrounding aneurysm wall on non-blood contacting surfaces. The external surface of polymer balloons, metal balloons, polymer-coated metal balloons, and metalized polymer balloons can be modified to promote attachment to the adjacent aneurysm wall and reduce the rate of balloon migration in vivo. Elongated bodies such as coils can be modified for use with polymer balloons, metal balloons, polymer-coated metal balloons, and metalized polymer balloons. These elongated bodies can be configured in a straight or mostly straight, soft, and flexible configuration, enabling the adjunctive use of one or a few long, straight or mostly straight coils to treat a wide range of aneurysm sizes and shapes with a relatively small number of balloon and coil sizes and shapes.

A flexible, low profile catheter or catheter assembly is disclosed herein, which can be used to deliver both detachable balloons and coils to aneurysms. Such a catheter assembly comprises a second catheter that is configured to accept both guidewires and coils, wherein this second catheter can be moved forward or backward while the expanded detachable balloon remains fixed in position. This feature provides the benefits of over-the-wire delivery along with the ability to place coils precisely both adjacent to and inside expanded detachable balloons. The result is a detachable, implantable balloon and coil assembly that can immediately and completely occlude the neck and sac of aneurysms in vivo and can maintain that occlusion over time by resisting degradation, migration, collapse, compression, or compaction without the need for a higher pressure inside the balloon or a valve to maintain that pressure.

In one example, a pleated and folded gold metal balloon is advanced over a guidewire into the sac of an aneurysm using an assembly of two catheters, a first catheter joined or operably coupled to the balloon and a second catheter configured for insertion of a guidewire and also for delivering elongated or expandable bodies. A fluid is injected under pressure from the hub of the first catheter, though a first lumen, and into the central void of the balloon, causing expansion of the balloon. The first catheter is then used to pull back the expanded balloon until it is pressed against the aneurysm neck. The second catheter is then advanced over the guidewire into the aneurysm lumen or sac, the guidewire is removed, and an elongated body of approximately 100 cm length (also called a "vascular coil") is advanced through the lumen of the second catheter and into the aneurysm sac behind the expanded balloon. Some segments of the vascular coil contact the inner surface of the wall of the aneurysm and other segments of the vascular coil contact the outer surface of the wall of expanded balloon. Loops of the vascular coil exert a force on the wall of the expanded balloon in a direction towards the aneurysm neck to aid in sealing the aneurysm neck and to reduce the risk of migration or movement of the expanded balloon. After confirming correct placement of the balloon and appropriate occlusion of the aneurysm neck and sac, the vascular coil is detached from its delivery system, the expanded balloon is detached from the first catheter, and the catheters along with the vascular coil delivery system are removed. Vascular coil detachment may occur by mechanical, electrolytic, or electrothermal means. In this example, the gold metal balloon is able to resist collapse, compression, or compaction without additional support materials placed inside the central void of the balloon. Using the approach described above, multiple elongated bodies, expandable bodies, or vascular coils may be placed into the aneurysm sac behind the expanded balloon anytime prior to detachment of the balloon from first catheter.

In another example, a pleated and folded polymer balloon is advanced over a guidewire into the sac of an aneurysm using an assembly of two catheters, a first catheter joined or operably coupled to the balloon and a second catheter configured for insertion of a guidewire and also for delivering elongated or expandable bodies. A fluid is injected under pressure from the hub of the first catheter though the first lumen and into the central void of the balloon, causing expansion of the balloon. The first catheter is then used to pull back the expanded balloon until it is pressed against the aneurysm neck. The second catheter is then advanced over the guidewire into the aneurysm lumen or sac, the guidewire is removed, and the distal portion of an approximately 100 cm long vascular coil elongated body is advanced through the lumen of the second catheter and into the aneurysm sac behind the expanded balloon. Some segments of the distal portion of the vascular coil contact the inner surface of the wall of the aneurysm and other segments of the distal portion of the vascular coil contact the outer surface of the wall of expanded balloon. Loops of the vascular coil exert a force on the outer surface of the wall of the expanded balloon in a direction towards the aneurysm neck to aid in sealing the aneurysm neck and to reduce the risk of migration or movement of the expanded balloon. The second catheter is then pulled back until its tip is in the central void of the expanded balloon and the remaining proximal portion of the vascular coil is placed inside the central void of the expandable balloon. Some segments of the proximal portion of the vascular coil contact the inner surface of the wall of the expanded balloon. Loops of the vascular coil exert an outward force on the inner surface of the wall of the expanded balloon to help the expanded balloon resist collapse, compression, or compaction; to maintain closure of the aneurysm neck; and to reduce the risk of balloon movement or migration. After confirming occlusion of the aneurysm neck and sac, the vascular coil is detached from its delivery system, the expanded balloon is detached from the first catheter, and the catheters and the vascular coil delivery system is removed. Vascular coil detachment may occur by mechanical, electrolytic, or electrothermal means. In some examples, one or more elongated bodies, expandable bodies, or vascular coils are placed in the aneurysm sac and one or more separate elongated bodies, expandable bodies, or vascular coils are placed in the expanded balloon. In some examples, the balloon is a metalized polymer balloon wherein an external layer of gold or titanium is present on the external surface of the polymer balloon at a thickness of 1 micron or less. In these examples, the polymer balloon or metalized polymer balloon is unable to resist collapse, compression, or compaction without additional support materials placed inside the central void of the balloon.

In another example, after placement of the expanded balloon at the aneurysm neck and placement of a single vascular coil, with the distal portion of the vascular coil in the aneurysm sac behind the expanded balloon and the remaining proximal portion of the vascular coil inside the central void of the expanded balloon, the physician concludes, prior to detachment of either, that the diameter of the balloon is too small and the length of the vascular coil is too short. The physician then removes the vascular coil from the patient, deflates the balloon by applying vacuum to the inflation port on the hub of the first catheter, and removes the balloon from the patient. Then, the physician selects a balloon with a larger diameter and a vascular coil with a longer length, places those in the aneurysm according to the method previously described, verifies that the balloon diameter and the coil length are appropriate, detaches the vascular coil and expanded balloon, and removes the catheters and any elongated body delivery systems.

The present disclosure presents devices, systems and methods to occlude, embolize, or reduce the flow of blood in arteries wherein a detachable balloon is placed in the lumen of an artery and maintained there in an expanded configuration. Optionally, one or more elongated or expandable bodies are placed adjacent to the expanded balloon, inside the central void of the expanded balloon, or both adjacent to the expanded balloon and inside the central void of the expanded balloon. Detachable polymer balloons, metal balloons, polymer-coated metal balloons, and metalized polymer balloons are described, wherein the balloons are made of low compliance polymer materials such as PET and metals such as gold that can be pleated and folded to achieve a low profile, are highly flexible, expand at low pressures, and promote rapid tissue incorporation and anchoring to the surrounding artery wall. The external surface of the polymer balloons, metal balloons, polymer-coated metal balloons, and metalized polymer balloons can be modified to promote attachment to the adjacent artery wall and reduce the rate of balloon migration in vivo. Elongated bodies such as coils can be modified for use with the detachable polymer balloons, metal balloons, polymer-coated metal balloons, and metalized polymer balloons. These elongated bodies can be configured in a straight or mostly straight, soft, and flexible configuration, enabling the adjunctive use of one or a few long, straight, or mostly straight coils to treat a wide range of artery sizes with a relatively small number of balloon and coil sizes.

A flexible, low profile catheter or catheter assembly is disclosed herein, which can be used to deliver both detachable balloons and coils to the target arterial segments. Such a catheter assembly comprises a second catheter that is configured to accept both guidewires and coils, wherein this second catheter can be moved forward or backward while the expanded detachable balloon remains fixed in position. This feature provides the benefits of over-the-wire delivery along with the ability to place coils precisely both adjacent to and inside expanded detachable balloons. The result is a detachable, implantable balloon and coil assembly that can immediately and completely occlude arteries in vivo and can maintain that occlusion over time by resisting degradation, migration, collapse, compression, or compaction without the need for a higher pressure inside the balloon or a valve to maintain that pressure.

In one example, a pleated and folded gold metal balloon is advanced over a guidewire into a selected arterial segment using an assembly of two catheters, a first catheter joined or operably coupled to the balloon and a second catheter configured for insertion of a guidewire. A fluid is injected under pressure from the hub of the first catheter, though a first lumen, and into the central void of the balloon, causing expansion of the balloon. After confirming correct placement of the balloon and appropriate occlusion of the selected arterial segment, the expanded balloon is detached from the first catheter and the guidewire and catheters are removed from the patient. Detachment may occur by mechanical, electrolytic, or electrothermal means. In this example, the gold metal balloon is able to resist collapse, compression, or compaction without additional support materials placed inside the central void of the balloon.

In another example, a pleated and folded polymer balloon is advanced over a guidewire into a selected arterial segment using an assembly of two catheters, a first catheter joined or operably coupled to the balloon and a second catheter configured for insertion of a guidewire and also for delivering elongated or expandable bodies. A fluid is injected under pressure from the hub of the first catheter though the first lumen and into the central void of the balloon, causing expansion of the balloon. After confirming correct placement of the balloon and appropriate occlusion of the selected arterial segment, the physician removes the guidewire and pulls the second catheter back until its tip is in the central void of the expanded balloon. The physician then places a vascular coil elongated body through the lumen of the second catheter and into the central void of the expandable balloon. Some segments of the vascular coil contact the inner surface of the wall of the expanded balloon. Loops of the vascular coil exert an outward force on the inner surface of the wall of the expanded balloon to help the expanded balloon resist collapse, compression, or compaction; to maintain occlusion of the arterial segment; and to reduce the risk of balloon movement or migration. After confirming occlusion of the selected arterial segment, the vascular coil is detached from its delivery system, the expanded balloon is detached from the first catheter, and the catheters and vascular coil delivery system are removed. Detachment may occur by mechanical, electrolytic, or electrothermal means. In some examples, more than one elongated body, expandable body, or vascular coil are placed in the expanded balloon. In some examples, the balloon comprises a distal neck assembly with an elastomeric or resilient valve that closes the distal opening in the balloon after retraction of the guidewire and second catheter. In addition to providing hemostasis within the expandable balloon, the valve may provide the primary means of attaching the balloon to the second catheter, the first catheter, or an assembly of the first and second catheters.

In some examples, the distal portion of an elongated body, expandable body, or vascular coil is placed in the lumen of the artery distal to the expanded polymer balloon and the proximal portion of the elongated body, expandable body or vascular coil is placed in the central void of the expanded balloon in order to close at least a portion of the distal opening of the balloon. In some examples, the balloon is a metalized polymer balloon wherein an external layer of gold or titanium is present on the external surface of the polymer balloon at a thickness of 1 micron or less. In these examples, the polymer balloon or metalized polymer balloon is unable to resist collapse, compression, or compaction without additional support materials placed inside the central void of the balloon.

The present disclosure presents devices, systems and methods to occlude, embolize, or reduce the flow of blood in veins wherein a detachable balloon is placed in the lumen of a vein and maintained there in an expanded configuration. Optionally, one or more elongated or expandable bodies are placed adjacent to the expanded balloon, inside the central void of the expanded balloon, or both adjacent to the expanded balloon and inside the central void of the expanded balloon. Detachable polymer balloons, metal balloons, polymer-coated metal balloons, and metalized polymer balloons are described, wherein the balloons are made of low compliance polymer materials such as PET and metals such as gold that can be pleated and folded to achieve a low profile, are highly flexible, expand at low pressures, and promote rapid tissue incorporation and anchoring to the surrounding vein wall. The external surface of the polymer balloons, metal balloons, polymer-coated metal balloons, and metalized polymer balloons can be modified to promote attachment to the adjacent vein wall and reduce the rate of balloon migration in vivo. Self-expanding structures can be added to the proximal or distal neck of the balloons wherein the self-expanding structures can make contact with wall of the adjacent vein segment, anchor the balloon to the vein wall, and reduce the risk of balloon migration. Elongated bodies such as coils can be modified for use with the detachable polymer balloons, metal balloons, polymer-coated metal balloons, and metalized polymer balloons. These elongated bodies can be configured in a straight, soft, and flexible configuration, enabling the adjunctive use of one or a few long, straight, or mostly straight coils to treat a wide range of vein sizes with a relatively small number of balloon and coil sizes.

A flexible, low profile catheter or catheter assembly is disclosed herein, which can be used to deliver both detachable balloons and coils to the target venous segments. Such a catheter assembly comprises a second catheter that is configured to accept both guidewires and coils, wherein this shaft can be moved forward or backward while the expanded detachable balloon remains fixed in position. This feature provides the benefits of over-the-wire delivery along with the ability to place coils precisely both adjacent to and inside expanded detachable balloons. The result is a detachable, implantable balloon and coil assembly that can immediately and completely occlude veins in vivo, and can maintain that occlusion over time by resisting degradation, migration, collapse, compression, or compaction without the need for a higher pressure inside the balloon or a valve to maintain that pressure.

In one example, a pleated and folded gold metal balloon is advanced over a guidewire into a selected venous segment using an assembly of three catheters: a first catheter joined or operably coupled to the balloon, a second catheter configured for insertion of a guidewire, and a third catheter configured to constrain a self-expanding retention structure joined to the distal neck or proximal neck of the balloon. The third catheter is retracted while the balloon remains in place, resulting in expansion of the self-expanding retention structure and engagement of a portion of the retention structure with the wall of the vein. A fluid is injected under pressure from the hub of the first catheter though a first lumen and into the central void of the balloon, causing expansion of the balloon. After confirming correct placement of the balloon and appropriate occlusion of the selected venous segment, the expanded balloon is detached from the first catheter and the guidewire and catheters are removed. Detachment may occur by mechanical, electrolytic, or electrothermal means. In this example, the gold metal balloon is able to resist collapse, compression, or compaction without additional support materials placed inside the central void of the balloon.

In another example, a pleated and folded polymer balloon is advanced over a guidewire into a selected venous segment using an assembly of three catheters: a first catheter joined or operably coupled to the balloon, a second catheter configured for insertion of a guidewire, and a third catheter configured to constrain a self-expanding retention structure joined to the distal neck or proximal neck of the balloon. The third catheter is retracted while the balloon remains in place, resulting in expansion of the self-expanding retention structure and engagement of a portion of the retention structure with the wall of the vein. A fluid is injected under pressure from the hub of the first catheter though a first lumen and into the central void of the balloon, causing expansion of the balloon. After confirming correct placement of the balloon and appropriate occlusion of the selected venous segment, the physician removes the guidewire and pulls the second catheter back until its tip is in the central void of the expanded balloon. The physician then places a vascular coil elongated body through the lumen of the second catheter and into the central void of the expandable balloon. Some segments of the vascular coil contact the inner surface of the wall of the expanded balloon. Loops of the vascular coil exert an outward force on the inner surface of the wall of the expanded balloon to help the expanded balloon resist collapse, compression, or compaction; to maintain occlusion of the venous segment; and to reduce the risk of balloon movement or migration. After confirming occlusion of the selected venous segment, the vascular coil is detached from its delivery system, the expanded balloon is detached from the first catheter, and the catheters and vascular coil delivery system are removed. Detachment may occur by mechanical, electrolytic, or electrothermal means. In some examples, more than one elongated body, expandable body, or vascular coil are placed in the expanded balloon. In some examples, the balloon comprises a distal neck assembly with an elastomeric or resilient valve that closes the distal opening in the balloon after retraction of the guidewire and second catheter. In addition to providing hemostasis within the expandable balloon, the valve may provide the primary means of attaching the balloon to the second catheter, the first catheter, or an assembly of the first and second catheters.

In some examples, the distal portion of an elongated body, expandable body, or vascular coil is placed in the lumen of the vein distal to the expanded balloon and the proximal portion of the elongated body, expandable body or vascular coil is placed in the central void of the expanded balloon in order to close at least a portion of the distal opening of the balloon. In some examples the retention structure is joined to a proximal neck of the balloon, while in other examples the retention structure is joined to a distal neck of the balloon. In some examples, the balloon is a metalized polymer balloon wherein an external layer of gold or titanium is present on the external surface of the polymer balloon at a thickness of 1 micron or less. In these examples, the polymer balloon or metalized polymer balloon is unable to resist collapse, compression, or compaction without additional support materials placed inside the central void of the balloon.

The present disclosure presents devices, systems and methods to occlude, embolize, or reduce the flow of blood in a LAA wherein a detachable balloon is placed in the lumen of a LAA and maintained there in an expanded configuration. Optionally, one or more elongated or expandable bodies are placed adjacent to the expanded balloon, inside the central void of the expanded balloon, or both adjacent to the expanded balloon and inside the central void of the expanded balloon. Detachable polymer balloons, metal balloons, polymer-coated metal balloons, and metalized polymer balloons are described, wherein the balloons are made of low compliance polymer materials such as PET and metals such as gold that can be pleated and folded to achieve a low profile, are highly flexible, expand at low pressures, and promote rapid tissue incorporation and anchoring to the surrounding LAA wall. The external surface of the polymer balloons, metal balloons, polymer-coated metal balloons, and metalized polymer balloons can be modified to promote attachment to the adjacent LAA wall and reduce the rate of balloon migration in vivo. Elongated bodies such as coils can be modified for use with the detachable polymer balloons, metal balloons, polymer-coated metal balloons, and metalized polymer balloons. These elongated bodies can be configured in a straight or mostly straight, soft, and flexible configuration, enabling the adjunctive use of one or a few long, straight or mostly straight coils to treat a range of LAA sizes with a relatively small number of balloon and coil sizes.

A flexible, low profile catheter or catheter assembly is disclosed herein, which can be used to deliver both detachable balloons and coils to the LAA. Such a catheter assembly comprises a second catheter that is configured to accept both guidewires and coils, wherein this second catheter can be moved forward or backward while the expanded detachable balloon remains fixed in position, thereby providing the benefits of over-the-wire delivery along with the ability to place coils precisely both adjacent to and inside expanded detachable balloons. The result is a detachable, implantable balloon and coil assembly that can immediately and completely occlude LAAs in vivo and can maintain that occlusion over time by resisting degradation, migration, collapse, compression without the need for a higher pressure inside the balloon or a valve to maintain that pressure.

In one example, a pleated and folded gold metal balloon is advanced over a guidewire into a LAA using an assembly of three catheters: a first catheter joined or operably coupled to the balloon, a second catheter configured for insertion of a guidewire, and a third catheter configured to constrain a self-expanding retention structure joined to the distal neck or proximal neck of the balloon. The third catheter is retracted while the balloon remains in place, resulting in expansion of the self-expanding retention structure and engagement of a portion of the retention structure with the wall of the LAA. A fluid is injected under pressure from the hub of the first catheter though a first lumen and into the central void of the balloon, causing expansion of the balloon. After confirming correct placement of the balloon and appropriate occlusion of the LAA, the expanded balloon is detached from the first catheter and the guidewire and catheters are removed. Detachment may occur by mechanical, electrolytic, or electrothermal means. In this example, the gold metal balloon is able to resist collapse, compression, or compaction without additional support materials placed inside the central void of the balloon.

In another example, a pleated and folded polymer balloon is advanced over a guidewire into a LAA using an assembly of three catheters: a first catheter joined or operably coupled to the balloon, a second catheter configured for insertion of a guidewire, and a third catheter configured to constrain a self-expanding retention structure joined to the distal neck of the balloon. The third catheter is retracted while the balloon remains in place, resulting in expansion of the self-expanding retention structure joined to the balloon and engagement of a portion of the retention structure with the wall of the LAA. A fluid is injected under pressure from the hub of the first catheter though a first lumen and into the central void of the balloon, causing expansion of the balloon. After confirming correct placement of the balloon and appropriate occlusion of the LAA, the physician removes the guidewire and pulls the second catheter back until its tip is in the central void of the expanded balloon. The physician then places a vascular coil elongated body through the lumen of the second catheter and into the central void of the expandable balloon. Some segments of the vascular coil contact the inner surface of the wall of the expanded balloon. Loops of the vascular coil exert an outward force on the inner surface of the wall of the expanded balloon to help the expanded balloon resist collapse, compression, or compaction; to maintain occlusion of the LAA; and to reduce the risk of balloon movement or migration. After confirming occlusion of the LAA, the vascular coil is detached from its delivery system, the expanded balloon is detached from the first catheter, and the catheters and vascular coil delivery system are removed. Detachment may occur by mechanical, electrolytic, or electrothermal means. In some examples, more than one elongated body, expandable body or vascular coil are placed in the expanded balloon. In some examples, the balloon is a metalized polymer balloon wherein an external layer of gold or titanium is present on the external surface of the polymer balloon at a thickness of 1 micron or less. In these examples, the polymer balloon or metalized polymer balloon is unable to resist collapse, compression, or compaction without additional support materials placed inside the central void of the balloon.

The present disclosure presents devices, systems and methods to occlude, embolize, or reduce the flow of blood in paravalvular leak paths wherein a detachable balloon is placed in the lumen of a paravalvular leak path and maintained there in an expanded configuration. Optionally, one or more elongated or expandable bodies are placed adjacent to the expanded balloon, inside the central void of the expanded balloon, or both adjacent to the expanded balloon and inside the central void of the expanded balloon. Detachable polymer balloons, metal balloons, polymer-coated metal balloons, and metalized polymer balloons are described, wherein the balloons are made of low compliance polymer materials such as PET and metals such as gold that can be pleated and folded to achieve a low profile, are highly flexible, expand at low pressures, and promote rapid tissue incorporation and anchoring to the surrounding artery wall. The external surface of the polymer balloons, metal balloons, polymer-coated metal balloons, and metalized polymer balloons can be modified to promote attachment to the adjacent tissue and reduce the rate of balloon migration in vivo. Elongated bodies such as coils can be modified for use with the detachable polymer balloons, metal balloons, polymer-coated metal balloons, and metalized polymer balloons. These elongated bodies can be configured in a straight or mostly straight, soft, and flexible configuration, enabling the adjunctive use of one or a few long, straight or mostly straight coils to treat a wide range of artery sizes with a relatively small number of balloon and coil sizes.

A flexible, low profile catheter or catheter assembly is disclosed herein, which can be used to deliver both detachable balloons and coils to the target paravalvular leak paths. Such a catheter assembly comprises a second catheter that is configured to accept both guidewires and coils, wherein this second catheter can be moved forward or backward while the expanded detachable balloon remains fixed in position. This feature provides the benefits of over-the-wire delivery along with the ability to place coils precisely both adjacent to and inside expanded detachable balloons. The result is a detachable, implantable balloon and coil assembly that can immediately and completely occlude paravalvular leak paths in vivo and can maintain that occlusion over time by resisting degradation, migration, collapse, compression, or compaction without the need for a higher pressure inside the balloon or a valve to maintain that pressure.

In one example, a detachable balloon catheter comprising a gold metal balloon, a first catheter joined or operably coupled to the balloon, and a second catheter configured for insertion of a guidewire is advanced over a guidewire until a pleated and folded gold metal balloon of the appropriate length is placed so that the distal portion of the balloon is distal to the paravalvular leak path and the proximal portion of the balloon is proximal to the paravalvular leak path. A fluid is injected under pressure from the hub of the first catheter though the first lumen and into the central void of the balloon, causing expansion of the balloon. After confirming correct placement of the balloon and appropriate occlusion of the leak path, the expanded balloon is detached from the first catheter and the guidewire and catheters are removed from the patient. Detachment may occur by mechanical, electrolytic, or electrothermal means. In this example, the gold metal balloon is able to resist collapse, compression, or compaction without additional support materials placed inside the central void of the balloon.

In another example, a detachable balloon catheter comprising a polymer balloon, a first catheter joined or operably coupled to the balloon, and a second catheter configured for insertion of a guidewire and also for delivering elongated or expandable bodies is advanced over a guidewire until a pleated and folded polymer balloon of the appropriate length is placed so that the distal portion of the balloon is distal to the paravalvular leak path and the proximal portion of the balloon is proximal to the paravalvular leak path. A fluid is injected under pressure from the hub of the first catheter though the first lumen and into the central void of the balloon, causing expansion of the balloon. After confirming correct placement of the balloon and appropriate occlusion of the paravalvular leak path, the physician removes the guidewire, and pulls the second catheter back until its tip is in the central void of the expanded balloon. The physician then places a vascular coil elongated body through the lumen of the second catheter and into the central void of the expandable balloon, wherein some portions of the proximal portion of the vascular coil contact the inner surface of the wall of the expanded balloon. Loops of the vascular coil exert an outward force on the inner surface of the wall of the expanded balloon to help the expanded balloon resist collapse, compression, or compaction; to maintain occlusion of the paravalvular leak path; and to reduce the risk of balloon movement or migration. After confirming occlusion of the paravalvular leak path, the vascular coil is detached from its delivery system and the expanded balloon is detached from the first catheter and the catheters and any vascular coil delivery systems are removed. Detachment could occur by mechanical, electrolytic, or electrothermal means.

In some examples, more than one elongated body, expandable body or vascular coil are placed in the expanded balloon. In some examples, the distal portion of an elongated body, expandable body, or vascular coil is placed in the paravalvular leak path distal to the expanded polymer balloon and the proximal portion of the elongated body, expandable body or vascular coil is placed in the central void of the expanded balloon in order to close at least a portion of the distal opening of the balloon. In some examples, the balloon comprises a distal neck assembly with an elastomeric or resilient valve that closes the distal opening in the balloon after retraction of the second catheter. In some examples, the balloon is a metalized polymer balloon wherein an external layer of gold or titanium is present on the external surface of the polymer balloon at a thickness of 1 micron or less. In these examples, the polymer balloon or metalized polymer balloon is unable to resist collapse, compression, or compaction without additional support materials placed inside the central void of the balloon.

The present disclosure presents devices, systems and methods to occlude, embolize, or reduce the flow of biological fluid or material in biological conduits wherein a detachable balloon is placed in the lumen of a biological conduit and maintained there in an expanded configuration, and optionally one or more elongated or expandable bodies are placed adjacent to the expanded balloon, inside the central void of the expanded balloon, or both adjacent to the expanded balloon and inside the central void of the expanded balloon. Detachable polymer balloons, metal balloons, polymer-coated metal balloons, and metalized polymer balloons are described, wherein the balloons are made of low compliance polymer materials such as PET and metals such as gold that can be pleated and folded down to a low profile, are highly flexible, expand at low pressures, and promote rapid tissue incorporation and anchoring to the surrounding biological conduit wall. The external surface of the polymer balloons, metal balloons, polymer-coated metal balloons, and metalized polymer balloons can be modified to promote attachment to the adjacent conduit wall and reduce the rate of balloon migration in vivo. Elongated bodies such as coils can be modified for use with the detachable polymer balloons, metal balloons, polymer-coated metal balloons, and metalized polymer balloons that are disclosed herein. These elongated bodies can be configured in a straight, soft and flexible configuration, enabling the adjunctive use of one or a few long, straight or mostly straight coils to treat a wide range of conduit sizes with a relatively small number of balloon and coil sizes.

A flexible, low profile catheter or catheter assembly is disclosed herein, which can be used to deliver both detachable balloons and coils to the target biological conduit segments, such assembly comprising a shaft that is configured to accept both guidewires and coils, wherein this shaft can be moved forward or backward while the expanded detachable balloon remains fixed in position. This feature provides the benefits of over-the-wire delivery along with the ability to place coils precisely both adjacent to, and inside expanded detachable balloons. The result is a detachable, implantable balloon and coil that can immediately and completely occlude biological conduits in vivo and can maintain that occlusion over time by resisting degradation, migration, collapse, compression, or compaction without the need for a higher pressure inside the balloon or a valve to maintain that pressure.

In one example, a pleated and folded gold metal balloon is advanced over a guidewire into a selected biological conduit segment using an assembly of three catheters, a first catheter joined or operably coupled to the balloon, a second catheter configured for insertion of a guidewire, and a third catheter configured to constrain a self-expanding retention structure joined to the distal neck or proximal neck of the balloon. The third catheter is retracted while the balloon remains in place, resulting in expansion of the self-expanding retention structure joined to the balloon and engagement of a portion of the retention structure with the wall of the biological conduit. A fluid is injected under pressure from the hub of the first catheter, though a first lumen, and into the central void of the balloon, causing expansion of the balloon. After confirming occlusion of the selected biological conduit segment, the expanded balloon is detached from the first catheter and the guidewire, and catheters are removed. Detachment may occur by mechanical, electrolytic, or electrothermal means. In this example, the gold metal balloon is able to resist collapse, compression, or compaction without additional support materials placed inside the central void of the balloon.

In another example, a pleated and folded polymer balloon is advanced over a guidewire into a selected biological conduit segment using an assembly of three catheters, a first catheter joined or operably coupled to the balloon, a second catheter configured for insertion of a guidewire, and a third catheter configured to constrain a self-expanding retention structure joined to the distal neck or proximal neck of the balloon. The third catheter is retracted while the balloon remains in place, resulting in expansion of the self-expanding retention structure joined to the balloon and engagement of a portion of the retention structure with the wall of the biological conduit. A fluid is injected under pressure from the hub of the first catheter, though a first lumen, and into the central void of the balloon, causing expansion of the balloon. After confirming correct placement of the balloon and appropriate occlusion of the selected biological conduit segment, the physician removes the guidewire and pulls the second catheter back until its tip is in the central void of the expanded balloon. The physician then places a vascular coil elongated body through the lumen of the second catheter and into the central void of the expandable balloon, wherein some segments of the proximal portion of the vascular coil contact the inner surface of the wall of the expanded balloon. Loops of the vascular coil exert an outward force on the inner surface of the wall of the expanded balloon to help the expanded balloon resist collapse, compression, or compaction; to maintain occlusion of the segment of biological conduit; and to reduce the risk of balloon movement or migration. After confirming occlusion of the selected biological conduit segment, the vascular coil is detached from its delivery system and the expanded balloon is detached from the first catheter and the catheters and vascular coil delivery system is removed. Detachment may occur by mechanical, electrolytic, or electrothermal means. In some examples, more than one elongated body, expandable body or vascular coil are placed in the expanded balloon.

In some examples, more than one elongated body, expandable body or vascular coil are placed in the expanded balloon. In some examples, the distal portion of an elongated body, expandable body, or vascular coil is placed in the lumen of the biological conduit distal to the expanded balloon and the proximal portion of the elongated body, expandable body or vascular coil is placed in the central void of the expanded balloon in order to close at least a portion of the distal opening of the balloon. In some examples, the balloon comprises a distal neck assembly with an elastomeric or resilient valve that closes the distal opening in the balloon after retraction of the second catheter. In some examples the retention structure is joined to a proximal neck of a balloon, while in other examples the retention structure is joined to a distal neck of a balloon. In some examples, the balloon is a metalized polymer balloon wherein an external layer of gold or titanium is present on the external surface of the polymer balloon at a thickness of 1 micron or less. In these examples, the polymer balloon or metalized polymer balloon is unable to resist collapse, compression, or compaction without additional support materials placed inside the central void of the balloon.

The present disclosure also relates to manufacturing detachable polymer balloons, detachable metal balloons, detachable polymer-coated metal balloons (including completely polymer-coated metal balloons and partially polymer-coated metal balloons) and detachable metalized polymer balloons (including completely metalized polymer balloons and partially metalized polymer balloons). Methods of applying one or more metals to the surface of a balloon comprising or substantially comprising a polymer such as PET, polyamide (nylon), or polyether block amide (Pebax) may include a mechanical process, such wrapping of metal in the form of wire coils or other patterns; an electrochemical process such as electroplating, electroforming, or sputtering; or various combinations of mechanical or electrochemical processes.

BRIEF DESCRIPTION OF FIGURES

FIGS. 2A-D are tables describing ranges of values for the overall geometric dimensions of the embodiment of a balloon shown in FIG. 1.

FIGS. 4A-C are tables describing ranges of values for the overall geometric dimensions of the embodiment of a balloon shown in FIG. 3.

FIGS. 6A-B are tables describing ranges of values for the proximal geometric dimensions of the embodiment of a balloon shown in FIG. 5A.

FIGS. 6C-D are tables describing ranges of values for the proximal geometric dimensions of the embodiment of a balloon shown in FIG. 5B.

FIGS. 13A-D are planar views showing one embodiment of a detachable balloon delivery system comprising a guidewire and three catheters, including details of the proximal configuration and purpose of each catheter.

FIGS. 26A-H are planar, perspective, cross-sectional, and detail views of the male tubular structure of a mechanical latch attachment system according to one embodiment, with its overall geometric dimensions defined.

FIG. 27 is a table describing ranges of values for the geometric dimensions of the embodiment of the male tubular structure of a mechanical latch attachment system shown in FIG. 26.

FIGS. 28A-G are planar, perspective, and cross-sectional views of the female tubular structure of a mechanical latch attachment system according to one embodiment, with its overall geometric dimensions defined.

FIG. 29 is a table of describing ranges of values for the geometric dimensions of the embodiment of the female tubular structure of a mechanical latch attachment system shown in FIG. 28.

FIGS. 30A-D are planar partial cross-sectional views showing the operation of an elastomeric tubular structure attachment system according to a first embodiment in which the elastomeric tubular structure is bonded within the balloon proximal neck and in frictional contact with the outside of the first catheter.

FIGS. 31A-D are planar partial cross-sectional views showing the operation of an elastomeric tubular structure attachment system according to a second embodiment in which the elastomeric tubular structure is bonded to the outside of the balloon proximal neck and in frictional contact with the outside of the first catheter.

FIGS. 32A-D are planar partial cross-sectional views showing the operation of an elastomeric tubular structure attachment system according to a third embodiment in which the elastomeric tubular structure is bonded to the outside of the first catheter and in frictional contact with the outside of the balloon proximal neck.

FIGS. 33A-B are cross-sectional views of the proximal portion of the embodiment of the balloon shown in FIG. 5A showing the operation of an elastomeric tubular structure attachment system according to the embodiment shown in FIG. 30.

FIGS. 34A-B are cross-sectional views of the proximal portion of the embodiment of the balloon shown in FIG. 5A showing the operation of an elastomeric tubular structure attachment system according to the embodiment shown in FIG. 31.

FIGS. 35A-B are cross-sectional views of the proximal portion of the embodiment of the balloon shown in FIG. 5A showing the operation of an elastomeric tubular structure attachment system according to the embodiment shown in FIG. 32.

FIGS. 36A-F are planar views showing a first sequence of operation of an elastomeric tubular structure attachment system according to the embodiment shown in FIG. 30.

FIGS. 37A-E are cross-sectional detail views showing a first sequence of operation of an elastomeric tubular structure attachment system according to the embodiment shown in FIG. 30.

FIGS. 38A-J are planar partial cross-sectional views showing a second sequence of operation of an elastomeric tubular structure attachment system according to the embodiment shown in FIG. 30.

FIGS. 39A-H are cross-sectional detail views showing a second sequence of operation of an elastomeric tubular structure attachment system according to the embodiment shown in FIG. 30.

FIGS. 40A-K are planar partial cross-sectional views showing a third sequence of operation of an elastomeric tubular structure attachment system according to the embodiment shown in FIG. 30.

FIGS. 41A-H are cross-sectional detail views showing a third sequence of operation of an elastomeric tubular structure attachment system according to the embodiment shown in FIG. 30.

FIGS. 42A-C show planar and cross-sectional views of an elastomeric or resilient tubular structure of a friction fit attachment system according to one embodiment, with its geometric dimensions defined.

FIG. 43 is a table describing ranges of values for the geometric dimensions of the embodiment of the elastomeric or resilient tubular structure of a friction fit attachment system shown in FIG. 42.

FIGS. 44A-B are cross-sectional views showing the operation of a valve assembly within a distal nose cone according to one embodiment in which retraction of the second catheter causes the valve to close, preventing fluid flow through the distal neck of the balloon.

FIGS. 45A-F are planar views showing a first sequence of operation of a friction fit attachment system comprising an elastomeric or resilient valve and an elastomeric or resilient tubular structure according to the embodiments shown in FIGS. 30 and 44.

FIGS. 46A-E are cross-sectional detail views showing a first sequence of operation of a friction fit attachment system comprising an elastomeric or resilient valve and an elastomeric or resilient tubular structure according to the embodiments shown in FIGS. 30 and 44.

FIGS. 47A-J are planar views showing a second sequence of operation of a friction fit attachment system comprising an elastomeric or resilient valve and an elastomeric or resilient tubular structure according to the embodiments shown in FIGS. 30 and 44.

FIGS. 48A-I are cross-sectional detail views showing a second sequence of operation of a friction fit attachment system comprising an elastomeric or resilient valve and an elastomeric or resilient tubular structure according to the embodiments shown in FIGS. 30 and 44.

FIGS. 49A-D are planar, cross-sectional, and perspective views of a distal nose cone incorporating a valve assembly according to one embodiment.

FIG. 51 is a table describing ranges of values for the geometric dimensions of the distal valve assembly shown in FIG. 50.

FIG. 56 is a table describing ranges of values for the geometric dimensions of the embodiment of the anode shown in FIG. 55.

FIGS. 57A-D show planar, cross-sectional, detail cross-sectional, and perspective views of the anode shown in FIG. 55.

FIGS. 58A-E are planar views showing a first sequence of operation of an electrolytic detachment system according to the embodiment shown in FIGS. 55 and 57.

FIGS. 59A-E are cross-sectional detail views showing a first sequence of operation of an electrolytic detachment system according to the embodiment shown in FIGS. 55 and 57.

FIGS. 60A-I are planar views showing a second sequence of operation of an electrolytic detachment system according to the embodiment shown in FIGS. 55 and 57.

FIGS. 61A-H are cross-sectional detail views showing a second sequence of operation of an electrolytic detachment system according to the embodiment shown in FIGS. 55 and 57.

FIGS. 62A-I are planar views showing a third sequence of operation of an electrolytic detachment system according to the embodiment shown in FIGS. 55 and 57.

FIGS. 63A-I are cross-sectional detail views showing a third sequence of operation of an electrolytic detachment system according to the embodiment shown in FIGS. 55 and 57.

FIGS. 64A-D are planar partial cross-sectional views showing the operation of an electrothermal detachment system according to a first embodiment in which a heat sensitive tubular structure is bonded within both the balloon proximal neck and the first catheter.

FIGS. 65A-D show cross-sectional and detail cross-sectional views of a heat sensitive tubular structure used in an electrothermal detachment system according to the embodiment shown in FIG. 64, with its overall geometric dimensions defined.

FIG. 66 is a table describing ranges of values for the geometric dimensions of the embodiment of the heat sensitive tubular structure shown in FIG. 65.

FIG. 69 is a table describing ranges of values for the geometric dimensions of the embodiment of the heat sensitive distal end of the first catheter shown in FIG. 68.

FIG. 72 is a table describing ranges of values for the geometric dimensions of the heat sensitive bond shown in FIG. 71.

FIG. 85 is a table describing ranges of values for the dimensions of balloons and their associated pleat designs including the embodiments shown in FIG. 84.

FIG. 87 is a table describing ranges of values for dimensions of the second catheter and second medical device serving as a coil delivery system shown in FIG. 86 when based on a 0.014" guidewire platform.

FIG. 88 is a table describing ranges of values for dimensions of the second catheter and second medical device serving as a coil delivery system shown in FIG. 86 when based on a 0.018" guidewire platform.

FIG. 89 is a table describing ranges of values for dimensions of the second catheter and second medical device serving as a coil delivery system shown in FIG. 86 when based on a 0.035/0.038" guidewire platform.

FIG. 90 is a table describing ranges of values for length dimensions of the second catheter and second medical device serving as a coil delivery system shown in FIG. 86 for three common guidewire platforms.

FIG. 91 is a table describing ranges of values for diameter dimensions of the second catheter and second medical device serving as a coil delivery system shown in FIG. 86 for three common guidewire platforms.

FIGS. 92A-C are cross-sectional views of a terminal bifurcation aneurysm according to one embodiment with its overall geometric dimensions defined.

FIGS. 93A-M are cross-sectional views of a terminal bifurcation aneurysm showing a sequence of treatment using a detachable balloon catheter according to one embodiment.

FIGS. 94A-M are cross-sectional views of a terminal bifurcation aneurysm, whose sac has a smaller daughter aneurysm, showing a sequence of treatment using a detachable balloon catheter according to one embodiment.

FIGS. 95A-B are cross-sectional views of a sidewall aneurysm, with its overall geometric dimensions defined, before and after treatment using a detachable balloon catheter according to one embodiment.

FIGS. 96A-B are cross-sectional views of a terminal bifurcation aneurysm, with its overall geometric dimensions defined, before and after treatment using a detachable balloon catheter according to one embodiment.

FIGS. 97A-B are schematics showing the direction of blood flow and luminal diameter tapering in arteries and veins.

FIGS. 98A-B are schematics showing the occlusion of arteries and veins using a detachable balloon catheter with adjunctive placement of vascular coils within the expanded balloon and an expandable retention structure deployed during vein treatment to secure the balloon.

FIGS. 101A-F are planar views showing a first sequence of operation of a detachable balloon catheter incorporating an expandable retention structure affixed to the proximal neck of the balloon and a mechanical latch attachment system according to one embodiment.

FIGS. 102A-J are planar views showing a second sequence of operation of a detachable balloon catheter incorporating an expandable retention structure affixed to the proximal neck of the balloon and a mechanical latch attachment system according to one embodiment.

FIGS. 103A-I are planar views showing a third sequence of operation of a detachable balloon catheter incorporating an expandable retention structure an expandable retention structure affixed to the proximal neck of the balloon and a mechanical latch attachment system according to one embodiment.

FIGS. 115A-B include images of the endothelialization of a canine terminal bifurcation aneurysm neck after balloon and coil placement according to one embodiment.

Figure 116:
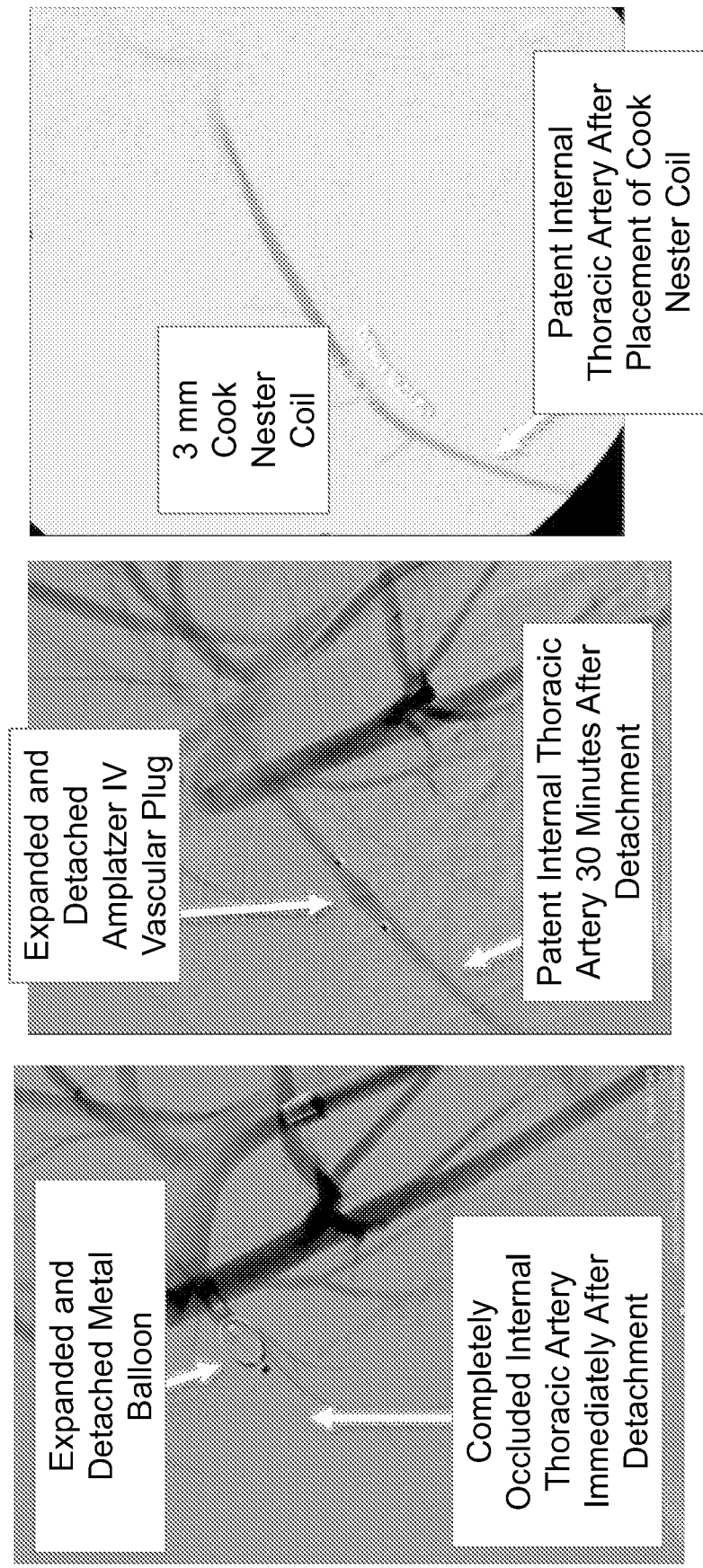

FIG. 116 includes images related to the immediate effect after treatment of canine internal thoracic artery according to one embodiment.

Figure 117:
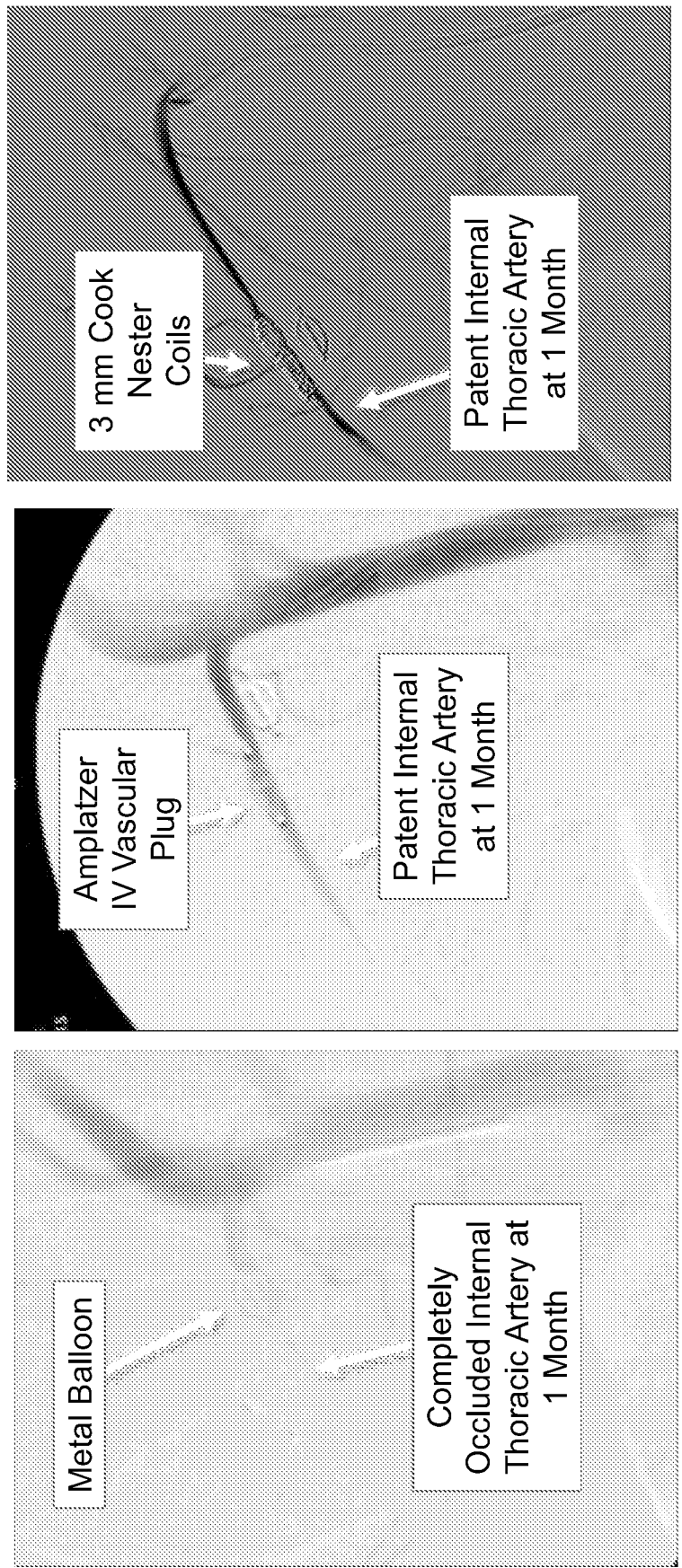

FIG. 117 includes images depicting 1 month after treatment of a canine internal thoracic artery according to one embodiment.

Figure 118:
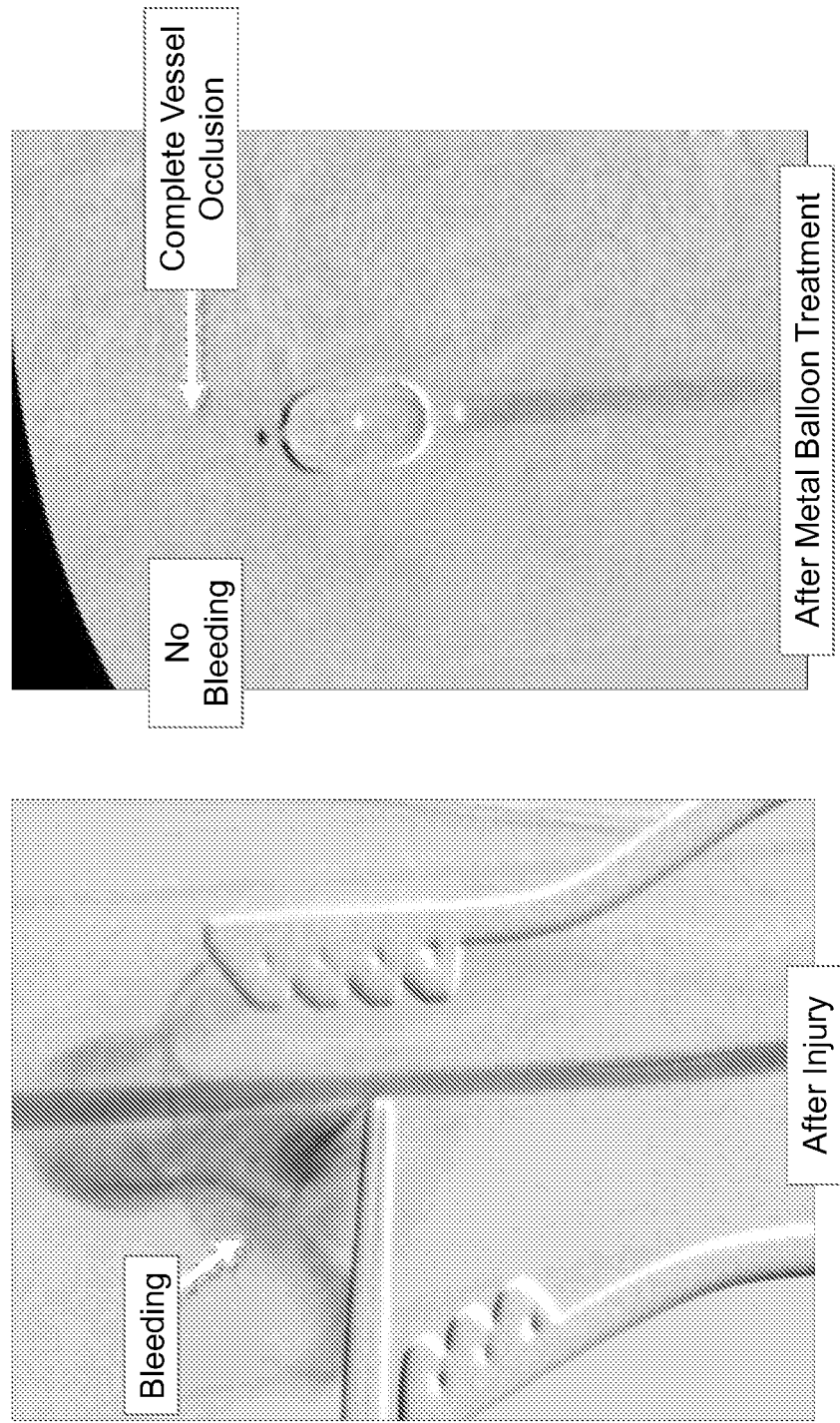

FIG. 118 includes images related to the effect of treatment of bleeding canine carotid artery with metal balloon according to one embodiment.

Figure 119:
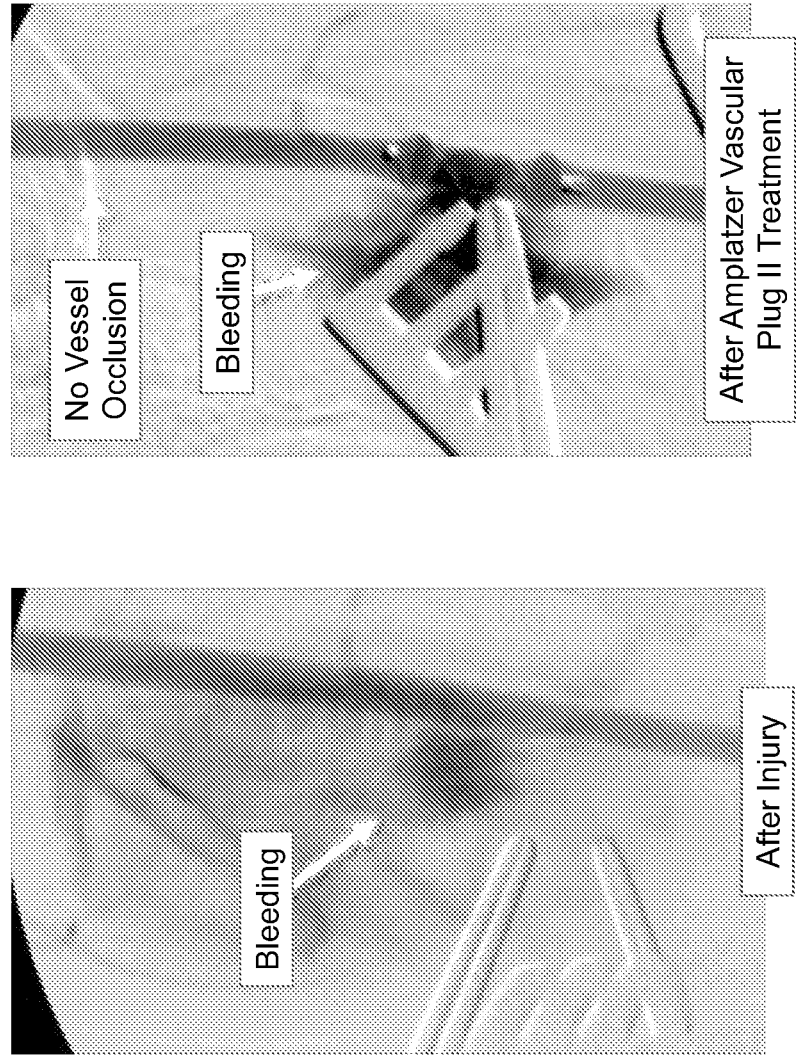

FIG. 119 includes images related to the effect of treatment of bleeding canine carotid artery with an Amplatzer vascular plug II according to one embodiment.

Figure 120:
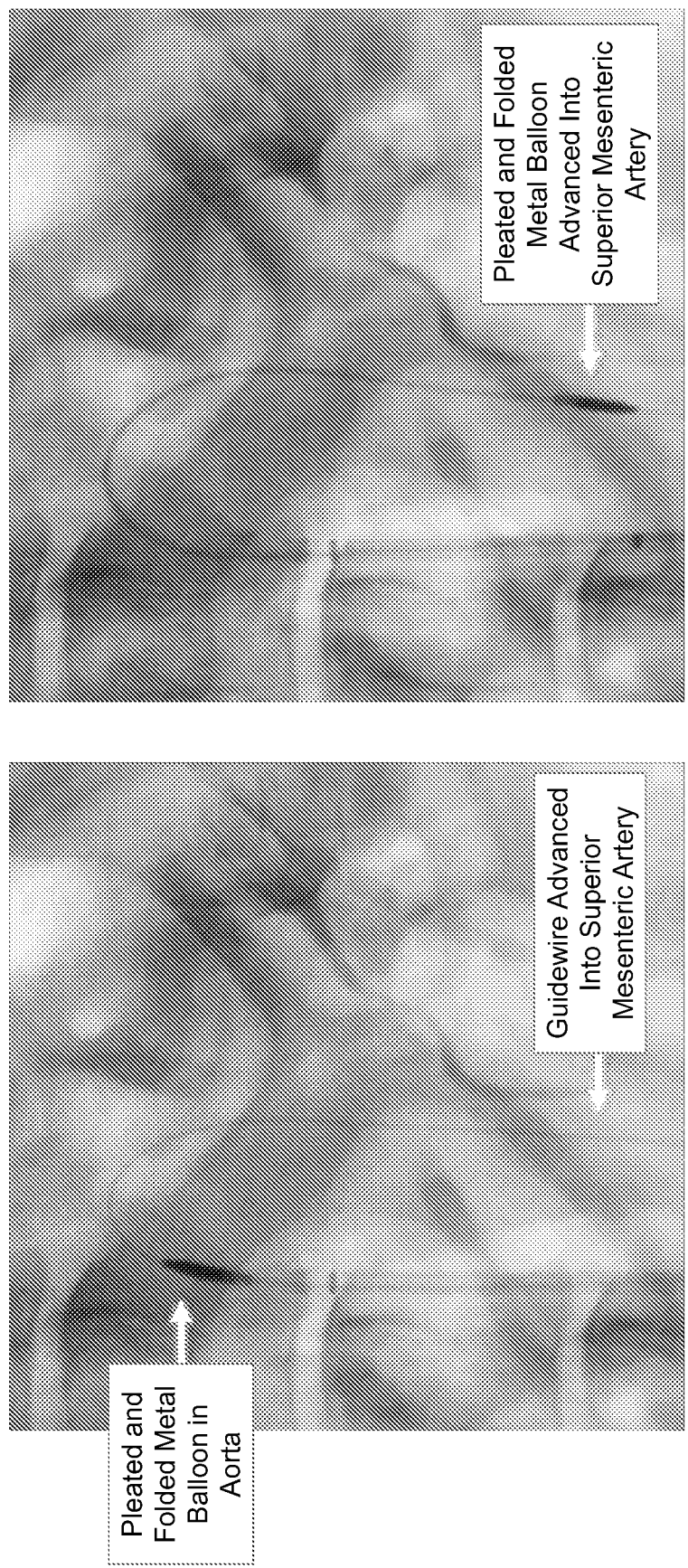

FIG. 120 includes images related to the advancement of metal balloon over guidewire into canine superior mesenteric artery according to one embodiment.

Figure 121A:
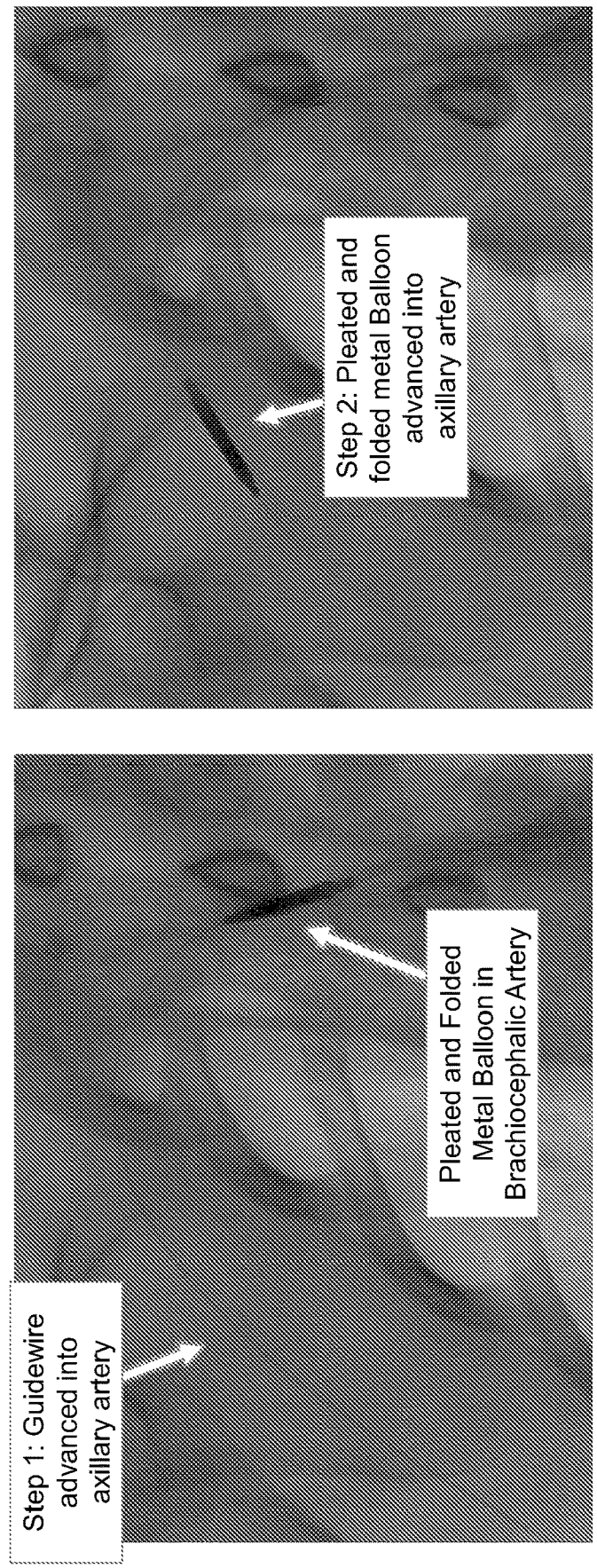
Figure 121B:
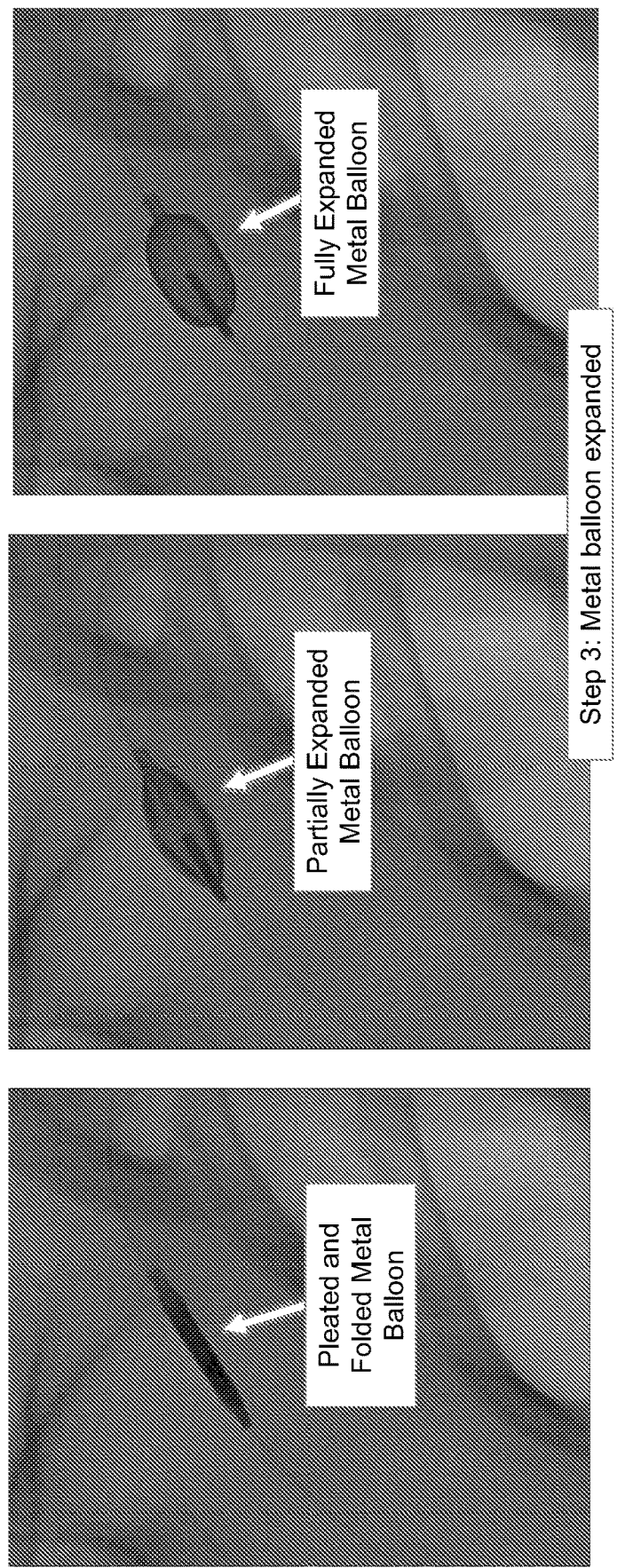

FIGS. 121A-B include images related to the treatment of canine axillary artery with metal balloon according to one embodiment.

Figure 122:
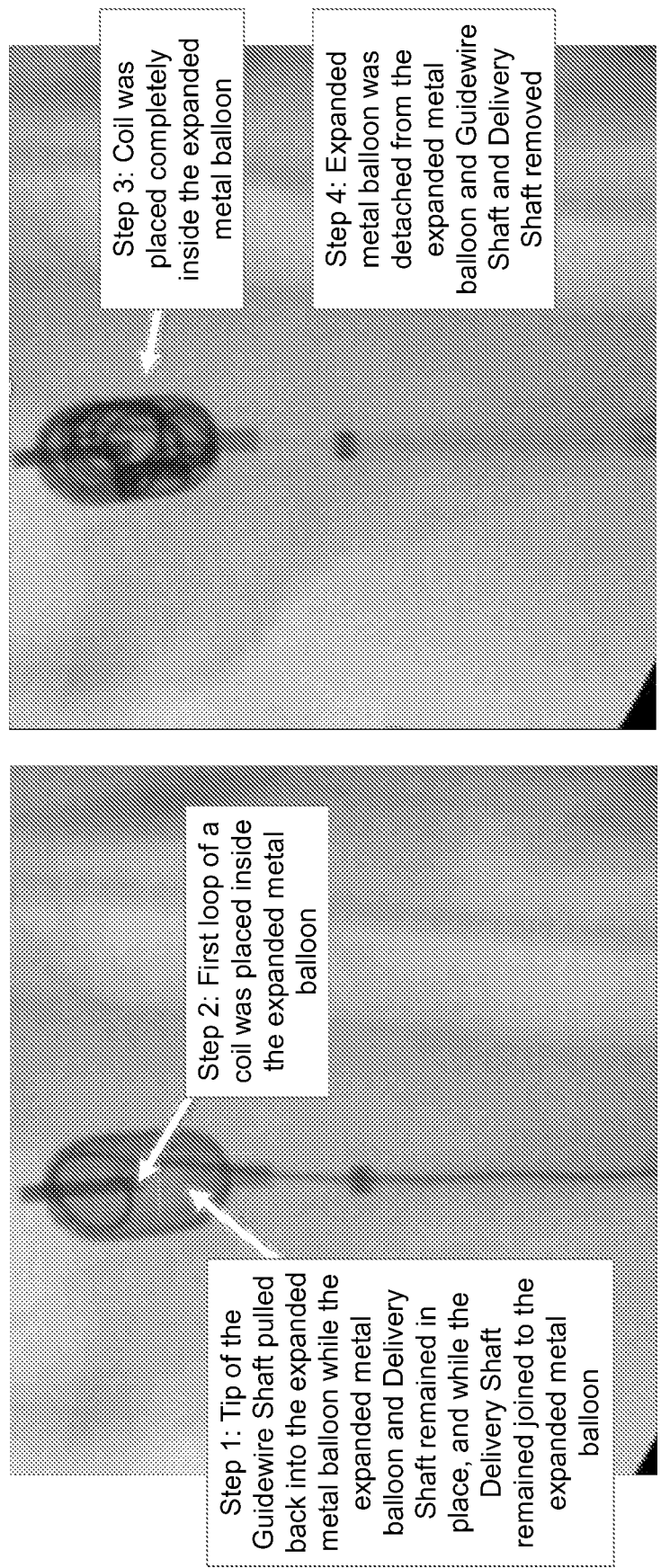

FIG. 122 includes images related to the placement of coil inside expanded metal balloon in canine carotid artery according to one embodiment.

Figure 123A:
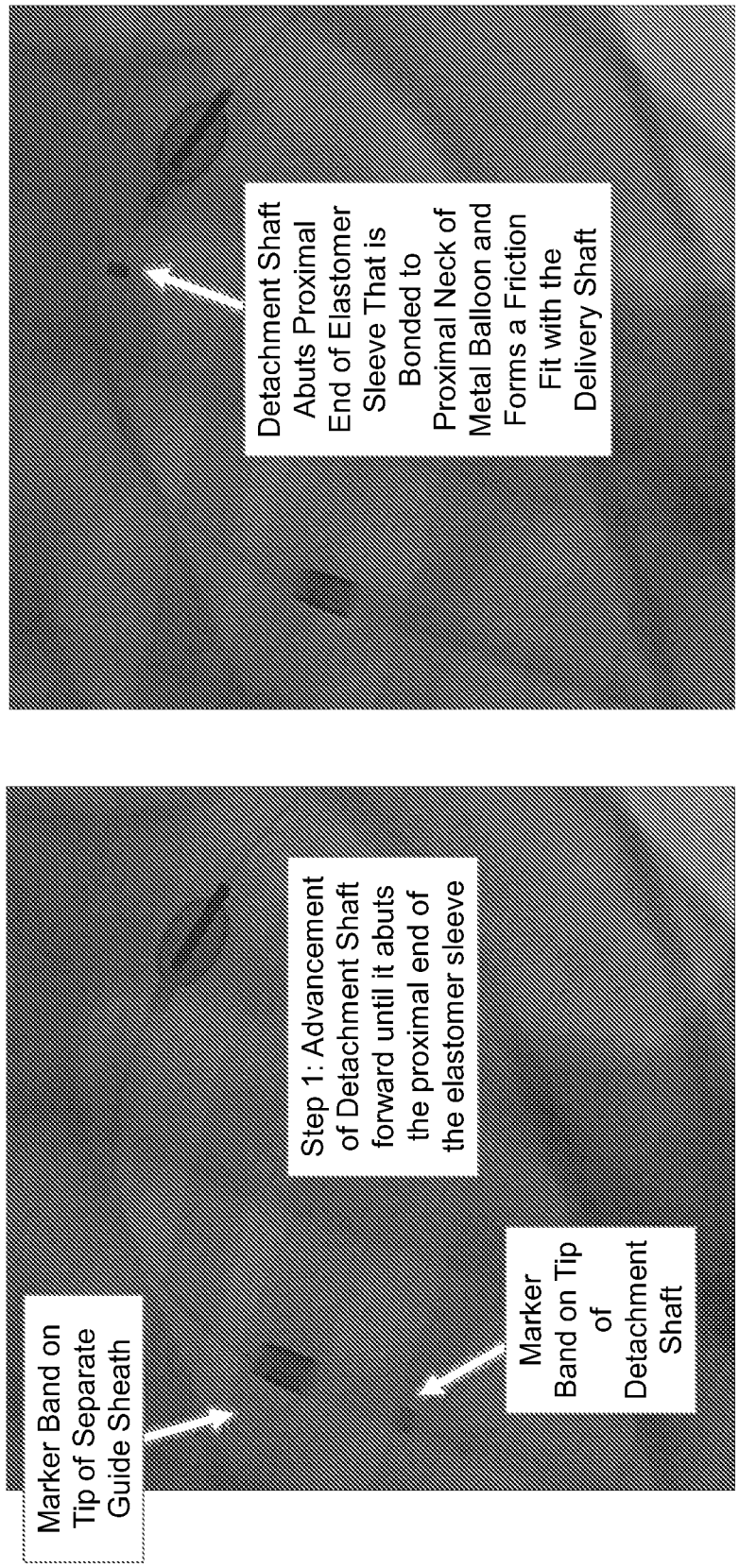
Figure 123B:
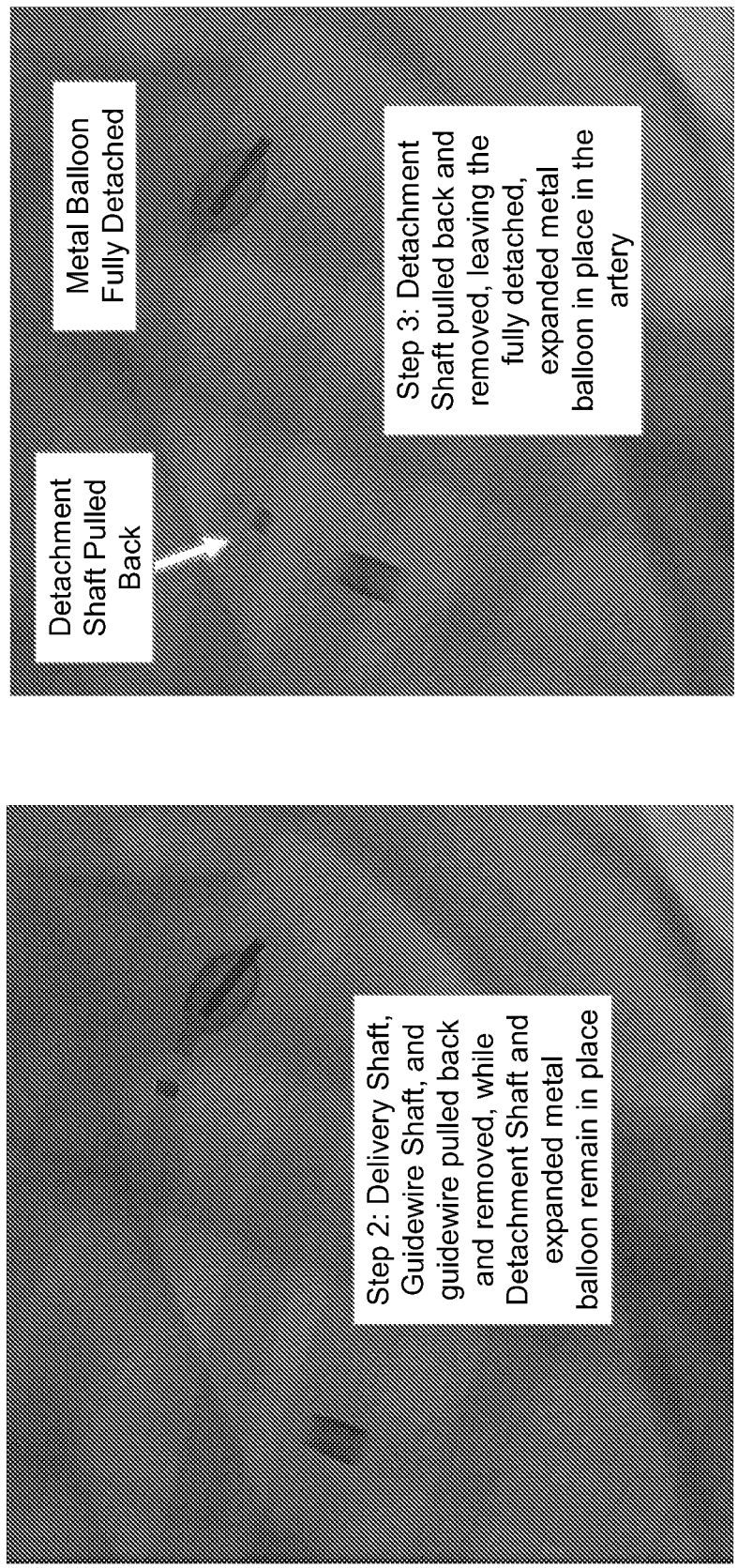
Figure 123C:
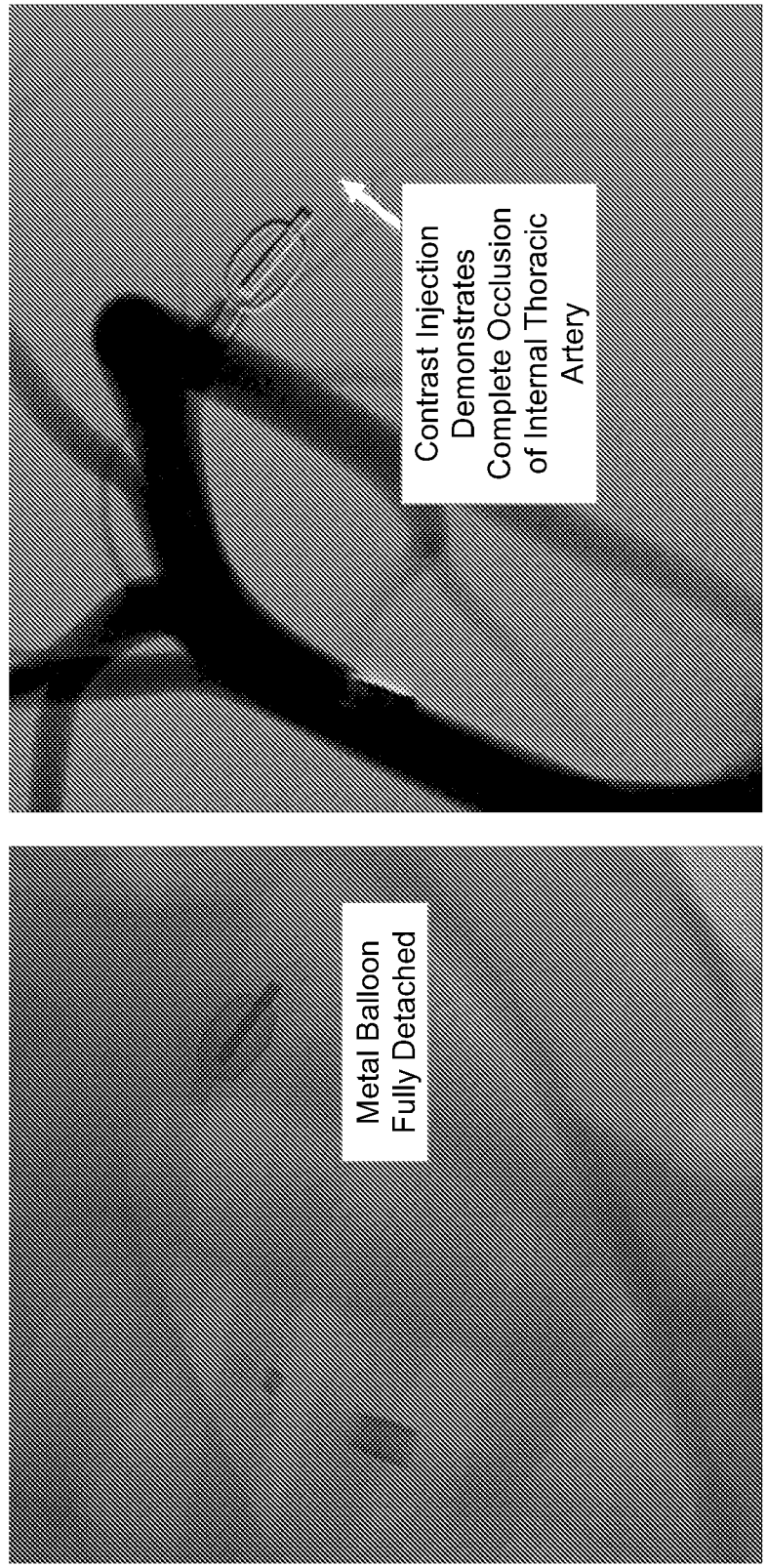

FIGS. 123A-C include images related to the detachment of metal balloon in canine internal thoracic artery according to one embodiment.

Figure 124:
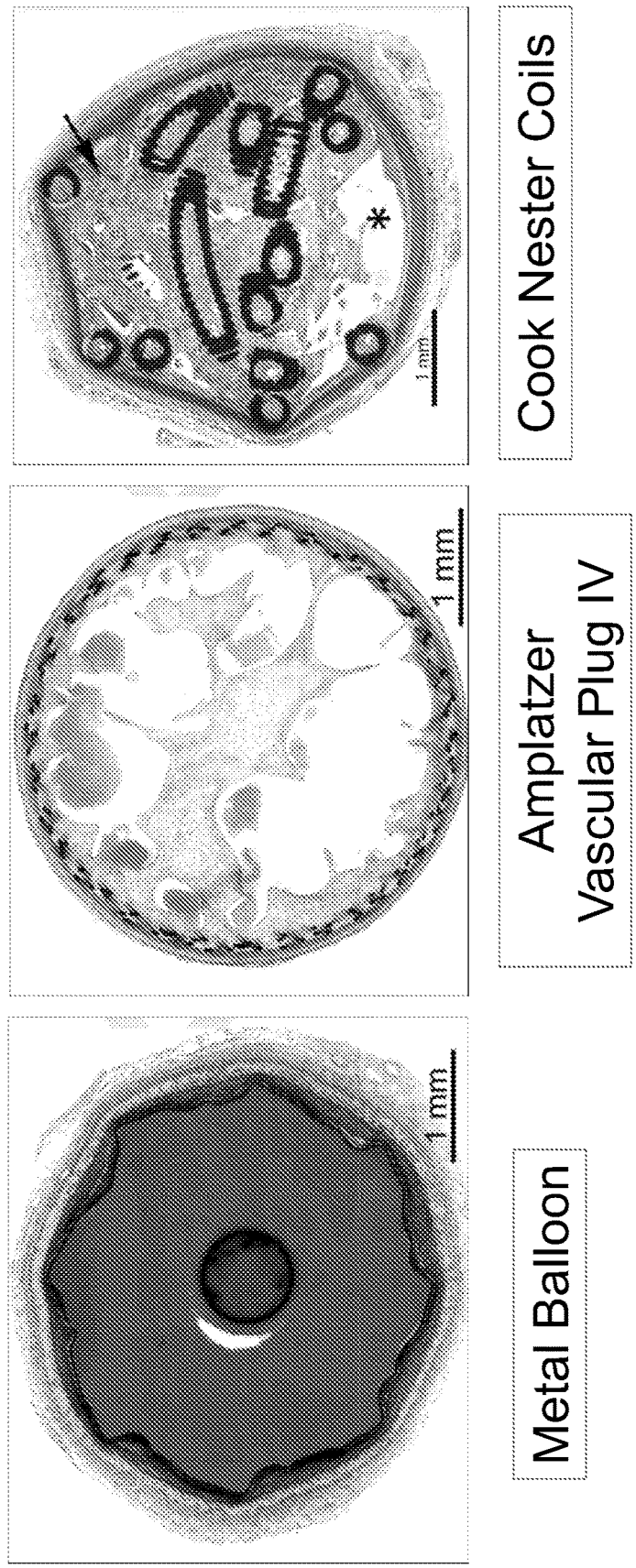

FIG. 124 includes images comparing histopathology at 1 month after the implants of various embodiments of the disclosed medical devices in a canine internal thoracic artery.

Figure 125:
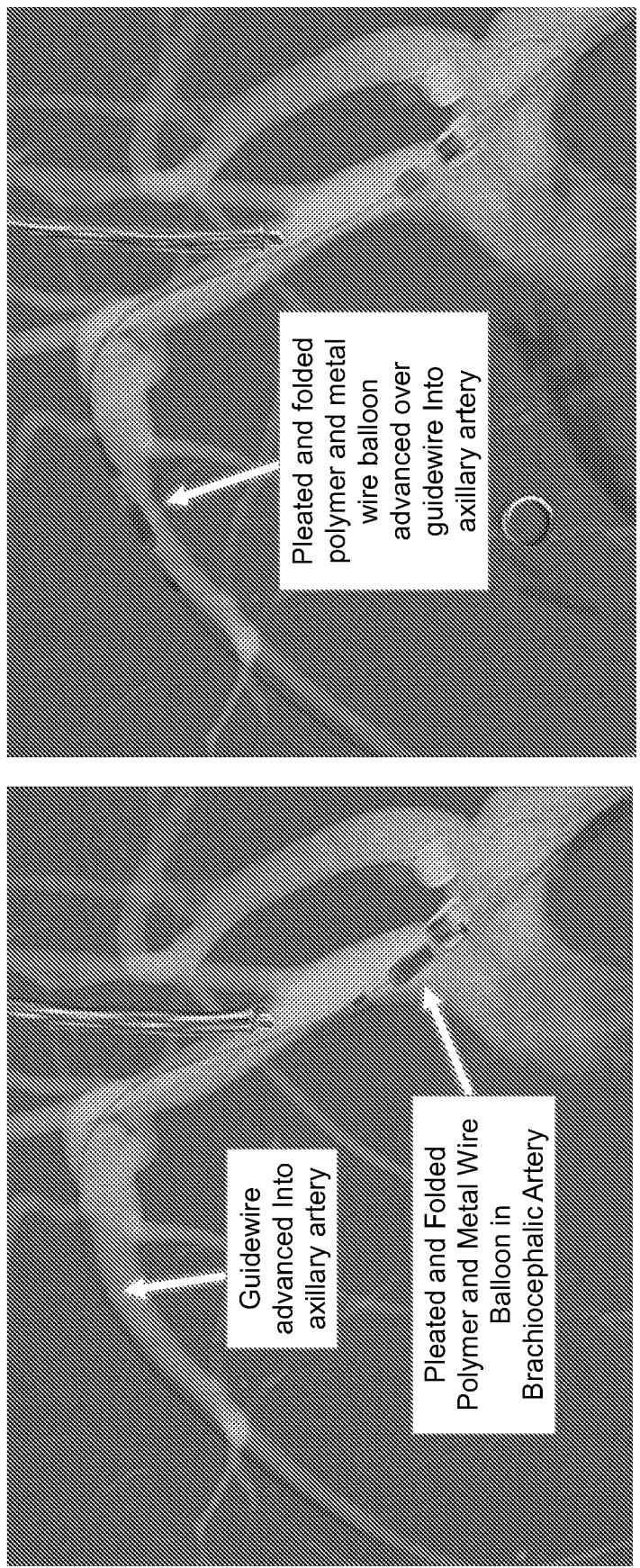

FIG. 125 includes images related to the advancement of polymer and metal wire balloon over guidewire into canine axillary artery according to one embodiment.

Figure 126:
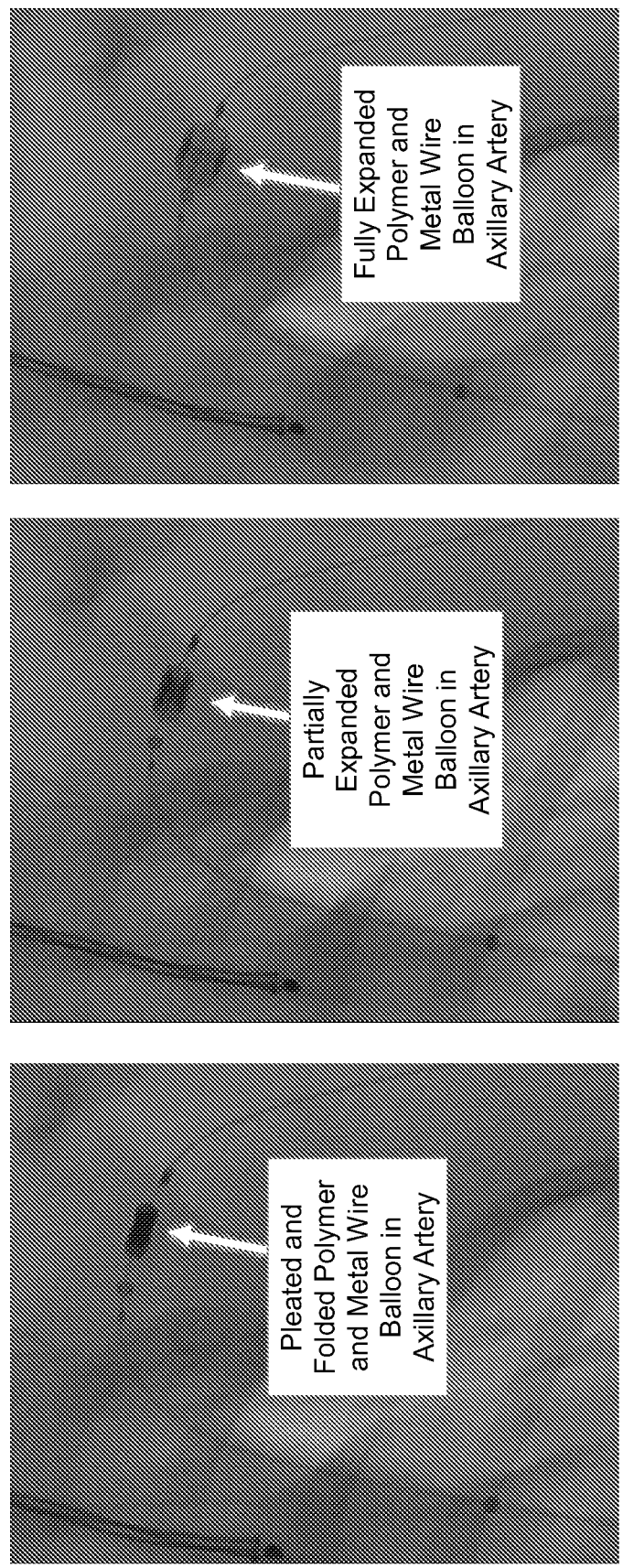

FIG. 126 includes images related to the expansion of polymer and metal wire balloon in canine axillary artery according to one embodiment.

Figure 127A:
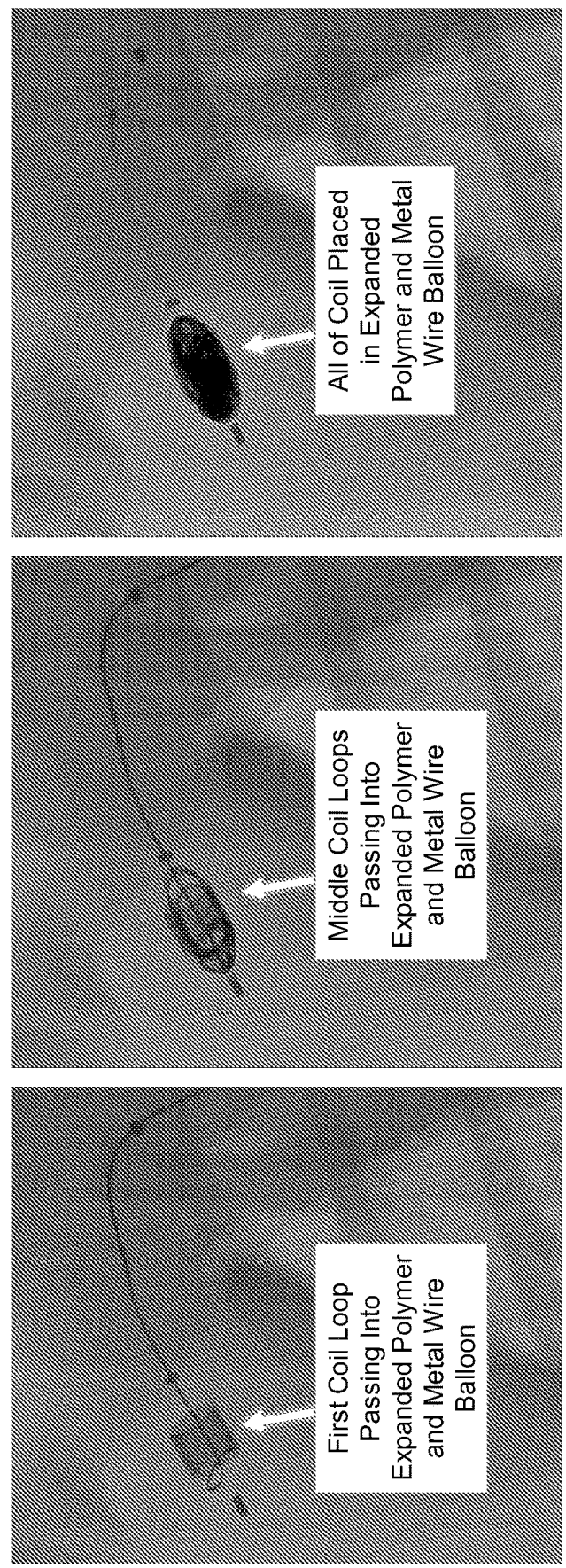
Figure 127B:
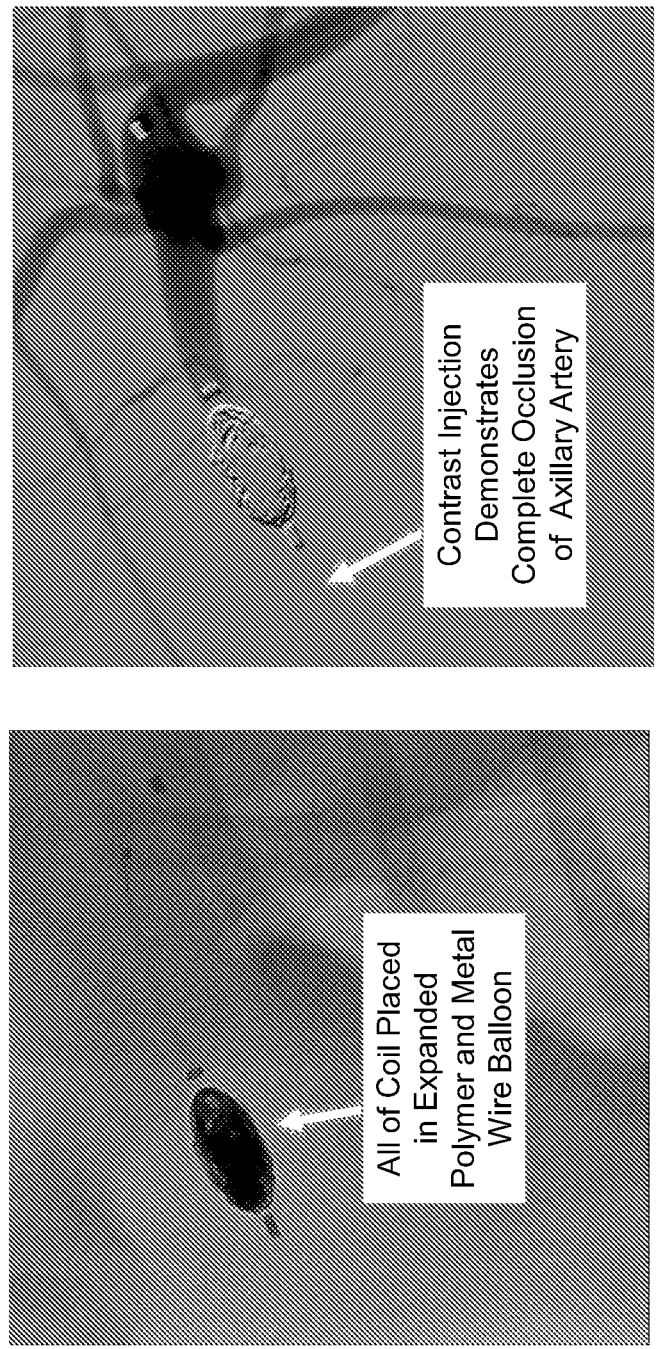
Figure 127C:
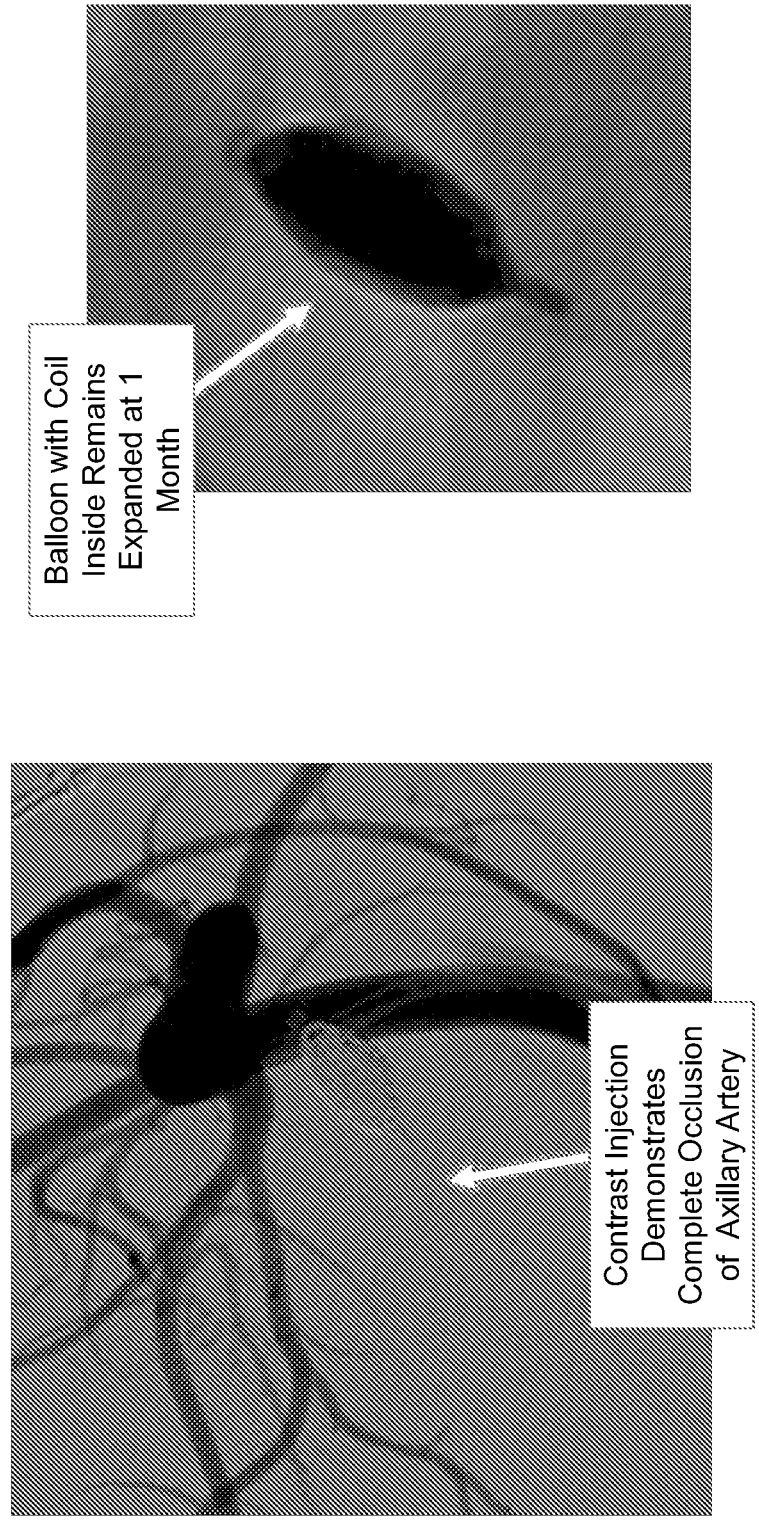
Figure 128A:
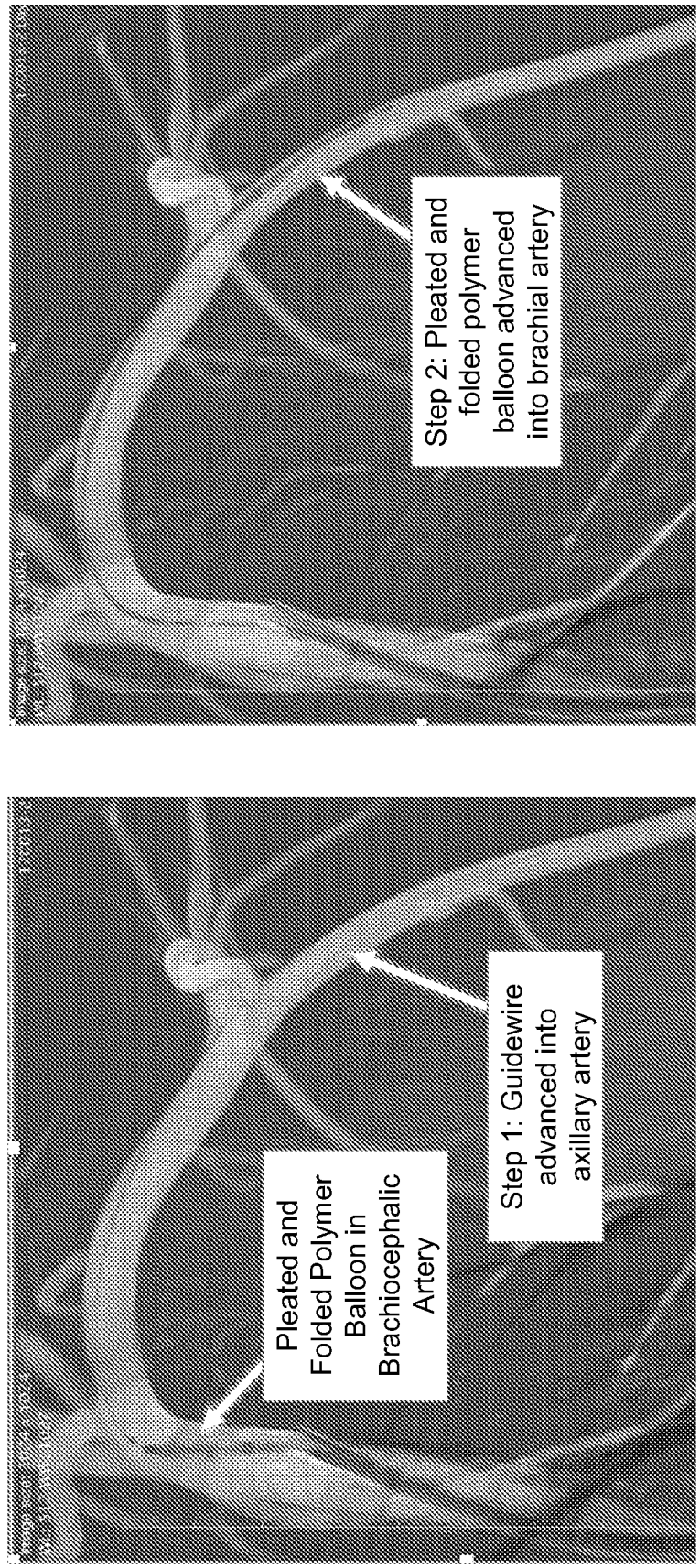
Figure 128B:
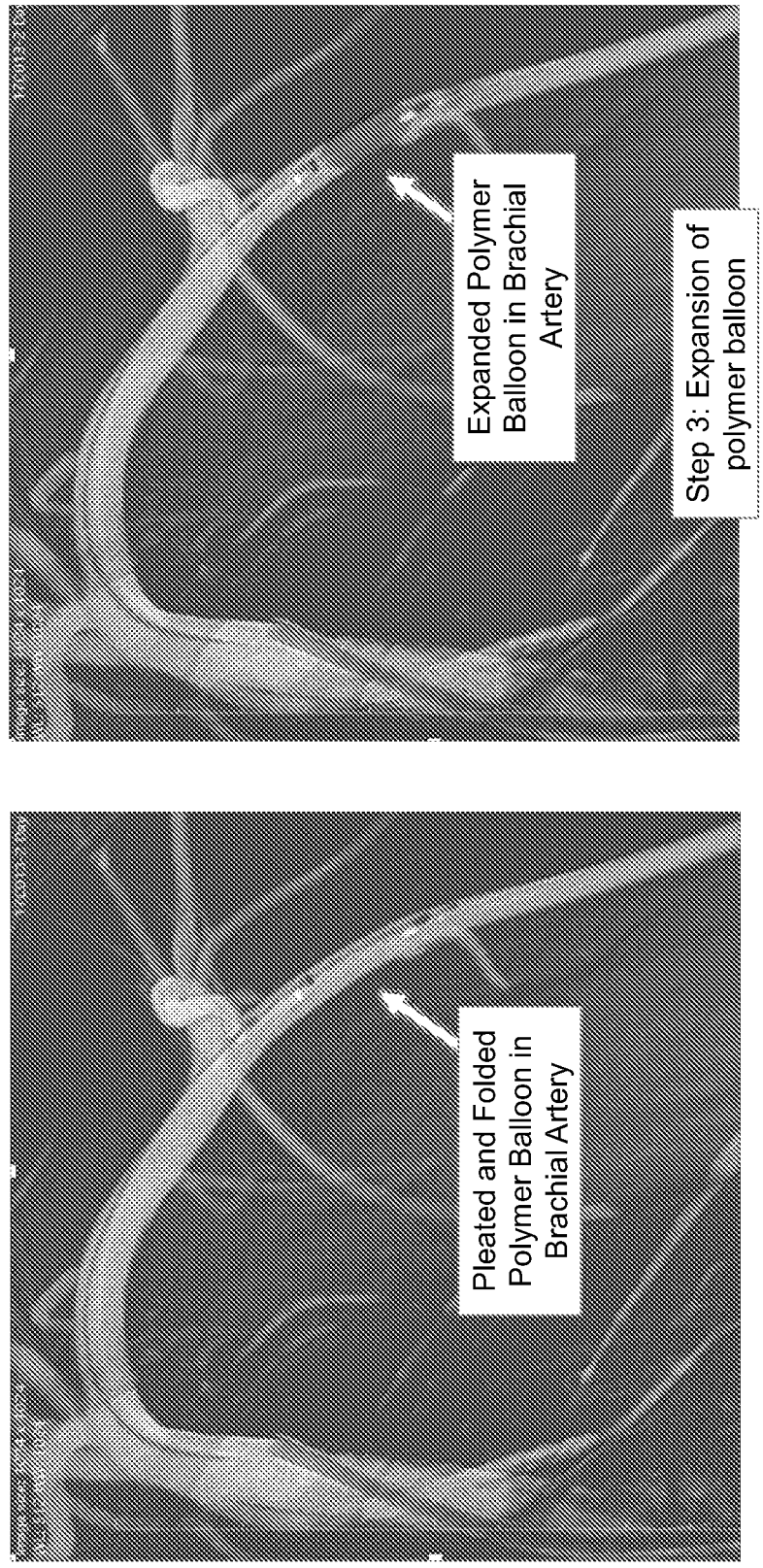
Figure 128C:
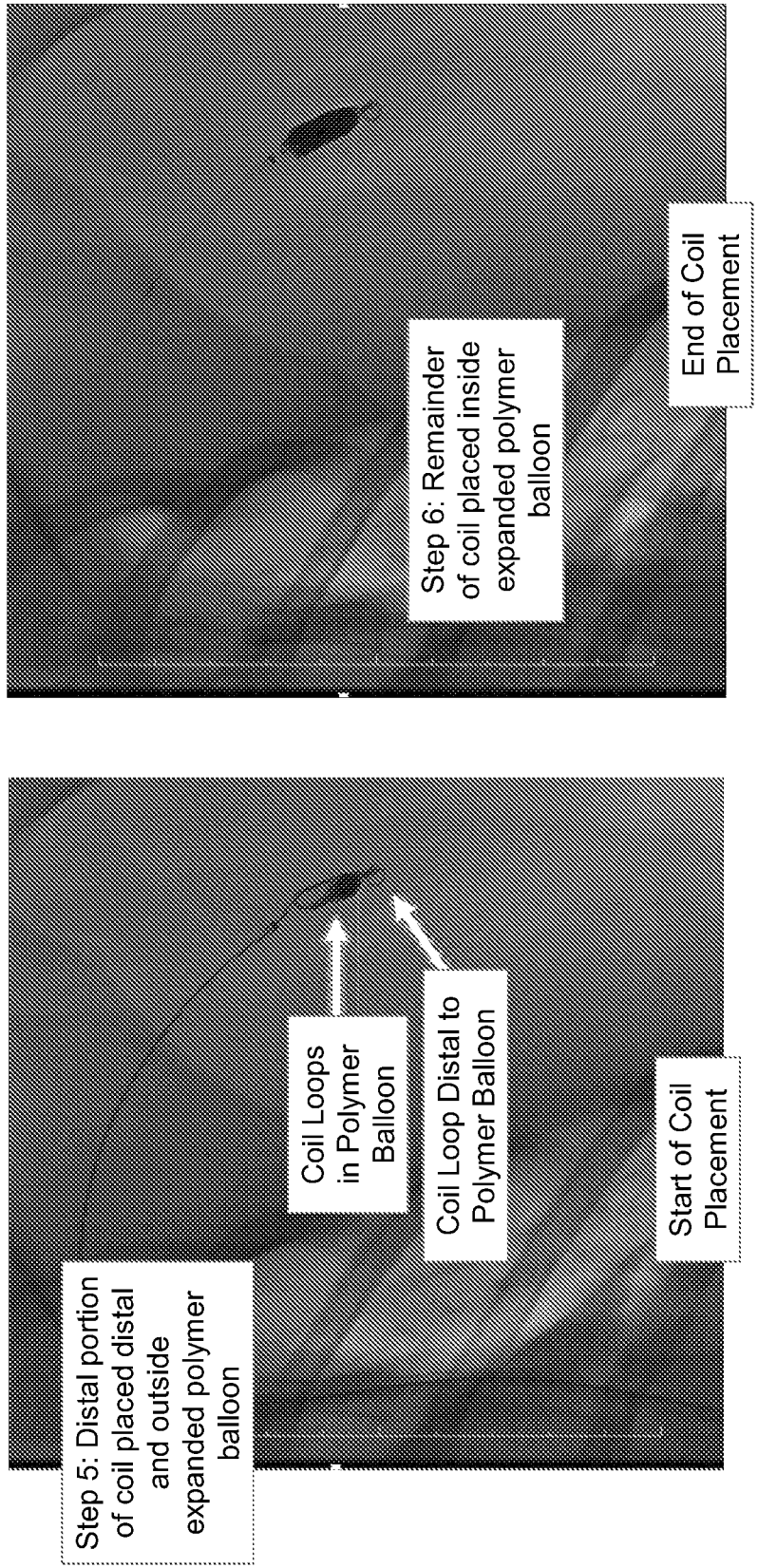
Figure 128D:

FIGS. 127A-C include images related to the placement of a coil in expanded polymer and metal wire balloon according to one embodiment.

FIGS. 128A-D include images related to the treatment of canine brachial artery with polymer only balloon and one coil according to one embodiment.

Figure 129:
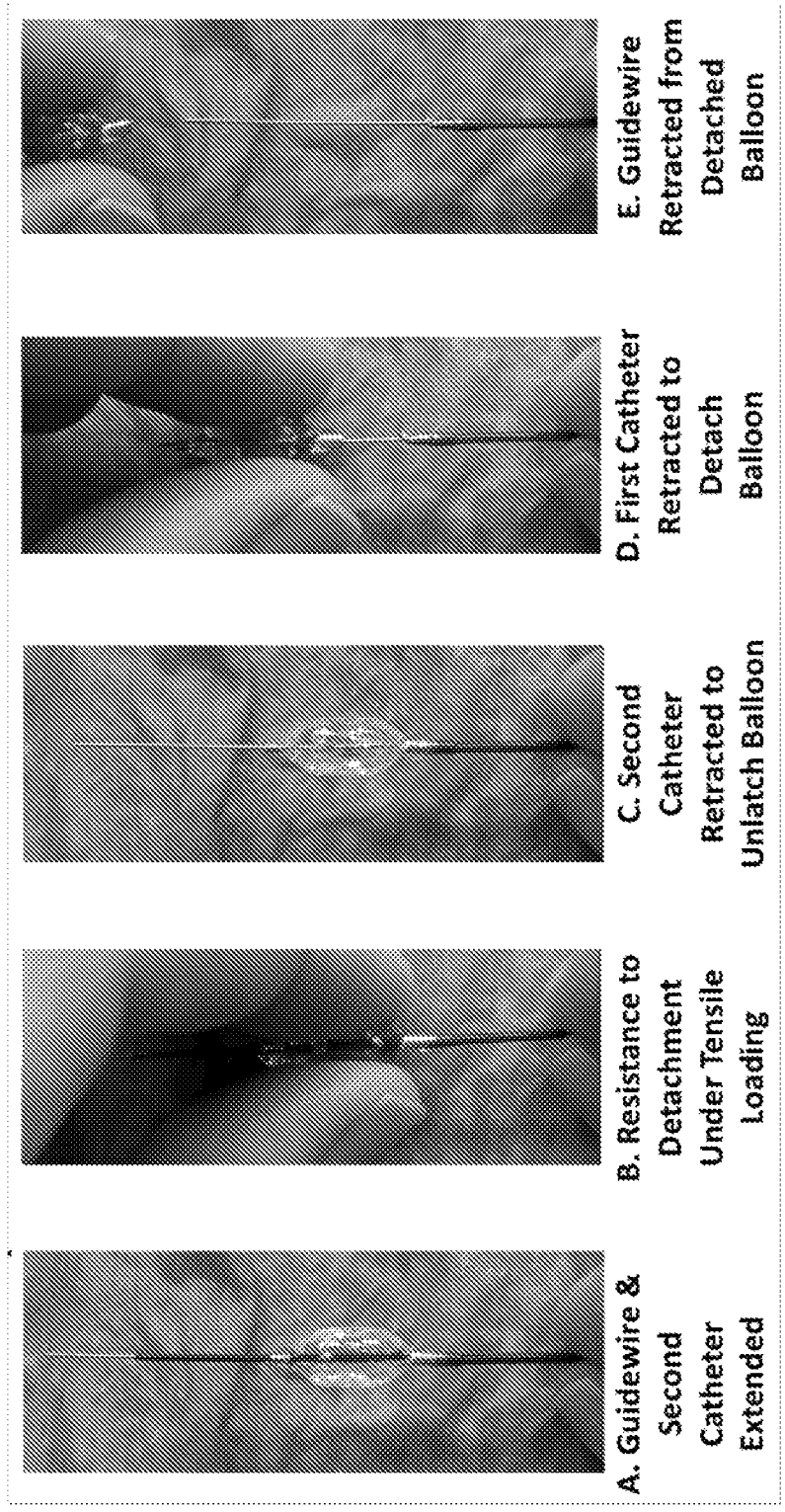

FIG. 129 includes images related to a mechanical latch detachment mechanism according to one embodiment.

DETAILED DESCRIPTION

Figure 1A:
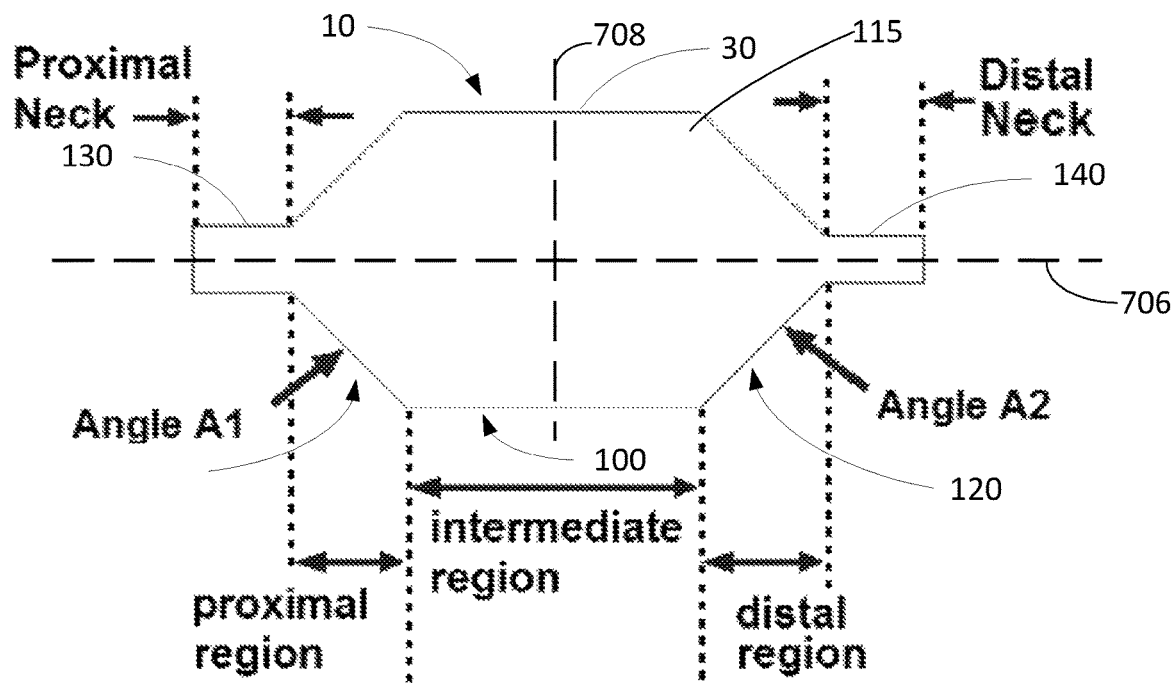
FIGS. 1A-B are planar views of one embodiment of a balloon having both proximal and distal necks with its overall geometric dimensions defined.
Figure 1B:
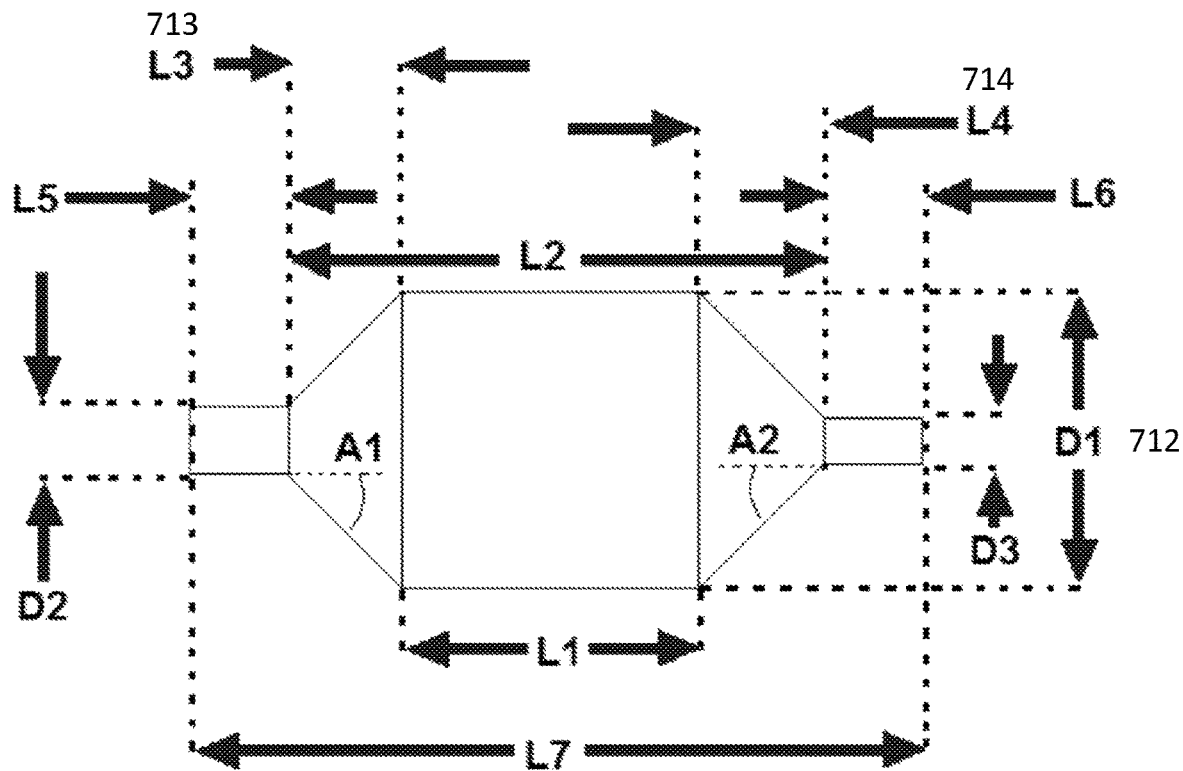
Figure 3A:
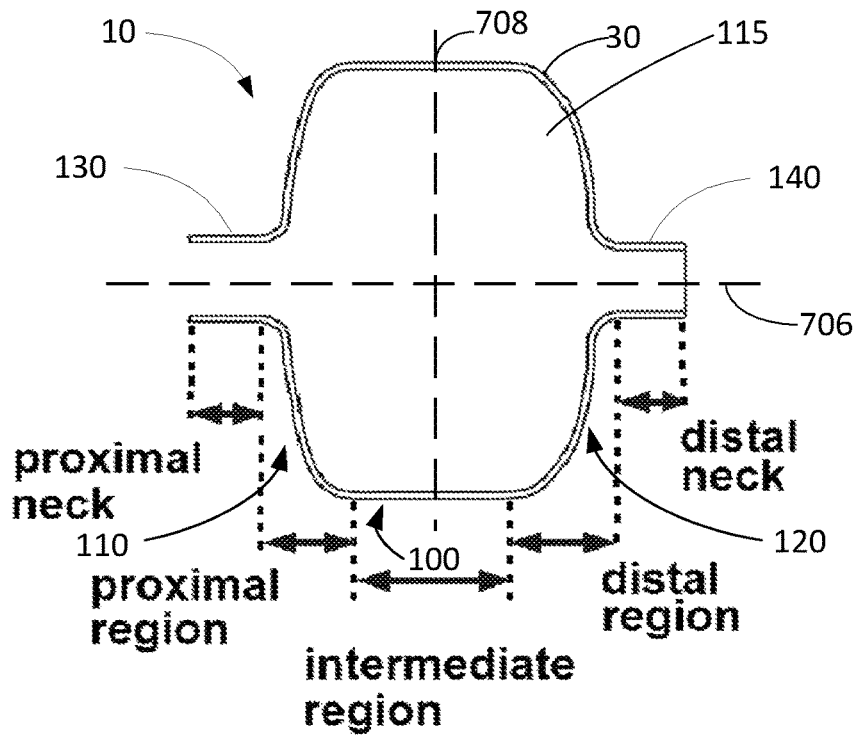
FIGS. 3A-B are planar views of another embodiment of a balloon having both proximal and distal necks with its overall geometric dimensions defined.

The present disclosure generally relates to medical devices 1 which can be used alone or in combination to treat human patients. When describing these medical devices, the proximal end generally refers to the end that remains outside of the patient and in the reach of the physician. The distal end generally refers to the end that is pushed or advanced into the patient. For individual components of medical devices described herein, this same proximal and distal orientation is generally maintained as shown in FIGS. 1A and 3A. In reference to the detachable balloon 10 portion of medical devices described herein, a first axis 706 extends along the centerline of the device between the proximal region 110 and the distal region 120 of the detachable balloon 10, and a second axis 708 extends perpendicular to the first axis 706.

The present disclosure relates to medical devices 1 that comprise a detachable balloon 10 and a catheter or catheter assembly 5, wherein the detachable balloon 10 is configured for expansion with fluid and detachment from the catheter or catheter assembly 5 in vivo. After separation of an expanded detachable balloon 10 from a catheter or catheter assembly 5, the detachable balloon 10 is configured to maintain an expanded configuration. Herein, these devices are also called "detachable balloon catheters" or "first medical devices" 1. The term balloon as used herein refers to a hollow structure with a nonporous wall 30 comprising a light or thin material that can be inflated or expanded, including with the injection of a fluid into a central void 115, as shown in FIGS. 1A and 3A. As used herein, a balloon may also be called a "hollow expandable structure" or "expandable hollow structure." Various shapes and sizes of detachable balloons 10 are described. Detachable balloons 10 with one or more layers, including polymer layers 99 and metal layers 90 are described, as shown in FIGS. 7, 8A-J, and 9A-L, along with various surface treatments and textures, as shown FIGS. 10A-D. Balloons with various retention structures 731, as shown in FIGS. 79A-B and 98B, and surface textures and that reduce the risk of detachable balloon 10 migration in vivo are described. Various catheters and catheter assemblies 5 for in vivo use are described, including catheters 5 configured for detachable balloon 10 inflation, catheters 5 configured to accept a guidewire 40, catheters 5 configured for delivery of expandable or elongated bodies 720, catheters 5 configured for injection of radiographic contrast, and catheters 5 configured to constrain retention structures 731 prior to placement as shown in FIGS. 13A-D, 14A-C, 15A-C, and 16A-D.

Various means of attaching detachable balloons 10 to catheters and catheter assemblies 5 are described, including a mating or coupling of parts, as shown in FIGS. 17A-C, 18A-D, 26A-H, and 28A-G; a friction fit 202 made using an elastomeric or resilient tubular structure 204 as shown in FIGS. 33A-B, 34A-B, 35A-B, and 42A-C; a friction fit 202 made using an elastomeric or resilient valve 192, as shown in FIGS. 44A-B, 46A-E, 49A-D, and 50; glues and adhesives; and other bonding methods. Various means of detaching balloons 10 from catheters and catheter assemblies 5 are described, including a decoupling of mated parts, as shown in FIGS. 19A-G, 20A-E, and 21A-E; a pulling of a catheter or catheter assembly 5 away from an expanded detachable balloon 10 by overcoming a friction fit 202, as shown in FIGS. 30A-D, 31A-D, 32A-D, 36A-F, and 37A-E; dissolution of a portion of a structure joining a detachable balloon 10 to a catheter or catheter assembly 5 by electrolysis, as shown in FIGS. 53A-C, 54A-C, 57A-D, 58A-E, and 59A-E; and melting a portion of a structure joining a detachable balloon 10 to a catheter or catheter assembly 5 by heating, as shown in FIGS. 64A-D, 67A-D, 70A-D, 73A-F, and 74A-E.

Various configurations of detachable balloons 10 and detachable balloon catheters 1 are described, along with the associated methods of manufacturing them. In one example, the detachable balloon 10 portion of a detachable balloon catheter 1 is configured in a compressed, collapsed, or pleated and folded form and configured for permanent implantation in a human patient. As shown in FIGS. 1A, 3A, and 5A-B, the detachable balloon 10 comprises a distal region 120, a proximal region 110 generally opposite the distal region 120, and an intermediate region 100 transitioning between the proximal and distal regions 110 & 120. A first axis 706 extends along the centerline of the device between the proximal region 110 and the distal region 120. A second axis 708 extends perpendicular to the first axis 706. A wall 30 extends generally continuously from the proximal region 110, through the intermediate region 100, to the distal region 120. The wall 30 has an exterior surface and an interior surface, the interior surface defining a central void 115 or interior volume. As shown in FIGS. 30A-D, The detachable balloon 10 has an opening in the wall 30 at the proximal region 110 that allows for the passage of fluid from a first catheter 173 into the central void 115 or interior volume of the balloon 10 and also allows for passage of a portion of a second catheter 174 into the central void 115 or interior volume of the balloon 10. As shown in FIGS. 37A-E and 44A, the detachable balloon 10 also has an opening in the wall 30 of the distal region 120 that allows for the passage of a portion of the second catheter 174 out of the central void 115 or interior volume of the balloon 10.

Various configurations of catheter assemblies are described. As shown in FIGS. 13B-C and 14A-C, the first catheter 173, along with the second catheter 174, defines a first lumen 162 of annular cross-section to allow passage of fluid from a proximal end of the first catheter 173 to a distal end of the first catheter 173, and into the central void 115 or interior volume of the detachable balloon 10. The first catheter 173 further comprises a proximal end that is coupled to a first proximal hub 179, and a distal portion that is operably coupled or joined to the opening in the wall 30 of the proximal region 110 of the balloon 10. The second catheter 174 defines a second lumen 163 of circular cross-section configured to accept at least one of a guidewire 40, an elongated or expandable body 720, or a solidifying fluid. The second catheter 174 comprises a proximal end that is coupled to a second proximal hub 178; a proximal portion that passes through the proximal hub 179 of the first catheter 173; a distal portion that passes through the proximal opening, central void 115, and distal opening of the balloon 10; and a distal end that is open. The passage of fluid through the first catheter 173 into the central void 115 or interior volume of the balloon 10 can result in expansion of the balloon 10.

The present disclosure also relates to medical devices that comprise an elongated or expandable body 720. Herein, these devices are also called "second medical devices" 700. As used herein, an elongated body 720 is a long, thin, flexible structure that can be pushed or carried through the lumen of a catheter and implanted in a patient. Elongated bodies 720 can occupy space and form complex shapes, but do not expand during or after placement. As used herein, an expandable body 720 is a long, thin, flexible structure that can be pushed or carried through the lumen of a catheter in a constrained, collapsed, compressed, or pleated and folded form and implanted in a patient, wherein at least portions of the expandable body 720 can expand in size during or after placement. Elongated and expandable bodies 720 that can be used with a first medical device comprising a detachable balloon catheter 1 are described.

In some embodiments, a solidifying fluid comprises an adhesive that can be injected as a fluid through the first lumen 162 or the second lumen 163 and into the central void 115 of the balloon 10 or injected into a biological space 904 adjacent to an expanded balloon 10, wherein the solidifying fluid become a solid or semi-solid after passing through the first lumen 162 or the second lumen 163. Some examples of solidifying fluids include adhesives such as cyanoacrylates or UV curable adhesives, ethylene vinyl alcohol, Onyx® copolymer, or particle that increases in viscosity at physiologic salinity. In some embodiments, the solid solidifying agent acts to help the expanded, detached balloon 10 of the detachable balloon catheter 1 resist collapse, compression, or compaction. In some embodiments, the solid solidifying agent acts to help maintain the position of the expanded, detached balloon 10 of the detachable balloon catheter 1. In some embodiments, the solid solidifying agent acts to reduce the flow of blood or other biological fluids or suspensions through treated arteries 317, veins 318, or other biological conduits 900. In some embodiments, the solid solidifying agent acts to occupy a biological space 904.

Continuing the deployment sequence following expansion of the detachable balloon 10, the second catheter 174 can be moved forward or backward while the balloon 10 remains fixed in position, as shown in FIGS. 14A-B and 19D-E. After removal of the guidewire 40, all or a portion of one or more second medical devices 700 comprising an elongated or expandable body 720 or solidifying fluid can be placed through the lumen 163 of the second catheter 174 into a biological space 904 adjacent to the balloon 10, as shown in FIGS. 16A-D and 41A-D. The second catheter 174 can then be pulled back until the distal tip of the second catheter 174 is located in the central void 115 of the balloon, while the first catheter 173 and the balloon 10 remain fixed in position. All or a portion of one or more second medical devices 700 comprising an elongated or expandable body 720, solidifying fluid, or other balloon support material can be passed through the second lumen 163 of the second catheter 174 and placed into the central void 115 of the balloon 10, as shown in FIG. 41E.

As shown in FIGS. 41 F-H, following placement of all or a portion of one or more second medical devices 700 comprising an elongated or expandable body 720, solidifying fluid, or other balloon support material, the first catheter 173 can be separated from the expanded balloon 10 and the first and second catheters 173 & 174 can be removed from the patient while the balloon and all or a portion of one or more elongated or expandable bodies 720, solidifying fluids or other balloon support materials remain in the patient.

In some embodiments, a compressed or collapsed balloon expandable body 10 comprises a balloon 10 wherein portions of the wall 30 of the balloon 10 are squeezed or pressed together or into a much smaller space than the expanded balloon 10, as shown in FIGS. 83A-D and 84A-B. In some embodiments, a constrained balloon 10 is forced and held into a smaller space or smaller diameter than the expanded balloon 10. In some embodiments, the balloon portion 10 of the detachable balloon catheter 1 is pleated, folded, or compressed into a shape that occupies a smaller space or smaller diameter than the expanded balloon 10, which is called a "deliverable configuration". In some embodiments, the expandable body portion 720 of the second medical device 700 is constrained or compressed into a shape that occupies a smaller space or smaller diameter than the expanded expandable body 720, which is also called a deliverable configuration.

Methods of treatment of saccular aneurysms 320, arteries 317, veins 318, left atrial appendages 800, paravalvular leaks 808, other blood containing structures, biological conduits 900, or other biological spaces 904 using a detachable balloon catheter 1 with or without adjunctively using one or more elongated or expandable bodies 720 are also described.

Figure 94B:
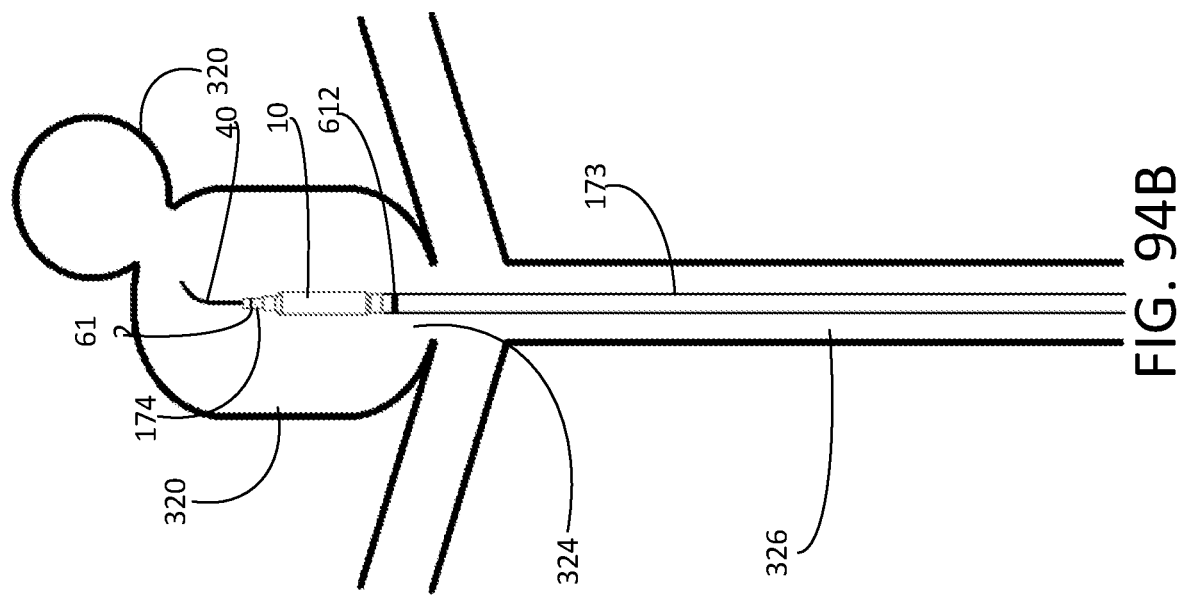
Figure 94A:
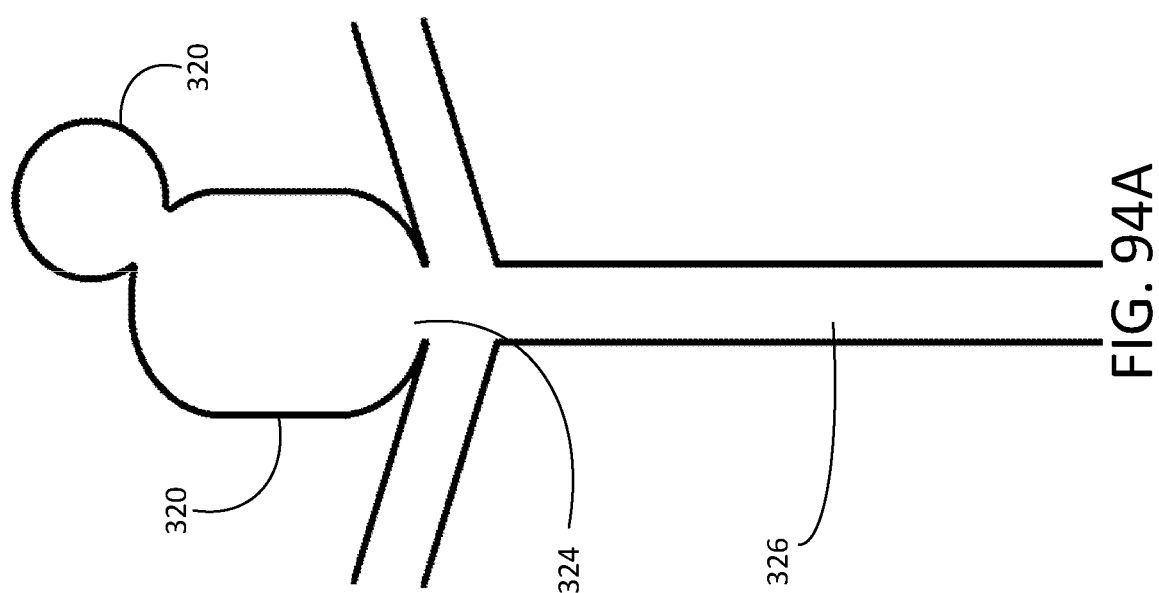
Figure 94F:
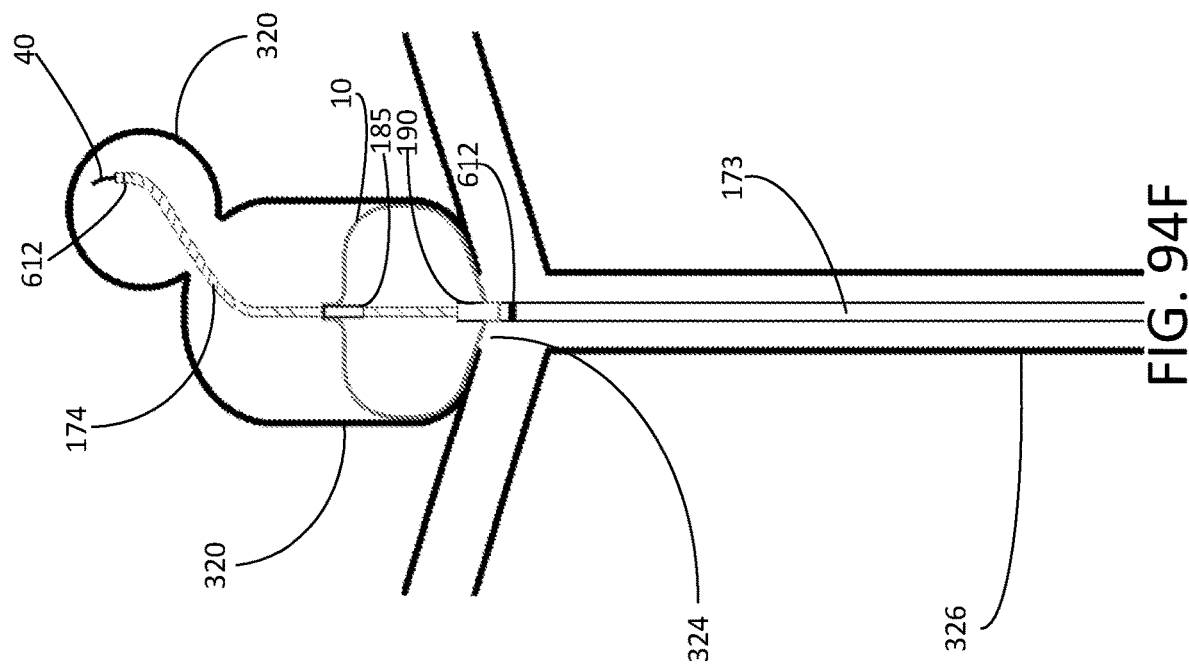
Figure 94E:
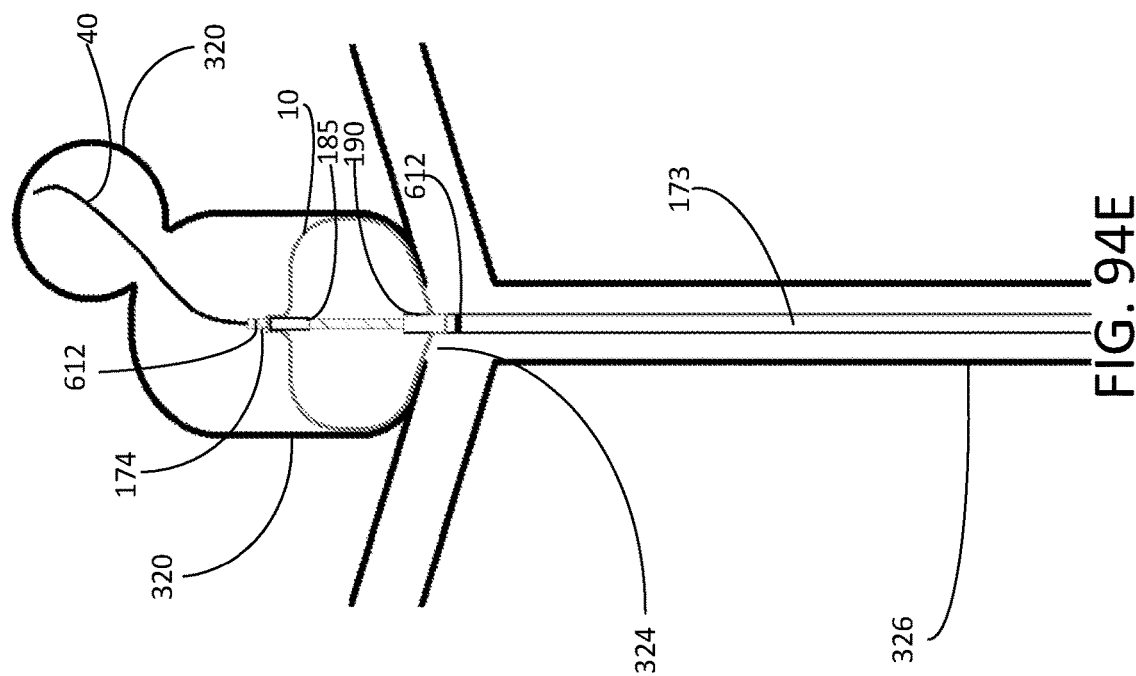
Figure 94H:
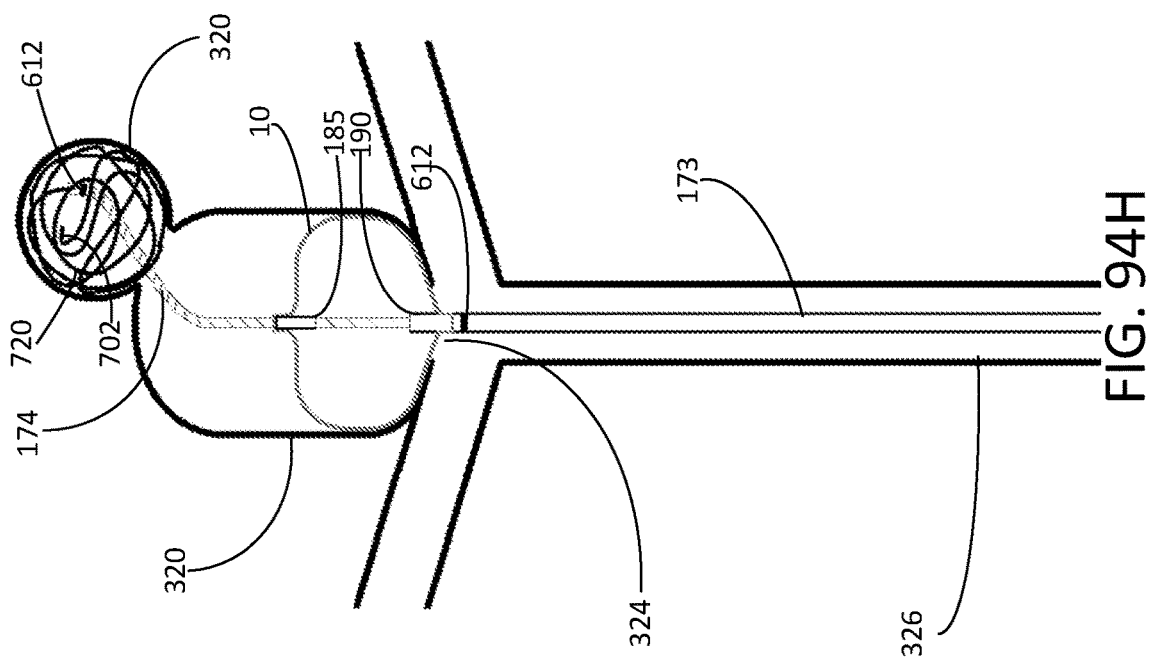
Figure 94G:
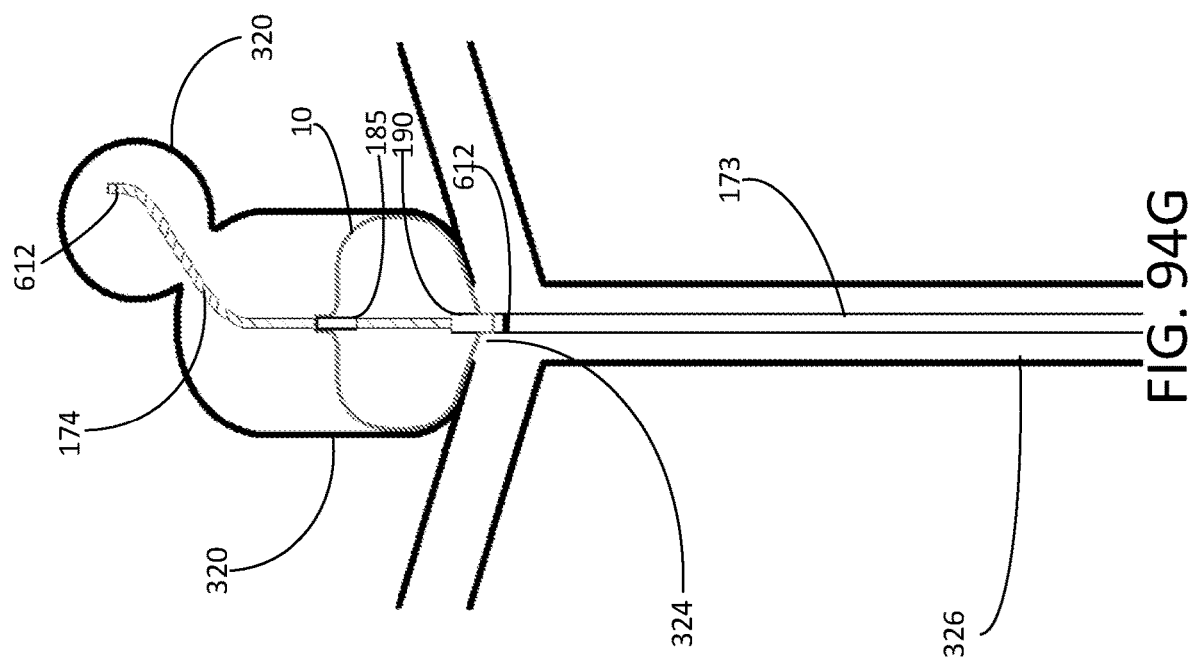
Figure 94K:
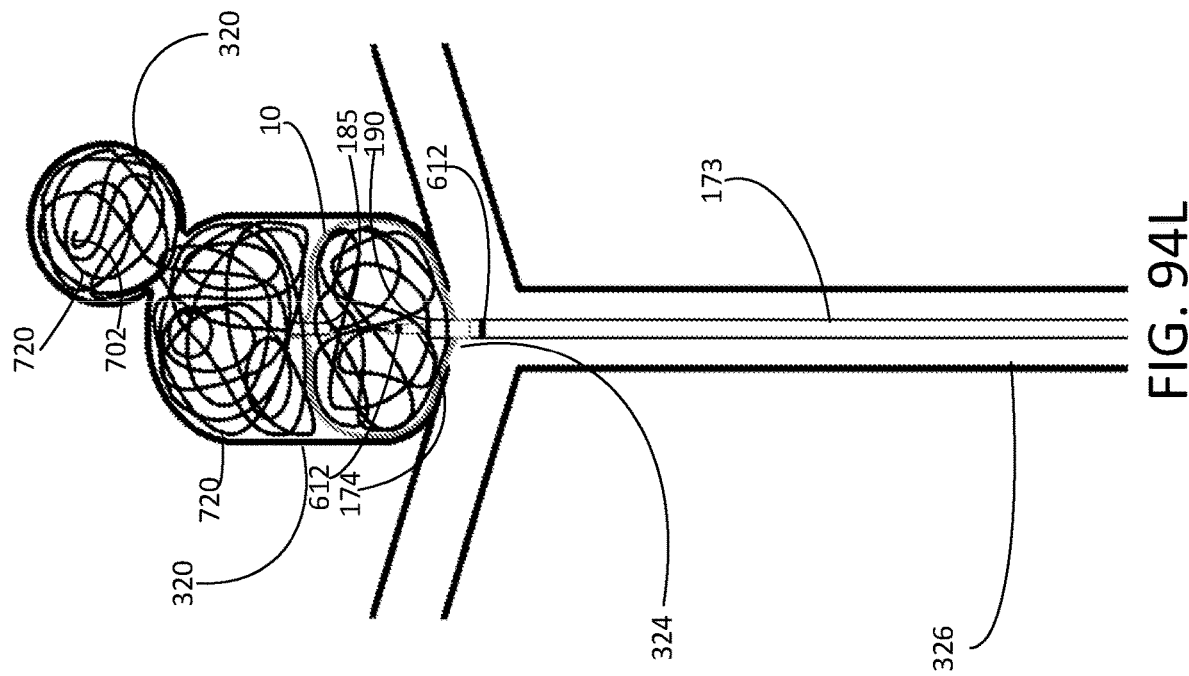
Figure 94L:
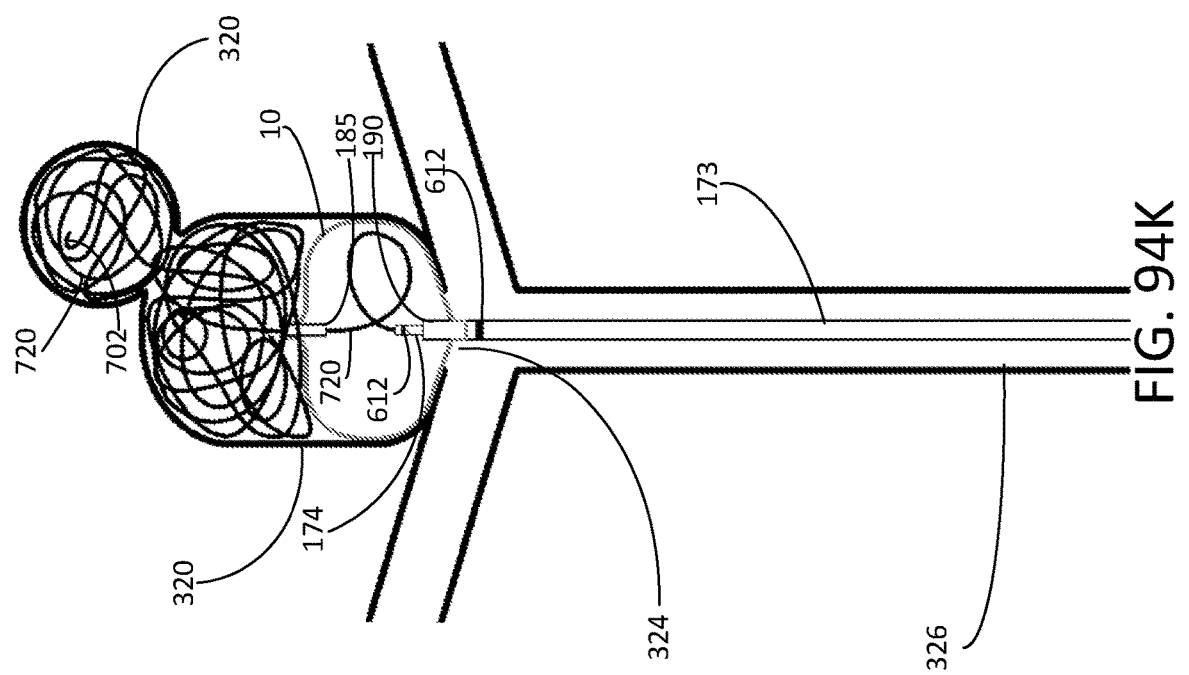
Figure 94M:
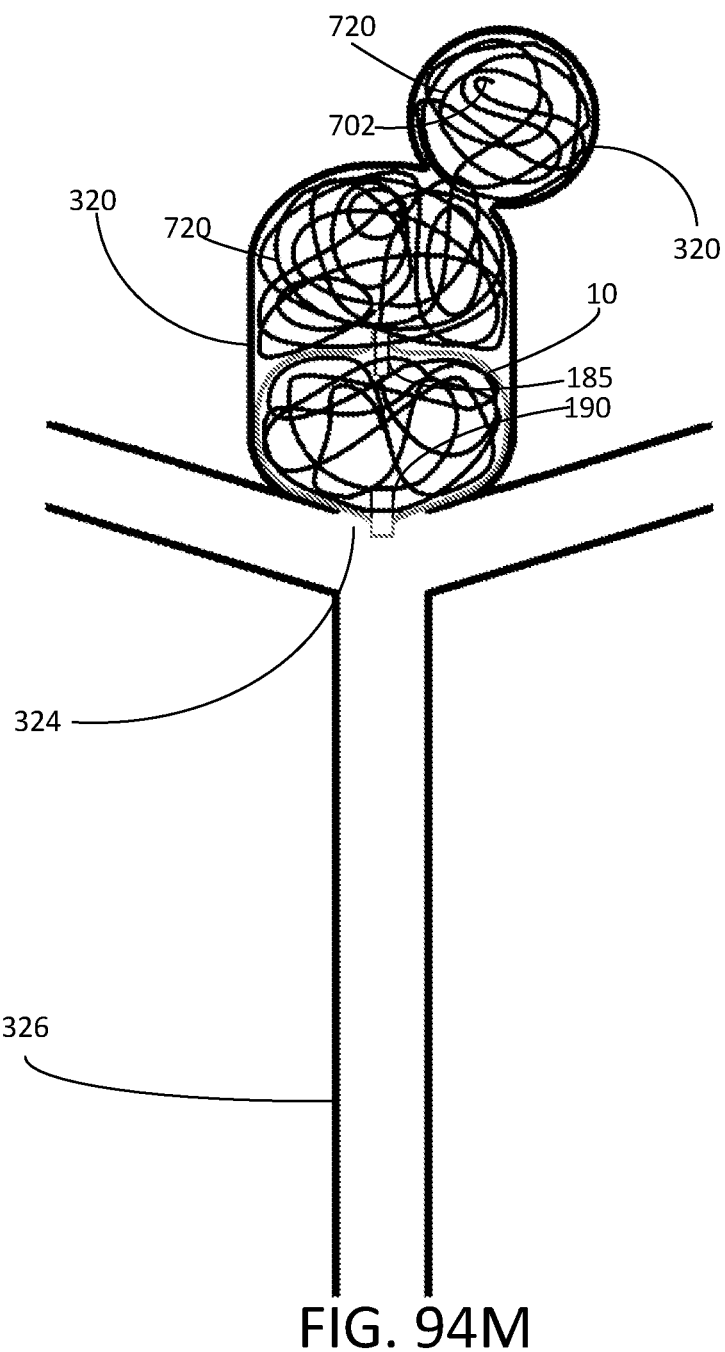

The general approach to treating a saccular aneurysm 320 using a detachable balloon catheter 1 and one or more elongated or expandable bodies 720 according to one embodiment is shown sequentially in FIGS. 93A-M. Based on standard imaging methods, a detachable balloon catheter 1 with an appropriated sized balloon 10 is selected. A guidewire 40 is placed into the aneurysm 320 using standard percutaneous delivery methods. The detachable balloon catheter 1 is advanced over the guidewire 40 and the balloon 10 is positioned and expanded within the aneurysm lumen 322. The detachable balloon catheter 1 is then pulled back to ensure close contact between the balloon 10 and the aneurysm neck 324. The guidewire 40 is then retracted. First and second elongated bodies 720 & 721 are advanced through the second catheter 174 and one or more coils or first elongated bodies are placed within the aneurysm lumen 322 distal to the expanded balloon 10. The second catheter 174 is then retracted. The first catheter 173 is then separated from proximal neck 130 of the balloon 10 using a detachment system, which may have various embodiments. Finally, the first catheter 173 is retracted. The expanded and detached balloon 10 and first elongated bodies 720 remain within the patient to provide complete and durable occlusion of the aneurysm 320. The above general approach may be applied to the treatment of saccular aneurysms 320 of different and more complex geometries, for example terminal bifurcation aneurysm 320 whose sac has a smaller daughter aneurysm, as shown in FIGS. 94A-M. By including the additional steps of retracting the distal tip of second catheter 174 into the void 115 of the balloon 10 and placing one or more coils or first elongated bodies 720 into the void 115 of the balloon 10, as shown in FIGS. 94K-L, the balloon 10 can be reinforced against external compression. The final configurations of treated aneurysms 320 containing an expanded and detached balloon 10, first elongated bodies 720 within the aneurysm lumen 322, and first elongated bodies 720 within void 115 of the balloon 10 are shown in FIGS. 94M, 95B, and 96B.

Balloons

A variety of detachable balloon shapes and sizes are described, as shown in FIGS. 1-6. In some embodiments the detachable balloons 10 can be characterized to include a proximal region 110, an intermediate region 100, and a distal region 120, wherein the proximal and distal regions 110 & 120 are generally opposite each other. For each body, the proximal region 110, the intermediate region 100, and the distal region 120 form the unitary construction of the detachable balloon 10. For this characterization, the proximal region 110, the intermediate region 100, and the distal region 120 together form a "main body" of the detachable balloon, 10, which excludes the proximal and distal necks 130 & 140. In some embodiments without an intermediate region 100 the detachable balloons can be characterized to include a proximal region 110 and a distal region, 120, wherein the proximal and distal regions 110 & 120 are generally opposite each other. For each of these bodies, the proximal region 110 and the distal region 120 form the unitary construction of the detachable balloon. 10. For this characterization, the proximal and distal regions 110 & 120 together form a "main body" of the detachable balloon 10, which excludes the proximal and distal necks 130 & 140. The detachable balloons 10 may further be defined by a first axis 706 and a second axis 708 transverse to the first axis. 706. In one aspect, the first axis 706 extends between the proximal neck 130 and distal neck 140.

In some embodiments, detachable balloons, 10, when expanded, are configured to assume a general shape comprising one lobe, excluding proximal and distal necks 130 & 140 or neck assemblies 135 & 142, if any. Some detachable balloons, when expanded, may be configured to assume a generally spherical, spheroid, oblate spheroid, prolate spheroid, ellipsoid, oblate ellipsoid, or a prolate ellipsoid shape, excluding proximal and distal necks 130 & 140 or neck assemblies 135 & 142, if any. Some detachable balloons, when expanded, comprise a proximal region 110, a distal region, 120, and an intermediate region 100. Other detachable balloons, when expanded, comprise a proximal region 110, a distal region 120, without an intermediate region 100. In some embodiments, the intermediate region 100 of a detachable balloon 10, when expanded, is generally cylindrical. In some embodiments, the detachable balloon 10, when expanded, is configured to assume a generally oblong or cylindrical shape, excluding proximal and distal necks 130 & 140 and neck assemblies 135 & 142, if any.

In some embodiments, the detachable balloons 10 may be defined and described by the proximal region 110 and the distal region 120, where each region is generally a hemispheroid. The hemispheroid formed by each region and is further defined by a semi-major axis and semi-minor axis that may be parallel with the first axis 706 or the second axis 708, depending upon the lengths of each axis. In various embodiments, the hemispheroid of the proximal region 110 has a semi-major axis and semi-minor axis different from that of the distal region 120. In other embodiments, the hemispheroid of the proximal region 110 has a semi-major axis and semi-minor axis the same as that in the distal region 120. Similarly, for each distal and proximal region 110 and, respectively, the semi-major and semi-minor axis may differ from one another or be identical, so the corresponding region may have a generally shape of an oblate hemispheroid, a prolate hemispheroid, or a hemisphere. The detachable balloons 10 may also be fabricated in many other configurations that have generally spheroid or ellipsoid shapes.

Figure 5A:
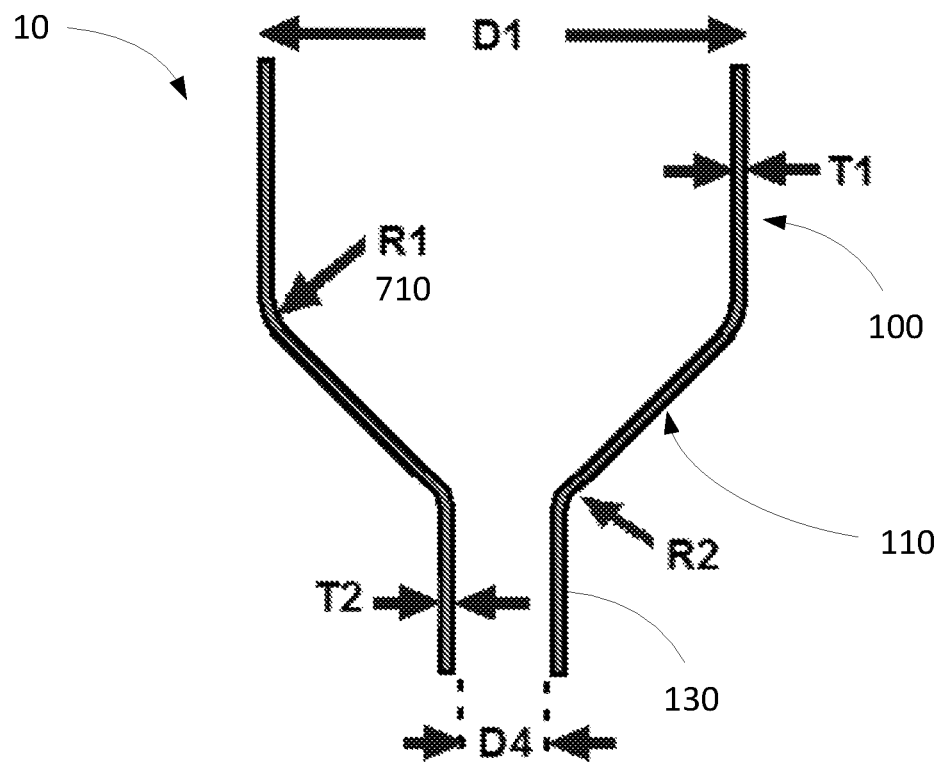
FIG. 5A is a cross-sectional view of the proximal portion of the embodiment of a balloon shown in FIG. 1 with its geometric dimensions defined.
Figure 5B:
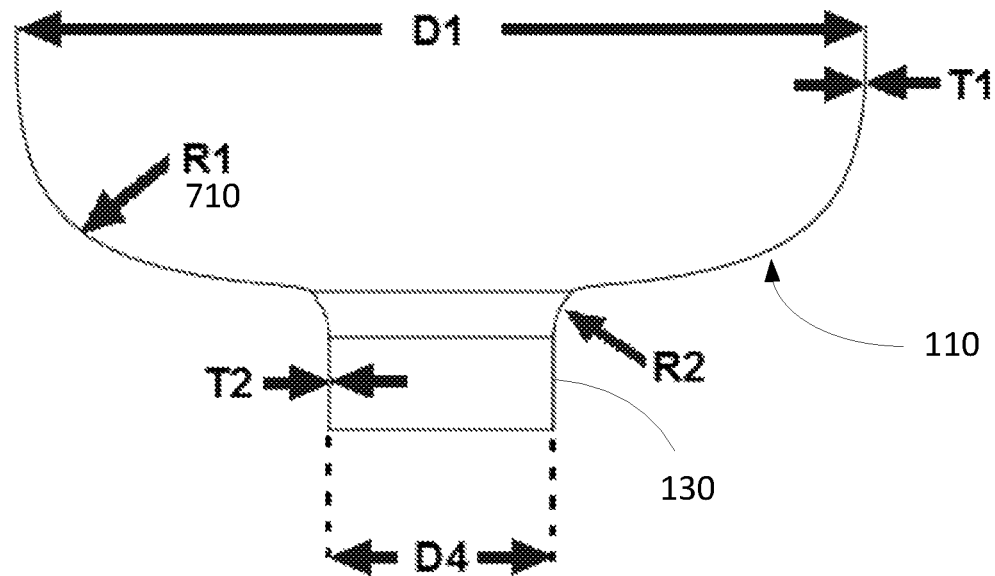
FIG. 5B is a cross-sectional view of the proximal portion of the embodiment of a balloon shown in FIG. 3 with its geometric dimensions defined.

The proximal region 110 of some detachable balloons 10, when expanded, are generally rounded in shape, excluding proximal and distal necks 130 & 140 or neck assemblies 135 & 142, if any, as shown in FIGS. 3A and 5B. The proximal region 110 of some detachable balloons 10, when expanded, are configured to form a hemisphere, an oblate hemispheroid, a prolate hemispheroid, hemiellipsoid, oblate hemiellipsoid, prolate hemiellipsoid, or a paraboloid shape, excluding proximal and distal necks 130 & 140 or neck assemblies 135 & 142, if any. The proximal region 110 of some detachable balloons 10, when expanded are generally conical in shape, excluding proximal and distal necks 130 & 140 or neck assemblies 135 & 142, if any, as shown in FIGS. 1A and 5A.

The distal region 120 of some detachable balloons 10, when expanded are generally rounded in shape, excluding proximal and distal necks 130 & 140 or neck assemblies 135 & 142, if any, as shown in FIG. 3A. The distal region 120 of some detachable balloons 10, when expanded, are configured to form a hemisphere, an oblate hemispheroid, a prolate hemispheroid, hemiellipsoid, oblate hemiellipsoid, prolate hemiellipsoid, or a paraboloid shape, excluding proximal and distal necks 130 & 140 or neck assemblies 135 & 142, if any. The distal region 120 of some detachable balloons 10, when expanded are generally conical in shape, excluding proximal and distal necks 130 & 140 or neck assemblies 135 & 142, if any. The distal region 120 of some detachable balloons 10, when expanded are generally conical in shape, excluding proximal and distal necks 130 & 140 or neck assemblies 135 & 142, if any, as shown in FIG. 1A.

For some embodiments, the detachable balloon 10, when expanded, is configured to assume a shape wherein the intermediate region 100 is generally cylindrical, and the proximal and distal regions 110 & 120 generally form a hemisphere, an oblate hemispheroid, a prolate hemispheroid, or a paraboloid, excluding proximal and distal necks 130 & 135 and neck assemblies 140 & 142, if any. For other embodiments, the detachable balloon 10, when expanded, is configured to assume a shape wherein the intermediate region is generally cylindrical, and the proximal region and distal regions 110 & 120 are generally conical, excluding proximal and distal necks 130 & 140 and neck assemblies 135 & 142, if any.

For some detachable balloons, as shown in FIGS. 1A-B, 2A-D, 5A, and 6A-B, wherein the intermediate region 100 is generally cylindrical and the proximal or distal regions 110 & 120 are conical, the proximal or distal regions 110 & 120 have a cone angle (defined as the angle between the wall 30 of the balloon and the first axis 706 of the balloon) of 20-75 degrees. In one embodiment, the shape of the intermediate region of the detachable balloons may be defined by the rotation, about the first axis 706, of a variable radius arc formed along the first axis 706, where the maximum radius for the variable arc is equal to either the maximum radius 711 of the distal region 720 or the maximum radius 710 of the proximal region 110, as measured along the second axis 708. For some embodiments, the expanded detachable balloon has a total length 709 along the first axis 706 that is less than or equal to the maximum diameter 712 of the expanded detachable balloon along the second axis 708.

As shown in FIGS. 1A-B, 2A-D, 3A-B, and 4A-C, some detachable balloons 10, when expanded, are configured to have a maximum diameter of 2-40 mm when measured parallel to the second axis 708. Some detachable balloons 10, when expanded, are configured to have a maximum length of 2-80 mm when measured parallel to the first axis 706, excluding proximal and distal necks 130 & 140 and neck assemblies 135 & 142, if any. Some detachable balloons comprising a proximal region 110, intermediate region 100, and distal region 120, when expanded, are configured to have a maximum length of the main body or intermediate region 100 of 2-40 mm when measured parallel to the first axis 706, excluding the lengths of proximal and distal necks 130 & 140 and neck assemblies 135 & 142, if any. Some detachable balloons 10, when expanded, have a largest diameter as measured parallel to the second axis 708 that is greater than the largest length as measured parallel to the first axis 706, excluding the lengths of proximal and distal necks 130 & 140 and neck assemblies 135 & 142, if any. Some detachable balloons 10, when expanded, have a largest diameter as measured parallel to the second axis 708 that is equal to the largest length as measured parallel to the first axis 706, excluding the lengths of proximal and distal necks 130 & 140 and neck assemblies 135 & 142, if any. Some detachable balloons 10, when expanded, have a largest length, as measured parallel to the first axis 706, that is greater than the largest diameter as measured parallel to the second axis 708, excluding the lengths of proximal and distal necks 130 & 140 and neck assemblies 135 & 142, if any. In some embodiments, the expanded detachable balloons 10 have a length from the proximal neck 130 to the distal neck 140 of approximately 4-30 mm, or larger, and a maximum diameter 712 of approximately 4-30 mm, or larger.

For some embodiments, the maximum radius lengths 710 & 711 for the proximal and distal regions 110 & 120 are equal, as shown in FIGS. 3A-B, 4A-C, 5B, and 6C-D, so the detachable balloons have a generally circular cross-section when viewed in cross-section along the first axis 706. For some other embodiments, the radius length at any equivalent location for the proximal and distal regions 110 & 120 may not be equal, so the expanded detachable balloons 10 may not have a generally circular cross-section when viewed in cross-section along the second axis 708.

In one aspect, various configurations of the detachable balloons 10 may be obtained by independently varying the maximum length (also called "height") along the first axis 706 of the proximal and distal regions 110 & 120, as shown in FIGS. 1A-B, 2A-D, 3A-B, and 4A-C. For example, the height 713 of the proximal region 110 may be smaller than the height 714 of the distal region 120. In other examples, the height 713 of the proximal region 110 may be equal to the height 714 of the distal region 120. In other examples, the height 713 for the proximal region 110 may be larger than the height 714 for the distal region 120. While both detachable balloons 10 and have the same maximum diameter 712, the difference in the heights 713 & 714 of the proximal and distal regions 110 & 120, respectively, of each detachable balloon 10 results in different overall shapes for the detachable balloon 10.

Figure 3B:
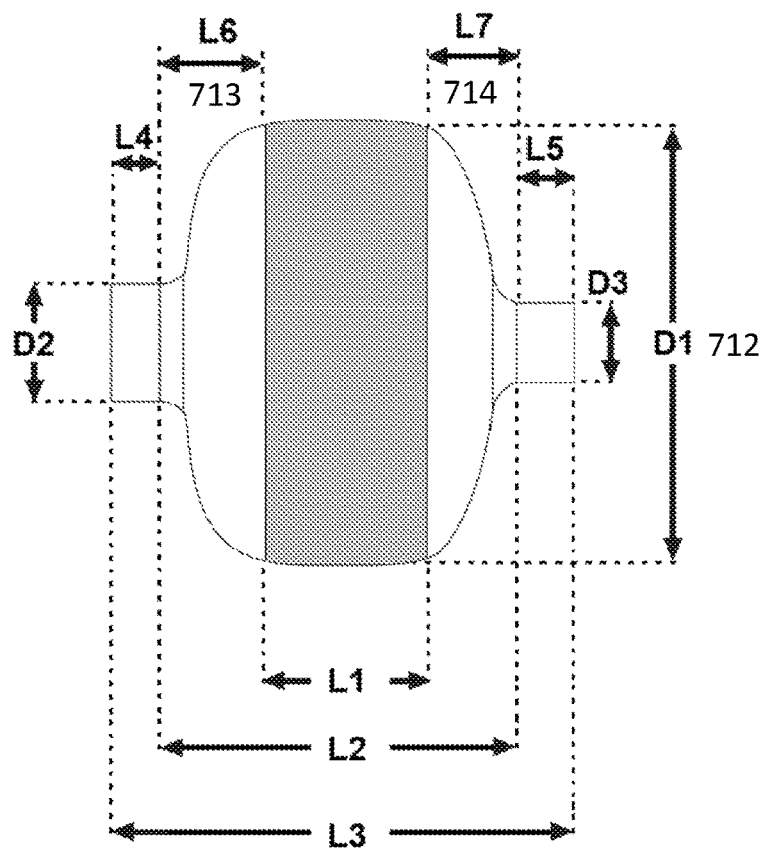

In other embodiments, the heights 713 & 714 of the proximal and distal regions 110 & 120, respectively, may be varied independently to produce a wide variety of configurations of the detachable balloons 10. In a first embodiment, the height 713 of the proximal region 110 may be approximately 2 mm, while the height 714 of the distal region 120 is approximately 4 mm. In a second embodiment, the height 713 of the proximal region 110 may be approximately 3 mm, while the height 714 of the distal region 120 is also approximately 3 mm. In a third embodiment, the height 713 of the proximal region 110 may be approximately 2 mm, while the height 714 of the distal region 120 is approximately 3.5 mm. In a fourth embodiment, the height 713 of the proximal region 110 may be approximately 3 mm, while the height 714 of the distal region 120 is approximately 4 mm. As shown in FIGS. 3A-B, the detachable balloons 10 may have several configurations that may be generally spheroid or generally spherical.

Figure 7:
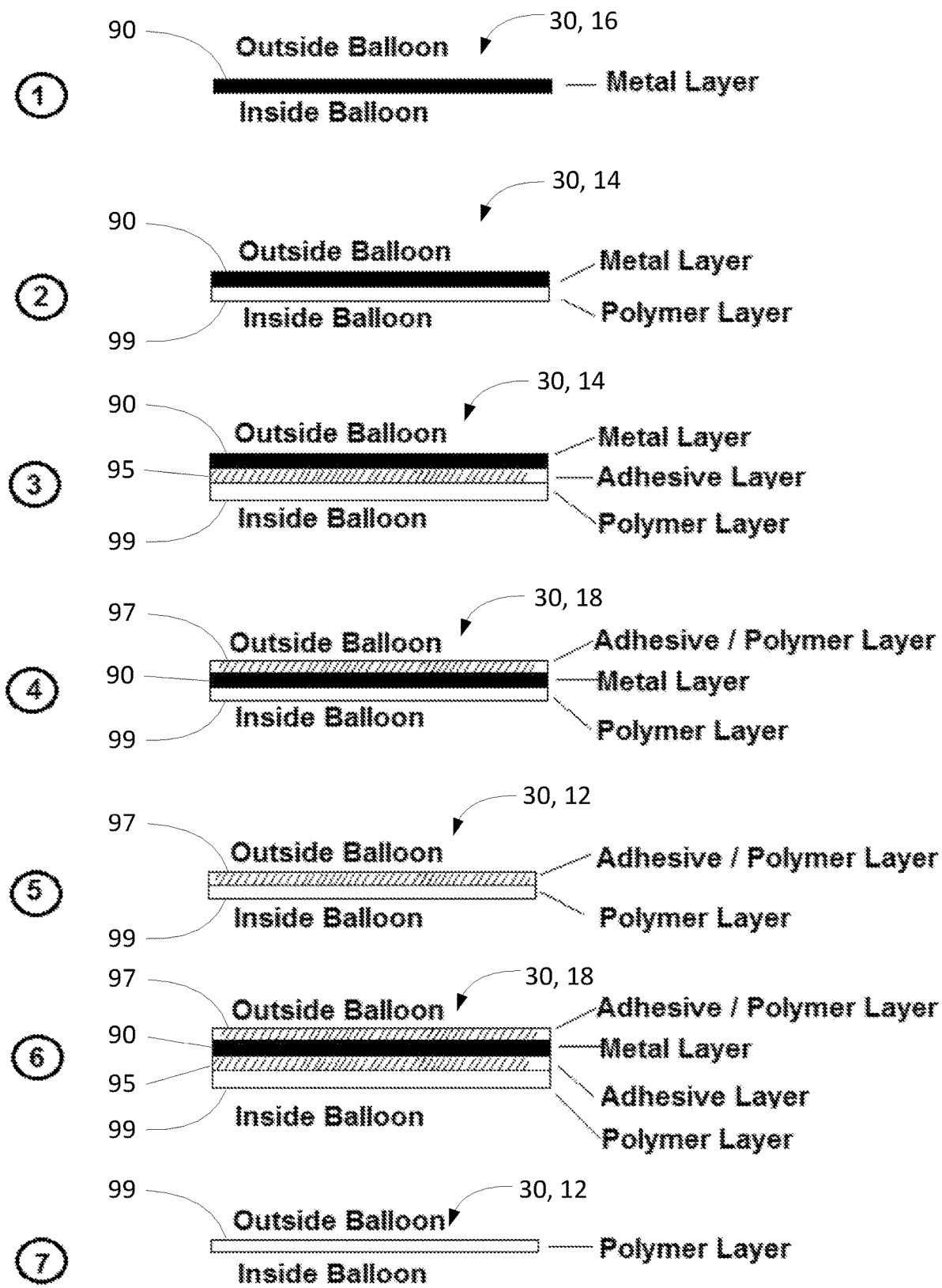
FIG. 7 provides cross-sectional views of a portion of the exterior wall of a metal, metalized, polymer, or hybrid balloon showing seven embodiments of layering.
Figure 8:
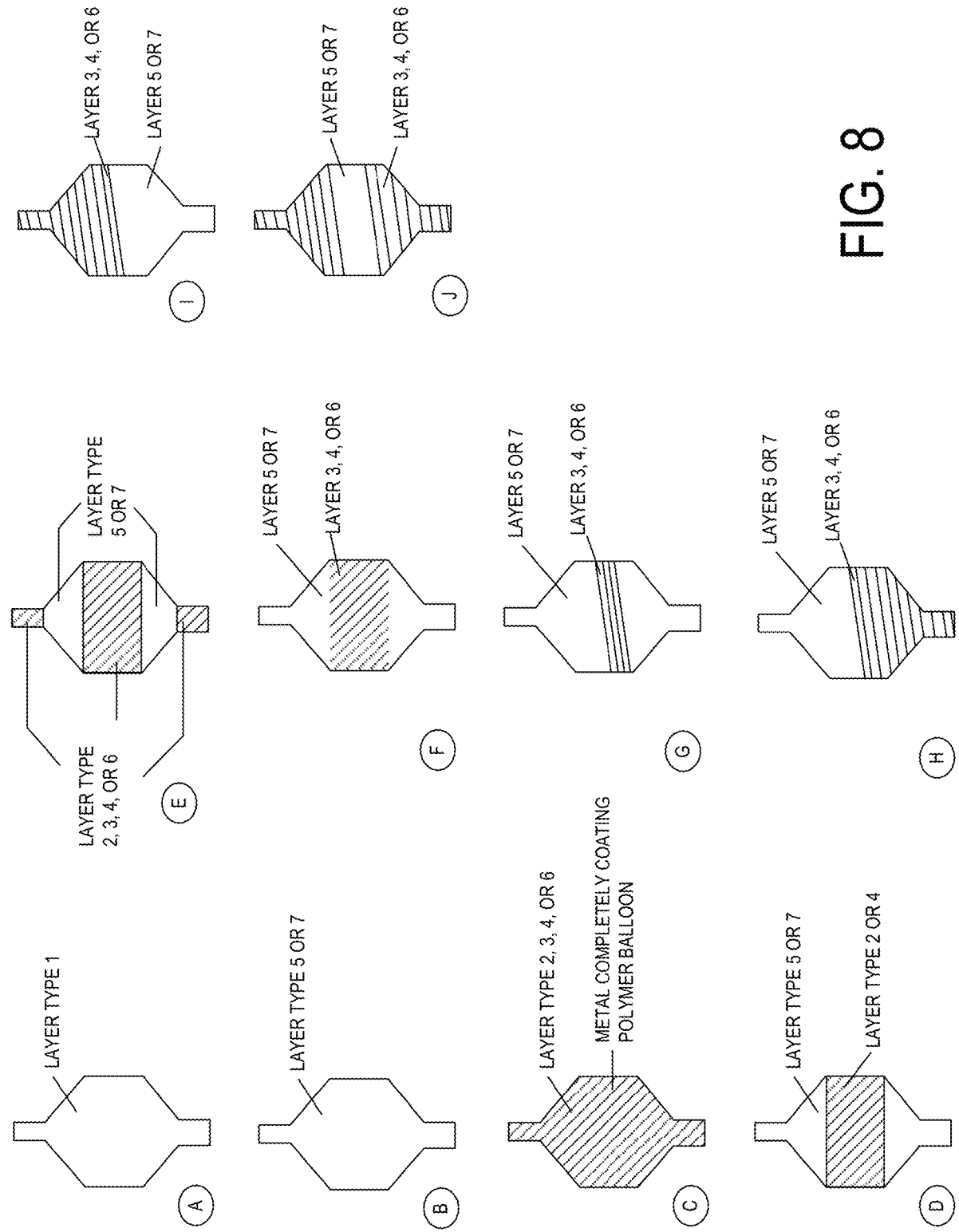
FIGS. 8A-J are planar views of embodiments of a balloon having the shape of the embodiment shown in FIG. 1 incorporating the various layer types defined in FIG. 7 in various regions of the balloon.
Figure 9:
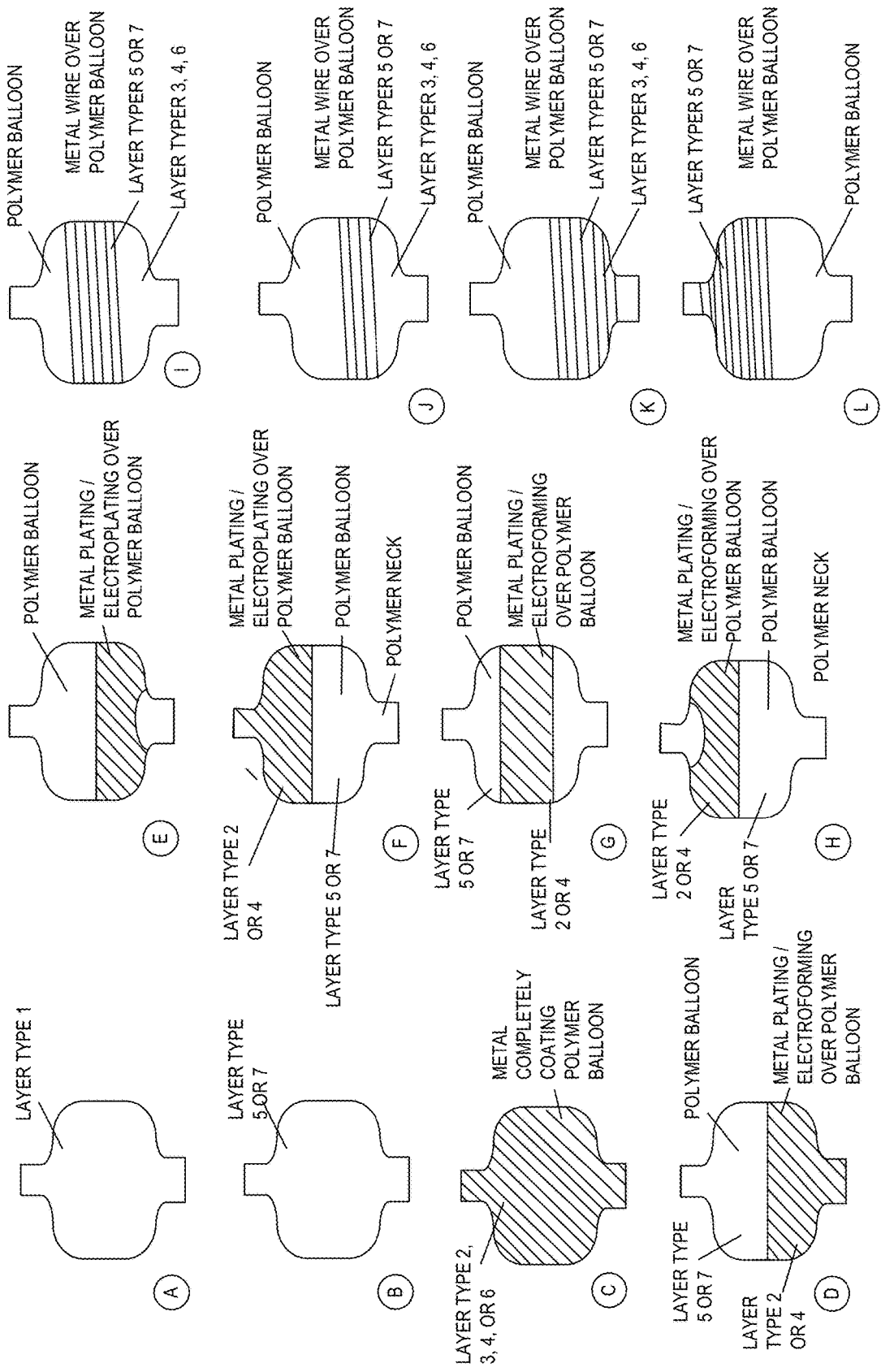
FIGS. 9A-L are planar views of embodiments of a balloon having the shape of the embodiment shown in FIG. 3 incorporating the various layer types defined in FIG. 7 in various regions of the balloon.

The walls 30 of the detachable balloons may comprise one or more layers, as shown in FIG. 7. The thickness of the walls 30 may range between 5-400 microns or between 0.0002-0.016 in, as shown in FIGS. 5A-B and 6A-D.

Figure 99A:
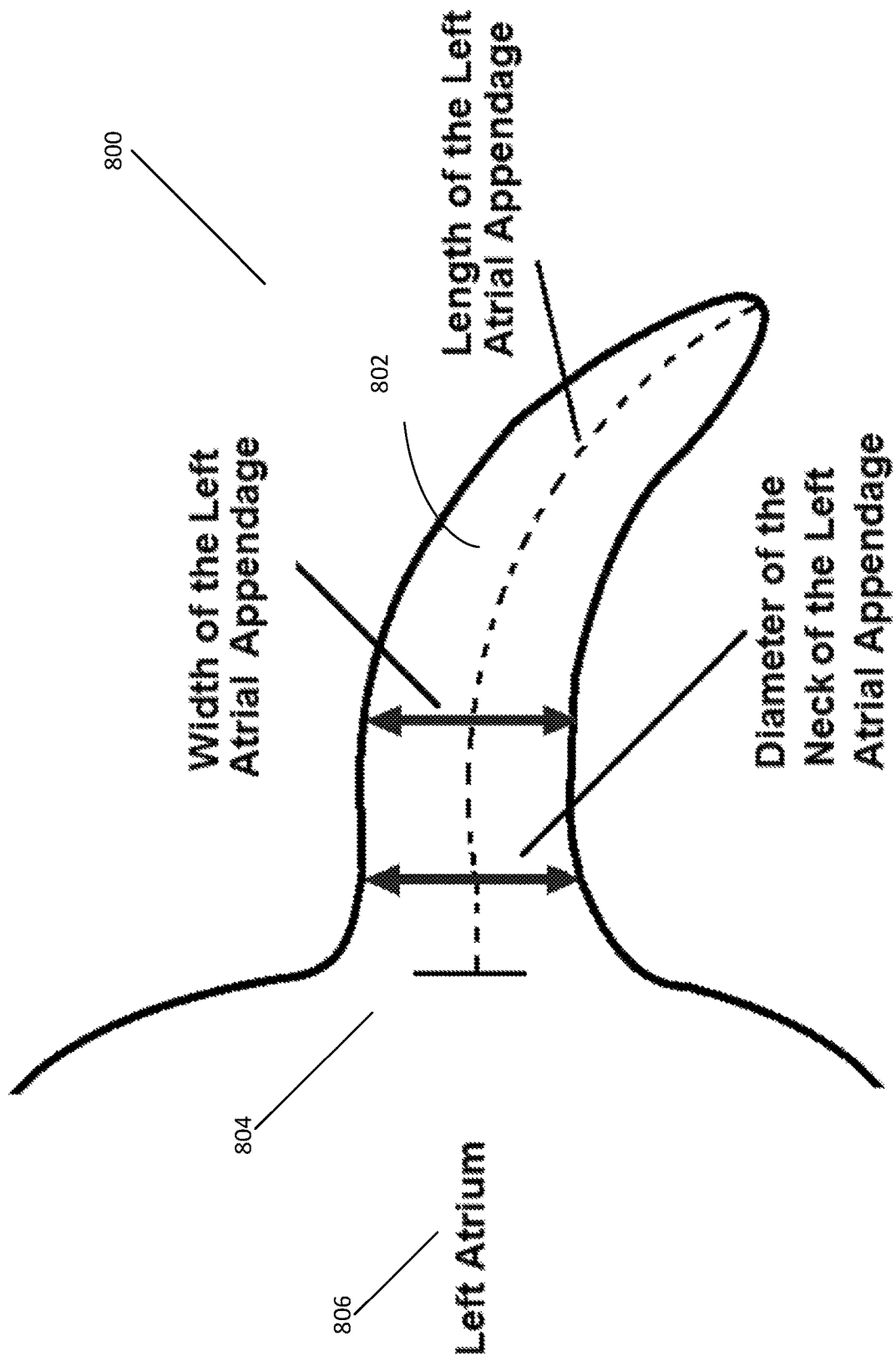
FIGS. 99A-B are cross-sectional views of a left atrial appendage, with its overall geometric dimensions defined, before and after treatment using a detachable balloon catheter with use of an expandable retention structure to secure the balloon and adjunctive placement of vascular coils within the expanded balloon according to one embodiment.
Figure 99B:
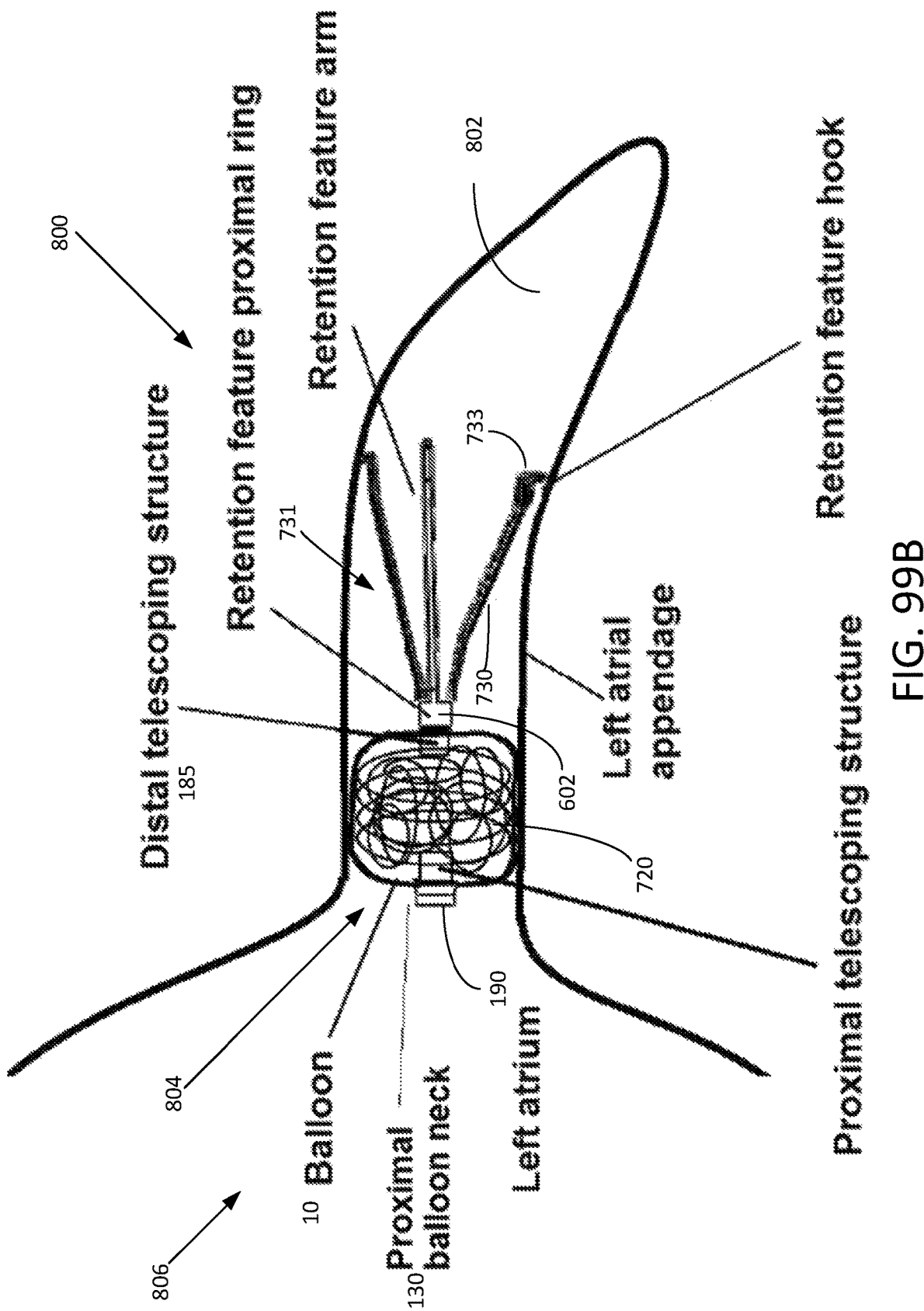
Figure 100A:
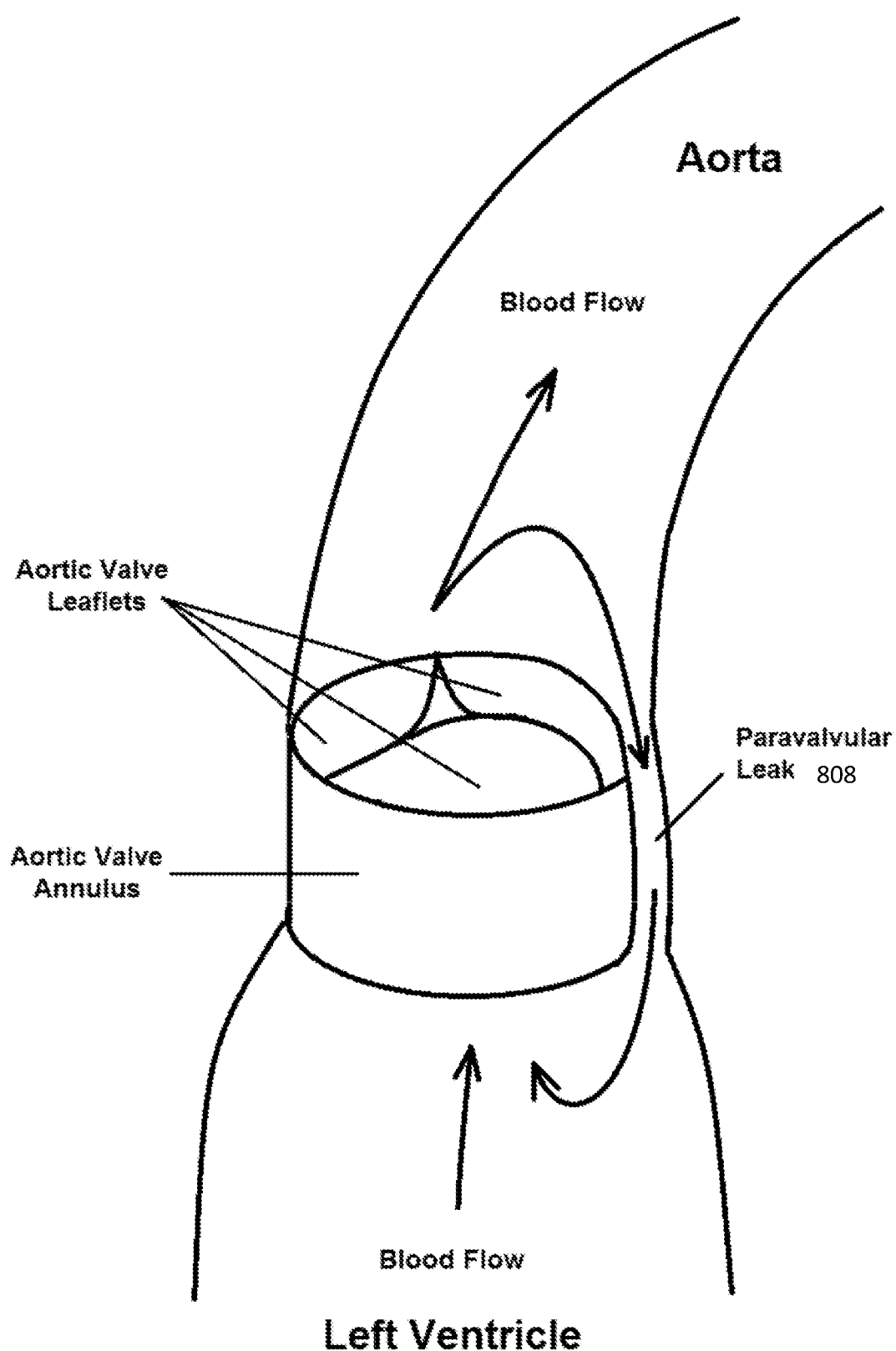
FIGS. 100A-B are partial cross-sectional views of an aortic valve with a paravalvular leak before and after treatment using a detachable balloon catheter with adjunctive placement of vascular coils within the expanded balloon according to one embodiment.
Figure 100B:
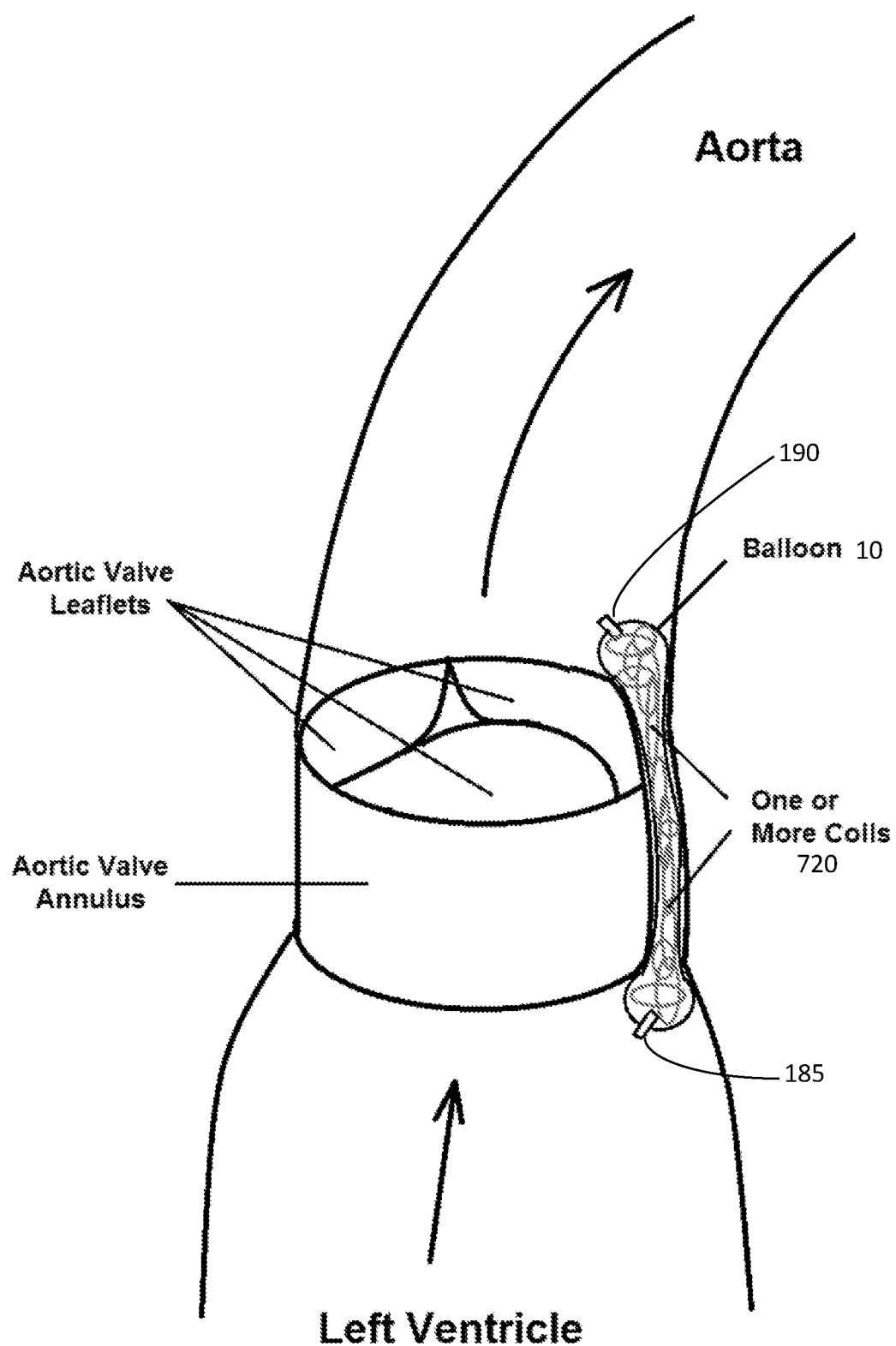
Figure 104:
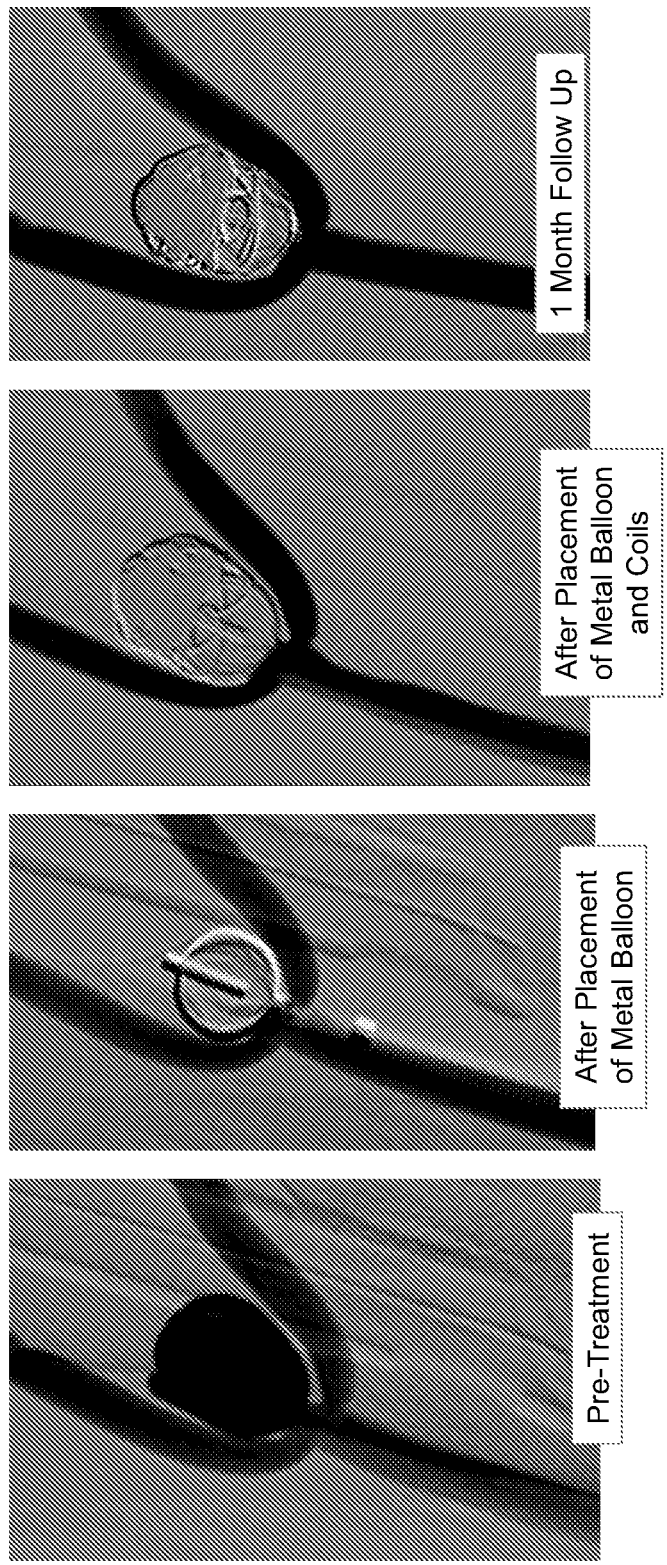
FIG. 104 includes images of the treatment of a canine terminal bifurcation aneurysm with a metal balloon and coils according to one embodiment.
Figure 105:
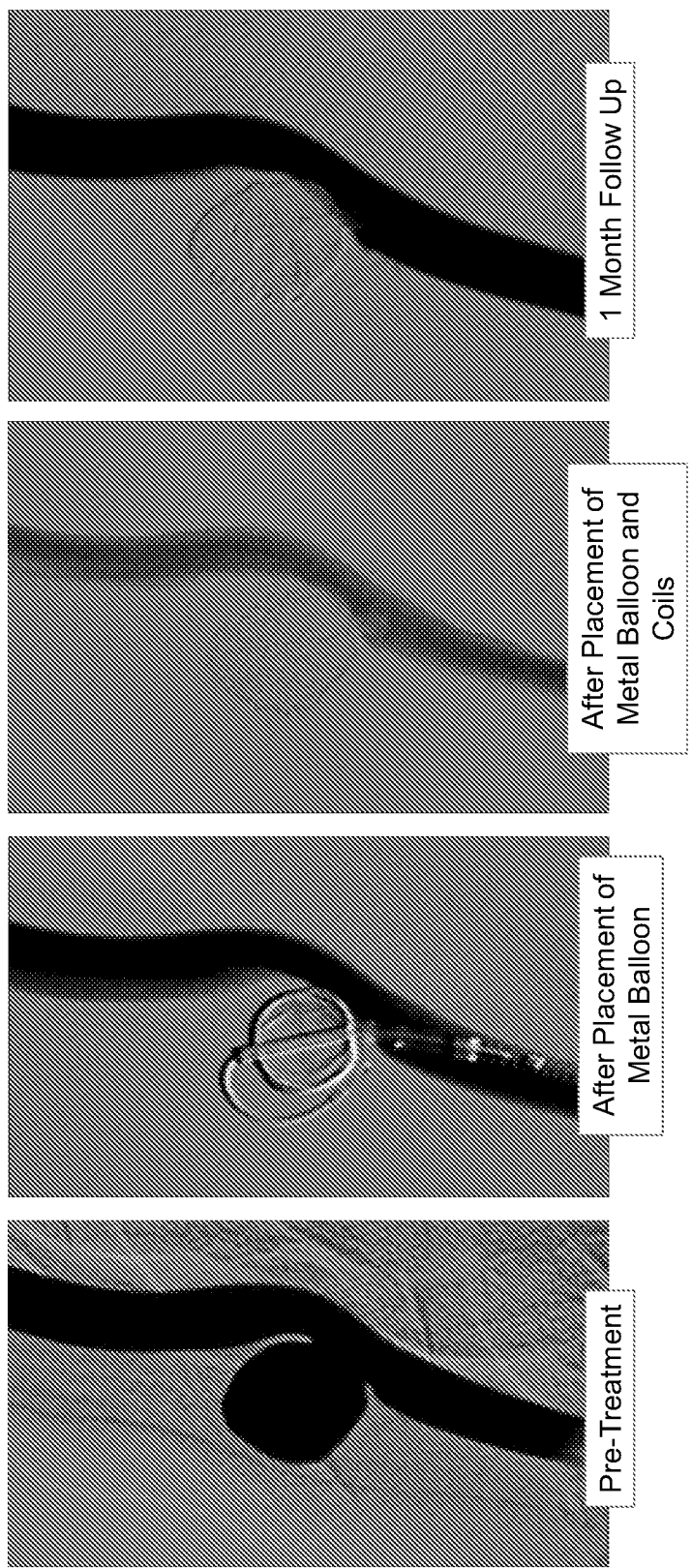
FIG. 105 includes images of the treatment of a canine side wall aneurysm with a metal balloon and coils according to one embodiment.
Figure 106:
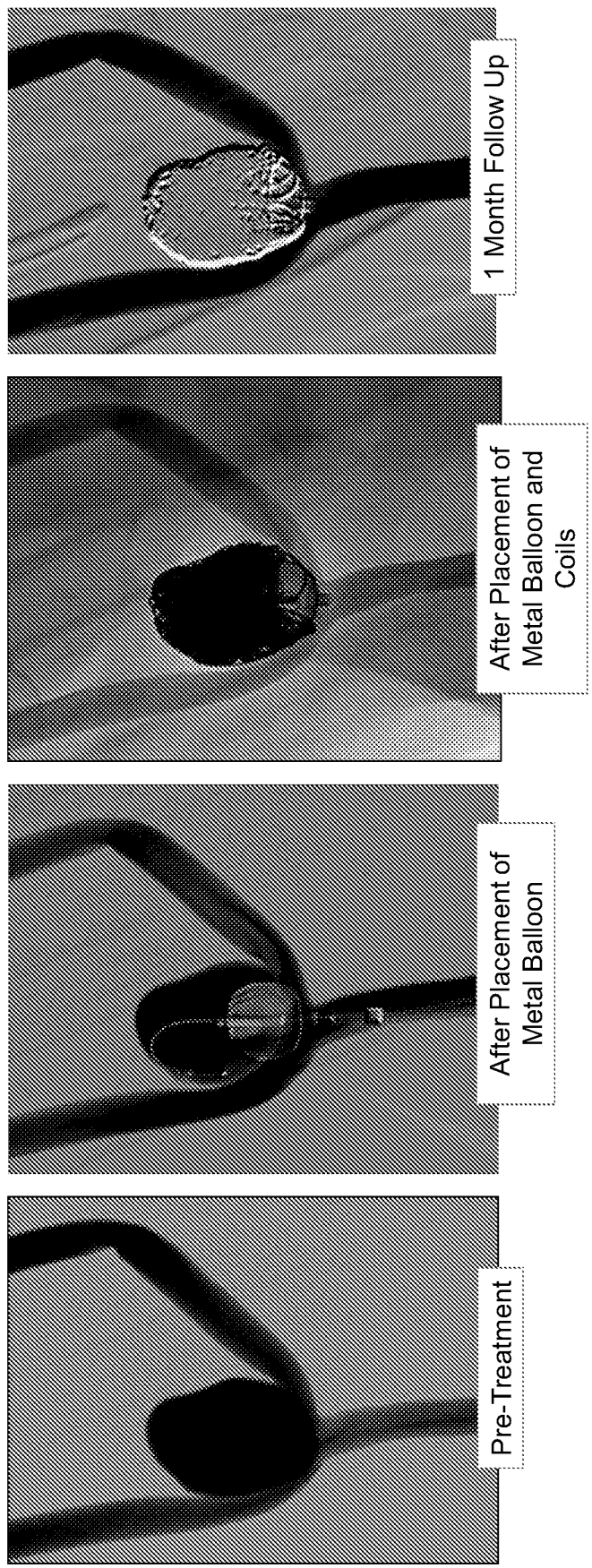
FIG. 106 includes images of the treatment of a canine complex bifurcation aneurysm with a metal balloon and coils according to one embodiment.
Figure 107A:
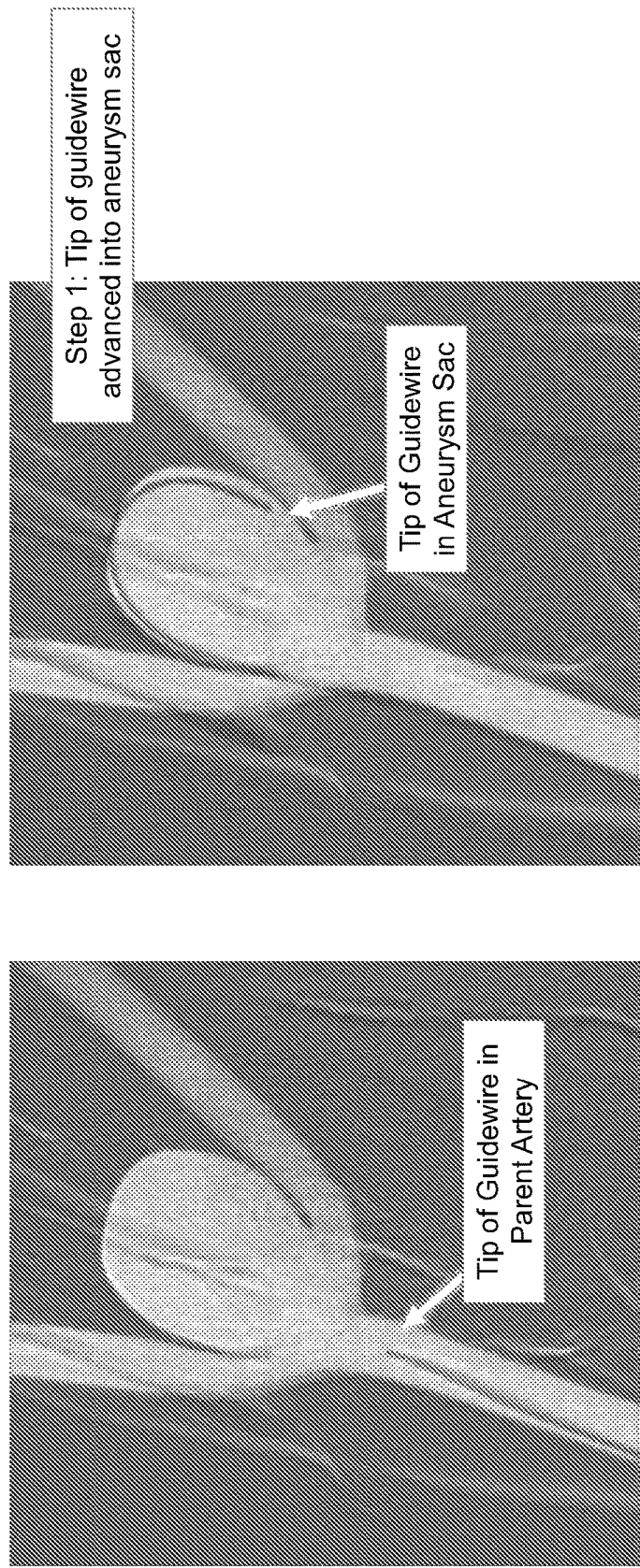
FIGS. 107A-E include images of various steps in the treatment of a canine complex bifurcation aneurysm according to one embodiment.
Figure 107B:
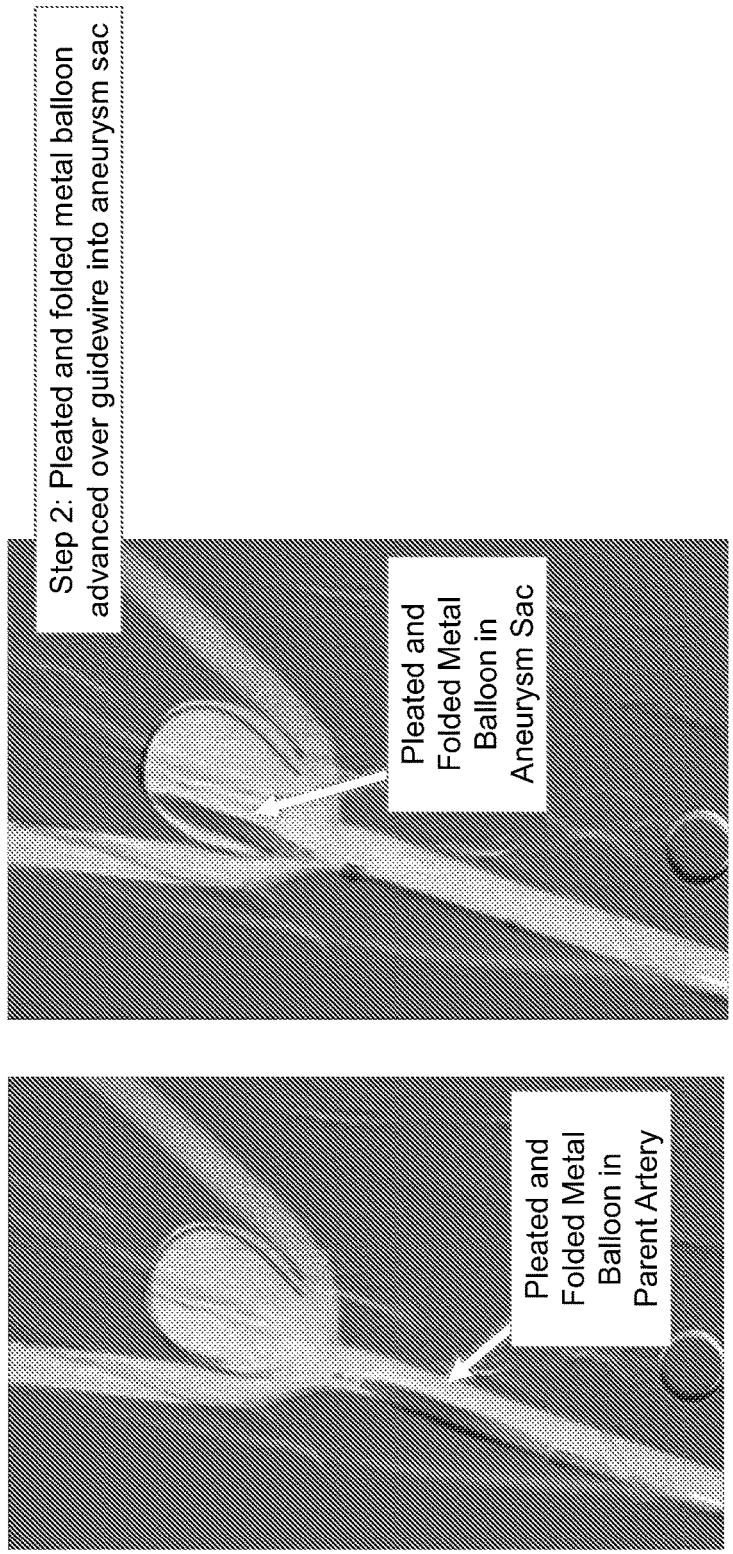
Figure 107C:
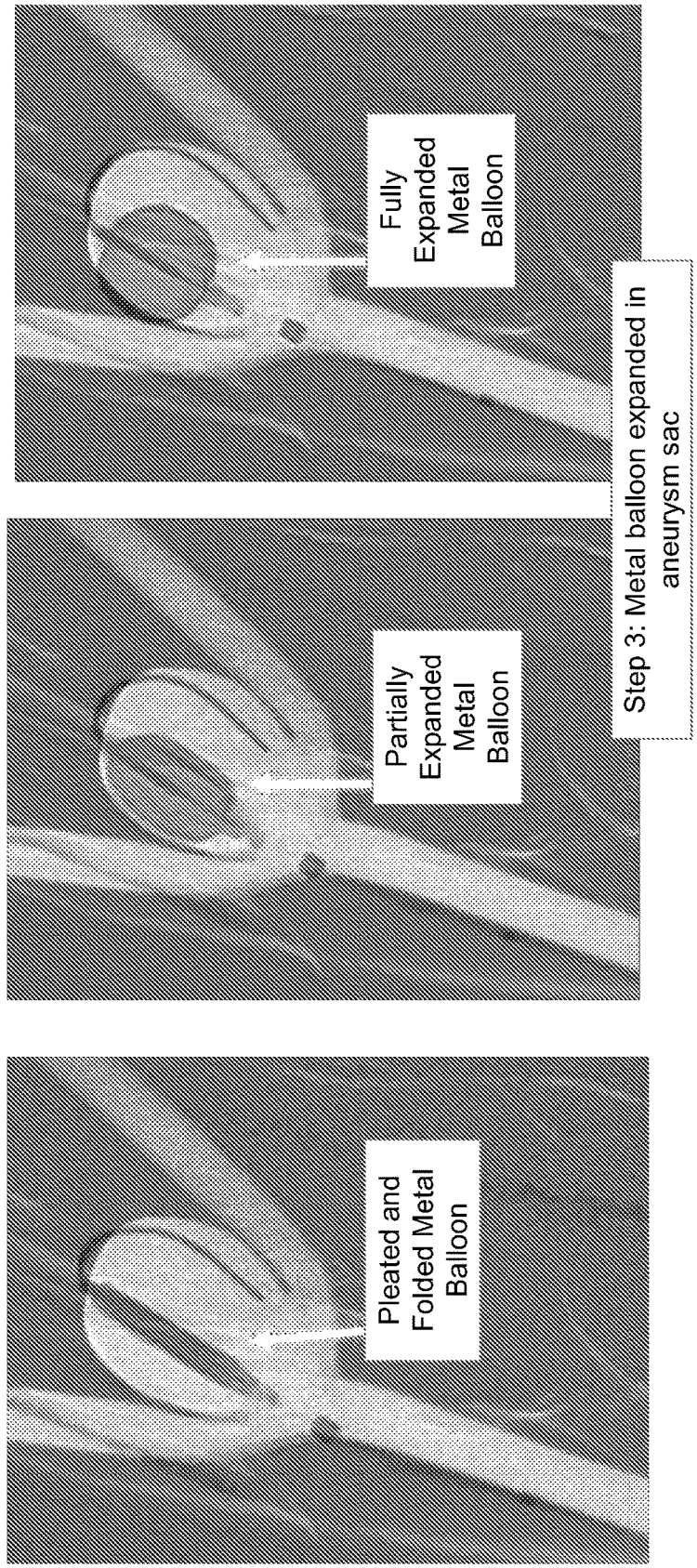
Figure 107D:
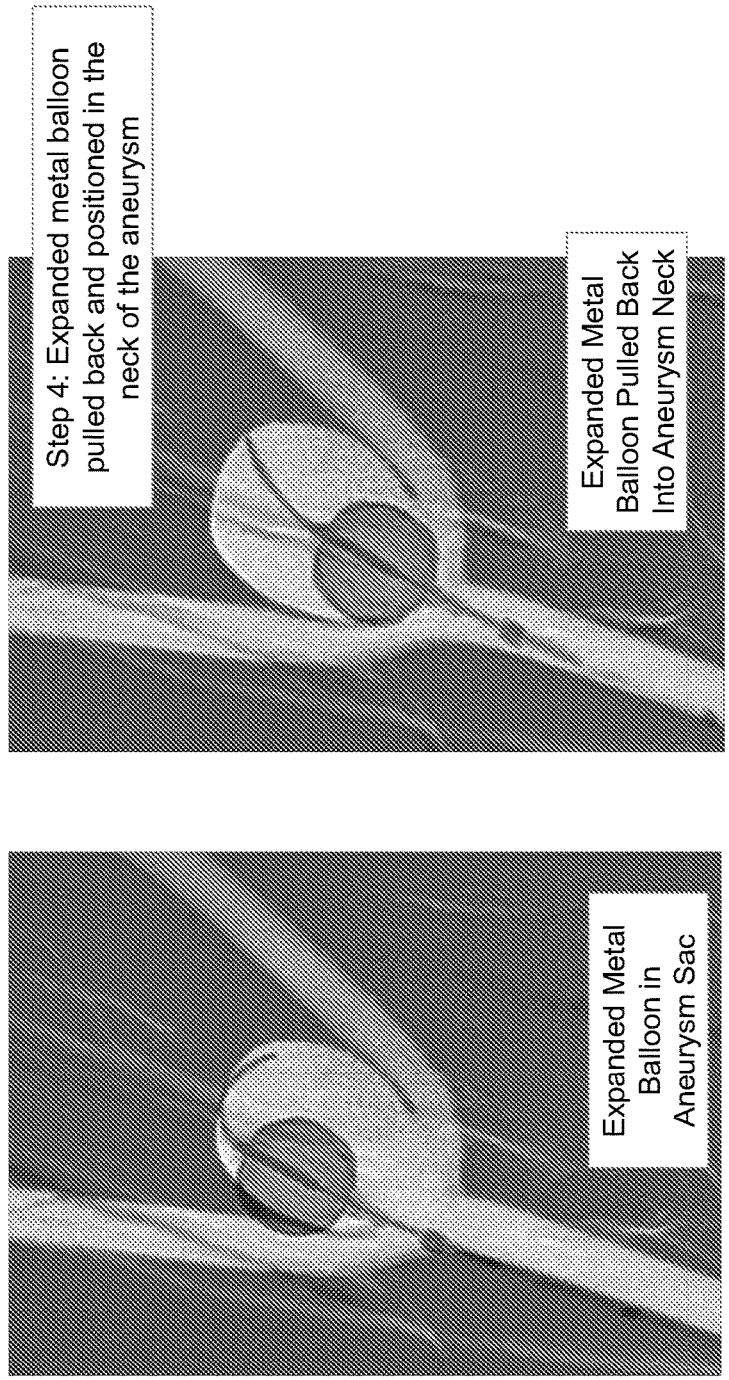
Figure 107E:
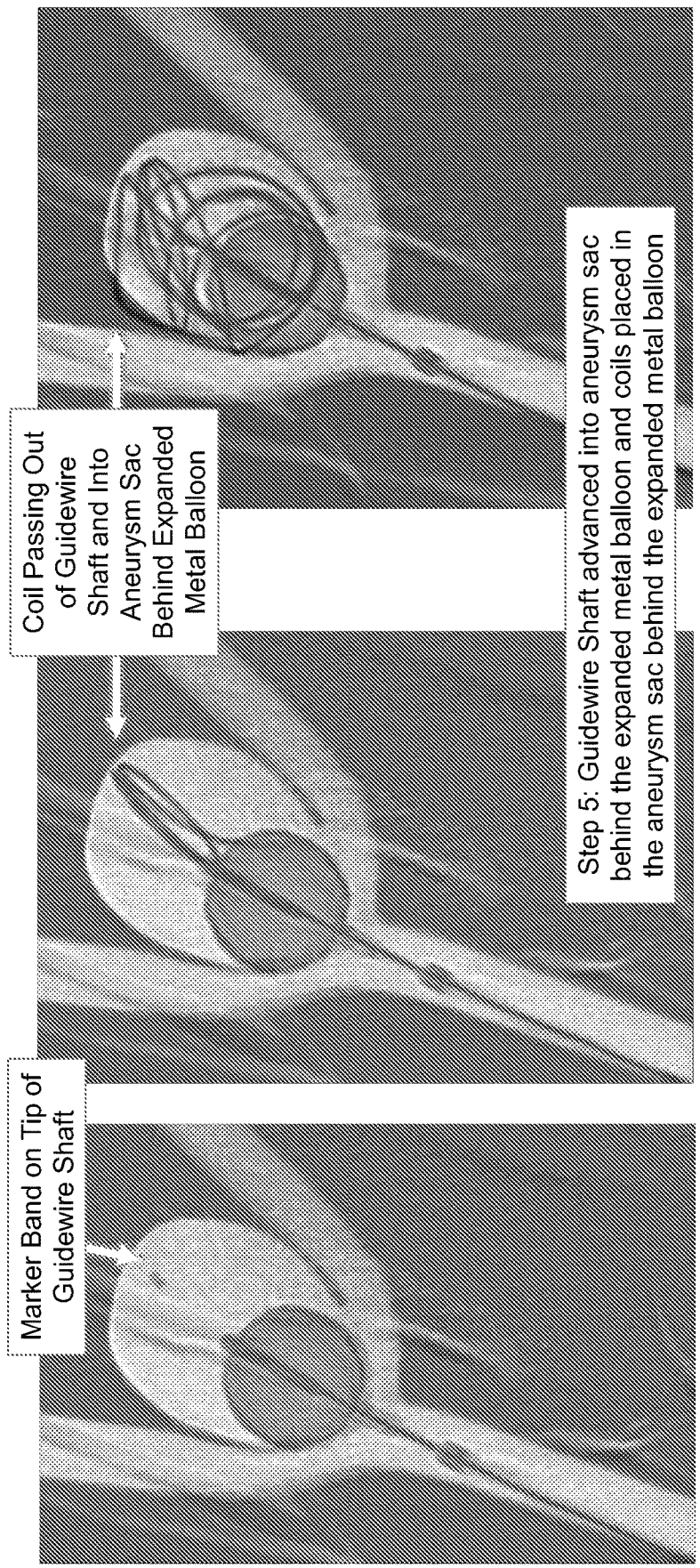
Figure 108:
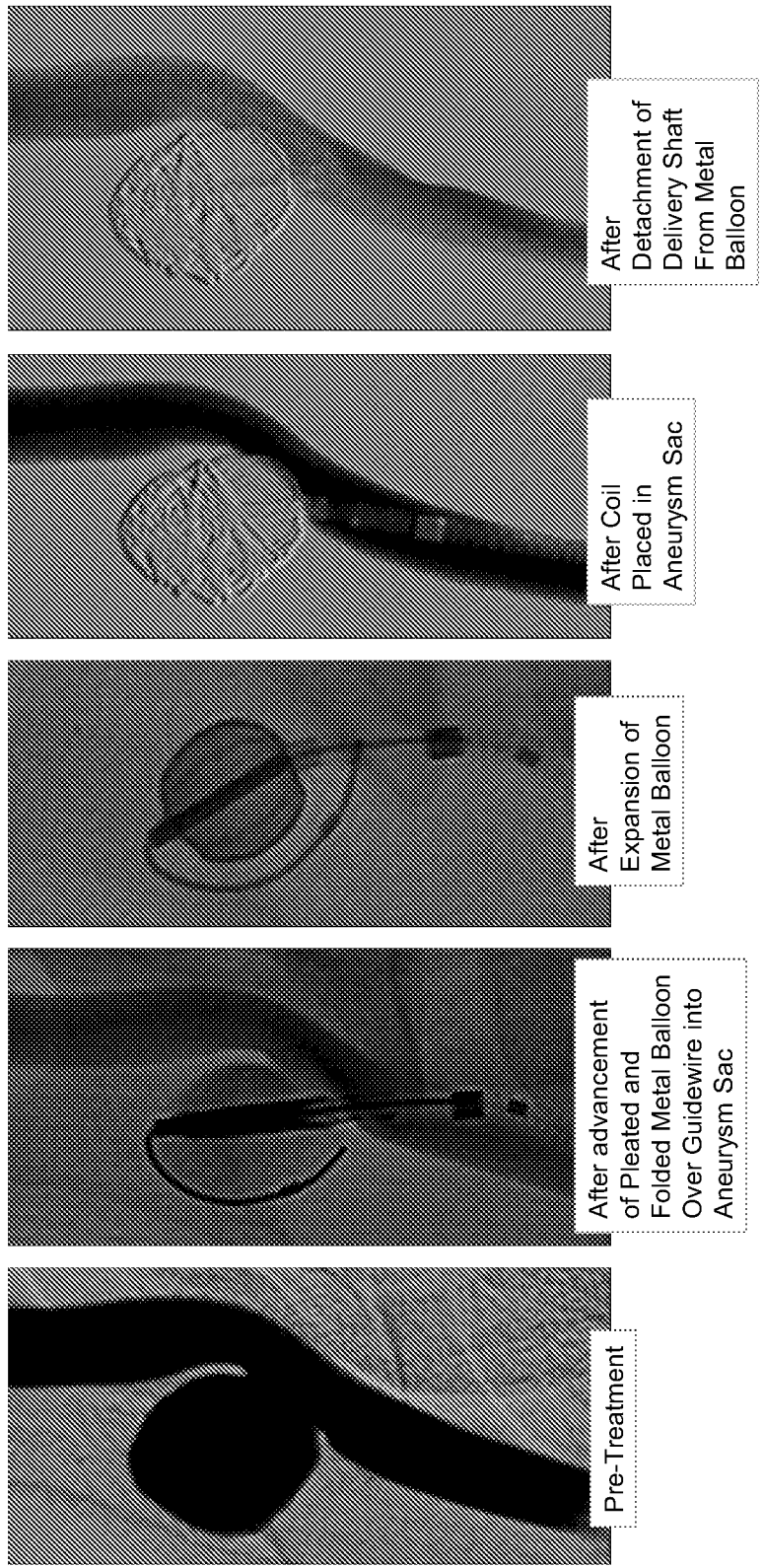
FIG. 108 includes images of various steps in the treatment of a canine side wall aneurysm according to one embodiment.
Figure 109:
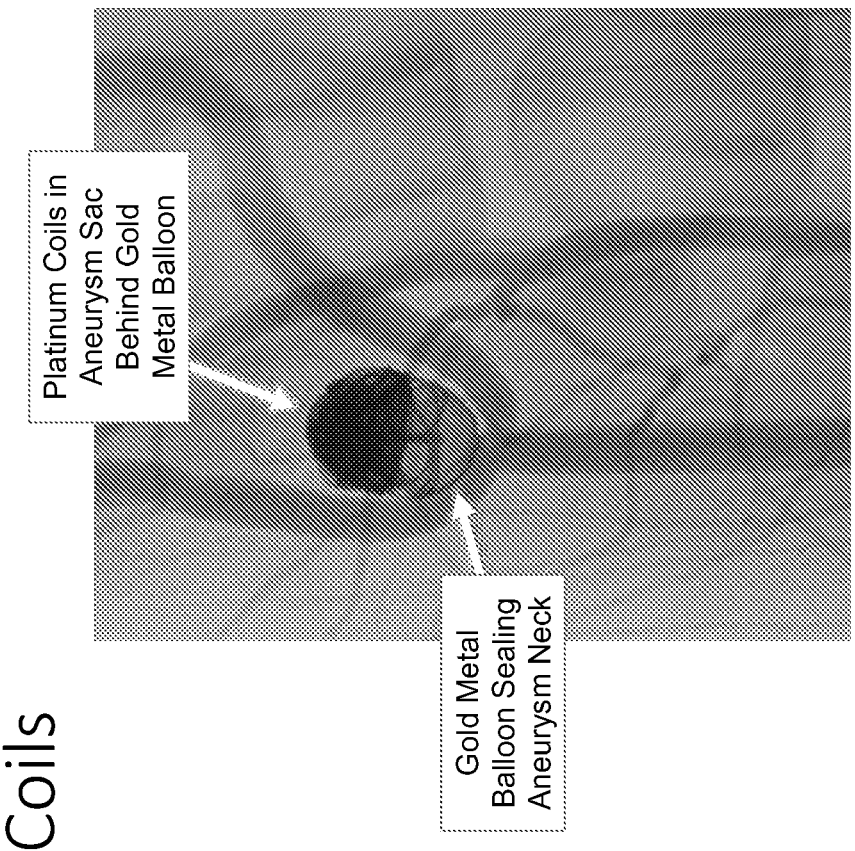
FIG. 109 illustrates radiographic differences between a metal balloon and platinum coils according to one embodiment.
Figure 110A:
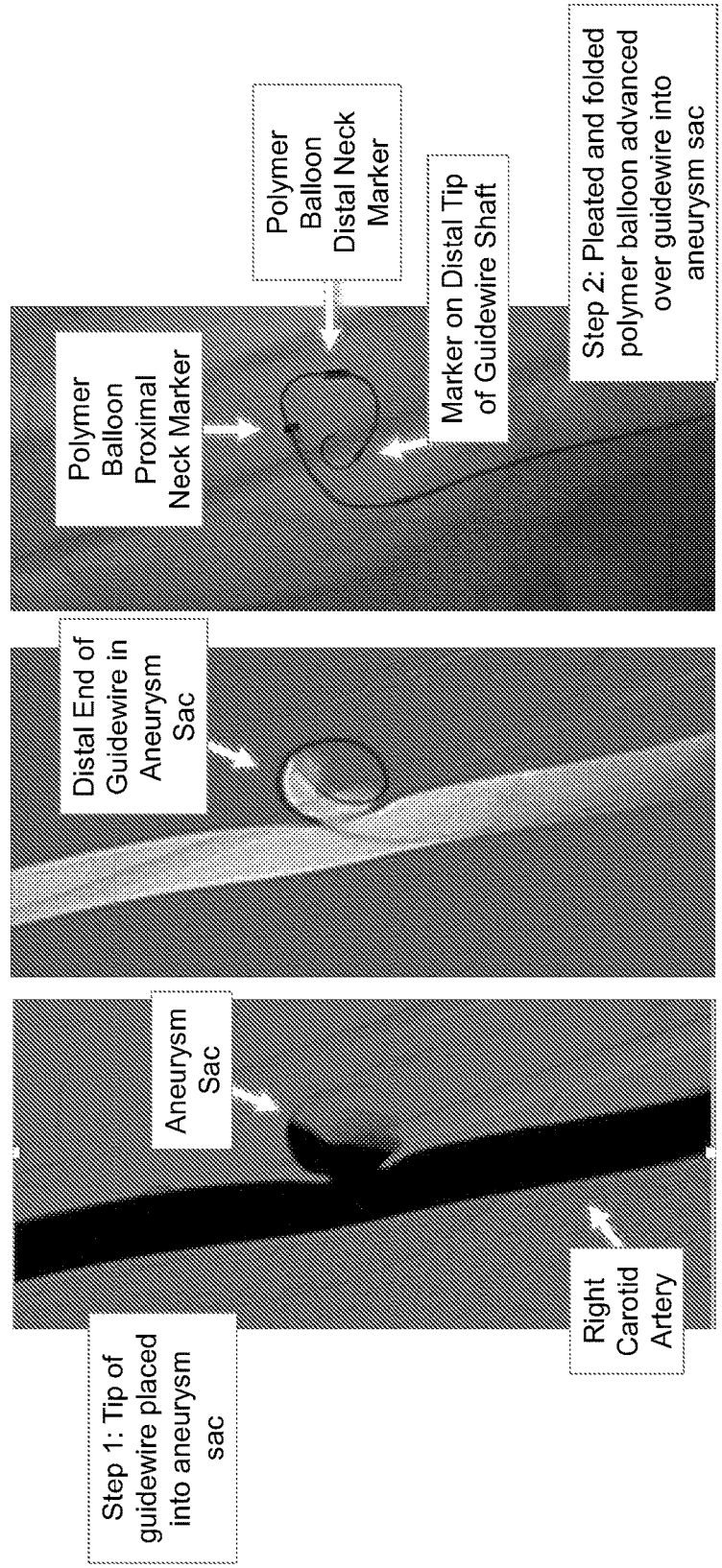
FIGS. 110A-D includes images of various steps in the treatment of a canine side wall aneurysm with a polymer balloon and coil according to one embodiment.
Figure 110B:
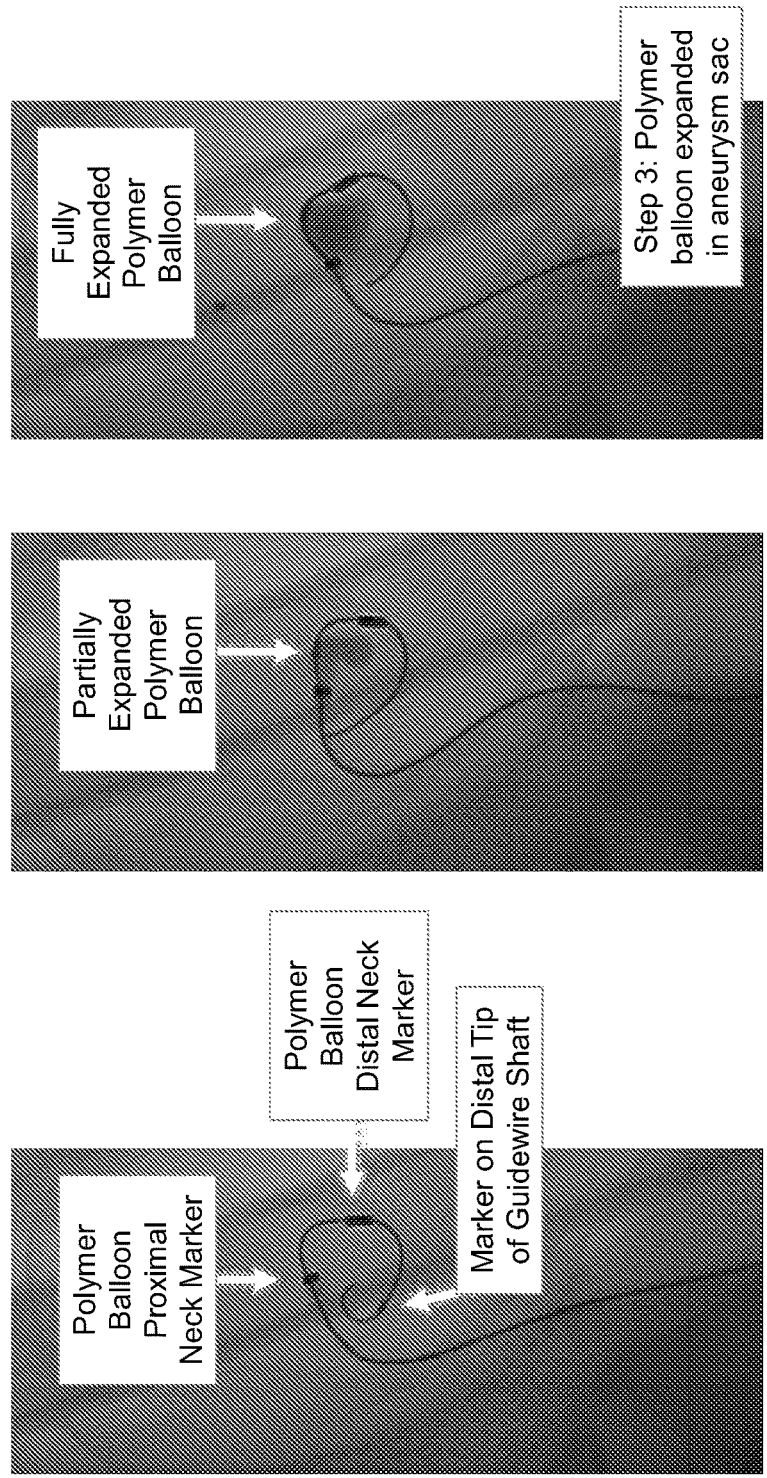
Figure 110C:
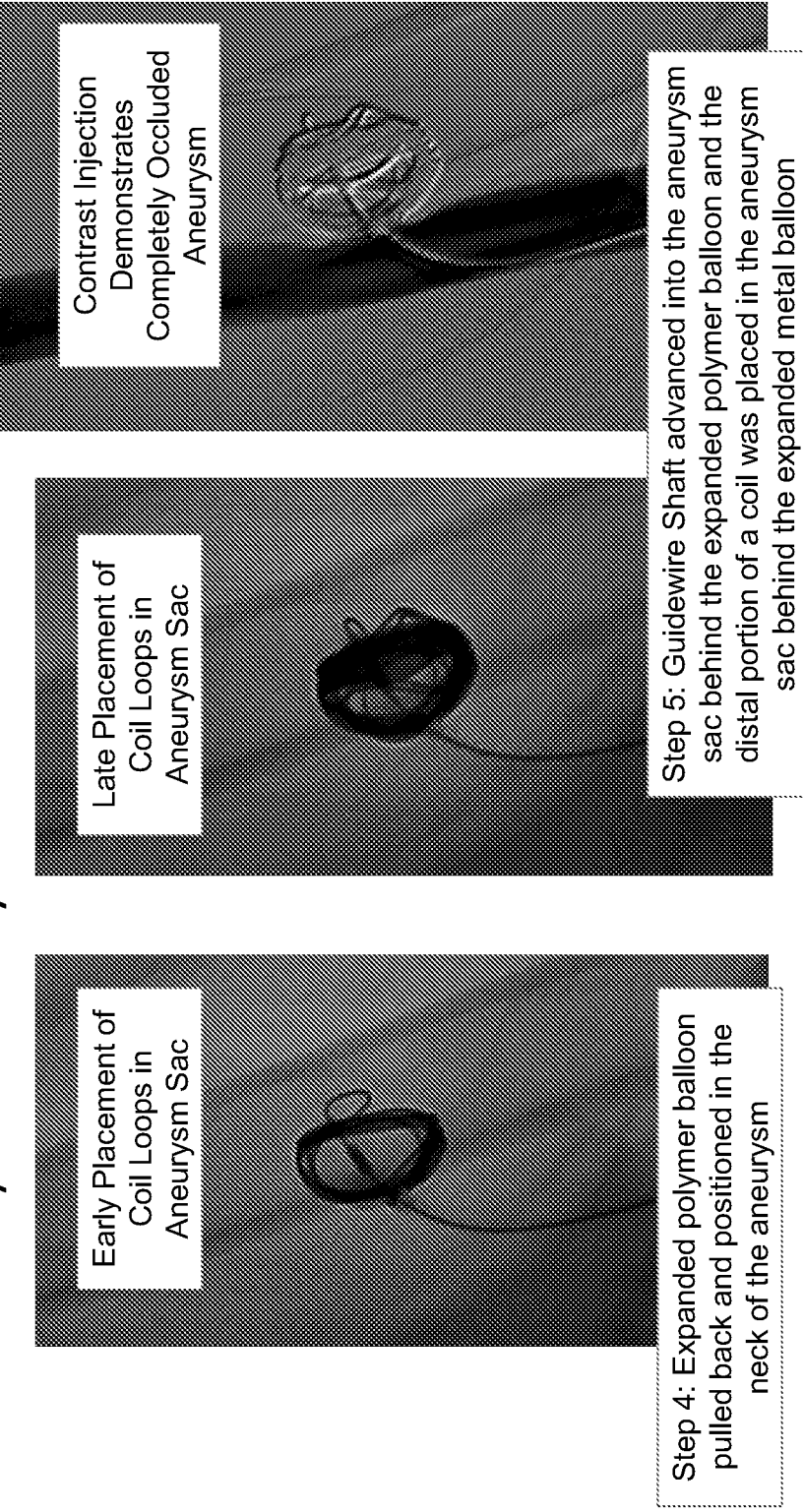
Figure 110D:
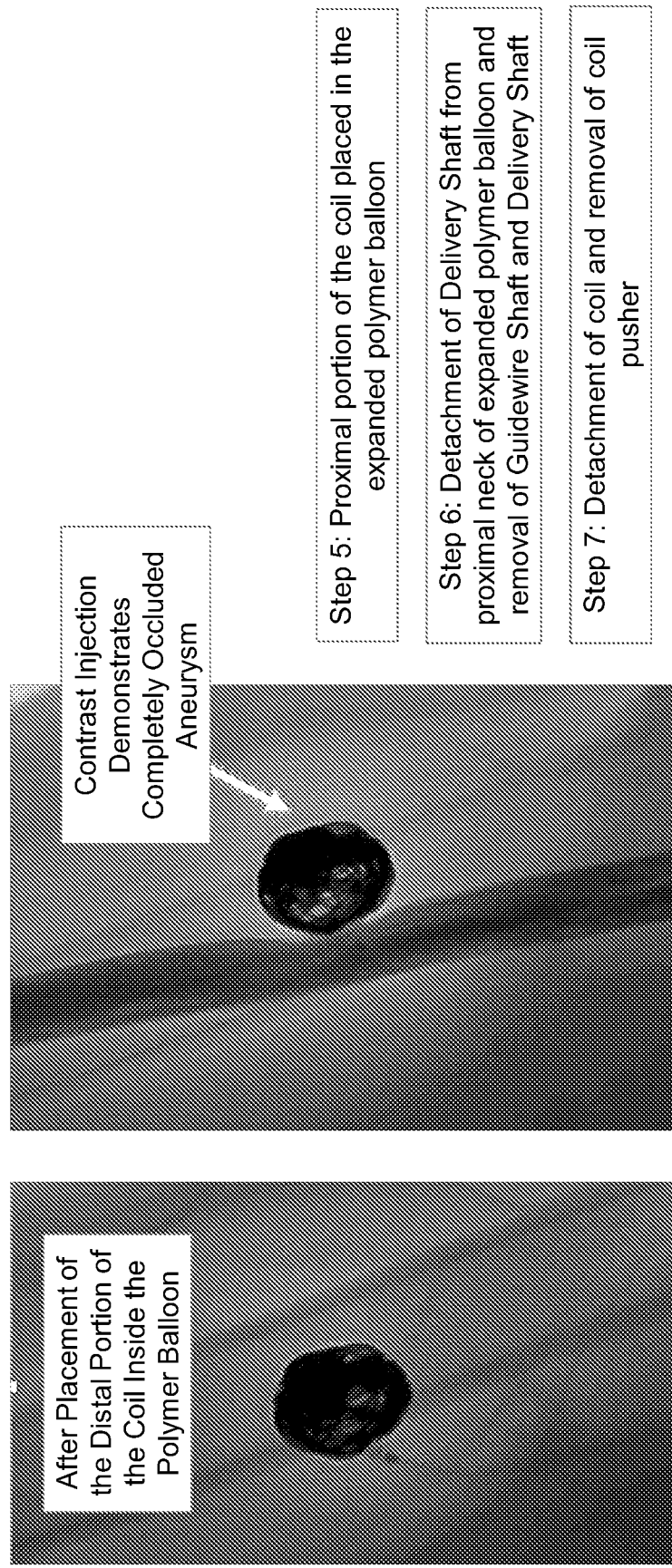
Figure 111:
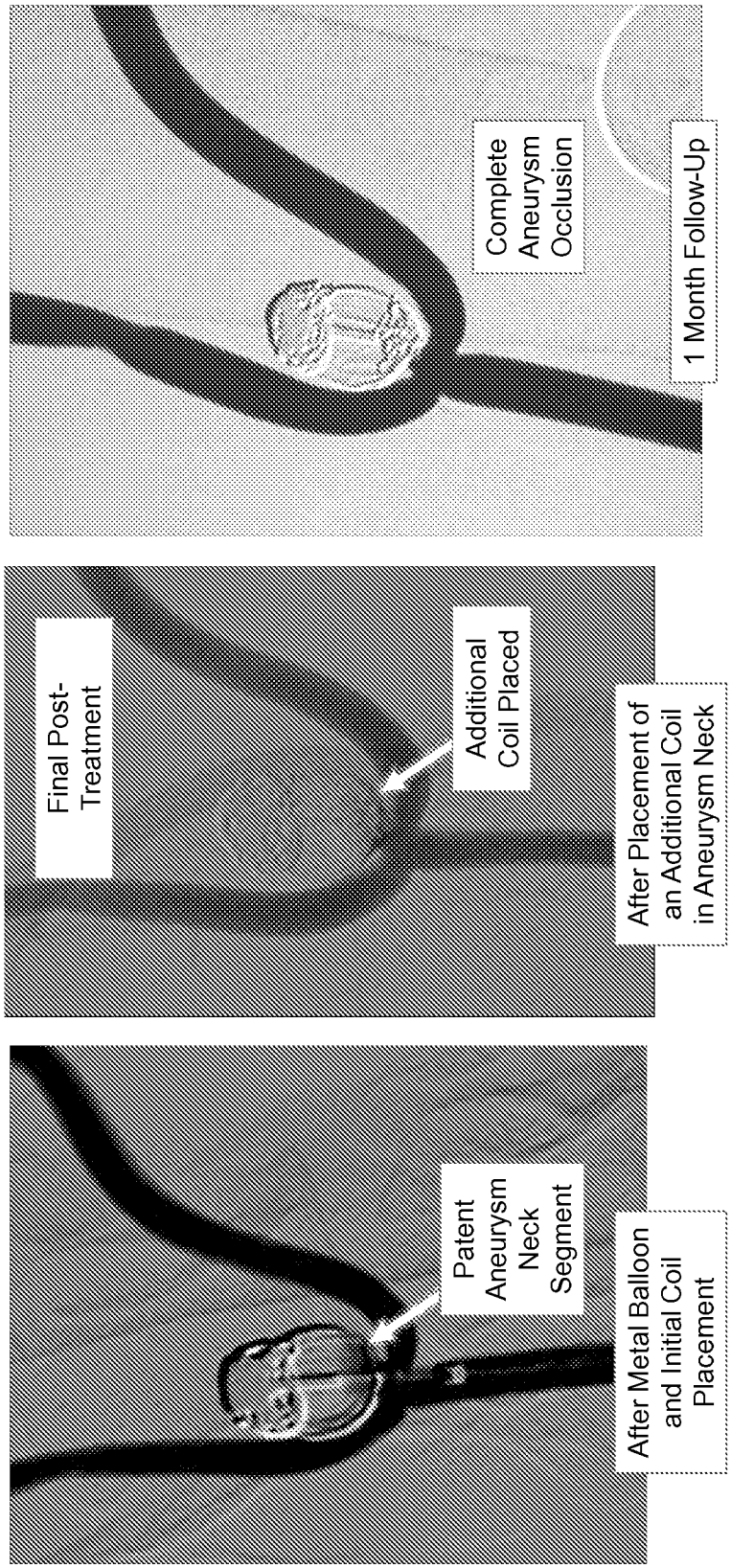
FIG. 111 includes images of the treatment of a patent aneurysm neck segment in a canine with additional coils according to one embodiment.
Figure 112:
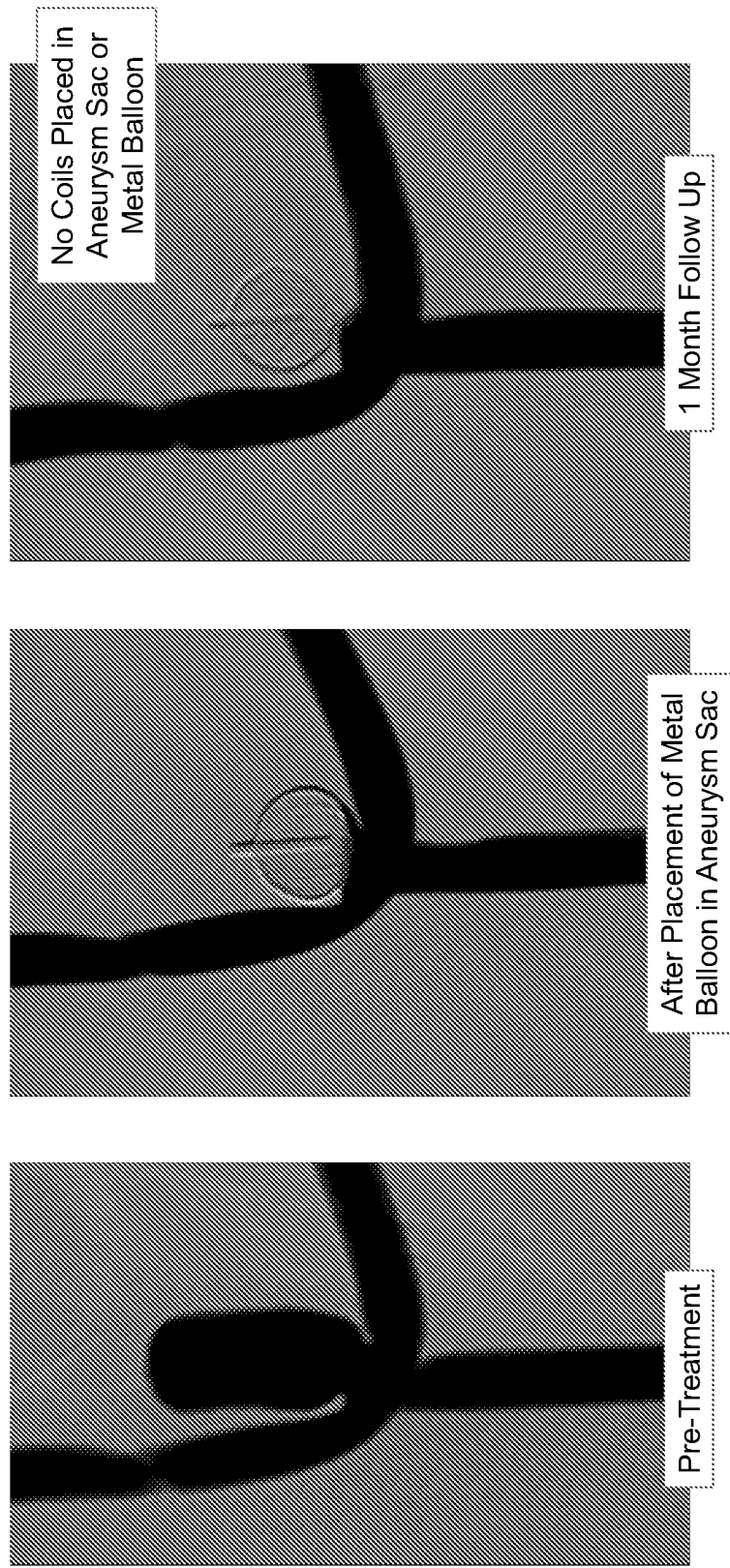
FIG. 112 includes images of the treatment of a canine terminal bifurcation aneurysm with only a metal balloon according to one embodiment.
Figure 113:
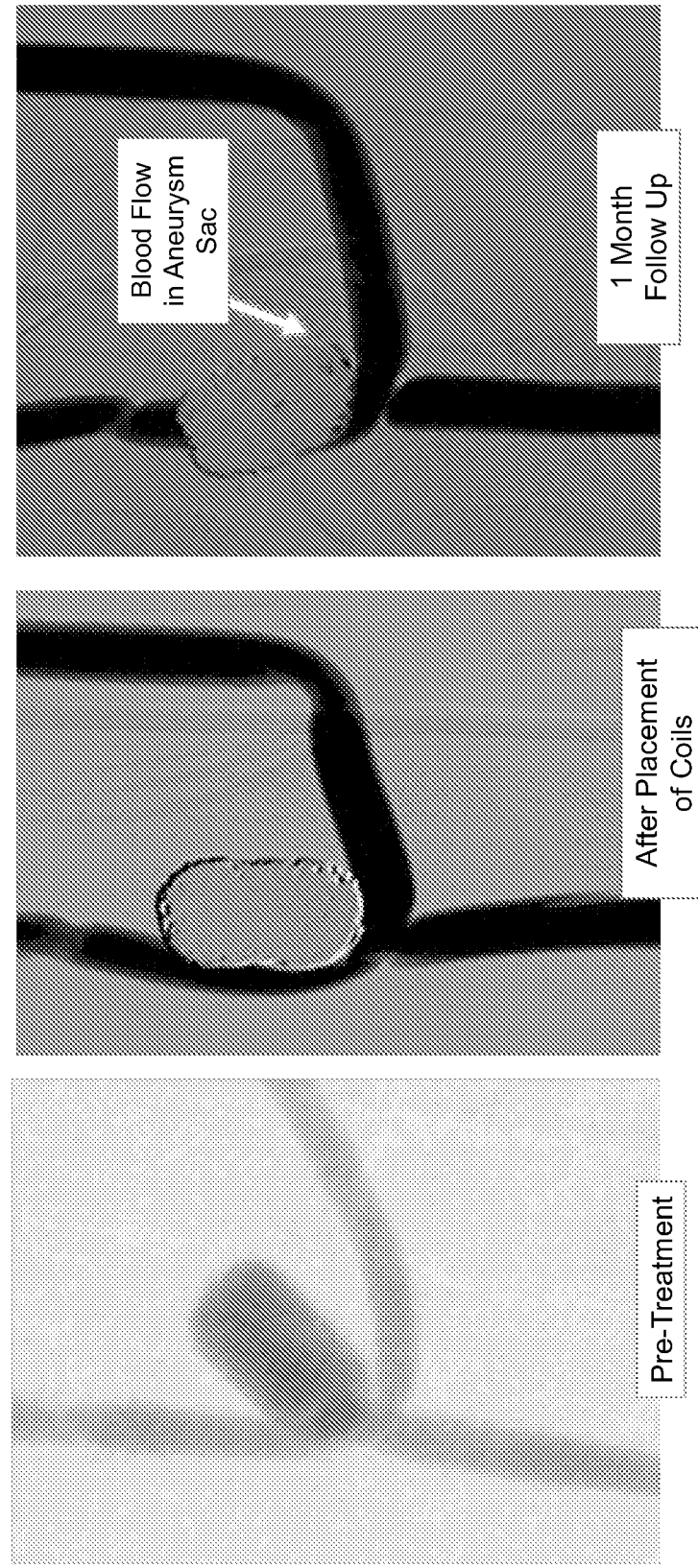
FIG. 113 includes images of the treatment of a canine terminal bifurcation aneurysm with only coils according to one embodiment.
Figure 114:
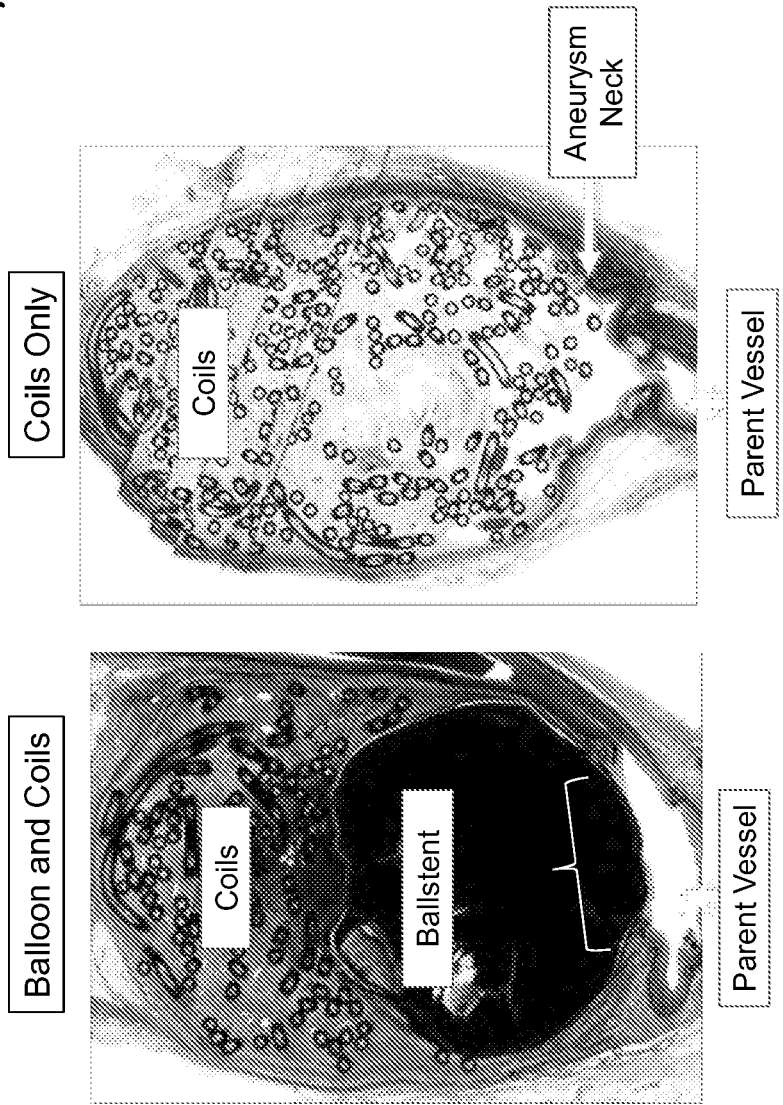
FIG. 114 includes images comparing treatments of a canine terminal bifurcation aneurysm with a metal balloon and coils against coils alone according to one embodiment.
Figure 115B:
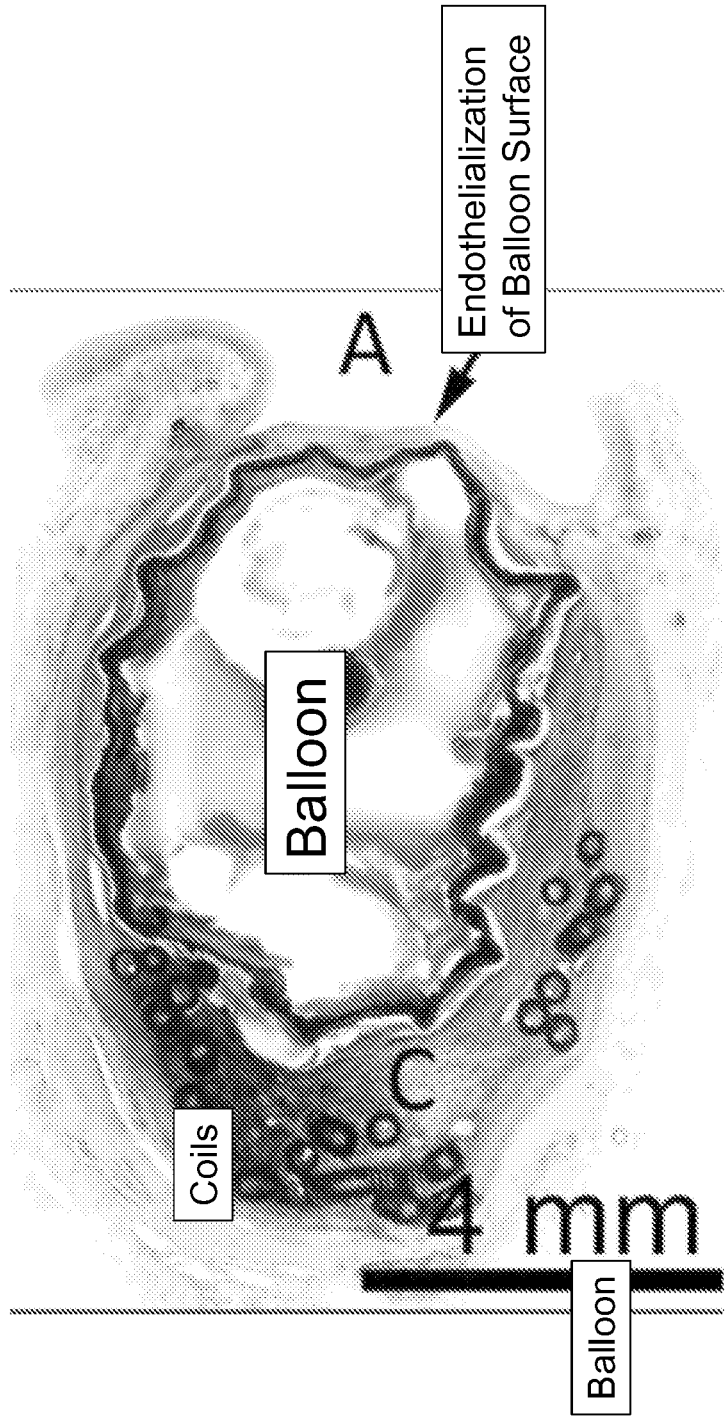

Some detachable balloon 10 sizes and shapes are better suited for the treatment of some conditions while others are better suited for the treatment of other conditions. For example, a rounded or spherical detachable balloon 10 may be better suited for treating saccular aneurysms 320, as shown in FIGS. 93A-M; and LAAs 800, as shown in FIGS. 99A-B. In contrast, a cylindrical detachable balloon may be better suited for treating arteries 317, as shown in FIG. 98A; veins 318, as shown in FIG. 98B; paravalvular leaks 808, as shown in FIGS. 100A-B; and biological conduits 900. For other clinical applications, detachable balloons may be configured to assume an expanded shape comprising two or more lobes, excluding proximal and distal necks 130 & 140 and neck assemblies 135 & 142, if any.

In some embodiments, all or a portion of a detachable balloon 10 of a detachable balloon catheter 1 is non-compliant. In some embodiments, all or a portion of a detachable balloon 10 of a detachable balloon catheter 1 is semi-compliant. In some embodiments, all or a portion of a detachable balloon 10 of a detachable balloon catheter 1 is compliant. In some embodiments, all or a portion of a detachable balloon 10 of a detachable balloon catheter 1 grows <2%, <4%, <6%, <8%, <10%, or >10% when inflated to a pressure of in a range of 1-20 atmospheres.

In some embodiments, the detachable balloon 10 comprises an opening in the proximal region 110 to enable fluid to pass from the catheter or catheter assembly 5 into the detachable balloon 10. In some embodiments, the proximal opening in the detachable balloon 10 further comprises a proximal neck 130 that extends away from the detachable balloon 10 or extends into the central void 115 of the detachable balloon 10, as shown in FIGS. 1A-B, 3A-B, and 5A-B.

As shown in FIGS. 11A-D, one or more ring structures, tubular structures, telescoping structures, catheter segments, or telescoping catheter segments may be joined to the proximal neck 130 of the detachable balloon 10. Such a structure is called a "proximal telescope" 190 and, along with the proximal neck 130, forms a proximal neck assembly 135.

Various configurations of proximal telescopes 190 may be employed to achieve various embodiments of a proximal neck assembly 135. The proximal telescope 190 may be longer than, shorter than, or the same length as the proximal neck 130 of the detachable balloon 10. The proximal telescope 190 may project distal to, proximal to, both distal and proximal to, or neither distal nor proximal to, the proximal neck 130. The outer surface of the proximal telescope 190 may be joined to the inner surface of the proximal neck 130. The inner surface of the proximal telescope 190 may be joined to the outer surface of the proximal neck 130. The proximal telescope 190 may be joined to the proximal neck 130 with an adhesive or glue. The proximal telescope 190 may be rigid, may comprise a metal, or may comprise a radiopaque metal that is visible during fluoroscopy. A metal proximal telescope 190 may comprise platinum, iridium, gold, silver, stainless steel, nitinol, titanium, or alloys or combinations thereof. The proximal telescope 190 may be flexible or may comprise a polymer. A polymer proximal telescope 190 may comprise Pebax, nylon, polyimide, PTFE, or combinations thereof. A polymer proximal telescope 190 may comprise a polymer or polymers with a Shore durometer hardness of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 D. The inner layer of the wall of a polymer proximal telescope 190 may comprise a lubricious polymer including, but not limited to, PTFE, polyimide, a composite, or a mixture of polyimide and PTFE. The wall of a polymer proximal telescope 190 may comprise a middle layer located between an outer layer and an inner layer, such middle layer comprising metal wire, including metal wire comprising nitinol or stainless steel, and including metal wire configured in a spiral, coil, braid, woven, or straight pattern. The proximal telescope 190 may comprise a lubricious coating on its inner surface, outer surface, or both inner and outer surfaces. The proximal telescope 190 may comprise a hydrophilic coating such as the Serene coating made by SurModics, Inc.

The proximal telescope 190 may comprise a marker band 612 that is conspicuous during fluoroscopy. The marker band 612 may comprise platinum, iridium, gold, silver, or alloys or combinations thereof. A marker band 612 may be joined to the distal, proximal, or both the proximal and distal ends of the proximal telescope 190.

Various dimensions of proximal telescopes 190 may be specified to achieve various embodiments of a proximal neck assembly 135. The internal or luminal diameter of the proximal telescope 190 may be 0.024-0.108 inch. The external or overall diameter of the proximal telescope 190 may be 0.026-0.110 inch. The proximal telescope 190 may have a length of 0.3-30 mm either prior to or after separation of the detachable balloon 10 from the first catheter 173, as measured parallel to the first axis 706. The internal diameter of the proximal neck 130 or proximal neck assembly 135 of the detachable balloon 10 may be 0.036-0.080 inch, as measured parallel to the second axis 708. The external diameter of the proximal neck 130 or proximal neck assembly 135 of the balloon may be 0.042-0.108 inch, as measured parallel to the second axis 708.

The proximal neck assembly 135 of detachable balloons 10 may further comprise a proximal nosecone 198 to reduce the risk of injury to the wall of a saccular aneurysm 320, artery 317, vein 318, LAA 800, other blood-containing structure, biological conduit 900, or biological space 904 when advancing or retracting the detachable balloon catheter 1. Although not illustrated, a proximal nosecone 198 is structurally and functionally similar to the distal nosecone shown in FIGS. 44A-B and 52A-B. The proximal nosecone 198 may have a tapered proximal end, a tapered distal end, or tapered proximal and distal ends. In some embodiments, the proximal nosecone 198 comprises one piece, while in other embodiments, the proximal nosecone 198 comprises two or more pieces that are bonded together, including bonded together with a glue or adhesive. In some embodiments, the proximal nosecone 198 comprises one or more polymers, including polyether ether ketone (PEEK), polycarbonate, nylon, polyimide, Pebax, PTFE, silicone, polyurethane, co-polyester polymer, thermoplastic rubber, silicone-polycarbonate copolymer, polyethylene ethyl-vinyl-acetate (PEVA) co-polymer, a biocompatible elastomer, biocompatible resilient material, or a biocompatible adhesive. In some embodiments, the length of the proximal nosecone 198 is 1-10 mm. In some embodiments, the proximal nosecone 198 has an outer diameter of 0.058-0.18 inch. In some embodiments, the proximal nosecone 198 is bonded to a proximal neck 130. In some embodiments, a proximal nosecone is bonded to a portion of a proximal neck assembly 135, including a proximal telescope 190. In some embodiments, a proximal nosecone 198 is bonded to both a proximal neck 130 and a portion of a proximal neck assembly 135. In some embodiments, a portion of the inner surface of a proximal nosecone 198 is bonded to a portion of the outer surface of a proximal balloon neck 130 or a portion of a proximal neck assembly 135. In some embodiments, at least a portion of the proximal neck 130 comprises a layer of radiopaque metal that is visible under fluoroscopy.

In some embodiments, the detachable balloon comprises an opening in the distal region 120 to enable a portion of a catheter or catheter assembly 5 to pass into and through the central void 115 of the detachable balloon 10 and optionally extend distal to the detachable balloon 10, thereby enabling a guidewire 40 and or second catheter 174 to pass completely through the detachable balloon 10. In some embodiments, the distal opening in detachable balloon 10 further comprises a distal neck 140 that extends away from the detachable balloon 10 or extends into the central void 115 of the detachable balloon 10, as shown in FIGS. 1A-B and 3A-B.

As shown in FIGS. 11E-H and 52C, one or more ring structures, tubular structures, telescoping structures, catheter segments, or telescoping catheter segments may be joined to the distal neck 140 of the detachable balloon 10. Such a structure is called a "distal telescope" 185 and, along with the distal neck 140, forms a distal neck assembly 142.

Various configurations of distal telescopes 185 may be employed to achieve various embodiments of a distal neck assembly 142. The distal telescope 185 may be longer than, shorter than, or the same length as the distal neck 140 of the detachable balloon 10. The distal telescope 185 may project proximal to, distal to, both distal and proximal to, or neither distal nor proximal to, the distal neck 140. The outer surface of the distal telescope 185 may be joined to the inner surface of the distal neck 140. The inner surface of the distal telescope 185 may be joined to the outer surface of the distal neck 140. The distal telescope 185 may be joined to the distal neck 140 with an adhesive or glue. The distal telescope 185 may be rigid, may comprise a metal, or may comprise a radiopaque metal that is visible during fluoroscopy. A metal distal telescope 185 may comprise platinum, iridium, gold, silver, stainless steel, nitinol, titanium, or alloys or combinations thereof. The distal telescope 185 may be flexible or may comprise a polymer. A polymer distal telescope 185 may comprise Pebax, nylon, polyimide, PTFE, or combinations thereof. A polymer distal telescope 185 may comprise a polymer or polymers with a Shore durometer hardness of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 D. The inner layer of the wall of a polymer distal telescope 185 may comprise a lubricious polymer including, but not limited to, PTFE, polyimide, a composite, or a mixture of polyimide and PTFE. The wall of a polymer distal telescope 185 may comprise a middle layer located between an outer layer and an inner layer, such middle layer comprising metal wire, including metal wire comprising nitinol or stainless steel, and including metal wire configured in a spiral, coil, braid, woven, or straight pattern. The distal telescope 185 may comprise a lubricious coating on its inner surface, outer surface, or both inner and outer surfaces. The distal telescope 185 may comprise a hydrophilic coating such as the Serene coating made by SurModics, Inc.

The distal telescope 185 may comprise a marker band 612 that is conspicuous during fluoroscopy. The marker band 612 may comprise platinum, iridium, gold, silver, or alloys or combinations thereof. A marker band 612 may be joined to the distal, proximal, or both the proximal and distal ends of the distal telescope 185.

Various dimensions of distal telescopes 185 may be specified to achieve various embodiments of a distal neck assembly 142. The internal or luminal diameter of the distal telescope 185 may be 0.024-0.108 inch. The external or overall diameter of the distal telescope 185 may be 0.026-0.110 inch. The distal telescope 185 may have a length of 0.3-30 mm either prior to or after separation of the detachable balloon 10 from the first catheter 173, as measured parallel to the first axis 706. The internal diameter of the distal neck 140 or distal neck assembly 142 may be 0.024-0.068 inch, as measured parallel to the second axis 708. The external diameter of the distal neck 140 or distal neck assembly 142 may be 0.030-0.096 inch, as measured parallel to the second axis 708.

In some embodiments of a detachable balloon catheter 1, the outer diameter of the distal telescope 185 is greater than the internal diameter of proximal telescope 190, such that the proximal portion of the distal telescope 185 cannot enter the first lumen 162. In some embodiments of a detachable balloon catheter 1, the outer diameter of the distal telescope 185 is greater than the internal diameter of the proximal neck 130, such that the proximal portion of the distal telescope 185 cannot enter the first lumen 162. In some embodiments of a detachable balloon catheter 1, the outer diameter of the distal telescope 185 is greater than the internal diameter of the first catheter 173, such that the proximal portion of the distal telescope 185 cannot enter the first lumen 162.

As shown in FIGS. 44A-B and 52A-B, the distal neck assembly 142 of detachable balloons 10 may further comprise a distal nosecone 191 to reduce the risk of injury to the wall of a saccular aneurysm 320, artery 317, vein 318, LAA 800, other blood-containing structure, biological conduit 900, or biological space 904 when advancing or retracting the detachable balloon catheter 1. The distal nosecone 191 may have a tapered proximal end, a tapered distal end, or tapered proximal and distal ends. In some embodiments, the distal nosecone 191 comprises one piece, while in other embodiments, the distal nosecone 191 comprises two or more pieces that are bonded together, as shown in FIGS. 49A-D, including bonded together with a glue or adhesive. In some embodiments, the distal nosecone 191 comprises one or more polymers, including polyether ether ketone (PEEK), polycarbonate, nylon, polyimide, Pebax, PTFE, silicone, polyurethane, co-polyester polymer, thermoplastic rubber, silicone-polycarbonate copolymer, polyethylene ethyl-vinyl-acetate (PEVA) co-polymer, a biocompatible elastomer, biocompatible resilient material, or a biocompatible adhesive. In some embodiments, the length of the distal nosecone 191 is 1-10 mm. In some embodiments, the distal nosecone 191 has an outer diameter of 0.058-0.18 inch. In some embodiments, the distal nosecone 191 is bonded to a distal neck 140. In some embodiments, a distal nosecone 191 is bonded to a portion of a distal neck assembly 142, including a distal telescope 185. In some embodiments, a distal nosecone 191 is bonded to both a distal neck 140 and a portion of a distal neck assembly 142. In some embodiments, a portion of the inner surface of a distal nosecone 191 is bonded to a portion of the outer surface of a distal balloon neck 140 or a portion of a distal neck assembly 142. In some embodiments, at least a portion of the distal neck 140 comprises a layer of radiopaque metal that is visible under fluoroscopy.

Detachable balloons 10 may be polymer balloons 12, wherein they comprise a continuous layer of polymer 99, excluding any proximal and distal openings in the detachable balloon 10, as shown in FIGS. 7.7, 8B, and 9B. The continuous polymer layer 99 of detachable polymer balloons 12 may comprise PET, nylon, or Pebax. The thickness of the polymer layer 99 of a detachable polymer balloon 12 may range between 5-300 microns or between 0.0002-0.012 inch. Detachable polymer balloons 12 may comprise additional layers of non-metallic coatings or polymers 97, which may be continuous or discontinuous, and which may be internal to the continuous polymer layer 99 or external to the continuous polymer layer 99, as shown in FIGS. 7.5, 8B, and 9B. The additional layers of non-metallic coatings or polymers 97 may comprise polyurethane, silicone, or poly(p-xylylene) (Parylene). The additional layers of non-metallic coatings or polymers 97 of detachable polymer balloons 12 may have a thickness of 0.1-100 microns. The overall thickness of the wall 30 of detachable polymer balloons 12 may range between 5-300 microns, or between 0.0002-0.012 inch. Detachable polymer balloons 12 may not possess sufficient strength to maintain an expanded or partially expanded configuration in vivo after separation from a catheter or catheter assembly 5. Detachable polymer balloons 12 may not possess sufficient strength to maintain an expanded or partially expanded configuration in vivo after separation from a catheter or catheter assembly 5 when no solid or semi-solid material, not derived from the patient, is present in the central void 115 of the expanded detachable polymer balloon after separation from the first and second catheters 173 & 174. Detachable polymer balloons 12 may not possess sufficient strength to maintain an expanded or partially expanded configuration in vivo after separation from a catheter or catheter assembly 5 when the detachable polymer balloon 12 is implanted in an unsealed configuration. Detachable polymer balloons 12 may not possess sufficient strength to maintain an expanded or partially expanded configuration in vivo after separation from a catheter or catheter assembly 5 when the pressure in the central void 115 or interior volume of the expanded detachable polymer balloon 12 is not greater than a pressure outside the expanded detachable polymer balloon 12. By using molds and balloon blowing techniques, detachable polymer balloons 12 that closely match the size and shape of various vascular structures, biological conduits 900, or biological spaces can be made, including but not limited to saccular aneurysms 320, segments of arteries 317, segments of veins 318, LAAs 800, paravalvular leak paths 808, segments of biological conduits, 900, or particular biological spaces.

In some embodiments, all or a portion of a detachable polymer balloon 12 of a detachable balloon catheter 1 is non-compliant. In some embodiments, all or a portion of a detachable polymer balloon 12 of a detachable balloon catheter 1 is semi-compliant. In some embodiments, all or a portion of a detachable polymer balloon 12 of a detachable balloon catheter 1 is compliant. In some embodiments, all or a portion of a detachable polymer balloon 12 of a detachable balloon catheter 1 grows <2%, <4%, <6%, <8%, <10%, or >10% when inflated to a pressure in a range from 1 to 20 atmospheres.

Figure 10:
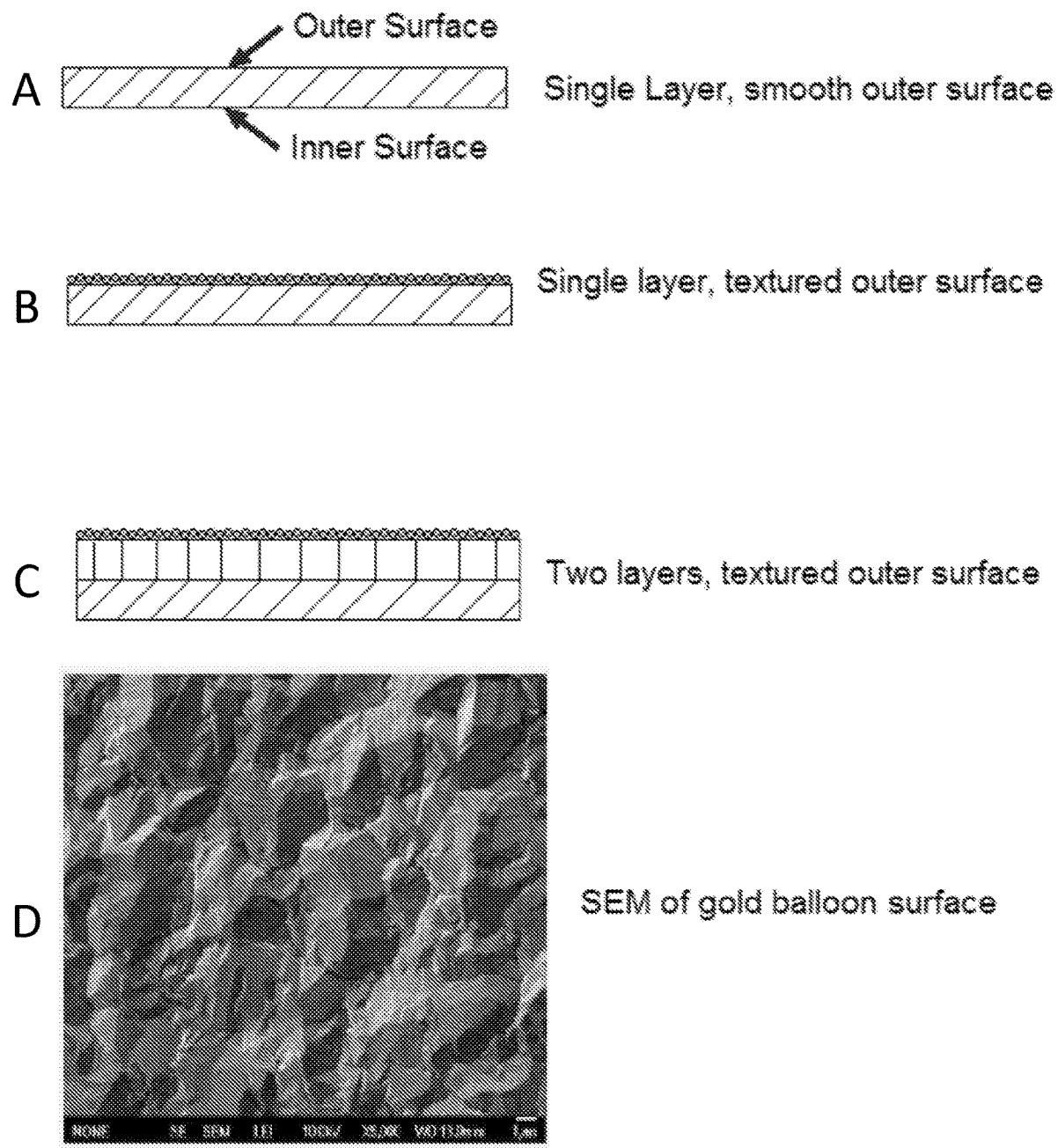
FIGS. 10A-C are cross-sectional views of a portion of the exterior wall of various embodiments of a balloon incorporating single or multiple layers and a smooth or textured outer surface.
FIG. 10D is a scanning electron micrograph showing the textured outer surface of an electroformed gold metal balloon.
Figure 11:
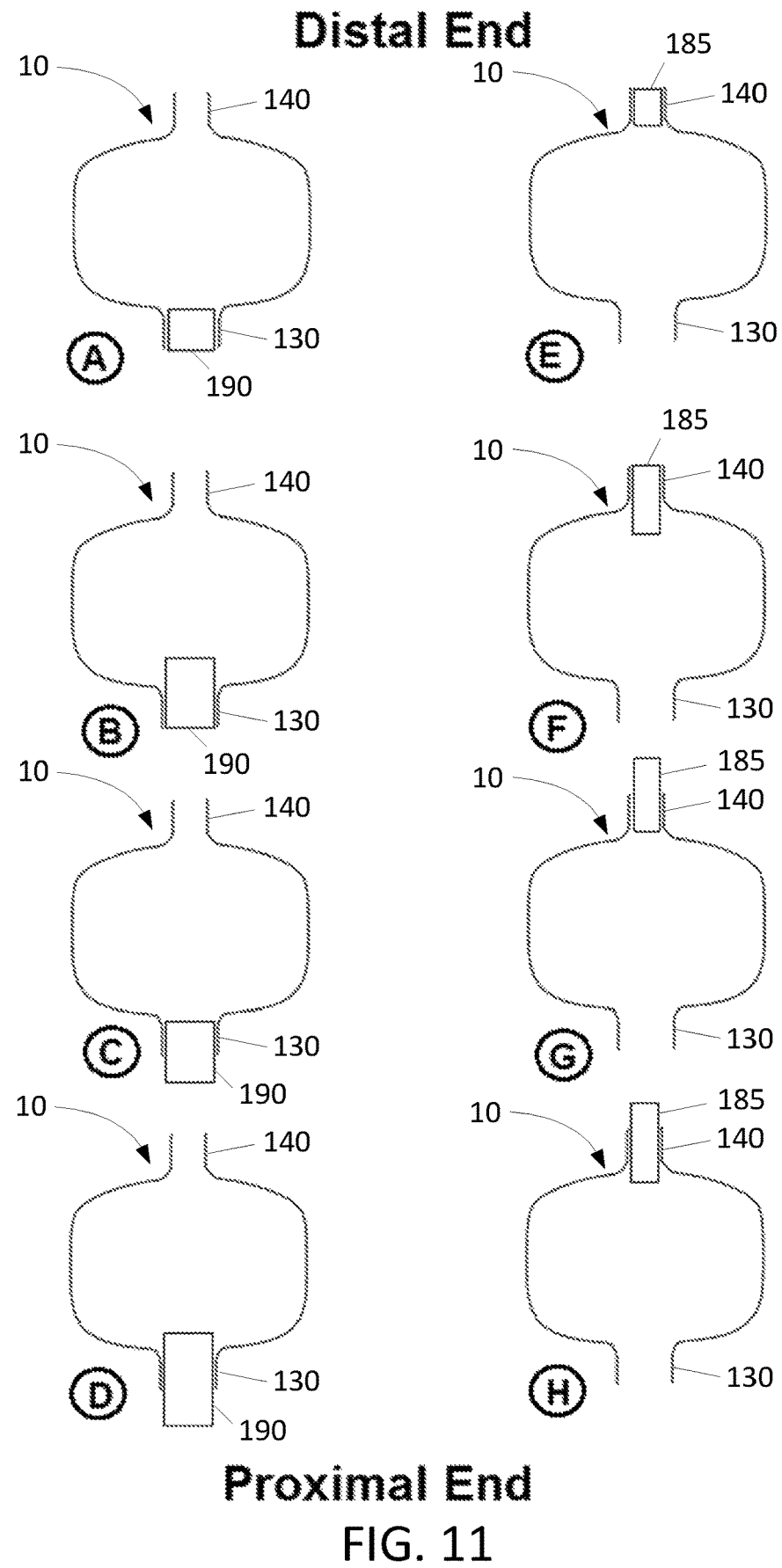
FIGS. 11A-H are partial cross-sectional views of balloons having the shape of the embodiment shown in FIG. 3 incorporating telescoping structures within their necks according to eight embodiments.

In some embodiments, the external surface of a polymer detachable balloon 12 of a detachable balloon catheter 1 comprises surface structures, as shown in FIGS. 10B-D. In some embodiments, the external surface of a polymer detachable balloon 12 of a detachable balloon catheter 1 comprises surface structures having a height of 0.01-1 microns. In some embodiments, the external surface of the proximal region 110 of a polymer detachable balloon 12 of a detachable balloon catheter 1 comprises surface structures or surface structures having a height of 0.01-1 microns, while the intermediate region 100 and distal region 120 are smooth or smoother than the proximal region 110, as shown in FIG. 10A. In some embodiments, the external surface of the proximal region 110 of a polymer detachable balloon 12 of a detachable balloon catheter 1 configured for implantation into a saccular aneurysm 320 or LAA 800 comprises surface structures or surface structures having a height of 0.01-1 microns, while the intermediate region 100 and distal region 120 are smooth or smoother than the proximal region 110.

Detachable balloons 10 may be metalized polymer balloons 14, wherein they comprise a continuous layer of polymer 99, excluding any proximal and distal openings in the detachable balloon, and a layer of metal 90, that may be continuous or discontinuous, as shown in FIGS. 7.2, 8C, 8E, 9C, and 9E. The continuous polymer layer 99 of detachable metalized polymer balloons 14 may comprise PET, nylon, or Pebax, and may have a thickness in a range between 5-300 microns, or between 0.0002-0.012 inch. The continuous polymer layer 99 may be an external layer. The metal layer 90 may comprise gold, titanium, platinum, or combinations or alloys thereof. The metal layer 90 may also comprise silver, vanadium, aluminum, nickel, tantalum, zirconium, chromium, silicon, magnesium, niobium, scandium, cobalt, palladium, manganese, molybdenum, alloys thereof, and combinations thereof. Other biocompatible rigid materials or combination of materials can be used.

The metal layer 90 may have a thickness in a range between 0.1-100 microns. The metal layer 90 may be an external layer. Detachable metalized polymer balloons 14 may comprise additional layers 97 of non-metallic coatings, polymers or adhesives, which may be continuous or discontinuous, and which may be internal to the continuous polymer layer 99 or external to the continuous polymer layer 99 and may be internal to the metal layer 90 or external to the metal layer 90, as shown in FIGS. 7.3, 7.4, 7.6, 8C-J, and 9C-J. The additional layers of non-metallic coatings, polymers, or adhesives may comprise polyurethane, silicone, or Parylene. The additional layers 97 of non-metallic coatings, polymers or adhesives may have a thickness of 0.1-100 microns. The additional layers 97 of non-metallic coatings, polymers, or adhesives may be an external layer, an internal layer, or both an external and internal layer. The overall thickness of the wall 30 of detachable metalized polymer balloons 14 may range between 5-300 microns or between 0.0002-0.012 inch. At least a portion of the outer surface of detachable metalized polymer balloons 14 may comprise a rounded, pebbled, or granular surface structure, as shown in FIGS. 10B-D, wherein the pebbles or granules have a surface height of 0.01-10 microns. At least a portion of the outer surface of detachable metalized polymer balloons 14 may comprise metal with a rounded, pebbled, or granular surface structure, wherein the pebbles or granules have a surface height of 0.01-10 microns. At least a portion of the wall 30 of a detachable metalized polymer balloon 14 may be formed by electroplating or electroforming. The electroplated or electroformed metal may be present on at least a portion of the intermediate region 100 of a detachable metalized polymer balloon 14, on at least a portion of the proximal region 110 of the detachable metalized polymer balloon 14, on at least a portion of the distal region 120 of the detachable metalized polymer balloon 14, on at least a portion of the proximal region 110 and intermediate 100 region of the detachable metalized polymer balloon 14, on at least a portion of the distal region 120 and intermediate region 100 of the detachable metalized polymer balloon 14, on at least a portion of the proximal region 110, intermediate region 100, and distal region 120 of the detachable metalized polymer balloon 14. In some embodiments, a fully metallized or fully plated detachable metalized polymer balloon 14 may be provided by plating the entire external surface of the continuous polymer detachable balloon 12 inner layer or base layer 99, producing various sizes and shapes of fully metallized or fully plated detachable metalized polymer balloons 14. In some embodiments, a partially metallized or partially plated detachable metalized polymer balloon 20 may be provided by plating a portion of the external surface of the continuous polymer detachable balloon 12 inner layer or base layer 99, producing various sizes and shapes of partially metallized or partially plated detachable metalized polymer balloons 20.

The metal portion 90 of a detachable metalized polymer balloon 14 may be formed as a wire and configured in a spiral, coil, braid, woven, or straight configuration, as shown in FIGS. 9I-L. The metal wire may be joined to the adjacent polymer layer 99 by a glue or adhesive 95. The metal wire may be present on at least a portion of the intermediate region 100 of a detachable metalized polymer balloon 14, on at least a portion of the proximal region 110 of a detachable metalized polymer balloon 14, on at least a portion of the distal region 120 of a detachable metalized polymer balloon 14, on at least a portion of the proximal region 110 and intermediate region 100 of a detachable metalized polymer balloon 14, on at least a portion of the distal region 120 and intermediate region 110 of a detachable metalized polymer balloon 14, on at least a portion of the proximal region 110, intermediate region 100, and distal region 120 of a detachable metalized polymer balloon 14. The cross-section profile of the metal wire can be circular, oval, square, or rectangular. The metal wire can have a diameter or width of 10-1000 microns. The overall thickness of the wall 30 of detachable metalized polymer balloon 14 may range between 5-1500 microns, or between 0.0002-0.060 inch.

In one example, the metal portion 90 of a detachable metalized polymer balloon 14 is formed as a wire and bonded to the external surface of the continuous polymer layer 99 by a glue or adhesive 95, as shown in FIG. 7.3. In another example, the metal portion 90 of a detachable metalized polymer balloon 14 is formed as a wire and bonded to the external surface of the continuous polymer layer 99 by a glue or adhesive 95, and one or more non-metallic layers comprising a coating or an adhesive 97 are applied to the external surface of the detachable polymer balloon 12 with metal wire, as shown in FIG. 7.6, wherein the coating or an adhesive 97 comprises polyurethane, silicone, or Parylene.

Detachable metalized polymer balloons 14 may possess sufficient strength to maintain an expanded or partially expanded configuration in vivo after separation from a catheter or catheter assembly 5. Detachable metalized polymer balloons 14 may possess sufficient strength to maintain an expanded or partially expanded configuration in vivo after separation from a catheter or catheter assembly 5 when no solid or semi-solid material, not derived from the patient, is present in the central void 115 of the detachable expanded metal balloon 16 after separation from the first and second catheters 173 & 174. Detachable metalized polymer balloons 14 may possess sufficient strength to maintain an expanded or partially expanded configuration in vivo after separation from a catheter or catheter assembly 5 when the detachable metalized polymer balloon 14 is implanted in an unsealed configuration. Detachable metalized polymer balloons 14 may possess sufficient strength to maintain an expanded or partially expanded configuration in vivo after separation from a catheter or catheter assembly 5 when the pressure in the central void 115 or interior volume of the expanded detachable metalized polymer balloon 14 is not greater than a pressure outside the expanded detachable metalized polymer balloon 14.

Detachable metalized polymer balloons 14 may not possess sufficient strength to maintain an expanded or partially expanded configuration in vivo after separation from a catheter or catheter assembly 5. Detachable metalized polymer balloons 14 may not possess sufficient strength to maintain an expanded or partially expanded configuration in vivo after separation from a catheter or catheter assembly 5 when no solid or semi-solid material, not derived from the patient, is present in the central void 115 of the expanded detachable metalized polymer balloon 14 after separation from the first and second catheters 173 & 174. Detachable metalized polymer balloons 14 may not possess sufficient strength to maintain an expanded or partially expanded configuration in vivo after separation from a catheter or catheter assembly 5 when the detachable metalized polymer balloon 14 is implanted in an unsealed configuration. Detachable metalized polymer balloons 14 may not possess sufficient strength to maintain an expanded or partially expanded configuration in vivo after separation from a catheter or catheter assembly 5 when the pressure in the central void 115 or interior volume of the expanded detachable metalized polymer balloon 14 is not greater than a pressure outside the expanded detachable metalized polymer balloon 14.

By using molds and balloon blowing techniques and then applying a layer of metal 90 by electroplating, electroforming, or bonding metal wire, detachable metalized polymer balloons 14 that closely match the size and shape of various vascular structures, biological conduits 900, or biological spaces can be made, including but not limited to saccular aneurysms 320, segments of arteries 317, segments of veins 318, LAAs 800, paravalvular leak paths 808, segments of biological conduits, 900, or particular biological spaces.

According to various embodiments of the partially or fully metallized detachable balloons 14, the metal layer 90 may be present on only a percentage of the wall 30 of the detachable balloon 10 up to a majority of the detachable metalized polymer balloon 14 as desired, as shown in FIGS. 7.1, 7.2, 7.3, 7.4, 7.6, 8A, 8C-J, 9A, and 9C-L. By way of example and not limitation, the metal layer 90 may cover 100% of the main body or intermediate region 100 or less than 100% of the main body or intermediate region 100 of a detachable metalized polymer balloon 14. Similarly, the metal layer 90 may cover 100% of the proximal region 110 or less than 100% of the proximal region 110 of a detachable metalized polymer balloon 14. Similarly, the metal layer 90 may cover 100% of the distal region 120 or less than 100% of the distal region 120 of a detachable metalized polymer balloon 14. The metal layer 90 may cover 1-99% of the detachable metalized polymer balloon 14.

In some embodiments, all or a portion of a detachable metalized polymer balloon 14 of a detachable balloon catheter 1 is non-compliant. In some embodiments, all or a portion of a detachable metalized polymer balloon 14 of a detachable balloon catheter 1 is semi-compliant. In some embodiments, all or a portion of a detachable metalized polymer balloon 14 of a detachable balloon catheter 1 is compliant. In some embodiments, all or a portion of a detachable metalized polymer balloon 14 of a detachable balloon catheter 1 grows <2%, <4%, <6%, <8%, <10%, or >10% when inflated to a pressure of <20 atmospheres.

In some embodiments, the external surface of a metalized polymer detachable balloon 14 of a detachable balloon catheter 1 comprises surface structures, as shown in FIGS. 10B-D. In some embodiments, the external surface of a metalized polymer detachable balloon 14 of a detachable balloon catheter 1 comprises surface structures having a height of 0.01-1 microns. In some embodiments, the external surface of the proximal region 110 of a metalized polymer detachable balloon 14 of a detachable balloon catheter 1 comprises surface structures or surface structures having a height of 0.01-1 microns, while the intermediate region 100 and distal region 120 are smooth or smoother than the proximal region 110. In some embodiments, the external surface of the proximal region 110 of a metalized polymer detachable balloon 14 of a detachable balloon catheter 1 configured for implantation into a saccular aneurysm 320 or LAA 800 comprises surface structures or surface structures having a height of 0.01-1 microns, while the intermediate region 100 and distal region 120 are smooth or smoother than the proximal region 110, as shown in FIG. 10A.

In some embodiments, the external surface of a metalized polymer detachable balloon 14 of a detachable balloon catheter 1 comprises a layer of titanium that is 5-500 angstroms thick. In some embodiments, the external surface of a metalized polymer detachable balloon 14 of a detachable balloon catheter 1 comprises a layer of gold that is 100-10,000 angstroms thick. In some embodiments, the outer layer of a metalized polymer detachable balloon 14 of a detachable balloon catheter 1 comprises a layer of gold that is 0.1-3 microns thick, or 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 microns. In some embodiments, the outer of a metalized polymer detachable balloon 14 of a detachable balloon catheter 1 comprises a layer of gold that is 0.1-3 microns thick and comprises an inner layer made by sputtering or vacuum deposition and an outer layer made by electroplating or electroforming. In some embodiments, the outer of a metalized polymer detachable balloon 14 of a detachable balloon catheter 1 comprises a layer of gold that is 0.1-3 microns thick and comprises an inner layer comprising titanium made by sputtering or vacuum deposition and an outer layer of gold made by electroplating or electroforming.

In some embodiments, the external surface of a metalized polymer detachable balloon 14 of a detachable balloon catheter 1 configured for implantation into a saccular aneurysm 320 or LAA 800 comprises a layer of titanium that is 5-500 angstroms thick. In some embodiments, the external surface of a metalized polymer detachable balloon 14 of a detachable balloon catheter 1 configured for implantation into a saccular aneurysm 320 or LAA 800 comprises a layer of gold that is 100-10,000 angstroms thick.

Detachable balloons 10 may be detachable metal balloons 16, wherein they comprise a continuous layer of metal 90, excluding any proximal and distal openings in the detachable metal balloon 16, as shown in FIGS. 7.1, 8A, and 9A. The continuous metal layer 90 of detachable metal balloons 16 may comprise gold, platinum, or combinations or alloys thereof. The overall thickness of the wall 30 of detachable metal balloons 16 may range between 5-300 microns or between 0.0002-0.012 inch. At least a portion of the outer surface of detachable metal balloons 16 may comprise a rounded, pebbled, or granular surface structure, as shown in FIGS. 10B-D, wherein the pebbles or granules have a surface height of 0.01-10 microns. At least a portion of the wall 30 of a detachable metal balloon 16 may be formed by electroplating or electroforming. At least a portion of the wall 30 of a detachable metal balloon 16 may be formed by electroplating or electroforming. At least a portion of the wall 30 of a detachable metal balloon 16 may have been annealed. In some embodiments a metal balloon 16 may be referred to as an expandable metal structure, a hollow metal structure, or a hollow, expandable metal structure.

Detachable metal balloons 16 may possess sufficient strength to maintain an expanded or partially expanded configuration in vivo after separation from a catheter or catheter assembly 5. Detachable metal balloons 16 may possess sufficient strength to maintain an expanded or partially expanded configuration in vivo after separation from a catheter or catheter assembly 5 when no solid or semi-solid material, not derived from the patient, is present in the central void 115 of the expanded detachable metal balloon 16 after separation from the first and second catheters 173 & 174. Detachable metal balloons 16 may possess sufficient strength to maintain an expanded or partially expanded configuration in vivo after separation from a catheter or catheter assembly 5 when the detachable metal balloon 16 is implanted in an unsealed configuration. Detachable metal balloons 16 may possess sufficient strength to maintain an expanded or partially expanded configuration in vivo after separation from a catheter or catheter assembly 5 when the pressure in the central void 115 or interior volume of the expanded detachable metal balloon 16 is not greater than a pressure outside the expanded detachable metal balloon 16.

Detachable metal balloons 16 may not possess sufficient strength to maintain an expanded or partially expanded configuration in vivo after separation from a catheter or catheter assembly 5. Detachable metal balloons 16 may not possess sufficient strength to maintain an expanded or partially expanded configuration in vivo after separation from a catheter or catheter assembly 5 when no solid or semi-solid material, not derived from the patient, is present in the central void 115 of the expanded detachable metal balloon 16 after separation from the first and second catheters 173 & 174. Detachable metal balloons 16 may not possess sufficient strength to maintain an expanded or partially expanded configuration in vivo after separation from a catheter or catheter assembly 5 when the detachable metal balloon 16 is implanted in an unsealed configuration. Detachable metal balloons 16 may not possess sufficient strength to maintain an expanded or partially expanded configuration in vivo after separation from a catheter or catheter assembly 5 when the pressure in the central void 115 or interior volume of the expanded detachable metal balloon 16 is not greater than a pressure outside the expanded detachable metal balloon 16.

By creating conductive mandrels 740 of various sizes and shapes and then applying a layer of metal 90 by electroplating or electroforming, detachable metal balloons 16 that closely match the size and shape of various vascular structures, biological conduits 900, or biological spaces can be made, including but not limited to saccular aneurysms, 320, segments of arteries 317, segments of veins 318, LAAs 800, paravalvular leak paths 808, segments of biological conduits, 900, or particular biological spaces.

In some embodiments, all or a portion of a detachable metal balloon 16 of a detachable balloon catheter 1 is non-compliant. In some embodiments, all or a portion of a detachable metal balloon 16 of a detachable balloon catheter 1 grows <2% during expansion.

In some embodiments, the external surface of a metal detachable balloon 16 of a detachable balloon catheter 1 comprises surface structures. In some embodiments, the external surface of a metal detachable balloon 16 of a detachable balloon catheter 1 comprises surface structures having a height of 0.01-1 microns. In some embodiments, the external surface the proximal region 110 of a metal balloon 16 of a detachable balloon catheter 1 comprises surface structures or surface structures having a height of 0.01-1 microns, while the intermediate and distal regions 120 are smooth or smoother than the proximal region 110. In some embodiments, the external surface of the proximal region 110 of a metal balloon 16 of a detachable balloon catheter 1 configured for implantation into a saccular aneurysm 320 or LAA 800 comprises surface structures or surface structures having a height of 0.01-1 microns, while the intermediate region 100 and distal region 120 are smooth or smoother than the proximal region 110.

Detachable balloons 10 may be polymer-coated metal balloons 18, wherein they comprise a continuous layer of metal 90, excluding any proximal and distal openings in the detachable polymer-coated metal balloon 18. The continuous metal layer 90 of detachable polymer-coated metal balloons 18 may comprise gold, platinum, or combinations or alloys thereof. Detachable polymer-coated metal balloons 18 may comprise additional layers of non-metallic coatings or polymers 97, which may be continuous or discontinuous, and which may be external to the continuous metal layer 90, internal to the continuous metal layer 90, or both external and internal to the continuous metal layer 90. The additional layers of non-metallic coatings or polymers 97 may comprise polyurethane, silicone, or Parylene. The additional layers of non-metallic coatings, polymers or adhesives 97 may comprise a material that insulates the metal layer 90 from passing an electrical current to the inner or outer surfaces of the detachable polymer-coated metal balloon 18. The additional layers of non-metallic coatings or polymers 97 of detachable polymer-coated metal balloons 18 may have a thickness of 0.1-100 microns. The overall thickness of the wall 30 of polymer-coated metal balloons 18 may range between 5-300 microns, or between 0.0002-0.012 inch. At least a portion of the wall 30 of a polymer-coated metal balloon 18 may be formed by electroplating or electroforming. At least a portion of the wall 30 of detachable polymer-coated metal balloons 18 may have been annealed.

Detachable polymer-coated metal balloons 18 may possess sufficient strength to maintain an expanded or partially expanded configuration in vivo after separation from a catheter or catheter assembly 5. Detachable polymer-coated metal balloons 18 may possess sufficient strength to maintain an expanded or partially expanded configuration in vivo after separation from a catheter or catheter assembly 5 when no solid or semi-solid material, not derived from the patient, is present in the central void 115 of the expanded detachable polymer-coated metal balloon 18 after separation from the first and second catheters 173 & 174. Detachable polymer-coated metal balloons 18 may possess sufficient strength to maintain an expanded or partially expanded configuration in vivo after separation from a catheter or catheter assembly 5 when the detachable polymer-coated metal balloon 18 is implanted in an unsealed configuration. Detachable polymer-coated metal balloons 18 may possess sufficient strength to maintain an expanded or partially expanded configuration in vivo after separation from a catheter or catheter assembly 5 when the pressure in the central void 115 or interior volume of the expanded detachable polymer-coated metal balloon 18 is not greater than a pressure outside the expanded detachable polymer-coated metal balloon 18.

Detachable polymer-coated metal balloons 18 may not possess sufficient strength to maintain an expanded or partially expanded configuration in vivo after separation from a catheter or catheter assembly 5. Detachable polymer-coated metal balloons 18 may not possess sufficient strength to maintain an expanded or partially expanded configuration in vivo after separation from a catheter or catheter assembly 5 when no solid or semi-solid material, not derived from the patient, is present in the central void 115 of the expanded detachable polymer-coated metal balloon 18 after separation from the first and second catheters 173 & 174. Detachable polymer-coated metal balloons 18 may not possess sufficient strength to maintain an expanded or partially expanded configuration in vivo after separation from a catheter or catheter assembly 5 when the detachable polymer-coated metal balloon 18 is implanted in an unsealed configuration. Detachable polymer-coated metal balloons 18 may not possess sufficient strength to maintain an expanded or partially expanded configuration in vivo after separation from a catheter or catheter assembly 5 when the pressure in the central void 115 or interior volume of the expanded detachable polymer-coated metal balloon 18 is not greater than a pressure outside the expanded detachable polymer-coated metal balloon 18.

By creating conductive mandrels 740 of various sizes and shapes, applying a layer of metal 90 by electroplating or electroforming, and then applying one or more layers of non-metallic coatings or polymers 97, detachable polymer-coated metal balloons 18 that closely match the size and shape of various vascular structures, biological conduits, 900, or biological spaces can be made, including but not limited to saccular aneurysms 320, segments of arteries 317, segments of veins 318, LAAs 800, paravalvular leak paths 808, segments of biological conduits 900, or particular biological spaces 904.

In some embodiments, all or a portion of a detachable polymer-coated metal balloon 18 of a detachable balloon catheter 1 is non-compliant. In some embodiments, all or a portion of a detachable polymer-coated metal balloon 18 of a detachable balloon catheter 1 grows <2% during expansion.

In some embodiments, the external surface of a polymer-coated metal detachable balloon 18 of a detachable balloon catheter 1 comprises surface structures. In some embodiments, the external surface of a polymer-coated metal detachable balloon 18 of a detachable balloon catheter 1 comprises surface structures having a height of 0.01-1 microns. In some embodiments, the external surface the proximal region 110 of a polymer-coated metal balloon 18 of a detachable balloon catheter 1 comprises surface structures or surface structures having a height of 0.01-1 microns, while the intermediate region 100 and distal region 120 are smooth or smoother than the proximal region 110. In some embodiments, the external surface the proximal region 110 of a polymer-coated metal balloon 18 of a detachable balloon catheter 1 configured for implantation into a saccular aneurysm 320 or LAA 800 comprises surface structures or surface structures having a height of 0.01-1 microns, while the intermediate region 110 and distal region 120 are smooth or smoother than the proximal region 110.

Detachable balloons 10 may further comprise an expandable metal retention structure 731 to reduce the risk of migration after placement in the lumen of a segment of a vein 318, a LAA 800, or other blood-containing structure, biological conduit 900 or biological space, as shown in FIG. 98B. Such a feature could provide an additional factor of safety when filling or occluding a vein segment 318, for example, because the lumen diameter of veins generally increases in the direction of flow as shown in FIG. 97B. Therefore, device migration in veins 318 is not self-limiting and the device may reach the right atrium, right ventricle, or a branch of a pulmonary artery branch, potentially leading to the symptoms of a pulmonary embolism. In contrast, the lumen diameter of arteries 317 generally decreases in the direction of flow as shown in FIG. 97A. Therefore, device migration in arteries 317 is self-limiting and the use of an expandable metal retention structure 731 may be less critical when filling or occluding an artery segment 317 with a detachable balloon 10, as shown in FIG. 98A.

An expandable metal retention structure 731 may be mounted to either the proximal neck 130 of the detachable balloon 10, as shown in FIGS. 79A and 100-103, or to the distal neck of 140 of the detachable balloon 10, as shown in FIGS. 79B and 80-82. A proximally mounted expandable metal retention structure 731 is favored when the detachable balloon catheter 1 is inserted in the direction of blood flow, whereas a distally mounted expandable metal retention structure 731 is favored when the detachable balloon catheter 1 is inserted in the direction opposite of blood flow. After expansion, the diameter of a portion of the metal retention structure 731 is equal to or greater than the diameter of the expanded detachable balloon 10. As shown in FIG. 98B, a portion of the expandable metal retention structure 731 is configured to make contact with the wall of an artery 317, vein 318, LAA 800, aneurysm 320, biological conduit, 900, or other blood containing space or biological space. The expandable metal retention structure 731 comprises a plurality of elongated ribs 604 or elongated arms 730. In the case of the proximally mounted expandable metal retention structure 731, as shown in FIG. 79A, the expandable metal retention structure 731 may comprise a plurality of elongated ribs 604 extending from both a proximal retention ring 602 and a distal retention ring 606. At least one elongated rib 604 may comprise a barb 608 configured to engage a portion of the wall of an artery 317, vein 318, LAA 800, aneurysm 320, biological conduit 900, or other blood containing space or biological space. In some embodiments, the elongated ribs 604 are biased outward. In the case of the distally mounted expandable metal retention structure 731, as shown in FIG. 79B, the expandable metal retention structure 731 may comprise a plurality of elongated arms 730 extending from a proximal retention ring 602. The free end of at least one elongated arm 730 may comprise a hook 733 configured to engage a portion of the wall of an artery 317, vein 318, LAA 800, aneurysm 320, biological conduit 900, or other blood containing space or biological space.

In some embodiments, the expandable metal retention structure 731 is self-expanding. The retention structure 731 may comprise nitinol or stainless steel. The external diameter of the ring structures when expanded, is in a range from 3-40 mm, and the diameter of the detachable balloon 10, when expanded, is 3-40 mm.

Detachable balloon catheters 1 comprising an expandable metal retention structure 731 may further comprise an outer catheter (also called a "third catheter") 175, as shown in FIGS. 15A-C and 16A-D, wherein a distal portion of the third catheter 175 passes over at least a portion of the expandable retention structure 731 and retains the expandable retention structure 731 in a constrained, compressed, or collapsed configuration, as shown in FIGS. 80A, 81A, 82A, 101A, 102A, and 103A. The third catheter 175 may further comprise a proximal hub. The proximal hub may be configured with a radiographic contrast injection port 177. The distal portion of the third catheter 175 may further comprise side holes, such that at least some of the radiographic contrast that is injected into the port 177 on hub of the third catheter 175 can exit through the side holes. In some embodiments, the distal end of the third catheter 175 can be retracted, while the constrained, compressed, or collapsed retention structure 731 remains fixed in position, resulting in expansion of the retention structure 731, as shown in FIGS. 80B, 81B, 82B, 101B, 102B, and 103B. In some embodiments, the third catheter 175 can be retracted before expansion of the detachable balloon 10. In some embodiments, the third catheter 175 can be retracted after expansion of the detachable balloon 10.

In one embodiment, the retention structure 731 is made of a highly elastic material such as nitinol and comprises a plurality of elongated arms 730 extending distally from a proximal retention ring 602 engaged to the distal neck 140 of the detachable balloon, as shown in FIG. 79B. Such an embodiment of the retention structure 731 is optimized to resist migration of the detachable balloon 10 where blood or other body fluids flow from the distal neck 140 toward the proximal neck 140 of the detachable balloon 10. The distal end of each elongated arm 730 further comprises a hook 733 configured to engage a portion of the wall of an artery 317, vein 318, LAA 800, or other blood-containing structure, biological conduit 900, or biological space when the retention structure 731 is expanded. FIGS. 80A-F, 81A-I, and 82A-I show various sequences of operation of a detachable balloon catheter 1 with such an embodiment of a retention structure 731. During the delivery of a detachable balloon 10 with a retention structure 731 by a detachable balloon catheter 1, the retention structure 731 is compressed by third catheter 175 with a distal marker band 612, as shown in FIGS. 80A, 81A, and 82A. After confirmation of proper positioning, the third catheter 175 is retracted to expand the retention structure 731, as shown in FIGS. 80B, 81B, and 82B. Subsequently, the detachable balloon is expanded, as shown in FIGS. 80C, 81C, and 82C. Optionally, placement of one or more coils or other elongated bodies 720 in the central void 115 of the expanded detachable balloon 10, as shown in FIGS. 81D-F and 82F, provides reinforcement against compression. Optionally, placement of one or more coils or other elongated bodies 720 (either different coils or other elongated bodies 720 or portions of the same coils or other elongated bodies 720 as placed in the central void 115 of the expanded detachable balloon 10), as shown in FIGS. 82D-E, promotes embolic occlusion of the biological space distal to the expanded detachable balloon 10. The expanded detachable balloon 10 is then detached from the first catheter 173, as shown in FIGS. 80D-F, 81G-I, and 82G-I.

In another embodiment, the retention structure 731 is made of a highly elastic material such as nitinol and comprises a plurality of elongated ribs 604 extending from proximal retention ring 602 engaged to the first catheter 173 to a distal retention ring 606 engaged to the proximal neck 130 of the detachable balloon 10, as shown in FIG. 79A. Such an embodiment of the retention structure 731 is optimized to resist migration of the detachable balloon 10 where blood or other body fluids flow from the proximal neck 130 toward the distal neck 130 of the detachable balloon 10. Each elongated rib 604 further comprises barbs 608 configured to engage a portion of the wall of an artery 317, vein 318, LAA 800, or other blood-containing structure, biological conduit 900, or biological space when the retention structure 731 is expanded. FIGS. 101A-F, 102A-J, and 103A-I show various sequences of operation of a detachable balloon catheter 1 with such an embodiment of a retention structure 731. During the delivery of a detachable balloon 10 with a retention structure 731 by a detachable balloon catheter 1, the retention structure 731 is compressed by third catheter 175 with a distal marker band 612, as shown in FIGS. 101A, 102A, and 103A. After confirmation of proper positioning, the third catheter 175 is retracted to expand the retention structure 731, as shown in FIGS. 101B, 102B, and 103B. Subsequently, the detachable balloon is expanded, as shown in FIGS. 101C, 102C, and 103C. Optionally, placement of one or more coils or other elongated bodies 720 in the central void 115 of the expanded detachable balloon 10, as shown in FIGS. 102D-G and 103F, provides reinforcement against compression. Optionally, placement of one or more coils or other elongated bodies 720 (either different coils or other elongated bodies 720 or portions of the same coils or other elongated bodies 720 as placed in the central void 115 of the expanded detachable balloon 10), as shown in FIGS. 103D-E, promotes embolic occlusion of the biological space distal to the expanded detachable balloon 10. The expanded detachable balloon 10 is then detached from the first catheter 173, as shown in FIGS. 101D-F, 102H-J, and 103G-I.

In some embodiments, the external surface of the detachable balloon 10 comprises surface structures. In certain instances, these surface structures increase surface roughness, increase frictional forces between the external surface of a detached balloon and the internal surface of a saccular aneurysm, 320, artery 317, vein 318, LAA 800, paravalvular leak path 808, other blood-containing structure, or biological conduit 900 or space, thereby reducing the risk of movement or migration of the detachable balloon 10 following its deployment. In some embodiments, the surface structures have a height of 0.01-1 micron. In some embodiments, the exterior surface of the detachable balloon 10 comprises a rounded, pebbled, or granular structure.

In some embodiments, the external surface of the detachable balloon 10 comprises a lubricous coating. In certain instances, this lubricous or hydrophilic coating reduces the frictional forces between the external surface of a detachable balloon 10 and the internal surface of a saccular aneurysm 320, artery 317, vein 318, LAA 800, paravalvular leak path 808, other blood-containing structure, or biological conduit 900 or space, thereby reducing the risk of tissue injury during placement and expansion of a detachable balloon 10. In some embodiments, the lubricous or hydrophilic coating is a hydrophilic coating, a Serene™ coating by SurModics, Inc. or an Assist™ coating by BioInteractions Ltd.

Catheter Assemblies

The present disclosure relates to embodiments of a first medical device 1 comprising a detachable balloon 10 and a catheter or catheter assembly 5; as shown in in FIGS. 13A-D, 14A-C, 15A-C, and 16A-D; wherein the detachable balloon 10 is configured for expansion with fluid and detachment from the catheter or catheter assembly 5 in vivo.

The first catheter 173 of the detachable balloon catheter 1 has a proximal end, a lumen configured to accept a second catheter 174, and a distal end that is joined or operably coupled to the proximal region 110 of the detachable balloon 10, as shown in in FIGS. 13C, 14A-C, and 16A-D. In various embodiments, the first catheter 173 is joined to a portion of the proximal neck 130 of a detachable balloon 10, joined to a portion of the proximal neck assembly 135 of the detachable balloon 10, or joined to a tubular segment that is interposed between the first catheter 173 and the proximal neck 130 or proximal neck assembly 135 of the detachable balloon 10.

In some embodiments, an outer layer of the wall of the first catheter 173 comprises a polymer, or comprises Pebax, nylon, polyimide, and PTFE. In some embodiments, an inner layer of the wall of the first catheter 173 comprises a lubricous polymer or comprises PTFE, polyimide, a composite, or mixture of polyimide and PTFE. In some embodiments, the first catheter 173 includes a middle layer comprising metal, wherein the middle layer is located between an outer layer and an inner layer. The metal of the middle layer of the first catheter 173 can be configured as wire, including metal or wire configured in a spiral, coil, braid, woven, or straight pattern, or combinations thereof. In some embodiments, the metal or metal wire comprises nitinol or stainless steel. In some embodiments, the wire is round and has a diameter of 0.0005-0.0030 inch. In some embodiments, the wire is configured in a coil with a pitch of 0.0010-0.0060 inch. In some embodiments, the wire is flat and has a thickness of 0.0005-0.0060 inch and a width of 0.001-0.030 inch. In some embodiments, wherein the wire is configured in a braid, the braid has a picks per inch of length (PPI) of 50-300, and in some embodiments, the wire is wound in a braid in an "under one, over two" pattern. In some embodiments, the proximal portion of the wire in the first catheter 173 is flat, and has a thickness of 0.0005-0.0060 inch and a width of 0.001-0.030 inch, and is configured in a braid configuration with a picks per inch of length of 50-300; and wherein the wire in the distal portion of the first catheter 173 is round, has a diameter of 0.0005-0.0030 inch, and is configured in a coil pattern with a pitch of 0.0010-0.0060 inch.

In some embodiments, the metal or metal wire is absent from the distal segment of the first catheter 173 that is joined to a tubular male structure, a tubular structure comprising a metal that is sensitive to electrolysis or corrosion (also called an "anode") 390, as shown in FIGS. 53A-C and 54A-C, or a heat sensitive tubular structure 410, as shown in FIGS. 64A-D.

In some embodiments, the first catheter 173 comprises a lubricous or hydrophilic coating, including a lubricous or hydrophilic coating that is present on the inner surface, the outer surface, or both the inner and outer surface of the first catheter 173. In some embodiments, the first catheter 173 comprises a Serene coating made by SurModics, Inc. In some embodiments, the lubricious or hydrophilic coating is present on the distal portion of the first catheter 173, but absent from the proximal portion of the first catheter 173.

In some embodiments, the outer layer of the proximal end of the first catheter 173 comprises a material with a Shore durometer hardness of 40-90 D. In some embodiments, the outer layer of the proximal end of the first catheter 173 comprises nylon. In some embodiments, the outer layer of the distal end of the first catheter 173 comprises a material with a Shore durometer hardness of 20-60 D. In some embodiments, the outer layer of the proximal end of the first catheter 173 comprises nylon.

Figure 53:
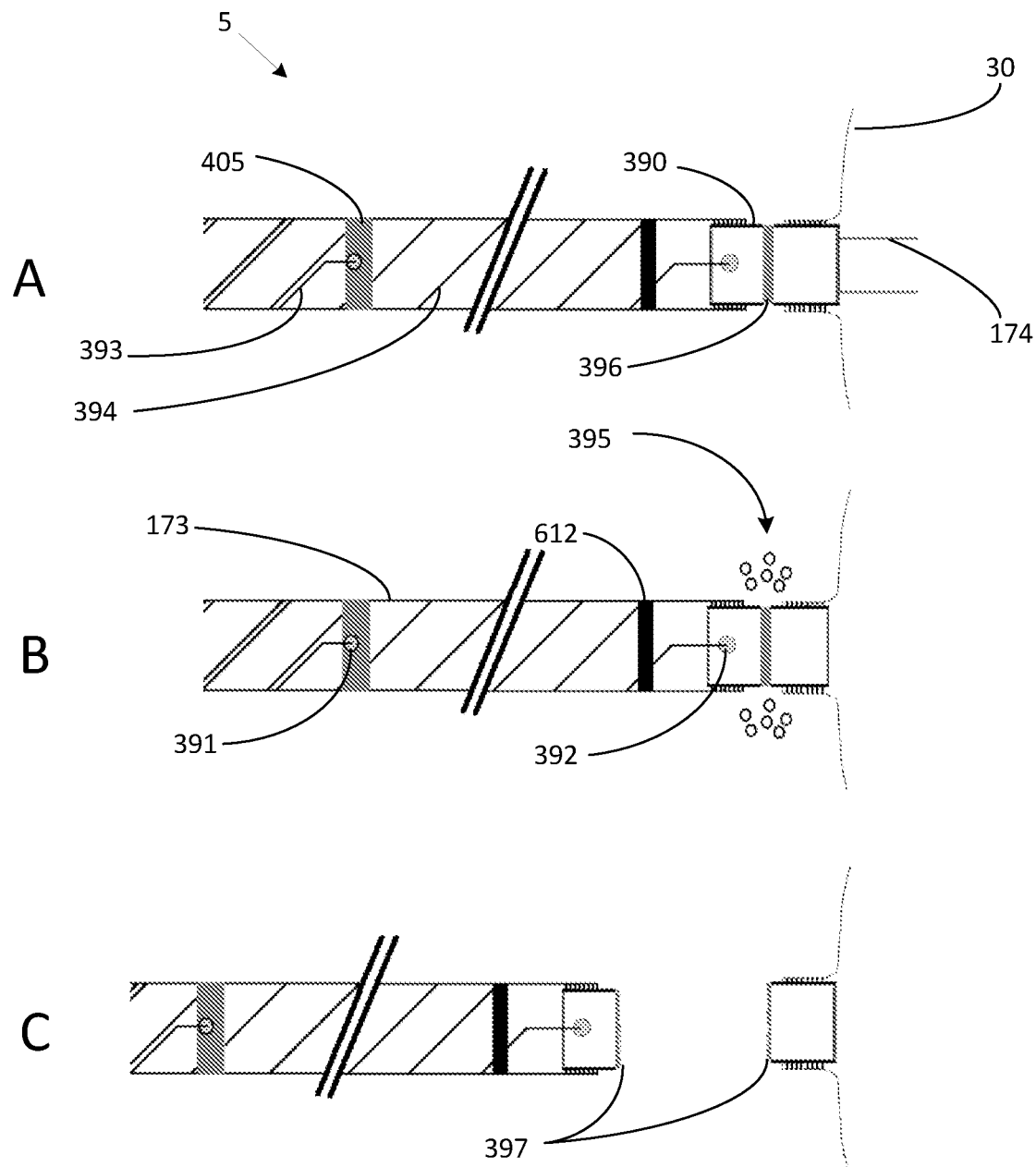
FIGS. 53A-C are planar partial cross-sectional views showing the operation of an electrolytic detachment system according to a first embodiment in which the tubular structure sensitive to electrolysis serving as an anode is bonded within both the balloon proximal neck and the first catheter.
Figure 54:
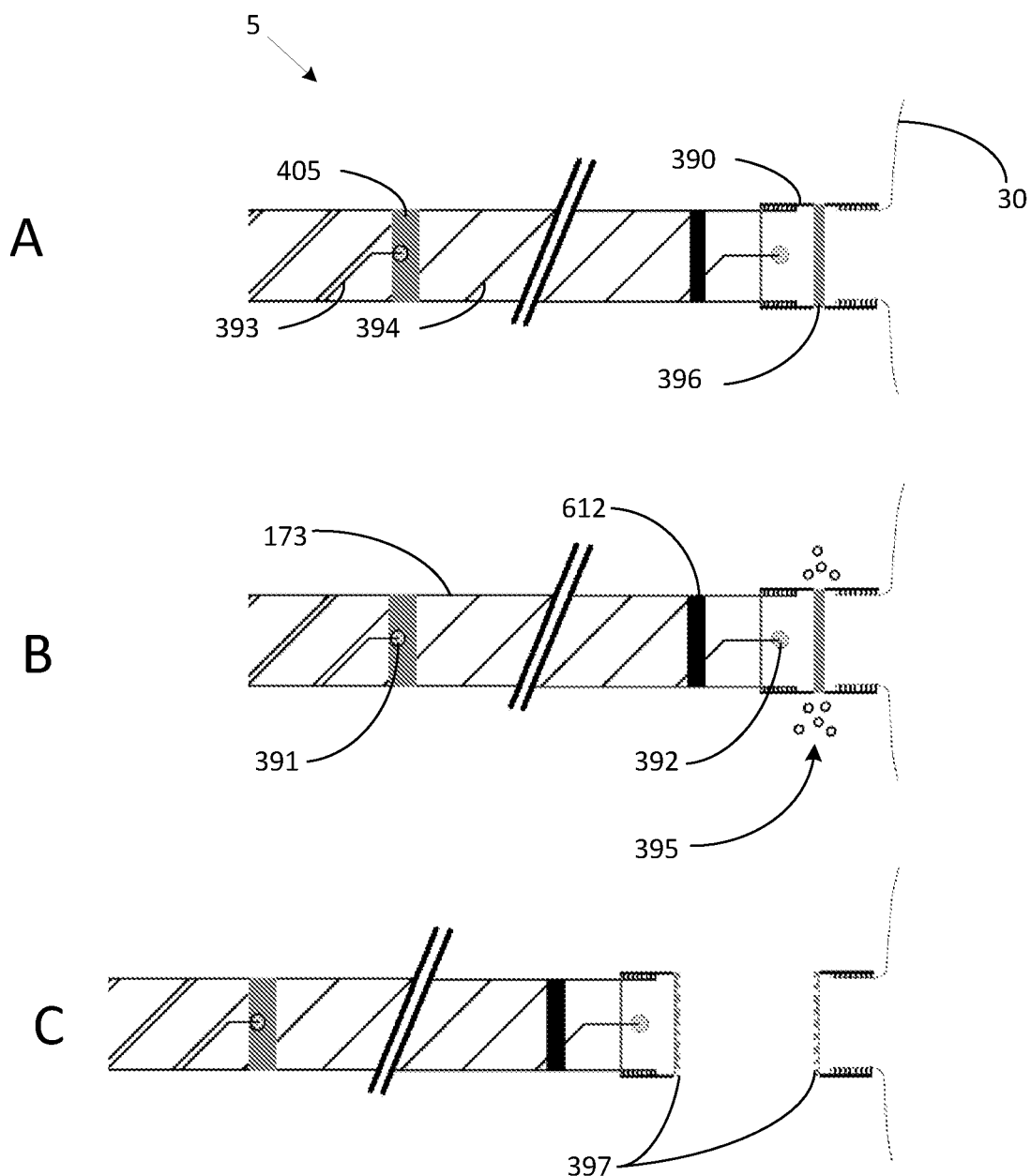
FIGS. 54A-C are planar partial cross-sectional views showing the operation of an electrolytic detachment system according to a second embodiment in which the tubular structure sensitive to electrolysis serving as an anode is bonded to the outside of both the balloon proximal neck and the first catheter.

In some embodiments, the distal end of the first catheter 173 comprises a marker band 612 that is conspicuous during fluoroscopy and is configured to identify the location wherein separation of the expanded balloon and the first catheter 173 is designed to occur, as shown in FIGS. 53B, 54B, and 64A.

In some embodiments, the first catheter 173 comprises a hub and a shaft. In some embodiments, proximal hub of the first catheter 173 comprises a valve, including a Tuohy-Borst adaptor 186 incorporating a valve. In some embodiments, the first catheter 173 comprises a tubular male structure joined to the distal end of the first catheter 173, thereby forming a first catheter assembly, as shown in FIGS. 30A-D, 31A-D, 32A-D, 33A-B, 34A-B, 35A-B, 37A-E, 42A-C, 43, 53A-C, 54A-C, 59A-E, 64A-D, 67A-D, 70A-D, and 74A-E. In some embodiments, an outer surface of a portion of the first catheter 173 or first catheter assembly is joined to a portion of the inner surface of the proximal neck 130 or proximal neck assembly 135 of the detachable balloon 10, as shown in FIGS. 30A-D, 33A-B, 37A-E, 53A-C, 54A-C, 59A-E, 64A-D, 67A-D, 70A-D, and 74A-E. In some embodiments, a portion of the first catheter 173 or first catheter assembly is joined to a portion of the distal neck 140 or distal neck assembly 142 of the detachable balloon. Although not illustrated, this distally joined configuration is structurally and functionally similar to the proximally joined configuration mentioned above. In some embodiments, an outer surface of a portion of the first catheter 173 or first catheter assembly is joined to a portion of the inner surface of the distal neck 140 or distal neck assembly 142 of the detachable balloon.

In some embodiments, the internal or luminal diameter of the first catheter 173 is 0.025-0.068 inch. In some embodiments, the external diameter of the first catheter 173 is 0.031-0.096 inch. In some embodiments, the length of the first catheter 173 is 45-245 cm.

In some embodiments, the wall of the first catheter 173 is continuous from the proximal end to the distal end. In one example, the outer layer of the proximal portion of the first catheter 173 comprises a nylon with a Shore durometer hardness of 40-90 D, the middle portion of the first catheter 173 comprises Pebax with a Shore durometer hardness of 20-60 D, and the distal portion of the first catheter 173 comprises nylon with a Shore durometer hardness of 40-90 D. The distal portion of the first catheter 173 is joined to a portion of the proximal neck 130 or proximal neck assembly 135 of the balloon 10 by a friction fit formed between the outer surface of the first catheter 173 and an elastomeric tubular segment 204 joined or bonded to the proximal neck 130 or proximal neck assembly 135 of the detachable balloon, as shown in FIGS. 30A-D, 31A-D, 33A-B, and 34A-B. In some embodiments, the distal portion of the first catheter 173 or first catheter assembly of a detachable balloon catheter 1 is coupled to the distal neck 140 or distal neck assembly 142 of the detachable balloon and the wall of the segment of the first catheter 173 that passes through the central void 115 or interior volume of the detachable balloon 10 comprises openings for fluid to pass out of the lumen 163 of the second catheter 174. Although not illustrated, this distally joined configuration is structurally and functionally similar to the proximally joined configuration mentioned above. In some embodiments, the proximal hub of the first catheter 173 or first catheter assembly of a detachable balloon catheter 1 comprises a port for the injection of fluids (also called an "inflation port") 176 into the first lumen (also called an "inflation lumen") 162, as shown in FIGS. 13C and 14A-C.

The second catheter 174 of the detachable balloon catheter 1 has a proximal end, a distal end that is open, and a lumen 163 configured to accept a guidewire 40, as shown in FIGS. 13B and 14A-C. In some embodiments, an outer layer of the wall of the second catheter 174 comprises a polymer, or comprises Pebax, nylon, polyimide, or PTFE. In some embodiments, an inner layer of the wall of the second catheter 174 comprises a lubricious polymer, or comprises PTFE, polyimide, a composite, or mixture of polyimide and PTFE. In some embodiments, the second catheter 174 includes a middle layer comprising metal, wherein the middle layer is located between an outer layer and an inner layer. In some embodiments, the middle layer comprising metal is configured as wire. In some embodiments, the middle layer comprising metal is configured in one or more of a spiral, coil, braid, woven, or straight pattern. In some embodiments, the middle layer comprises nitinol or stainless steel. In some embodiments, the wire of the middle layer is round and has a diameter of 0.0005-0.0030 inch. In some embodiments, the wire of the middle layer is configured in a coil with a pitch of 0.0010-0.0060 inch. In some embodiments, the wire of the middle layer is flat and has a thickness of 0.0005-0.0060 inch and a width of 0.001-0.030 inch. In some embodiments, the wire of the middle layer is configured in a braid with a picks per inch of length (PPI) of 50-300, or configured in a braid that is wound in an "under one, over two" pattern. In one example, the wire in the middle layer of the proximal portion of the second catheter 174 is flat, has a thickness of 0.0005-0.0060 inch and a width of 0.001-0.030 inch, and is configured in a braid configuration with a picks per inch of length of 50-300; and the wire in the middle layer of the distal portion of the second catheter 174 is round, has a diameter of 0.0005-0.003 inch, and is configured in a coil pattern with a pitch of 0.0010-0.0060 inch. In some embodiments, the second catheter 174 comprises a lubricious or hydrophilic coating, or comprises a lubricious or hydrophilic coating on the inner surface, the outer surface, or both the inner and outer surface of the second catheter 174. In some embodiments, the lubricious or hydrophilic coating comprises a Serene coating made by SurModics, Inc. In some embodiments, a lubricious or hydrophilic coating is present on the distal portion of the second catheter 174, but absent from the proximal portion of the second catheter 174. In some embodiments, the proximal end of the second catheter 174 comprises a material with a Shore durometer hardness of 40-90 D. In some embodiments, the outer layer of the proximal end of the second catheter 174 comprises nylon. In some embodiments, the outer layer of the proximal end of the second catheter 174 comprises nylon with a Shore durometer hardness of 40-90 D. In some embodiments, the distal end of a second catheter 174 comprises a material with a Shore durometer hardness of 20-60 D, or Pebax with a Shore durometer hardness of 20-60 D. In some embodiments, the distal end of the second catheter 174 comprises a material with a Shore durometer hardness of 40-90 D, or nylon with a Shore durometer hardness of 40-90 D. In some embodiments, the second catheter 174 comprises at least two marker bands 612 that are conspicuous during fluoroscopy and are configured to assist in the passage of coils through the lumen of the second catheter 174 and to assist the detachment of coils that are passed through the lumen of the second catheter 174. In some embodiments, a first marker band 612 is 0.3-1.5 mm from the distal end of the second catheter 174 and a second marker band 612 is 2.0-4.0 mm proximal to the distal end of the second catheter 174. In some embodiments, the internal or luminal diameter of the second catheter 174 is 0.025-0.068 inch. In some embodiments, the internal or luminal diameter of the second catheter 174 is 0.012-0.048 inch. In some embodiments, the external diameter of the second catheter 174 is 0.018-0.068 inch. In some embodiments, the second catheter 174 comprises a hub and a shaft. In some embodiments, the length of the second catheter 174 is 50-250 cm. In some embodiments, the wall of the second catheter 174 is continuous from the proximal end to the distal end. In some embodiments of a detachable balloon catheter 1, the wall of a segment of the second catheter 174 that passes through the central void 115 or interior volume of the balloon comprises openings for fluid to pass out of the lumen of the second catheter 174. In one example, the outer layer of the proximal portion of the second catheter 174 comprises a material with a Shore durometer hardness of 40-90 D and the outer layer of the distal end of the second catheter 174 comprises a material with a Shore durometer hardness of 40-90 D, and wherein the distal end of the second catheter 174 comprising a material with a Shore durometer hardness of 20-60 D is interposed with a segment of material with a Shore durometer hardness of 40-90 D. In another example, the outer layer of the proximal portion of the second catheter 174 comprises nylon with a Shore durometer hardness of 40-90 D and the outer layer of the distal end of the second catheter 174 comprises Pebax with a Shore durometer hardness of 20-60 D, and wherein the Pebax at the distal end of the second catheter 174 is interposed with a segment of nylon with a Shore durometer hardness of 40-90 D. In some embodiments, the distal portion of a second catheter 174 of a detachable balloon catheter 1 is joined or operably coupled to a portion of the one or more elastomeric valves 192 by a friction fit 202. In some embodiments, the distal portion of a second catheter 174 of a detachable balloon catheter 1 is joined or operably coupled to a portion of the one or more elastomeric valves 192 by a friction fit 202, wherein the elastomeric valves 192 are contained within a distal nosecone 191 bonded to the distal neck 140 or the distal neck assembly 142 of the detachable balloon. In some embodiments, the distal portion of a second catheter 174 of a detachable balloon catheter 1 is joined or operably coupled to a portion of the one or more elastomeric valves 192 and spacers 196 & 197 by a friction fit 202. In some embodiments, the distal portion of a second catheter 174 of a detachable balloon catheter 1 is joined or operably coupled to a portion of the one or more elastomeric valves 192 or spacers 196 & 197 by a friction fit 202, wherein the elastomeric valves 192 and spacers 196 & 197 are contained within a distal nosecone 191 bonded to the distal neck 140 or the distal neck assembly 142 of the detachable balloon. In some embodiments, the distal portion of a second catheter 174 of a detachable balloon catheter 1 is joined or operably coupled to a portion of the one or more elastomeric valves 192 by a friction fit 202, wherein the one or more elastomeric valves 192 and the one or more spacers 196 & 197 overlap the segment of material in the second catheter 174 with a Shore durometer hardness of 40-90 D that is interposed into the material in the second catheter 174 with a Shore durometer hardness of 20-60 D. In some embodiments, the distal portion of the second catheter 174 of the detachable balloon catheter 1 is angled. In some embodiments, the angle between the distal portion of the second catheter 174 and the proximal portion of the second catheter 174 of the detachable balloon catheter 1 is 1-70 degrees. In some embodiments, the proximal hub of the second catheter 174 of a detachable balloon catheter 1 is configured for the injection of fluids into the second lumen. In some embodiments, the color of the external surface of a first 173, second 174, or third 175 catheter is configured to help physicians use the device safely. In some embodiments, the color of the most proximal portion of the second catheter 174 could be of one color (the first color), while the more distal portion of the second catheter 174 could be another color (the second color). The length of the most proximal portion would be chosen to correspond to the length from the distal end of the second catheter 174 (as packaged) to the distal end of the male tubular structure 510 or from the distal end of the second catheter 174 (as packaged) to a location 1-10 mm distal to the distal end of the male tubular structure 510, such that while retracting the second catheter 174, if the physician sees the second color then stops retracting to avoid inadvertent detachment of the balloon 510. In some embodiments, a flexible elongated structure could be joined to the hub 179 of the first catheter 173 and the hub 178 of the second catheter 174, such that the extended length of the flexible elongated structure could correspond to the length from the distal end of the second catheter 174 (as packaged) to the distal end of the male tubular structure, or from the distal end of the second catheter 174 (as packaged) to a location 1-10 mm distal to the distal end of the male tubular structure 510, such that while retracting the second catheter 174, the flexible elongated structure prevents the physician from retracting the second catheter 174 too far, risking inadvertent detachment of the balloon 510. To proceed with detachment, the physician could first remove, disconnect, or cut the flexible elongated structure and then retract the second catheter 174 further.

The third catheter 175 of the detachable balloon catheter 1 has a proximal end, a distal end that is open, and a lumen 164 configured to accept a first catheter 173. The inner surface of the third catheter 175 and the outer surface of the first catheter 173 define a third lumen 164 to allow for passage of fluid from the proximal hub 180 of the third catheter 175 to the distal end of the third catheter 175 and into the space adjacent to the distal end of the third catheter 175. In some embodiments, the third lumen 164 is configured for the injection of fluids, including water, saline, radiographic contrast, solutions comprising therapeutic agents or drugs, and mixtures therein. In some embodiments, an outer layer of the wall of the third catheter 175 comprises a polymer, Pebax, nylon, polyimide, or PTFE. In some embodiments, an inner layer of the wall of the third catheter 175 comprises a lubricious polymer, PTFE, polyimide, or a composite, or mixture of polyimide and PTFE. In some embodiments, the third catheter 175 comprises a middle layer comprising metal, wherein the middle layer is located between an outer layer and an inner layer. In some embodiments, the metal of the middle layer is configured as wire. In some embodiments, the metal wire of the middle layer is configured in spiral, coil, braid, woven, or straight pattern. In some embodiments, the metal or metal wire of the middle layer comprises nitinol or stainless steel. In some embodiments, the metal wire of the middle layer is round and has a diameter of 0.0005-0.0030 inch. In some embodiments, the metal wire of the middle layer is configured in a coil with a pitch of 0.0010-0.0060 inch. In some embodiments, the metal wire of the middle layer is flat and has a thickness of 0.0005-0.0060 inch and a width of 0.001-0.030 inch. In some embodiments, the metal wire of the middle layer is configured in a braid with a "picks per inch" of length (PPI) of 50-300, including a braid wound in an "under one, over two' pattern. In one example, the wire in the proximal portion of the third catheter 175 is flat, has a thickness of 0.0005-0.0060 inch and a width of 0.001-0.030 inch, and is configured in a braid configuration with a picks per inch of length of 50-300; and the wire in the distal portion of the third catheter 175 is round, has a diameter of 0.0005-0.003 inch, and is configured in a coil pattern with a pitch of 0.0010-0.0060 inch. In some embodiments, the third catheter 175 comprises a lubricious or hydrophilic coating that is present on the inner surface, the outer surface, or both the inner and outer surface of the third catheter 175. In some embodiments, the third catheter 175 comprises a Serene coating made by SurModics, Inc. In some embodiments, a lubricious or hydrophilic coating is present on the distal portion of the third catheter 175, but absent from the proximal portion of the third catheter 175. In some embodiments, the proximal end of the third catheter 175 comprises a material with a Shore durometer hardness of 40-90 D. In some embodiments the outer layer of the proximal end of the third catheter 175 comprises nylon. In some embodiments, the outer layer of the proximal end of the third catheter 175 comprises nylon with a Shore durometer hardness of 40-90 D. In some embodiments, the distal end of the third catheter 175 comprises a material with a Shore durometer hardness of 20-60 D. In some embodiments, the outer layer of the distal end of the third catheter 175 comprises Pebax. In some embodiments, the outer layer of the distal end of the third catheter comprises Pebax with a Shore durometer hardness of 40-90 D. In some embodiments, the distal end of the third catheter 175 comprises a marker band 612 that is conspicuous during fluoroscopy and is configured to identify the location of the tip of the third catheter 175. In some embodiments, the internal or luminal diameter of the third catheter 175 is 0.033-0.098 inch. In some embodiments, the external diameter of the third catheter 175 is 0.039-0.114 inch. In some embodiments, the third catheter 175 comprises a proximal hub 180 and a shaft. In some embodiments, the length of the third catheter 175 is 40-235 cm. In some embodiments, the wall of the third catheter 175 is continuous from the proximal end to the distal end. In some embodiments, the wall of a distal portion of the third catheter 175 comprises openings for the fluid to pass out of the lumen 164 of the third catheter 175.

In some embodiments, a detachable balloon catheter 1 comprises a detachable balloon 10 and a catheter assembly 5. In some embodiments of a detachable balloon catheter 1 comprising a catheter assembly 5, a first lumen is defined by an annular gap between an inner surface of the first catheter 173 and an outer surface of the second catheter 174. In some embodiments of a detachable balloon catheter 1 comprising a catheter assembly 5, a fluid communication can be made between the proximal hub 179 of the first catheter 173, the first lumen 162, and the central void 115 or interior volume of the balloon. In some embodiments of a detachable balloon catheter 1 comprising a catheter assembly 5, the internal diameter of the first catheter 173 is 0.003-0.012 inch larger than the outer diameter of the second catheter 174. In some embodiments of a detachable balloon catheter 1 comprising a catheter assembly 5, a second lumen 163 is defined by the inner surface of the second catheter 174. In some embodiments of a detachable balloon catheter 1 comprising a catheter assembly 5, a fluid communication can be made between the proximal hub 178 of the second catheter 174 and space adjacent to the distal end of the second catheter 174. In some embodiments of a detachable balloon catheter 1 comprising a catheter assembly 5, a portion of the second catheter 174 is inserted through the one or more elastomeric or resilient valves 192. In some embodiments of a detachable balloon catheter 1 comprising a catheter assembly 5, an external surface of a portion of the second catheter 174 is in contact with the inner surface of the one or more elastomeric valves 192. In some embodiments of a detachable balloon catheter 1 comprising a catheter assembly 5, the one or more elastomeric valves 192 seal against the second catheter 174. In some embodiments of a detachable balloon catheter 1 comprising a catheter assembly 5, the second catheter 174 is longer than the first catheter 173. In some embodiments of a detachable balloon catheter 1 comprising a catheter assembly 5, a second catheter 174 is longer than a first catheter 173, and a first catheter 173 is longer than a third catheter 175. In some examples of a detachable balloon catheter 1 comprising a catheter assembly 5, the wall of a first catheter 173 is continuous from the proximal end to the distal end and the wall of the second catheter 174 is continuous from the proximal end to the distal end. In some embodiments of a detachable balloon catheter 1 comprising a catheter assembly 5, the wall of the first catheter 173 is continuous and the wall of the segment of the second catheter 174 that passes through the central void 115 or interior volume of the balloon 10 comprises openings for fluid to pass out of the lumen 162 of the second catheter 174. In some embodiments of a detachable balloon catheter 1 comprising a catheter assembly 5, the proximal hub 178 of the second catheter 174 is proximal to the proximal hub 179 of the first catheter 173, a portion of the second catheter 174 passes through the lumen 162 of the first catheter 173, and the distal end of the second catheter 174 is distal to the distal end of the first catheter 173. In some embodiments of a detachable balloon catheter 1 comprising a catheter assembly 5, a portion of the second catheter 174 passes through a valve or a Tuohy-Borst adaptor 186 with a valve that is joined to the hub 179 of the first catheter 173. In some embodiments of a detachable balloon catheter 1 comprising a catheter assembly 5, an outer surface of a portion of the second catheter 174 makes contact with an inner surface of the valve. In some embodiments of a detachable balloon catheter 1 comprising a catheter assembly 5, a portion of the second catheter 174 is received within the distal neck 140 of the balloon 10. In some embodiments of a detachable balloon catheter 1 comprising a catheter assembly 5, a portion of the second catheter 174 passes through the distal neck 140 of the balloon 10. In some embodiments of a detachable balloon catheter 1 comprising a catheter assembly 5, the internal diameter of the distal neck 140 of the balloon 10 is 0.001, 0.002, 0.003, or 0.004 inch larger than the external diameter of the second catheter 174. In some embodiments of a detachable balloon catheter 1 comprising a catheter assembly 5, a portion of the second catheter 174 is received within a ring structure, tubular structure, telescoping structure, catheter segment, or telescoping catheter segment 185 joined to the distal balloon neck 140. In some embodiments of a detachable balloon catheter 1 comprising a catheter assembly 5, a portion of the second catheter 174 is inserted through a ring structure, tubular structure, telescoping structure, catheter segment, or telescoping catheter 185 joined to the distal balloon neck 140. In some embodiments of a detachable balloon catheter 1 comprising a catheter assembly 5, the internal diameter of the ring structure, tubular structure, telescoping structure, catheter segment, or telescoping catheter segment 185 joined to the distal neck 140 of the balloon 10 is 0.001-0.004 inch larger than the external diameter of the second catheter 174. In some embodiments of a detachable balloon catheter 1 comprising a catheter assembly 5, the length of the ring structure, tubular structure, telescoping structure, catheter segment, or telescoping catheter segment joined to the distal neck 140 of the balloon 10 is 0.3-6.0 mm.

In some embodiments of a detachable balloon catheter 1 comprising a catheter assembly 5, the proximal hub of the third catheter 175 can be joined to the proximal hub 179 of the first catheter 173. In some embodiments of a detachable balloon catheter 1 comprising a catheter assembly 5, the engagement or joining of the proximal hubs 179 & 180 of the first and third catheters 173 & 175 prevents or reduces leaking during injection of fluid into the third lumen 164. In some embodiments of a detachable balloon catheter 1 comprising a catheter assembly 5, once joined, the proximal hub 180 of the third catheter 175 and the proximal hub 179 of the first catheter 173 can be separated or can be separated after rotating a lock. In some embodiments of a detachable balloon catheter 1 comprising a catheter assembly 5, the third catheter 175 can be moved forward or backward while the first catheter 173 remains fixed in position. In some embodiments of a detachable balloon catheter 1 comprising a catheter assembly 5, when the proximal hub 180 of the third catheter 175 and the proximal hub 179 of the first catheter 173 are separated, the third catheter 175 can be moved forward or backward while the first catheter 173 remains fixed in position. In some embodiments of a detachable balloon catheter 1 comprising a catheter assembly 5, when the proximal hub 180 of the third catheter 175 and the proximal hub 179 of the first catheter 173 are separated, the proximal hub 180 of the third catheter 175 comprises a valve to prevent leaking during injection of fluids into the third lumen. In some embodiments of a detachable balloon catheter 1 comprising a catheter assembly 5, the proximal hub 180 of the third catheter 175 comprises a Tuohy-Borst adaptor 186 with a valve. In some embodiments of a detachable balloon catheter 1 comprising a catheter assembly 5, the first portions of the first and second catheters 173 & 174 pass through the valve or Tuohy-Borst adaptor 186 of the third catheter 175. In some embodiments of a detachable balloon catheter 1 comprising a catheter assembly 5, the external surface of a portion of the first catheter 173 makes contact with an inner surface of the valve. In some embodiments of a detachable balloon catheter 1 comprising a catheter assembly 5, the proximal hub 179 of the first catheter 173 and the proximal hub 178 of the second catheter 174 are proximal to the proximal hub 180 of the third catheter 175. In some embodiments of a detachable balloon catheter 1 comprising a catheter assembly 5, portions of the first and second catheters pass 173 & 174 through the proximal hub 180 of the third catheter 175. In some embodiments of a detachable balloon catheter 1 comprising a catheter assembly 5, portions of the first and second catheters 173 & 174 pass through the lumen 164 of the third catheter 175. In some embodiments of a detachable balloon catheter 1 comprising a catheter assembly 5, portions of the first and second catheters 173 & 174 are distal to the distal end of the third catheter 175. In some embodiments, the proximal hub 180 of the third catheter 175 of a detachable balloon catheter 1 comprises a port 177 for the injection of fluids into the third lumen 164.

Attachment/Detachment Systems

The present disclosure relates to medical devices 1 comprising a detachable balloon 10 and a catheter or catheter assembly 5, wherein the detachable balloons 10 are configured for detachment from the catheter or catheter assembly 5 in vivo. In some embodiments, a distal end of the first catheter assembly and a portion of a proximal neck assembly 135 of the balloon combine to form a mechanical attachment 500 between the first catheter 173 and the balloon 10, as shown in FIGS. 17A-C, 18A-D, 19A-G, 20A-E, 21A-E, 26A-H, 27, 28A-G, and 29. The mechanical attachment is configured to be engaged when the second catheter 174 passes through the attachment site, as shown in FIGS. 17A, 18A, and 20A-C, and is configured to be disengaged when the second catheter 174 is removed from the attachment site, as shown in FIGS. 17B-C, 18B-D, and 20D-E.

In some embodiments, the detachable balloon 10 is operably coupled and decoupled from the first catheter 173 by the opening and closing of a mechanical latch 500, as shown in FIGS. 17A-C, 18A-D, and 20A-E. The mechanical latch 500 comprises a tubular male structure 510 bonded to the distal end of the first catheter 173. The tubular male structure 510 defines a detachable assembly lumen extending from a male proximal end 506 to a male distal end 508, as shown in FIGS. 26A-H and 27. The male distal end 508 comprises at least one movable arm 512 having a distal tab 513 projecting radially outward from an exterior surface. Between the arms 512 are longitudinal recesses 514 to allow fluid to allow fluid to flow radially through the tubular male structure 510. By way of example and not limitation, nominal dimensions, along with allowable and preferred ranges of dimensions, for various potential embodiments of the tubular male structure 510 described in FIGS. 26A-H are presented in tabular form in FIG. 27. The mechanical latch 500 further comprises a tubular female structure 520 bonded to a proximal neck 130 or proximal neck assembly 135 of the balloon. The tubular female structure 520 defines a second detachable assembly lumen extending from a female proximal end 524 to a female distal end 528, as shown in FIGS. 28A-G and 29. By way of example and not limitation, nominal dimensions, along with allowable and preferred ranges of dimensions, for various potential embodiments of the tubular female structure 510 described in FIGS. 28A-G are presented in tabular form in FIG. 29.

The male tubular structure may also have two arms and tabs, four arms and tabs, five arms and tabs, or six arms and tabs. 528. The second catheter 174 of the detachable balloon catheter 1 is configured such that the tubular male structure 510 can be fixed to the tubular female structure 520 in one configuration, and wherein, in a second configuration, the tubular male structure 510 is free to move relative to the tubular female structure. 520. When the tubular male structure 510 is received within the second detachable assembly lumen of the tubular female structure 520 and a portion of the shaft of the second catheter 174 is received within the first detachable assembly lumen of the male structure, the second catheter 174 exerts a radially outward force on the at least one arm of the tubular male structure 510 resulting in an engaged configuration wherein the tubular male structure 510 is joined to the tubular female structure. 520. When the tubular male structure 510 is received within the second detachable assembly lumen of the tubular female structure 520 and the shaft of the second catheter 174 is withdrawn from within the first detachable assembly lumen of the male structure, the detachable assembly changes from an engaged to a disengaged configuration and the assembly of the first catheter 173 and the tubular male structure 510 can be separated from the assembly of the tubular female structure 520 and the proximal neck 130 of the balloon, and the first catheter 173 and the balloon 10 can be pulled apart. In some embodiments, the internal diameter of the female tubular structure 520 is 0.0005, 0.001, 0.002, or 0.003 inch larger than the external diameter of the male tubular structure 510, and the male tubular structure and female tubular structure 510 & 520 are capable of engaging in a slip-fit engagement. In some embodiments, the male tubular structure 510 and female tubular structure 520 are made by machining, casting, or other suitable methods. In some embodiments, the proximal end of the female tubular structure 520 comprises an annular flange 526. In some embodiments, In the male tubular structure 510 comprises one or more depth stop projections extending from an exterior surface and the annular flange 526 of the female tubular structure 520 defines one or more corresponding depth stop recesses 514, wherein the depth stop projections of the male tubular structure 510 are received in the depth stop recesses 514 of the female tubular structure 520 to limit insertion of the male structure 510 in the female structure 520. In some embodiments, the depth stop projections of the male tubular structure 510 and the corresponding depth stop recesses 514 of the female tubular structure 520 are operatively engaged, and wherein rotation of the male structure 510 rotates the female structure 520. In some embodiments, the male tubular structure 510 comprises metal, radiopaque metal, nitinol, stainless steel, platinum, iridium, gold, silver, titanium, or combinations or alloys thereof. In some embodiments, the female tubular structure 520 comprises a metal, a radiopaque metal, platinum, iridium, gold, silver, stainless steel, nitinol, titanium, or alloys or combinations thereof. In some embodiments, the male tubular structure 510 comprises two movable arms 512. In some embodiments, the two movable arms 512 are disposed at antipodal points of the distal end of the male tubular structure 510. In some embodiments, the male tubular structure 510 comprises three movable arms 512. In some embodiments, the three movable arms 512 are disposed at equidistant points of the distal end 508 of the male tubular structure 510. In some embodiments, at least one movable arm 512 of the tubular male structure 510 is biased inwards when the detachable assembly is in the disengaged configuration. In some embodiments, at least one movable arm 512 of the tubular male structure 510 is biased inwards when the detachable assembly is in the disengaged configuration and is displaced outward radially when the detachable assembly is in the engaged configuration. When the detachable assembly is in the engaged configuration, at least a portion of at least one distal tab 513 of a movable arm 512 of the tubular male structure 510 extends distally beyond at least a portion of the distal end 528 of the female tubular structure 520, and at least a portion of one distal tab 513 of at least one movable arm 512 of the tubular male structure 510 extends radially beyond at least a portion of the outer surface of the female tubular structure 520, thereby retaining the male tubular structure 510 within the female tubular structure 520. When the second catheter 174 is withdrawn from within the first detachable assembly lumen of the male structure and the detachable assembly changes from an engaged to a disengaged configuration, the assembly of the first catheter and the tubular male structure 510 can be separated from the assembly of the proximal neck 130 of the balloon 10 and the tubular female structure 520 by pulling the first catheter 173 and the balloon 10 apart.

In some embodiments, internal or luminal diameter of the tubular male structure 510 is 0.025-0.068 inch. In some embodiments, the external diameter of the tubular male structure 510 is 0.028-0.093 inch. In some embodiments, the internal the external diameter of the tubular female structure 520 is 0.031-0.096 inch.

In one embodiment, the attachment and detachment assembly for a detachable balloon catheter 1 includes mated parts. The male tubular structure is received within the female tubular structure. The male tubular structure is a generally tubular structure having a wall that defines a lumen or conduit. The lumen extends from a proximal end of the male tubular structure 510 to the distal end. The lumen is dimensioned to receive the mobile second catheter 174 while also providing a conduit for fluid through the detachment assembly for inflation of the detachable balloon. The male and female tubular structures, are machined with close tolerances to engage each other in a slip-fit engagement.

The proximal end of the male tubular structure is received in and bonded to a distal end of the delivery device. The distal end of the male tubular structure is defined by two or more fingers 513, which may have different lengths in various embodiments. Each finger 513 having an outwardly-oriented projection that extends beyond the outer diameter of the wall. Among others, the fingers 513 are biased inward towards the central axis of the male tubular structure. As such, the projections generally do not extend beyond the outer diameter of the wall without application of a radially outward force. To retain the male tubular structure to the female tubular structure, the radially outward force is provided by the mobile second catheter 174 when disposed within the assembly. In one aspect, the mobile second catheter 174 directly exerts a radially outward force on at least one of the fingers 513. Other embodiments of the male tubular structure, also include support bars 516 positioned between the fingers 513. The support bars 516 aid in the alignment of the male tubular structure 510 and the female tubular structure 520, as well as preventing the guidewire 40 from becoming entangled in the detachment assembly, when the second catheter 174 is withdrawn.

The wall also includes one or more depth stop projections that engage complimentary recesses 514 in the proximal face of the female tubular structure. In addition to limiting insertion of the male tubular structure into the female tubular structure, the depth stop projections also permit rotation of the female tubular structure and detachable balloon, when the delivery device is rotated. In various embodiments, the male tubular structure is constructed of nitinol or stainless steel. When the mechanical latch is mated, the annular shoulder of the male component contacts the annular shoulder of the female component, among others, allowing the transmission of axial compressive force from the first catheter 173 to the proximal neck 130 of the detachable balloon 10.

The female tubular structure 520 includes a tubular wall defining a lumen that is dimensioned to receive the male tubular structure. The proximal end of the female tubular structure includes an annular flange that defines the one or more recesses 514. The distal end of the female tubular structure is bonded to the proximal neck 130 of the detachable balloon. In various embodiments, the female tubular structure is composed of a radiopaque metal including but not limited to platinum, rhodium, or alloys thereof.

Figure 17:
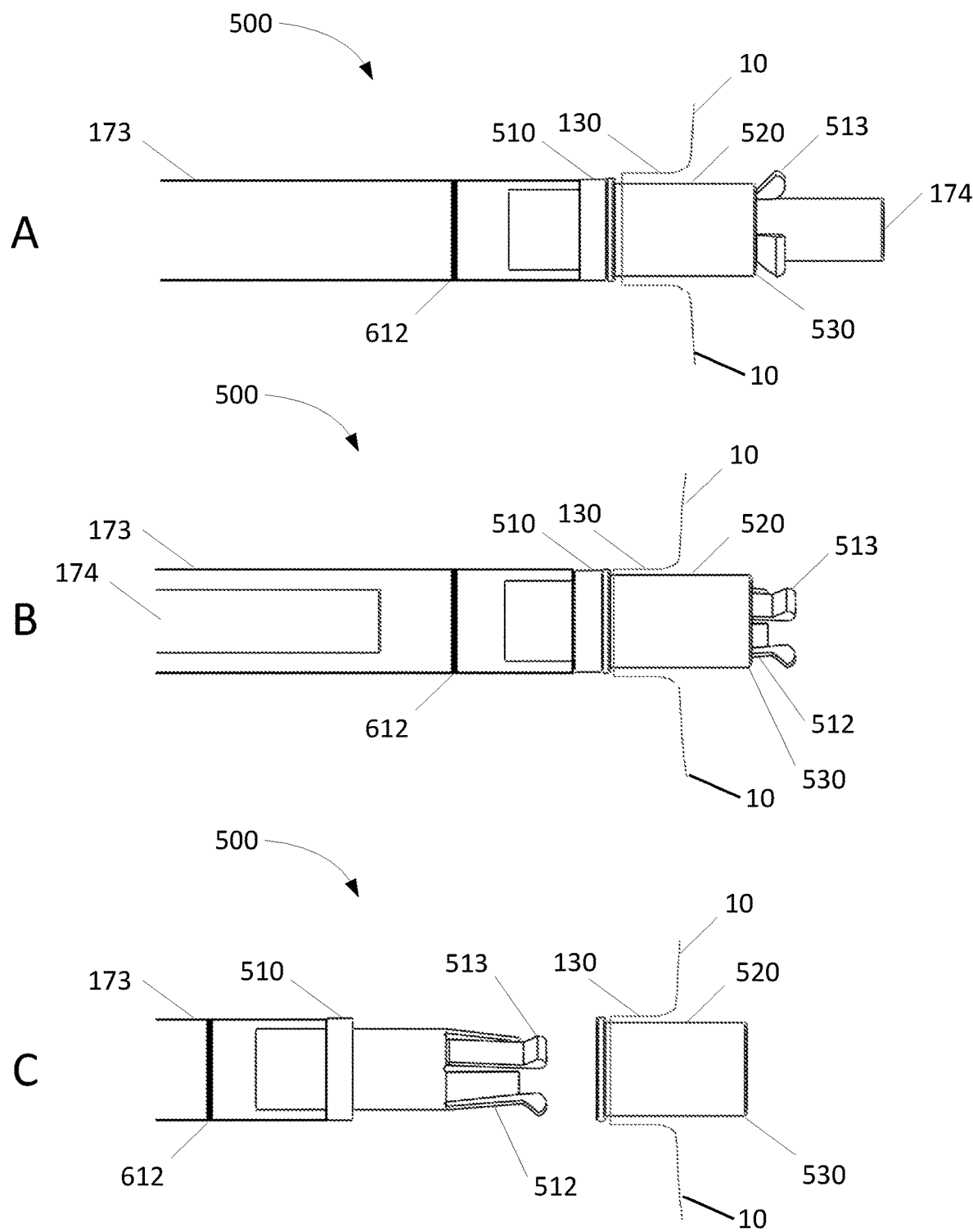
FIGS. 17A-C are partial cross-sectional views showing the operation of a mechanical latch attachment system with the guidewire previously retracted, according to one embodiment.
Figure 18:
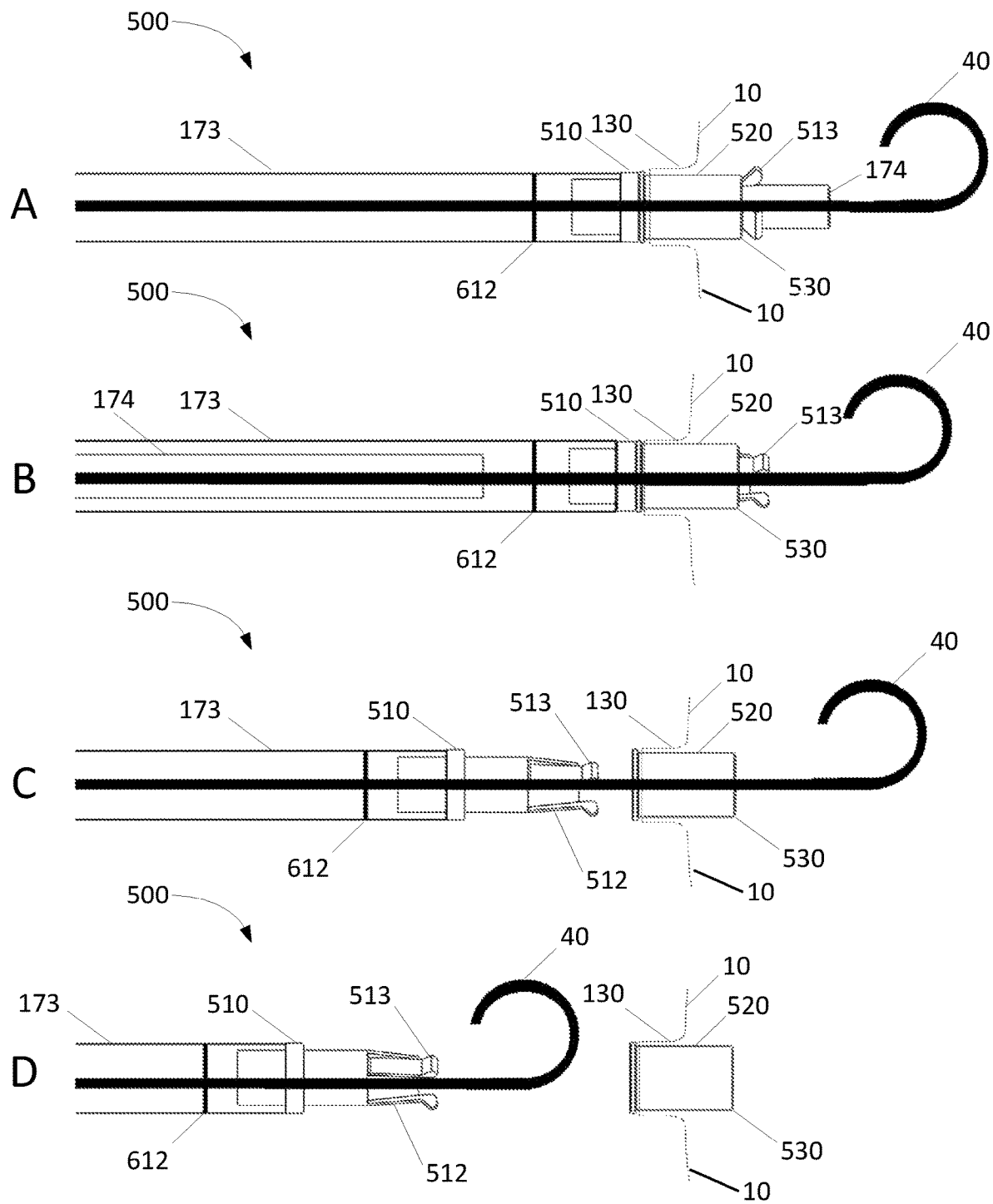
FIGS. 18A-D are partial cross-sectional views showing the operation of a mechanical latch attachment system with the guidewire remaining inserted, according to one embodiment.
Figure 19:
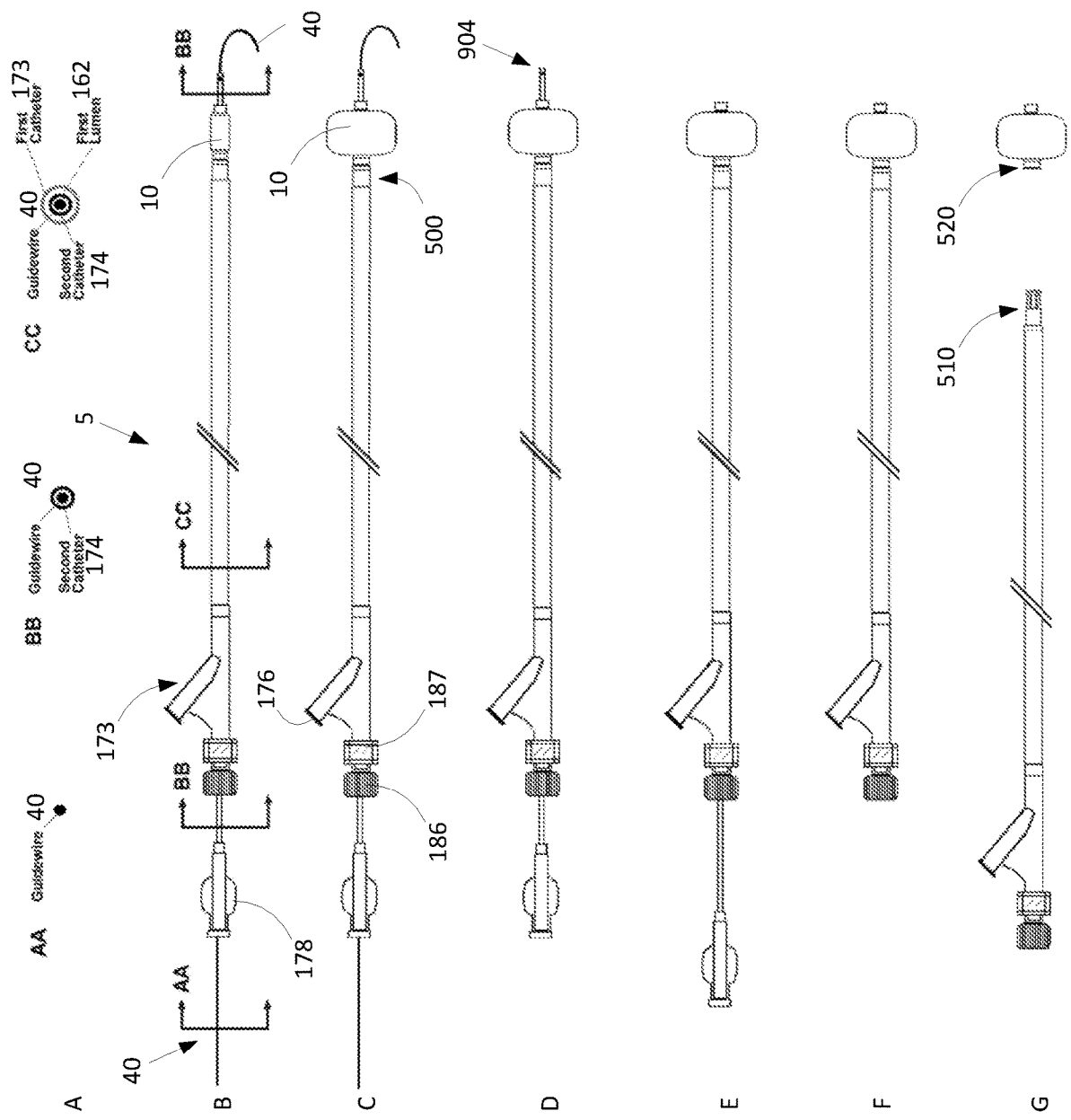
FIGS. 19A-G are planar views showing a first sequence of operation of a mechanical latch attachment system according to one embodiment.
Figure 20:
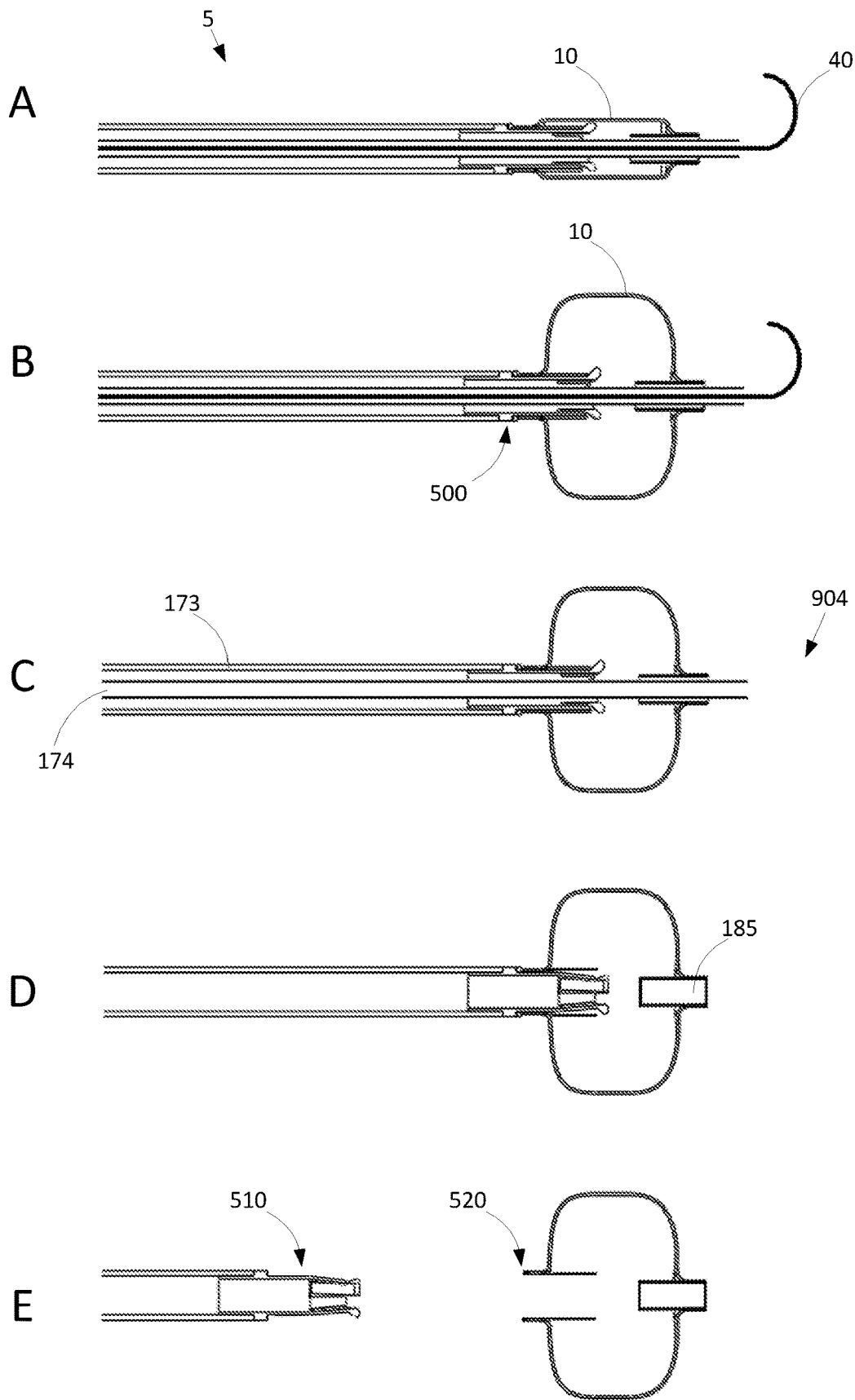
FIGS. 20A-E are cross-sectional detail views showing a first sequence of operation of a mechanical latch attachment system according to one embodiment.
Figure 21:
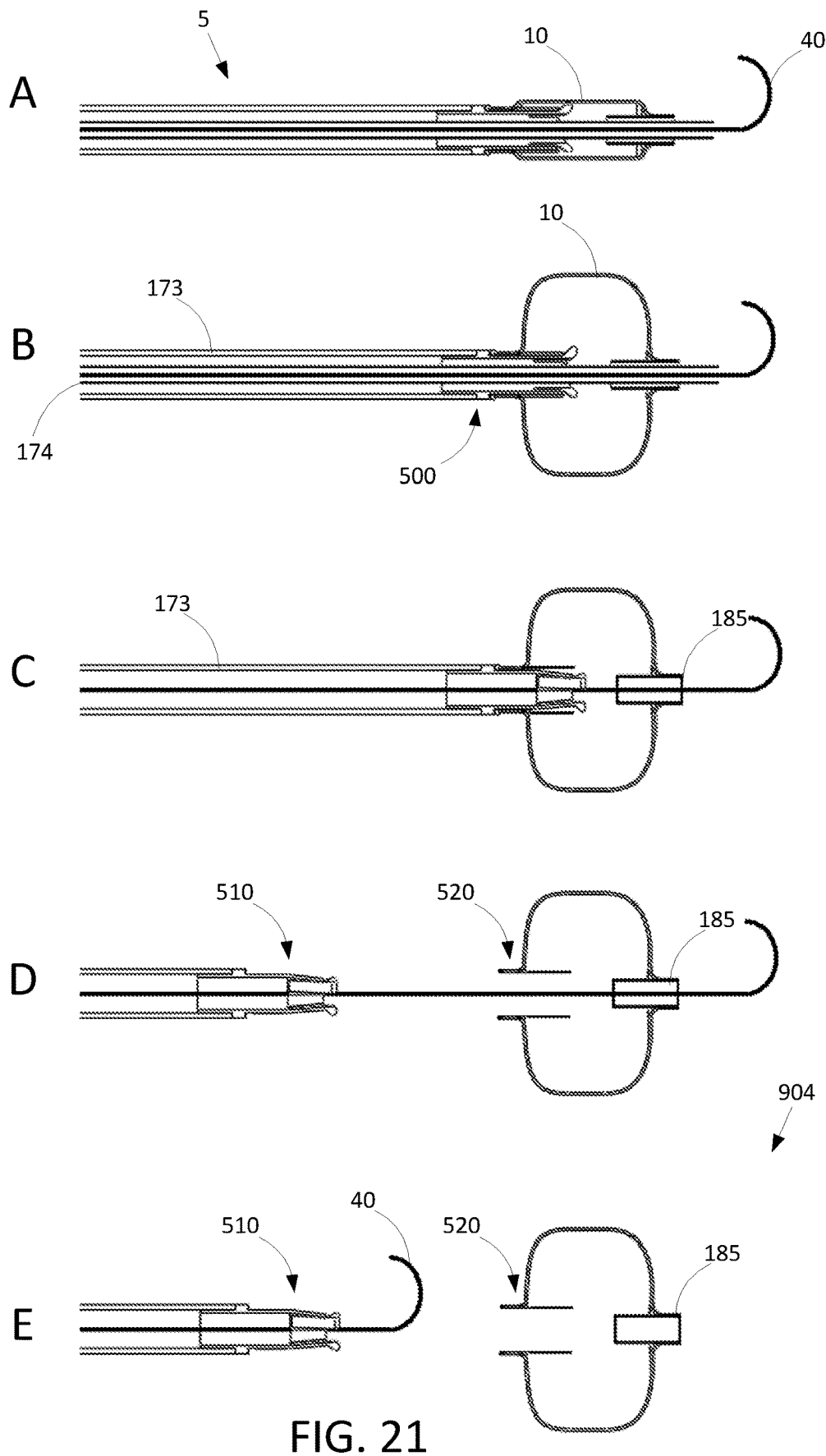
FIGS. 21A-E are cross-sectional detail views showing a second sequence of operation of a mechanical latch attachment system according to one embodiment.
Figure 22:
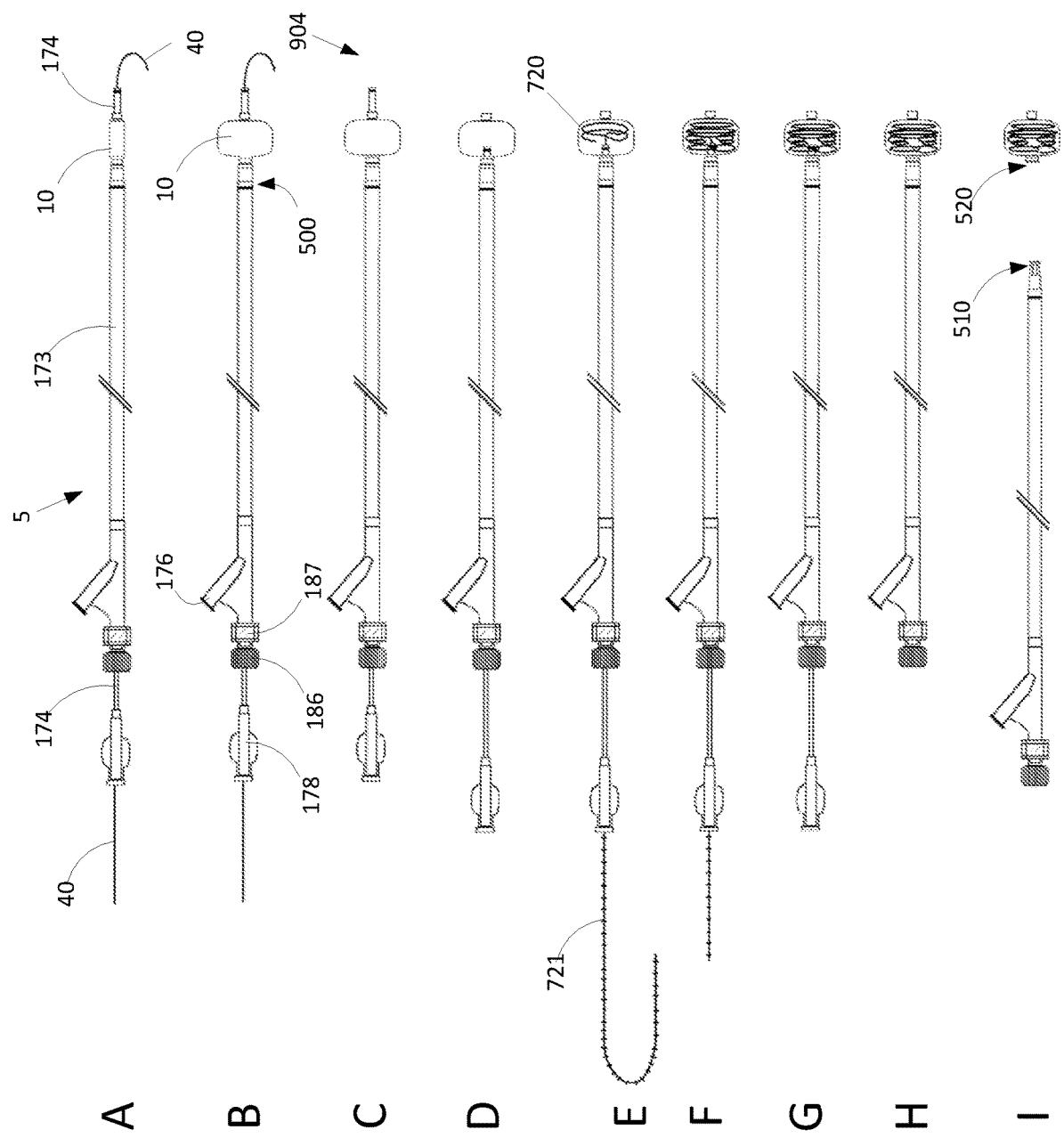
FIGS. 22A-I are planar views showing a third sequence of operation of a mechanical latch attachment system according to one embodiment.
Figure 23:
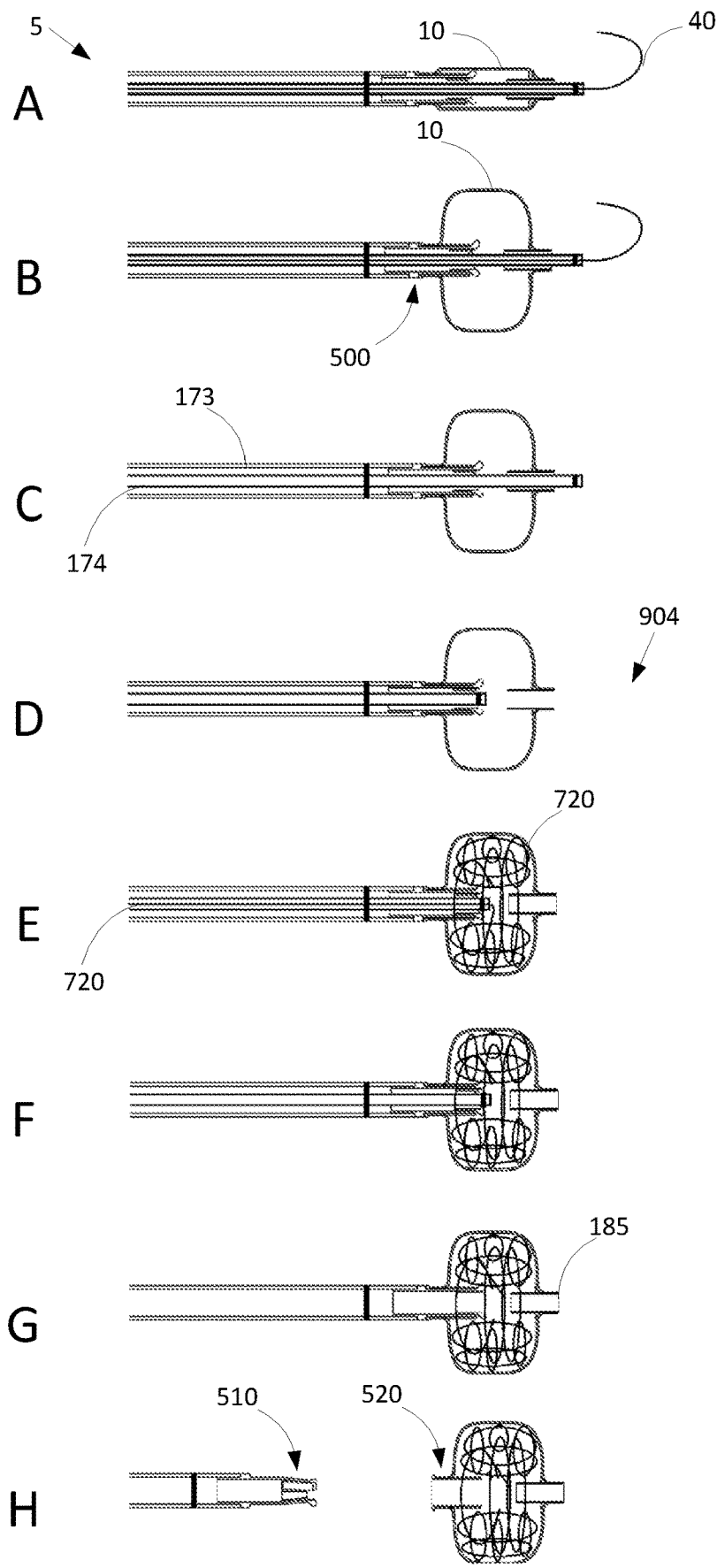
FIGS. 23A-H are cross-sectional detail views showing a third sequence of operation of a mechanical latch attachment system according to one embodiment.
Figure 24:
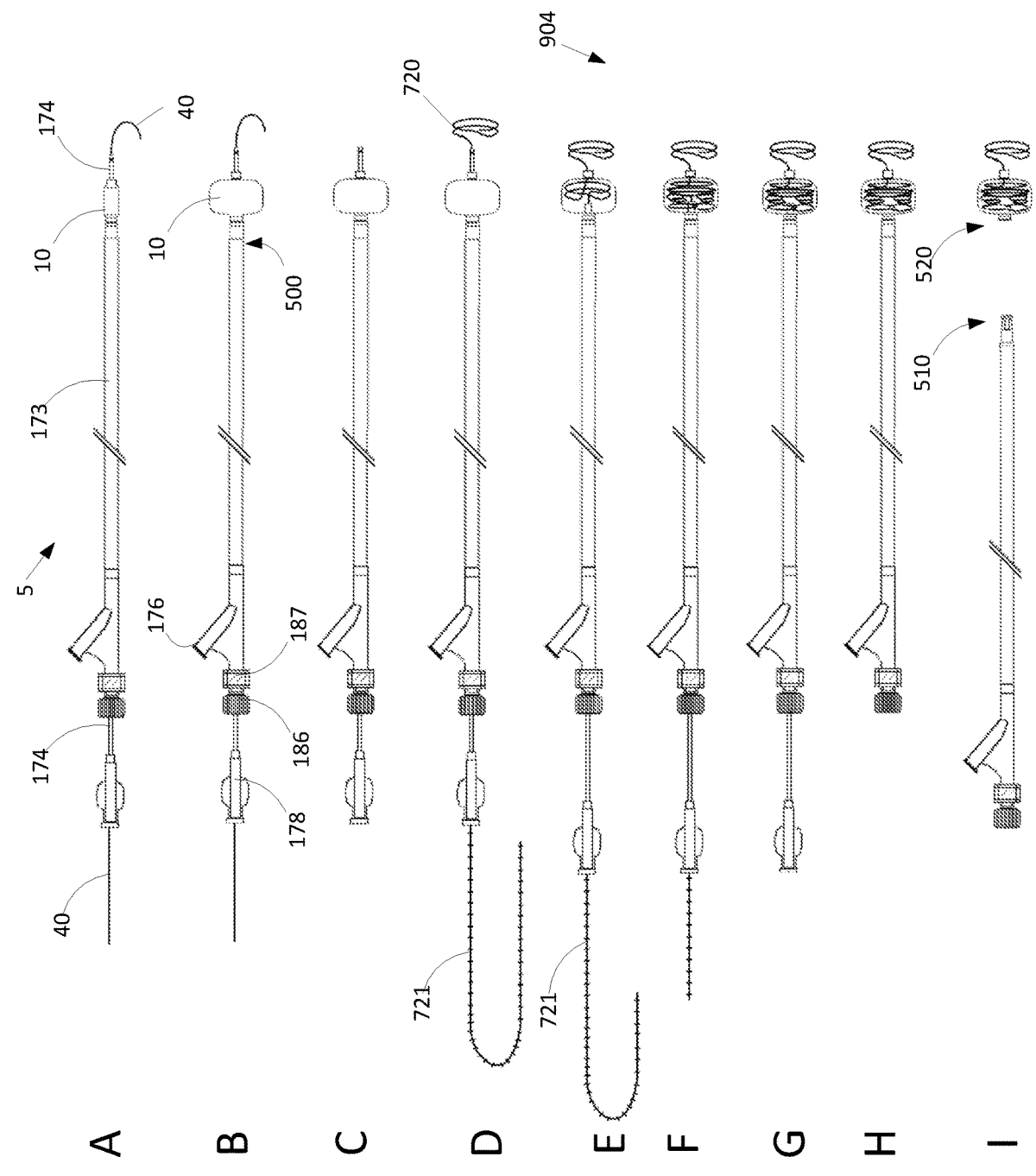
FIGS. 24A-I are planar views showing a fourth sequence of operation of a mechanical latch attachment system according to one embodiment.
Figure 25:
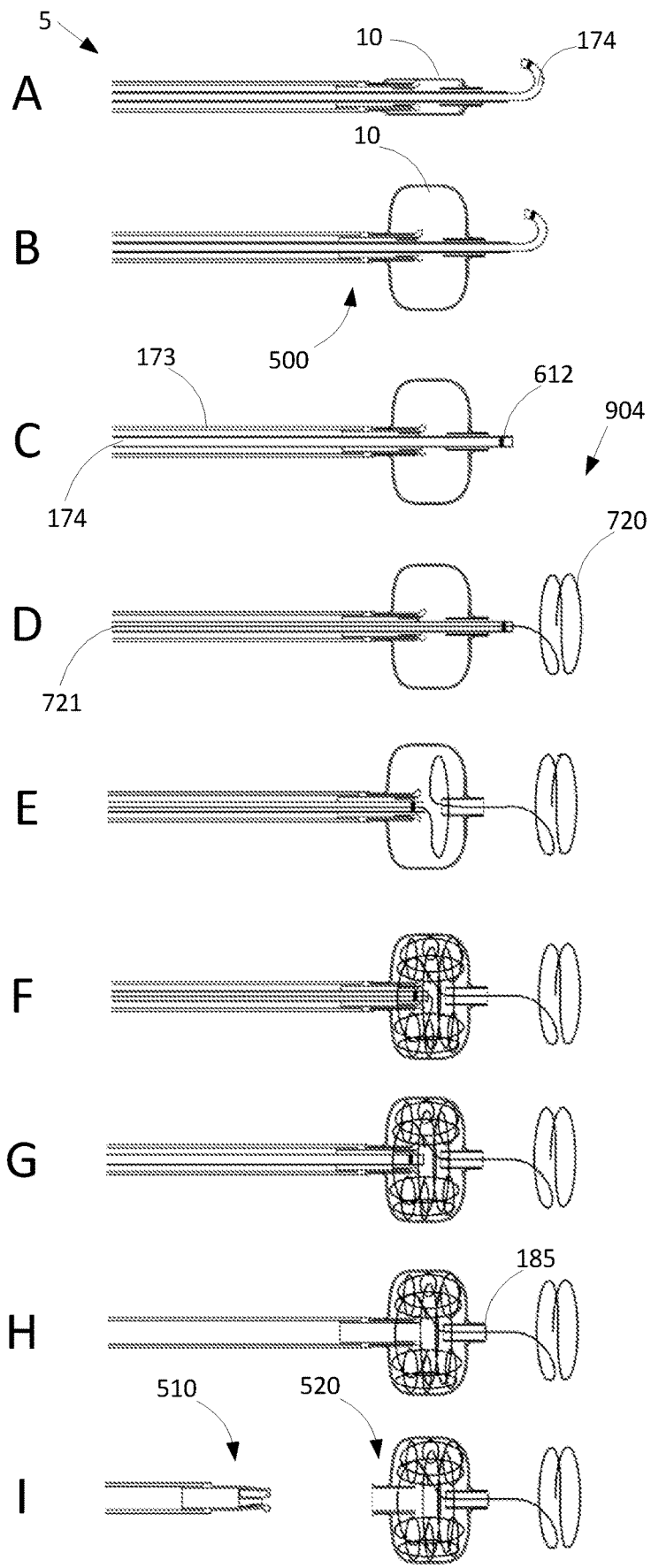
FIGS. 25A-I are cross-sectional detail views showing a fourth sequence of operation of a mechanical latch attachment system according to one embodiment.
Figure 26E:
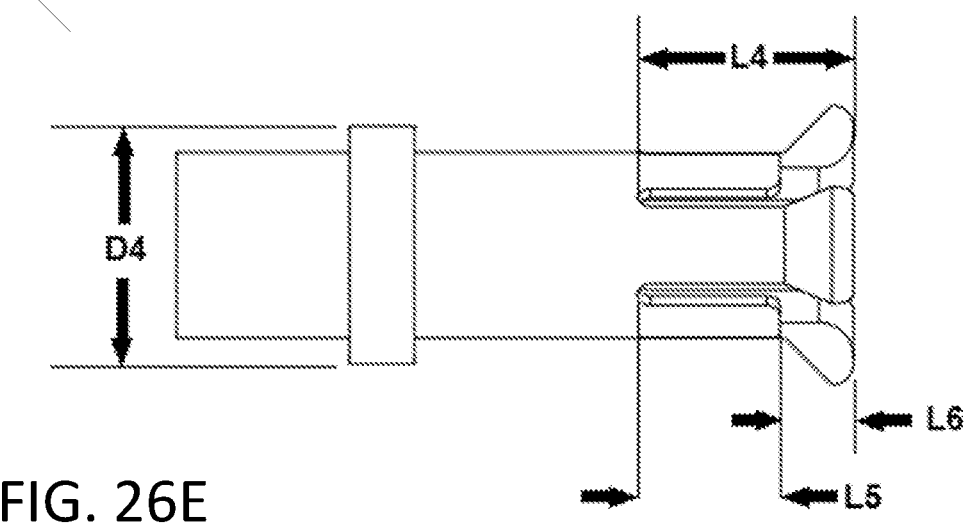
Figure 26F:
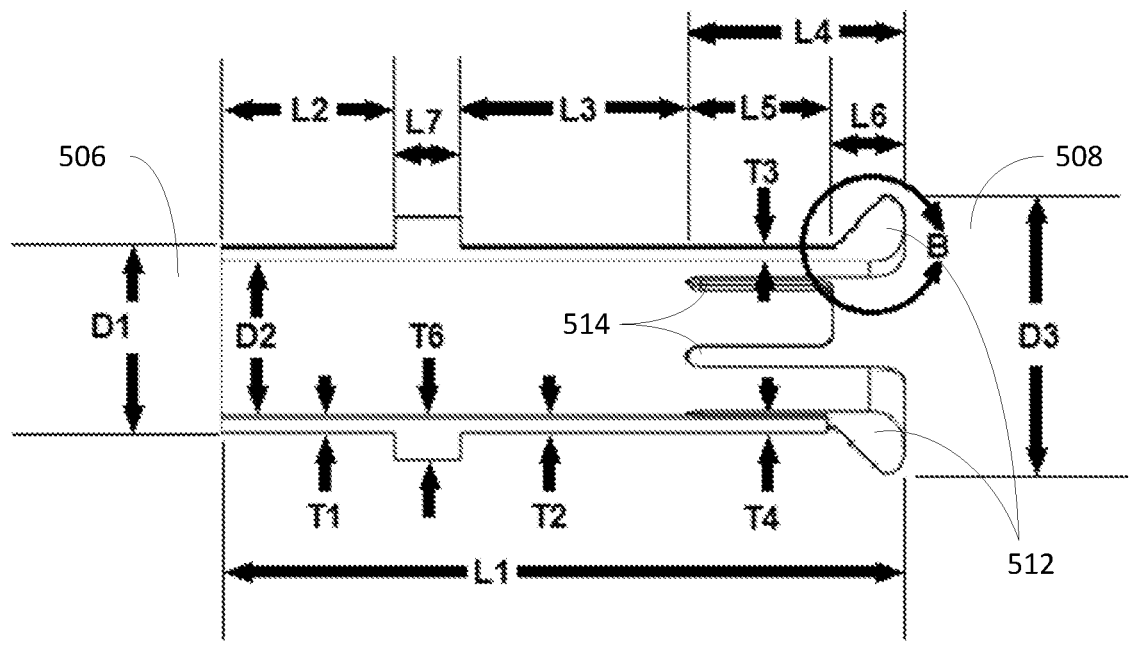
Figure 26G:
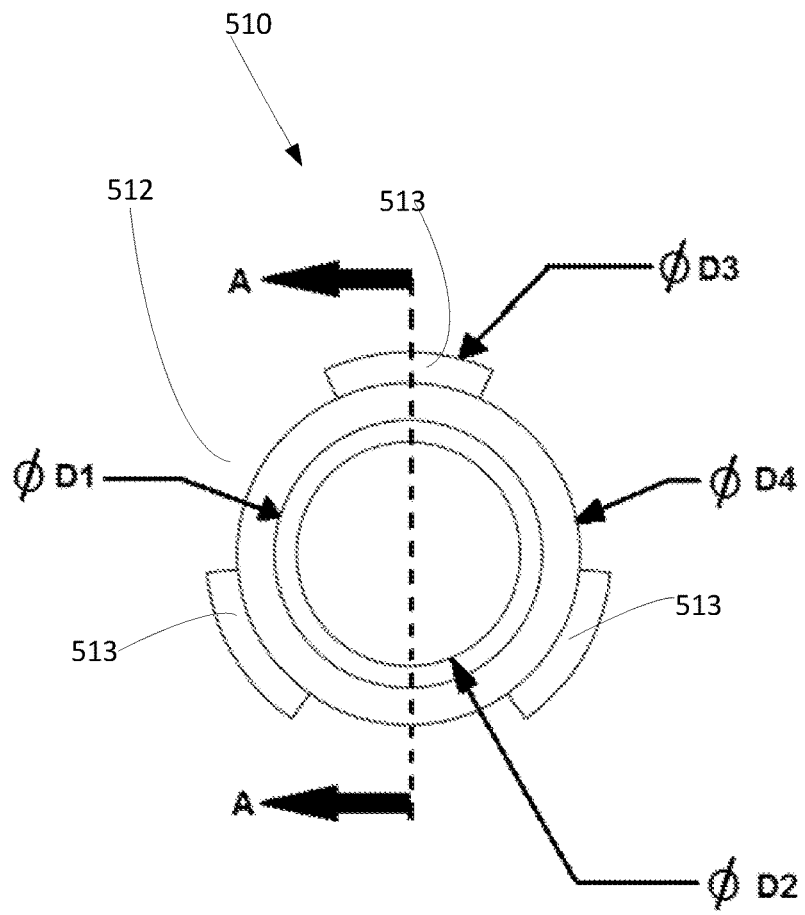
Figure 26H:
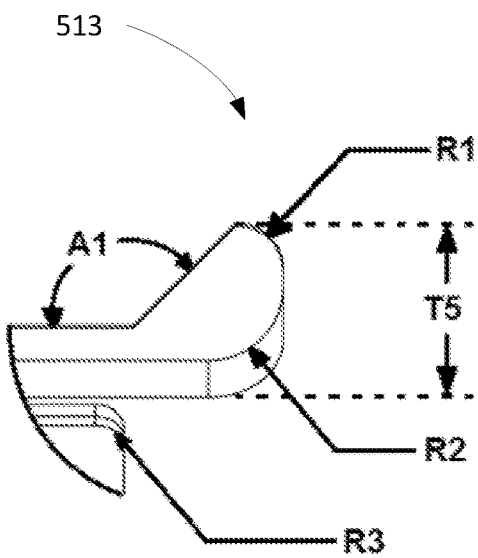
Figure 28E:
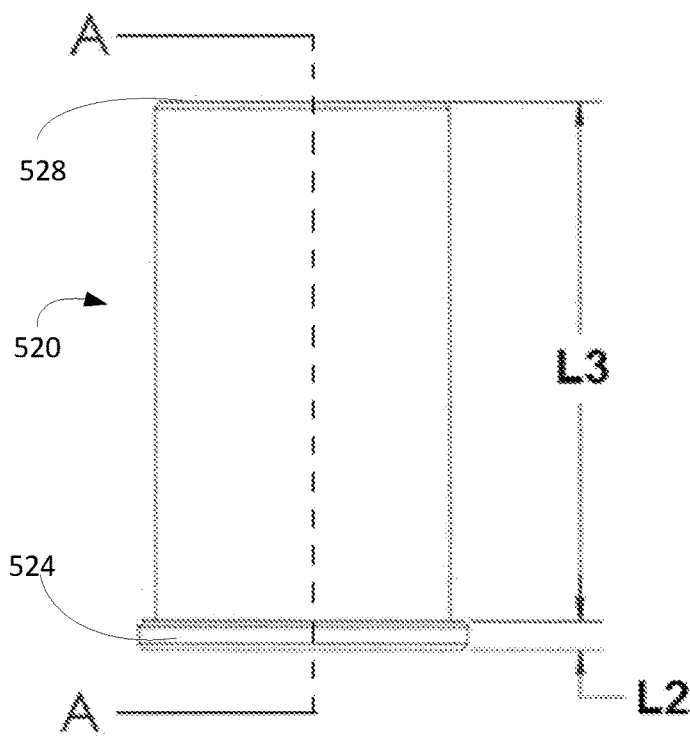
Figure 28F:
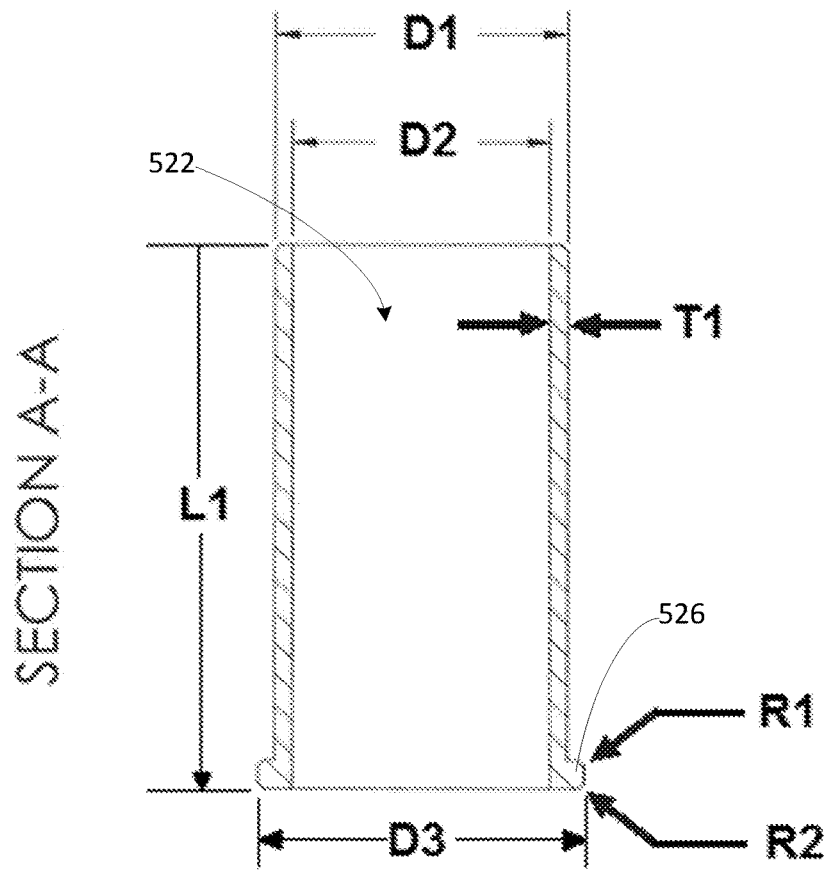
Figure 28G:
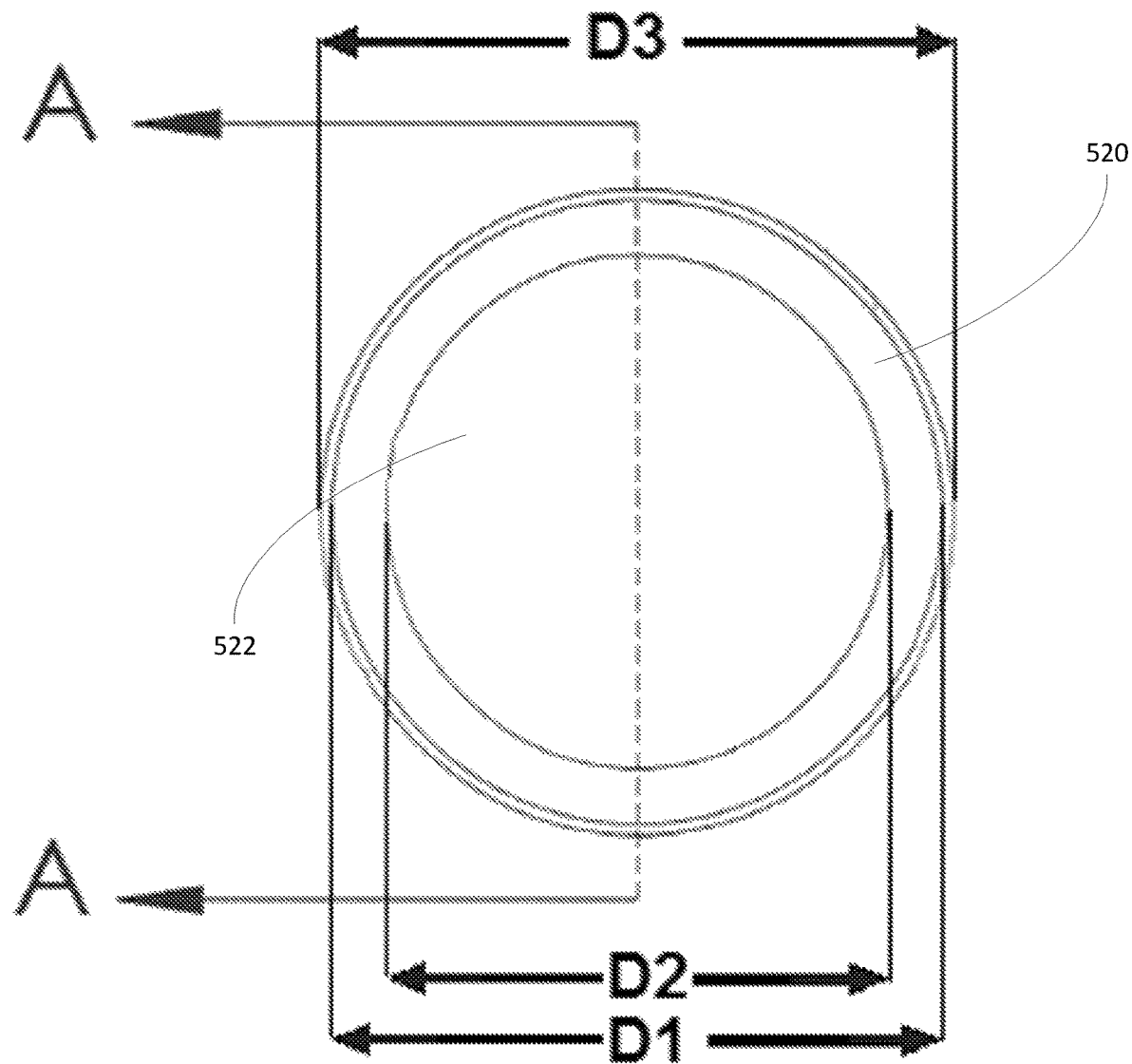

To allow detachment of the detachable balloon 10 from the first catheter 173, the second catheter 174 is retracted from the first catheter 173. This action removes the interference between the fingers 513 of the male component 510 and the distal edge 530 of the female component 520. The first catheter 173 is then retracted, unmating the mechanical latch 500. It should be noted that the detachment process may occur either with the guidewire 40 in place, as shown in FIG. 17A-C, or without the guidewire 40 in place, as shown in FIG. 18A-D. It should also be noted that the detachment process may occur with a coil or other elongated or expandable body 720 in place of the guidewire 40. The mechanical latch 500 may be used for the attachment of detachable balloons 10 and other expandable bodies of various sizes and shapes to catheter systems.

The mechanical latch 500 is compatible with deployment of the detachable balloon 10 when it is used alone, as shown in FIGS. 19A-G and 20A-E; used in combination with one or more elongated bodies 720 placed within the balloon 10, as shown in FIGS. 22A-I and 23A-H; or used in combination with one or more elongated bodies 720 placed both within and distal to the balloon 10, as shown in FIGS. 24A-I and 25A-I.

FIGS. 19A-G and 20A-E show a first sequence of operation of a detachable balloon catheter 1 with a mechanical latch 500 attachment system according to one embodiment. The balloon 10 is positioned and expanded. The guidewire 40 is retracted. The second catheter 174 is retracted from the male and female tubular structures 510 & 520 of the latch to detach the first catheter 173 from the proximal neck 130 of the balloon 10. Finally, the first catheter 173 is retracted.

FIGS. 21A-E and 22A-I show a second sequence of operation of a detachable balloon catheter 1 with a mechanical latch 500 attachment system according to one embodiment. The balloon 10 is positioned and expanded. The second catheter 174 is retracted from the male and female tubular structures 510 & 520 of the latch to detach the first catheter 173 from the proximal neck 130 of the balloon 10. The first catheter 173 is retracted. Finally, the guidewire 40 is retracted.

FIGS. 22A-I and 23A-H show a third sequence of operation of a detachable balloon catheter 1 with a mechanical latch 500 attachment system according to one embodiment. The balloon 10 is positioned and expanded. The guidewire 40 is retracted. The second catheter 174 is partially retracted. One or more coils or first elongated bodies 720 are placed within the central void 115 of the expanded balloon 10. The second catheter 174 is retracted from the male and female tubular structures 510 & 520 of the latch to detach the first catheter 173 from the proximal neck 130 of the balloon 10. Finally, the first catheter 173 is retracted.

FIGS. 24A-I and 25A-I show a fourth sequence of operation of a detachable balloon catheter 1 with a mechanical latch 500 attachment system according to one embodiment. The balloon 10 is positioned and expanded. The guidewire 40 is retracted. One portion of a coil or first elongated body 720 is placed distal to the expanded balloon 10. The second catheter 174 is partially retracted. The remaining portion of the first elongated body 720 is placed within the central void 115 of the expanded balloon 10. The second catheter 174 is retracted from the male and female tubular structures 510 & 520 of the latch to detach the first catheter 173 from the proximal neck 130 of the balloon 10. Finally, the first catheter 173 is retracted.

The present disclosure relates to medical devices comprising a detachable balloon 10 and a catheter or catheter assembly 5, wherein the detachable balloons 10 are configured for detachment from the catheter or catheter assembly 5 in vivo. In some embodiments, the balloon 10 is joined or operably coupled to the first catheter 173 by an elastomeric tubular structure 204.

In some embodiments, the elastomeric tubular segment 204 is bonded to a proximal neck 130 of the balloon 10 and configured to make a friction fit with the distal end of the first catheter 173. In some examples, the detachable balloon of a detachable balloon catheter 1 is expanded in an artery 317, vein 318, LAA 800, aneurysm 320, biological conduit 900, or other blood containing space or biological space 904 and at least a portion of the external surface of the detachable balloon 10 or a portion of the external surface of an expandable retention structure 731 attached to the balloon 10 is in contact with at least a portion of the wall of the artery 317, vein 318, LAA 800, aneurysm 320, biological conduit 900, or other blood containing space or biological space 904, and the first catheter 173 is be separated from an assembly of the proximal neck 130 of the balloon 10 and the elastomeric tubular segment 204 by pulling the first catheter 173 away from the assembly of the proximal neck 130 of the balloon 10 and the elastomeric tubular structure 204. In some embodiments, the elastomeric tubular structure 204 is configured to make a friction fit 202 with the distal end of the first catheter 173, wherein, when the detachable balloon is expanded in an artery, vein, LAA 800, aneurysm 320, biological conduit 900, or other blood containing space or biological space and at least a portion of the external surface of the balloon or a portion of the external surface of an expandable retention structure 731 attached to the balloon is in contact with at least a portion of the wall of the artery 317, vein 318, LAA 800, aneurysm 320, biological conduit, 900, or other blood containing space or biological space 904, the first catheter 173 can be separated from an assembly of the proximal neck 130 of the detachable balloon 10 and the elastomeric tubular segment 204 by pulling the first catheter 173 away from the assembly of the proximal neck 130 of the detachable balloon 10 and the elastomeric tubular segment 204. In some embodiments, the distal end of the elastomeric tubular segment 204 is inserted into the proximal neck 130 or proximal neck assembly 135 of the detachable balloon 10 and the elastomeric tubular segment 204 is bonded to the inner surface of the proximal neck 130 or proximal neck assembly 135 of the detachable balloon 10. In some embodiments, the distal end of the elastomeric tubular structure 204 is inserted over the proximal neck 130 or proximal neck assembly 135 of the balloon and the first tubular structure is bonded to the outer surface of the proximal neck 130 or proximal neck assembly 135 of the balloon. In some embodiments, the distal portion of the elastomeric tubular segment 204 is bonded to the proximal neck 130 or proximal neck assembly 135 of the detachable balloon with a glue or adhesive. In some embodiments, when assembling a detachable balloon catheter 1, the proximal end of the elastomeric tubular structure 204 is stretched open and the distal end of the first catheter 173 is inserted into the proximal end of the stretched first friction fit 202 structure, forming a friction fit 202 between a proximal portion of the elastomeric tubular structure 204 and a distal portion of the first catheter 173. In some embodiments, an external surface of a ring structure, tubular structure, telescoping structure, catheter segment, or telescoping catheter segment is bonded to an internal surface of the proximal neck 130, forming a proximal neck assembly 135 and the friction fit structure is bonded or joined to the ring structure, tubular structure, telescoping structure, catheter segment, or telescoping catheter segment. In some embodiments, an internal surface of a ring structure, tubular structure, telescoping structure, catheter segment, or telescoping catheter segment is bonded to the external surface of the proximal neck 130, forming a proximal neck assembly 135. In some embodiments, a ring structure, tubular structure, telescoping structure, catheter segment, or telescoping catheter segment comprises metal, platinum, iridium, gold, silver, stainless steel, nitinol, titanium, or alloys or combinations thereof. In some embodiments, at least a portion of a ring structure, tubular structure, telescoping structure, catheter segment, or telescoping catheter segment is radiopaque and visible under fluoroscopy and can assist a physician in confirming that a first catheter 173 has separated from the detachable balloon 10. In some embodiments, the friction fit 202 between the elastomeric tubular structure 204 and the first catheter 173 is made without glue, adhesive, or a weld.

In some embodiments, an elastomeric tubular structure 204 is bonded to the distal end of the first catheter 173 and configured to make a friction fit 202 with a proximal neck 130 of the detachable balloon 10 such that, when the detachable balloon is expanded in an artery, vein, LAA, 800, aneurysm, 320, biological conduit, 900, or other blood containing space or biological space and at least a portion of the external surface of the balloon or a portion of the external surface of an expandable retention structure 731 attached to the balloon is in contact with at least a portion of the wall of the artery 317, vein 318, LAA 800, aneurysm 320, biological conduit 900, or other blood containing space or biological space 904, the assembly of the first catheter 173 and the elastomeric tubular structure 204 can be separated from the proximal neck 130 of the detachable balloon 10 by pulling the assembly of the first catheter 173 and the elastomeric tubular structure 204 and the detachable balloon 10 apart. In some embodiments, the proximal end of the elastomeric tubular structure 204 is inserted into the distal end of the first catheter 173 and the elastomeric tubular structure 204 is bonded to the inner surface of the distal end of the first catheter 173. In some embodiments, the proximal end of the elastomeric tubular structure 204 is inserted over the distal end of the first catheter 173 and the elastomeric tubular structure 204 is bonded to the outer surface of the distal end of the first catheter 173. In some embodiments, the elastomeric tubular structure 204 is bonded to distal end of the first catheter 173 with a glue or adhesive. In some embodiments, when assembling a detachable balloon catheter 1, the distal end of the elastomeric tubular structure 204 is stretched open, the proximal neck 130 or proximal neck assembly 135 of the detachable balloon 10 is inserted into the stretched open elastomeric tubular structure 204, forming a friction fit 202 between the distal portion of the elastomeric tubular structure 204 and the proximal neck 130 or proximal neck assembly 135 of the detachable balloon 10. In some embodiments, the internal surface of a ring structure, tubular structure, telescoping structure, catheter segment, or telescoping catheter segment 190 is bonded to the external surface of the proximal neck 130 of a detachable balloon 10, forming a proximal neck assembly 135. In some embodiments, a ring structure, tubular structure, telescoping structure, catheter segment, or telescoping catheter segment 190 comprises metal, platinum, iridium, gold, silver, stainless steel, nitinol, titanium, or alloys or combinations thereof. In some embodiments, at least a portion of a ring structure, tubular structure, telescoping structure, catheter segment, or telescoping catheter segment 190 is radiopaque and visible under fluoroscopy and can assist a physician in confirming that a first catheter 173 has separated from the detachable balloon 10. In some embodiments, the friction fit 202 between the elastomeric tubular structure 204 and the proximal neck 130 or proximal neck assembly 135 of the detachable balloon 10 is made without glue, adhesive, or a weld.

In some embodiments, the elastomeric tubular segment 204 is a sleeve or wrap. In some embodiments, the elastomeric tubular segment 204 is elastic or resilient. In some embodiments, the elastomeric tubular segment 204 comprises an elastomer or a resilient material. In some embodiments, the elastomeric tubular structure 204 comprises a biocompatible thermoplastic elastomer material. In some embodiments, the elastomeric tubular segment 204 comprises nylon, Pebax, polyurethane, thermoplastic polyurethane, silicone, ChronoPrene, or other biocompatible elastomers or resilient materials. In some embodiments, the elastomeric tubular segment 204 comprises a material with a Shore durometer of 25 D-80 D.

By way of example and not limitation, nominal dimensions, along with allowable and preferred ranges of dimensions, for various potential embodiments of the elastomeric tubular segment 204 described in FIGS. 42A-C are presented in tabular form in FIG. 43. In some embodiments, the external diameter of an elastomeric tubular segment 204 is 0.031-0.096 inch after insertion of a first catheter 173. In some other embodiments, the external diameter of an elastomeric tubular segment 204 is 0.035-0.100 inch after insertion of a first catheter 173.

It should be noted that, with a elastomeric tubular segment 204, the detachment process may occur either with the guidewire 40 extending through the central void 115 of the expanded detachable balloon and terminating distal to the expanded detachable balloon, or without the guidewire 40 present. It should also be noted that the detachment process may occur with a coil or other elongated or expandable body 10 in the lumen of the first catheter 173 or the second catheter 174. The elastomeric tubular structure 204 may be used for attachment of detachable balloons 10 of various sizes and shapes.

The elastomeric tubular segment 204 is compatible with deployment of the detachable balloon 10 when it is used alone, as shown in FIGS. 36A-F and 37A-E; used in combination with one or more first elongated bodies 720 placed within the balloon 10, as shown in FIGS. 38A-J and 39A-H; or used in combination with one or more first elongated bodies 720 placed both within and distal to the balloon 10, as shown in FIGS. 40A-K and 41A-H.

FIGS. 36A-F and 37A-E show a first sequence of operation of a detachable balloon catheter 1 with an elastomeric tubular segment 204 attachment system according to the embodiment shown in FIG. 30. An elastomeric tubular segment 204 is bonded within the proximal neck 130 of the balloon 10 and in frictional contact 202 with the outside of the first catheter 173. The balloon 10 is positioned and expanded. With the elastomeric tubular segment 204 held in place by the third catheter 175, retraction of the first catheter 173 allows detachment of the first catheter 173 from the proximal neck 130 of the balloon 10. Finally, the guidewire 40 is retracted.

FIGS. 38A-J and 39A-H show a second sequence of operation of a detachable balloon catheter 1 with an elastomeric tubular segment 204 attachment system according to the embodiment shown in FIG. 30. An elastomeric tubular segment 204 is bonded within the proximal neck 130 of the balloon 10 and in frictional contact 202 with the outside of the first catheter 173. The balloon 10 is positioned and expanded. The guidewire 40 is retracted. One or more coils or first elongated bodies 720 are placed within the expanded balloon 10. With the elastomeric tubular segment 204 held in place by the third catheter 175, retraction of the first catheter 173 allows detachment of the first catheter 173 from the proximal neck 130 of the balloon 10.

FIGS. 40A-K and 41A-H show a third sequence of operation of a detachable balloon catheter 1 with an elastomeric tubular segment 204 attachment system according to the embodiment shown in FIG. 30. An elastomeric tubular segment 204 is bonded within the balloon proximal neck 130 and in frictional contact 202 with the outside of the first catheter 173. The balloon 10 is positioned and expanded. The guidewire 40 is retracted. One portion of a coil or first elongated body 720 is placed distal to the expanded balloon 10. The second catheter 174 is partially retracted. The remaining portion of the first elongated body 720 is placed within the expanded balloon 10. With the elastomeric tubular segment 204 held in place by the third catheter 175, retraction of the first catheter 173 (along with the second catheter 174) allows detachment of the first catheter 173 from the proximal neck 130 of the balloon 10.

The present disclosure relates to medical devices comprising a detachable balloon 10 and a catheter or catheter assembly 5, wherein the detachable balloons 10 are configured for detachment from the catheter or catheter assembly 5 in vivo. In some embodiments, the balloon 10 is joined or operably coupled to the second catheter 174 by a friction fit 202 provided by an elastomeric or resilient valve 192, as shown in FIGS. 44A-B and 52A-B. In some embodiments, a detachable balloon catheter 1 comprises a detachable assembly for joining the detachable balloon 10 to the second catheter 174, the detachable assembly comprising one or more elastomeric valves 192 joined to a distal neck 140 or distal neck assembly 142 of the detachable balloon 10, wherein the one or more elastomeric valves 192 are configured to make a friction fit 202 with the distal portion of the second catheter 174.

Figure 50:
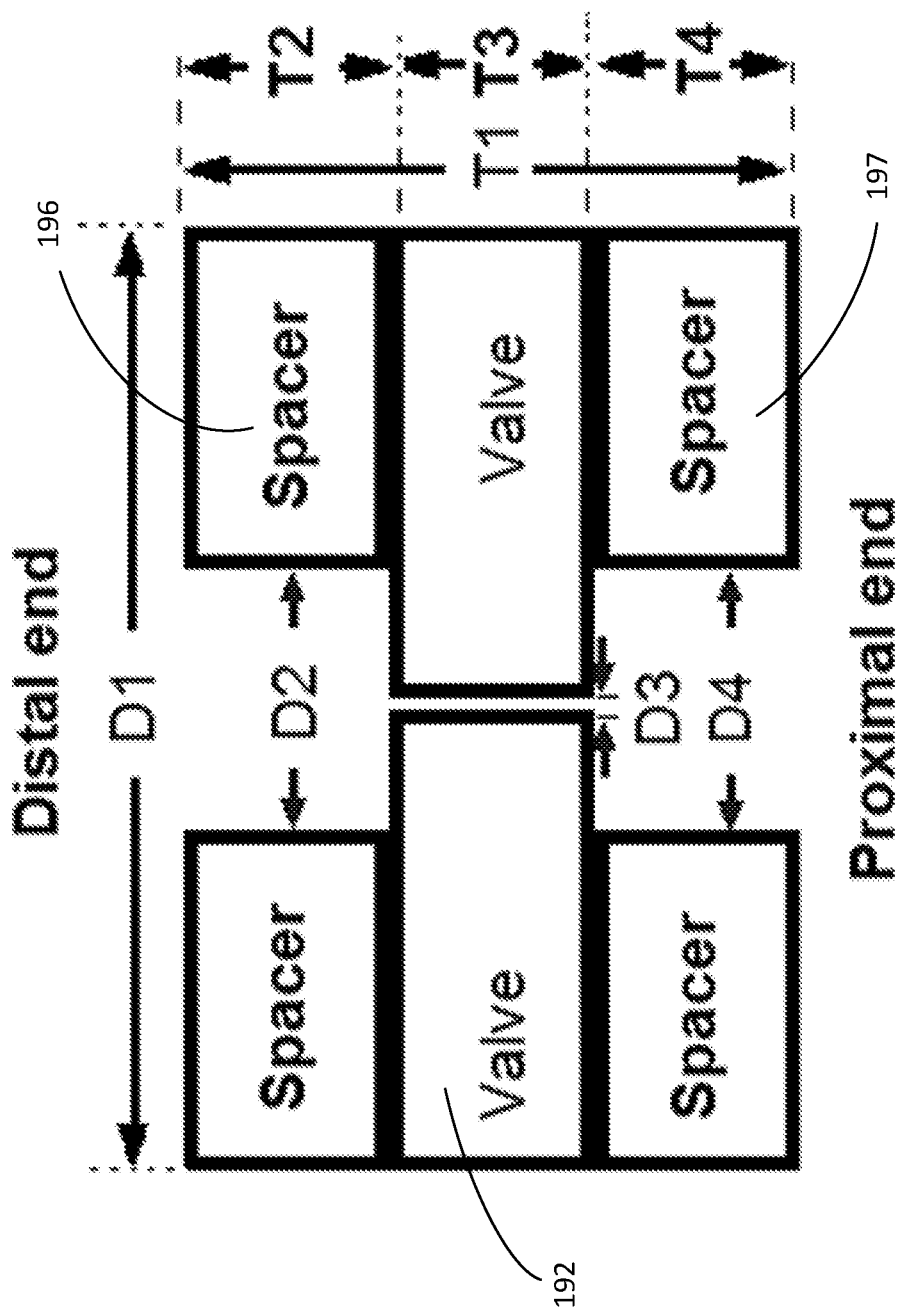
FIG. 50 is a cross-sectional view of the distal valve assembly shown in FIGS. 49A-D, with its overall geometric dimensions defined.
Figure 52:
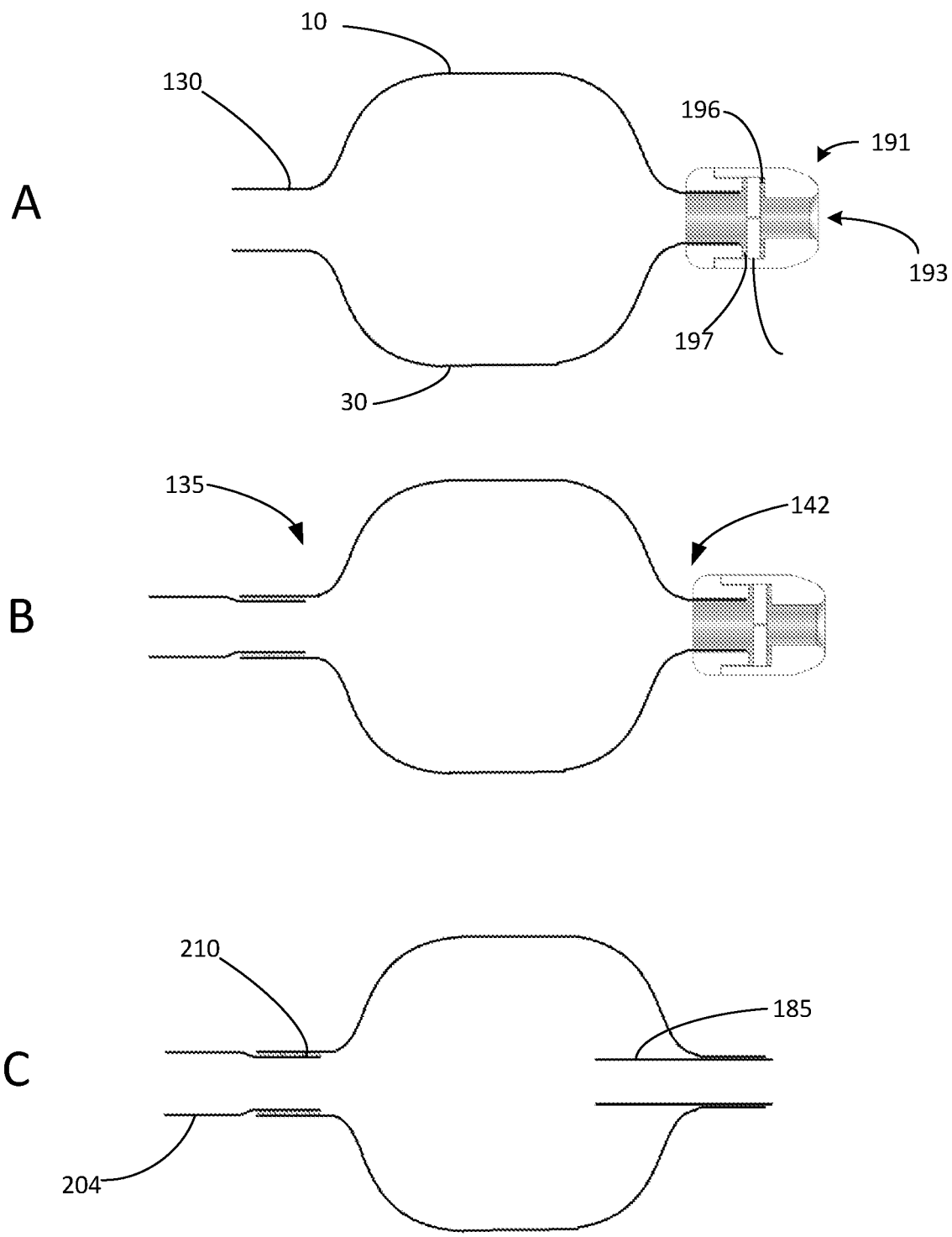
FIGS. 52A-C are cross-sectional views of embodiments of a balloon with various components attached to its proximal and distal necks.

In some embodiments, one or more elastomeric or resilient valves 192 are in the shape of a disc with a central orifice, such central orifice or aperture comprising a round puncture, a slit along an axis, or orthogonal slits across two axes, as shown in FIGS. 49A-D. The central orifice or aperture through the full thickness of the valve 192 may be a slit resembling a plus or minus sign, or a round puncture. In some embodiments, the one or more elastomeric valves 192 comprise polymer, silicone, polyurethane, or rubber. In one embodiment, a single valve 192 is used which comprises a silicone rubber disk of durometer ranging from about 40 Shore A to about 90 Shore A with 0.010 inch thickness and a round puncture central aperture. In some embodiments, one or more washers or spacers are located proximal to 197, distal to 196, or both proximal and distal 197 & 196 to the one or more elastomeric valves 192, as shown in FIGS. 44A-B, 50, and 52A-B. In some embodiments, the proximal and distal spacers 197 & 196 are in the shape of a disc with a central orifice, such central orifice comprising a round puncture, a slit along a diameter, or orthogonal slits across two diameters. In some embodiments, the proximal and distal spacers 197 & 196 may comprise an elastomeric or other resilient material such as a polymer including silicone, polyurethane, or rubber. By way of example and not limitation, nominal dimensions, along with allowable and preferred ranges of dimensions, for various potential embodiments of the elastomeric or resilient valves 192 and proximal and distal spacers 197 & 196 described in FIG. 50 are presented in tabular form in FIG. 51.

In some embodiments, one or more elastomeric or resilient valves 192 and proximal and distal spacers 197 & 196 are contained within a distal nosecone 191, as shown in FIGS. 44A-B and 52A-B. In some embodiments, a lumen or inner surface 193 of a distal nosecone 191 comprising one or more elastomeric valves 192, proximal spacers 197, and distal spacers 196 is bonded to a distal neck 140, distal neck assembly 142, or distal telescoping structure 185 of a detachable balloon 10. The nosecone 191 may contain multiple valves 192 placed in series with various combinations of central aperture geometry.

An attachment system comprising an elastomeric or resilient valve 192 within a distal nosecone 191 and an elastomeric tubular segment 204 integrated with a proximal neck assembly 135 is compatible with deployment of the detachable balloon 10 when it is used alone, as shown in FIGS. 45A-F and 46A-E; used in combination with one or more first elongated bodies 720 placed within the balloon 10, as shown in FIGS. 47A-J and 48A-I; or used in combination with one or more first elongated bodies 720 placed both within and distal to the balloon 10, which is structurally and functionally similar to what is shown in FIGS. 40A-K, 41A-H, 47A-J, and 48A-I.

FIGS. 45A-F and 46A-E show a first sequence of operation of an attachment system comprising an elastomeric or resilient valve 192 and an elastomeric or resilient tubular segment 204 according to the embodiments shown in FIGS. 30 and 44. The balloon 10 is positioned and expanded. With the elastomeric tubular segment 204 held in place by the third catheter 175, retraction of the first catheter 173 (along with the second catheter 174) allows detachment of the first catheter 173 from the proximal neck 130 of the balloon 10. Finally, retraction of the guidewire 40 causes the valve 192 to close.

FIGS. 47A-J and 48A-I show a second sequence of operation of an attachment system comprising an elastomeric or resilient valve 192 and an elastomeric or resilient tubular segment 204 according to the embodiments shown in FIGS. 30 and 44. The balloon 10 is positioned and expanded. The guidewire 40 is retracted. The second catheter 174 is partially retracted, causing the valve 192 to close. One or more coils or first elongated bodies 720 are placed within the expanded balloon 10. With the elastomeric tubular segment 204 held in place by the third catheter 175, retraction of the first catheter 173 (along with the second catheter 174) allows detachment of the first catheter 173 from the proximal neck 130 of the balloon 10.

In some embodiments, when an expanded detachable balloon 10 of a detachable balloon catheter 1 comprising one or more elastomeric or resilient valves 192 joined to a distal neck 140 or distal neck assembly 142 of the detachable balloon 10 is expanded in an artery 317, vein 318, LAA 800, aneurysm 320, biological conduit 900, or other blood containing space or biological space 904 and at least a portion of the external surface of the balloon 10 or a portion of the external surface of an expandable retention structure 731 attached to the balloon 10 is in contact with at least a portion of the wall of the artery 317, vein 318, LAA 800, aneurysm 320, biological conduit 900, or other blood containing space or biological space 904, the second catheter 174 can be separated from the expanded detachable balloon 10 by pulling the second catheter 174 and the expanded detachable balloon 10 apart.

In some examples, when the detachable balloon 10 of a detachable balloon catheter 1 is expanded in an artery 317, vein 318, LAA 800, aneurysm 320, biological conduit 900, or other blood containing space or biological space 904 and at least a portion of the external surface of the expanded detachable balloon 10 or a portion of the external surface of an expandable retention structure 731 attached to the balloon 10 is in contact with at least a portion of the wall of the artery 317, vein 318, LAA 800, aneurysm 320, biological conduit 900, or other blood containing space or biological space 904, the second catheter 174 can be separated from the expanded detachable balloon 10 by pulling the second catheter 174 and the expanded balloon 10 apart.

In some examples, when the detachable balloon 10 of a detachable balloon catheter 1 is expanded in an artery 317, vein 318, LAA 800, aneurysm 320, biological conduit 900, or other blood containing space or biological space 904 and at least a portion of the external surface of the expanded detachable balloon 10 or a portion of the external surface of an expandable retention structure 731 attached to the balloon 10 is in contact with at least a portion of the wall of the artery 317, vein 318, LAA 800, aneurysm 320, biological conduit 900, or other blood containing space or biological space 904, an assembly of the second catheter 174 and the first catheter 173 can be separated from the expanded detachable balloon 10 by pulling the assembly of the second catheter 174, the first catheter 173, and the expanded balloon 10 apart.

In some examples, one or more elastomeric or resilient valves 192 are configured to close a distal opening, distal neck 140, distal telescoping segment 185, or distal neck assembly 142 of the expanded detachable balloon 10 when the second catheter 174 is separated from the expanded detachable balloon 10. In some examples, one or more elastomer or resilient valves 192 are configured to reduce blood flow through the central void 115 or interior volume of the expanded detachable balloon 10 following removal of the second catheter 174 from the expanded detachable balloon 10.

In some embodiments, the external diameter of one or more elastomeric or resilient valves 192 is 0.018-0.068 inch. It should be noted that, with a valve 192 configured for a friction fit 202, the detachment process may occur either with the guidewire 40 extending through the valve 192 and terminating distal to the expanded detachable balloon 10, or without the guidewire 40 present. It should also be noted that the detachment process may occur with a coil or other elongated or expandable body 720 in the lumen 162 of the first catheter 173 or in the lumen 163 of the second catheter 174. The valve 192 may be used for attachment of detachable balloons 10 of various sizes and shapes.

The present disclosure relates to medical devices comprising a detachable balloon 10 and a catheter or catheter assembly 5, wherein the detachable balloons 10 are configured for detachment from the catheter or catheter assembly 5 in vivo. In some embodiments, the balloon is joined or operably coupled to the first catheter 173 by a tubular structure sensitive to electrolysis, also called an "anode" 390. In some embodiments, the detachable balloon catheter 1 may comprise an electrolytic detachment system that includes an anode 390 placed between the first catheter 173 and the detachable balloon 10. In some embodiments, the anode 390 is also sensitive to corrosion, electrochemical corrosion, electrochemical dissolution, and electrochemical metal dissolution.

One example of a detachable balloon catheter 1 comprises an anode 390, a conductor extends from the hub or proximal end of a first catheter 173 that makes an electrical connection with the anode 390, the proximal end of the anode 390 is bonded to the distal end of the first catheter 173 and the distal end of the anode 390 is bonded to a proximal neck 130 or proximal neck assembly 135 of the balloon 10. When an electrical current is passed through the conductor while the anode 390 is immersed in a fluid containing electrolytes for a sufficient time to cause dissolution of at least a portion of the anode 390 and separation of the proximal and distal ends of the anode 390, the first catheter 173 can be separated from the detachable balloon by pulling apart the assembly of the first catheter 173 and the proximal portion of the anode 390 and the assembly of the proximal neck 130 or proximal neck assembly 135 of the detachable balloon 10 and the distal portion of the anode 390.

In some embodiments, the bond between the first catheter 173 and the anode 390 is made using adhesive or glue, the bond between the anode 390 and the proximal neck 130 or proximal neck assembly 135 of the detachable balloon 10, or both bonds are made using adhesive or glue, or adhesive or glue that is electrically non-conductive or insulating. In some embodiments, the adhesive or glue between the anode 390 and the proximal neck 130 or proximal neck assembly 135 of the detachable balloon 10, electrically insulates the balloon from the anode 390. In some embodiments, the adhesive or glue between the first catheter 173 and the anode 390, electrically insulates the first catheter 173 from the anode 390. In some embodiments, the wall of the anode 390 comprises an inner layer that is more sensitive to electrolysis and an outer layer that defines an exterior surface that is less sensitive to electrolysis or corrosion. In some embodiments, the inner layer of the anode 390 comprises stainless steel. In some embodiments, the outer layer of the anode 390 that is less sensitive to electrolysis or corrosion comprises gold, silver, platinum, iridium, titanium, electrically non-conductive polymers, electrically non-conductive coatings, or alloys or combinations thereof. In some embodiments, the wall of the anode 390 comprises an inner layer that defines an interior surface that is less sensitive to electrolysis or corrosion, a middle layer that is more sensitive to electrolysis or corrosion, and an outer layer that defines an exterior surface that is less sensitive to electrolysis or corrosion. In some embodiments, the inner layer of the anode 390 comprises gold, silver, platinum, iridium, titanium, electrically non-conductive polymers, electrically non-conductive coatings, or alloys or combinations thereof. In some embodiments, the outer layer of the anode 390 comprises gold, silver, platinum, iridium, titanium, electrically non-conductive polymers, electrically non-conductive coatings, or alloys or combinations thereof. In some embodiments, the electrically non-conductive polymer is Parylene, polyurethane, or silicone. In some embodiments, the middle layer of the anode 390 comprises stainless steel, 300 series stainless steel, 400 series stainless steel, 302 stainless steel, 304 stainless steel, 316 stainless steel, 316L stainless steel, or 316LVM stainless steel. In some embodiments, at least a portion of the stainless steel portion of the anode 390 is heat-treated. In some embodiments, the outer layer of the anode 390 is absent and the middle layer or a stainless steel layer is exposed on the outer surface of a ring-shaped region of the anode 390. In some embodiments, the inner and outer layers of the anode 390 are absent and a middle layer or stainless steel layer is exposed on the inner and outer surface of a ring-shaped region of the anode 390. In some embodiments, a stress concentration line or strip is formed in the ring-shaped region, enabling a physician to break the anode 390 in vivo. In some embodiments, at least a portion of the inner surface of the anode 390 is shielded from electrolysis or corrosion by having an outer surface of a distal portion of the first catheter 173 covering the portion of the inner surface of the anode 390. In some embodiments, at least a portion of the outer surface of the anode 390 is shielded from electrolysis or corrosion by having an inner surface of a distal portion of the first catheter 173 covering the portion of the outer surface of the anode 390. In some embodiments, at least a portion of the inner surface of the anode 390 is shielded from electrolysis or corrosion by having an outer surface of a proximal neck 130 or proximal neck assembly 135 covering the portion of the inner surface of the anode 390. In some embodiments, at least a portion of the outer surface of the anode 390 is shielded from electrolysis or corrosion by having an inner surface of a proximal neck 130 or proximal neck assembly 135 covering the portion of the outer surface of the anode 390.

In some embodiments, the detachable balloon catheter 1 comprises an electrolytic detachment subsystem comprising an electrical circuit, wherein a portion of the electrical circuit is supported on the first catheter 173 and configured to cause separation of the anode 390, and thereby separation of the expanded detachable balloon 10 from the first catheter 173. In some embodiments, at least a portion of the electrical circuit is supported on the first catheter 173 and configured to cause electrolysis or corrosion in the ring-shaped region of the anode 390 and separation of the portion of the anode 390 distal to the ring-shaped region from the portion of the anode 390 proximal to the ring-shaped region, and thereby separation of the expanded balloon 10 from the first catheter 173. In some embodiments, the electrolytic detachment subsystem is configured to apply an electrical current in a manner that creates an anode 390 in the region of the ring-shaped region of the anode 390 to cause the anode 390 to separate such that the distal end of the first catheter 173 can separate from the balloon 10. In some examples, a portion of the anode 390 distal to the ring-shaped region is separated from the portion of the anode 390 proximal to the ring-shaped region. In some embodiments, the electrolytic detachment subsystem is configured to deliver a constant current of 1-10 mA, including delivering current to an anode. 390. In some embodiments, the anode 390 is a ring-shaped region of the anode 390 comprising stainless steel on the outer surface of the ring-shaped region.

In some embodiments, an external surface of a ring structure, tubular structure, telescoping structure, catheter segment, or telescoping catheter segment is bonded to an internal surface of the proximal neck 130, forming a proximal neck assembly 135 and the anode 390 is bonded or joined to the ring structure, tubular structure, telescoping structure, catheter segment, or telescoping catheter segment. In some embodiments, an internal surface of a ring structure, tubular structure, telescoping structure, catheter segment, or telescoping catheter segment is bonded to the external surface of the proximal neck 130 of the detachable balloon 10, forming a proximal neck assembly 135. In some embodiments, a ring structure, tubular structure, telescoping structure, catheter segment, or telescoping catheter segment comprises metal, platinum, iridium, gold, silver, stainless steel, nitinol, titanium, or alloys or combinations thereof. In some embodiments, at least a portion of a ring structure, tubular structure, telescoping structure, catheter segment, or telescoping catheter segment is radiopaque and visible under fluoroscopy and can assist a physician in confirming that a first catheter 173 has separated from the detachable balloon 10. In some embodiments, an internal surface of a ring structure, tubular structure, telescoping structure, catheter segment, or telescoping catheter segment 190 is bonded to an external surface of a proximal neck 130 of a detachable balloon 10, forming a proximal neck assembly 135. In some embodiments, a ring structure, tubular structure, telescoping structure, catheter segment, or telescoping catheter segment comprises metal, platinum, iridium, gold, silver, stainless steel, nitinol, titanium, or alloys or combinations thereof. In some embodiments, at least a portion of a ring structure, tubular structure, telescoping structure, catheter segment, or telescoping catheter segment is radiopaque and visible under fluoroscopy and can assist a physician in confirming that a first catheter 173 has separated from the detachable balloon. In some embodiments, a tubular structure or ring-shaped structure 185 present in the wall of the distal portion of the first catheter 173. In some embodiments, the tubular structure or ring-shaped structure 190 present in the wall of the distal portion of the first catheter 173 comprises metal, platinum, iridium, gold, silver, stainless steel, nitinol, titanium, or alloys or combinations thereof. In some embodiments, at least a portion of the tubular structure or ring-shaped structure 190 present in the wall of the distal portion of the first catheter 173 is radiopaque and visible under fluoroscopy and can assist a physician in confirming that a first catheter 173 has separated from a detachable balloon 10. In some embodiments, a tubular structure or ring-shaped structure 190 is present in the wall of the distal portion of the first catheter 173 and in other embodiments a tubular structure or ring-shaped structure 190 is bonded or joined to the external surface of the distal portion of the first catheter 173.

In some embodiments, the detachable balloon catheter 1 further comprises a conductor extending from the hub or proximal end of the first catheter 173 and making an electrical connection with a cathode tubular structure 405. In some embodiments, at least a portion of one or more conductors are embedded in the wall of the first catheter 173 and act as electrical conductors for the electrolytic detachment subsystem and provide structural reinforcement for the wall of the first catheter 173. In some embodiments, at least the portion of a conductor is routed through the wall of the first catheter 173 in a spiral, coiled, braided, or straight configuration. In some embodiments, one or more of the conductors are wires, or are copper wires with an electrically insulating polymer coating. In some embodiments, the electrolytic detachment subsystem is configured to deliver constant current to the anode 390. In some embodiments, the proximal hub 179 of the first catheter 173 comprises an electrical jack and the proximal end of the conductor wire connected to the anode 390 is connected to the electrical jack. In some embodiments, the proximal hub 179 of the first catheter 173 comprises an electrical jack and the proximal end of the conductor wire connected to the cathode tubular structure 405 on the first catheter is connected to the electrical jack.

In some examples, after electrolysis or corrosion of a portion of the anode 390, an assembly of the distal portion of the anode 390, the proximal neck 130 or proximal neck assembly 135 of the detachable balloon, and the expanded detachable balloon can be separated from an assembly of the proximal portion of the anode 390 and the first catheter 173 by pulling on the first catheter 173 while the expanded detachable balloon 10 remains fixed in place. In some examples, after electrolysis or corrosion of a portion of the anode 390, an assembly of the distal portion of the anode 390, the proximal neck 130 or proximal neck assembly 135 of the detachable balloon 10, and the expanded detachable balloon can be separated from an assembly of the proximal portion of the anode 390, the first catheter 173, and the second catheter 174 by pulling on the first and second catheters 173 & 174 while the expanded detachable balloon 10 remains fixed in place. In some examples, the first catheter 173 assembly and the detachable balloon 10 assembly are pulled apart when the expanded detachable balloon 10 is engaged to the wall of a saccular aneurysm 320, artery 317, vein 318, LAA 800, other blood containing structure, biological conduit 900, or biological space 904.

By way of example and not limitation, nominal dimensions, along with allowable and preferred ranges of dimensions, for various potential embodiments of the anode described in FIGS. 55A-E and 57A-D are presented in tabular form in FIG. 56. In some embodiments, the internal or luminal diameter of the anode is 0.025-0.068 inch. In some embodiments, the external diameter of the anode is 0.029-0.072 inch.

It should be noted that, with a anode 390, the detachment process may occur either with the guidewire 40 extending through the central void 115 of the expanded detachable balloon and terminating distal to the expanded detachable balloon, or without the guidewire 40 present. It should also be noted that the detachment process may occur with a coil or other elongated or expandable body 10 in the lumen 162 of the first catheter 173 or lumen 163 of the second catheter 174. The anode 390 may be used for attachment of detachable balloons 10 of various sizes and shapes.

The electrolytic detachment system comprising an anode 390 is compatible with deployment of the detachable balloon 10 when it is used alone, as shown in FIGS. 58A-E and 59A-E; used in combination with one or more elongated bodies 720 placed within the balloon 10, as shown in FIGS. 60A-I and 61A-H; or used in combination with one or more elongated bodies 720 placed both within and distal to the balloon 10, as shown in FIGS. 62A-I and 63A-I.

Figure 55:
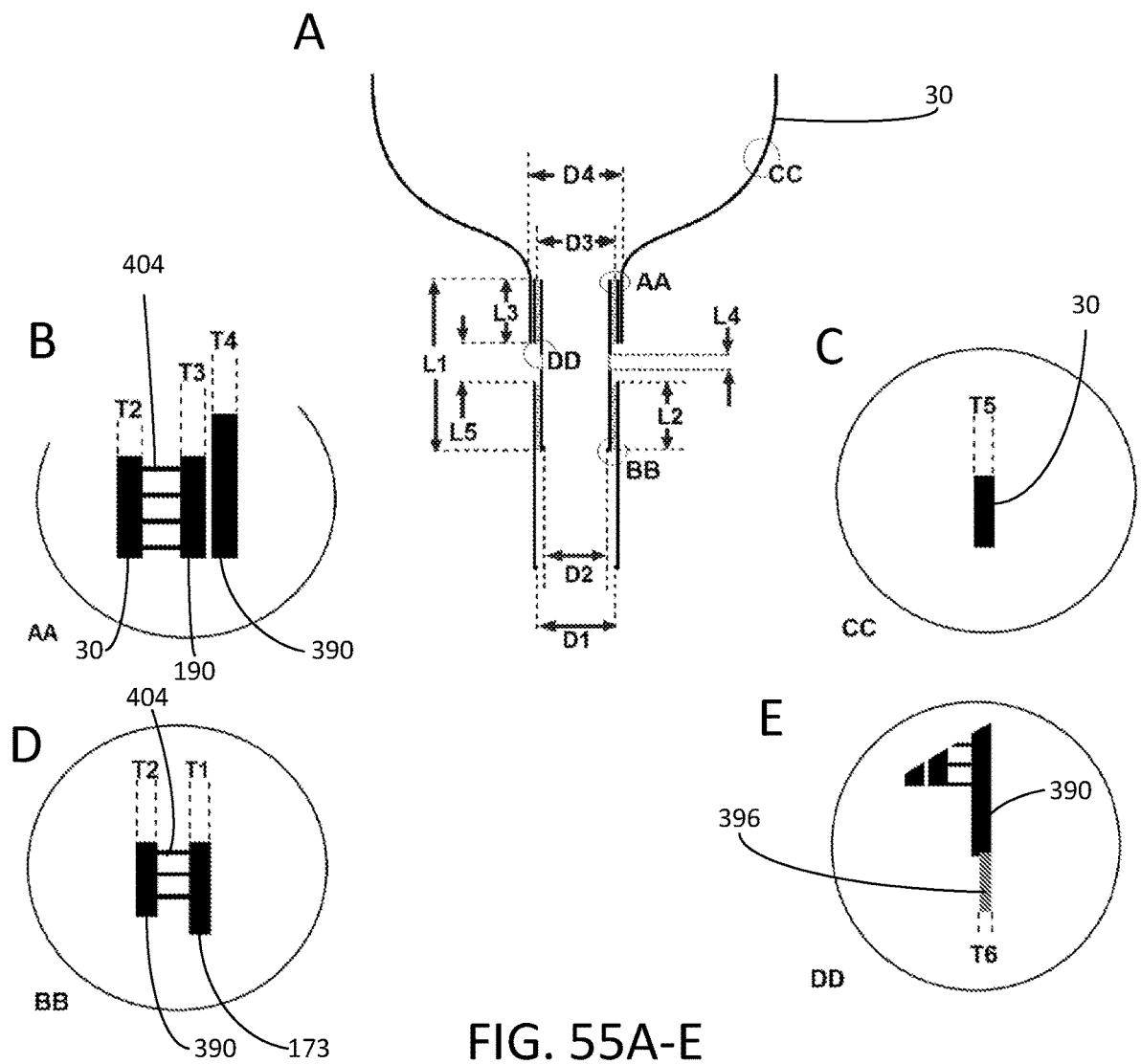
FIGS. 55A-E show cross-sectional and detail cross-sectional views of a tubular structure sensitive to electrolysis which serves as the anode of an electrolytic detachment system according to one embodiment, with its overall geometric dimensions defined.
Figure 67:
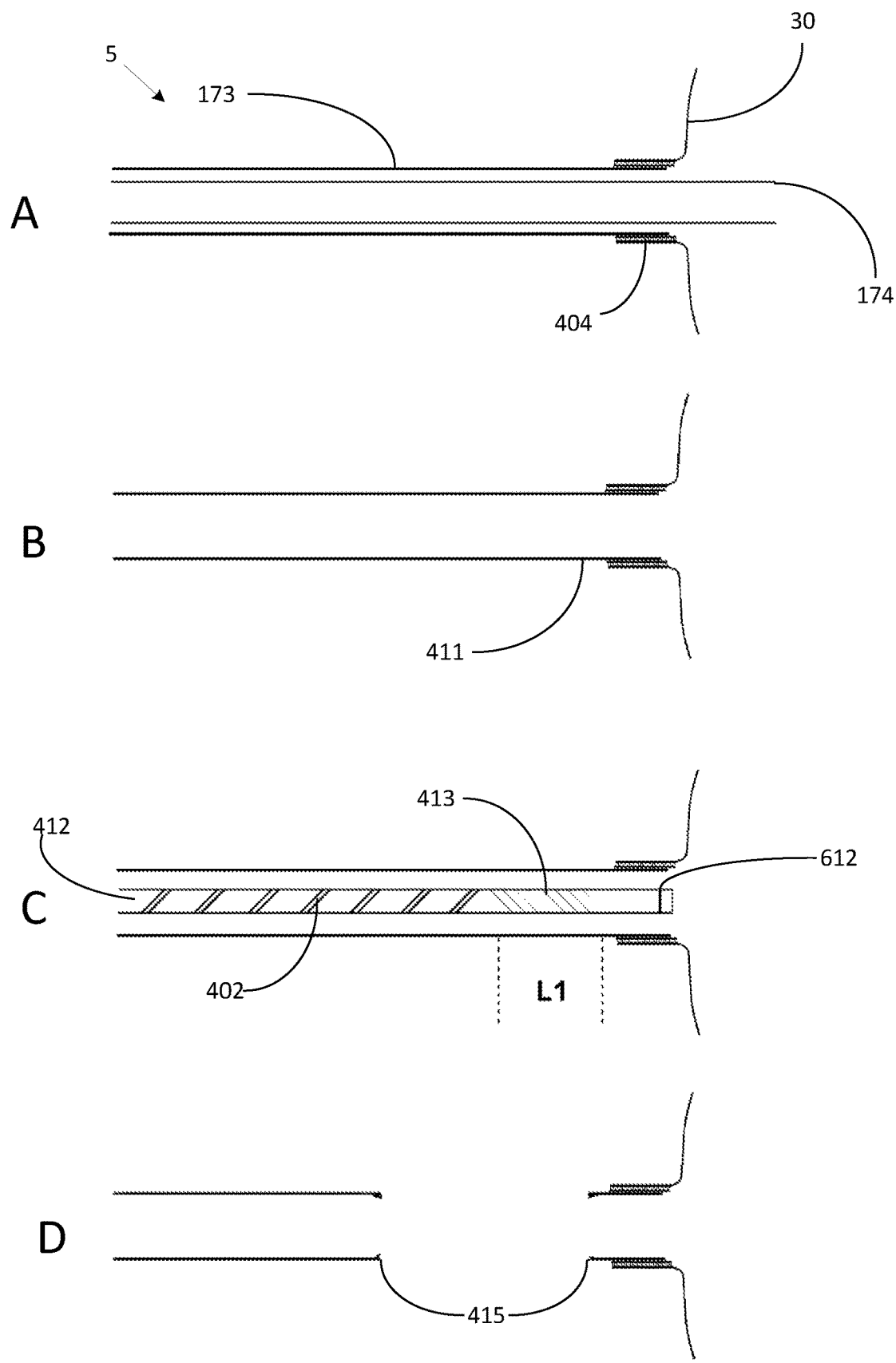
FIGS. 67A-D are planar partial cross-sectional views showing the operation of an electrothermal detachment system according to a second embodiment in which the distal end of the first catheter is heat sensitive.
Figure 68:
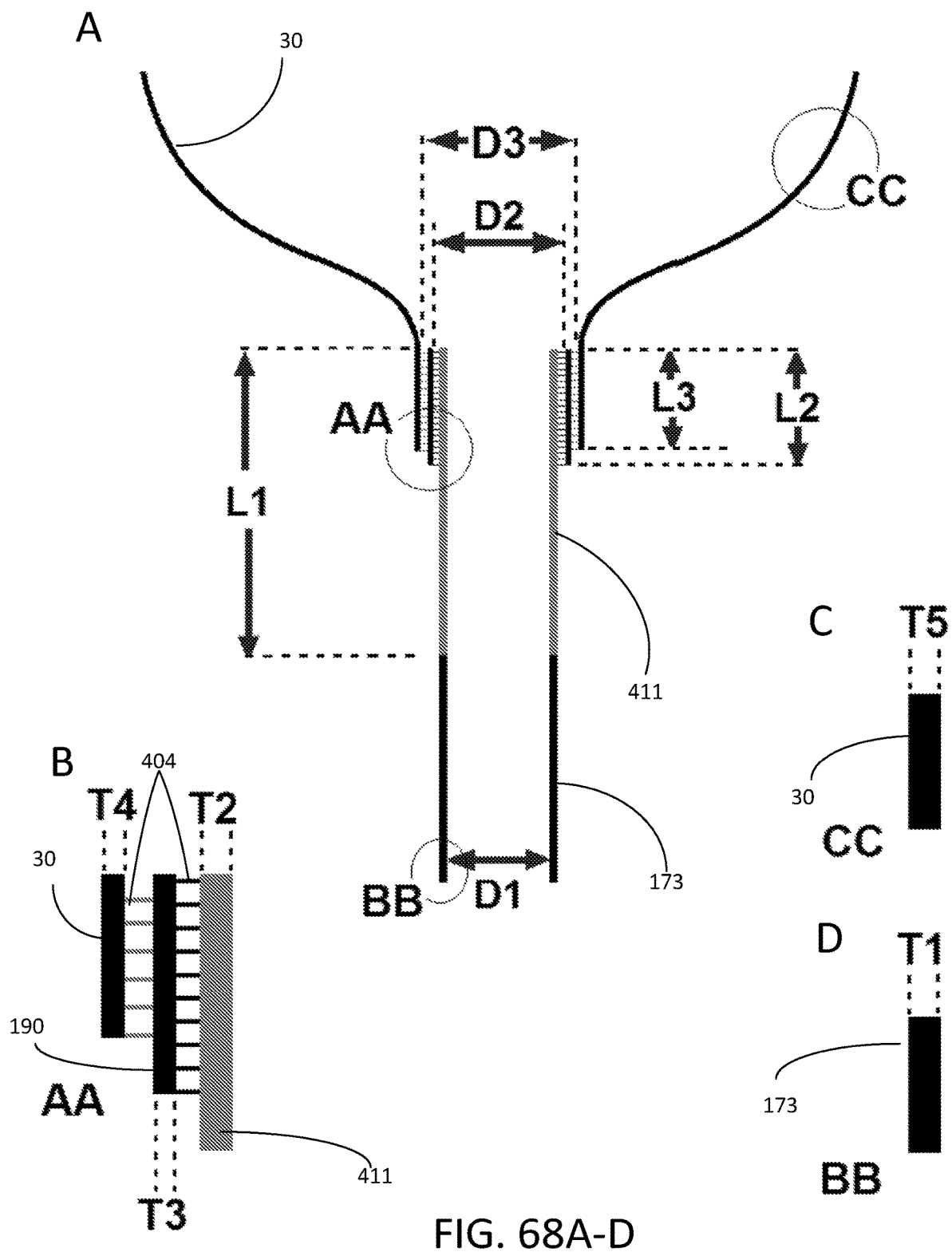
FIGS. 68A-D show cross-sectional and detail cross-sectional views of a heat sensitive distal end of the first catheter used in an electrothermal detachment system according to the embodiment shown in FIG. 67, with its overall geometric dimensions defined.
Figure 70:
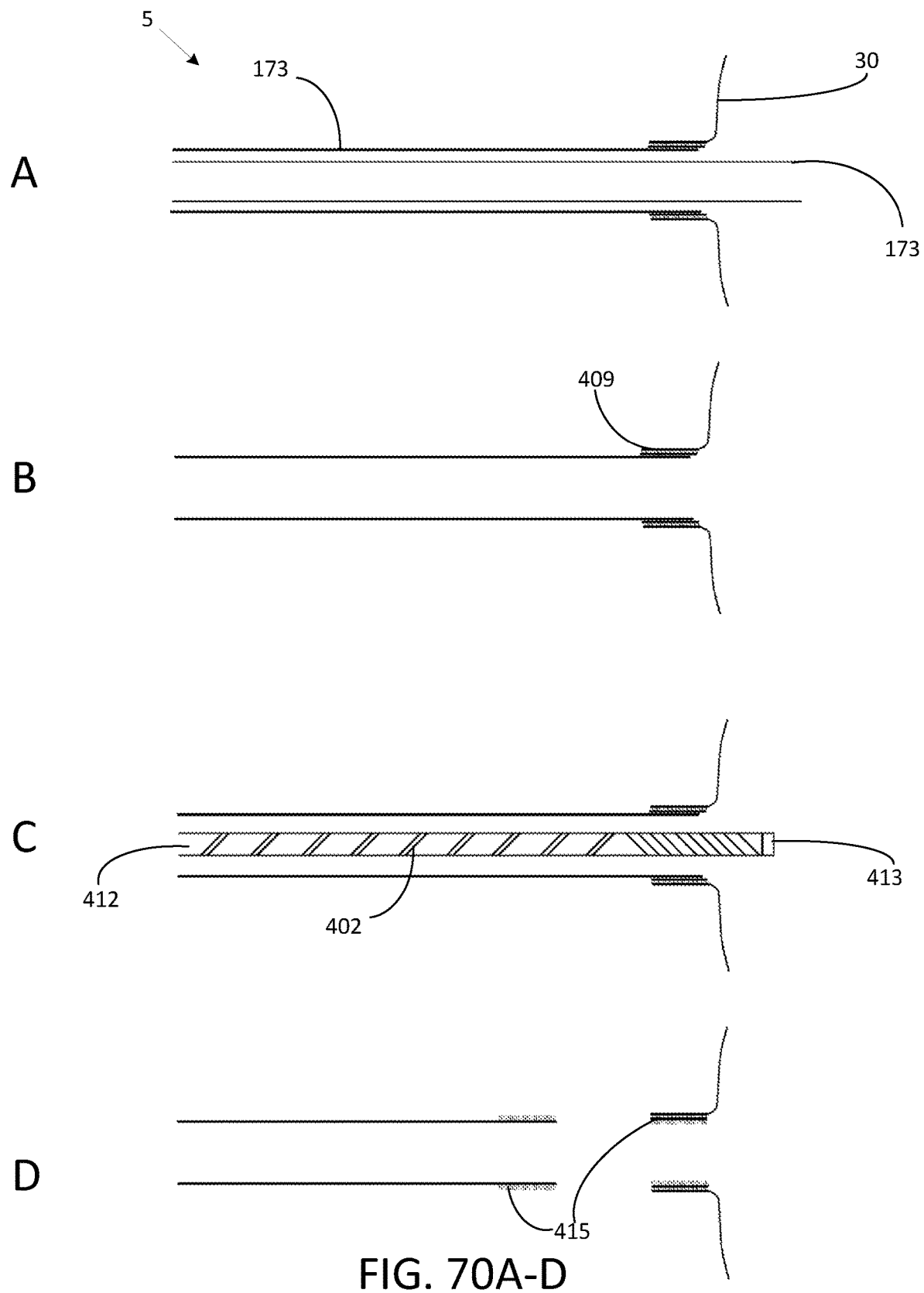
FIGS. 70A-D are planar partial cross-sectional views showing the operation of an electrothermal detachment system according to a third embodiment in which a heat sensitive material bonds the first catheter to a telescoping structure within the proximal balloon neck.

FIGS. 58A-E and 59A-E show a first sequence of operation of an electrolytic detachment system according to the embodiment shown in FIGS. 55 and 57. The balloon 10 is positioned and expanded. An electrolytic detachment controller 406 is connected to the hub 179 of the first catheter 173 by a cable 407 and the balloon 10 is detached by electrolysis. Finally, the guidewire 40, first catheter 173, and second catheter 174 are simultaneously retracted.

FIGS. 60A-I and 61A-H show a second sequence of operation of an electrolytic detachment system according to the embodiment shown in FIGS. 55 and 57. The balloon 10 is positioned and expanded. The guidewire 40 is retracted. The second catheter 174 is partially retracted and one or more coils or first expandable bodies 720 are placed within the expanded balloon 10. An electrolytic detachment controller 406 is connected to the hub 179 of the first catheter 173 by a cable 407 and the balloon 10 is detached by electrolysis. Finally, the guidewire 40, first catheter 173, and second catheter 174 are simultaneously retracted.

FIGS. 62A-I and 63A-I show a third sequence of operation of an electrolytic detachment system according to the embodiment shown in FIGS. 55 and 57. The balloon 10 is positioned and expanded. The guidewire 40 is retracted. One portion of a coil or first expandable body 720 is placed distal to the expanded balloon 10. The second catheter 174 is partially retracted and the remaining portion of the first expandable body 720 is placed within the expanded balloon 10. An electrolytic detachment controller 406 is connected to the hub 179 of the first catheter 173 by a cable 407 and the balloon 10 is detached by electrolysis. Finally, the guidewire 40, first catheter 173, and second catheter 174 are simultaneously retracted.

In one embodiment, as shown in FIGS. 55A-E, and 57A-D, a stainless steel (SST) ring, is attached to the proximal neck 130 of the detachable balloon 10 and the first catheter 173. The SST ring 224 may be composed of any biocompatible stainless steel alloy, including but not limited to 300 series stainless steel or 400 series stainless steel and preferably 304, 316, 316L, or 316LVM stainless steel. In another embodiment, a stainless steel (SST) ring 224 is attached to the proximal neck 130 via welding or gluing after the formation of the detachable balloon 10. In other embodiments, the neck 215 may be composed of stainless steel and may be incorporated during the formation of the detachable balloon, 10, or subsequently welded or glued to the body. The SST ring 224 or the SST neck 215 may be composed of any biocompatible stainless steel alloy, including but not limited to 300 series stainless steel or 400 series stainless steel and preferably 304, 316, 316L, or 316LVM stainless steel. In various embodiments, the SST ring 224 includes an insulating coating. 226. The insulating coating 226 may be any biocompatible polymer coating. In one aspect, the insulating coating 226 is a dielectric material. A portion of the polymer coating is removed from the exterior surface of the ring 224 to expose a metal surface that may have a strip or ring 228 configuration. In other embodiments, the exposed metal surface may be formed by masking this region of the ring 228 before applying the coating, and then removing the masking material. Upon application of a desired electrical current, electrolysis can occur to sever the uncoated metal strip thereby separating the expanded detachable balloon 10 from the first catheter 173. The metallic strip may be exposed by any suitable method, including but not limited to laser etching or laser ablation. In other embodiments, the metallic strip of the detachment site may be exposed before or after the folding or compression of the detachable balloon. 10. By way of example and not limitation, in one embodiment, the exposed metal in the region may be gold plated, while in other embodiments the exposed metal is stainless steel. In one embodiment, the neck 215 or ring 224 has an average wall thickness of 23 microns±5 microns and the laser etched detachment site has an average wall thickness of about 15 microns, a width of about 125 microns, and is located about 1 mm from the end of the neck 215. In this embodiment, the laser etched portion is subsequently masked during the electroforming process. The width W of the detachment site (i.e. the exposed metal surface in a strip or ring configuration) may be in a range between about 0.1 mm and about 0.4 mm. The detachment site may be located anywhere along the length N1 of the neck. In some embodiments W may be located in the region of the neck 215 formed by the metallic ring 224. In one particular embodiment, the exposed strip of the detachment site has a width W of 0.25 mm+0.03 mm and is located at a length of approximately 0.51 mm+0.03 mm from the end of the neck.

The present disclosure relates to medical devices comprising a detachable balloon 10 and a catheter or catheter assembly 5, wherein the detachable balloons 10 are configured for detachment from the catheter or catheter assembly 5 in vivo. In some embodiments, the balloon 10 is joined or operably coupled to the first catheter 173 by a heat sensitive tubular structure 204 or a tubular structure that is a solid at body temperature but melts after the application of heat increases the temperature above body temperature.

In some embodiments, a detachable balloon catheter 1 comprises a detachable assembly for joining the detachable balloon to the first catheter 173, the detachable assembly comprising a heat sensitive tubular structure comprising a material that melts at a temperature between 50° C. and 100° C. In some examples, when the heat sensitive tubular structure is warmed to a temperature above its melting point for a sufficient time to cause melting of at least a portion of the heat sensitive tubular structure and separation of the heat sensitive tubular structure, an assembly of the distal portion of the heat sensitive tubular structure, the proximal neck 130 or proximal neck assembly 135 of the detachable balloon 10, and the expanded detachable balloon can be separated from an assembly of the proximal portion of the heat sensitive tubular structure and the first catheter 173 by pulling on the first catheter 173 while the expanded detachable balloon 10 remains fixed in place. In some examples, when the heat sensitive tubular structure is warmed to a temperature above its melting point for a sufficient time to cause melting of at least a portion of the heat sensitive tubular structure and separation of the heat sensitive tubular structure, an assembly of the distal portion of the heat sensitive tubular structure, the proximal neck 130 or proximal neck assembly 135 of the detachable balloon 10, and the expanded detachable balloon can be separated from an assembly of the proximal portion of the heat sensitive tubular structure 410, the first catheter 173, and the second catheter 174 by pulling on the first and second catheters 173 & 174 while the expanded detachable balloon 10 remains fixed in place. In some examples, the first catheter 173 assembly and the detachable balloon 10 assembly are pulled apart when the expanded detachable balloon 10 is engaged to the wall of a saccular aneurysm 320, artery 317, vein 318, LAA 800, other blood containing structure, biological conduit 900, or biological space 904.

In some embodiments, the heat sensitive tubular structure comprises a polymer segment. In some embodiments, the proximal end of the heat sensitive tubular structure is bonded to the distal end of the first catheter 173 and the distal end of the heat sensitive tubular structure 410 is bonded to a proximal neck 130 or proximal neck assembly 135 of the detachable balloon 10. In some embodiments, the distal end of the first catheter 173 is joined or bonded to the heat sensitive tubular structure using glue or adhesive. In some embodiments, the distal end of the heat sensitive tubular structure and the proximal neck 130 or proximal neck assembly 135 of the detachable balloon 10 are joined or bonded using glue or adhesive. In some embodiments, the distal end of the first catheter 173 is joined or bonded to the heat sensitive tubular structure 410 and the distal end of the heat sensitive tubular structure 410 and the proximal neck 130 or proximal neck assembly 135 of the detachable balloon 10 are joined or bonded using glue or adhesive.

In some embodiments, the heat sensitive tubular structure comprises material that forms at least a portion of the distal end of the first catheter 173. In some embodiments, the distal end of the heat sensitive tubular structure portion 411 of the first catheter 173 and the proximal neck 130 or proximal neck assembly 135 of the detachable balloon 10 are joined or bonded using glue or adhesive.

In some embodiments, the heat sensitive tubular structure comprises material that forms a bond 409 between the distal end of the first catheter 173 and the proximal neck 130 or proximal neck assembly 135 of the detachable balloon 10, and wherein the first catheter 173 can be separated from the detachable balloon 10 when at least a portion of the heat sensitive bond 409 melts.

In some embodiments, the detachable balloon catheter 1 comprises an electrothermal detachment subsystem with an electrical circuit wherein a portion of the electrical circuit is supported on the first catheter 173 and configured to supply energy to a heat sensitive tubular structure in a manner that increases at least a portion of the heat sensitive tubular structure to a temperature between 50° C. and 100° C. In some embodiments, the electrothermal detachment subsystem comprises an electrical circuit wherein at least a portion of the first circuit is supported on the first catheter 173, the electrical circuit comprises a resistance heating element, and the electrothermal detachment subsystem is configured to deliver an electrical current to the resistance heating element. In some embodiments, when electrical current is passed through a resistance heating element, the resistance heating element warms to a temperature between 50° C. and 100° C. In some examples, when a resistance heating element warms to a temperature between 50° C. and 100° C., at least a portion of the heat sensitive tubular structure warms to a temperature between 50° C. and 100° C. In some embodiments, the resistance heating element comprises a wire, a wire comprising nickel, chromium, iron, aluminum, copper, or combinations thereof, a Nichrome wire, a Kanthal wire, a Constantan wire, an Evanohm wire, a Balco wire, a Cupron wire, or a Manganin wire. In some embodiments, at least or portion of the resistive heating element or wire is located adjacent to the heat sensitive tubular structure. In some embodiments, the electrothermal detachment subsystem comprises one or more conductors, including conductors which are wires or insulated wires. In some embodiments, at least a portion of the one or more conductors is embedded in the wall of the first catheter 173 and act as both conductors for the first electrothermal detachment subsystem and structural reinforcement for the wall of the first catheter 173. In some embodiments, the conductors are routed through at least a portion of the wall of the first catheter 173 in a spiral, coiled, braided, or straight configuration. In some embodiments, the electrothermal detachment subsystem is configured to deliver constant current or a constant voltage to a resistive heating element or wire.

In some embodiments, a third medical device 1 comprises an electrothermal detachment subsystem for use with a detachable balloon catheter 1 comprising a heat sensitive tubular structure. In some embodiments, the third medical device 1 comprises an electrical circuit wherein a portion of the electrical circuit is supported on the third medical device 412 and configured to supply energy to the distal portion of the third medical device 412 in a manner that increases a distal portion of the third medical device 412 to a temperature between 50° C. and 100° C. In some embodiments, a third medical device 412 comprises an electrical circuit wherein at least a portion of the electrical circuit is supported on the third medical device 412, the electrical circuit comprises a resistance heating element, and the third medical device 412 is configured to deliver an electrical current to a resistance heating element. In some embodiments, the electrothermal detachment subsystem of the third medical device 412 is configured to deliver an electrical current to the resistance heating element in a manner that causes the temperature of the resistance heating element to increase to a temperature between 50° C. and 100° C. In some examples, a first medical device 1 is configured such that, when the third medical device 412 is inserted into the lumen 162 of the first catheter 173 of the first medical device 1 and advanced until the resistive heating element portion of the third medical device 412 is located within or adjacent to the heat sensitive tubular structure 410 of the first medical device 1 that melts at a temperature between 50° C. and 100° C., and an electrical current is passed through the resistive heating element of the third medical device 412 in a manner that results in the temperature of the resistance heating element increasing to a temperature between 50° C. and 100° C., then at least a portion of the heat sensitive tubular structure 410 of the first medical device 1 melts and the first catheter 173 of the first medical device 1 can be separated from the proximal neck 130 or proximal neck assembly 135 of the detachable balloon 10 of the first medical device 1. In some embodiments, the outer diameter of the portion of the third medical device 1 that warms to a temperature between 50° C. and 100° C. is 0.001, 0.002, 0.003, 0.004, 0.005, 0.006, 0.007, 0.008, 0.009, or 0.010 inch less than the internal diameter of the first catheter 173 of the first medical device 1 in or near the heat sensitive tubular structure 410. In some embodiments, the resistance heating element of the third medical device 1 is a wire, a wire comprising nickel, chromium, iron, aluminum, copper, or combinations thereof, a Nichrome wire, a Kanthal wire, a Constantan wire, an Evanohm wire, a Balco wire, a Cupron wire, or a Manganin wire. In some embodiments, a resistive heating element or wire is located on the external surface of the third medical device 1 or the external surface of the catheter of the third medical device 412. In some embodiments, the third medical device 412 comprises one or more second conductors, wherein at least a portion of one or more second conductors are embedded in the wall of the third medical device 412 or the catheter of the third medical device 412 and act as both electrical conductors for the second electrothermal detachment subsystem and structural reinforcement for the wall of the third medical device 412 or the catheter of the third medical device 412. In some embodiments, at least a portion of the conductors of the third medical device 412 are routed through the wall of the third medical device 412 or the catheter of the third medical device 412 in a spiral, coiled, braided, or straight configuration. In some embodiments, the conductors of the third medical device 412 are wires. In some embodiments, the electrothermal detachment subsystem of the third medical device 412 is configured to deliver constant current or constant voltage to the resistive heating element or wire of the third medical device 412.

In some examples, after melting of a portion of the heat sensitive tubular structure, an assembly of the distal portion of the heat sensitive tubular structure, the proximal neck 130 or proximal neck assembly 135 of the detachable balloon 10, and the expanded detachable balloon can be separated from an assembly of the proximal portion of the heat sensitive tubular structure and the first catheter 173 by pulling on the first catheter 173 while the expanded detachable balloon 10 remains fixed in place. In some examples, melting of a portion of the heat sensitive tubular structure 410, an assembly of the distal portion of the heat sensitive tubular structure 410, the proximal neck 130 or proximal neck assembly 135 of the detachable balloon 10, and the expanded detachable balloon 10 can be separated from an assembly of the proximal portion of the heat sensitive tubular structure 410, the first catheter 173, and the second catheter 174 by pulling on the first and second catheters 173 & 174 while the expanded detachable balloon 10 remains fixed in place. In some examples, the first catheter 173 assembly and the detachable balloon 10 assembly are pulled apart when the expanded detachable balloon 10 is engaged to the wall of a saccular aneurysm 320, artery 317, vein 318, LAA 800, other blood containing structure, biological conduit 900, or biological space 904.

It should be noted that, with a heat sensitive tubular structure, the detachment process may occur either with the guidewire 40 extending through the central void 115 of the expanded detachable balloon and terminating distal to the expanded detachable balloon, or without the guidewire 40 present. It should also be noted that the detachment process may occur with a coil or other elongated or expandable body 10 in the lumen of the first catheter 173 or the second catheter 174. The heat sensitive tubular structure may be used for attachment of detachable balloons of various sizes and shapes.

The electrothermal detachment system comprising a heat sensitive tubular structure 410, heat sensitive distal portion 411 of the first catheter 173, or heat sensitive bond 409 between distal end of the first catheter 173 and the proximal neck 130 of the detachable balloon 10 is compatible with deployment of the balloon 10 when it is used alone, as shown in FIGS. 73A-F and 74A-E; used in combination with one or more elongated bodies 720 placed within the balloon 10, as shown in FIGS. 75A-I and 76A-K; or used in combination with one or more elongated bodies 720 placed both within and distal to the balloon 10, as shown in FIGS. 77A-I and 78A-K.

FIGS. 73A-F and 74A-E show a first sequence of operation of an electrothermal detachment system according to the embodiment shown in FIGS. 64 and 65. The balloon 10 is positioned and expanded. The guidewire 40 and second catheter 174 are retracted and replaced with a heating catheter 412. The electrothermal detachment controller 406 is connected to heating catheter 412 by a cable 407 and the balloon 10 is detached by melting the heat sensitive first tubular structure 410. Finally, the first catheter 173 and heating catheter 412 are simultaneously retracted.

FIGS. 75A-I and 76A-K show a second sequence of operation of an electrothermal detachment system according to the embodiment shown in FIGS. 64 and 65. The balloon 10 is positioned and expanded. The guidewire 40 is retracted. The second catheter 174 is partially retracted and one or more coils or expandable bodies 720 are placed within the expanded balloon 10. The guidewire 40 and second catheter 174 are retracted and replaced with a heating catheter 412. The electrothermal detachment controller 406 is connected to the heating catheter 412 by a cable 407 and the balloon 10 is detached by melting the heat sensitive first tubular structure 410. Finally, the first catheter 173 and heating catheter 412 are simultaneously retracted.

FIGS. 77A-I and 78A-K show a third sequence of operation of an electrothermal detachment system according to the embodiment shown in FIGS. 64 and 65. The balloon 10 is positioned and expanded. The guidewire 40 is retracted. One portion of a coil or elongated body 720 is placed distal to the expanded balloon 10. The second catheter 174 is partially retracted and the remaining portion of the elongated body 720 is placed within the expanded balloon 10. The guidewire 40 and second catheter 174 are retracted and replaced with a heating catheter 412. The electrothermal detachment controller 406 is connected to the heating catheter 412 by a cable 407 and the balloon 10 is detached by melting the heat sensitive first tubular structure 410. Finally, the first catheter 173 and heating catheter 412 are simultaneously retracted.

In one embodiment, a resistance wire 400 is incorporated into a third medical device 1 that is coaxial and internal to the first catheter 173. A thermally sensitive coupling 410 joins the proximal neck 130 of the detachable balloon 10 to the first catheter 173. In one aspect, the thermally sensitive coupling 410 is a tubular structure wherein one end is affixed or bonded to the detachable balloon and the other end is affixed or bonded to first catheter 173. In another aspect, the thermal sensitive coupling is a heat sensitive distal end 411 of the first catheter 173 and the first catheter 173 is affixed or bonded to the proximal neck 130 or proximal neck assembly 135 of the detachable balloon 10. In another aspect, the thermally sensitive coupling is a heat sensitive bond 409 between the first catheter 173 and the proximal neck 130 or proximal neck assembly 135 of the detachable balloon 10. During placement of the detachable balloon and one or more elongated bodies or coils 720, the second catheter 174 remains within the first catheter 173. After expansion of the detachable balloon 10 and placement of one or more elongated bodies or coils 720 at one or more desire locations, the second catheter 174 is replaced with the third medical device 412. At its distal tip, the third medical device 412 features both a marker band 612 a resistance wire 400 segment that is electrically engaged to a pair of conductive wires 402 that are embedded within the catheter and run out to its proximal end for connection to a detachment controller 406. Using the detachment controller 406, a current is applied through the conductive wires 402 and through the resistance wire 400. The applied current is sufficient to heat the resistance wire 400 segment and the nearby thermally sensitive tubular structure 410 to a temperature in a range between about 40° C. and about 95° C. which melts the thermally sensitive coupling 409, 410, or 411 and detaches the expanded detachable balloon 10 from the first catheter 173. Optionally, the distal neck 140 of the detachable balloon 10 may be held to the distal end 194 of the second catheter 174 by a valve 192 mounted within a distal nosecone 191. This valve 191 closes the distal neck 140 of the detachable balloon 10 when the second catheter 174 is removed, blocking blood flow through the central void 115 or interior volume of the expanded detached balloon 10.

In another embodiment, a resistance wire 400 segment is placed adjacent to, or incorporated into, a thermally sensitive coupling between the first catheter 173 and the proximal neck 130 or proximal neck assembly 135 of the detachable balloon 10, and the resistance wire segment 400 is electrically engaged to a pair of conductive wires 402 that are embedded within the wall of the first catheter 173 or are placed within the first lumen 162 of the detachable balloon catheter 1, and run out to the proximal end of the detachable balloon catheter 1 for connection to a detachment controller 406 using a cable 407.

In one aspect shown in FIGS. 64A-D and 65A-D, the thermally sensitive coupling is a heat sensitive tubular structure 410 wherein one end is affixed or bonded to the detachable balloon and the other end is affixed or bonded to first catheter 173. By way of example and not limitation, nominal dimensions, along with allowable and preferred ranges of dimensions, for various potential embodiments of the heat sensitive tubular structure 410 described in FIGS. 65A-D are presented in tabular form in FIG. 66. In some embodiments, the internal or luminal diameter of the heat sensitive tubular structure 410 is 0.025-0.078 inch. In some embodiments, the external diameter of the heat sensitive tubular structure 410 is 0.027-0.080 inch.

In another aspect shown in FIGS. 67A-D and 68A-D, the thermal sensitive coupling is integrated into the distal end of the first catheter 173 and the first catheter 173 is affixed or bonded to the proximal neck 130 or proximal neck assembly 135 of the detachable balloon 10. By way of example and not limitation, nominal dimensions, along with allowable and preferred ranges of dimensions, for various potential embodiments of the heat sensitive distal end of the first catheter 173 described in FIGS. 68A-D are presented in tabular form in FIG. 69.

Figure 71:
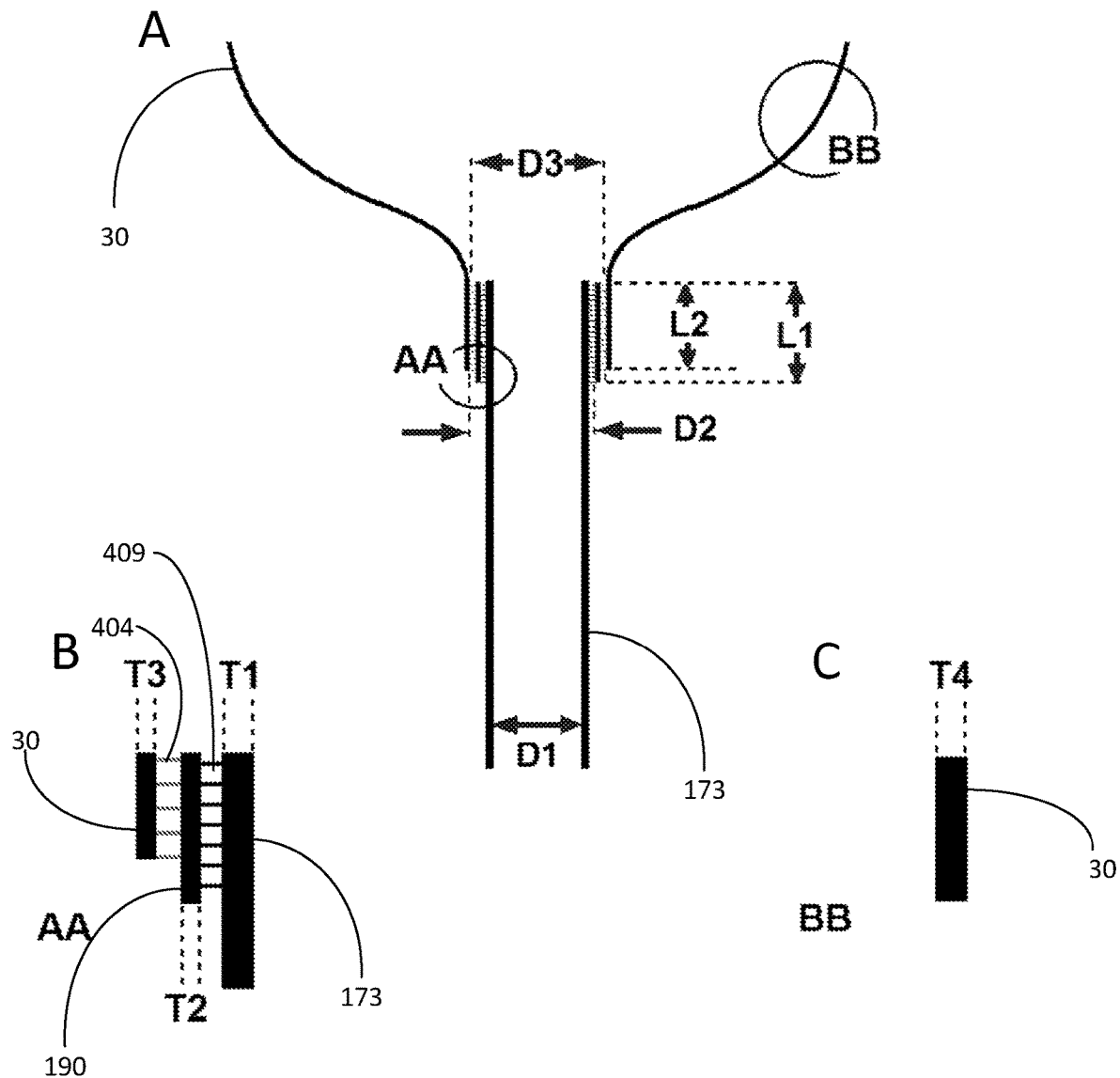
FIGS. 71A-C show cross-sectional and detail cross-sectional views of a heat sensitive bond used in an electrothermal detachment system according to the embodiment shown in FIG. 70, with its overall geometric dimensions defined.
Figure 73:
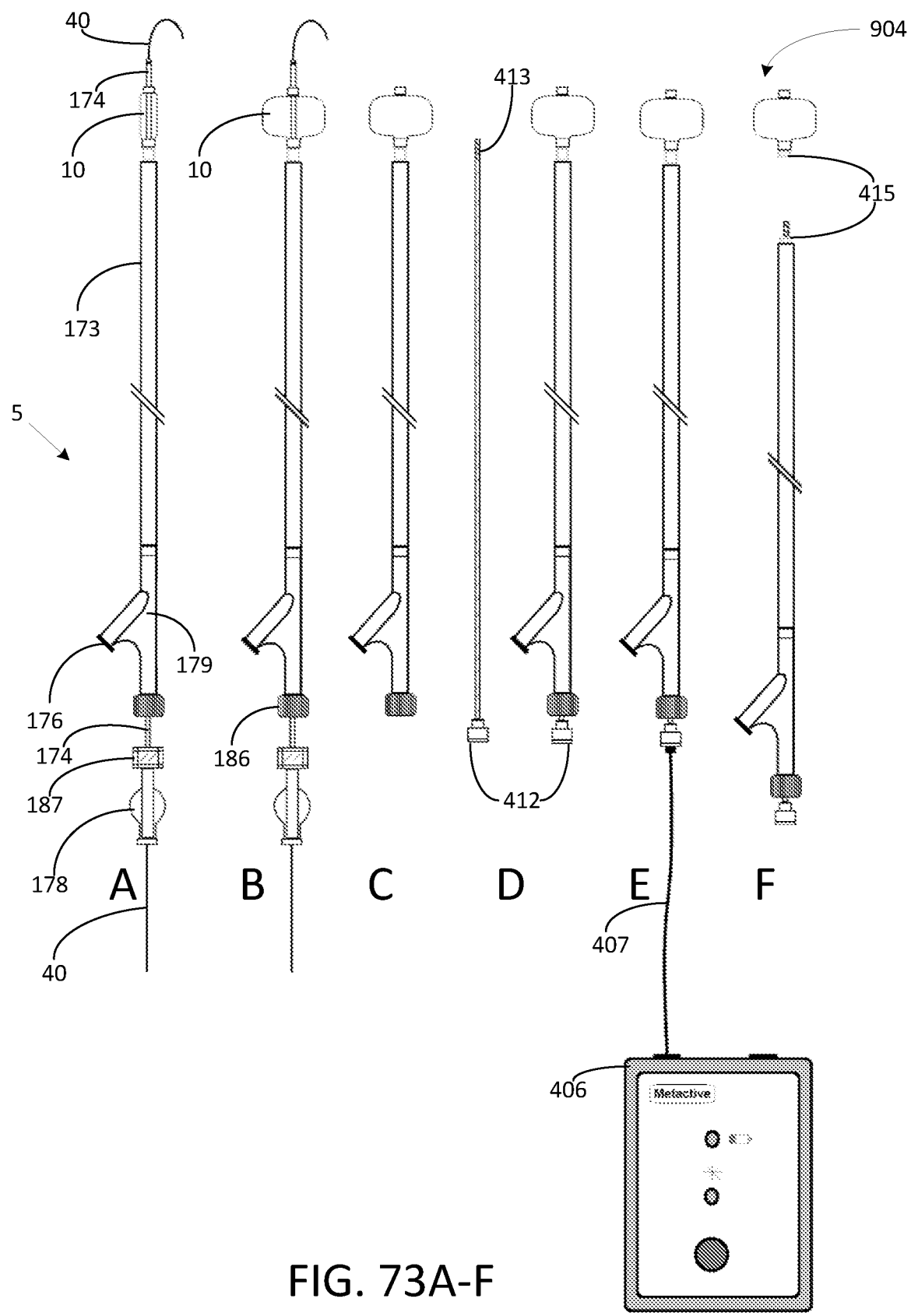
FIGS. 73A-F are planar views showing a first sequence of operation of an electrothermal detachment system according to the embodiment shown in FIGS. 64 and 65.
Figure 74:
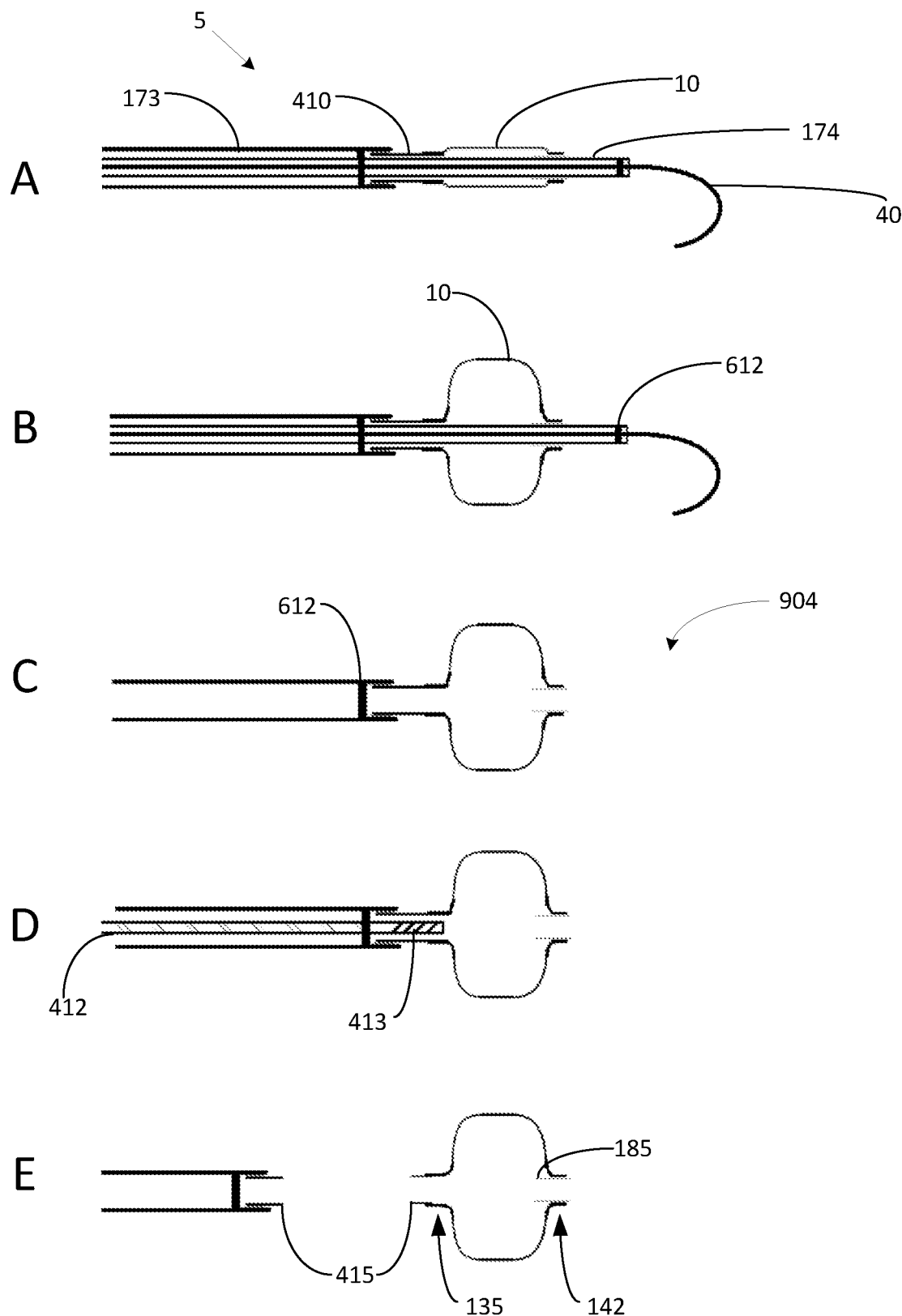
FIGS. 74A-E are cross-sectional detail views showing a first sequence of operation of an electrothermal detachment system according to the embodiment shown in FIGS. 64 and 65.
Figure 75:
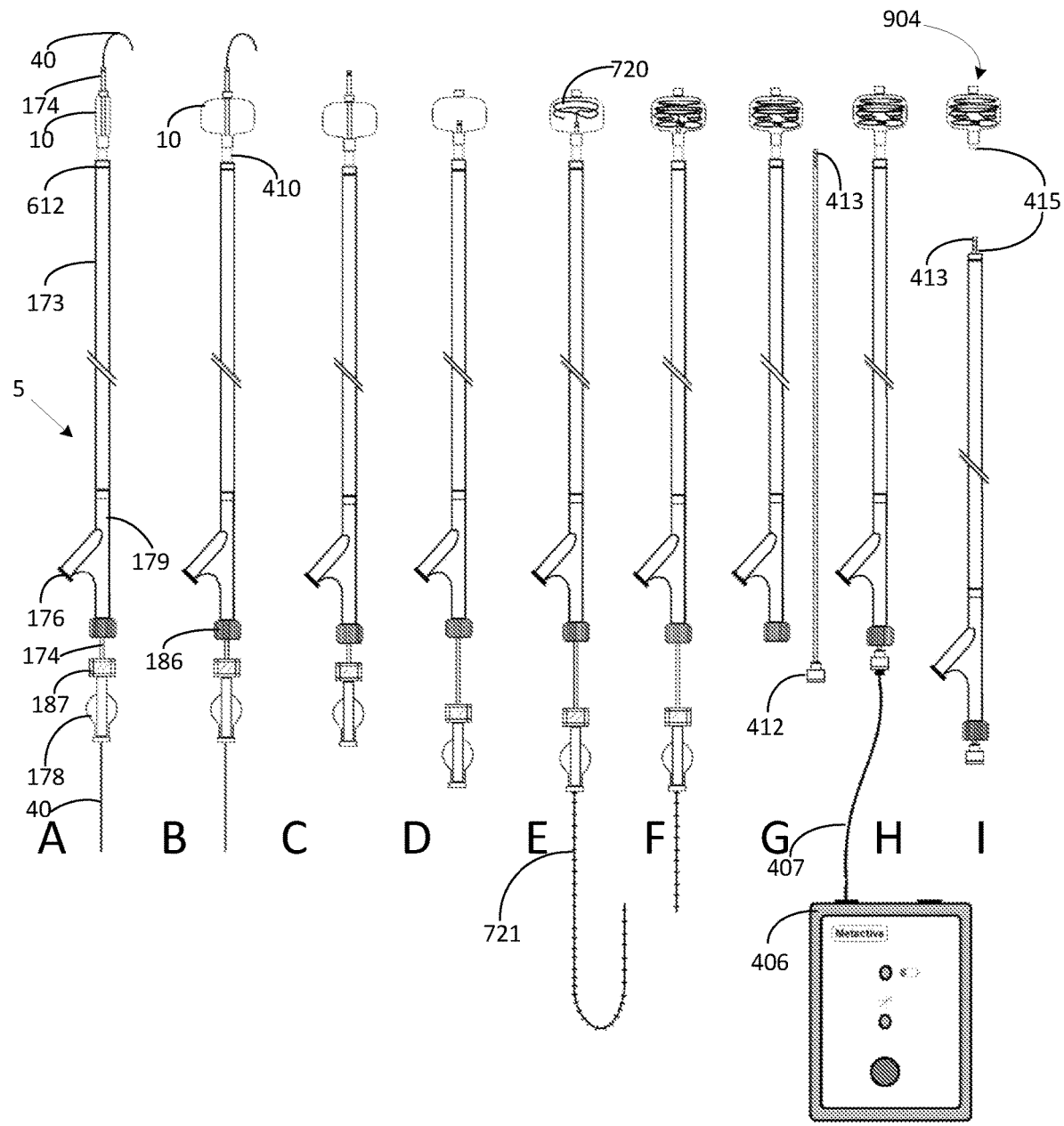
FIGS. 75A-I are planar views showing a second sequence of operation of an electrothermal detachment system according to the embodiment shown in FIGS. 64 and 65.
Figure 76:
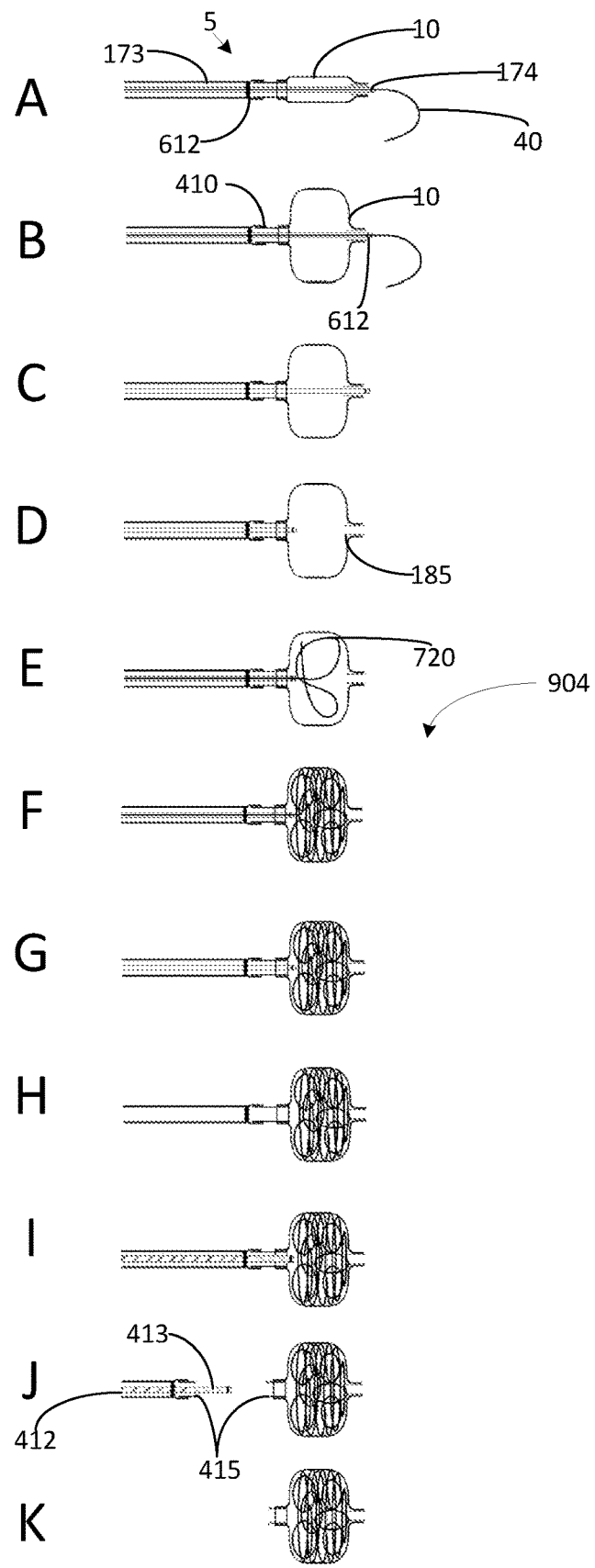
FIGS. 76A-K are cross-sectional detail views showing a second sequence of operation of an electrothermal detachment system according to the embodiment shown in FIGS. 64 and 65.

In another aspect shown in FIGS. 70A-D and 71A-C, the thermally sensitive coupling 410 is a bond between the first catheter 173 and the proximal neck 130 or proximal neck assembly 135 of the detachable balloon 10. By way of example and not limitation, nominal dimensions, along with allowable and preferred ranges of dimensions, for various potential embodiments of the heat sensitive bond to the first catheter 173 described in FIGS. 71A-C are presented in tabular form in FIG. 72.

After placement of the detachable balloon 10 and optionally one or more elongated bodies or coils, the second catheter 174 can be removed or can remain within the first catheter 173. A current is applied through the conductive wires 402 and through the resistance wire 400. The applied current is sufficient to heat the resistance wire 400 segment and the nearby thermally sensitive coupling 410 to a temperature in a range between about 40° C. and about 95° C. which melts the thermally sensitive coupling 410 and detaches the expanded detachable balloon 10 from the first catheter 173. Optionally, the distal neck 140 of the detachable balloon may be held to the distal end of the second catheter 174 by a valve 192 mounted within a distal nosecone 191. This valve 192 closes the distal neck 140 of the detachable balloon 10 when the second catheter 174 is removed, blocking blood flow through the central void 115 or interior volume of the expanded detached balloon 10.

Complete Detachable Balloon Catheters or First Medical Devices

A medical device 1 comprising a detachable balloon may further comprise a first catheter 173 that is coupled to the proximal end of the detachable balloon 10. In some embodiments, the first catheter is coupled to a proximal neck 130 of the detachable balloon 10. In some embodiments, the first catheter 173 is coupled to the detachable balloon 10 by a friction fit 202. In some embodiments, the first catheter 173 is coupled to the detachable balloon 10 by a glue, adhesive, solder, or weld.

A medical device 1 comprising a detachable balloon may further comprise a second catheter 174 that passes through the central void 115 of the detachable balloon and couples with the distal end or distal neck 140 of the detachable balloon. In some embodiments, the second catheter 174 is coupled to the detachable balloon by a friction fit through an elastomeric or resilient valve 192, including through an elastomeric or resilient valve 192 that is part of a distal nosecone 191 assembly. In some embodiments, the tip of the second catheter 174 further comprises one or two marker bands 612 that are conspicuous during fluoroscopy and configured to assist in the delivery and detachment of first elongated bodies 720 or expandable bodies from second elongated bodies 721.

In some embodiments of a medical device comprising a detachable balloon 10, the tip of the second catheter 174 can be rendered mobile and advanced into the biological space 904 adjacent or distal to the expanded detachable balloon 10. As used herein, rendering the second catheter 174 mobile may refer to manipulating a control mechanism on its proximal hub 178, or turning the hemostatic valve of a Tuohy Borst adaptor 186 on a first catheter 173 to reduce friction between the hemostatic valve and the external surface of the adjacent second catheter 174, such that the second catheter 174 may be advanced forward into the biological space 904 distal to the remaining fixed assembly of the detachable balloon 10 and the first catheter 173, and steered or guided to a desired location. The second catheter 174 may also be rendered mobile and navigable by any other suitable means including but not limited to mechanical arrangements, magnetic interaction, or the use of an electrical current, or combinations thereof, among others.

In some embodiments of a medical device 1 comprising a detachable balloon 10, the tip of the second catheter 174 can be advanced into the biological space distal to the detachable balloon 10 when expanded. One or more first elongated bodies 720 or expandable bodies can be placed through the lumen 163 of the second catheter 174 and into the biological space 904 adjacent to the expanded balloon 10 prior to detachment of the first catheter 173 from the detachable balloon 10. When used in this way, the second catheter 174 may also be referred to as a "coiling catheter." In some embodiments of a medical device 1 comprising a detachable balloon 10, the tip of the second catheter 174 can be pulled back into the central void 115 of the detachable balloon 10 when expanded. One or more first elongated bodies 720 or expandable bodies can be placed through the lumen 163 of the second catheter 174 and into the central void 115 of the detachable balloon 10 prior to detachment of the first catheter 173 from the detachable balloon 10. One or more first elongated bodies or expandable bodies 720 can be placed through the lumen 163 of the second catheter 174 and into the remaining portion of the lumen 322 of the aneurysm 320 that is not filled with the expanded balloon 10. The tip of the second catheter 174 can be repositioned in the remaining portion of the lumen 322 of the aneurysm 320 that is not filled with the expanded balloon 10 and then one or more additional first elongated bodies or expandable bodies 720 or medical devices can be placed. The tip of the second catheter 174 can be repositioned again in the remaining portion of the lumen 322 of the aneurysm 320 that is not filled with the expanded balloon 10 and then one or more additional first elongated bodies or expandable bodies 720 or medical devices can be placed. The assembly of the first and second catheters 173 & 174 can be separated or detached from the expanded balloon 10 and the first and second catheters 173 & 174 can be removed. Manipulation of components at the hub can cause the advancement or retraction of the second catheter 174 relative to the expanded balloon 10, first catheter 173, or third catheter 175. The second catheter 174 can be rendered mobile and advanced forward relative to the expanded balloon 10, first catheter 173, or third catheter 175 to facilitate the placement of one or more first elongated bodies or expandable bodies 720 or medical devices in the unfilled lumen 322 of the aneurysm 320 behind the expanded balloon 10. The second catheter 174 may further comprise one or more radiopaque marker bands 612 to help identify the catheter tip position using fluoroscopy, helping facilitate the placement and detachment of the first elongated bodies or expandable bodies 720 or medical devices that are placed through the lumen 163 of the second catheter 174.

In some embodiments, a ring structure, tubular structure, telescoping structure, catheter segment, or telescoping catheter segment 185 is bonded to the distal neck 140 of the detachable balloon and helps to form a tight seal between the outer surface of the second catheter 174 and the distal neck 140 or neck assembly of the detachable balloon 10 to facilitate expansion of the detachable balloon 10 or to facilitate the sliding of the distal neck 140 of the detachable balloon 10 on the second catheter 174 during expansion of the detachable balloon 10. During expansion of the detachable balloon 10, the ring structure, tubular structure, telescoping structure, catheter segment, or telescoping catheter structure 185 allows the body of the detachable balloon 10 to shorten in the axial direction 706. For a medical device 1 comprising a detachable balloon 10 intended for use in the treatment of saccular aneurysms, 320, this maximizes the distance between the distal end of the expanded detachable balloon 10 and the dome of the aneurysm 320 so that a first elongated body 720 or an expandable body 10 may be placed in the sac or lumen of the aneurysm 322 distal to the expanded detachable balloon 10 with the least risk of injuring, rupturing, or puncturing the often fragile dome of the aneurysm 320. The ring structure, tubular structure, telescoping structure, catheter segment, or telescoping catheter segment 185 may also reduce leakage of the injected fluid medium from the detachable balloon during expansion, which reduces the pressure required for expansion and reduces the rate of collapse of detachable polymer balloons and detachable flexible metalized polymer balloons 14 after expansion in vivo. In some embodiments, the ring structure, tubular structure, or telescoping structure 185 may be a section of metal tubing comprising gold, platinum, iridium, tantalum, or combinations or alloys thereof that may also function as a radiopaque marker that is visible under fluoroscopy. In one aspect, the radiopaque ring structure, tubular structure, or telescoping structure enhances the visibility of the detachable balloon 10 under fluoroscopic imaging. In another aspect, the radiopaque ring structure, tubular structure, or telescoping structure 185 may help a physician in positioning the tip of the second catheter 174 prior to the placement of all or a portion of a first elongated body 720 or expandable body 10 in vivo, including placement within the central void 115 of, or adjacent to, an expanded detachable balloon 10. Alternatively, the ring structure, tubular structure, telescoping structure, catheter segment, or telescoping catheter segment 185 may be composed of a polymer and include a radiopaque marker spot or band 612 to enhance the visibility of the detachable balloon 10 under fluoroscopic imaging. In another aspect, the radiopaque marker spot or band 612 or the ring structure, tubular structure, or telescoping structure 185 may help a physician in positioning the tip of the second catheter 174 prior to the placement of all or a portion of a first elongated body 720 or expandable body 10 in vivo, including placement within the central void 115 of, or adjacent to, an expanded detachable balloon 10.

Manufacturing of Detachable Balloon Catheters—Fabricating Detachable Polymer Balloons and Detachable Metalized Polymer Balloons Methods of manufacturing first medical devices 1 as disclosed herein, including methods of manufacturing detachable polymer balloons 12, detachable metalized polymer balloons 14, detachable flexible metalized polymer balloons, detachable rigid metalized polymer balloons, detachable metal balloons 16, and detachable polymer-coated metal balloons 18.

In one embodiment, a first medical device 1 is made by manufacturing a first catheter 173, manufacturing a second catheter 174, manufacturing a detachable polymer balloon 12 with a proximal and a distal opening, thereby creating a first polymer layer 99 of the detachable polymer balloon 12 that is continuous, except for the proximal and distal openings, forming the wall 30 of the detachable polymer balloon 12 into a pleated and folded configuration, joining or operably coupling the pleated and folded detachable polymer balloon to the first catheter 173 in a manner that allows for the separation of the detachable polymer balloon 12 from the first catheter 173 after expansion in a patient. In another example, the expanded detachable metalized polymer balloon 14 is joined or operably coupled to the first catheter 173 in a manner that allows for the separation of the detachable metalized polymer balloon 14 from the first catheter 173 after expansion in a patient, and then the wall 30 of the detachable metalized polymer balloon 14 is formed into a pleated and folded configuration. Detachable balloons 10 wherein the polymer layer 99 is continuous except for the proximal and distal openings and there is no metal layer 90 are called "detachable polymer balloons", "polymer balloons", "detachable polymer-only balloons", or "polymer-only balloons" 12.

In some embodiments, the polymer layer 99 of a detachable polymer balloon 12 comprises PET, nylon, or Pebax. In some embodiments, a detachable polymer balloon 12 is manufactured by blow molding. In some embodiments, a detachable polymer balloon 12 is formed with a distal region 120, a proximal region 110 generally opposite the distal region 120, and an intermediate region 100 transitioning from the distal region 120 to the proximal region 110, while in other embodiments, a detachable polymer balloon 12 is formed with a distal region 120 and a proximal region 110 without an intermediate region 100. In some embodiments, the rated burst pressure of a detachable polymer balloon 12 is 1-30 atmospheres. In some embodiments, the thickness of the wall 30 of the detachable polymer balloon 12 is 5-75 microns. In some embodiments, at least a portion of the external surface of a detachable polymer balloon 12 comprises a textured surface. In some embodiments, at least a portion of the external surface of a detachable polymer balloon 12 comprises a textured surface, wherein the distance between the highest portions of the external surface of the detachable balloon 10 and the lowest portions of the external surface of the detachable balloon 10 is 0.0001-1 microns.

In one embodiment, a first medical device 1 is made by manufacturing a first catheter 173, manufacturing a second catheter 174, manufacturing a detachable polymer balloon 12 with a proximal opening and a distal opening, thereby creating a first polymer layer 99 of the detachable polymer balloon 12 that is continuous, except for the proximal and distal openings, expanding the detachable polymer balloon 12, adding a first layer of metal 90 with a thickness in the range of 0.0005 to 1 micron to at least a portion of the external surface of the detachable polymer balloon 12 through a sputter coating or vapor deposition process, forming the wall 30 of the detachable metalized polymer balloon 14 into a pleated and folded configuration, joining or operably coupling the pleated and folded detachable metalized polymer balloon 14 to the first catheter 173 in a manner that allows for the separation of the detachable metalized polymer balloon 14 from the first catheter 173 after expansion in a patient. In another example, the expanded detachable metalized polymer balloon 14 is joined or operably coupled to the first catheter 173 in a manner that allows for the separation of the detachable metalized polymer balloon 14 from the first catheter 173 after expansion in a patient, and then the wall 30 of the detachable metalized balloon 14 is formed into a pleated and folded configuration. Detachable metalized polymer balloons 14 without a structural metal layer 90 are also referred to as "flexible metalized polymer balloons" or "detachable flexible metalized polymer balloons." In some embodiments, a structural metal layer 90 is a metal layer 90 wherein the primary purpose of the metal is load bearing, rather than for other purposes such as increasing fluoroscopic visualization, enhancing biocompatibility, inducing a biological response in the adjacent tissue (such as stimulating growth of an endothelial layer on the surface of the balloon 10), or the conduction of electricity, among other purposes. In some embodiments, a structural metal layer 90 is a metal layer 90 with a thickness greater than 1 micron.

In some embodiments, the first metal layer 90 is gold, titanium, or combinations thereof. In some embodiments, the first metal layer 90 that is continuous, in other embodiments the first metal layer 90 that is discontinuous. In some embodiments, a first metal layer 90 is formed on the proximal region 110, the intermediate region, the distal region, 120, the proximal and intermediate regions, the intermediate and distal regions, 120, or the proximal, intermediate, and distal regions. 120. In some embodiments, one or more masks are applied to an outer surface of the detachable polymer balloon prior to creating the first metal layer 90 such that only a portion of the external surface of the detachable polymer balloon is covered by a first metal layer. 90. In some embodiments, the rated burst pressure of a detachable flexible metalized polymer balloon is 1-30 atmospheres. In some embodiments, the thickness of the wall 30 of a detachable flexible metalized polymer balloon is 5-75 microns. In some embodiments, at least a portion of the external surface of a detachable flexible metalized polymer balloon comprises a textured surface. In some embodiments, at least a portion of the external surface of a detachable flexible metalized polymer balloon comprises a textured surface, wherein the distance between the highest portions of the external surface of the balloon and the lowest portions of the external surface of the balloon is 0.0001-1 microns.

In another embodiment, a first medical device 1 is made by manufacturing a first catheter 173, manufacturing a second catheter 174, manufacturing a detachable polymer balloon 12 with a proximal and a distal opening, thereby creating a first polymer layer 99 of the detachable polymer balloon 12 that is continuous, except for the proximal and distal openings, expanding the polymer balloon 12, adding a first layer of metal 90 with a thickness in the range of 0.0005 to 1 micron to at least a portion of the external surface of the detachable balloon 10 through a sputter coating or vapor deposition process, adding a second layer of metal 90 with a thickness of 1 to 50 microns to at least a portion of the external surface of the first metal layer 90; through an electroforming or electroplating process, forming the wall 30 of the detachable metalized polymer balloon 14 into a pleated and folded configuration, joining or operably coupling the pleated and folded detachable metalized polymer balloon 14 to the first catheter 173 in a manner that allows for the separation of the detachable metalized polymer balloon 14 from the first catheter 173 after expansion in a patient. In another example, the expanded detachable metalized polymer balloon 14 is joined or operably coupled to the first catheter 173 in a manner that allows for the separation of the detachable metalized polymer balloon 14 from the first catheter 173 after expansion in a patient, and then the wall 30 of the detachable metalized balloon 14 is formed into a pleated and folded configuration. Detachable metalized polymer balloons 14 with a structural metal layer 90 are also referred to as "rigid metalized polymer balloons" or "detachable rigid metalized polymer balloons." In this context, a structural metal layer 90 is a metal layer 90 wherein the primary purpose of the metal is load bearing, rather than for other purposes such as increasing fluoroscopic visualization, enhancing biocompatibility, inducing a biological response in the adjacent tissue (such as stimulating growth of an endothelial layer on the surface of the balloon 10), or the conduction of electricity, among other purposes. In some embodiments, a structural metal layer 90 is a metal layer 90 with a thickness greater than 1 micron.

In some embodiments, wherein a detachable rigid metalized polymer balloon is produced by an electroforming or electroplating process, the second metal layer 90 comprises gold, platinum, or combinations thereof. In some embodiments, wherein a detachable rigid metalized polymer balloon is produced by an electroforming or electroplating process, the second metal layer 90 is continuous, in other embodiment, wherein a detachable rigid metalized polymer balloon is produced by an electroforming or electroplating process, the second metal layer 90 that is discontinuous. In some embodiments, wherein a detachable rigid metalized polymer balloon is produced by an electroforming or electroplating process, the second metal layer 90 is formed on the proximal region 110; the intermediate region 100; the distal region 120; the proximal region 110 and intermediate region 100; the intermediate region 100 and distal region 120; or the proximal region 110, intermediate region 100, and distal region 120. In some embodiments, wherein a detachable rigid metalized polymer balloon is produced by an electroforming or electroplating process, one or more masks are applied to an outer surface of the detachable metalized balloon prior to creating the second metal layer 90 such that only a portion of the external surface of the detachable metalized balloon is covered by a second metal layer. 90. In some embodiments, the rated burst pressure of a detachable rigid metalized polymer balloon produced by an electroforming or electroplating process is 5-50 atmospheres. In some embodiments, the thickness of the wall 30 of a detachable flexible metalized polymer balloon produced by an electroforming or electroplating process is 6-100 microns. In some embodiments, at least a portion of the external surface of a detachable rigid metalized polymer balloon produced by an electroforming or electroplating process comprises a textured surface. In some embodiments, at least a portion of the external surface of a detachable rigid metalized polymer balloon produced by an electroforming or electroplating process comprises a textured surface, wherein the distance between the highest portions of the external surface of balloon and the lowest portions of the external surface of the balloon is 0.0001-1 microns.

In another embodiment, a first medical device 1 is made by manufacturing a first catheter 173, manufacturing a second catheter 174, manufacturing a detachable polymer balloon 12 with a proximal and a distal opening, thereby creating a first polymer layer 99 of the detachable polymer balloon 12 that is continuous, except for the proximal and distal openings, expanding the detachable polymer balloon 12, adding a first adhesive layer 95 to at least a portion of the external surface of the balloon 10, applying metal wire with a thickness of 25-100 microns to the external, adhesive-coated surface of the expanded balloon 10 in a spiral, coil, braid, woven, or straight pattern, thereby creating a first metal layer 90, adding a second adhesive layer 95 to at least a portion of the external adhesive-coated surface and at least a portion of the external metal wire covered surface of the expanded balloon, drying, hardening, or curing the adhesive layers 95, forming the wall 30 of the detachable metalized balloon 14 into a pleated and folded configuration, joining or operably coupling the detachable metalized polymer balloon 14 to the first catheter 173 in a manner that allows for the separation of the detachable metalized polymer balloon 14 from the first catheter 173 after expansion in a patient. In another example, the expanded detachable metalized polymer balloon 14 is joined or operably coupled to the first catheter 173 in a manner that allows for the separation of the detachable metalized polymer balloon 14 from the first catheter 173 after expansion in a patient, and then the wall 30 of the detachable metalized balloon 14 is formed into a pleated and folded configuration. Detachable metalized polymer balloons 14 with a structural metal layer 90 are also referred to as "rigid metalized polymer balloons" or "detachable rigid metalized polymer balloons." In this context, a structural metal layer 90 is a metal layer 90 wherein the primary purpose of the metal is load bearing, rather than for other purposes such as increasing fluoroscopic visualization, enhancing biocompatibility, inducing a biological response in the adjacent tissue (such as stimulating growth of an endothelial layer on the surface of the detachable balloon 10), or the conduction of electricity, among other purposes. In some embodiments, a structural metal layer 90 is a metal layer 90 wherein the thickness of metal wire applied to a polymer base layer 99 is greater than 1 micron.

In some embodiments, wherein a detachable rigid metalized polymer balloon is produced by applying metal wire to the surface of a detachable polymer balloon, the first layer of adhesive comprises urethane. In some embodiments, wherein a detachable rigid metalized polymer balloon is produced by applying metal wire to the surface of a detachable polymer balloon, the first adhesive layer that is continuous, while in other embodiments, the first adhesive layer is discontinuous. In some embodiments, wherein a detachable rigid metalized polymer balloon is produced by applying metal wire to the surface of a detachable polymer balloon, a first adhesive layer is formed on the proximal region 110, the intermediate region 100, the distal region 120; the proximal region 10 and intermediate region 100; the intermediate region 100 and distal region 110120; or the proximal region 110, intermediate region 100, and distal region 120. In some embodiments, wherein a detachable rigid metalized polymer balloon is produced by applying metal wire to the surface of a detachable polymer balloon, one or more masks are applied to an outer surface of the detachable polymer balloon prior to applying the first layer of adhesive such that only a portion of the external surface of the detachable polymer balloon is coated by a first adhesive layer. In some embodiments, wherein a detachable rigid metalized polymer balloon is produced by applying metal wire to the surface of a detachable polymer balloon, the first adhesive layer is formed by dipping the balloon in a solution comprising urethane in a solvent having a concentration of urethane in a range of 1-20%, or by spraying the balloon in a solution comprising urethane in a solvent having a concentration of urethane in a range of 1-20%. Wherein a detachable rigid metalized polymer balloon is produced by applying metal wire to the surface of a detachable polymer balloon, the metal wire is wound onto the expanded detachable balloon. Wherein a detachable rigid metalized polymer balloon is produced by applying metal wire to the surface of a detachable polymer balloon, the first metal layer 90 comprises gold, platinum, or combinations thereof. In some embodiment, wherein a detachable rigid metalized polymer balloon is produced by applying metal wire to the surface of a detachable polymer balloon, the pitch and angle of the winding of the wire is uniform, and in other embodiments, the pitch and angle of the winding of the wire is non-uniform. In some embodiment, wherein a detachable rigid metalized polymer balloon is produced by applying metal wire to the surface of a detachable polymer balloon, the second layer of adhesive comprises urethane. In some embodiment, wherein a detachable rigid metalized polymer balloon is produced by applying metal wire to the surface of a polymer balloon 12, the second adhesive layer that is continuous, while in other embodiments, the second adhesive layer that is discontinuous. In some embodiment, wherein a detachable rigid metalized polymer balloon is produced by applying metal wire to the surface of a detachable polymer balloon, the second adhesive layer is formed on the proximal region 110; the intermediate region 100; the distal region 120; the proximal region 110 and intermediate region 100; the intermediate region 100 and distal region 120; or the proximal region 110, intermediate region 100, and distal region 120. In some embodiment, wherein a detachable rigid metalized polymer balloon is produced by applying metal wire to the surface of a detachable polymer balloon, one or more masks are applied to an outer surface of the detachable metalized balloon prior to applying the second layer of adhesive such that only a portion of the external surface of the detachable metalized balloon is coated by a second adhesive layer. In some embodiment, wherein a detachable rigid metalized polymer balloon is produced by applying metal wire to the surface of a detachable polymer balloon, the second adhesive layer is formed by dipping the balloon in a solution comprising urethane in a solvent having a concentration of urethane in a range of 1-20%, while in other embodiments the second adhesive layer is formed by spraying the balloon in a solution comprising urethane in a solvent having a concentration of urethane in a range of 1-20%. In some embodiment, wherein a detachable rigid metalized polymer balloon is produced by applying metal wire to the surface of a detachable polymer balloon, the second adhesive layer is formed on the proximal region 110; the intermediate region 100; the distal region 120, the proximal region 110 and intermediate region 100; the intermediate region 100 and distal region 120; or the proximal region 110, intermediate region 100, and distal region 120. In some embodiment, wherein a detachable rigid metalized polymer balloon is produced by applying metal wire to the surface of a detachable polymer balloon, one or more masks are applied to an outer surface of the detachable metalized balloon prior to applying the second layer of adhesive such that only a portion of the external surface of the detachable metalized balloon is coated by a second adhesive layer. In some embodiments, the rated burst pressure of a detachable rigid metalized polymer balloon produced by applying metal wire to the surface of a detachable polymer balloon is 5-50 atmospheres. In some embodiments, the thickness of the wall 30 of a detachable flexible metalized polymer balloon produced by applying metal wire to the surface of a detachable polymer balloon is 6-400 microns. In some embodiments, at least a portion of the external surface of a detachable rigid metalized polymer balloon produced by applying metal wire to the surface of a detachable polymer balloon comprises a textured surface. In some embodiments, at least a portion of the external surface of a detachable rigid metalized polymer balloon produced by applying metal wire to the surface of a polymer balloon 12 comprises a textured surface, wherein the distance between the highest portions of the external surface of the balloon 10 and the lowest portions of the external surface of the balloon 10 is 0.0001-1 microns.

Methods for manufacturing a detachable polymer balloon, a detachable metallized polymer balloon, a detachable metal balloon 16, and a detachable polymer-coated metal balloon 18 are disclosed herein. Detachable balloons may be comprised solely of polymer, solely of metal, or a combination of polymer and metal. Detachable balloons may be comprised solely of a single polymer, solely of a single metal, or a combination of a single polymer and a single metal. Detachable balloons may be comprised solely of multiple polymers, solely of multiple metals, or a combination of multiple polymers and multiple metals. Detachable balloons may be comprised a combination of a single polymer and multiple metals or multiple polymers and single metal. As used herein, a detachable metallized polymer balloon includes detachable metallic polymer balloons, detachable metal plated polymer balloons, detachable partially metallized polymer balloons, detachable partially metallic plated polymer balloons, detachable partially metal plated polymer balloons, and detachable wire wound or wrapped polymer balloons and refer to a detachable polymer balloon with at least one metallic region incorporated into the wall 30 of a detachable polymer balloon 12 or a detachable balloon 10 with a continuous layer of polymer 99, except for a proximal or distal opening, if any.

In some embodiments, the metal portion of a detachable metalized polymer balloon 14 or polymer coated metal balloon 18 may be the most exterior surface of the detachable balloon 10 or may not be the most exterior surface of the detachable balloon 10. In various embodiments, the detachable balloon 10 may also include a thin polymer coating over the polymer 99 or metal 90 layers, including detachable polymer-coated polymer balloons 12, detachable metallized polymer balloons 14, detachable metal balloons 16, and detachable polymer-coated metal balloons 18.

One method includes manufacturing a detachable balloon composed of metal or comprising metal, having a distal region 120, a proximal region 110 generally opposite the distal region 120, and an optional intermediate region 100 transitioning from the distal region 120 to the proximal region 110. A center or first axis 706 extends between the proximal neck 130 and the distal neck 140 of the detachable balloon 10. A wall 30 of the detachable balloon 10 extends continuously from the proximal region 110 through the intermediate region 100, and to the distal region 120 to define an exterior surface of the detachable balloon 10 and an interior surface of the detachable balloon 10. The interior surface defines a central void 115 or interior volume of the detachable balloon 10. The method may include fabricating a detachable polymer balloon and applying a metal layer 90 to the detachable polymer balloon, including by sputtering, electroplating, electroforming, use of adhesives, mechanical means, or combinations thereof. In one embodiment, the metal portion of the wall 30 of a detachable balloon 10 may be continuous throughout the entire balloon. In another embodiment, the metal portion of the wall 30 of a detachable balloon 10 may be discontinuous or may comprise only one or more portions of the wall 30 of a detachable balloon 10. In one embodiment, all or a portion of the external surface of a detachable balloon 10 may comprise metal. In another embodiment, all or a portion of the internal surface of a detachable balloon 10 may comprise metal. In another embodiment, the all or a portion of the exterior and interior surfaces of a detachable balloon 10 may comprise metal. In one embodiment, none of the external surface of a detachable balloon 10 may comprise metal. In another embodiment, none of the internal surface of a detachable balloon 10 may comprise metal. In another embodiment, none of the exterior and interior surfaces of a detachable balloon 10 may comprise metal.

In some embodiments, detachable metalized polymer balloons 14 may be fabricated from one or more base polymer materials. In various embodiments, the base material may comprise PET, nylon, Pebax, or other aliphatic or semi-aromatic polyamides that can be melt-processed, polyurethane (including Pellethane or Carbothane), polyvinyl chloride, polyethylene, silicone elastomer, PTFE, and combinations thereof. One of skill in the art will appreciate that the polymer or polymer layer of a detachable metalized balloon, may be fabricated from any synthetic or natural polymer known in the art. The detachable metalized balloon may be fabricated using a single metal, a single metal alloy or amalgam, two different metals, two different metal alloys or amalgams, or more than two different metals, or metal alloys or amalgams. Metals that may be used include but are not limited to gold, platinum, iridium, silver, nickel, stainless steel, titanium, and combinations or alloys thereof.

In one embodiment, a detachable metalized balloon may comprise a continuous base layer of PET (except for openings in the proximal and distal regions 110 & 120, if any) and a continuous outer layer of gold, wherein the gold layer is <1 micron thick. In one embodiment, a detachable metalized balloon may comprise a continuous base layer of PET (except for openings in the proximal and distal regions 110 & 120, if any) and a continuous outer layer of gold, wherein the gold layer is >1 micron thick. In one embodiment, a detachable metalized balloon may comprise a continuous base layer of nylon (except for openings in the proximal and distal regions 110 & 120, if any) and a continuous outer layer of gold, wherein the gold layer is <1 micron thick. In one embodiment, a detachable metalized balloon may comprise a continuous base layer of nylon (except for openings in the proximal and distal regions 110 & 120, if any) and a continuous outer layer of gold, wherein the gold layer is >1 micron thick. In one embodiment, a detachable metalized balloon may comprise a continuous base layer of Pebax (except for openings in the proximal and distal regions 110 & 120, if any) and a continuous outer layer of gold, wherein the gold layer is <1 micron thick. In one embodiment, a detachable metalized balloon may comprise a continuous base layer of Pebax (except for openings in the proximal and distal regions 110 & 120, if any) and a continuous outer layer of gold, wherein the gold layer is >1 micron thick.

In one embodiment, a detachable metalized balloon may comprise a continuous base layer of PET (except for openings in the proximal and distal regions 110 & 120, if any) and an outer layer of gold, wherein the gold layer is <1 micron thick and covers only a portion of the PET base layer. In one embodiment, a detachable metalized balloon may comprise a continuous base layer of PET (except for openings in the proximal and distal regions 110 & 120, if any) and an outer layer of gold, wherein the gold layer is >1 micron thick and covers only a portion of the PET base layer. In one embodiment, a detachable metalized balloon may comprise a continuous base layer of nylon (except for openings in the proximal and distal regions 110 & 120, if any) and an outer layer of gold, wherein the gold layer is <1 micron thick and covers only a portion of the nylon base layer. In one embodiment, a detachable metalized balloon may comprise a continuous base layer of nylon (except for openings in the proximal and distal regions 110 & 120, if any) and an outer layer of gold, wherein the gold layer is >1 micron thick and covers only a portion of the nylon base layer. In one embodiment, a detachable metalized balloon may comprise a continuous base layer of Pebax (except for openings in the proximal and distal regions 110 & 120, if any) and an outer layer of gold, wherein the gold layer is <1 micron thick and covers only a portion of the Pebax base layer. In one embodiment, a detachable metalized balloon may comprise a continuous base layer of Pebax (except for openings in the proximal and distal regions 110 & 120, if any) and an outer layer of gold, wherein the gold layer is >1 micron thick and covers only a portion of the Pebax base layer.

In one embodiment, a detachable metalized balloon may comprise a continuous base layer of PET (except for openings in the proximal and distal regions 110 & 120, if any) a middle layer of gold, wherein the gold layer is >1 micron thick and covers only a portion of the PET base layer, and an outer layer of polymer, polyurethane or silicone. In one embodiment, a detachable metalized balloon may comprise a continuous base layer of nylon (except for openings in the proximal and distal regions 110 & 120, if any) a middle layer of gold, wherein the gold layer is >1 micron thick and covers only a portion of the nylon base layer, and an outer layer of polymer, polyurethane or silicone. In one embodiment, a detachable metalized balloon may comprise a continuous base layer of Pebax (except for openings in the proximal and distal regions 110 & 120, if any) a middle layer of gold, wherein the gold layer is >1 micron thick and covers only a portion of the Pebax base layer, and an outer layer of polymer, polyurethane or silicone.

In one embodiment, a detachable metalized balloon may comprise a continuous base layer of PET (except for openings in the proximal and distal regions 110 & 120, if any) a middle layer of gold, wherein the gold layer is >1 micron thick and covers all of the PET base layer, and an outer layer of polymer, polyurethane or silicone. In one embodiment, a detachable metalized balloon may comprise a continuous base layer of nylon (except for openings in the proximal and distal regions 110 & 120, if any) a middle layer of gold, wherein the gold layer is >1 micron thick and covers all of the nylon base layer, and an outer layer of polymer, polyurethane or silicone. In one embodiment, a detachable metalized balloon may comprise a continuous base layer of Pebax (except for openings in the proximal and distal regions 110 & 120, if any) a middle layer of gold, wherein the gold layer is >1 micron thick and covers all of the Pebax base layer, and an outer layer of polymer, polyurethane or silicone.

In one embodiment, a detachable metalized balloon may comprise a continuous base layer of PET (except for openings in the proximal and distal regions 110 & 120, if any) and a continuous outer layer of titanium, wherein the titanium layer is <1 micron thick. In one embodiment, a detachable metalized balloon may comprise a continuous base layer of nylon (except for openings in the proximal and distal regions 110 & 120, if any) and a continuous outer layer of titanium, wherein the titanium layer is <1 micron thick. In one embodiment, a detachable metalized balloon may comprise a continuous base layer of Pebax (except for openings in the proximal and distal regions 110 & 120, if any) and a continuous outer layer of titanium, wherein the titanium layer is <1 micron thick.

In one embodiment, a detachable metalized balloon may comprise a continuous base layer of PET (except for openings in the proximal and distal regions 110 & 120, if any) and an outer layer of titanium, wherein the titanium layer is <1 micron thick and covers only a portion of the PET base layer. In one embodiment, a detachable metalized balloon may comprise a continuous base layer of nylon (except for openings in the proximal and distal regions 110 & 120, if any) and a continuous outer layer of titanium, wherein the titanium layer is <1 micron thick and covers only a portion of the nylon base layer. In one embodiment, a detachable metalized balloon may comprise a continuous base layer of Pebax (except for openings in the proximal and distal regions 110 & 120, if any) and an outer layer of titanium, wherein the titanium layer is <1 micron thick and covers only a portion of the Pebax base layer.

In various embodiments, a detachable metalized balloon may comprise a continuous inner layer of PET, nylon, or Pebax, a continuous middle layer comprising gold, platinum, iridium, or silver, and a continuous exterior layer of polyurethane or silicone. In various embodiments, a detachable metalized balloon may comprise a continuous inner layer of PET, nylon, or Pebax, a discontinuous middle layer comprising gold, platinum, iridium, or silver, and a continuous exterior layer of polyurethane or silicone. In various embodiments, a detachable metalized balloon may comprise a continuous inner layer of PET, nylon, or Pebax, a continuous middle layer comprising gold, platinum, iridium, or silver, and a discontinuous exterior layer of polyurethane or silicone.

The polymer materials of detachable polymer balloons 12 or detachable metalized polymer balloons 14 may be fabricated by extruding one or more polymer materials to form a detachable balloon 10. Extrusion may be accomplished by forcing one or more polymer materials through a die to form a tube. In some embodiments, the polymer materials may be warmed or heated to soften the polymer material prior to extrusion. In some embodiments, the polymer material may have melting point approximately 238° C. In other embodiments, the polymer material may have a melting point 178° C. One of skill in the art will appreciate that the polymer material may have a melting point above the temperatures used for depositing or attaching metal onto the detachable balloon 10.

Fabrication of the polymer material of detachable polymer balloons or detachable metalized polymer balloons 14 may include preparation of a mold. A mold may be dimensioned so a polymer material (e.g., a balloon inner layer or base layer material) of the detachable polymer balloons or detachable metalized polymer balloons 14 fabricated from the mold will have a desired shape and size for a desired use (e.g., a balloon inner layer or base layer structure). The use may include but is not limited to treating, occluding, or sealing a saccular aneurysm, artery, vein, LAA, 800, paravalvular leak path, other blood-containing structure, or other biological conduit 900 or space. In one example, a detachable balloon intended for use in occluding cerebral aneurysms may have a generally spherical shape and may have a diameter from 2-12 mm, or larger than 12 mm. In another example, a detachable balloon intended for use in occluding arteries and veins may have a generally cylindrical shape and may have a diameter from 2-24 mm, or larger than 24 mm. In another example, a detachable balloon intended for use in occluding a LAA may have a generally spherical or cylindrical shape and may have a diameter from 16-36 mm, or larger than 36 mm.

A mold may be used for fabrication of a detachable polymer balloon, with a proximal opening only, or a proximal and distal opening. A mold may be used for fabrication of a detachable polymer balloon, with a proximal opening and proximal neck 130 only, or a proximal opening, a proximal neck 130, a distal opening, and a distal neck 140. Fluid from outside a detachable polymer balloon can pass through the proximal opening of a detachable balloon 10 and enter the central void 115 or space defined by the interior surface of the detachable balloon. When fluid enters the central void 115 or space of the detachable balloon 10 under pressure, and the detachable balloon 10 is not constrained by external forces, the detachable balloon 10 can expand.

Detachable balloons 10 can expand by an unfolding of the balloon wall 30 or can expand by a stretching of the material of the balloon wall 30, or by both unfolding of the balloon wall 30 and by a stretching of the material of the balloon wall 30. Detachable rigid balloons, such as detachable metal balloons 16 or detachable polymer-coated metal balloons 18, expand primarily by unfolding only. Detachable compliant balloons, such as detachable silicone balloons, expand primary by a stretching of the material of the balloon wall 30 only. Detachable semi-compliant balloons, such as PET, nylon, or Pebax detachable balloons expand by unfolding and by a stretching of the material of the balloon wall 30, with unfolding predominating. In various embodiments, one or both necks can project away from the wall 30 of the detachable balloon 10, or they can project into the central void 115 or space of the detachable balloon 30.

Detachable balloon necks 130 & 140 and neck assemblies 135 & 142 can be used for attaching a detachable balloon 10 to a first catheter 173 and for attaching a detachable balloon 10 to a second catheter 174. Detachable balloon necks 130 & 140 and neck assemblies 135 & 142 may be involved in separating an expanded detachable balloon 10 from the first catheter 173. In one example, an elastomeric tubular structure 204 can be bonded to the proximal neck 130 of a detachable balloon 10 and used to form a friction fit 202 with the distal end of the first catheter 173. After expansion of a detachable balloon 10, a third catheter 175 can be advanced forward until it abuts the proximal end of the elastomeric tubular structure 204, and the first catheter 173 can be retracted to effect separation of the detachable expanded balloon 10 and the first catheter 173. In another example, an elastomeric or resilient valve 192 can be bonded to the distal neck 140 or distal neck assembly 142 of a detachable balloon 10 and used to form a friction fit 202 with a distal portion of the second catheter 174. After expansion of a detachable balloon 10, a third catheter 175 can be advanced forward until it abuts the proximal neck 130 of the detachable balloon 10 or the proximal region 110 of the detachable balloon 10 and the second catheter 174 can be retracted to effect separation of the expanded detachable balloon 10 and the second catheter 174. In another example, a tubular female structure 520 can be bonded to the proximal neck 130 of a detachable balloon 10, a tubular male structure 510 can be bonded to the distal end of a first catheter 173 and the detachable balloon 10, and the first catheter 173 and the detachable balloon 10 can be joined by a mating of the male and female tubular structures 510 & 520 and an insertion of a second catheter 174 through the lumen of the mated parts. After expansion of the detachable balloon 10 in vivo, the second catheter 174 can be retracted, and the first catheter 173 can be separated from the expanded detachable balloon 10.

Detachable balloon necks and neck assemblies can be designed and dimensioned to provide a point of attachment for a retention structure 731 to the detachable balloon. In one embodiment, a self-expanding, nitinol retention structure 731 comprising a proximal ring and distal arms and hooks 733 can be bonded to the distal neck 140 of a detachable balloon. In another embodiment, a self-expanding, nitinol retention structure 731 comprising a proximal and distal ring with elongated structures comprising barbs 608 or hooks 733 interposed between the proximal and distal rings can be bonded to the proximal neck 130 of a detachable balloon 10.

Detachable balloon necks and neck assemblies can be designed and dimensioned to reduce the leaking of fluid from the central void 115 of a detachable balloon 10 portion of a detachable balloon catheter 1 during balloon expansion. In some embodiments, a tubular structure 185 with an internal or luminal diameter that closely matches the external diameter of the second catheter 174 can be bonded to the distal neck 140 of a detachable balloon. When a second catheter 174 extends through this tubular structure 185, the length of the tubular structure and the width of the clearance gap between the tubular structure 185 and the second catheter 174 can affect the rate of the leakage of fluid injected into the central void 115 of the balloon, reducing the time required for a detachable balloon 10 to become fully expanded. In some embodiments, a tubular structure 190 with an internal or luminal diameter that closely matches the external diameter of the first catheter 173 can be bonded to the proximal neck 130 of a detachable balloon 10. When the distal end of first catheter 173 is inserted this proximal neck tubular structure 190, the length of the tubular structure 190 and the width of the clearance gap between the tubular structure 190 and the first catheter 173 can affect the rate of the leakage of fluid injected into the central void 115 of the balloon 10, reducing the time required for a detachable balloon 10 to become fully expanded.

Detachable balloon necks and neck assemblies can be designed and dimensioned to increase the fluoroscopic conspicuity of the balloon necks and neck assemblies. In some embodiments, a ring-shaped or tubular structure comprising a radiopaque metal that is visible during fluoroscopy can be bonded to the internal or external surface of the proximal or distal neck 130 & 140 to improve visualization of the detachable balloon portion of a detachable balloon catheter 1 in vivo. In some embodiments, during electroforming or electroplating of a polymer detachable balloon, a layer of a radiopaque metal that is visible during fluoroscopy can be applied to the proximal or distal neck 130 & 140 of a detachable balloon 10 to improve visualization of the detachable balloon portion of a detachable balloon catheter 1 in vivo.

Figure 12:
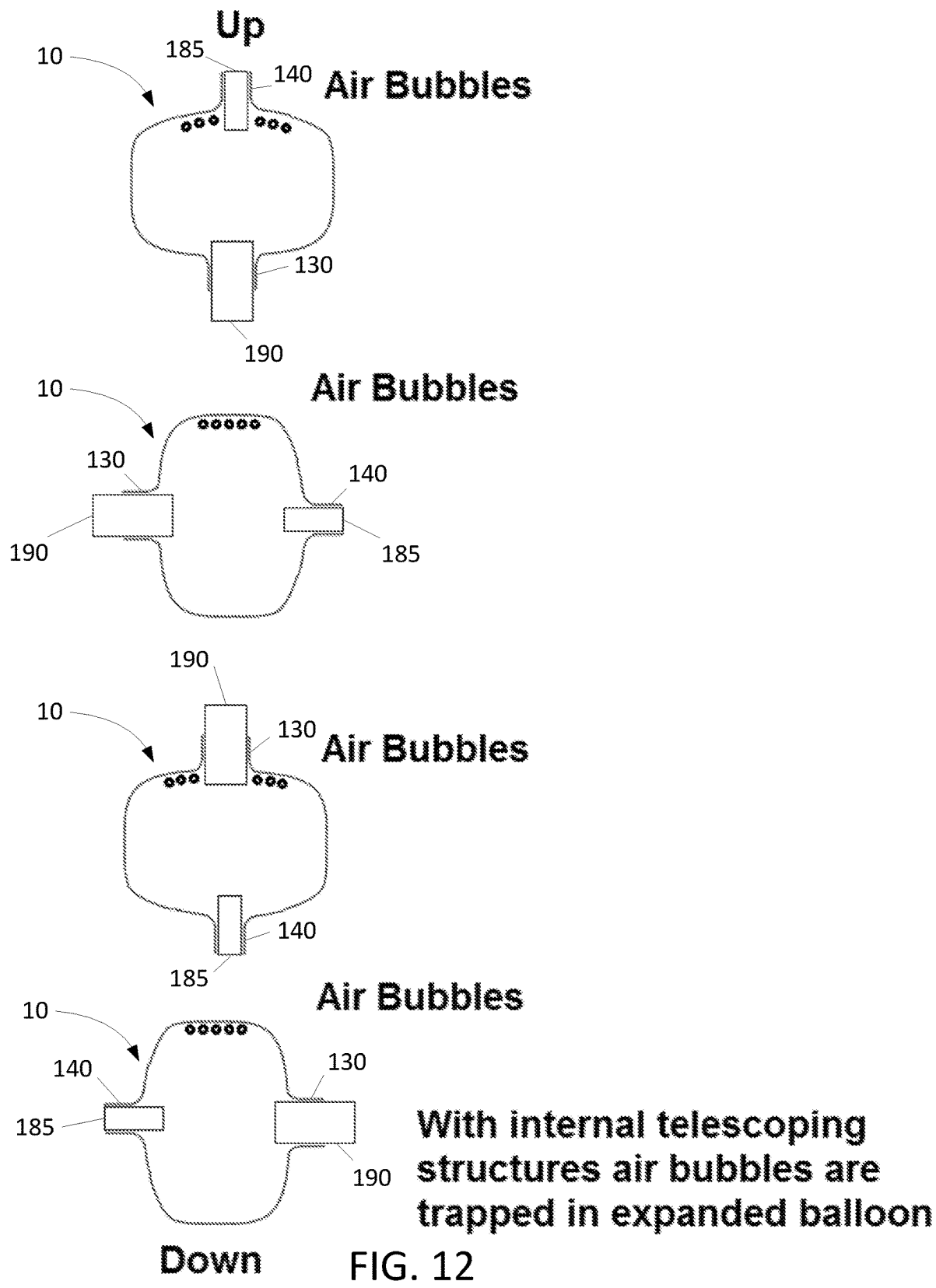
FIG. 12 provides cross-sectional views of a balloon having the shape of the embodiment shown in FIG. 3 incorporating telescoping structures within both its proximal and distal necks, which shows its ability to trap air bubbles while in four distinct orientations.
Figure 14:
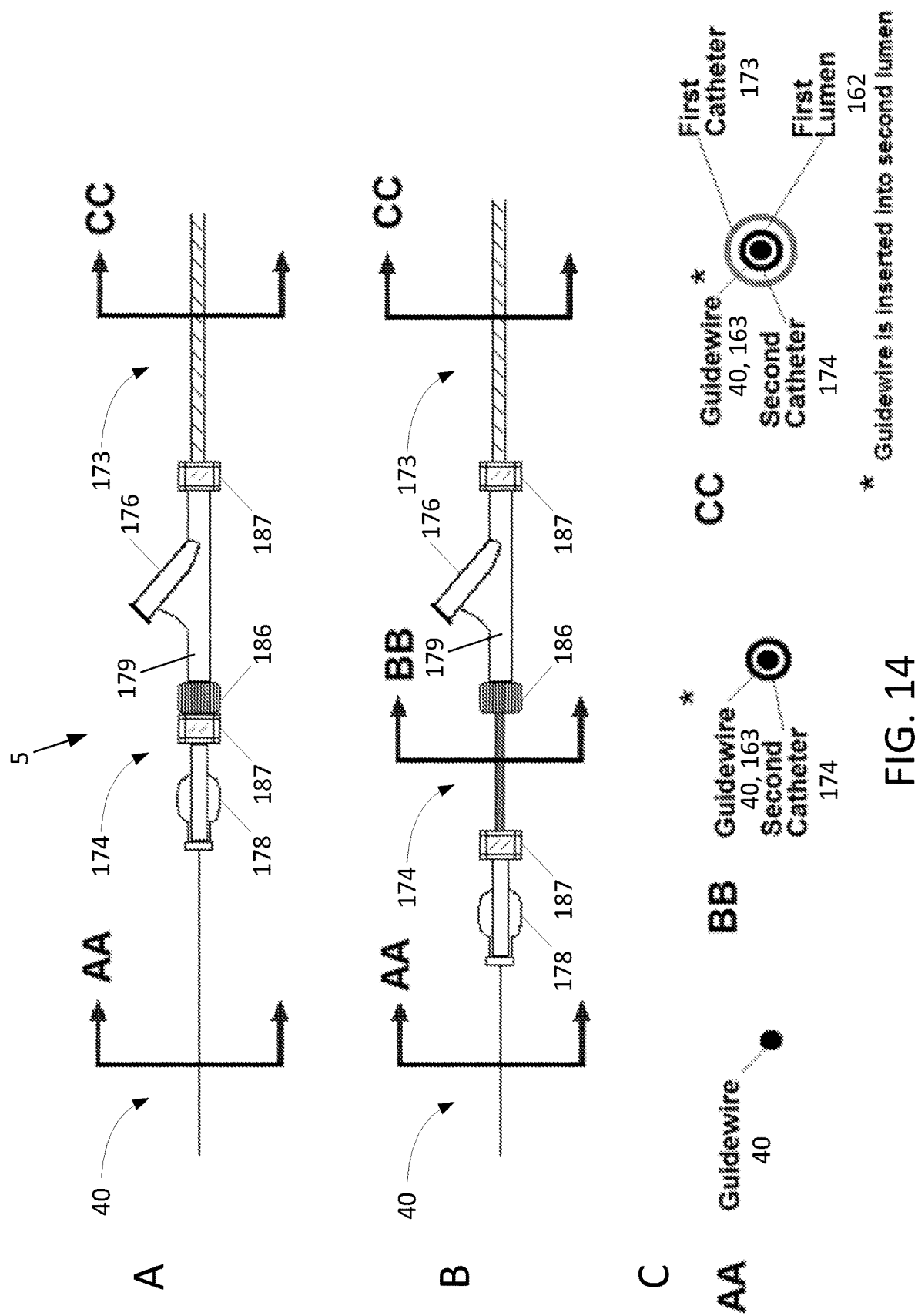
FIGS. 14A-C are planar and cross-sectional views showing proximal hub configurations of one embodiment of a detachable balloon delivery system before and after unlocking & retracting the second catheter from the first catheter.
Figure 15:
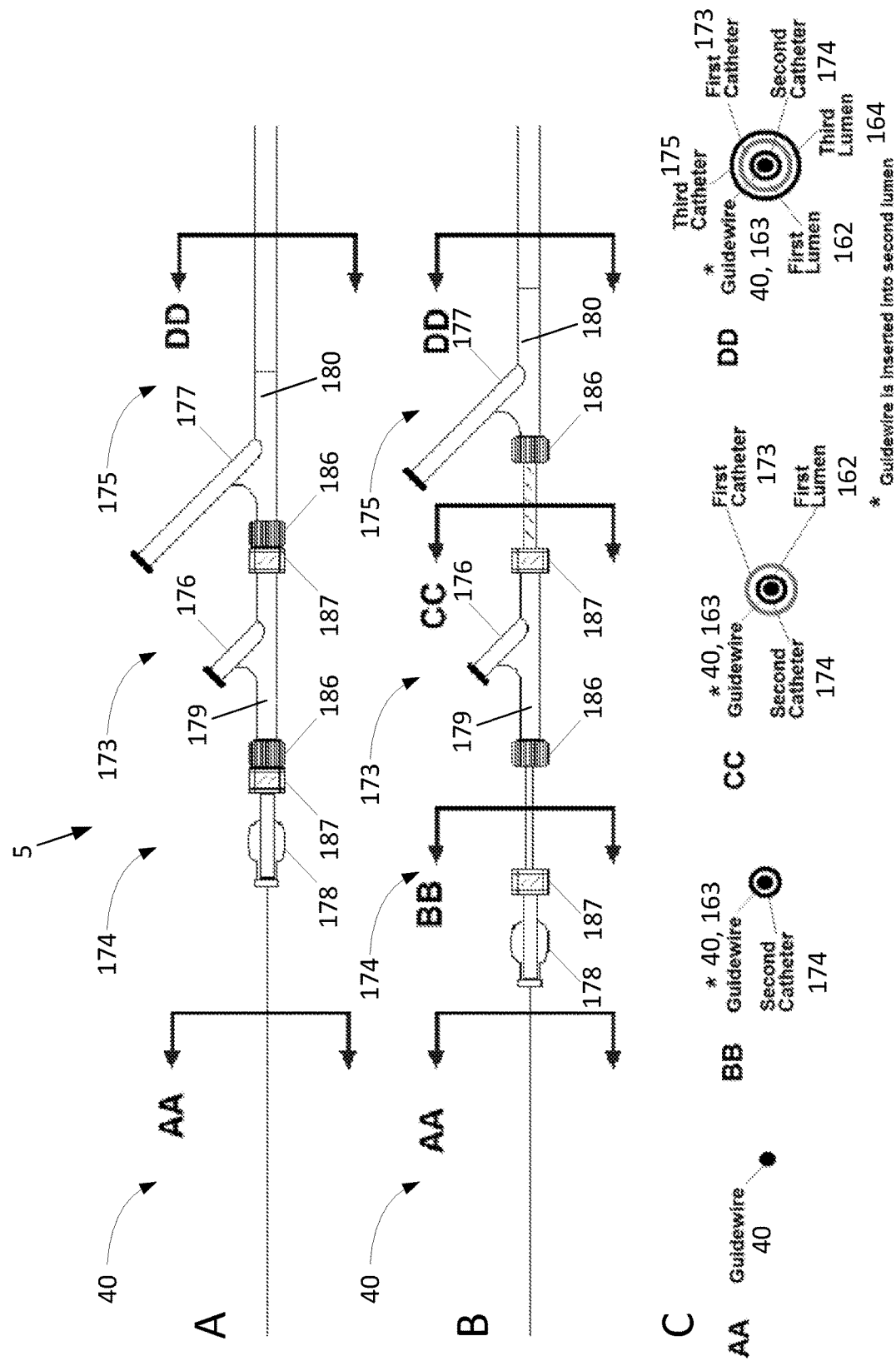
FIGS. 15A-C are planar and cross-sectional views showing proximal hub configurations of one embodiment of a detachable balloon delivery system before and after unlocking & retracting the second catheter from the first catheter and the first catheter from the third catheter.
Figure 16:
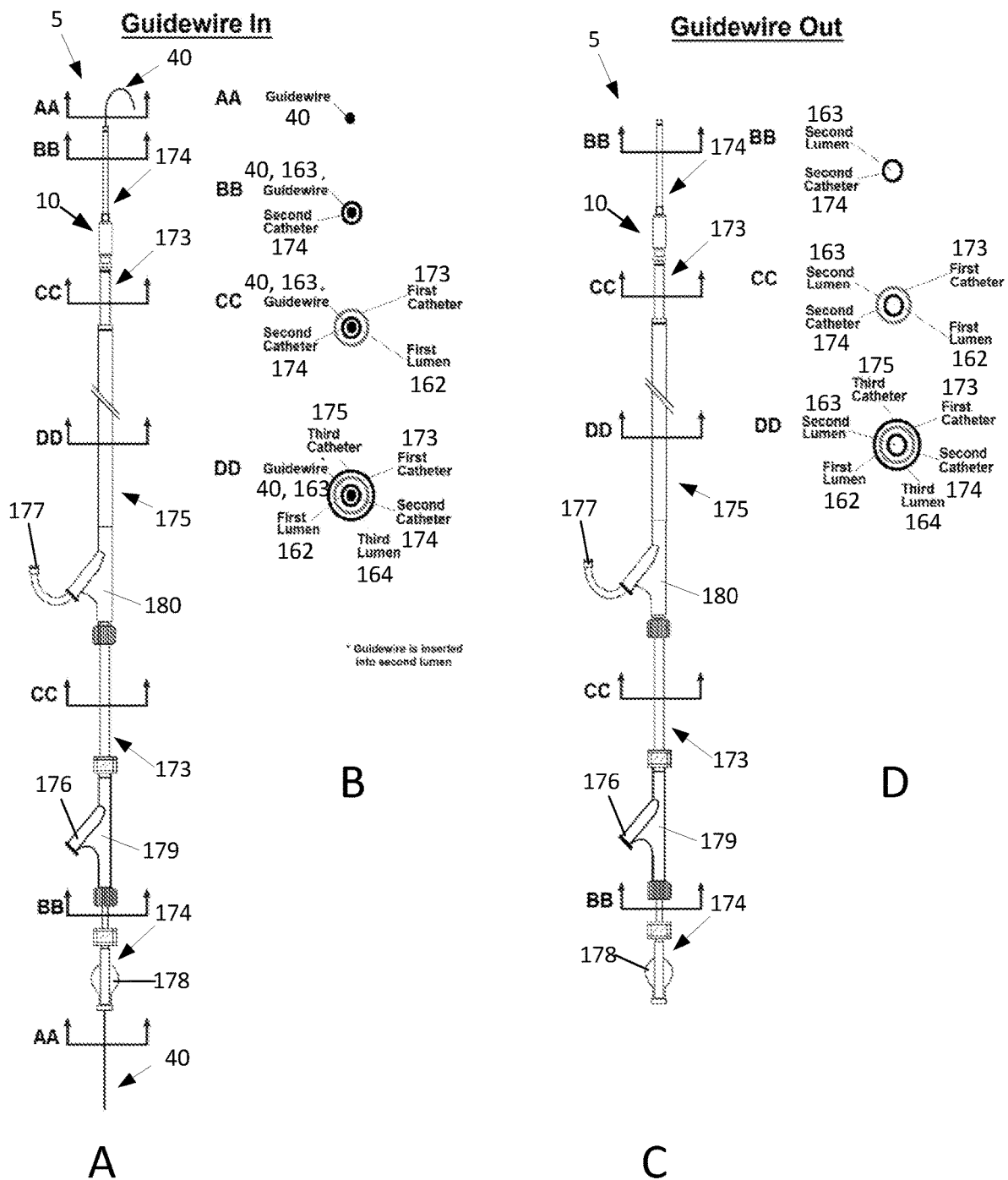
FIGS. 16A-B are planar and cross-sectional views showing one embodiment of a detachable balloon delivery system comprising a guidewire, three catheters, and three lumens, with the guidewire inserted.
FIGS. 16C-D are planar and cross-sectional views showing one embodiment of a detachable balloon delivery system comprising a guidewire, three catheters, and three lumens, with the guidewire retracted.

Detachable balloon necks and neck assemblies can be designed and dimensioned to reduce the risk of air embolization in vivo. In most interventional procedures using a balloon catheter a small amount of air remains in the balloon during use. For standard angioplasty balloon catheters, with the exception of inadvertent balloon rupture, this air remains trapped in the balloon during use, and then removed with the removal of the angioplasty balloon catheter. With detachable balloon catheters 1, residual air trapped in a balloon remains in the patient with the balloon, with a concomitant risk of embolization of that air into the distal circulation, which can cause serious effects, especially in the cerebral circulation. As illustrated in FIG. 12, the bonding of tubular structures to the proximal and distal neck 130 &140 of a detachable balloon wherein the tubular structures extend into the central void 115 of the detachable balloon can reduce the escape of air trapped in a detached balloon.

In some embodiments, one or more of the necks or neck assemblies can be designed and dimensioned to comprise an opening that can be closed or partially closed before, during, or after separation of the expanded detachable balloon from the first catheter 173. For example, an elastomeric or resilient valve 192 can be contained within a distal nosecone 191, optionally with one or more spacers 196 on the proximal side, the distal side, or both the proximal and the distal side of the valve. 192. The distal nosecone 191 containing the valve can be bonded to the distal neck 140 or distal neck assembly 142 of a detachable balloon. During assembly of a detachable balloon catheter 1, a second catheter 174 can be inserted through the valve 192, creating an over-the-wire device, and increasing the strength of attachment between the catheter assembly 5 of a detachable balloon catheter 1 and a detachable balloon 10 of a detachable balloon catheter 1. After expansion of the detachable balloon in an artery 317 or vein 318, and detachment of the expanded balloon from the catheter assembly 5, the elastomeric or resilient valve 192 closes, thereby stopping or reducing the flow of blood through the central void 115 of the expanded balloon 10.

Detachable balloon necks may have a length ranging between about 0.5 mm and 60 mm, preferably a length between about 0.5 mm and about 5 mm. The necks may define the openings, having diameters between about 0.25 mm and about 5 mm. The necks may protrude into the central void 115 or space for a length ranging between about 1 mm and 60 mm, and preferably for a length between about 0.5 mm and 5 mm, while defining the openings having diameters between about 0.25 mm and about 5 mm, and preferably having diameters between about 0.25 mm and about 5 mm. The thickness of the wall of either or both necks may be the same as the main body of the detachable balloon, thinner than the wall 30 of main body 100 of the detachable balloon, or thicker than the wall 30 of main body 100 of the detachable balloon. Preferably, either or both necks have a wall 30 thickness between about 3 m and about 300 m, with a typical thickness of 60 m or less. With an embodiment of the detachable balloon wherein the proximal and distal necks 130 & 140 extend into the central void 115 or space of the detachable balloon 10, the external surface of the detachable balloon 10 retains a more rounded surface contour, and therefore there may be a reduced risk of damage to the blood vessel wall or the adjacent tissue with placement of the detachable balloon 10.

Various expanded detachable balloon shapes are acceptable, as required to treat saccular aneurysms, blood vessel segments, LAAs, other blood-containing structures, biological conduits, 900, or biological spaces, of various shapes. In various embodiments, a mold may be used to fabricate detachable polymer balloons or portions of detachable polymer balloons where the dimensions of the detachable polymer balloons or detachable polymer balloon portions are selected based upon the size and shape of the saccular aneurysms, artery or vein segments, LAAs, other blood-containing structures, or biological conduit 900 segment or spaces being treated.

Preferred shapes of the detachable balloons for the treatment of arteries, veins, and other biological conduits 900 include cylindrical shapes with conical ends, as there is no need to present a rounded surface to the flow of blood or other biological fluids, and conical end shapes generally provide the lowest profile and outer diameter after pleating and folding. The length of the intermediate region of detachable balloons can affect occlusion performance. Longer intermediate regions are generally preferred when possible, due to the reduced leakage of blood around an expanded balloon with a long contact surface with adjacent tissues. For the occlusion of arteries and veins, a longer intermediate region is preferred, especially with detachable polymer balloons and detachable, flexible metalized polymer balloons which are flexible. Therefore, detachable balloons for the occlusion of arteries, veins, and other biological conduits 900 are often longer than they are wide. With detachable rigid metalized polymer balloons 14, detachable metal balloons 14, and detachable polymer-coated metal balloons 18, increasing the length of the intermediate region 100 of the detachable balloon can increase stiffness in the distal portion of detachable balloon catheters 1, reducing deliverability.

The dimensions of typical saccular aneurysms 320, including a terminal bifurcation aneurysm and a sidewall aneurysm, are defined in FIGS. 92A-C, 95A, and 96A. Preferred shapes of the detachable balloons for the treatment of saccular aneurysms 320 are spherical, or cylindrical with short intermediate regions. The length or diameter of detachable balloons 10 along the second axis 708 is critical, as this determines the diameter of an aneurysm neck 324 that can be covered and occluded. The length or diameter of balloons 10 along the first axis 706 is also critical as longer lengths and diameters along this axis brings the tip of the second catheter 174 closer to the dome of an aneurysm 320, which is usually the most fragile portion of the aneurysm 320 and the most susceptible to rupture or puncture. Therefore, when choosing a balloon 10 to treat a saccular aneurysm 320, a balloon 10 with a length or diameter in the second axis 708 that is long enough to cover the aneurysm neck 324 but not longer than the aneurysm width is important, as is choosing a balloon 10 with the smallest length or diameter along the first axis 706 that is still effective is also important. When using this shape of balloon 10 to treat a saccular aneurysm 320, the unfilled body and dome of the aneurysm 320 can be filled with one or more coils or elongated bodies 720, which are generally softer and less traumatic to the aneurysm wall than the distal neck 140 or second catheter 174 of a detachable balloon catheter 1. Detachable balloons 10 for the treatment of saccular aneurysms 320 are therefore frequently wider than they are long. The proximal region 110 of detachable balloon 10 placed in a saccular aneurysm 320 is blood-facing and therefore a rounded proximal region 110 is preferred. Given that the dome of an aneurysm 320 is often fragile, a rounded distal region 120 is also preferred over a conical or square shaped distal end.

Preferred shapes of detachable balloons 10 for the treatment of LAAs 800 include cylindrical shapes with intermediate regions that are of intermediate length and rounded ends. LAAs 800 are generally long and the "dome" of the LAA 800 is not particularly fragile or susceptible to rupture or puncture, so a detachable balloon 10 with longer intermediate region is acceptable. The proximal end 110 of a detachable balloon 10 placed in a LAA 800 is blood-facing and therefore a rounded proximal region 110 is preferred. Preferred shapes of detachable balloons 10 for the treatment of paravalvular leaks include cylindrical shapes with long intermediate regions and rounded ends or cone-shaped ends. Paravalvular leaks paths are sometimes long and have flow so a detachable balloon with long intermediate region is desirable to achieve a long region that is sealed by the balloon. Both the proximal and distal ends of a detachable balloon placed in a paravalvular leak are blood-facing and therefore rounded proximal and distal regions 110 & 120 are preferred.

For example, the detachable balloon 10 or a portion of the detachable balloon 10 may be configured as a cylinder with rounded, hemispherical, coned, or flat ends. The diameter of the cylindrical expanded detachable balloon 10 or portion of a detachable balloon 10 may range from about 2 mm to about 30 mm. The expanded length of oblong detachable balloons may range between about 5 mm to about 60 mm. The detachable balloon may have an expanded volume that ranges between about 0.005 mL to about 65 mL. The expanded diameter of the cylindrical detachable balloon may range from about 2 mm to about 40 mm, the expanded volume may range from about 0.004 mL to about 40 mL, and the expanded length of the spherical detachable balloon may range from about 2 mm to about 20 mm.

The detachable balloon has one or more openings defined by the wall 30 or by one or more necks 130 & 140. In various embodiments, one or both necks 130 & 140 can project away from the wall of the detachable balloon 10 or they can project into the central void 115 or space of the detachable balloon. Additionally, a neck 130 or 140 can be designed and dimensioned, so the opening can be closed or partially closed before, during, or after separation of the expanded detachable balloon 10 from the first catheter 173. The necks have a length ranging between about 0.5 mm and 60 mm, preferably a length between about 0.5 mm and about 5 mm. The necks 130 & 140 may define the openings having diameters between about 0.25 mm and about 5 mm. The necks 130 & 140 may protrude into the central void 115 or space for a length ranging between about 1 mm and 60 mm, and preferably for a length between about 0.5 mm and 5 mm, while defining the openings, having diameters between about 0.25 mm and about 5 mm, and preferably having diameters between about 0.25 mm and about 5 mm. The thickness of the wall 30 of either or both necks 130 & 140 may be the same, thinner, or thicker than the wall 30 of main body 100 of the detachable balloon 10. Either one or both necks 130 & 140 have a wall thickness 30 between about 3 m and about 500 m. In one embodiment of the detachable balloon 10 wherein the necks 130 & 140 extend into the central void 115 or space of the detachable balloon 10, the external surface of the detachable balloon 10 retains a more rounded surface contour, and therefore there may be a reduced risk of damage to the blood vessel wall or the adjacent tissue with placement of the detachable balloon 10.

In other embodiments, one or more portions of the detachable balloon wall 30 may be thicker than the remaining portions of the wall 30. By way of example and not limitation, the wall 30 in the body or intermediate region 100 of the detachable balloon 10 may be thicker than the wall in the proximal 110 and distal 120 regions of the detachable balloon 10, or in the necks 130 & 140. By way of example and not limitation, the wall 30 in the proximal region 120 of the detachable balloon may be thicker than the wall in the distal region 140 of the detachable balloon 10, or in the necks 130 & 140. By way of example and not limitation, the wall 30 in the distal region 120 of the detachable balloon 10 may be thicker than the wall 30 in the proximal region 110 of the detachable balloon 10, or in the necks 130 & 140. By way of example and not limitation, the wall 30 in the intermediate region 100 of the detachable balloon 10 and the wall of the proximal and distal necks 130 & 140 may be thicker than the walls in the proximal and distal regions 110 & 120 of the detachable balloon 10. By way of example and not limitation, the wall 30 in the proximal and distal necks 130 & 140 may be thicker than the wall 30 in the intermediate region 100 of the detachable balloon 10.

A detachable metalized polymer balloon 14 may be fabricated using an "inner layer" material or "base layer" material, using various extrusion and molding techniques, wherein the inner layer or base layer material is formed into a detachable balloon or a portion of a detachable balloon, and the material used to fabricate the detachable balloon inner layer or base layer structure is a polymer. One of skill in the art will appreciate that a detachable balloon inner layer or base layer structure may be fabricated using any process known in the art for making balloons.

The detachable balloon inner layer or base layer structure may be fabricated by using various types of molding process. In some embodiments, the detachable balloon may be fabricated using blow molding, compression molding, extrusion molding, injection molding, matrix molding, rotational molding, thermoforming, transfer molding, vacuum assisted resin transfer molding, vacuum forming, or any molding means known in the art. The detachable balloon inner layer or base layer structure may be made using various extrusion molding techniques. One of skill in the art will appreciate that any fabrication method known in the art may be used.

The material used to form the detachable balloon inner layer or base layer structure may start in the form a billet that may be placed in a container and pushed through a die opening. Fabrication of the detachable balloon inner layer or base layer structure mold may be accomplished using direct or forward extrusion techniques known in the art wherein the billet is pushed through a stationary container. Fabrication of the detachable balloon inner layer or base layer structure may also be accomplished by using indirect or backwards extrusion wherein the billet and the container move together pushing the billet through a die. Fabrication of the detachable balloon inner layer or base layer structure mold may also be accomplished through hydrostatic extrusion wherein the billet is surrounded by a pressurized liquid. Any extrusion method used may include the use of one or more die configured to provide an extruded material that has both internal and external surface. One of skill in the art will appreciate that a mold for the detachable balloon inner layer or base layer structure may be fabricated by any extrusion means known in the art.

Detachable balloons comprising a detachable polymer balloons or detachable balloon inner layer or base layer structures may be fabricated from various materials, including polymers, using blow-molding techniques. Blow molding techniques may include heating the detachable balloon inner layer or a base layer material to a temperature that makes the detachable balloon inner layer or base layer material soft or pliable. This temperature may be the melting point of the detachable balloon inner layer or base layer material. Suitable temperatures for softening or melting the detachable balloon inner layer or base layer material may vary based on the detachable balloon inner layer or base layer material. When PET is the detachable balloon inner layer or base layer material, the detachable balloon inner layer or base layer material may be heated to approximately 238° C. The detachable balloon inner layer or base layer material may be a material without a defined melting point. When the detachable balloon inner layer or base layer material does not have a melting point, the base material may be heated to its Vicat softening temperature.

Blow molded detachable balloon inner layer or base layer structures may be fabricated from a cut section of extruded detachable balloon inner layer or base layer material. The cut section may be approximately 18 inches long. The cut section may be 10 inches long. The cut section may be 24 inches long. One of skill in the art will appreciate that the cut section may be any length known in the art. The cut section may also have any diameter known in the art. In some embodiments, the blow-molded detachable balloon inner layer or base layer structure may be fabricated using a preform.

The cut section of extruded detachable balloon inner layer or base layer material may be heated to a temperature suitable for softening the material. The heated detachable balloon inner layer or base layer material may be extruded into a hollow tube or a parison. The softened parison may be placed in the detachable balloon inner layer or base layer structure mold, which is closed around the softened parison. Once in the detachable balloon inner layer or base layer structure mold, fluid or air may be pushed or blown into the parison causing the parison to assume the shape of the detachable balloon inner layer or base layer structure mold. The air pushed into the parison should provide enough pressure to the inner diameter of the parison to cause the parison to expand to the mold surface. One with skill in the art will appreciate that fluid or air may be blown into either end of the parison. The detachable balloon mold may have a temperature that is less than the temperature of the softened parison. The detachable balloon inner layer or base layer structure mold may have a temperature sufficient for allowing the softened parison to remain soft until the softened parison has been filled with enough air to make the parison conform to the detachable balloon inner layer or base layer structure mold. In some embodiments, the detachable balloon inner layer or base layer structure mold may have a temperature lower than that of the warm soft parison before the softened parison is placed in the detachable balloon inner layer or base layer structure mold. The heated base material should be properly oriented. Proper positioning of the parison requires the softened section to be contained in the cavity to allow the parison to be reshaped against the inner structure of the detachable balloon inner layer or base layer structure mold.

The detachable balloon may be fabricated using injection blow molding wherein the softened detachable balloon inner layer or base layer material is injection molded onto a core pin. The core pin may be configured to provide pressure to the internal surface of the detachable balloon inner layer or base layer material. After the detachable balloon inner layer or base layer material has been deposited onto a core pin, the core pin may be placed in a detachable balloon inner layer or base layer structure mold that is closed around the core pin and the base material. Fluid may be forced or blown into the internal surface of the detachable balloon inner layer or base layer material causing the detachable balloon inner layer or base layer material to expand and conform to the internal shape of the detachable balloon inner layer or base layer structure mold. The detachable balloon inner layer or base layer structure mold may have an initial temperature that keeps the detachable balloon inner layer or base layer material soft. The detachable balloon inner layer or base layer structure mold may have a temperature low enough to lock the molded shape. One of skill in the art will appreciate that the detachable balloon inner layer or base layer structure mold may vary to keep the detachable balloon inner layer or base layer material soft until it has been molded into a desired shape at which point the detachable balloon inner layer or base layer structure mold temperature may decrease to lock the detachable balloon inner layer or base layer material into a detachable balloon inner layer or base layer structure shape. In some embodiments, the detachable balloon inner layer or base layer structure may be reheated to stretch the detachable balloon inner layer or base layer structure using a suitable apparatus such as a core rod.

The formed detachable balloon inner layer or base layer structure may be further processed and shaped using a process such as spin trimming excess material may be trimmed off by spinning a knife or blade around the detachable balloon inner layer or base layer structure. At this point, the detachable balloon inner layer or base layer structure may be fabricated into a detachable balloon of a detachable balloon catheter 1, without applying additional layers or surface coatings to the detachable balloon inner layer or base layer structure. For these embodiments, the detachable balloon inner layer or base layer structure is a polymer balloon and can be used to make a detachable balloon catheter 1 with a detachable polymer balloon 10. Alternatively, additional layers or coatings can be applied to the polymer balloon 12 inner layer or base layer 99 structure to make a polymer-coated polymer balloon or a metalized polymer balloon 14.

Fabrication of the inner layer or detachable balloon base layer 99 structure may include bonding a needle to a detachable balloon inner layer or base layer structure. Bonding a needle to the detachable balloon inner layer or base layer structure may be important for part processing. The bonded needle may be useful for facilitating simplified processing and testing of the detachable balloon inner layer or base layer structure assembly. In this regard, a proximal end of the detachable balloon inner layer or base layer structure may be flared and bonded to a needle. The needle may also be bonded to the distil end of the detachable balloon inner layer or base layer structure. In some embodiments, a needle may be bonded to both the proximal and distal ends of the detachable balloon inner layer or base layer structure. Bonding may be accomplished by any means known in the art. One bonding method may include providing a UV cured adhesive and applying the adhesive to an end of the detachable balloon inner layer or base layer structure. In embodiments where only one end of the detachable balloon inner layer or base layer structure is bonded to a needle, the opposite end may be plugged. Plugging may be accomplished using a UV cured adhesive. Plugging may also be accomplished by heating the end of the detachable balloon inner layer or base layer structure until the end is pliable, at which point the end of the detachable balloon inner layer or base layer structure is sculpted until it is closed. One of skill in the art will appreciate that plugging and bonding may be accomplished by any means known in the art. One of skill in the art will also appreciate that a needle may be replaced by any tools known in the art for aiding in simplified processing and testing of a detachable balloon inner layer or base layer structure, or polymer balloon.

The detachable balloon inner layer or base layer structure may be coated using various techniques. In some embodiments, the detachable balloon inner layer or base layer structure may be coated using one or more of these processes: sputter coating or deposition, vapor deposition, electroforming, or electroplating. The method for forming the external layer may further include methods to form pores or projections.

Coating the detachable balloon inner layer or base layer structure may be accomplished by physical vapor deposition. In some embodiments, the physical vapor deposition is accomplished using sputter deposition, where a material is ejected from a source material and deposited on the detachable balloon. Sputter deposition is a process carried out in a vacuum chamber environment. Handling the detachable balloon inner layer or base layer structure in the vacuum environment requires special process consideration. It is important to maintain the shape of the detachable balloon inner layer or base layer structure while under vacuum so that the detachable balloon inner layer or base layer structure is sufficiently coated. To maintain the shape of the detachable balloon inner layer or base layer structure in a vacuum environment, the pressure inside the detachable balloon inner layer or base layer structure should be equal to or above the pressure outside the detachable balloon inner layer or base layer structure. In some embodiments, the detachable balloon inner layer or base layer structure will be vented to the vacuum chamber, thus providing an equal pressure inside and outside the detachable balloon inner layer or base layer structure. In other embodiments, the detachable balloon inner layer or base layer structure will be attached to a manifold that will allow the detachable balloon inner layer or base layer structure to maintain a positive pressure in relation to the vacuum chamber pressure without exceeding a pressure that would cause detachable balloon inner layer or base layer structure deformation or bursting. To maintain pressure equilibrium or positive pressure between the inside and outside of the detachable balloon, the detachable balloon may be fluidly connected to an apparatus that aids in maintaining pressure equilibrium. The apparatus for maintaining pressure equilibrium may be a sputter rack. A sputtering rack may be flat to allow sputtering of one side at a time. A sputtering rack may be configured in such a way to enable two-sided simultaneous sputtering. The sputter rack may include a manifold. The manifold may be fluidly connected to one or more detachable balloons in parallel. The detachable balloons may also be fluidly connected to the manifold in series. The detachable balloon inner layer or base layer structure may be fluidly connected to the manifold via needles connected to the detachable balloons. In some embodiments, the needle may be connected to the manifold using a Luer connection. One of skill in the art will appreciate that the needles may be connected to the manifold using any means known in the art for fluidly connecting a needle. To maintain equilibrium between the inner and outer portion of the detachable balloon inner layer or base layer structure, a balancing balloon may be fluidly connected to the manifold. The balancing balloon may expand as the pressure inside the chamber falls. The balancing balloon may provide pressure to the interior surface or central void 115 of the one or more detachable balloon inner layer or base layer structures fluidly connected to the manifold. In some embodiments, the sputter rack is fluidly connected to one, two to six, seven to twelve, twelve to forty, or more than forty detachable balloon inner layer or base layer structures. One of skill in the art will appreciate that the sputter rack may be fluidly connected to any number of detachable balloon inner layer or base layer structures.

Sputter deposition may be accomplished using several steps. Components such as the detachable balloon inner layer or base layer structure, the needles, and the manifold may be marked to identify various aspects of the detachable balloon inner layer or base layer structure. The markings may be used for identifying the detachable balloon inner layer or base layer structure composition. The markings may identify the composition of the detachable balloon inner layer or base layer structure. After marking the various components, the sputtering rack may be loaded with the detachable balloon inner layer or base layer structures. The detachable balloon inner layer or base layer structure may be fluidly connected to the rack via the Luer connection of the needles. One of skill in the art will appreciate that the connection between the rack and the needles may be any connection known in the art. Once the detachable balloon inner layer or base layer structures have been placed, pressure may be increased in the manifold. Increasing the pressure of the manifold may cause increased pressure within the detachable balloon inner layer or base layer structures. This increased pressure may remove wrinkles and folds in the detachable balloon inner layer or base layer structures. One of skill in the art will appreciate that the pressure increase should be increased enough to remove wrinkles but not enough pressure to damage the detachable balloon inner layer or base layer structures. In some embodiments, the pressure is increased by fluidly connecting a syringe to the manifold. The pressure may also be increased by pumping air into the manifold. One of skill in the art will appreciate that the pressure may be increased using any means known in the art.

After the wrinkles or folds have been removed from the detachable balloon inner layer or base layer structures, the syringe or other pumping apparatus may be detached and removed from the sputter rack. The balancing balloon may be deflated and placed on the manifold and tucked into the tunnel. The balancing balloon may be fluidly connected the rack via a tubing or hose by suitable means. The balancing balloon may be placed into a tube or other method of containment that allows a balancing balloon to expand under vacuum while controlling the location of the balancing balloon during the vacuum phase. The balancing balloon may be placed in a containment chamber to prevent the balancing balloon from becoming too large during the sputtering process. The balancing balloon may be placed in a containment chamber by lowering via gravity or by pushing into place or pulling into place by well-known means. The sputter rack may then be placed in a vacuum chamber and the air pumped out of the vacuum chamber until at or near vacuum pressure. The sputter deposition process may include a target that is the source of the coating material. The sputter deposition process may also include a substrate that is positioned in a location such that material from the target is ejected towards the substrate. The substrates within the vacuum chamber are the individual detachable balloon inner layer or base layer structures. The target may be bombarded by a high-speed plasma stream of gas. The etch species may be any etch species known in the art. In some embodiments, the etch species may be charged or neutral. One of skill in the art will appreciate that the etch species may be any gas appropriate for plasma etching the source or target. The duration of etching process may vary from no etching to a maximum amount of etching allowed without deforming the detachable balloon inner layer or base layer structures.

The target or source may be made of metal selected from the group consisting of gold, platinum, silver, titanium, vanadium, aluminum, nickel, tantalum, zirconium, chromium, silicon, magnesium, niobium, scandium, cobalt, palladium, manganese, molybdenum, alloys thereof, and combinations thereof. Other biocompatible rigid materials or combination of materials can be used. The target or source may be bombarded for a duration of time that is sufficient to deposit titanium onto the surface of the detachable balloon inner layer or base layer structures at a thickness of 1 angstrom to 10,000 angstroms, preferably a thickness of 50 to 500 angstroms. The source may also be bombarded for a time that is sufficient to deposit gold onto the surface of the detachable balloon inner layer or base layer structure at a thickness of 1 angstroms to 10,000 angstroms, preferably a thickness of 250-5000 angstroms, or 1000 angstroms. In some embodiments, the titanium may be deposited on the detachable balloon inner layer or base layer structures prior to deposition of the gold. In some embodiments, the gold may be deposited onto the surface of the detachable balloon inner layer or base layer structures prior to the titanium deposition. In some embodiments, once a sufficient coating of metal has been deposited on one side of the detachable balloon inner layer or base layer structures, the detachable balloon inner layer or base layer structures can be moved into an anti-chamber where vacuum may be released. The pallet may be turned over, turned around, or otherwise moved to coat the other side of the detachable balloon inner layer or base layer structures using the method used for coating the first side of the detachable balloon inner layer or base layer structures. In some embodiments, the detachable balloon inner layer or base layers structures may also be placed into a sputtering environment where both sides of the detachable balloon inner layer or base layers structures can be coated without the need to change the position of the sputtering rack. The coated detachable balloon inner layer or base layer structures may be placed in custom packaging tubes. One of skill in the art will appreciate that the coated detachable balloon inner layer or base layers structures may be placed in any packaging known in the art.

Detachable balloon inner layer or a base layer structures may also be coated using electroplating techniques. This includes, electroplating a detachable balloon inner layer or base layer structure that has an external surface layer of metal, including an external surface layer of metal produced by vapor deposition or sputtering. Electroplating generally involves dissolving a metal in a circulating solution and submerging detachable balloon inner layer or base layer structures with a metal surface layer or coating in the solution until at least a portion of the metal surface layer or coating of the detachable balloon inner layer or base layer structures are covered or coated with the metal circulating in the solution. One of skill in the art will understand that an additional surface layer of metal can be added to a metal surface layer or coating of a detachable balloon inner layer or base layer structure using any electrodeposition method known in the art. As in traditional electroplating, an anode 390 and a cathode 405 are submerged into a circulating metal solution. In the present disclosure, the anode 390 may be any traditional anode known in the art of electrodeposition. The surface of the metal coated detachable balloon inner layer or base layer structure acts as the cathode 405 and is coated externally by the metal circulating in the solution. To achieve the electrical conductivity required for electroplating of the surface of the metal coated detachable balloon inner layer or base layer structure, support fixturing, or other support structures, are used to create an electrical contact to the negative side of the electroplating power supply. In some embodiments, a hypodermic tube splint may be inserted into the needle. The hypodermic tube splint may include one or more apertures that allow fluid to pass from an external source to the inner void of the metal coated detachable balloon inner layer or base layer structure. The hypodermic tube splint may also include a connection for attachment to the female Luer hub. The assembly may further include a one-way injection port. One of skill in the art will appreciate that the hypodermic tube splint may have any means of connecting to the needle known in the art. To enhance the even deposition of metal to the external surface of a metal coated detachable balloon inner layer or base layer structure during electroforming or electroplating, the metal coated detachable balloon inner layer or base layer structure may be rotated during electroforming or electroplating. The hypodermic tube splint may be attached to a rack or similar apparatus that includes means for rotating the metal coated detachable balloon inner layer or base layer structure assembly. The hypodermic tube splint may be connected to a needle injection port and the rack assembly, suspending the metal coated detachable balloon inner layer or base layer structure in the bath. A support structure that allows for an electrical connection of the needles, while maintaining their position within the electroforming or electroplating solution is preferred. The support structure may permit one or more of individual metal coated detachable balloon inner layer or base layer structures to rotate using gears, belts, pulleys or other suitable means. The support structure also provides for a common electrical connection such that the metal coated detachable balloon inner layer or base layer structure may be referenced at an electrical potential that facilitates electroforming or electroplating. The metal coated detachable balloon inner layer or base layer structures may be submerged in an electroforming or electroplating bath with a temperature of 100° F. to 250° F., or about 160° F. One of skill in the art will appreciate that the bath may be any temperature necessary for successfully electroforming or electroplating the metal coated detachable balloon inner layer or base layer structure with the metal circulating in the solution. The metal circulating in the solution may be a metal selected from the group consisting of gold, platinum, silver, titanium, vanadium, aluminum, nickel, tantalum, zirconium, chromium, silicon, magnesium, niobium, scandium, cobalt, palladium, manganese, molybdenum, alloys thereof, and combinations thereof, or any other conductive, biocompatible, rigid, or semi-rigid materials or combination of materials.

The central layer of the wall 30 of a detachable balloon 10, the interior layer of the wall 30 of a detachable balloon 10, and an exterior layer of the wall 30 of the detachable balloon 10 may be formed by any suitable method. In some preferred embodiments, the wall 30 of the detachable balloon 10 has two layers. The inner layer of the wall 30 of the detachable balloon 10 comprises PET, nylon, or Pebax and is formed by blow molding fabrication. The outer layer of the wall 30 of the detachable balloon 10 comprises a metal layer 90 comprising gold or titanium formed by sputter deposition or vapor deposition. In some preferred embodiments, the detachable balloon 10 has three layers. The inner layer of the wall 30 of the detachable balloon 10 comprises PET, nylon, or Pebax and is formed by blow molding fabrication. The central layer of the wall 30 of the detachable balloon 10 comprises gold or titanium formed by sputter deposition or vapor deposition. The outer layer of the wall 30 of the detachable balloon 10 comprises gold or platinum formed by electroforming or electroplating.

In some embodiments, a conductive mandrel 740 is placed in a solution of metal ions, which coat the external surface of the mandrel 740 to form a layer of a detachable balloon. For example, in some preferred embodiments, the conductive mandrel 740 is a detachable balloon inner layer or base layer structure comprising polymer formed by blow molding fabrication. The detachable balloon inner layer or base layer structure is coated with gold or titanium on its external surface by sputter deposition or vapor deposition. The shape of the mandrel 740 (and thereby the shape of the detachable balloon) can be modified by modifying the shape of the polymer inner layer or base layer that is formed by blow molding fabrication. The thickness of any layer of the detachable balloon, including but not limited to a metal or metallic layer, can be modified by varying the process time or conditions. An additional surface layer may be formed by additional electroplating or electroforming. An additional surface layer may be formed by vapor deposition or sputter deposition, wherein material is eroded from a target (e.g., a metal or metal alloy) and is then deposited onto a substrate, such as a mandrel 740 or mold, forming a thin layer on the substrate. Similarly, an inner layer may be formed by additional electroplating or electroforming, or by vapor deposition or sputter deposition. In other exemplary methods of forming the detachable balloon, the central layer of the wall 30 of the detachable balloon 10 may be formed by vapor deposition, wherein vapors from one or more polymers, pure metals, or metal alloys are condensed upon a substrate or mold. The mold may be removed to provide a hollow shell composed of the polymer, pure metal or metal alloy. In various embodiments, the exterior surface of a detachable balloon, after deposition or formation of the one or more metal layers, 90, may be further coated with a polymer, including by using a polymer containing solution. This additional coating may include an external coating of a urethane containing solution that may further act to secure the metal or metallic layers to the detachable balloon, including to the inner layer or base layers.

In various embodiments, only desired portions or regions of the detachable balloon comprise a metal layer 90 deposited by electroforming or electroplating. In various embodiments, only portions or regions of the metal coated detachable balloon inner layer or base layer structure are further coated with additional metal by electroforming or electroplating. In various embodiments, various portions or regions of the detachable balloon may have different wall composition or thickness. In some embodiments, the different wall composition or thickness is produced by masking portions or regions of the detachable balloon inner layer or base layer structure prior to vapor deposition or sputter deposition. In some of these embodiments, additional metal may be applied to the portions or regions of the detachable balloon inner layer or base layer structures that have been covered with metal by vapor deposition or sputter deposition. In some embodiments, the different wall composition or thickness is produced by masking or coating regions of the metal coated detachable balloon inner layer or base layer structure prior to electroforming or electroplating. In some of these embodiments, additional metal may be applied to the portions or regions of the metal coated detachable balloon inner layer or base layer structures that have not been masked or coated prior to electroforming or electroplating.

According to various embodiments, metal layers 90 of detachable balloons may comprise a variety of patterns. For example, one or more masks may be applied to the exterior surface of the detachable balloon inner layer or base layer structure prior to further coating with polymer or metal. In some embodiments, a first metal or metallic layer is applied by sputter deposition and then a second metal layer 90 is formed by electroforming or electroplating, wherein one or more masks may be applied before or after the forming of the first metallic layer. For these embodiments, various portions of the detachable balloon inner layer or base layer structure may have a no metal layer, 90, one metal, layer or two or more metal layers. 90. The external metallic layer or layers may be deposited as one or more narrow bands, arcuate configurations, multiple bands of uniform different widths, multiple bands of different widths, or combinations thereof. One having skill in the art can appreciate that other configurations may be provided.

In some embodiments, detachable balloons may comprise a metallized polymer balloon wherein a metal layer 90 is incomplete, discontinuous or present in only a portion of the wall 30 of the detachable balloon 10. Such incomplete or discontinuous layers can be produced by electroplating, electroplating, vapor deposition, or sputter deposition. In some detachable balloon embodiments, a metal layer 90 is formed over a polymer inner layer or base layer structure wherein some regions or portions of the wall 30 of the detachable balloon 10 have a metal layer 90 produced by electroforming or electroplating and other regions or portions of the detachable balloon without a metal layer 90 produced by electroforming or electroplating. In some embodiments, a detachable partially metallized polymer balloon 20 has a central or intermediate region 100 that comprises a layer of gold produced by electroforming or electroplating that is rigid or semi-rigid, while the proximal and distal regions 110 & 120 of the detachable balloon comprise a polymer layer but do not comprises a layer of gold produced by electroforming or electroplating, and are more flexible, with the polymer layer comprising PET, nylon, Pebax, or other polymers. The proximal region 110 may have a generally tapered configuration that terminates in a proximal neck 130 with a metal layer 90 produced by electroforming or electroplating, or a proximal neck 130 that does not have a metal layer 90 produced by electroforming or electroplating. The distal region 120 may have a generally tapered configuration that terminates in a distal neck 140 with a metal layer 90 produced by electroforming or electroplating, or a distal neck 140 that does not have a metal layer 90 produced by electroforming or electroplating. A partially metallized detachable balloon may comprise a proximal or distal "fluted" portion of the detachable balloon between the proximal neck 130 and the proximal region 110 or the distal neck 140 and the distal region 120. In some embodiments, a fluted portion 150 may not comprise metal or may comprise a layer of metal <1 micron in thickness, that serves as a flexible "hinge" region that remains flexible when the partially metallized polymer detachable balloon is pleated, folded, mounted on a delivery system, and advanced inside the body of a patient. In some embodiments, all or a portion of the fluted region may or may not comprise metal produced by electroforming or electroplating or metal with a thickness >1 micron.

In some embodiments, a partially metallized polymer balloon in a pleated and folded configuration joined or operably coupled to a first or second catheter 174 may comprise alternating regions of stiffer material (including metal produced by electroforming or electroplating or metal with a thickness >1 micron) and more flexible material (including flexible polymer only or flexible polymer with metal having a thickness >1 micron) which produces a pleated and folded partially metallized polymer balloon with rigid or semi-rigid regions 170 interposed with flexible regions 165 to facilitate advancement into the body of a patient, including advancement over guidewires 40, advancement through guide catheters, and advancement through tortuous paths. A detachable balloon with alternating flexible and rigid or semi-rigid regions 170 provides a detachable balloon that is strong enough to resist compression, compaction, or collapse after expansion in vivo, and yet flexible enough when pleated and folded to maneuver through tortuous paths and traverse the twists and turns of the vascular system when joined or operably coupled to a catheter or catheter assembly 5.

The wall thickness for the polymer only and metalized portions of partially metallized detachable balloons may be uniform, or each portion may have a different thickness. For example, the wall 30 of a metallized portion of a detachable partially metalized polymer balloon 20 may have a uniform thickness of 3, 5, 10, 15, 20, 30, 40, 50, 60, 70, 80, 90, 100, or up to 200 microns, including any value between 3 microns and 200 microns, regardless of material. Alternatively, the thickness of the wall 30 of a metallized portion of a detachable partially metalized polymer balloon 20 at different locations along the detachable balloon 10 may vary. The thickness may vary among each individual metalized region and each polymer only or non-metalized region. The wall thickness may vary within each individual metalized region and each polymer or non-metalized region according to some embodiments. In some embodiments, the metalized portions of detachable partially metallized polymer balloons may be 3-100 microns in thickness, including metalized regions wherein the metal is deposited by electroplating or electroforming. In some embodiments, the wall 30 of the polymer or non-metalized portions of detachable partially metallized polymer balloons 20 may have a thickness in the range of approximately 3-60 microns. In some embodiments, a cross-sectional view of the wall 30 of a pleated and folded detachable partially metallized polymer balloon 20 may show more flexible regions 165 comprising polymer only or comprising one or more polymer layers and one or more metal layers with a thickness <1 micron interposed between more rigid regions 170 comprising a metal layer 90 produced by electroplating or electroforming, or a metal layer 90 with a thickness greater than 1 micron. In some embodiments of a detachable partially metallized polymer balloon 20, the proximal neck 130 and proximal region 110 of the partially metallized polymer balloon 20 comprises a polymer layer 99 and a metal layer 90 produced by electroplating or electroforming, or a metal layer 90 with a thickness greater than 1 micron, while the distal region 120 comprises polymer only or comprises a polymer layer 99 and a metal layer 90 with a thickness <1 micron.

In various embodiments, all or a portion of the exterior or interior surface of detachable balloons 10, including polymer balloons 12, metalized polymer balloons 14, metal balloons 16, and polymer-coated metal balloons 18 may be coated with a variety of materials having properties ranging from hydrophobic to hydrophilic, urethanes, other metals or combinations thereof, by well-known means. Coating can achieve various objectives including enhanced biocompatibility, blood contact enhancement, surface texturing, or conformal coating to improve part durability, including a coating to reduce the risk of delamination of a metal layer 90 from a polymer layer 99.

In some embodiments of a detachable metalized polymer balloon 14, a metal wire or metal ribbon may be applied to all or portions of the exterior surface of a polymer balloon 12 or a polymer inner layer or base layer structure. The metal wire may be provided in a variety of thickness and shapes. By way of example and not limitation, the metal wire may have a circular cross-section and a diameter in a range between 25 microns to 600 microns. In a preferred embodiment, round metal wires have a diameter of approximately 50-200 microns. Alternatively, the metal wire may be provided as a flat ribbon or a semi-flat "half round" wire. The width for the flat wire is typically in a range of about 25 microns to about 600 microns in width and about 20 microns to about 300 microns, in thickness. In particular, the width of a flat ribbon wire may be 25, 50, 75, 100, 125, 150, 175, 200, 225, 250, 275, 300, 325, 350, 375, 400, 425, 450, 475, 500, 525, 550, 575, or up to 600 microns, including any value between 25 microns and 600 microns. Similarly, the thickness of the flat ribbon projecting away from the surface of the detachable balloon, may be 20, 30, 40, 50, 60, 70, 80, 90, 100, 110, 120, 130, 140, 150, 160, 170, 180, 190, 200, 210, 220, 230, 240, 250, 260, 270, 280, and 300 microns, including any value between 20 microns and 300 microns. Other wire shapes may be used, including wires with non-linear or irregular cross sectional profiles. The pitch and number of wire loops (loop density), and the angle of winding may be varied both between and within embodiments. As such, the metal wire may be uniformly wound and positioned in some embodiments of the detachable metalized balloon, while in other embodiments, the pitch, number of loops, the angle of winding, or a combination thereof, may be varied.

For some embodiments, after positioning metal wire or ribbon on the external surface of a polymer balloon 12 or polymer inner layer or base layer 99 structure, the resulting metalized polymer balloon 14 is coated with a polymer or adhesive. In some embodiments, a coating comprising a urethane composition is used to further adhere the metal wire to the detachable polymer balloon 12 or inner layer or base layer 99 structure. The urethane composition may be provided at a concentration range of 2% to 10% urethane in a solvent. By way of the example and not limitation, the solvent may comprise tetrahydrofuran ("THF") or oxolane; however other solvents may be used. In one aspect, a solvent, such as THF, may chemically modify, react with, or bond to the surface of the detachable polymer balloon 12 or inner layer or base layer 99 structure. As such, forming a strong bond is formed between the urethane layer and the detachable polymer balloon 12 or the polymer inner layer or base layer 99 structure to further secure the wire to the exterior surface of the detachable balloon 10. The urethane coating may be applied by any suitable method, including but not limited to dip coating or spray coating. Preferred methods result in a more even or uniform distribution of the urethane composition over and between the metal wires applied to the surface of the detachable polymer balloon 12 or the polymer inner layer or base layer 99 structure. Preferred methods increase the force required to induce delamination of the metal wire from the detachable balloon 10. Preferred methods reduce the risk of fracturing or breaking of the metal wire. Preferred methods permit the simultaneous coating of multiple metalized polymer balloons 14. Preferred methods can be used to manufacture coated metalized polymer balloons 14 at a reasonable cost.

In one embodiment, a detachable polymer balloon 12 or a polymer inner layer or base layer 99 structure is prepared in a manner similar to that of a common angioplasty balloon. For example, a tubular polymer material is cut to a desired length, including material to form the distal neck 140 and proximal neck 130 at opposing ends of the balloon. One end of the balloon is adhered to a tubular structure, (e.g., a blunt needle) that forms a leak-free conduit to the balloon interior. The tubular structure also permits passage of additional tubing into the balloon interior. This additional tubing provides a means to inflate the balloon and also functions as a splint to secure the balloon during fabrication processes. The additional tubing may be engaged to a valve, such as a Luer valve such that the balloon may be inflated and remain inflated during processes that add metal. To complete the fabrication of the detachable polymer balloon 12 or polymer inner layer or base layer 99 structure, the remaining neck or opening is filled and sealed. In one embodiment, the remaining opening is filled with an ultraviolet (UV) curable adhesive that is cured to seal the balloon. The detachable polymer balloon 12 or polymer inner layer or base layer 99 structure is then pressurized or inflated and positioned with in a device that can apply wire to the surface of the detachable polymer balloon 12 or polymer inner layer or base layer 99 structure. Optionally, the pressurized detachable polymer balloon 12 or polymer inner layer or base layer 99 structure may be coated in a urethane solution prior to applying the metal wire. In one embodiment, the device that can apply wire to the surface of the detachable polymer balloon 12 or polymer inner layer or base layer 99 structure is a wrapping system that is similar to a lathe, such that a mounted balloon 10 rotates about a longitudinal axis. Once a balloon is mounted, one end of the wire is adhered to the polymer balloon 12 and the polymer balloon 12 is rotated. While the polymer balloon 12 is rotating, the wire is wrapped around the desired portions of the polymer balloon 12 at the desired pitch, loop density, and angle. After the wrapping, the terminal end of the wire is adhered to the polymer balloon 12. The wire wrapped polymer balloon is removed from the wire wrapping assembly and coated at least once in a urethane based composition. In one embodiment, the entire wire wrapped polymer balloon may be coated in the urethane composition, as described herein. In other embodiments, masks may be placed over the portions of the wire wrapped polymer balloon such that only the wrapped portions are coated. After the urethane coating cures, the wire wrapped polymer balloon may be depressurized (deflated), pleated and folded. The pleated and folded detachable wire wrapped polymer balloon may take a collapsed configuration or delivery configuration.

Manufacturing of Detachable Balloon Catheters—Fabricating Detachable Metal Balloons and Detachable Polymer-Coated Balloons A hollow metallic expandable body 10 may be manufactured by a method wherein a metal such as gold is deposited by electroforming over a sacrificial mandrel 740 made from an electrically conductive material such as aluminum. The sacrificial mandrel 740 may then be removed from the interior of the expandable body 10 by processes such as drilling and acid etching. The electroforming process may produce rounded, pebbled, or granular structures on the exterior surface of the expandable body. 10. The metallic expandable body 10 may further undergo an annealing process to improve its pliability of the expandable body. 10. In one embodiment, a gold expandable body 10 is heated to approximately 300° C. for approximately 1 hour and then immediately quenched in a bath of distilled water at room temperature. Finally, a polymer coating may be applied to the expandable body 10 to modify its mechanical, electrical, or biocompatibility characteristics. The polymer coating may comprise Parylene, polyurethane, PTFE, silicone, or other biocompatible polymers. The coating may be applied by dipping, spinning, spraying, or other deposition processes specialized for the specific polymer. The coating may be applied to the entire exterior of the expandable body 10 or to only selected regions by masking the regions not to be coated.

Figure 84:
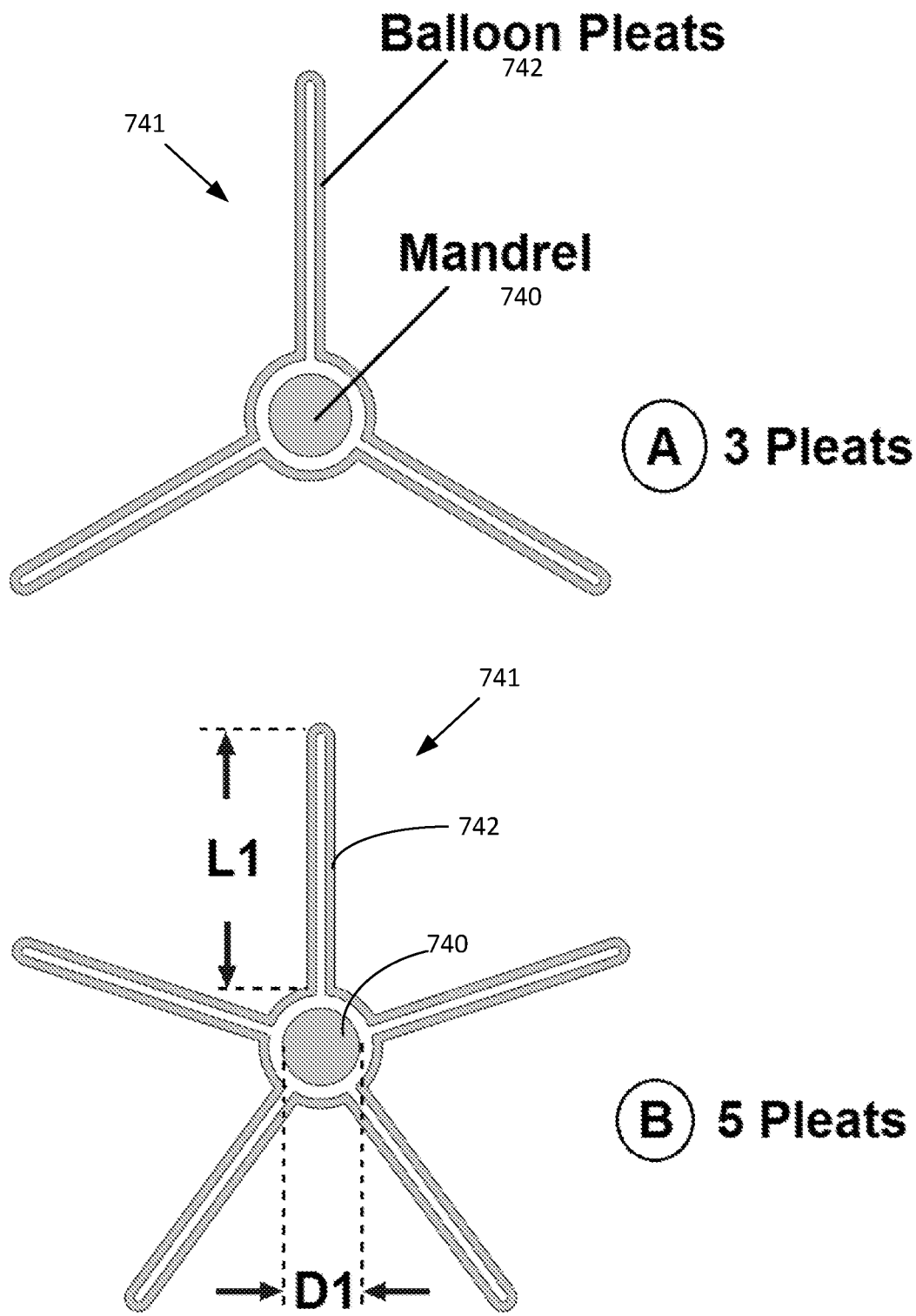
FIGS. 84A-B are cross-sectional views showing a pleated balloon according to embodiments using three or five pleats with certain geometric dimensions defined.

Manufacturing of Detachable Balloon Catheters—Pleating and Folding Detachable Balloons To facilitate advancement of the partially or fully metallized, or partially or fully plated detachable balloon through the vascular system, the detachable balloon can be compressed into various shapes and dimensions, as shown in FIGS. 83A-D and 84A-B. For example, partially or fully metallized, or partially or fully plated detachable balloon can be pleated, folded, and optionally compressed to a diameter small enough to pass through 3-9 Fr, or larger guide catheters or maneuvered through arteries, veins, chambers of the heart (including atrial and ventricular chambers), other blood-containing structures, biological conduits, or other biological spaces. The pleating, folding, and optional compression can include various forms and patterns. As shown in FIGS. 84A-B and 85, the number and length of pleats can be optimized to suit the expanded diameter and wall thickness of the detachable balloon. For example, partially or fully metallized, or partially or fully plated detachable balloon can be pleated folded and compressed to a diameter small enough to pass through 3-8 Fr guide catheters or maneuvered through cerebral arteries. Optionally, this compression can include various forms and patterns of pleating, folding, or compression.

In some embodiments, the detachable balloon of a detachable balloon catheter 1 is configured to expand from a compressed or collapsed configuration to an expanded configuration and wherein, when the detachable balloon is in the compressed or collapsed configuration, the wall 30 of the detachable balloon 10 assumes a pleated configuration comprising a plurality of pleats folded over in a clockwise direction relative to the first axis 706 or a counterclockwise direction relative to the first axis 706 to form a folded-over region of the detachable balloon. In some embodiments, when the detachable balloon of a detachable balloon catheter 1 is in a compressed or collapsed configuration, the wall 30 of the detachable balloon 10 assumes a pleated configuration comprising a plurality of pleats folded over in a clockwise direction relative to the first axis 706 or a counterclockwise direction relative to the first axis 706 to form a folded-over region of the detachable balloon; and wherein, when the detachable balloon is in the expanded configuration, the plurality of pleats is not folded over. In some embodiments, each pleat 742 of the plurality of pleats of detachable balloon of a detachable balloon catheter 1 comprises a ridge line extending proximal-distal and radially away from the first axis. 706. In some embodiments, each pleat 742 comprises a ridge line extending proximal to distal and each pleat 742 of the plurality of pleats of detachable balloon of a detachable balloon catheter 1 is separated from any immediately adjacent pleat 742 by an interposed trough extending proximal to distal. In some embodiments, the pleated configuration of a pleated balloon of a detachable balloon catheter 1 comprises an alternating ridge-trough arrangement. In some embodiments, each pleat 742 of the plurality of pleats of a pleated balloon of a detachable balloon catheter 1 is folded over an immediately adjacent pleat 742 in a clockwise direction relative to the first axis, 706, or a counterclockwise direction relative to the first axis. 706. In some embodiments, the detachable balloon of a detachable balloon catheter 1 is configured to assume the expanded configuration by substantially eliminating the pleated configuration or a plurality of pleats that are present in the collapsed or compressed configuration.

In some embodiments, the compressed or collapsed detachable balloon of a detachable balloon catheter 1 can be expanded by injection of water, saline, radiographic contrast, or combinations thereof, into the central void 115 or interior volume of the detachable balloon. In some embodiments, the detachable balloon of a detachable balloon catheter 1 is configured to be expanded from the compressed or collapsed configuration to the expanded configuration by applying a pressure of less than 10 atmospheres, less than 5 atmospheres, less than 4 atmospheres, less than 3 atmospheres, less than 2 atmospheres, or less than 1 atmosphere to the central void 115 or interior volume of the detachable balloon. In some embodiments, the central void 115 or interior volume of a detachable balloon of a detachable balloon catheter 1 can be pressurized during the passage of a fluid from the proximal hub of the first catheter 173, through the first lumen 162, and into the central void 115 or interior volume of the detachable balloon 10. In some embodiments, a detachable balloon catheter 1 is configured to enable the injection of fluid from the hub 179 of the first catheter 173, through the lumen 162 of the first catheter 173, and into the central void 115 or interior volume of the detachable balloon 10 at a rate higher than the leaking of fluid from the central void 115 or interior volume of the detachable balloon 10 into the space adjacent to the detachable balloon 10. In some embodiments, the expansion of a detachable balloon 10 of a detachable balloon catheter 1 results in a foreshortening of the detachable balloon 10 along a plane parallel to the first axis 706.

Various methods can be used to pleat, fold, and compress the partially or fully metallized, or partially or fully plated detachable balloon and enable it to travel through various lumens and conduits. These include, but are not limited to, the lumen of guide catheter, arteries 317, veins 318, chambers of the heart (including atrial and ventricular chambers), other blood-containing structures, biological conduits 900, or other biological spaces 904.

In one embodiment, the partially or fully metallized, or partially or fully plated detachable balloon is folded to form one or more pleats prior to or after attaching the partially or fully metallized, or partially or fully plated detachable balloon to a first catheter 173, and the pleats are rolled and compressed, like the folding of a non-compliant angioplasty balloon. In another embodiment, the partially or fully metallized, or partially or fully plated detachable balloon is flattened into a planar shape and rolled into a cylindrical shape. In certain embodiments, the partially or fully metallized, or partially or fully plated detachable balloon may be folded and wrapped around the first catheter 173.

For example, one or more pleats can be made in the partially or fully metallized, or partially or fully plated detachable balloon and then the pleats can be wrapped into a cylindrical shape. The partially or fully metallized, or partially or fully plated detachable balloon may be flattened into a planar shape and then rolled into a cylindrical shape. Alternatively, the partially or fully metallized, or partially or fully plated detachable balloon may be compressed into a compact spherical shape. Additionally, the portions of the partially or fully metallized, or partially or fully plated detachable balloon may be twisted or braided during compression. In certain instances, the partially or fully metallized, or partially or fully plated detachable balloon may be compressed around a first catheter 173. Sometimes, the partially or fully metallized, or partially or fully plated detachable balloon 741 may be compressed around a mandrel. In other embodiments, the partially or fully metallized, or partially or fully plated detachable balloon may be compressed on itself, without a central mandrel, including a catheter mandrel.

In another embodiment, the partially or fully metallized, or partially or fully plated detachable balloon is pleated, then the pleats are wrapped around the hollow cylindrical member of the first catheter 173, and the partially or fully metallized, or partially or fully plated detachable balloon 14 or 20 is compressed against the first catheter 173. In another embodiment, the partially or fully metallized, or partially or fully plated detachable balloon 14 or 20 is pleated, then the pleats are wrapped around a removable wire mandrel, and then the partially or fully metallized, or partially or fully plated detachable balloon 14 or 20 is compressed against the removable wire mandrel. In another embodiment, the partially or fully metallized, or partially or fully plated detachable balloon 14 or 20 is pleated, and then the pleats are rolled into a generally cylindrical shape without a removable wire or catheter acting as central fixation point or mandrel.

In various embodiments, the partially or fully metallized, or partially or fully plated detachable balloon is attached to a first catheter 173, then pleated, and then the pleats are folded, wrapped or compressed onto the first catheter 173. In another embodiment, the partially or fully metallized, or partially or fully plated detachable balloon is first pleated, attached to the first catheter 173, and then the pleats are wrapped or compressed onto the outer surface of the first catheter 173.

In some embodiments, excess material may be removed from one or both ends of the proximal end of the proximal neck 130 or the distal end of the distal neck 140 of a detachable balloon inner layer or base layer structure or a partially or fully metallized, or partially or fully plated detachable balloon prior to pleating. The excess material may be removed by cutting the necks. Cutting can be accomplished by means of rotating the detachable balloon inner layer or base layer structure or a partially or fully metallized, or partially or fully plated detachable balloon under a fixed blade or by rotating the blade over the proximal or distal neck 130 & 140 of a detachable balloon inner layer or base layer 99 structure or a partially or fully metallized, or partially or fully plated detachable balloon 14 or 20. In some instances, heat may be used to soften the necks or the ends of the necks prior to cutting. One of skill in the art will appreciate that the excess material at the ends of the necks of a detachable balloon inner layer or base layer structure or a partially or fully metallized, or partially or fully plated detachable balloon may be removed by means known in the art.

A partially or fully metallized, or partially or fully plated detachable balloon may be mounted on a pleating and folding mandrel, either before or after removing excess material from the proximal or distal necks. 130 & 140. In this regard, the needle hub that the partially or fully metallized, or partially or fully plated detachable balloon was previously mounted on as part of the custom packaging system is replaced by a mandrel. To keep the mandrel 740 stationary during shipping, a stopper or other means of stabilizing the mandrel 740 may be placed over the tip of the mandrel 740 when the mandrel 740 and partially or fully metallized, or partially or fully plated detachable balloon are placed in a shipping tube. The stopper may be a piece of foam or any other material known in the art. The pleating and folding mandrel 740 reduces the risk of compression of the partially or fully metallized, or partially or fully plated detachable balloon during shipment and setup and prevents the partially or fully metallized, or partially or fully plated detachable balloon from being overly compressed during pleating, folding, and compression. This is accomplished by sizing the outer diameter of the mandrel 740 to the desired final internal dimension corresponding to the outer diameter of the second catheter 174, or the telescoping segment 185 that will be used during assembly of a complete medical device, 1, including but not limited to those disclosed co-owned PCT applications having serial Nos. PCT/US2014/030869 and PCT/US2015/050783, commonly referred to as Blockstent Microcatheter devices and a Ballstent Microcatheter devices.

Figure 77:
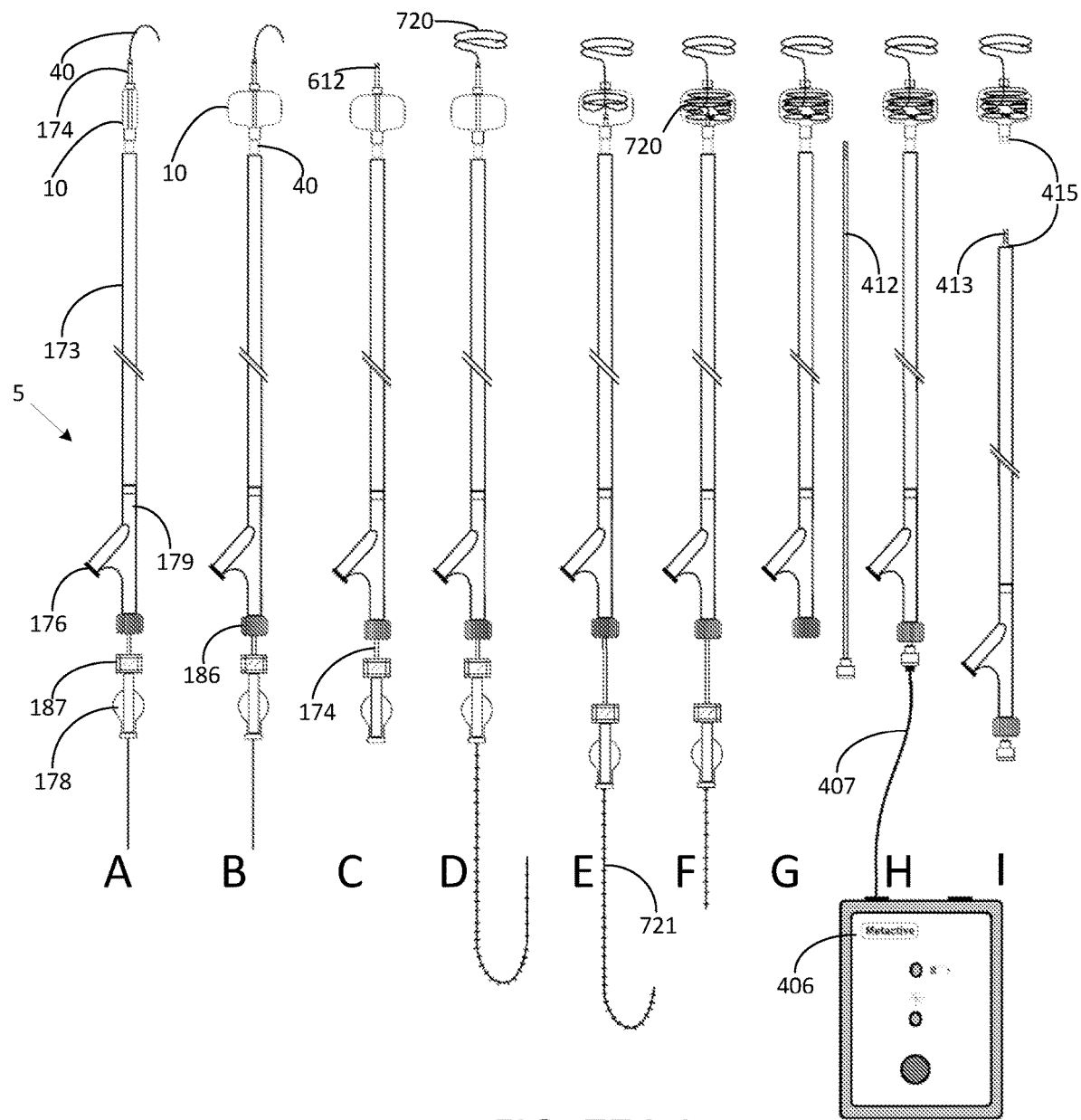
FIGS. 77A-I are planar views showing a third sequence of operation of an electrothermal detachment system according to the embodiment shown in FIGS. 64 and 65.
Figure 78:
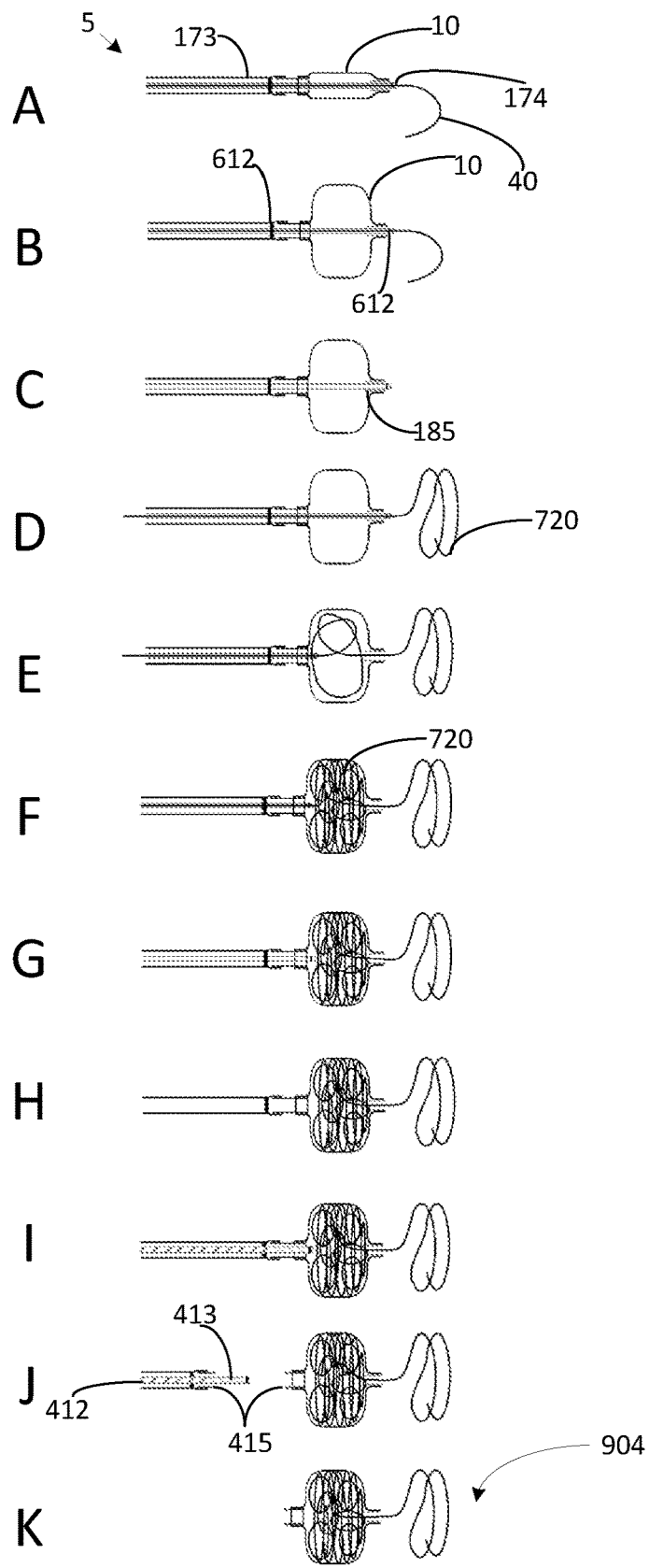
FIGS. 78A-K are cross-sectional detail views showing a third sequence of operation of an electrothermal detachment system according to the embodiment shown in FIGS. 64 and 65.
Figure 79:
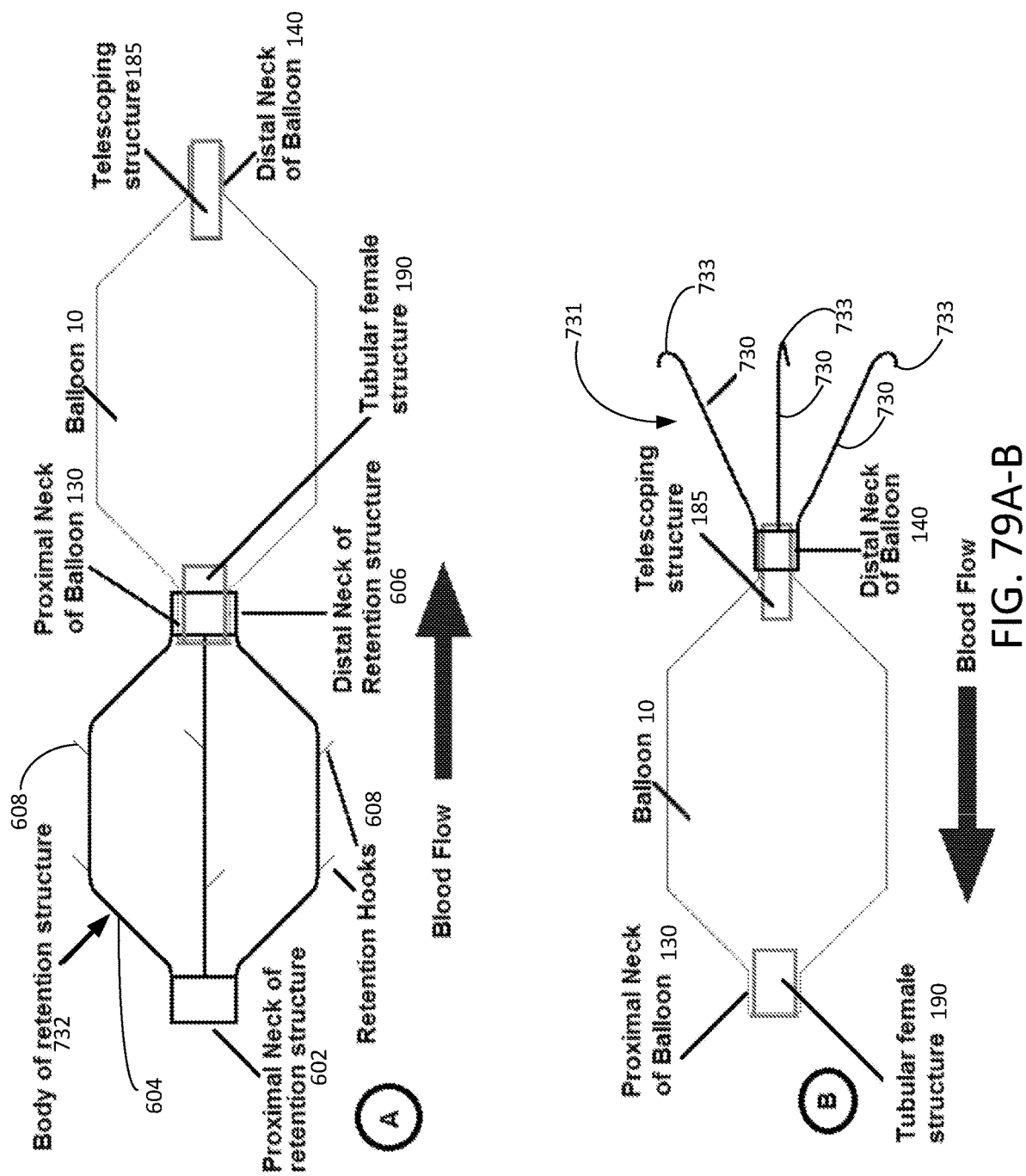
FIGS. 79A-B are partial cross-sectional views of balloons equipped with two embodiments of expandable retention structures.
Figure 80:
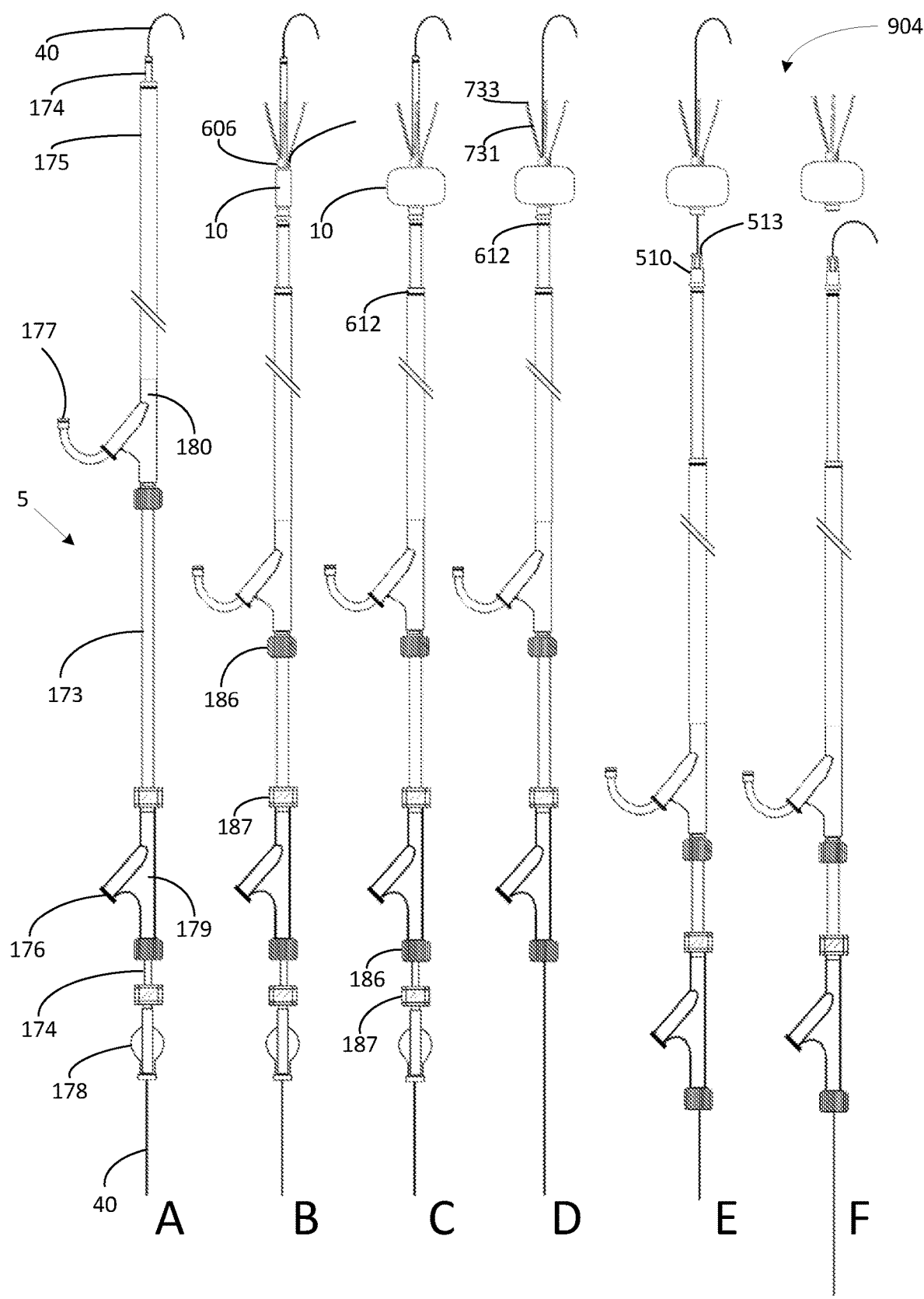
FIGS. 80A-F are planar views showing a first sequence of operation of a detachable balloon catheter incorporating an expandable retention structure affixed to the distal neck of the balloon and a mechanical latch attachment system according to one embodiment.
Figure 81:
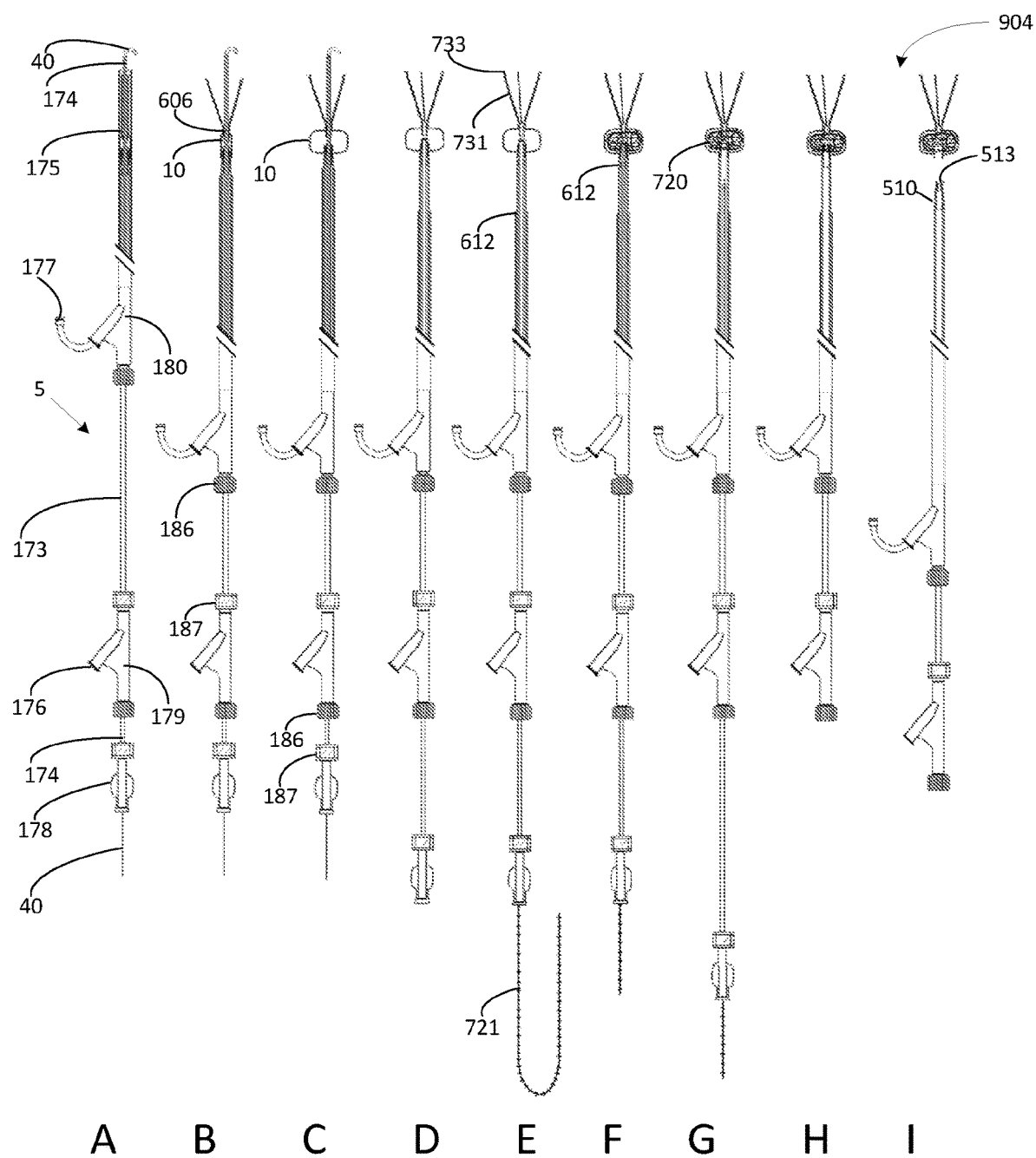
FIGS. 81A-I are planar views showing a second sequence of operation of a detachable balloon catheter incorporating an expandable retention structure affixed to the distal neck of the balloon and a mechanical latch attachment system according to one embodiment.
Figure 82:
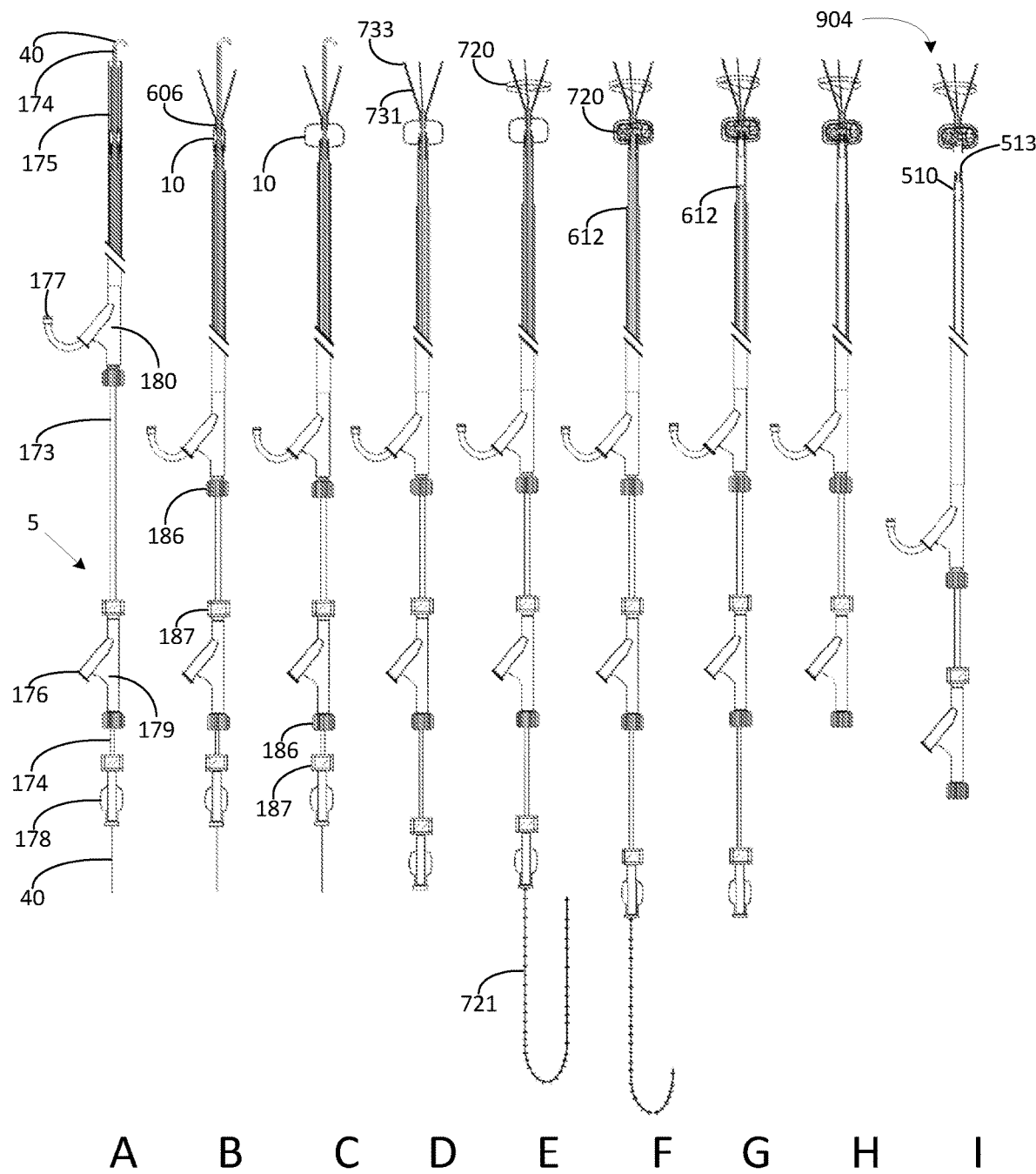
FIGS. 82A-I are planar views showing a third sequence of operation of a detachable balloon catheter incorporating an expandable retention structure affixed to the distal neck of the balloon and a mechanical latch attachment system according to one embodiment.
Figure 83:
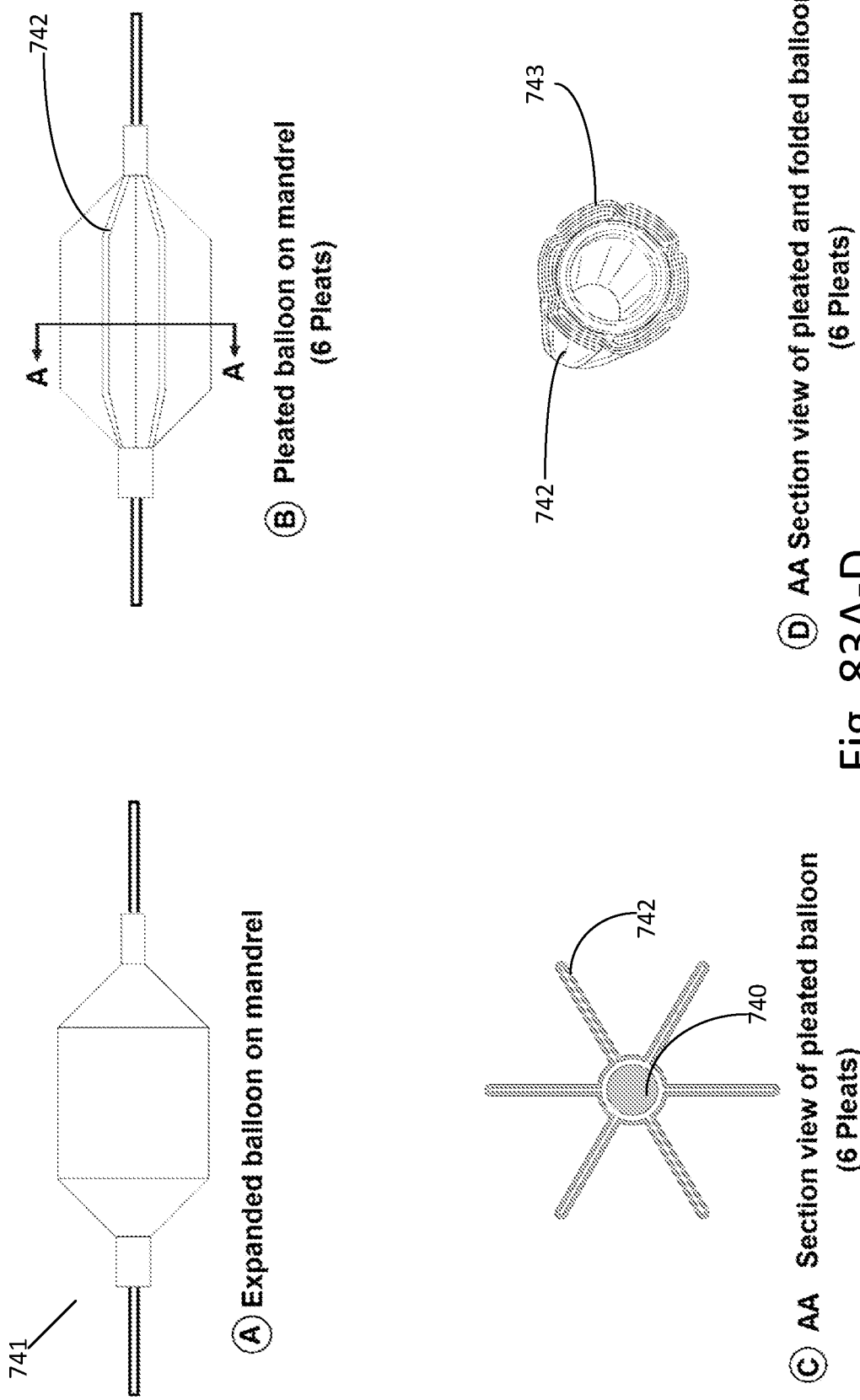
FIGS. 83A-D are planar, cross-sectional, and perspective views showing the sequence of pleating and folding a balloon according to one embodiment.

Once the partially or fully metallized, or partially or fully plated detachable balloon 741 and mandrel 740 have been placed in a shipping tube along with a stabilizing means, the shipping tube may be sent to a third party where the partially or fully metallized, or partially or fully plated detachable balloon is removed and pleated. As illustrated in FIGS. 77-79, the pleated partially or fully metallized, or partially or fully plated detachable balloon may have a plurality of pleats. In a preferred embodiment, the pleated partially or fully metallized, or partially or fully plated detachable balloon may have three pleats. In some instances, the pleated partially or fully metallized, or partially or fully plated detachable balloon may have as few as one pleat, 742, or as many as ten pleats. One of skill in the art will appreciate that the partially or fully metallized, or partially or fully plated detachable balloon may have as many pleats as necessary to compress the partially or fully metallized, or partially or fully plated detachable balloon into a size that allows the pleated and folded partially or fully metallized, or partially or fully plated detachable balloon to be advanced through the vascular system using a delivery system.

In some embodiments, the partially or fully metallized, or partially or fully plated detachable balloon may be pleated with no head heating. In some embodiments, it may be advantageous to pleat the partially or fully metallized, or partially or fully plated detachable balloon with no extended dwell time in pleat head. By pleating the partially or fully metallized, or partially or fully plated detachable balloon without head heating and without extended dwell time in the pleat head, the partially or fully metallized, or partially or fully plated detachable balloon may be expanded without permanent folds. The partially or fully metallized, or partially or fully plated detachable balloon 741 may be folded to the mandrel 740 while in fold-head. In some embodiments, the partially or fully metallized, or partially or fully plated detachable balloon may be pleated and removed from the mandrel. 740. After the partially or fully metallized, or partially or fully plated detachable balloon have been pleated and folded they may be packaged for shipping, documenting the pleat and fold information on the packaging tube.

Pleating is accomplished by compressing the partially or fully metallized, or partially or fully plated detachable balloon between two or more plates. This compression causes the partially or fully metallized, or partially or fully plated detachable balloon to achieve a single or multi-lobular shape. These lobes are then folded around the central axis of the partially or fully metallized, or partially or fully plated detachable balloon in one direction which causes the partially or fully metallized, or partially or fully plated detachable balloon to be formed into a tubular shape that is concentric with its ends and approximates the dimensions of one or both ends.

Manufacturing of Detachable Balloon Catheters—Assembly of Detachable Balloon Catheters The partially or fully metallized, or partially or fully plated detachable balloon may be attached to the delivery system, first catheter 173, or second catheter 174 using a variety of materials, components, systems, and methods. The partially or fully metallized, or partially or fully plated detachable balloon can be attached to the first catheter 173 in a manner wherein the size and shape of the distal end of the first catheter 173 and the size and shape of the opening in the wall 30 of the partially or fully metallized, or partially or fully plated detachable balloon 14 or 20 are matched so that a friction fit 202 is formed between partially or fully metallized, or partially or fully plated detachable balloon 14 or 20 and the first catheter 173. In an embodiment of a friction fit 202, the elastic sleeve or wrap 204 can be affixed, generally indicated as 206, within the proximal neck 130 of the detachable balloon 10 and the sleeve engages the first catheter 173. Alternatively, the elastic sleeve or wrap 204 can be placed around the proximal neck 130 of the partially or fully metallized, or partially or fully plated detachable balloon 14 or 20 and used to hold the partially or fully metallized, or partially or fully plated detachable balloon 14 or 20 and the first catheter 173 together. In another embodiment of a friction fit 173, the partially or fully metallized, or partially or fully plated detachable balloon 14 or 20 can be attached to the first catheter 173 using an adhesive or glue, or a weld or solder. The partially or fully metallized, or partially or fully plated detachable balloon 14 or 20 can be attached to the first catheter 173 by a fitting of mechanical parts on the partially or fully metallized, or partially or fully plated detachable balloon 14 or 20 and the first catheter 173, such as with a clamp that can be released or with a wire, polymer strand, filament, thread, or string that can be loosened or removed.

The method may also include welding or joining all or a portion of the proximal or distal neck 130 & 140 segments to the partially or fully metallized, or partially or fully plated detachable balloon 14 or 20, or both the proximal and distal neck 130 & 140 segments. In other embodiments, a proximal neck segment 130, a distal neck segment 140, or both a proximal and distal neck segments 130 & 140 may be joined during an electroforming process to form the partially or fully metallized, or partially or fully plated detachable balloon 14 or 20.

Elongated and Expandable Bodies

The present disclosure relates to medical devices 1 that comprise an elongated or expandable body 720. Herein, these devices are also called "second medical devices." As used herein, an elongated body 720 is a long, thin, flexible structure that can be pushed or carried through the lumen of a catheter and implanted in a patient. Elongated bodies 720 can occupy space and form complex shapes, but do not expand during or after placement. As used herein, an expandable body 720 is a long, thin, flexible structure that can be pushed or carried through the lumen of a catheter in a constrained, collapsed, compressed, or pleated and folded form and implanted in a patient, wherein at least portions of the expandable body 720 can expand in size during or after placement. Elongated and expandable bodies 720 that can be used with detachable balloon catheters 1 are described.

Figure 86:
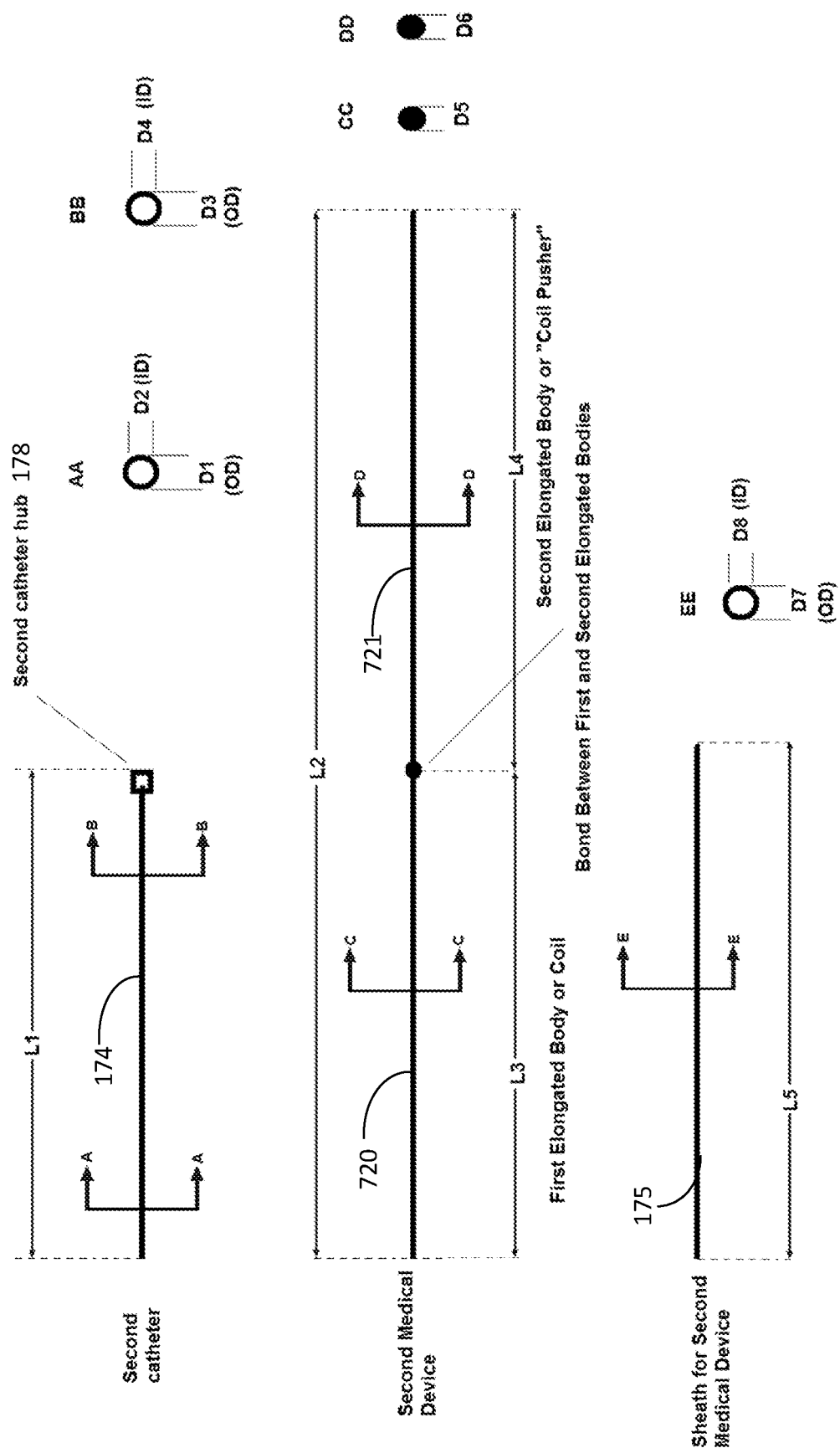
FIG. 86 is a schematic of a second catheter and second medical device serving as a coil delivery system according to one embodiment with overall geometric dimensions defined.
Figure 93B:
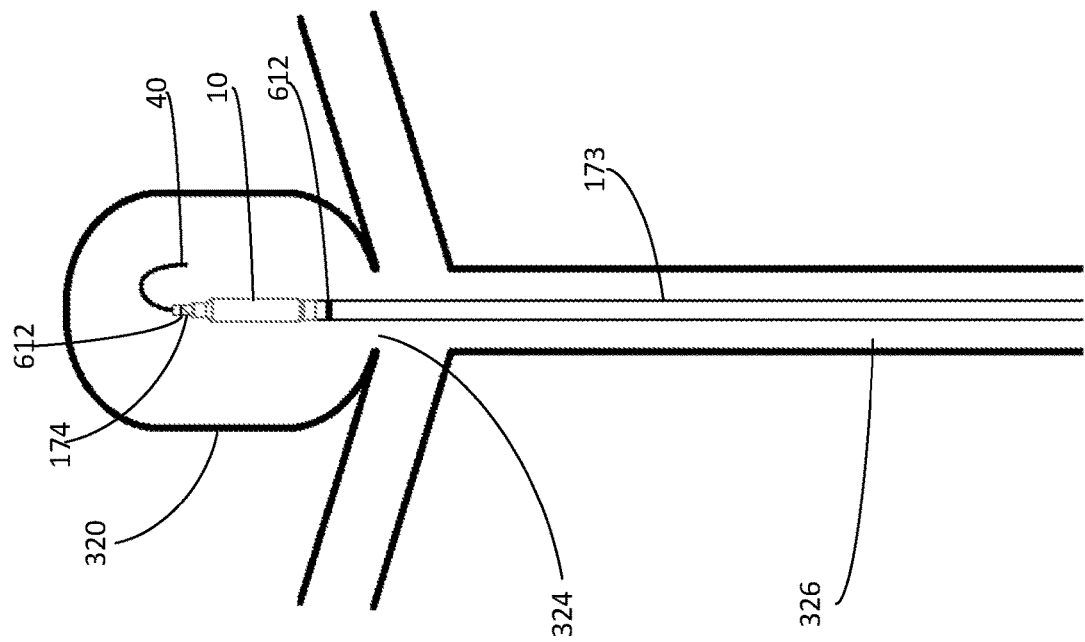
Figure 93A:
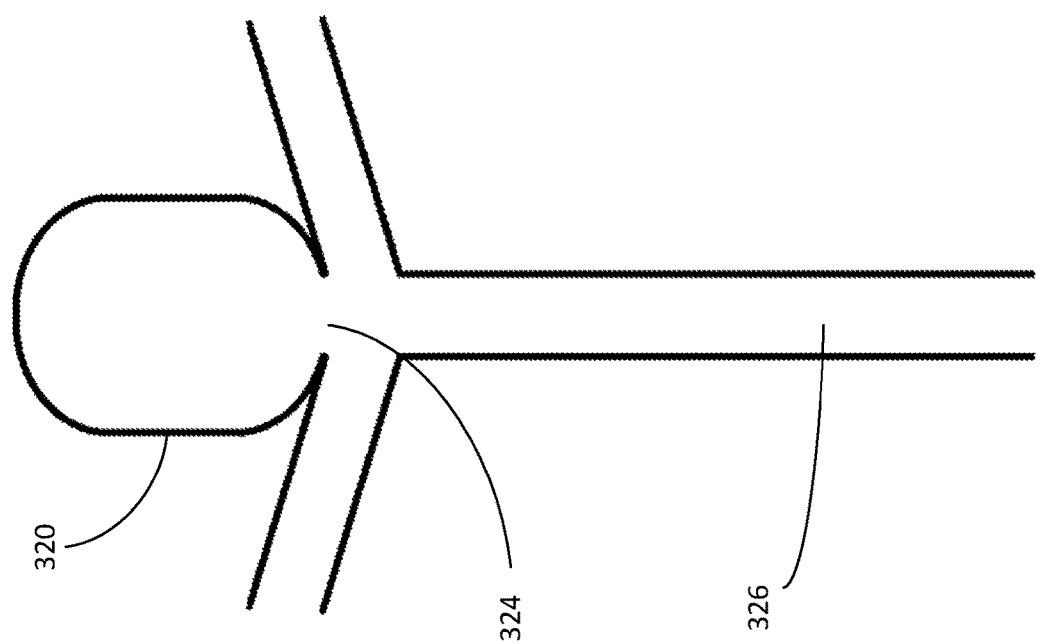
Figure 93D:
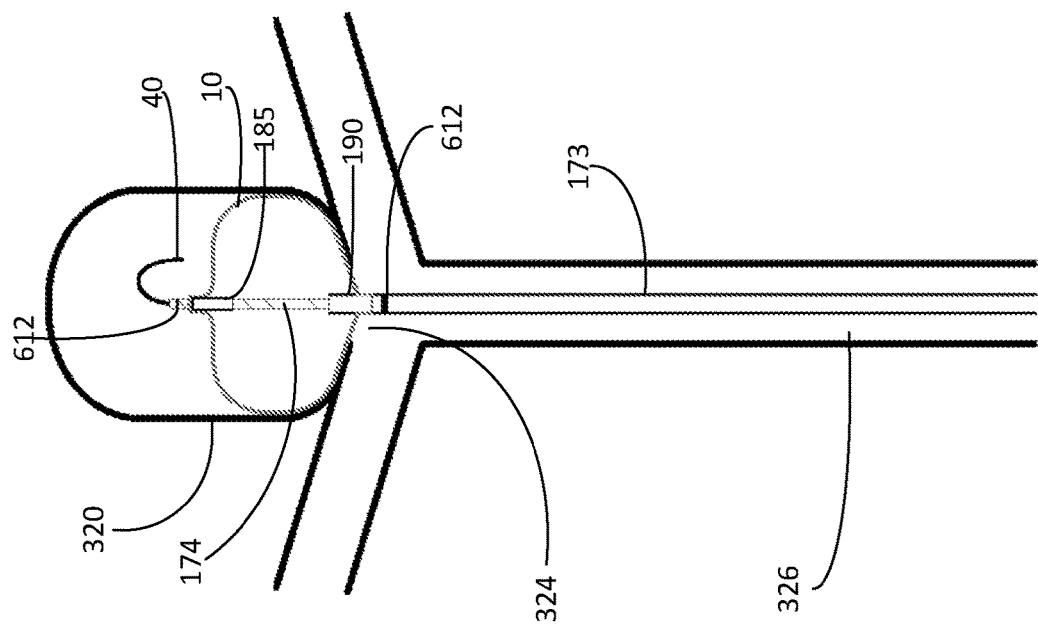
Figure 93C:
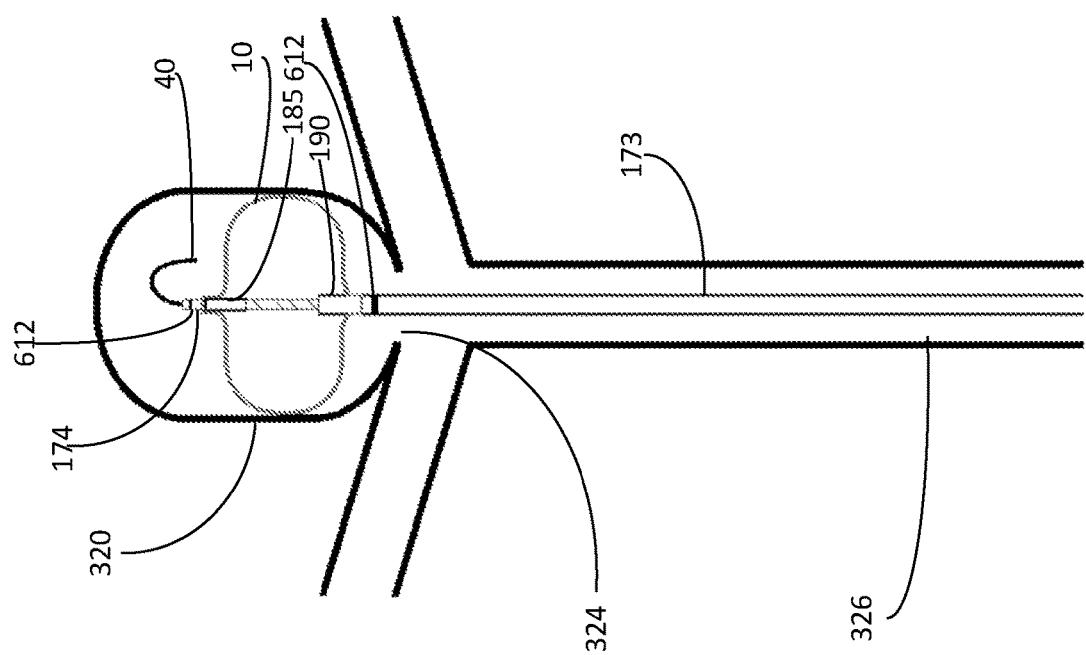
Figure 93H:
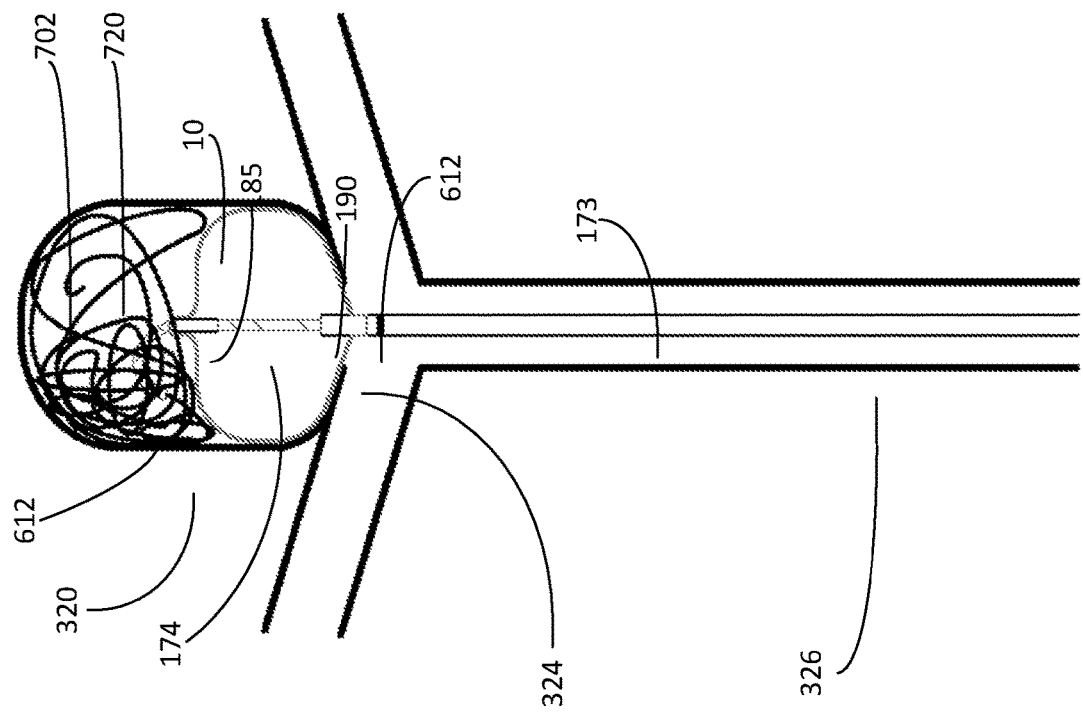
Figure 93G:
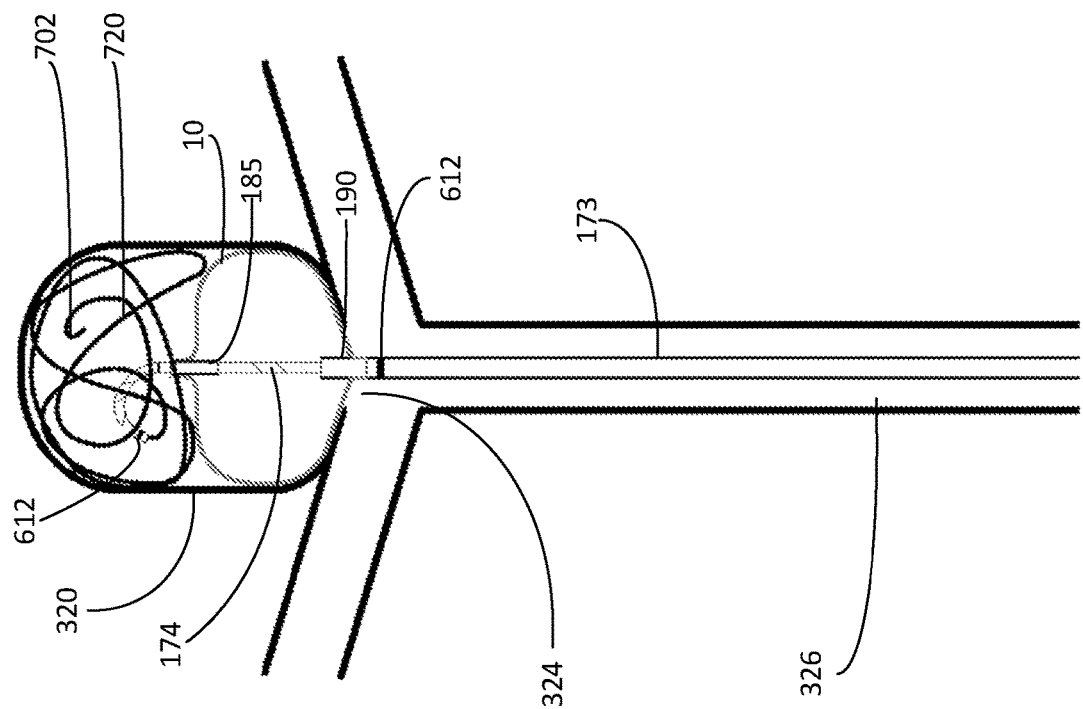
Figure 93I:
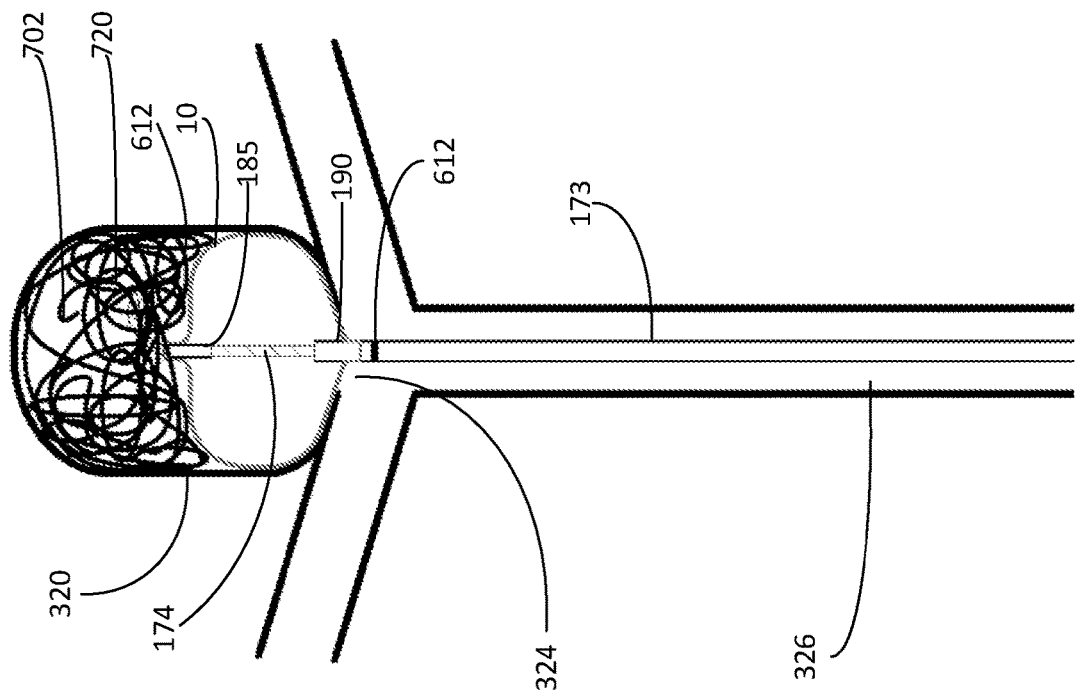
Figure 93J:
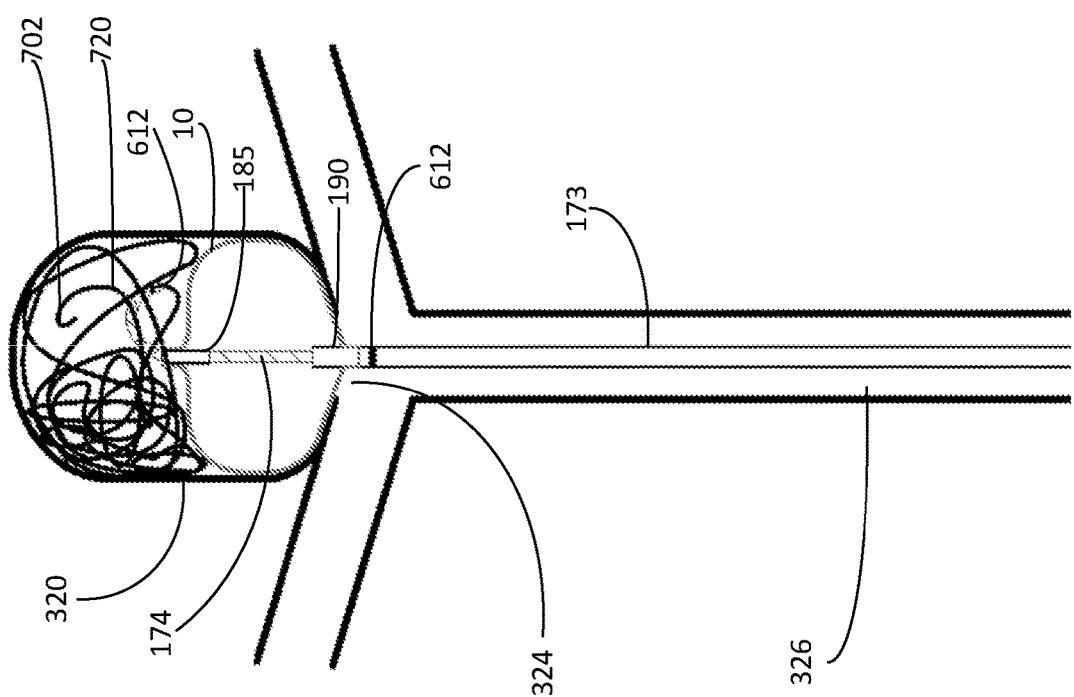
Figure 93L:
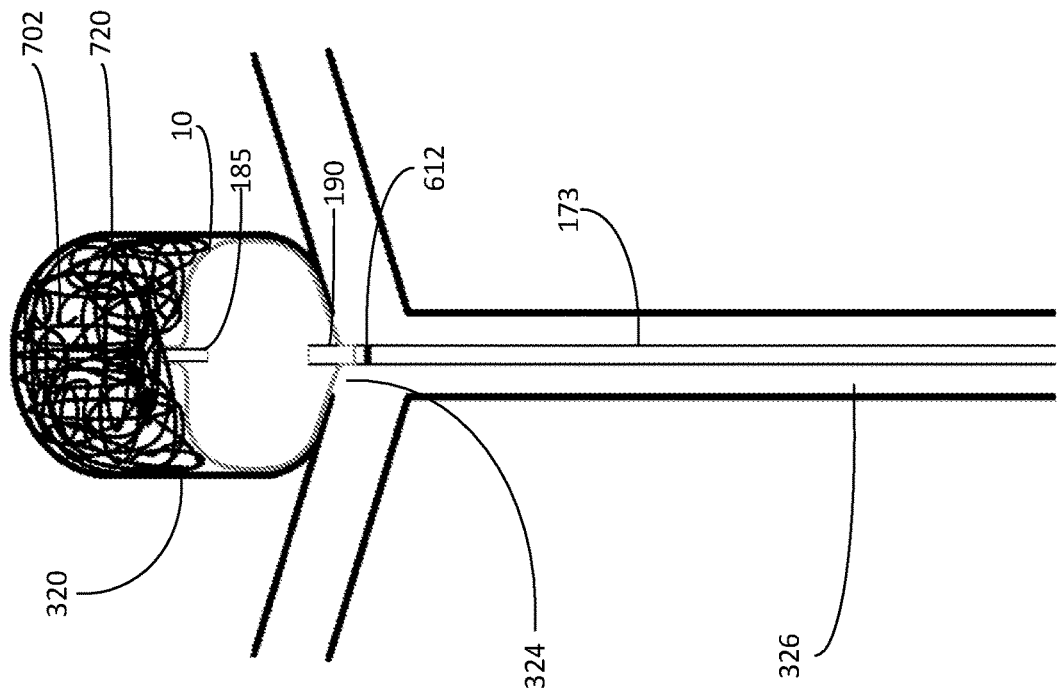
Figure 93K:
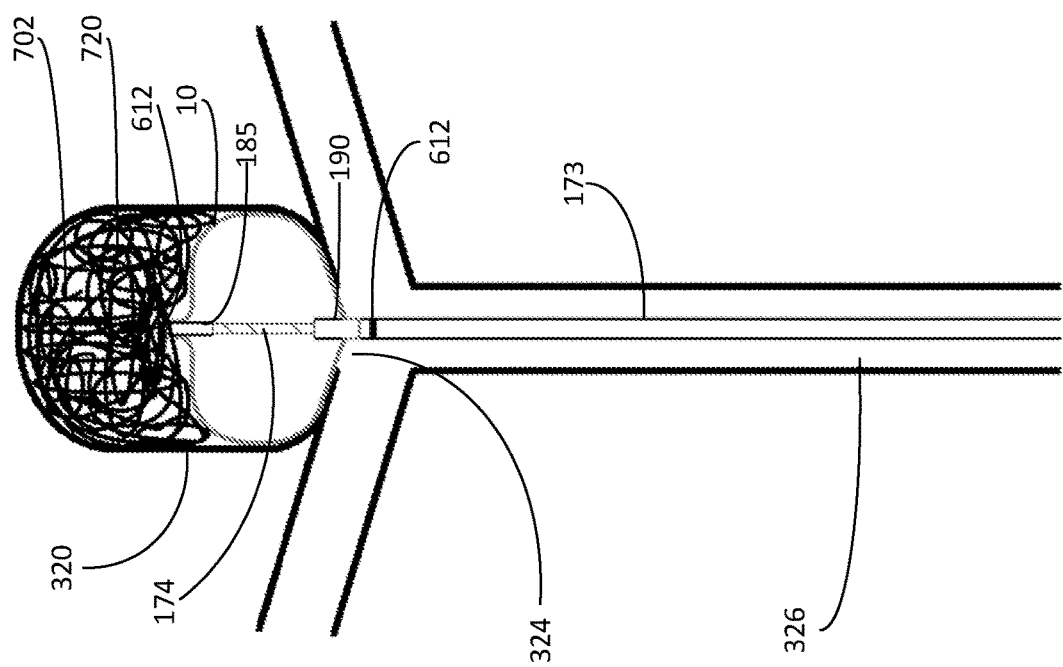
Figure 93M:
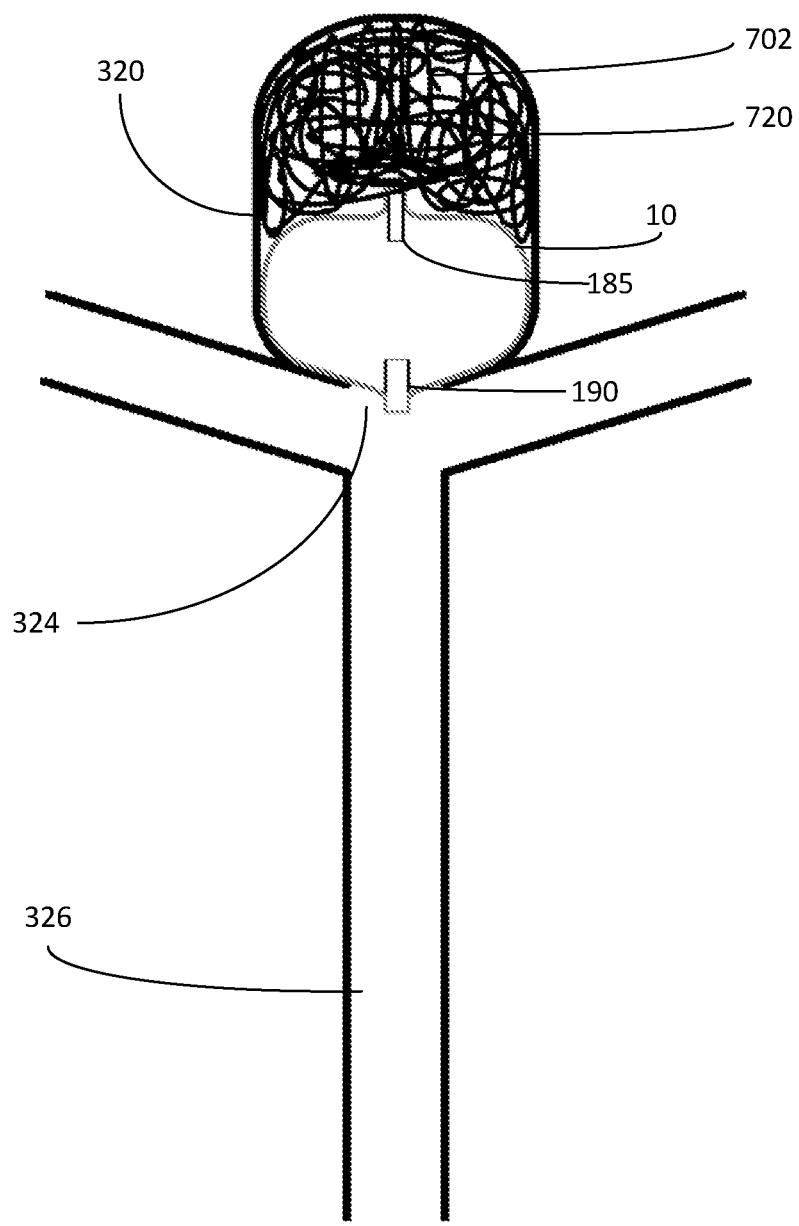

As shown in FIG. 86, the first elongated or expandable body 10 of the second medical device 1 is joined to the second elongated body of the second medical device 1 by a bond or joint that can be separated after placement of the first elongated or expandable body 10 into a saccular aneurysm, artery, vein, LAA, paravalvular leak, blood-containing space, biological conduit 900 or space, or the central void 115 or interior volume of the expanded detachable balloon of the first medical device. 1. The first elongated or expandable body 10 of the second medical device 1 is joined to the second elongated body of the second medical device 1 and wherein, after expulsion of the first elongated or expandable body 10 of the second medical device 1 from the distal end of the second catheter 174 of the first medical device 1, the second elongated body of the second medical device 721 can be separated from the first elongated or expandable body 720 of the second medical device 700 and the second elongated body 721 can be removed from the patient while the first elongated or expandable body 720 remains in the patient. In some embodiments, the first elongated or expandable bodies 720 act to stimulate thrombus formation and fibrosis in an aneurysm lumen or sac 722.

The first elongated bodies or coils may comprise a primary wire having a diameter of 0.00175-0.003 inches. This primary wire may be wound against itself to provide an overall or secondary diameter of the coil that is 0.010-0.040 inches in diameter. Furthermore, this secondary shape of the first elongated bodies or coils may be formed into tertiary shapes having a diameter of approximately 2-100 mm or 0.1 to 4 inches.

Standard nominal values for guidewire 40 diameters (and their associated coil sizes) are 0.014", 0.018", and 0.035"/0.038". FIG. 91 summarizes the minimum and maximum values for diameters of the second various catheter 173 (or guidewire shaft), first elongated body 720 (or coil), and second elongated body 721 (or pusher wire) for embodiments of first and second medical devices 1 & 700 accommodating these three guidewire platforms. FIG. 90 summarizes the minimum and maximum values for the lengths of these elements. FIGS. 87-89 detail the nominal dimensions, along with allowable and preferred ranges of dimensions, for these elements.

In various embodiments, the first elongated bodies or coils are not provided with a tertiary shape, but rather elongated straight, yet flexible first elongated bodies or coils that may have a length between about 10 cm and about 400 cm. The straight first elongated bodies or coils may be deployed within an aneurysm, within a detachable balloon, or the first elongated bodies or coils may extend into both the aneurysm and the detachable balloon. The straight flexible first elongated bodies or coils may be used with various balloons of any size and shape. In one aspect, the first elongated bodies or coils are formed into a secondary shape by the expanded detachable balloon. The balloon gives the first elongated bodies or coils the ideal secondary shape by constraining them inside the balloon.

Straight coils are desirable as they reduce friction during passage through the various catheter and/or delivery devices. The long straight first elongated bodies or coils also permit the use of only a single first elongated body or coil for each balloon. When treating aneurysms with a single detachable balloon and one first elongated body or coil, users have increased flexibility to reposition a balloon and a first elongated body or coil during treatment. The single detachable balloon and first elongated body or coil combination also reduces overall treatment times.

In various embodiments, the first elongated bodies or coils may be manufactured to include one or more distal loops. The loops may be deformed under tension for delivery through one or more catheters and return to their natural loop shape as they exit the catheter. The loops on the elongated straight first elongated bodies or coils also protect the back wall of an aneurysm 320 from spearing or puncturing that could occur when using a first elongated bodies or coils lacking loops. In various other embodiments, the first elongated bodies or coils may include 1, 2, 3, 4 or more than 4 end loops or may include no end loops. As the first elongated bodies or coils will remain within the desired location, the first elongated bodies or coils may be advanced and deployed by a second elongated body, pusher wire, or pusher catheter that is joined to or contacts the proximal end of the first elongated body or coil. Similarly, for embolization of a peripheral artery or vein, using a low friction straight first elongated bodies or coils with 0, 1, 2, 3, or 4 loops on the distal end enables the use of a single first elongated body or coil and makes it simple to plug the distal neck opening of the balloon with the first elongated body or coil, reducing the flow of blood through the balloon. A first elongated body or coil may be positioned such that one loop is positioned outside the detachable balloon, while another loop is positioned within the neck or in the central void of the detachable balloon.

In some methods, the operator can gently push the first loop out of the second catheter 174 to plug the distal neck opening of the balloon, pull the tip of the second catheter 174 back into the central void of the balloon, and then deploy the remainder of the first elongated body or coil within the balloon. At this point, the operator may release any remaining tension in the delivery system, acquire an angiogram to confirm complete occlusion. If the size or location of the detachable balloon or the first elongated body or coil is not appropriate then the first elongated body or coil can be removed or reposition, and the detachable balloon can be deflated and repositioned, removed or replaced, and the first elongated body or coil can be reinserted, or a new first elongated body or coil can be inserted. When the operator is satisfied with the placement of the detachable balloon and the first elongated body or coil, the operator may detach the first elongated body or coil and the expanded balloon and remove the first catheter 173 and the second elongated body 721.

In some methods, the operator can gently push the distal loops of the first elongated body or coil out of the second catheter 174 to frame the aneurysm sac 722, then push some of the straight portion of the first elongated body or coil into the aneurysm sac behind or adjacent to the expanded balloon, then pull the tip of the second catheter 174 back into the central void 115 of the balloon 10 and deploy the remainder of the first elongated body or coil within the balloon. At this point, the operator may release any remaining tension in the delivery system, acquire an angiogram to confirm complete occlusion. If the size or location of the detachable balloon or the first elongated body or coil is not appropriate then the first elongated body or coil can be removed or reposition, and the detachable balloon can be deflated and repositioned, removed or replaced, and the first elongated body or coil can be reinserted, or a new first elongated body or coil can be inserted. When the operator is satisfied with the placement of the detachable balloon and the first elongated body or coil, the operator may detach the first elongated body or coil and the expanded balloon and remove the first catheter 173 and the second elongated body 721.

In various embodiments, as shown in FIG. 93F, the first elongated bodies or coils 720 may be manufactured to include one or more distal loops 702 and one or more proximal loops. The loops may be deformed under tension for delivery through one or more catheters and return to their natural loop shape as they exit the catheter. The distal loop or loops 702 can be configured to present a flatter surface to the adjacent tissue or balloon wall 30 as the first elongated body or coil 720 as it is pushed forward, reducing the risk of wall puncture. The proximal loop or loops can be configured to present a shape that is more easily grasped by a snare catheter. For example, when placing a first elongated body or coil with both distal and proximal loops into the central void of detachable balloon expanded in a blood vessel, the distal loop or loops 702 can be placed in the vessel lumen distal to the expanded balloon 10 to fill at least a portion of the opening in the distal neck 140 of the balloon and the middle portion of the first elongated body or coil 720 can be placed in the central void 115 of the expanded detachable balloon. Then, the first catheter 173 can be detached from the proximal neck 130 of the expanded detachable balloon 10. Then the proximal loop or loops can be placed in the vessel lumen proximal to the expanded balloon 10. For embodiments, wherein a first elongated body or coil 720 is joined to a second elongated body 721, then the first elongated body or coil 720 can be detached from the second elongated body 721. In situations wherein it is determined, after detachment of the expanded detachable balloon 10 and the first elongated body or coil 720, that the placement of a detachable balloon 10 was undesirable, a snare catheter can be used to grasp the proximal loop or loops of the detached first elongated body or coil 720 and the first elongated body or coil 720 can be removed from the patient. Then, the snare catheter can be used to grasp the proximal neck 130 of the expanded, detached balloon 10 and the balloon 10 can be collapsed and removed from the patient by pulling it into a guide catheter or sheath.

In some embodiments, the detachable balloon 10 and single first elongated body or coil combination 720 may be used to fully occlude a wide-necked bifurcation aneurysm with a width of 12 mm and a height of less than 10 mm. In one aspect, one or more first elongated bodies or coils 720 may be provided in a kit. The kit may include first elongated bodies or coils 720 that range from approximately 10 cm to 400 cm. By way of example and not limitation, a single kit may include approximately 1-30 first elongated bodies or coils 720 having lengths of 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 cm.

When treating a patient using a detachable balloon and single first elongated body or coil, the length of the first elongated body or coil used may be determined by the desired coil packing density of an aneurysm, detachable balloon, or both. As used herein, the packing density refers to the percentage of the void defined by the aneurysm, detachable balloon, or both that is filled by the first elongated body or coil. In various embodiments, the packing density may be in a range from approximately 5% to 75% (e.g. 5%, 10%, 15%, 20%, 25%, 30%, 35%, 40%, 45%, 50%, 55%, 60%, 65%, 70%, or 75% packing density).

In some embodiments, a second medical device 700 comprises a first elongated or expandable body 720 configured for permanent implantation in a human patient joined to a second elongated body 721 configured to push or carry the first elongated or expandable body 720 into the lumen 163 of the second catheter 174 of the first medical device comprising a detachable balloon catheter 1 and pull or carry the first elongated or expandable body 720 from the lumen 163 of second catheter 174. The first elongated and second elongated bodies 720 & 721 are configured to pass through the lumen 163 of the second catheter 174 and into a human patient in an elongated form. In some embodiments, a second medical device 700 comprises an expandable body 720 configured for permanent implantation in a human patient joined to a second elongated body 721 configured to push or carry the expandable body 720 into the lumen 163 of the second catheter 174 and pull or carry the expandable body 720 from the lumen 163 of the second catheter 174. The expandable body 720 is configured to pass through the lumen 163 of the second catheter 174 and into a human patient in an elongated, constrained, compressed, or collapsed form.

In some embodiments, at least a portion of the first elongated or expandable body 720 is configured for implantation into the central void 115 or interior volume of the detachable balloon 10 of the first medical device 1. In all embodiments, the first elongated or expandable body 720 can be separated from the second elongated body 721, which can be removed from the lumen 163 of the second catheter 174 while the first or expandable elongated body 720 remains in place in the patient. In some embodiments, the second elongated body 720 can be a wire, coiled wire, catheter, or laser cut tube comprising nitinol. In some embodiments of a second medical device 700, wherein the second elongated body is a catheter or laser cut tube comprising nitinol, at least a portion of the first elongated body 720 is within the lumen of the catheter or laser cut tube comprising nitinol of the second elongated body 721.

Elongated bodies may be made from wire, polymer, and other flexible materials, and combinations therein. Elongated bodies are not generally formed from self-expanding materials and not generally formed in a manner that renders an elongated body self-expanding. Examples of elongated bodies include coils, metal coils, metallic coils, polymer coils, coils comprising metal and polymer, coiled wires, coiled metal wires, coiled metallic wires, coiled wires comprising metal and polymer, strands, polymer strands, metal strands, metallic strands, strands comprising polymer and metal, vascular coils, assemblies of wires, assemblies of metal wires, assemblies of metallic wires, assemblies of polymer strands, assemblies of wires or strands comprising metal and polymer, assemblies of coiled wires, assemblies of coiled metal wires, assemblies of coiled metallic wires, assemblies of coiled polymer strands, assemblies of coiled structures comprising metal and wire, assemblies of strands, assemblies of polymer strands, assemblies of metal strands, assemblies of metallic strands, and assemblies of strands comprising polymer and metal, assemblies of braided wires, assemblies of braided metal wires, assemblies of braided metallic wires, assemblies of braided wires comprising metal and polymer, assemblies of braided strands, assemblies of braided polymer strands, assemblies of braided strands comprising polymer and metal, assemblies of woven wires, assemblies of woven metal wires, assemblies of woven metallic wires, assemblies of woven wires comprising metal and polymer, assemblies of woven strands, assemblies of woven polymer strands, and assemblies of woven strands comprising polymer and metal, and combinations thereof.

Expandable bodies may be made from wire, polymer, and other flexible materials, and combinations therein. Expandable bodies are generally formed from self-expanding materials or generally formed in a manner that renders the expandable body 10 self-expanding. Examples of expandable bodies include self-expanding wires, nitinol wires, assemblies of wires, assemblies of metal wires, assemblies of metallic wires, assemblies of polymer strands, assemblies of wires or strands comprising metal and polymer, assemblies of coiled wires, assemblies of coiled metal wires, assemblies of coiled metallic wires, assemblies of coiled polymer strands, assemblies of coiled structures comprising metal and wire, assemblies of strands, assemblies of polymer strands, assemblies of metal strands, assemblies of metallic strands, and assemblies of strands comprising polymer and metal, assemblies of braided wires, assemblies of braided metal wires, assemblies of braided metallic wires, assemblies of braided wires comprising metal and polymer, assemblies of braided strands, assemblies of braided polymer strands, assemblies of braided strands comprising polymer and metal, assemblies of woven wires, assemblies of woven metal wires, assemblies of woven metallic wires, assemblies of woven wires comprising metal and polymer, assemblies of woven strands, assemblies of woven polymer strands, assemblies of woven strands comprising polymer and metal, balloons, and combinations thereof.

In some embodiments, the wires, strands, coils, coiled wires, assemblies of wires, assemblies of strands, assemblies of coils, assemblies of coiled wires, woven assemblies of wires, woven assemblies of strands, woven assemblies of coils, woven assemblies of coiled wires, braided assemblies of wires, braided assemblies of strands, braided assemblies of coils, braided assemblies of coiled wires, and combinations thereof, of expandable bodies are self-expanding. In some embodiments, the wires, strands, coils, coiled wires, assemblies of wires, assemblies of coils, assemblies of coiled wires, woven assemblies of wires, woven assemblies of coils, woven assemblies of coiled wires, braided assemblies of wires, braided assemblies of coils, braided assemblies of coiled wires and combinations thereof, of expandable bodies comprise nitinol.

In some embodiments, the first elongated or expandable body 10 of the second medical device 1 comprises a coiled wire, wherein the primary diameter of the coiled wire is 0.00175-0.003 inch in diameter, and the secondary diameter of the coiled wire is 0.010-0.050 inch in diameter. In some embodiments, the first elongated or expandable body 10 has a tertiary structure without pre-formed loops or shapes, is configured to form a straight or unformed tertiary shape when relaxed, or is configured as a straight vascular coil. In some embodiments, at least a portion of the first elongated or expandable body 10 has a helical, spherical, or complex tertiary structure. In some embodiments, at least a portion of the first elongated or expandable body 10 is configured to form a coiled, helical, or complex tertiary shape when relaxed. In some embodiments, the coiled wire is a vascular coil. In some embodiments, the distal portion of the first elongated or expandable body 10 comprises one loop of tertiary structure and the remainder of the first elongated or expandable body 10 comprises a tertiary structure without pre-formed loops or shapes when relaxed; or the distal portion of the first elongated or expandable body 10 comprises one loop of tertiary structure and the remainder of the first elongated or expandable body 10 comprises a tertiary structure configured to form a straight or unformed tertiary shape when relaxed. In some embodiments, the distal portion of the first elongated or expandable body 10 comprises two loops of tertiary structure and the remainder of the first elongated or expandable body 10 comprises a tertiary structure without pre-formed loops or shapes when relaxed, or the distal portion of the first elongated or expandable body 10 comprises two loops of tertiary structure and the remainder of the first elongated or expandable body 10 comprises a tertiary structure configured to form a straight or unformed tertiary shape, when relaxed. In some embodiments, the distal portion of the first elongated or expandable body 10 comprises three loops of tertiary structure and the remainder of the first elongated or expandable body 10 comprises a tertiary structure without pre-formed loops or shapes when relaxed, or the first elongated or expandable body 10 comprises three loops of tertiary structure and the remainder of the first elongated or the expandable body 10 comprises a tertiary structure configured to form a straight or unformed tertiary shape, when relaxed. In some embodiments, the distal portion of the first elongated or expandable body 10 comprises four or more loops of tertiary structure when relaxed and the remainder of the first elongated or expandable body 10 comprises a tertiary structure without preformed loops or shapes when relaxed, or the first elongated or expandable body 10 comprises four loops of tertiary structure and the remainder of the first elongated or the expandable body 10 comprises a tertiary structure configured to form a straight or unformed tertiary shape, when relaxed. The tertiary diameter of the looped, coiled, formed, or tertiary portion of the first elongated or expandable body 10 can be 2-100 mm. In some embodiments, the first elongated or expandable body 10 comprises platinum, iridium, nickel, tungsten or combinations thereof.

In some embodiments, the first elongated or expandable body 10 of the second medical device 1 is a wire with a primary diameter of 0.005-0.050 inch. In some embodiments, the first elongated or expandable body 10 is a wire without a secondary or tertiary diameter or shape. In some embodiments, the first elongated or expandable body 10 is a wire and without pre-formed loops or shapes. In some embodiments, the first elongated or expandable body 10 is a wire that is configured to form a straight or unformed tertiary shape when relaxed. In some embodiments, the first elongated or expandable body 10 is a straight vascular coil. In some embodiments, the first elongated or expandable body 10 is a wire and at least a portion of the first elongated or expandable body 10 has a helical, spherical, or complex tertiary structure. In some embodiments, the first elongated or expandable body 10 is a wire, has a portion of the first elongated or expandable body 10 has a helical, spherical, or complex tertiary structure, with the remainder of the first elongated or expandable body 10 comprises a tertiary structure without pre-formed loops or shapes, when relaxed. In some embodiments, the first elongated or expandable body 10 is a wire wherein the distal portion of the first elongated or expandable body 10 comprises one loop of tertiary structure and the remainder of the first elongated or expandable body comprises a tertiary structure configured to form a straight or unformed tertiary shape when relaxed, or the distal portion of the first elongated or expandable body comprises one loop of tertiary structure and the remainder of the first elongated or expandable body comprises a tertiary structure without pre-formed loops or shapes, when relaxed. In some embodiments, the first elongated or expandable body is a wire, wherein the distal portion of the first elongated or expandable body comprises two loops of tertiary structure and the remainder of the first elongated or expandable body comprises a tertiary structure without pre-formed loops or shapes when relaxed, or the distal portion of the first elongated or expandable body comprises two loops of tertiary structure and the remainder of the first elongated or expandable body comprises a tertiary structure configured to form a straight or unformed tertiary shape, when relaxed. In some embodiments, the first elongated or expandable body is a wire, wherein the distal portion of the first elongated or expandable body comprises three loops of tertiary structure and the remainder of the first elongated or expandable body comprises a tertiary structure without pre-formed loops or shapes when relaxed, or the distal portion of the first elongated or expandable body comprises three loops of tertiary structure and the remainder of the first elongated or expandable body comprises a tertiary structure configured to form a straight or unformed tertiary shape, when relaxed. In some embodiments, the first elongated or expandable body is a wire, wherein the distal portion of the first elongated or expandable body 10 comprises a tertiary structure configured to form a straight or unformed tertiary shape when relaxed, or the distal portion of the first elongated or expandable body 10 comprises one loop of tertiary structure and the remainder of the first elongated or expandable body 10 comprises a tertiary structure without pre-formed loops or shapes, when relaxed. In some embodiments, the first elongated or expandable body 10 is a wire, wherein the distal portion of the first elongated or expandable body 10 comprises two loops of tertiary structure and the remainder of the first elongated or expandable body 10 comprises a tertiary structure without pre-formed loops or shapes when relaxed, or the distal portion of the first elongated or expandable body 10 comprises two loops of tertiary structure and the remainder of the first elongated or expandable body 10 comprises a tertiary structure configured to form a straight or unformed tertiary shape, when relaxed. In some embodiments, the first elongated or expandable body 10 is a wire, wherein the distal portion of the first elongated or expandable body 10 comprises three loops of tertiary structure and the remainder of the first elongated or expandable body 10 comprises a tertiary structure without pre-formed loops or shapes when relaxed, or the distal portion of the first elongated or expandable body 10 comprises three loops of tertiary structure and the remainder of the first elongated or expandable body 10 comprises a tertiary structure configured to form a straight or unformed tertiary shape, when relaxed. In some embodiments, the first elongated or expandable body 10 is a wire, wherein the distal portion of the first elongated or expandable body 10 comprises four or more loops of tertiary structure, and the remainder of the first elongated or expandable body 10 comprises a tertiary structure without pre-formed loops or shapes when relaxed, or the distal portion of the first elongated or expandable body 10 comprises four loops of tertiary structure and the remainder of the first elongated or expandable body 10 comprises a tertiary structure configured to form a straight or unformed tertiary shape, when relaxed. In some embodiments, the first elongated or expandable body 10 is a wire and the tertiary diameter of the looped, coiled, or formed portion of the first elongated or expandable body 10 is 2-100 mm. In some embodiments, the first elongated or expandable body 10 is a wire comprising nitinol, a nitinol wire is plated or coated with platinum or gold, or a nitinol wire further with one or more radiopaque markers that are visible during fluoroscopy, including wherein the radiopaque marker comprises platinum, iridium, gold, tungsten, or combinations thereof, or is a radiopaque marker in the form of a ring or band around a portion of the wire.

In some embodiments, the second medical device 1 comprises a first elongated or expandable body 10 that is configured to be carried through the lumen 163 of the second catheter 174 of the detachable balloon catheter 1 by the catheter of the second medical device 700. In some embodiments, the catheter of the second medical device 700 comprises a radiopaque marker band 612 that is visible during fluoroscopy, including wherein the radiopaque marker comprises platinum, iridium, gold, tungsten, or combinations thereof.

In some embodiments, the first elongated body 720 of the second medical device 720 comprises a wire assembly, coiled wire assembly, braided wire assembly, woven wire assembly, or other expandable body 720. In some embodiments, the expandable body 720 of the second medical device 700 comprises a wire assembly, coiled wire assembly, braided wire assembly, woven wire assembly, or other expandable body 720. In some embodiments, the first expandable body 720 of the second medical device 700 comprises a self-expanding wire assembly, coiled wire assembly, braided wire assembly, woven wire assembly, or other expandable body 720. In some embodiments, the wire assembly, coiled wire assembly, braided wire assembly, or woven wire assembly expandable body 720 is configured to form into the shape of a generally cylindrical form when not in a compressed, collapsed, constrained, or elongated form. In some embodiments, the wire assembly, coiled wire assembly, braided wire assembly, or woven wire assembly expandable body 720 is configured to form into the shape of a generally spherical shape when not in a compressed, collapsed, constrained, or elongated form. In some embodiments, the wire assembly, coiled wire assembly, braided wire assembly, or woven wire assembly expandable body 720 is configured to form into a general shape and size with a largest diameter of 2-100 mm when not in a compressed, collapsed, constrained, or elongated form. In some embodiments, the expandable body 720 of the second medical device 700 comprises nitinol, a nitinol wire, or a nitinol wire that is plated or coated with platinum or gold. In some embodiments, the nitinol wire expandable body 720 further comprises one or more radiopaque markers that are visible during fluoroscopy, including radiopaque marker comprising platinum, iridium, gold, tungsten, or combinations thereof.

In some embodiments, the first elongated or expandable body 10 of the second medical device 1 comprises a polymer strand or a polymer strand plated or coated with platinum or gold. In some embodiments, the polymer strand portion of the first elongated or expandable body 10 of the second medical device 1 further comprises one or more radiopaque markers that are visible during fluoroscopy, including radiopaque marker comprised of platinum, iridium, gold, tungsten, or combinations thereof, and including radiopaque markers in the form of a ring or band around a portion of the polymer strand.

In some embodiments, the first elongated or expandable body 10 is 10-400 cm in length, 70-400 cm, or 10-70 cm in length. In some embodiments, the first elongated or expandable body 10 comprises a lubricious or hydrophilic layer or coating, a Serene™ coating sold by SurModics, Inc, or an Assist™ coating sold by BioInteractions Ltd. In some embodiments, the first elongated or expandable body 10 comprises a lubricious outer layer, a PTFE outer layer, a polyimide outer layer, or an outer layer comprising a PTFE and polyimide composite. In some embodiments, the second elongated body of the second medical device 1 comprises a lubricious or hydrophilic layer or coating, a Serene™ coating sold by SurModics, Inc, or an Assist™ coating sold by BioInteractions Ltd. In some embodiments, the second elongated body of the second medical device 1 comprises a PTFE outer layer, a polyimide outer layer, or an outer layer comprising a PTFE and polyimide composite. In some embodiments, the second elongated body of the second medical device 1 comprises visual or tactile markings that enable a user to determine the length of the first elongated or expandable body 10 that has been pushed distal to the distal tip of the second catheter 174.

In some embodiments, the first elongated or expandable body 10 of the second medical device 1 and the second elongated body of the second medical device 1 are configured to separate by mechanical means. In some embodiments, the first elongated or expandable body 10 of the second medical device 1 and the second elongated body of the second medical device 1 are configured to separate by electrolysis or corrosion. In some embodiments, the first elongated or expandable body 10 of the second medical device 1 and the second elongated body of the second medical device 1 are configured to separate in a region between the first elongated or expandable body 10 and second elongated body that is sensitive to electrolysis or corrosion, or are configured to separate in a region between the first elongated or expandable body 10 and second elongated body comprising stainless steel. In some embodiments, the second elongated body of the second medical device 1 is configured to enable the passage of an electrical current from a proximal portion of the second elongated body to the region that is sensitive to electrolysis or corrosion. In some embodiments, at least a portion of the second elongated body of the second medical device 1 is configured to enable the passage of a direct electrical current. In some embodiments, at least a portion of the second elongated body of the second medical device 1 is covered with a substance that insulates it from electrical conduction. In some embodiments, at least a portion of the segment sensitive to electrolysis or corrosion, or configured for dissolution by electrolysis, is not covered with a substance that insulates it from electrical conduction. In some embodiments, the first elongated or expandable body 10 of the second medical device 1 and the second elongated body of the second medical device 1 are configured to separate by an electrothermal process. In some embodiments, the separation occurs in a region between the first elongated or expandable body 10 and the second elongated body can melt with heating. In some embodiments, the second medical device 1 is configured to enable the passage of an electrical current from a proximal portion of the second elongated body to a resistive heating element on or near the region between the first elongated or expandable body 10 and the second elongated body that can melt with heating. In some embodiments, at least a portion of the second elongated body of the second medical device 1 is covered with a substance that insulates it from electrical conduction. In some embodiments, the first elongated or expandable body 10 of the second medical device 1 and the second elongated body of the second medical device 1 are not joined and the second elongated body of the second medical device 1 is configured to push the first elongated or expandable body 10 of the second medical device 1 through the lumen of the second catheter 174 of the first medical device 1. In some embodiments, the second elongated body 721 of the second medical device 700 is configured to expel the first elongated or expandable body 720 of the second medical device 700 from the distal end of the lumen 163 of the second catheter 174 of the first medical device 1. In some embodiments, the second elongated body 721 of the second medical device 700 can be removed from the lumen 163 of the second catheter 174 of the first medical device 1 after expulsion of the first elongated or expandable body 720 of the second medical device 700 from the distal end of the lumen 163 of the second catheter 174 of the first medical device 1.

In some examples, beads, balls, microspheres, bioresorbable materials, adhesives, glues, solidifying polymers, solidifying foams, or combinations thereof are passed from the proximal end of the second catheter 174, through the lumen 163 of the second catheter 174, and into the central void 115 or interior volume of the detachable balloon 10 of a detachable balloon catheter 1 to help maintain the expanded size and shape of the detached balloon 10.

Guidewires

The lumen 163 of the second catheter 174 can be configured to accept guidewires 40 with a diameter of 0.010-0.038 inch, including guidewires with a diameter of 0.010, 0.011, 0.012, 0.013, 0.014, 0.015, 0.016, 0.017, 0.018, 0.033, 0.034, 0.035, 0.036, 0.037, or 0.038 inch. The lumen 163 of the second catheter 174 can be configured to accept guidewires 40 with a length of 50-500 cm or 200-400 cm.

Systems Comprising a First Medical Device and One or More Second Medical Devices In some embodiments, the first elongated or expandable body 10 of the second medical device 1 comprises a wire assembly, coiled wire assembly, braided wire assembly, woven wire assembly, or other expandable body. 10. In some embodiments, the first elongated or expandable body 10 of the second medical device 1 comprises a self-expanding wire assembly, coiled wire assembly, braided wire assembly, woven wire assembly, or other expandable body. 10. In some embodiments, the wire assembly, coiled wire assembly, braided wire assembly, or woven wire assembly expandable body 10 is configured to form into the general shape and size of the expanded detachable balloon of the first medical device 1 when not in a compressed, collapsed, constrained, or elongated form.

In some embodiments, the second elongated body 721 of the second medical device 700 comprises visual or tactile markings that enable a user to determine the length of the first elongated or expandable body 720 that has been pushed distal to the distal tip of the second catheter 174. In some embodiments, the hub 178 of the second catheter 174 of the detachable balloon catheter 1 is configured to allow for the insertion of the distal end of a first elongated body or an expandable body 720 into the lumen 163 of the second catheter 174 of the detachable balloon catheter 1, and also configured to be joined with the distal end of a carrier structure or carrier that houses, constrains, or otherwise engages the first elongated or expandable body 720 and at least a portion of the second elongated body 721. This helps a physician use long or very long coils, up to 400 cm or more in length by providing a longer rigid pathway to guide the coil or first elongated body 720 into the patient. In one example, the second catheter 174 of the detachable balloon catheter 1 is 130 cm in length and the carrier structure is 300 cm in length. If the hub 178 of the second catheter 174 of the detachable balloon catheter 1 is joined to the carrier, then a 400 cm first elongated or expandable body 720 can be used, with a second elongated body 721 that is 430 cm long. Once the distal end of the second elongated body 721 is pushed into the proximal end of the second catheter 174 of the detachable balloon catheter 1, then the carrier and the second catheter 174 of the detachable balloon catheter 1 can be separated, the second elongated body 721 can be removed from the carrier and used to push the remainder of the first elongated or expandable body 720 out of the second catheter 174 of the detachable balloon catheter 1. In some embodiments, the carrier is configured into a coiled shape. In some embodiments, a portion of the first or expandable elongated body 720 of the second medical device 1 is configured to contact the interior surface of the expanded detachable balloon 10 of the first medical device 1. In some embodiments, the largest overall diameter or tertiary diameter of the first elongated or expandable body 720 of the second medical device 700 is in a range from 5% smaller than the largest diameter of the expanded detachable balloon 10 of the first medical device 1 to 20% larger than the largest diameter of the expanded detachable balloon 10 of the first medical device 1. In some embodiments, the largest overall or tertiary diameter of the first elongated or expandable body 720 of the second medical device 700 is 1, 2, 3, 4, 5, 6, 7, 8, 9, or 10 mm larger than the largest diameter of the expanded detachable balloon 10 of the first medical device 1. In some embodiments, the volume of the one or more first elongated or expandable bodies of the second medical device 1 would fill 5-75% of the volume of the central void 115 of the expanded detachable balloon 10.

Kits Comprising a First Medical Device and One or More Second Medical Devices

Aspects and embodiments related to kits incorporating first and second medical devices 1 & 700 as disclosed herein. Such kits comprise at least one first medical device 1 and one or more second medical devices 700, configured for use with the first medical device 1.

In one example, a kit may contain one first medical device 1 configured for use with a 0.014" guidewire 40 with a detachable polymer balloon 12 that is 6 mm in diameter and 10 mm in length and a second medical device 700 wherein the first elongated body 720 is a coiled wire or coil with a secondary diameter of 0.014" that is configured without a tertiary shape or structure and a length that, when placed entirely within the central void 115 of the expanded detachable balloon 10 of the first medical device 1 results in a filling density of 25%.

Such kits may further comprise additional medical devices. In one embodiment, a kit may comprise a first medical device 1, a second medical device 700, and a guidewire 40 that is configured for use with the first medical device 1, including configured for passage through the lumen 163 of the second catheter 174 of the first medical device 1 and with a length that is longer than the length of the second catheter 174 of the first medical device 1.

In some embodiments, a kit may comprise a first medical device 1, a second medical device 700, and a detachment controller 406 that is configured to i) cause separation of the first catheter 173 and the detachable balloon 10 of the first medical device 1, ii) cause separation of the first elongated body or expandable body 720 from the second elongated body 721, or iii) cause separation of the first catheter 173 and the detachable balloon 10 of the first medical device 1 and also to cause separation of the first elongated body or expandable body 720 from the second elongated body 721. In some embodiments, a kit may further comprise one or more cables 407 or connectors that make an electrical connection between i) the first medical device 1 and a controller 406, ii) the second medical device 700 and a controller 406, or iii) the first medical device 1 and a controller 406, and the second medical device 700 and a controller 406.

Examples of Device Use

A sequence of steps is associated with the deployment of the detachable balloon in a saccular aneurysm. Initially, a guidewire may be placed so that its distal tip lies within the lumen of the aneurysm sac. Next, the first medical device comprising a pleated and folded detachable balloon may be advanced over the guidewire and through the neck or mouth of the aneurysm. After the pleated and folded detachable balloon has been placed in the lumen of the aneurysm sac, radiographic or X-ray contrast agent may be injected into the parent artery during fluoroscopy to evaluate the position of the pleated and folded detachable balloon. Once proper positioning of the detachable balloon in the lumen of the aneurysm sac has been achieved and confirmed, then the detachable balloon is inflated or expanded. A fluid medium source, such as syringe, inflation device (e.g. Endoflator® by Karl Storz, not shown) or, pump is connected to the inflation port on the hub of the first catheter and a fluid medium is injected into the central void of the detachable balloon, which results in expansion of the detachable balloon until it fills at least a portion of the lumen of the aneurysm sac. After expansion, the first catheter is pulled back in the aneurysm lumen to draw the expanded detachable balloon towards the neck of the aneurysm. After the expanded balloon has been positioned in the neck of the aneurysm, radiographic or X-ray contrast agent may be injected into the parent artery during fluoroscopy to evaluate the position of the expanded balloon and to confirm aneurysm neck occlusion. The second catheter may then be advanced into the lumen of the aneurysm sac, the guidewire removed, and one or more first elongated bodies or coils may be fed through the lumen of the second catheter (second lumen) into the lumen of the aneurysm sac. The first elongated bodies or coils exert a continuous force on the detachable balloon which provides a tight seal between the expanded balloon and the aneurysm neck. After placement of elongated bodies or coils into the lumen of the aneurysm sac, radiographic or X-ray contrast agent may be injected into the parent artery during fluoroscopy to evaluate the position of the first elongated bodies or coils and to confirm aneurysm neck occlusion. The second catheter may then be retracted into the central void of the detachable balloon and one or more first elongated bodies or coils may be fed through the lumen of the second catheter (second lumen) into the central void of the expanded detachable balloon. The first elongated bodies or coils exert an outward force on the inner wall of the expanded detachable balloon to keep the expanded detachable balloon expanded; maintain contact between the outer wall of the detachable balloon and the inner wall of the aneurysm; and prevent collapse, compression, or compaction of the detachable balloon due to external compressive forces, including external compressive forces from portions of the first elongated bodies or coils that are present in the lumen of the aneurysm sac. The first elongated bodies or coils placed within the lumen of the aneurysm sac and central void or interior volume of the detachable balloon may either be separate or the same. In some embodiments, the same first elongated bodies or coils are placed in both locations, and the distal portion of the first elongated body or coil is first placed in the lumen of the aneurysm sac and then the second catheter is retracted to allow the proximal portion of the first elongated body or coil to be placed in the central void of the detachable balloon. Finally, the first catheter is detached from the detachable balloon and removed (along with the second catheter), leaving the detachable balloon and the elongated bodies or coils within the lumen of the aneurysm sac and the central void of the detachable balloon to occlude the neck and sac the aneurysm.

A sequence of steps is associated with the deployment of a detachable balloon in an artery, vein, or biological conduit. Initially, a guidewire may be placed so that its distal tip lies within the lumen of the artery, vein, or biological conduit. Next, the first medical device comprising a pleated and folded detachable balloon may be advanced over the guidewire and into a segment of the artery, vein, or biological conduit that is selected for occlusion. After the pleated and folded detachable balloon has been placed in the lumen of the selected segment of artery, vein, or biological conduit, radiographic or X-ray contrast agent may be injected into the artery, vein, or biological conduit during fluoroscopy to evaluate the position of the pleated and folded detachable balloon. Once proper positioning of the detachable balloon in the lumen of the artery, vein, or biological conduit has been achieved and confirmed, then the detachable balloon is inflated or expanded. A fluid medium source, such as syringe, inflation device (e.g. Endoflator® by Karl Storz, not shown) or, pump is connected to the inflation port on the hub of the first catheter and a fluid medium is injected into the central void of the detachable balloon, which results in expansion of the detachable balloon until it fills at least a portion of the lumen of the artery, vein, or biological conduit. After the expanded balloon has been positioned in the lumen of the artery, vein, or biological conduit, radiographic or X-ray contrast agent may be injected into the lumen of the artery, vein, or biological conduit during fluoroscopy to evaluate the position of the expanded balloon and to confirm artery, vein, or biological conduit occlusion. The guidewire may be removed. Optionally, a solution comprising a drug or therapeutic agent, a solution or suspension comprising embolic particles, or combinations thereof injected into the lumen of the target segment of artery, vein, or biological conduit. The distal end of a first elongated body or coil may be fed through the lumen of the second catheter (second lumen) into the lumen of the artery, vein, or biological conduit adjacent and distal to the expanded detachable balloon. The second catheter may then be retracted into the central void of the detachable balloon and the remained of the first elongated body or coil may be fed through the lumen of the second catheter (second lumen) into the central void of the expanded detachable balloon. Optionally, additional first elongated bodies or coils may be fed through the lumen of the second catheter (second lumen) into the central void of the expanded detachable balloon. The first elongated bodies or coils exert an outward force on the inner wall of the expanded detachable balloon to keep the expanded detachable balloon expanded; maintain contact between the outer wall of the detachable balloon and the inner wall of the artery, vein, or biological conduit; and prevent collapse, compression, or compaction of the detachable balloon due to external compressive forces, including external compressive forces from portions of the first elongated bodies or coils that are present in the lumen of the artery, vein, or biological conduit. The first elongated bodies or coils placed within the lumen of the artery, vein, or biological conduit and central void or interior volume of the detachable balloon may either be separate or the same. Finally, the first catheter (along with the second catheter) is detached from the detachable balloon leaving the detachable balloon and the elongated bodies or coils within the lumen of the artery, vein, or biological conduit and the central void of the detachable balloon to occlude the artery, vein, or biological conduit.

After access into the left atrium, a sequence of steps is associated with the deployment of the detachable balloon in a left atrial appendage (LAA). Initially, a guidewire may be placed so that its distal tip lies within the lumen of the LAA. Next, the first medical device comprising a pleated and folded detachable balloon may be advanced over the guidewire and through the neck or mouth of the LAA. After the pleated and folded detachable balloon has been placed in the lumen of the LAA sac, radiographic or X-ray contrast agent may be injected into the parent artery during fluoroscopy to evaluate the position of the pleated and folded detachable balloon. Once proper positioning of the detachable balloon in the lumen of the LAA sac has been achieved and confirmed, then the third catheter is retracted, leading to expansion of the retention structure and engagement of the arms and hooks of the retention structure in the wall of the LAA. A gentle tug on the first catheter confirms adequate wall engagement. The detachable balloon is inflated or expanded. A fluid medium source, such as syringe, inflation device (e.g. Endoflator® by Karl Storz, not shown) or, pump is connected to the inflation port on the hub of the first catheter and a fluid medium is injected into the central void of the detachable balloon, which results in expansion of the detachable balloon until it fills at least a portion of the lumen of the LAA sac. After expansion of the detachable balloon, radiographic or X-ray contrast agent may be injected into the left atrium during fluoroscopy to evaluate the position of the expanded balloon and to confirm LAA occlusion. The second catheter may be retracted into the central void of the expanded detachable balloon and one or more first elongated bodies or coils may be fed through the lumen of the second catheter (second lumen) into the central void of the expanded detachable balloon. The first elongated bodies or coils exert an outward force on the inner wall of the expanded detachable balloon to keep the expanded detachable balloon expanded; maintain contact between the outer wall of the detachable balloon and the inner wall of the LAA; and prevent collapse, compression, or compaction of the detachable balloon due to external compressive forces, including external compressive forces. Finally, the first catheter is detached from the detachable balloon and removed (along with the second catheter and third catheter), leaving the detachable balloon, the retention structure, and the elongated bodies or coils within the central void of the detachable balloon to occlude the neck and sac of the LAA.

After access into the left atrium, a sequence of steps is associated with the deployment of the detachable balloon in a LAA. Initially, a guidewire may be placed so that its distal tip lies within the lumen of the LAA sac. Next, the first medical device comprising a pleated and folded detachable balloon may be advanced over the guidewire into the lumen of the LAA and positioned such that the proximal end of the pleated and folded detachable balloon is in the neck of the LAA. After positioning of the pleated and folded detachable balloon, radiographic or X-ray contrast agent may be injected into the parent artery during fluoroscopy to evaluate the position of the pleated and folded detachable balloon. Once proper positioning of the detachable balloon in the lumen of the LAA has been achieved and confirmed, then the detachable balloon is inflated or expanded. A fluid medium source, such as syringe, inflation device (e.g. Endoflator® by Karl Storz, not shown) or, pump is connected to the inflation port on the hub of the first catheter and a fluid medium is injected into the central void of the detachable balloon, which results in expansion of the detachable balloon until it occludes the neck of the LAA and fills at least a portion of the lumen of the LAA sac. After the expanded balloon has been positioned in the neck of the LAA, radiographic or X-ray contrast agent may be injected into the parent artery during fluoroscopy to evaluate the position of the expanded balloon and to confirm LAA neck occlusion. The second catheter may then be advanced into the lumen of the LAA sac, the guidewire removed, and one or more first elongated bodies or coils may be fed through the lumen of the second catheter (second lumen) into the lumen of the LAA sac. The first elongated bodies or coils exert a continuous force on the detachable balloon which provides a tight seal between the expanded balloon and the LAA neck. After placement of elongated bodies or coils into the lumen of the LAA sac, radiographic or X-ray contrast agent may be injected into the parent artery during fluoroscopy to evaluate the position of the first elongated bodies or coils and to confirm LAA neck occlusion. The second catheter may then be retracted into the central void of the detachable balloon and one or more first elongated bodies or coils may be fed through the lumen of the second catheter (second lumen) into the central void of the expanded detachable balloon. The first elongated bodies or coils exert an outward force on the inner wall of the expanded detachable balloon to keep the expanded detachable balloon expanded; maintain contact between the outer wall of the detachable balloon and the inner wall of the LAA; and prevent collapse, compression, or compaction of the detachable balloon due to external compressive forces, including external compressive forces from portions of the first elongated bodies or coils that are present in the lumen of the LAA sac. The first elongated bodies or coils placed within the lumen of the LAA sac and central void or interior volume of the detachable balloon may either be separate or the same. In some embodiments, the same first elongated bodies or coils are placed in both locations, and the distal portion of the first elongated body or coil is first placed in the lumen of the LAA sac and then the second catheter is retracted to allow the proximal portion of the first elongated body or coil to be placed in the central void of the detachable balloon. Finally, the first catheter is detached from the detachable balloon and removed (along with the second catheter), leaving the detachable balloon and the elongated bodies or coils within the lumen of the LAA sac and the central void of the detachable balloon to occlude the neck and sac the LAA.

Various figures, drawings, and images related to various aspects of the use, deployment, assembly, and experimental testing of various embodiments of the devices, systems and methods disclosed herein are shown in FIGS. 104-129. The figures relate to Examples 1-26 as described more fully below.

Examples of Bench and In Vivo Use

Examples 1, 6, and 11 demonstrate the treatment of a canine vein pouch terminal bifurcation aneurysm with a metal balloon and coils. Animal 15C035 was treated in Study GNA1504W. The effect of the treatment was evaluated by angiography and histology.

A surgical procedure was performed to create a carotid artery bifurcation in the right neck and a single venous pouch terminal bifurcation aneurysm was created using a segment of external jugular vein. Following creation of the aneurysm, angiography was used to assess parent vessel and aneurysm size, shape, patency, and blood flow. Parent vessel diameter and aneurysm size (including neck diameter and aneurysm width, height, and depth) were determined using QVA on the day of aneurysm creation.

The terminal carotid artery bifurcation aneurysm in Animal 15C035 was treated with an 8 mm×6 mm metal balloon Ballstent Microcatheter (gold body, stainless steel and gold proximal neck and gold distal neck). After expansion of the balloon, four Barricade coils (Blockade Medical) were placed through the lumen of the second catheter of the Ballstent Microcatheter, and into the dome of the aneurysm behind the expanded balloon. The Barricade coils were detached by electrolysis using a standard Barricade Detachment Box and Handheld Detachment Cable (Blockade Medical). After the placement of the Barricade coils, the expanded balloon was detached from the first catheter by electrolysis using a modified Barricade Detachment Box with a duty cycle of 3 minutes and a modified Barricade Handheld Detachment Cable adapted to connect with the proximal hub of the Ballstent Microcatheter. Immediately after treatment, the interventionalist estimated that the aneurysm was 95% occluded. Terminal angiography for Animal 15C035 was performed 28 days after treatment. Angiography was used to visually assess % aneurysm occlusion, aneurysm size (including neck diameter and aneurysm width, height, and depth), parent vessel patency and diameter, and protrusion of the balloon or Barricade coils into the parent vessels. To assess parent vessel diameter and aneurysm size, QVA was performed. On the day of termination, Animal 15C035 was subjected to limited necropsy. The right neck aneurysm tissues and the adjacent vessel segments were collected, inclusive of the Test Article. On terminal follow up, the interventionalist estimated that the aneurysm was 95-100% occluded.

The aneurysm site and reference vessels were trimmed and processed in paraffin. The remaining explants were processed and embedded in Spurr resin. The resulting blocks were then sectioned to include three sequential in-aneurysm levels. Two slides were generated at each level in each aneurysm and in the reference artery segments and stained with hematoxylin and eosin (H&E) and elastin trichrome (ET). All resulting slides were evaluated for aneurysm occlusion, parent vessel patency, endothelialization of the implanted balloon and coils, tissue reaction and inflammatory reaction around the implanted balloon and coils, and aneurysm sac healing. Histologic analysis showed advanced to complete coverage of the balloon by endothelialized neointima. The neointima was generally fully mature and fibromuscular, with no residual fibrin. There was complete aneurysm neck occlusion (100% occlusion).

Examples 2, 5, and 12B demonstrate the treatment of a canine vein pouch sidewall aneurysm with a metal balloon and coils. Animal 15C036 was treated in Study GNA1504W. The effect of the treatment was evaluated by angiography and histology.

A surgical procedure was performed to create a carotid artery wide neck sidewall aneurysm on the left carotid artery using a segment of external jugular vein. Following creation of the aneurysm, angiography was used to assess parent vessel and aneurysm size, shape, patency, and blood flow. Parent vessel diameter and aneurysm size (including neck diameter and aneurysm width, height, and depth) were determined using QVA on the day of aneurysm creation.

The left carotid artery sidewall aneurysm in Animal 15C036 was treated with a 6 mm×4.5 mm metal balloon Ballstent Microcatheter (gold body, stainless steel and gold proximal neck and gold distal neck). After expansion of the balloon the second catheter of the Ballstent Microcatheter was advanced into the aneurysm sac while the expanded balloon and first catheter remained fixed in position. Four Barricade coils (Blockade Medical) were placed through the lumen of the second catheter of the Ballstent Microcatheter and into the dome of the aneurysm behind the expanded balloon. The Barricade coils were detached by electrolysis using a standard Barricade Detachment Box and Handheld Detachment Cable (Blockade Medical). After the placement of the Barricade coils, the expanded balloon was detached from the first catheter by electrolysis using a modified Barricade Detachment Box with a duty cycle of 3 minutes and a modified Barricade Handheld Detachment Cable adapted to connect with the proximal hub of the Ballstent Microcatheter. Immediately after treatment, the interventionalist estimated that the aneurysm was 95% occluded.

Interim and terminal angiography for Animal 15C036 was performed on Day 36 and Day 63, respectively. Angiography was used to visually assess % aneurysm occlusion, aneurysm size (including width, height, depth and neck), parent vessel patency and diameter, and protrusion of the balloon or Barricade coils into the parent vessel prior to termination. To assess parent vessel diameter and aneurysm size, QVA was performed. On the day of termination, Animal 15C036 was subjected to limited necropsy. The left neck aneurysm tissues and the adjacent vessel segments were collected, inclusive of Test Articles. On terminal follow up, the interventionalist estimated that the aneurysm was 100% occluded.

The aneurysm site and reference vessels were trimmed and processed in paraffin. The remaining explant was processed and embedded in Spurr resin. The resulting blocks were then sectioned to include three sequential in-aneurysm levels. Two slides were generated at each level in each aneurysm and in the reference artery segments and stained with H&E and ET. All resulting slides were evaluated for aneurysm occlusion, parent vessel patency, endothelialization of the implanted balloon and coils, tissue reaction and inflammatory reaction around the implanted balloon and coils, and aneurysm sac healing. Histologic analysis showed complete coverage of the balloon by endothelialized neointima. The neointima was fully mature and fibromuscular, with no residual fibrin. There was complete aneurysm neck occlusion (100% occlusion).

Example 3 demonstrates the treatment of a canine vein pouch complex bifurcation aneurysm with a metal balloon and coils. Animal 15C026 was treated in Study GNA1502W. The effect of the treatment was evaluated by angiography.

A surgical procedure was performed to create a carotid artery bifurcation in the right neck, followed by creation of a complex bifurcation aneurysm using a segment of external jugular vein. Following creation of the aneurysm, angiography was used to assess parent vessel and aneurysm size, shape, patency, and blood flow. Parent vessel diameter and aneurysm size (including neck diameter and aneurysm width, height, and depth) were determined using quantitative vascular analysis (QVA) on the day of aneurysm creation.

The complex bifurcation carotid artery bifurcation aneurysm in Animal 15C026 was treated with an 8 mm×6 mm metal balloon Ballstent Microcatheter (gold body, stainless steel and gold proximal neck and gold distal neck). After expansion of the balloon the second catheter of the Ballstent Microcatheter was advanced into the aneurysm sac while the expanded balloon and first catheter remained fixed in position. The 0.014" guidewire was removed from the second catheter and seventeen Barricade coils (Blockade Medical) were then placed through the lumen of the second catheter and into the dome of the aneurysm behind the expanded balloon. The Barricade coils were detached by electrolysis using a standard Barricade Detachment Box and Handheld Detachment Cable (Blockade Medical). After the placement of the Barricade coils, the expanded balloon was detached from the first catheter by electrolysis using a modified Barricade Detachment Box with a duty cycle of 3 minutes and a modified Barricade Handheld Detachment Cable adapted to connect with the proximal hub of the Ballstent Microcatheter. Immediately after treatment, the interventionalist estimated that the aneurysm was 75% occluded.

Terminal angiography for Animal 15C026 was performed on Day 35. Angiography was used to visually assess % aneurysm occlusion, aneurysm size (including width, height, depth and neck), parent vessel patency and diameter, and protrusion of the balloon or Barricade coils into the parent vessel prior to termination. To assess parent vessel diameter and aneurysm size, QVA was performed. On the day of termination, Animal 15C026 was subjected to limited necropsy. The right neck aneurysm tissues and the adjacent vessel segments were collected, inclusive of Test Articles. On terminal follow up, the interventionalist estimated that the aneurysm was 100% occluded.

Example 4 demonstrates the treatment of a canine vein pouch complex bifurcation aneurysm with a metal balloon and coils. Animal 15C027 was treated in Study GNA1502W. The effect of the treatment was evaluated by angiography.

A surgical procedure was performed to create a carotid artery bifurcation in the right neck, followed by creation of a complex bifurcation aneurysm using a segment of external jugular vein. Following creation of the aneurysm, angiography was used to assess parent vessel and aneurysm size, shape, patency, and blood flow. Parent vessel diameter and aneurysm size (including neck diameter and aneurysm width, height, and depth) were determined using QVA on the day of aneurysm creation.

The complex bifurcation carotid artery bifurcation aneurysm in Animal 15C027 was treated with an 8 mm×6 mm metal balloon Ballstent Microcatheter (gold body, stainless steel and gold proximal neck and gold distal neck). After expansion of the balloon, the tip of the second catheter was advanced forward into the aneurysm sac while the expanded balloon and first catheter remained fixed in position, and ten Barricade coils (Blockade Medical) were placed through the lumen of the second catheter of the Ballstent Microcatheter and into the dome of the aneurysm behind the expanded balloon. The Barricade coils were detached by electrolysis using a standard Barricade Detachment Box and Handheld Detachment Cable (Blockade Medical). After the placement of the Barricade Coils, the expanded balloon was detached from the first catheter by electrolysis using a modified Barricade Detachment Box with a duty cycle of 3 minutes and a modified Barricade Handheld Detachment Cable adapted to connect with the proximal hub of the Ballstent Microcatheter. Immediately after treatment, the interventionalist estimated that the aneurysm was 80% occluded.

Interim and terminal angiography for Animal 15C027 was performed on Day 35. Angiography was used to visually assess % aneurysm occlusion, aneurysm size (including width, height, depth and neck), parent vessel patency and diameter, and protrusion of the balloon, Metactive Accessory coils, or Barricade coils into the parent vessel prior to termination. To assess parent vessel diameter and aneurysm size, QVA was performed. On the day of termination, Animal 15C027 was subjected to limited necropsy. The right neck aneurysm tissues and the adjacent vessel segments were collected, inclusive of Test Articles. On terminal follow up, the interventionalist estimated that the aneurysm was 100% occluded.

Example 7 demonstrates the treatment of a canine vein pouch sidewall aneurysm with a polymer balloon and coils. Animal 17C013 was treated in Study GNA1802N. The effect of the treatment was evaluated by angiography.

A surgical procedure was performed to create a carotid artery wide neck sidewall aneurysm on the left carotid artery using a segment of external jugular vein. Following creation of the aneurysm, angiography was used to assess parent vessel and aneurysm size, shape, patency, and blood flow. Parent vessel diameter and aneurysm size (including neck diameter and aneurysm width, height, and depth) were determined using QVA on the day of aneurysm creation.

The left carotid artery sidewall aneurysm in 17C013 was treated with a 6 mm×4.5 mm polymer balloon Ballstent Microcatheter. After expansion of the balloon, the tip of the second catheter was advanced forward into the aneurysm sac. The distal portion of one Blockade Barricade coil (50 cm long straight coil with one 4 mm pre-formed loop on the distal end) was placed through the lumen of the second catheter of the Ballstent Microcatheter and into the aneurysm sac behind the expanded balloon. Then, the tip of the second catheter was pulled back into the central void of the expanded balloon and the remainder of the coil was placed in the central void of the expanded balloon.

Example 8 demonstrates the treatment of a canine vein pouch terminal bifurcation aneurysm with a metal balloon and coils. A patent aneurysm neck segment that remained after the initial treatment was treated with an additional coil. Animal 15C033 was treated in Study GNA1504W. The effect of the treatment was evaluated by angiography.

A surgical procedure was performed to create a carotid artery bifurcation in the right neck and then a single venous pouch terminal bifurcation aneurysm was created using a segment of external jugular vein. Following creation of the aneurysm, angiography was used to assess parent vessel and aneurysm size, shape, patency, and blood flow. Parent vessel diameter and aneurysm size (including neck diameter and aneurysm width, height, and depth) were determined using QVA on the day of aneurysm creation.

The terminal carotid artery bifurcation aneurysm in Animal 15C033 was treated with an 8 mm×6 mm metal balloon Ballstent Microcatheter (gold body, stainless steel and gold proximal neck and gold distal neck). After expansion of the balloon, one Metactive Medical nitinol coil and three Barricade coils (Blockade Medical) were then placed through the lumen of the second catheter of the Ballstent Microcatheter, and into the dome of the aneurysm behind the expanded balloon. The Metactive nitinol coil was pushed out of an Accessory Coil Delivery Catheter advanced into the aneurysm sac using a pusher wire. The Barricade coils were detached by electrolysis using a standard Barricade Detachment Box and Handheld Detachment Cable (Blockade Medical). After the placement of the Metactive and Barricade coils, the expanded balloon was detached from the first catheter by electrolysis using a modified Barricade Detachment Box with a duty cycle of 3 minutes and a modified Barricade Handheld Detachment Cable adapted to connect with the proximal hub of the Ballstent Microcatheter. After detachment of the expanded balloon, an assembly of the first and second catheters was removed from the animal, the second catheter was removed from first catheter, reinserted into the animal, and advanced over a 0.014" guidewire into a residual aneurysm neck segment adjacent to the expanded balloon. A fourth Barricade coil was placed into the residual aneurysm neck segment and detached in the manner described above. Immediately after treatment, the interventionalist estimated that the aneurysm was 95% occluded.

Terminal angiography for Animal 15C033 was performed on Day 29. Angiography was used to visually assess % aneurysm occlusion, aneurysm size (including neck diameter and aneurysm width, height, and depth), parent vessel patency and diameter, and protrusion of the balloon or Barricade coils into the parent vessels. To assess parent vessel diameter and aneurysm size, QVA was performed. On the day of termination, Animal 15C033 was subjected to limited necropsy. The right neck aneurysm tissues and the adjacent vessel segments were collected, inclusive of Test Articles. On terminal follow up, the interventionalist estimated that the aneurysm was 95-100% occluded.

Example 9 demonstrates the treatment of a canine vein pouch terminal bifurcation aneurysm with a metal balloon only. Animal 15C005 was treated in Study GNA1502W. The effect of the treatment was evaluated by angiography.

A surgical procedure was performed to create a carotid artery bifurcation in the right neck and then a single venous pouch terminal bifurcation aneurysm was created using a segment of external jugular vein. Following creation of the aneurysm, angiography was used to assess parent vessel and aneurysm size, shape, patency, and blood flow. Parent vessel diameter and aneurysm size (including neck diameter and aneurysm width, height, and depth) were determined using QVA on the day of aneurysm creation.

The terminal carotid artery bifurcation aneurysm in Animal 15C005 was treated with an 8 mm×6 mm metal balloon Ballstent Microcatheter (gold body, stainless steel and gold proximal neck and gold distal neck). The expanded balloon was detached from the first catheter by electrolysis using a modified Barricade Detachment Box (Blockade Medical) with a duty cycle of 3 minutes and a modified Barricade Handheld Detachment Cable adapted to connect with the proximal hub of the Ballstent Microcatheter. No coils were placed in the aneurysm sac or expanded balloon. Immediately after treatment, the interventionalist estimated that the aneurysm was 90% occluded.

Terminal angiography for Animal 15C005 was performed on Day 27. Angiography was used to visually assess % aneurysm occlusion, aneurysm size (including neck diameter and aneurysm width, height, and depth), parent vessel patency and diameter, and protrusion of the balloon into the parent vessels. To assess parent vessel diameter and aneurysm size, QVA was performed. On the day of termination, Animal 15C005 was subjected to limited necropsy. The right neck aneurysm tissues and the adjacent vessel segments were collected, inclusive of Test Articles. On terminal follow up, the interventionalist estimated that the aneurysm was 95% occluded.

Examples 10 and 11 demonstrate the treatment of a canine vein pouch terminal bifurcation aneurysm with coils only. Animal 13C009 was treated in Study GNA1307W. The effect of the treatment was evaluated by angiography and histology.

For Animal 13C009, a surgical procedure was performed to create a carotid artery bifurcation in the right neck and then a single venous pouch terminal bifurcation aneurysm was created using a segment of external jugular vein. Following creation of the aneurysm, angiography was used to assess parent vessel and aneurysm size, shape, patency, and blood flow. Parent vessel diameter and aneurysm size (including neck diameter and aneurysm width, height, and depth) were determined using QVA on the day of aneurysm creation.

The terminal carotid artery bifurcation aneurysm in Animal 13C009 was treated with seventeen Axium coils (Medtronic), delivered into the aneurysm sac using a 2.4 F Rebar-18 microcatheter (ev3) and an Instant Detacher (ev3). The calculated volume of the coils delivered was 225 mm$^3$ compared to an estimated aneurysm volume of 351 mm$^3$ resulting in a coil packing of 64% of the estimated aneurysm volume. The Interventionalist noted minor blood flow into the coil complex in the aneurysm neck at the end of the procedure but no additional coils could be delivered. Immediately after treatment, the interventionalist estimated that the aneurysm was 85-99% occluded.

Terminal angiography for Animal 13C009 was performed on Day 25. Angiography was used to visually assess % aneurysm occlusion, aneurysm size (including neck diameter and aneurysm width, height, and depth), parent vessel patency and diameter, and protrusion of the balloon into the parent vessels. To assess parent vessel diameter and aneurysm size, QVA was performed. On the day of termination, Animal 15C005 was subjected to limited necropsy. The right neck aneurysm tissues and the adjacent vessel segments were collected, inclusive of Axium coils. On terminal follow up, the interventionalist estimated that the aneurysm was 85-99% occluded.

The aneurysm sites and reference vessels were trimmed and processed in paraffin. The remaining explants were processed and embedded in Spurr resin. The resulting blocks were then sectioned to include three sequential in-aneurysm levels. Two slides were generated at each level in each aneurysm and in the reference artery segments and stained with H&E and ET. All resulting slides were evaluated for aneurysm occlusion, parent vessel patency, endothelialization of the implanted balloon and coils, tissue reaction and inflammatory reaction around the implanted balloon and coils, and aneurysm sac healing. Histologic analysis showed incomplete coverage of the coil mass by endothelialized neointima due to prominent recanalization at the neck. The neck occlusion rate was low (50% in two of three section levels) due to the presence of a dense network of wide recanalization channels into the aneurysm body extending down in the sac to its center. There was prominent neovascularization in the sac between the coils. The upper half of the aneurysm showed a dense network of wide vascular channels.

For the treatment of Animal 15C035, see Example 1.

Example 12A demonstrates the treatment of a canine vein pouch terminal bifurcation aneurysm with a metal balloon and coils. Animal 15C008 was treated in Study GNA1502W. The effect of the treatment was evaluated by histology.

A surgical procedure was performed to create a carotid artery bifurcation in the right neck and then a single venous pouch terminal bifurcation aneurysm was created using a segment of external jugular vein. Following creation of the aneurysm, angiography was used to assess parent vessel and aneurysm size, shape, patency, and blood flow. Parent vessel diameter and aneurysm size (including neck diameter and aneurysm width, height, and depth) were determined using QVA on the day of aneurysm creation.

The terminal carotid artery bifurcation aneurysm in Animal 15C008 was treated with an 8 mm×6 mm metal balloon Ballstent Microcatheter (gold body, stainless steel and gold proximal neck and gold distal neck). After expansion of the balloon, twelve Barricade coils (Blockade Medical) were then placed through the lumen of the second catheter of the Ballstent Microcatheter, and into the dome of the aneurysm behind the expanded balloon. The Barricade coils were detached by electrolysis using a standard Barricade Detachment Box and Handheld Detachment Cable (Blockade Medical). After the placement of the Barricade coils, the expanded balloon was detached from the first catheter by electrolysis using a modified Barricade Detachment Box with a duty cycle of 3 minutes and a modified Barricade Handheld Detachment Cable adapted to connect with the proximal hub of the Ballstent Microcatheter.

Terminal angiography for Animal 15C035 was performed on Day 85. On the day of termination, Animal 15C008 was subjected to limited necropsy. The right neck aneurysm tissues and the adjacent vessel segments were collected, inclusive of Test Articles. The aneurysm site and reference vessels were trimmed and processed in paraffin. The remaining explant was processed and embedded in Spurr resin. The resulting blocks were then sectioned to include three sequential in-aneurysm levels. Two slides were generated at each level in each aneurysm and in the reference artery segments and stained with H&E and ET. All resulting slides were evaluated for aneurysm occlusion, parent vessel patency, endothelialization of the implanted balloon and coils, tissue reaction and inflammatory reaction around the implanted balloon and coils, and aneurysm sac healing. Histologic analysis showed complete coverage of the balloon by endothelialized neointima. The neointima was fully mature and fibromuscular, with no residual fibrin. There was complete aneurysm neck occlusion (100% occlusion).

Examples 13 and 14 demonstrate the treatment of a segment of canine internal thoracic artery with a metal balloon, an Amplatzer Vascular Plug IV, or Cook Nester coils. Animals 15C001, 15C004, 17C006, and 17C008 were treated in Studies GNA1501W and GNA1701W. The effect of the treatment was evaluated by angiography.

On the day of treatment (Day 0), all animals underwent an interventional procedure in which bilateral occlusion of the internal thoracic arteries was attempted with the Test and Control Articles. The animals were prepped for surgery per the protocol. Contrast angiography was performed on Day 0 prior to treatment, during treatment (when possible) and following treatment. QVA was performed prior to placement of the Test and Control Articles to ensure that the targeted vessels segments were selected such that the diameter of the Test and Control Articles would be 25-50% larger than that of the target vessel.

A single 4 mm metal balloon Blockstent Microcatheter (gold body and necks), a single 4 mm Amplatzer Vascular Plug IV, or two 3 mm Cook Nester coils were implanted in the internal thoracic artery in dogs. The treated vessel segments were monitored, as needed, with serial angiography until complete occlusion of the target vessel segment was observed or 60 minutes had passed. In Study GNA1501W, 100% immediate occlusion was observed in 2 of 4 Blockstent treatments (4 mm) and 0 of 4 Cook Nester coil treatments. In Study GNA1701W, 100% immediate occlusion was observed in 4 of 4 Blockstent treatments (4 mm) and 0 of 4 Amplatzer Vascular Plug IV treatments. Average balloon inflation pressure was 3 atm. Mean time to complete occlusion was >30 minutes with Amplatzer Vascular Plug IV treatments.

At the terminal follow-up time point of 27 days, all animals were evaluated using contrast angiography to determine the degree of occlusion of the vessels treated with Test and/or Control Articles. On the day of termination, animals were subjected to limited necropsy. The treated tissues and the adjacent vessel segments were collected, inclusive of Test Articles. In Study GNA1501W, 100% chronic occlusion was observed in 4 of 4 Blockstent treatments (4 mm) and 0 of 4 Cook Nester coil treatments. In Study GNA1701W, 100% chronic occlusion was observed in 3 of 4 Blockstent treatments (4 mm) and 0 of 4 Amplatzer Vascular Plug IV treatments.

Example 15 demonstrates the treatment of a bleeding canine carotid artery with a metal balloon. Animal 17C002 was treated in Study GNA1701W. The effect of the treatment was evaluated by angiography.

The right carotid artery was exposed and an arteriotomy made with a 4 Fr introducer sheath to induce controlled bleeding, followed by treatment with a 6 mm metal balloon Blockstent Microcatheter (gold body and necks). The time to complete hemostasis was assessed using serial angiography to detect extravasation and direct visualization to detect vessel bleeding. There was complete cessation of bleeding immediately after balloon placement.

Example 16 demonstrates the treatment of a bleeding canine carotid artery with an Amplatzer Vascular Plug II. Animal 17C001 was treated in Study GNA1701W. The effect of the treatment was evaluated by angiography.

The right carotid artery was exposed and an arteriotomy made with a 4 Fr introducer sheath to induce controlled bleeding, followed by treatment with a 6 mm Amplatzer Vascular Plug II. The time to complete hemostasis was assessed using serial angiography to detect extravasation and direct visualization to detect vessel bleeding. There was persistent bleeding after treatment with the Amplatzer Vascular Plug II.

Example 17 demonstrates advancement of metal balloon over a guidewire into a canine superior mesenteric artery. Animal 17C005 was treated in Study GNA1701W. The advancement was evaluated by angiography.

A 0.014" guidewire was placed into the superior mesenteric artery and a pleated and folded 4 mm metal balloon Blockstent Microcatheter (gold body and necks) was advanced over the guidewire into the superior mesenteric artery without difficulty.

Example 18 demonstrates the treatment of a canine axillary artery with a metal balloon. Animal 17C003 was treated in Study GNA1701W. The effect of the treatment was evaluated by angiography.

On the day of treatment (Day 0), Animal 17C003 underwent an interventional procedure in which bilateral occlusion of the axillary arteries was attempted with Test and Control Articles. Contrast angiography was performed on Day 0 prior to treatment, during treatment (when possible) and following treatment. QVA was performed prior to placement of the Test and Control Articles to ensure that the targeted vessels segments were selected such that the diameter of the Test and Control Articles would be 25-50% larger than that of the target vessel.

A single 6 mm metal balloon Blockstent Microcatheter (gold body and necks) or a single Amplatzer Vascular Plug II was implanted in the axillary artery in dogs. The treated vessel segments were monitored, as needed, with serial angiography until complete occlusion of the target vessel segment was observed or 60 minutes had passed. In Study GNA1701W, 100% immediate occlusion was observed in 4 of 4 Blockstent treatments (6 mm) and 0 of 4 Amplatzer Vascular Plug II treatments. Average balloon inflation pressure was <4 atm. Mean time to complete occlusion was >30 minutes with Amplatzer Vascular Plug II treatments.

At the terminal follow-up time point of 28 days, animals were evaluated using contrast angiography to determine the degree of occlusion of the vessels treated. On the day of termination, animals were subjected to limited necropsy. The treated tissues and the adjacent vessel segments were collected, inclusive of the Test and Control Articles. In Study GNA1701W, 100% chronic occlusion was observed in 4 of 4 Blockstent treatments (6 mm) and 0 of 4 Amplatzer Vascular Plug II treatments.

Example 19 demonstrates the placement of a coil inside an expanded metal balloon in a canine carotid artery. Animal 17C008 was treated in Study GNA1701W. The effect of the treatment was evaluated by angiography.

A single 6 mm metal balloon Blockstent Microcatheter (gold body and necks) was implanted in a right carotid artery in a dog. The treated vessel segment was monitored with serial angiography. After complete occlusion of the carotid artery was confirmed, the guidewire was removed and the second catheter of the Blockstent Microcatheter was retracted until its tip was inside the expanded balloon, detaching the second catheter from an elastomeric valve present in a distal nosecone bonded to the distal neck of the balloon. A 6 mm coil was placed through the lumen of the second catheter and into the expanded balloon. The coil was detached by electrolysis using a standard Barricade Detachment Box and Handheld Detachment Cable (Blockade Medical).

Example 20 demonstrates the treatment of a canine internal thoracic artery with a metal balloon. Animal 17C006 was treated in Study GNA1701W. The effect of the treatment was evaluated by angiography.

On the day of treatment (Day 0), the animals underwent an interventional procedure to occlude the internal thoracic arteries bilaterally. The animals were prepped for surgery per the protocol. Contrast angiography was performed on Day 0 prior to treatment, during treatment (when possible) and following treatment. QVA was performed prior to placement of the Test and Control Articles to ensure that the targeted vessel segment was selected such that the diameter of the Test and Control Article would be 25-50% larger than that of the target vessel.

A single 4 mm metal balloon Blockstent Microcatheter (gold body and necks) or a single 4 mm Amplatzer Vascular Plug IV, was implanted in the internal thoracic artery in dogs. The treated vessel segment was monitored, as needed, with serial angiography. See Examples 13 and 14 for acute results from this study.

At the terminal follow-up time point of 28 days, the animals were evaluated using contrast angiography to determine the degree of occlusion of the treated vessel. On the day of termination, the animals were subjected to limited necropsy. The treated tissues and the adjacent vessel segments were collected, inclusive of the Test and Control Articles. See Examples 13 and 14 for chronic results from this study.

Example 21 demonstrates the treatment of a segment of canine internal thoracic artery with a metal balloon, an Amplatzer Vascular Plug IV, or Cook Nester coils. Animals 15C004, 17C005, and 17C006 were treated in Studies GNA1501W and GNA1701W. The effect of the treatment was evaluated by histopathology.

On the day of treatment (Day 0), all animals underwent an interventional procedure in which bilateral occlusion of the internal thoracic arteries was attempted with Test and Control Articles. The animals were prepped for surgery per the protocol. Contrast angiography was performed on Day 0 prior to treatment, during treatment (when possible) and following treatment. QVA was performed prior to placement of the Test and Control Articles to ensure that the targeted vessels segments were selected such that the diameter of the Test and Control Articles would be 25-50% larger than that of the target vessel.

A single 4 mm Blockstent Microcatheter (gold body and necks), a single 4 mm Amplatzer Vascular Plug IV, or two 3 mm Cook Nester coils were implanted in the internal thoracic artery in dogs. See Examples 13 and 14 for acute angiography results from this study.

At the terminal follow-up time point of 27-28 days, all animals were evaluated using contrast angiography to determine the degree of occlusion of the vessels treated with Test and Control Articles. On the day of termination, animals were subjected to limited necropsy. The treated tissues and the adjacent vessel segments were collected, inclusive of Test and Control Articles. See Examples 13 and 14 for chronic angiography results from this study.

All vessels were trimmed, processed, and embedded. The device regions were embedded in epoxy resin (Spurr), and the reference levels were embedded in paraffin. Resulting blocks were sectioned and stained with H&E and ET for recognition of local tissue reaction, evidence of infection and/or immunological response provoked by the experimental procedures or devices. Three implanted levels (proximal, middle, and distal) and two reference levels (Proximal Reference and Distal Reference) were collected from each vessel. Histology showed 98% vessel occlusion with the metal Blockstent balloon (n=4), 55% for the Amplatzer Vascular Plug IV (n=4), and 81% for the Cook Nester coils (n=4).

Examples 22, 23 and 24 demonstrates the treatment of a canine axillary artery with a metalized polymer balloon. Animal 17C014 was treated in Study GNA1703N. The effect of the treatment was evaluated by angiography.

On the day of treatment (Day 0), all animals underwent an interventional procedure in which bilateral occlusion of the internal thoracic arteries was attempted with Test Articles. The animals were prepped for surgery per the protocol. Contrast angiography was performed on Day 0 prior to treatment, during treatment (when possible) and following treatment. QVA was performed prior to placement of the Test Article to ensure that the targeted vessel segment was selected such that the diameter of the Test Article would be 25-50% larger than that of the target vessel.

For Animal 17C014, a single 4 mm polymer and metal Blockstent Microcatheter (gold wire applied to the external surface of the intermediate region of a PET balloon) was implanted in the internal thoracic artery. After expansion of the balloon, the third catheter of the Blockstent Microcatheter was advanced forward until the distal tip abutted the proximal end of an elastomeric tubular segment that was bonded to the proximal neck of the balloon, while the first and second catheters remained fixed in position. The tip of the second catheter was pulled back, while the expanded balloon and the first and third catheters of the Blockstent Microcatheter remained fixed in position, resulting in separation of the second catheter from an elastomeric valve in the distal nosecone joined to the distal neck of the balloon. The 0.014" guidewire was removed from the second catheter and two 6 mm Barricade coils (Blockade Medical) were advanced through the lumen of the second catheter and placed inside the central void of the balloon. The Barricade coils were detached by electrolysis using a standard Barricade Detachment Box and Handheld Detachment Cable (Blockade Medical). An assembly of the first and second catheters was retracted while the third catheter remained fixed in position, resulting in detachment of the expanded, coiled balloon from the first catheter. There was 100% occlusion of the treated vessel segment immediately after detachment for Animal 17C014.

At the terminal follow-up time point of 30 days, the animals were evaluated using contrast angiography to determine the degree of occlusion of the treated vessel. On the day of termination, Animal 17C014 was subjected to limited necropsy. The treated tissues and the adjacent vessel segments were collected, inclusive of the Test Article. There was 100% chronic occlusion of the treated vessel segment for Animal 17C014.

Example 25 demonstrates the treatment of a canine brachial artery with a polymer balloon. Animal 17C013 was treated in Study GNA1802N. The effect of the treatment was evaluated by angiography.

On the day of treatment (Day 0), Animal 17C013 underwent an interventional procedure to occlude the brachial arteries bilaterally. The animal was prepped for surgery per the protocol. Contrast angiography was performed on Day 0 prior to treatment, during treatment (when possible) and following treatment. QVA was performed prior to placement of the Test Article to ensure that the targeted vessel segment was selected such that the diameter of the Test Article would be 25-50% larger than that of the target vessel.

For Animal 17C013, a single 6 mm polymer Blockstent Microcatheter (PET balloon without metal) was implanted in the left brachial artery. The pleated and folded balloon was positioned over a 0.014" guidewire in the axillary artery and expanded with a pressure <2 atm. The Blockstent did not have a distal nosecone or elastomeric valve. The 0.014" guidewire was removed from the second catheter and one straight Barricade coil with two 4 mm loops on the distal end (Blockade Medical) was advanced through the lumen of the second catheter. The distal 4 mm loop was placed in the artery distal to the expanded balloon. The tip of the second catheter was pulled back into the central void of the expanded balloon, while the expanded balloon and the first catheter remained fixed in position. The proximal 4 mm loop of the coil and the remainder of the coil (straight portion) was placed inside the central void of the balloon. There was 100% occlusion of the treated vessel segment immediately after insertion of the coil.

Example 26 demonstrates the use of a mechanical latch to attach a polymer balloon to a first catheter and the use of a mechanical latch to detach a polymer balloon from a first catheter.

A benchtop test was conducted using a detachable balloon catheter incorporating a mechanical latch attachment system. Starting with both the guidewire and the second catheter extended past the distal nose cone, saline was injected into the proximal hub and through the annular lumen between the first and second catheters to expand the balloon as shown in frame A. In this configuration, the balloon resisted detachment from the first catheter under tensile loading as shown in frame B. The second catheter was then retracted past the proximal neck of the balloon as shown in frame C, unlatching the male tubular structure on the first catheter from the female tubular structure mounted within proximal neck of the balloon. The first catheter was then retracted, detaching the first catheter from the balloon as shown in frame D. Finally, the guidewire was retracted from the detached balloon as shown in frame E.

It will be appreciated that the devices and methods of the present disclosure can be incorporated in many embodiments, only a few of which have been illustrated and described above. The disclosures herein may be embodied in other specific forms without departing from its spirit or essential characteristics. The described embodiments are to be considered only as illustrative and not restrictive and the scope of the present disclosure is, therefore indicated by the appended claims rather than by the foregoing description. All changes that come within the meaning and range of equivalency of the claims are to be embraced within their scope.

Examples of Treatment of Human Patients

Example 27: Treatment of a Basilar Tip Aneurysm Using a Detachable Flexible Metalized Polymer Balloon Catheter and a Single Elongated Body A detachable balloon catheter (or first medical device) is provided, comprising a pleated and folded detachable flexible metalized polymer balloon and a catheter assembly comprising a first catheter and a second catheter.

The detachable balloon has a proximal neck and a distal neck. A female tubular structure is joined to proximal neck of the detachable flexible metalized polymer balloon. The distal portion of the female tubular structure projects into the central void of the balloon. A telescoping catheter segment with proximal and distal marker bands is joined to the distal neck of the detachable balloon. The proximal portion of the telescoping catheter segment projects into the central void of the detachable balloon. The diameter of the detachable balloon (measured in a plane parallel to the second axis) is 8 mm and the length is 5.3 mm (measured in a plane parallel to the first axis), excluding the length of the proximal and distal necks. The proximal and distal regions 110 & 120 of the detachable balloon are rounded. The wall of the detachable balloon comprises an inner layer of PET with a single wall thickness of 10 microns made by blow molding, and an outer layer of gold with a single wall thickness of 1000 angstroms, made by sputter deposition on the external surface of the PET base layer.

The first catheter comprises a proximal end with a hub comprising a port for the injection of fluid and a distal end generally opposite the proximal end, wherein the distal end of the first catheter is joined to the proximal end of a male tubular structure with three arms and tabs. The distal end of the male tubular structure is operably coupled to the tubular female structure that is joined to the proximal neck of the detachable balloon. The distal end of the first catheter further comprises a fluoroscopic marker band. The hub of the first catheter also comprises a rotating, valved lock configured to secure the hub of the first catheter to the shaft of the second catheter. The second catheter comprises a proximal end with a hub comprising a port for accepting a 0.014" guidewire, and a distal end that is open. The second catheter further comprises two fluoroscopic marker bands to facilitate the placement and detachment of a first elongated body. The second catheter is longer than the first catheter. A proximal portion of the second catheter passes through the hub of the first catheter and is secured to the hub of the first catheter by a rotating valved lock. A middle portion of the second catheter passes through the lumen of the first catheter. A distal portion of the second catheter passes through the proximal neck opening, central void, distal neck opening, and telescoping catheter segment of the pleated and folded detachable balloon and extends distal to the distal end of the distal neck telescoping catheter segment of the detachable balloon. The internal surface of the first catheter and the external surface of the second catheter define a first lumen to allow for passage of a fluid medium from the proximal end of the first catheter to the distal end of the first catheter, and into the central void of the detachable balloon. The lumen of the second catheter defines the second lumen.

A physician advances a needle into the right femoral artery in a patient with a saccular terminal aneurysm of the basilar artery and advances a 0.035" guidewire into the artery in a retrograde fashion. The needle is removed, and a 6 Fr introducer sheath is placed into the right femoral artery. A 6 Fr guide catheter with a Tuohy-Borst adaptor is inserted into the introducer sheath and advanced over the guidewire to the origin of the right vertebral artery. Standard digital subtraction angiography is performed, and the aneurysm dimensions are confirmed. The neck of the aneurysm measures 6 mm in diameter, the width and depth of the aneurysm measure 9 mm and the height of the aneurysm measures 12 mm. The 0.035" guidewire is removed and a 300 cm 0.014" guidewire is inserted and advanced until its tip is in the sac of the aneurysm. The physician removes residual air from the detachable balloon catheter and advances it over the guidewire until the pleated and folded detachable balloon is positioned in the center of the aneurysm sac. An inflation device filled with a mixture of 50% saline and 50% radiographic contrast (by volume) is attached to the inflation port on the first catheter and the inflation device is used to inject the saline and contrast mixture through the first catheter lumen and into the central void of the balloon at a pressure of 2 atmospheres, resulting in full expansion of the balloon. The physician then pulls the expanded detachable balloon back by pulling on the assembly of the first and second catheters, until the proximal surface of the expanded detachable balloon makes contact with the aneurysm neck. An injection of radiographic contrast through the 6 Fr guide catheter using the side arm of the Tuohy-Borst confirms occlusion of the neck of the aneurysm by the expanded detachable balloon. The physician opens the valved, rotating lock on the hub of the first catheter to enable movement of the second catheter and advances the tip of the second catheter over the guidewire into the distal end of the aneurysm sac not filled by the expanded detachable balloon, while maintaining the position of the expanded detachable balloon and the first catheter. The 0.014" guidewire is removed. An injection of radiographic contrast into the hub of the second catheter, through the lumen of the second catheter, and into the lumen of the vein distal to the expanded detachable balloon confirms occlusion of the aneurysm by the expanded detachable balloon. The physician then selects a second medical device comprising a 100 cm long first elongated body comprising a coiled platinum wire joined to a second elongated body comprising a pusher wire. The first elongated body has a 0.014" secondary diameter and comprises a single 4 mm tertiary loop at the distal end, with the remainder of the first elongated body having no tertiary shape, when related. The first elongated body is joined to the second elongated body (a pusher wire) by a mechanical attachment. The guidewire is removed from the lumen of the second catheter and the first elongated body is inserted into the lumen of the second catheter and advanced into the aneurysm sac under fluoroscopic guidance. The physician advances the distal 70 cm of the first expandable body into the aneurysm sac, using visual marks on the second elongated body of the second medical device for guidance. During the advancement of the first expandable body into the aneurysm sac, the physician increases the pressure in the inflation device and in the detachable balloon to maintain full balloon expansion. An injection of radiographic contrast through the 6 Fr guide catheter using the side arm of the Tuohy-Borst adaptor confirms continued occlusion of the neck of the aneurysm by the expanded detachable balloon, and appropriate placement of the expanded detachable balloon and the first elongated body. Under fluoroscopic guidance, the second catheter is withdrawn until its tip is within the central void of the expanded detachable balloon and proximal to the proximal portion of the telescoping catheter segment bonded to the distal neck of the expanded detachable balloon, while the position of the expanded detachable balloon and first catheter remain fixed and unchanged. The physician then advances the remaining 30 cm of the first expandable body into the central void of the expanded detachable balloon. An injection of radiographic contrast through the 6 Fr guide catheter using the side arm of the Tuohy-Borst adaptor confirms continued occlusion of the neck of the aneurysm by the expanded detachable balloon, and appropriate placement of the expanded detachable balloon and the first elongated body. The physician places the proximal end of the second elongated body of the second medical device into a handle provided with the second medical device, detaches the first elongated body from the second elongated body and removes the second elongated body from the patient. The physician then withdraws the tip of the second catheter until it is proximal to the coupling of the male and female tubular structures, which unlocks the coupling between the male and female structures. The physician then withdraws the first catheter and second catheter from the patient, using the marker bands on each catheter and the radiopaque female tubular structure bonded to proximal neck of the detachable balloon to confirm separation, leaving the expanded detached balloon and the first elongated body in the aneurysm sac. An injection of radiographic contrast through the 6 Fr guide catheter using the side arm of the Tuohy-Borst adaptor confirms complete occlusion of the neck and sac of the aneurysm by the expanded detachable balloon, and appropriate placement of the expanded detachable balloon and the first elongated body. The physician then removes the introducer sheath in the right femoral artery and seals the hole in the right femoral artery with a closure device, having successfully occluded the saccular aneurysm. Over the next few months the elongated body within the central void of the balloon helps the balloon resist collapse, compression, or compaction. The thin outer layer of gold on the surface of the balloon induces a complete layer of new endothelium over the blood-contacting surfaces of the balloon which completely seals the neck of the aneurysm and also induces the formation of a capsule of tissue that holds the balloon in place.

Example 28: Treatment of a Basilar Tip Aneurysm Using a Detachable Rigid Metalized Polymer Balloon Catheter and a Single Elongated Body A detachable balloon catheter (or first medical device) is provided, comprising a pleated and folded detachable rigid metalized polymer balloon and a catheter assembly comprising a first catheter and a second catheter.

The detachable balloon has a proximal neck and a distal neck. A female tubular structure is joined to proximal neck of the detachable flexible metalized polymer balloon. The distal portion of the female tubular structure projects into the central void of the balloon. A telescoping catheter segment with proximal and distal marker bands is joined to the distal neck of the detachable balloon. The proximal portion of the telescoping catheter segment projects into the central void of the detachable balloon. The diameter of the detachable balloon (measured in a plane parallel to the second axis) is 8 mm and the length is 5.3 mm (measured in a plane parallel to the first axis), excluding the length of the proximal and distal necks. The proximal and distal regions 110 & 120 of the detachable balloon are rounded. The wall of the detachable balloon comprises an inner layer of PET with a single wall thickness of 10 microns made by blow molding, a middle layer of gold with a single wall thickness of 1000 angstroms, made by sputter deposition on the external surface of the PET base layer, and an outer layer of gold with a single wall thickness of 12.5 microns, made by electroforming.

The first catheter comprises a proximal end with a hub comprising a port for the injection of fluid and a distal end generally opposite the proximal end, wherein the distal end of the first catheter is joined to the proximal end of a male tubular structure with three arms and tabs. The distal end of the male tubular structure is operably coupled to the tubular female structure that is joined to the proximal neck of the detachable balloon. The distal end of the first catheter further comprises a fluoroscopic marker band. The hub of the first catheter also comprises a rotating, valved lock configured to secure the hub of the first catheter to the shaft of the second catheter. The second catheter comprises a proximal end with a hub comprising a port for accepting a 0.014" guidewire, and a distal end that is open. The second catheter further comprises two fluoroscopic marker bands to facilitate the placement and detachment of a first elongated body. The second catheter is longer than the first catheter. A proximal portion of the second catheter passes through the hub of the first catheter and is secured to the hub of the first catheter by a rotating, valved lock. A middle portion of the second catheter passes through the lumen of the first catheter. A distal portion of the second catheter passes through the proximal neck opening, central void, distal neck opening, and telescoping catheter segment of the pleated and folded detachable balloon and extends distal to the distal end of the distal neck telescoping catheter segment of the detachable balloon. The internal surface of the first catheter and the external surface of the second catheter define a first lumen to allow for passage of a fluid medium from the proximal end of the first catheter to the distal end of the first catheter, and into the central void of the detachable balloon. The lumen of the second catheter defines the second lumen.

A physician advances a needle into the right femoral artery in a patient with a saccular terminal aneurysm of the basilar artery and advances a 0.035" guidewire into the artery in a retrograde fashion. The needle is removed, and a 6 Fr introducer sheath is placed into the right femoral artery. A 6 Fr guide catheter with a Tuohy-Borst adaptor is inserted into the introducer sheath and advanced over the guidewire to the origin of the right vertebral artery. Standard digital subtraction angiography is performed, and the aneurysm dimensions are confirmed. The neck of the aneurysm measures 6 mm in diameter, the width and depth of the aneurysm measure 9 mm and the height of the aneurysm measures 12 mm. The 0.035" guidewire is removed and a 300 cm 0.014" guidewire is inserted and advanced until its tip is in the sac of the aneurysm. The physician removes residual air from the detachable balloon catheter and advances it over the guidewire until the pleated and folded detachable balloon is positioned in the center of the aneurysm sac. An inflation device filled with a mixture of 50% saline and 50% radiographic contrast (by volume) is attached to the inflation port on the first catheter and the inflation device is used to inject the saline and contrast mixture through the first catheter lumen and into the central void of the balloon at a pressure of 5 atmospheres, resulting in full expansion of the balloon. The physician then pulls the expanded detachable balloon back by pulling on the assembly of the first and second catheters, until the proximal surface of the expanded detachable balloon makes contact with the aneurysm neck. An injection of radiographic contrast through the 6 Fr guide catheter using the side arm of the Tuohy-Borst confirms occlusion of the neck of the aneurysm by the expanded detachable balloon. The physician opens the valved, rotating lock on the hub of the first catheter to enable movement of the second catheter and advances the tip of the second catheter over the guidewire into the distal end of the aneurysm sac not filled by the expanded detachable balloon, while maintaining the position of the expanded detachable balloon and the first catheter. The 0.014" guidewire is removed. An injection of radiographic contrast into the hub of the second catheter, through the lumen of the second catheter, and into the lumen of the vein distal to the expanded detachable balloon confirms occlusion of the aneurysm by the expanded detachable balloon. The physician then selects a second medical device comprising a 70 cm long first elongated body comprising a coiled platinum wire joined to a second elongated body comprising a pusher wire. The first elongated body has a 0.014" secondary diameter and comprises a single 4 mm tertiary loop at the distal end, with the remainder of the first elongated body having no tertiary shape, when related. The first elongated body is joined to the second elongated body (a pusher wire) by a mechanical attachment. The guidewire is removed from the lumen of the second catheter and the first elongated body is inserted into the lumen of the second catheter and advanced into the aneurysm sac under fluoroscopic guidance. The physician advances the entire 70 cm of the first expandable body into the aneurysm sac, using visual marks on the second elongated body of the second medical device for guidance. An injection of radiographic contrast through the 6 Fr guide catheter using the side arm of the Tuohy-Borst adaptor confirms continued occlusion of the neck of the aneurysm by the expanded detachable balloon, and appropriate placement of the expanded detachable balloon and the first elongated body. The physician places the proximal end of the second elongated body of the second medical device into a handle provided with the second medical device, detaches the first elongated body from the second elongated body and removes the second elongated body from the patient. The physician then withdraws the tip of the second catheter until it is proximal to the coupling of the male and female tubular structures, which unlocks the coupling between the male and female structures. The physician then withdraws the first catheter and second catheter from the patient, using the marker bands on each catheter and the radiopaque female tubular structure bonded to proximal neck of the detachable balloon to confirm separation, leaving the expanded detached balloon and the first elongated body in the aneurysm sac. An injection of radiographic contrast through the 6 Fr guide catheter using the side arm of the Tuohy-Borst adaptor confirms complete occlusion of the neck and sac of the aneurysm by the expanded detachable balloon, and appropriate placement of the expanded detachable balloon and the first elongated body. The physician then removes the introducer sheath in the right femoral artery and seals the hole in the right femoral artery with a closure device, having successfully occluded the saccular aneurysm. Over the next few months the elongated body within the central void of the balloon helps the balloon resist collapse, compression, or compaction. The thin outer layer of gold on the surface of the balloon induces a complete layer of new endothelium over the blood-contacting surfaces of the balloon which completely seals the neck of the aneurysm and also induces the formation of a capsule of tissue that holds the balloon in place.

Example 29: Treatment of a Gastroduodenal Artery Using a Detachable Flexible Metalized Polymer Balloon Catheter and a Single Elongated Body A detachable balloon catheter (or first medical device) is provided, comprising a pleated and folded detachable flexible metalized polymer balloon and a catheter assembly comprising a first catheter and a second catheter.

The detachable balloon has a proximal neck and a distal neck. A female tubular structure is joined to proximal neck of the detachable flexible metalized polymer balloon. The distal portion of the female tubular structure projects into the central void of the balloon. A telescoping catheter segment with proximal and distal marker bands is joined to the distal neck of the detachable balloon. The proximal portion of the telescoping catheter segment projects into the central void of the detachable balloon. The diameter of the detachable balloon (measured in a plane parallel to the second axis) is 4 mm and the length is 6.8 mm (measured in a plane parallel to the first axis), excluding the length of the proximal and distal necks. The proximal and distal regions 110 & 120 of the detachable balloon are cone shaped, with a 45° cone angle. The wall of the detachable balloon comprises an inner layer of PET with a single wall thickness of 10 microns made by blow molding, and an outer layer of gold with a single wall thickness of 1000 angstroms, made by sputter deposition on the external surface of the PET base layer.

The first catheter comprises a proximal end with a hub comprising a port for the injection of fluid and a distal end generally opposite the proximal end, wherein the distal end of the first catheter is joined to the proximal end of a male tubular structure with three arms and tabs. The distal end of the male tubular structure is operably coupled to the tubular female structure that is joined to the proximal neck of the detachable balloon. The distal end of the first catheter further comprises a fluoroscopic marker band. The hub of the first catheter also comprises a rotating, valved lock configured to secure the hub of the first catheter to the shaft of the second catheter. The second catheter comprises a proximal end with a hub comprising a port for accepting a 0.014" guidewire, and a distal end that is open. The second catheter further comprises two fluoroscopic marker bands to facilitate the placement and detachment of a first elongated body. The second catheter is longer than the first catheter. A proximal portion of the second catheter passes through the hub of the first catheter and is secured to the hub of the first catheter by a rotating, valved lock. A middle portion of the second catheter passes through the lumen of the first catheter. A distal portion of the second catheter passes through the proximal neck opening, central void, distal neck opening, and telescoping catheter segment of the pleated and folded detachable balloon and extends distal to the distal end of the distal neck telescoping catheter segment of the detachable balloon. The internal surface of the first catheter and the external surface of the second catheter define a first lumen to allow for passage of a fluid medium from the proximal end of the first catheter to the distal end of the first catheter, and into the central void of the detachable balloon. The lumen of the second catheter defines the second lumen.

A physician advances a needle into the right femoral artery in a patient with liver metastasis for liver cancer who is scheduled for radioembolization and advances a 0.035" guidewire into the artery in a retrograde fashion. The needle is removed, and a 6 Fr introducer sheath is placed into the right femoral artery. A 6 Fr guide catheter with a Tuohy-Borst adaptor is inserted into the introducer sheath and advanced over the guidewire and used to engage the proximal portion origin of the celiac artery. Standard digital subtraction angiography is performed, and the diameter of the gastroduodenal artery is measured at 3 mm. The 0.035" guidewire is removed and a 300 cm 0.014" guidewire is inserted and advanced through the gastroduodenal artery and into the distal superior mesenteric artery. The physician removes residual air from the detachable balloon catheter and advances it over the guidewire until the proximal end of the pleated and folded detachable balloon is positioned at the origin of the gastroduodenal artery. An inflation device filled with a mixture of 50% saline and 50% radiographic contrast (by volume) is attached to the inflation port on the first catheter and the inflation device is used to inject the saline and contrast mixture through the first catheter lumen and into the central void of the balloon at a pressure of 2 atmospheres, resulting in full expansion of the balloon. An injection of radiographic contrast through the 6 Fr guide catheter using the side arm of the Tuohy-Borst confirms occlusion of the gastroduodenal artery by the expanded detachable balloon. The physician then removes a second medical device provided with the detachable balloon catheter as a kit, the second medical device comprising a 20 cm long first elongated body comprising a coiled platinum wire joined to a second elongated body comprising a pusher wire. The first elongated body has a 0.014" secondary diameter and comprises a single 4 mm tertiary loop at the distal end, with the remainder of the first elongated body having no tertiary shape, when related. The first elongated body is joined to the second elongated body (a pusher wire) by a mechanical attachment. The guidewire is removed from the lumen of the second catheter and the first elongated body is inserted into the lumen of the second catheter and advanced until the distal 4 mm loop is advanced distal to the tip of the second catheter. The physician used fluoroscopy to conform that the distal portion of the first elongated body of the second medical device is located in the lumen of the gastroduodenal artery adjacent and distal to the expanded detachable balloon. The physician opens the valved, rotating lock on the hub of the first catheter to enable movement of the second catheter and under fluoroscopic guidance, the second catheter is withdrawn until its tip is within the central void of the expanded detachable balloon and proximal to the proximal portion of the telescoping catheter segment bonded to the distal neck of the expanded detachable balloon, while the position of the expanded detachable balloon and first catheter remain fixed and unchanged. The physician advances the remaining portion of the first expandable body into the central void of the expanded detachable balloon, using the fluoroscopic marker bands on the second catheter for guidance. An injection of radiographic contrast through the 6 Fr guide catheter using the side arm of the Tuohy-Borst adaptor confirms continued occlusion of the gastroduodenal artery by the expanded detachable balloon, and appropriate placement of the expanded detachable balloon and the first elongated body. The physician places the proximal end of the second elongated body of the second medical device into a handle provided with the kit comprising the detachable balloon catheter and the second medical device, detaches the first elongated body from the second elongated body and removes the second elongated body from the patient. The physician then withdraws the tip of the second catheter until it is proximal to the coupling of the male and female tubular structures, which unlocks the coupling between the male and female structures. The physician then withdraws the first catheter and second catheter from the patient, using the marker bands on each catheter and the radiopaque female tubular structure bonded to proximal neck of the detachable balloon to confirm separation, leaving the expanded detached balloon and the first elongated body in the gastroduodenal artery. An injection of radiographic contrast through the 6 Fr guide catheter using the side arm of the Tuohy-Borst adaptor confirms complete occlusion of the gastroduodenal artery by the expanded detachable balloon, and appropriate placement of the expanded detachable balloon and the first elongated body. The physician then removes the introducer sheath in the right femoral artery and seals the hole in the right femoral artery with a closure device, having successfully occluded the gastroduodenal artery. Over the next few months the elongated body within the central void of the balloon helps the balloon resist collapse, compression, or compaction. The thin outer layer of gold on the surface of the balloon induces the formation of a capsule of tissue that seals the segment of artery and holds the balloon in place.

Example 30: Treatment of a Gastroduodenal Artery Using a Detachable Metal Balloon Catheter A detachable balloon catheter (or first medical device) is provided comprising a pleated and folded detachable metal balloon and a catheter assembly comprising a first catheter, a second catheter, and a third catheter.

The detachable balloon has a proximal neck and a distal neck. The outer surface of the distal end of an elastomeric tubular segment is joined to inner surface of the proximal neck of the detachable balloon. The distal end of the first catheter is inserted into the proximal end of the elastomeric tubular segment, forming a friction fit. The inner surface of the proximal portion of a distal nosecone is joined to the outer surface of the distal end of the distal neck of the detachable balloon. The distal nosecone contains an elastomeric valve and two spacers, one proximal and one distal, forming a friction fit. The diameter of the detachable balloon (measured in a plane parallel to the second axis) is 4 mm and the length is 6.8 mm (measured in a plane parallel to the first axis), excluding the length of the proximal and distal necks. The proximal and distal regions 110 & 120 of the detachable balloon are cone shaped, with a 45° cone angle. The wall of the detachable balloon comprises an inner layer of PET with a single wall thickness of 10 microns made by blow molding, and an outer layer of gold with a single wall thickness of 1000 angstroms, made by sputter deposition on the external surface of the PET base layer.

The first catheter comprises a proximal end with a hub comprising a port for the injection of fluid and a distal end that is operably coupled to the proximal end of the elastomeric tubular segment portion of the proximal neck assembly. The distal end of the first catheter further comprises a fluoroscopic marker band. The hub of the first catheter also comprises a rotating, valved lock configured to secure the hub of the first catheter to the shaft of the second catheter. The second catheter comprises a proximal end with a hub comprising a port for accepting a 0.014" guidewire, and a distal end that is open. The second catheter further comprises a fluoroscopic marker at the distal end. The third catheter comprises a proximal end with a hub comprising a port for injection of radiographic contrast, and a distal end that is open. The hub of the third catheter also comprises a rotating, valved lock configured to secure the hub of the third catheter to the shaft of the first catheter. The distal end of the third catheter further comprises a fluoroscopic marker band.

The first catheter is longer than the third catheter. A proximal portion of the first catheter passes through the hub of the third catheter and is secured to the hub of the third catheter by a rotating, valved lock. A middle portion of the first catheter passes through the lumen of the third catheter. A distal portion of the first catheter extends distal to the distal end of the third catheter. The internal surface of the third catheter and the external surface of the first catheter define a third lumen to allow for passage of a fluid medium, including a radiographic contrast solution, from the proximal end of the third catheter to the distal end of the third catheter where it can exit the third catheter and enter the lumen of an artery or vein, when used in vivo.

The second catheter is longer than the first catheter. A proximal portion of the second catheter passes through the hub of the first catheter and is secured to the hub of the first catheter by a rotating, valved lock. A middle portion of the second catheter passes through the lumen of the first catheter. A distal portion of the second catheter passes through the proximal neck opening, central void, distal neck opening, distal neck radiopaque tubular structure, and the friction fit valve and spacers of the distal nosecone of the pleated and folded detachable balloon and extends distal to the distal end of the distal nosecone of the detachable balloon. A portion of the shaft of the second catheter is operably coupled to the elastomeric valve of the distal nosecone of the detachable balloon by a friction fit. The internal surface of the first catheter and the external surface of the second catheter define a first lumen to allow for passage of a fluid medium from the proximal end of the first catheter to the distal end of the first catheter, and into the central void of the detachable balloon. The lumen of the second catheter defines the second lumen.

A physician advances a needle into the right femoral artery in a patient with liver metastasis for liver cancer who is scheduled for radioembolization and advances a 0.035" guidewire into the artery in a retrograde fashion. The needle is removed, and a 6 Fr introducer sheath is placed into the right femoral artery. A 6 Fr guide catheter with a Tuohy-Borst adaptor is inserted into the introducer sheath and advanced over the guidewire and used to engage the proximal portion origin of the celiac artery. Standard digital subtraction angiography is performed, and the diameter of the gastroduodenal artery is measured at 3 mm. The 0.035" guidewire is removed and a 300 cm 0.014" guidewire is inserted and advanced through the gastroduodenal artery and into the distal superior mesenteric artery. The physician removes residual air from the detachable balloon catheter and advances it over the guidewire until the proximal end of the pleated and folded detachable balloon is positioned at the origin of the gastroduodenal artery. An inflation device filled with a mixture of 50% saline and 50% radiographic contrast (by volume) is attached to the inflation port on the first catheter and the inflation device is used to inject the saline and contrast mixture through the first catheter lumen and into the central void of the balloon at a pressure of 4 atmospheres, resulting in full expansion of the balloon. The physician opens the rotating, valved lock on the hub of the third catheter, advances the tip of the third catheter forward until it is in the celiac artery, while the first catheter, second catheter, and detachable balloon remain fixed in place. The physician closes the rotating, valved lock on the hub of the third catheter. An injection of radiographic contrast into the hub of the third catheter confirms occlusion of the gastroduodenal artery by the expanded detachable balloon. The physician opens the rotating, valved lock on the hub of the third catheter, advances the tip of the third catheter forward until it abuts the proximal end of the elastomeric tubular segment. While holding the third catheter fixed in position, the physician pulls an assembly of the first catheter and the second catheter, while leaving the detachable balloon, the third catheter, and the guidewire in place. An injection of radiographic contrast into the hub of the third catheter confirms closure of the elastomeric valve of the distal nosecone and complete occlusion of the gastroduodenal artery by the expanded detachable balloon. The physician removes the third catheter and the guidewire from the patient. The physician then removes the introducer sheath in the right femoral artery and seals the hole in the right femoral artery with a closure device, having successfully occluded the gastroduodenal artery. Over the next few months the elongated body within the central void of the balloon helps the balloon resist collapse, compression, or compaction and the thin outer layer of gold on the surface of the balloon induces the formation of a capsule of tissue that seals the segment of artery and holds the balloon in place.

Example 31: Treatment of a Left Ovarian Vein Using a Detachable Flexible Metalized Polymer Balloon Catheter with a Distal Neck Retention Structure, and a Single Elongated Body A detachable balloon catheter (or first medical device) is provided, comprising a pleated and folded detachable flexible metalized polymer balloon and a catheter assembly comprising a first catheter, a second catheter, and a third catheter.

The detachable balloon has a proximal neck and a distal neck. A female tubular structure is joined to proximal neck of the detachable flexible metalized polymer balloon. The distal portion of the female tubular structure projects into the central void of the balloon. A telescoping catheter segment with proximal and distal marker bands is joined to the distal neck of the detachable balloon. The proximal portion of the telescoping catheter segment projects into the central void of the detachable balloon. The internal surface of a proximal ring of a nitinol retention structure is bonded to the external surface of the distal neck of the detachable balloon. The arms and hooks of the nitinol retention structure extend distally from the proximal ring. The diameter of the detachable balloon (measured in a plane parallel to the second axis) is 10 mm and the length is 16.8 mm (measured in a plane parallel to the first axis), excluding the length of the proximal and distal necks. The proximal and distal regions of the detachable balloon are cone shaped, with a 45° cone angle. The wall of the detachable balloon comprises an inner layer of PET with a single wall thickness of 20 microns made by blow molding, and an outer layer of gold with a single wall thickness of 1000 angstroms, made by sputter deposition on the external surface of the PET base layer.

The first catheter comprises a proximal end with a hub comprising a port for the injection of fluid and a distal end that is operably coupled to the proximal end of the elastomeric tubular segment portion of the proximal neck assembly. The distal end of the first catheter further comprises a fluoroscopic marker band. The hub of the first catheter also comprises a rotating, valved lock configured to secure the hub of the first catheter to the shaft of the second catheter. The second catheter comprises a proximal end with a hub comprising a port for accepting a 0.014" guidewire, and a distal end that is open. The second catheter further comprises a fluoroscopic marker at the distal end. The third catheter comprises a proximal end with a hub comprising a port for injection of radiographic contrast, and a distal end that is open. There are side holes in the distal end of the third catheter configured to allow fluid injected into the third catheter to exit the catheter lumen. The hub of the third catheter also comprises a rotating, valved lock configured to secure the hub of the third catheter to the shaft of the first catheter. The distal end of the third catheter further comprises a fluoroscopic marker band.

A proximal portion of the first catheter passes through the hub of the third catheter and is secured to the hub of the third catheter by a rotating, valved lock. The middle and distal portion of the first catheter are within the lumen of the third catheter. For the proximal and middle portions of the third catheter, the internal surface of the third catheter and the external surface of the first catheter define a third lumen to allow for passage of a fluid medium, including a radiographic contrast solution, from the proximal end of the third catheter to the distal end of the third catheter where it can exit the third catheter and enter the lumen of an artery or vein, when used in vivo. For the distal portion of the third catheter, the internal surface of the third catheter and the external surfaces of the pleated and folded detachable balloon, the retention structure, and the second catheter define a third lumen to allow for passage of a fluid medium, including a radiographic contrast solution, from the proximal end of the third catheter to the distal end of the third catheter where it can exit the third catheter and enter the lumen of an artery or vein, when used in vivo. The arms and hooks of the nitinol retention structure extend distally from the proximal ring are completely covered and constrained by the third catheter.

The second catheter is longer than the first catheter and the third catheter. A proximal portion of the second catheter passes through the hub of the first catheter and is secured to the hub of the first catheter by a rotating, valved lock. A middle portion of the second catheter passes through the lumen of the first catheter. A distal portion of the second catheter passes through the proximal neck opening, central void, and distal neck opening, and extends distal to the distal end of the third catheter. The internal surface of the first catheter and the external surface of the second catheter define a first lumen to allow for passage of a fluid medium from the proximal end of the first catheter to the distal end of the first catheter, and into the central void of the detachable balloon. The lumen of the second catheter defines the second lumen.

A physician advances a needle into the right femoral vein in a patient with pelvic pain and left ovarian vein varices and advances a 0.035" guidewire into the vein in an anterograde fashion. The needle is removed, and a 7 Fr introducer sheath is placed into the right femoral vein. A 7 Fr guide catheter with a Tuohy-Borst adaptor is inserted into the introducer sheath and advanced over the guidewire and into the distal portion of a dilated left ovarian vein. Standard digital subtraction angiography is performed, and the diameter of the left ovarian is measured at 7 mm. The 0.035" guidewire is removed and a 300 cm long 0.014" guidewire is inserted and advanced into the distal left ovarian vein. The physician removes residual air from the detachable balloon catheter and advances it over the guidewire until the proximal end of the pleated and folded detachable balloon is positioned in the distal left ovarian vein. The physician opens the rotating, valved lock on the hub of the third catheter, pulls back the tip of the third catheter until both the retention structure and the pleated and folded balloon are uncovered, while the first catheter, second catheter, and detachable balloon remain fixed in place. The physician closes the rotating, valved lock on the hub of the third catheter. An injection of radiographic contrast into the hub of the third catheter and a gentle tub on the first catheter confirms the position of the pleated and folded detachable balloon and adequate engagement of the hooks of the retention structure to the vein wall. An inflation device filled with a mixture of 50% saline and 50% radiographic contrast (by volume) is attached to the inflation port on the first catheter and the inflation device is used to inject the saline and contrast mixture through the first catheter lumen and into the central void of the balloon at a pressure of 2 atmospheres, resulting in full expansion of the balloon. An injection of radiographic contrast into the hub of the third catheter, through the lumen of the third catheter, and into the lumen of the vein adjacent to the expanded detachable balloon confirms occlusion of the left ovarian vein by the expanded detachable balloon. The 0.014" guidewire is removed. An injection of radiographic contrast into the hub of the second catheter, through the lumen of the second catheter, and into the lumen of the vein distal to the expanded detachable balloon confirms occlusion of the left ovarian vein by the expanded detachable balloon. The physician then removes a second medical device provided with the detachable balloon catheter as a kit, the second medical device comprising a 100 cm long first elongated body comprising a coiled platinum wire joined to a second elongated body comprising a pusher wire. The first elongated body has a 0.014" secondary diameter and comprises a single 4 mm tertiary loop at the distal end, with the remainder of the first elongated body having no tertiary shape, when related. The first elongated body is joined to the second elongated body (a pusher wire) by a mechanical attachment. The guidewire is removed from the lumen of the second catheter and the first elongated body is inserted into the lumen of the second catheter and advanced until the distal 4 mm loop is advanced distal to the tip of the second catheter. The physician used fluoroscopy to conform that the distal portion of the first elongated body of the second medical device is located in the lumen of the left ovarian vein adjacent and distal to the expanded detachable balloon. The physician opens the valved, rotating lock on the hub of the first catheter to enable movement of the second catheter and under fluoroscopic guidance, the second catheter is withdrawn until its tip is within the central void of the expanded detachable balloon and proximal to the proximal portion of the telescoping catheter segment bonded to the distal neck of the expanded detachable balloon, while the position of the expanded detachable balloon, first catheter, and the third catheter remain fixed and unchanged. The physician advances the remaining portion of the first expandable body into the central void of the expanded detachable balloon, using the fluoroscopic marker bands on the second catheter for guidance. An injection of radiographic contrast into the hub of the third catheter, through the lumen of the third catheter, and into the lumen of the vein adjacent to the expanded detachable balloon confirms occlusion of the left ovarian vein by the expanded detachable balloon, and appropriate placement of the expanded detachable balloon and the first elongated body. The physician places the proximal end of the second elongated body of the second medical device into a handle provided with the kit comprising the detachable balloon catheter and the second medical device, detaches the first elongated body from the second elongated body and removes the second elongated body from the patient. The physician then withdraws the tip of the second catheter until it is proximal to the coupling of the male and female tubular structures, which unlocks the coupling between the male and female structures. The physician then withdraws the first catheter and second catheter from the patient, using the marker bands on each catheter and the radiopaque female tubular structure bonded to proximal neck of the detachable balloon to confirm separation, leaving the expanded detached balloon and the first elongated body in the left ovarian vein. An injection of radiographic contrast into the hub of the third catheter, through the lumen of the third catheter, and into the lumen of the vein adjacent to the expanded detachable balloon confirms occlusion of the left ovarian vein by the expanded detachable balloon, and appropriate placement of the expanded detachable balloon and the first elongated body. The physician removes the third catheter and then removes the introducer sheath in the right femoral vein and seals the hole in the right femoral vein by applying manual pressure, having successfully occluded the left ovarian vein. Over the next few months the elongated body within the central void of the balloon helps the balloon resist collapse, compression, or compaction and the thin outer layer of gold on the surface of the balloon induces the formation of a capsule of tissue that that seals the segment of vein and holds the balloon in place.

Example 32: Treatment of Gastroesophageal Venous Varices Using a Detachable Flexible Metalized Polymer Balloon Catheter with a Proximal Neck Retention Structure, and a Single Elongated Body A detachable balloon catheter (or first medical device) is provided, comprising a pleated and folded detachable flexible metalized polymer balloon and a catheter assembly comprising a first catheter, a second catheter, and a third catheter.

The detachable balloon has a proximal neck and a distal neck. A female tubular structure is joined to proximal neck of the detachable flexible metalized polymer balloon. The distal portion of the female tubular structure projects into the central void of the balloon. A telescoping catheter segment with proximal and distal marker bands is joined to the distal neck of the detachable balloon. The proximal portion of the telescoping catheter segment projects into the central void of the detachable balloon. The internal surface of a distal ring of a nitinol retention structure is bonded to the external surface of the proximal neck of the detachable balloon. The elongated arms and barbs of the nitinol retention structure extend distally from the distal ring and then come together in a proximal ring. The diameter of the detachable balloon (measured in a plane parallel to the second axis) is 10 mm and the length is 16.8 mm (measured in a plane parallel to the first axis), excluding the length of the proximal and distal necks. The proximal and distal regions of the detachable balloon are cone shaped, with a 45° cone angle. The wall of the detachable balloon comprises an inner layer of PET with a single wall thickness of 20 microns made by blow molding, and an outer layer of gold with a single wall thickness of 1000 angstroms, made by sputter deposition on the external surface of the PET base layer.

The first catheter comprises a proximal end with a hub comprising a port for the injection of fluid and a distal end that is operably coupled to the proximal end of the elastomeric tubular segment portion of the proximal neck assembly. The distal end of the first catheter further comprises a fluoroscopic marker band. The hub of the first catheter also comprises a rotating, valved lock configured to secure the hub of the first catheter to the shaft of the second catheter. The second catheter comprises a proximal end with a hub comprising a port for accepting a 0.014" guidewire, and a distal end that is open. The second catheter further comprises a fluoroscopic marker at the distal end. The third catheter comprises a proximal end with a hub comprising a port for injection of radiographic contrast, and a distal end that is open. There are side holes in the distal end of the third catheter configured to allow fluid injected into the third catheter to exit the catheter lumen. The hub of the third catheter also comprises a rotating, valved lock configured to secure the hub of the third catheter to the shaft of the first catheter. The distal end of the third catheter further comprises a fluoroscopic marker band.

A proximal portion of the first catheter passes through the hub of the third catheter and is secured to the hub of the third catheter by a rotating, valved lock. The middle and distal portion of the first catheter are within the lumen of the third catheter. For the proximal and middle portions of the third catheter, the internal surface of the third catheter and the external surface of the first catheter define a third lumen to allow for passage of a fluid medium, including a radiographic contrast solution, from the proximal end of the third catheter to the distal end of the third catheter where it can exit the third catheter and enter the lumen of an artery or vein, when used in vivo. For the distal portion of the third catheter, the internal surface of the third catheter and the external surfaces of the retention structure, the pleated and folded detachable balloon, and the second catheter define a third lumen to allow for passage of a fluid medium, including a radiographic contrast solution, from the proximal end of the third catheter to the distal end of the third catheter where it can exit the third catheter and enter the lumen of an artery or vein, when used in vivo. The nitinol retention structure joined to the proximal neck of the detachable balloon is completely covered and constrained by the third catheter.

The second catheter is longer than the first catheter and the third catheter. A proximal portion of the second catheter passes through the hub of the first catheter and is secured to the hub of the first catheter by a rotating, valved lock. A middle portion of the second catheter passes through the lumen of the first catheter. A distal portion of the second catheter passes through the proximal neck opening, central void, and distal neck opening, and extends distal to the distal end of the third catheter. The internal surface of the first catheter and the external surface of the second catheter define a first lumen to allow for passage of a fluid medium from the proximal end of the first catheter to the distal end of the first catheter, and into the central void of the detachable balloon. The lumen of the second catheter defines the second lumen.

A physician advances a needle into liver in a patient with liver cirrhosis and bleeding gastroesophageal varices under fluoroscopy and locates a branch of the right hepatic vein. The physician advances a 0.035" guidewire into the hepatic vein in a retrograde fashion and inserts a 7 Fr introducer sheath into the hepatic vein. A flexible curved needle is then inserted in the 7 Fr introducer sheath and advanced from a hepatic vein branch through the parenchyma of the liver and into a portal vein branch. The physician advances a 0.035" guidewire into the portal vein in a retrograde fashion, removes the needle, and places a stent from the portal vein, through the parenchyma of the liver, and into the hepatic vein to lower the blood pressure in the portal vein. A 5 Fr diagnostic catheter is then advanced into the largest gastroesophageal venous collateral arising from the portal vein over the 0.035" guidewire. The 0.035" guidewire is removed, a 300 cm 0.014" guidewire is inserted and advanced into the gastroesophageal collateral and the 5 Fr diagnostic catheter is removed. The physician removes residual air from the detachable balloon catheter and advances it over the guidewire until the proximal end of the pleated and folded detachable balloon is positioned in the gastroesophageal collateral vein. The physician opens the rotating, valved lock on the hub of the third catheter, pulls back the tip of the third catheter until both the pleated and folded balloon and the retention structure are uncovered, while the first catheter, second catheter, and detachable balloon remain fixed in place. The physician closes the rotating, valved lock on the hub of the third catheter. An injection of radiographic contrast into the hub of the third catheter and a gentle tub on the first catheter confirms the position of the pleated and folded detachable balloon and adequate engagement of the barbs of the retention structure to the vein wall. An inflation device filled with a mixture of 50% saline and 50% radiographic contrast (by volume) is attached to the inflation port on the first catheter and the inflation device is used to inject the saline and contrast mixture through the first catheter lumen and into the central void of the balloon at a pressure of 2 atmospheres, resulting in full expansion of the balloon. An injection of radiographic contrast into the hub of the third catheter, through the lumen of the third catheter, and into the lumen of the vein adjacent to the expanded detachable balloon confirms occlusion of the gastroesophageal collateral vein by the expanded detachable balloon. The 0.014" guidewire is removed. An injection of radiographic contrast into the hub of the second catheter, through the lumen of the second catheter, and into the lumen of the vein distal to the expanded detachable balloon confirms occlusion of the left ovarian vein by the expanded detachable balloon. The physician then removes a second medical device provided with the detachable balloon catheter as a kit, the second medical device comprising a 100 cm long first elongated body comprising a coiled platinum wire joined to a second elongated body comprising a pusher wire. The first elongated body has a 0.014" secondary diameter and comprises a single 4 mm tertiary loop at the distal end, with the remainder of the first elongated body having no tertiary shape, when related. The first elongated body is joined to the second elongated body (a pusher wire) by a mechanical attachment. The guidewire is removed from the lumen of the second catheter and the first elongated body is inserted into the lumen of the second catheter and advanced until the distal 4 mm loop is advanced distal to the tip of the second catheter. The physician used fluoroscopy to conform that the distal portion of the first elongated body of the second medical device is located in the lumen of the gastroesophageal collateral vein adjacent and distal to the expanded detachable balloon. The physician opens the valved, rotating lock on the hub of the first catheter to enable movement of the second catheter and under fluoroscopic guidance, the second catheter is withdrawn until its tip is within the central void of the expanded detachable balloon and proximal to the proximal portion of the telescoping catheter segment bonded to the distal neck of the expanded detachable balloon, while the position of the expanded detachable balloon, first catheter, and the third catheter remain fixed and unchanged. The physician advances the remaining portion of the first expandable body into the central void of the expanded detachable balloon, using the fluoroscopic marker bands on the second catheter for guidance. An injection of radiographic contrast into the hub of the third catheter, through the lumen of the third catheter, and into the lumen of the vein adjacent to the expanded detachable balloon confirms occlusion of the gastroesophageal collateral vein by the expanded detachable balloon, and appropriate placement of the expanded detachable balloon and the first elongated body. The physician places the proximal end of the second elongated body of the second medical device into a handle provided with the kit comprising the detachable balloon catheter and the second medical device, detaches the first elongated body from the second elongated body and removes the second elongated body from the patient. The physician then withdraws the tip of the second catheter until it is proximal to the coupling of the male and female tubular structures, which unlocks the coupling between the male and female structures. The physician then withdraws the first catheter and second catheter from the patient, using the marker bands on each catheter and the radiopaque female tubular structure bonded to proximal neck of the detachable balloon to confirm separation, leaving the expanded detached balloon and the first elongated body in the gastroesophageal collateral vein. An injection of radiographic contrast into the hub of the third catheter, through the lumen of the third catheter, and into the lumen of the vein adjacent to the expanded detachable balloon confirms occlusion of the gastroesophageal collateral vein by the expanded detachable balloon, and appropriate placement of the expanded detachable balloon and the first elongated body. The physician removes the third catheter and then removes the introducer sheath from the liver and seals the hole in liver with pledgets, having successfully reduced the blood pressure in the portal vein and occluded the major gastroesophageal collateral vein. Over the next few months the elongated body within the central void of the balloon helps the balloon resist collapse, compression, or compaction. The thin outer layer of gold on the surface of the balloon seals the segment of vein and induces the formation of a capsule of tissue that holds the balloon in place.

Example 33: Treatment of a Left Atrial Appendage Using a Detachable Flexible Metalized Polymer Balloon Catheter with a Distal Neck Retention Structure and a Single Elongated Body A detachable balloon catheter (or first medical device) is provided, comprising a pleated and folded detachable flexible metalized polymer balloon and a catheter assembly comprising a first catheter, a second catheter, and a third catheter.

The detachable balloon has a proximal neck and a distal neck. A female tubular structure is joined to proximal neck of the detachable flexible metalized polymer balloon. The distal portion of the female tubular structure projects into the central void of the balloon. A telescoping catheter segment with proximal and distal marker bands is joined to the distal neck of the detachable balloon. The proximal portion of the telescoping catheter segment projects into the central void of the detachable balloon. The internal surface of a proximal ring of a nitinol retention structure is bonded to the external surface of the distal neck of the detachable balloon. The arms and hooks of the nitinol retention structure extend distally from the proximal ring. The diameter of the detachable balloon (measured in a plane parallel to the second axis) is 26 mm and the length is 32 mm (measured in a plane parallel to the first axis), excluding the length of the proximal and distal necks. The proximal and distal regions 110 & 120 of the detachable balloon 10 are rounded. The wall of the detachable balloon comprises an inner layer of PET with a single wall thickness of 30 microns made by blow molding, and an outer layer of gold with a single wall thickness of 1000 angstroms, made by sputter deposition on the external surface of the PET base layer.

The first catheter comprises a proximal end with a hub comprising a port for the injection of fluid and a distal end that is operably coupled to the proximal end of the elastomeric tubular segment portion of the proximal neck assembly. The distal end of the first catheter further comprises a fluoroscopic marker band. The hub of the first catheter also comprises a rotating, valved lock configured to secure the hub of the first catheter to the shaft of the second catheter. The second catheter comprises a proximal end with a hub comprising a port for accepting a 0.038" guidewire, and a distal end that is open. The second catheter further comprises a fluoroscopic marker at the distal end. The third catheter comprises a proximal end with a hub comprising a port for injection of radiographic contrast, and a distal end that is open. There are side holes in the distal end of the third catheter configured to allow fluid injected into the third catheter to exit the catheter lumen. The hub of the third catheter also comprises a rotating, valved lock configured to secure the hub of the third catheter to the shaft of the first catheter. The distal end of the third catheter further comprises a fluoroscopic marker band.

A proximal portion of the first catheter passes through the hub of the third catheter and is secured to the hub of the third catheter by a rotating, valved lock. The middle and distal portion of the first catheter are within the lumen of the third catheter. For the proximal and middle portions of the third catheter, the internal surface of the third catheter and the external surface of the first catheter define a third lumen to allow for passage of a fluid medium, including a radiographic contrast solution, from the proximal end of the third catheter to the distal end of the third catheter where it can exit the third catheter. For the distal portion of the third catheter, the internal surface of the third catheter and the external surfaces of the pleated and folded detachable balloon, the retention structure, and the second catheter define a third lumen to allow for passage of a fluid medium, including a radiographic contrast solution, from the proximal end of the third catheter to the distal end of the third catheter where it can exit the third catheter. The arms and hooks of the nitinol retention structure extend distally from the proximal ring are completely covered and constrained by the third catheter.

The second catheter is longer than the first catheter and the third catheter. A proximal portion of the second catheter passes through the hub of the first catheter and is secured to the hub of the first catheter by a rotating valved lock. A middle portion of the second catheter passes through the lumen of the first catheter. A distal portion of the second catheter passes through the proximal neck opening, central void, and distal neck opening, and extends distal to the distal end of the first catheter. The internal surface of the first catheter and the external surface of the second catheter define a first lumen to allow for passage of a fluid medium from the proximal end of the first catheter to the distal end of the first catheter, and into the central void of the detachable balloon. The lumen of the second catheter defines the second lumen.

A physician advances a needle into the right femoral vein in a patient with atrial fibrillation with a contraindication to chronic anticoagulation and advances a 300 cm long 0.038" guidewire into the vein in an anterograde fashion. The needle is removed, and an 8 Fr introducer sheath is placed into the right femoral vein. An 8 Fr guide catheter with a Tuohy-Borst adaptor is inserted into the introducer sheath and advanced over the guidewire and into the right atrium. A puncture is made in the inter-atrial septum under transesophageal ultrasound guidance, the puncture tract is dilated using serial fascial dilators, and the 8 Fr guide catheter is advanced into the left atrium. Using a 5 Fr diagnostic catheter, the guidewire is advanced deep into the left atrial appendage (LAA). The diameter of the LAA is measured using transesophageal ultrasound, demonstrating a diameter of 20 mm near the neck. The physician removes residual air from the detachable balloon catheter and advances it over the guidewire until the proximal end of the pleated and folded detachable balloon is positioned in the LAA just distal to the neck of the LAA. The physician opens the rotating valved lock on the hub of the third catheter, pulls back the tip of the third catheter until both the retention structure and the pleated and folded balloon are uncovered, while the first catheter, second catheter, and detachable balloon remain fixed in place. The physician closes the rotating valved lock on the hub of the third catheter. An injection of radiographic contrast into the hub of the third catheter and a gentle tub on the first catheter confirms the position of the pleated and folded detachable balloon and adequate engagement of the hooks of the retention structure to the wall of the LAA. Transesophageal ultrasound is used to confirm. An inflation device filled with a mixture of 50% saline and 50% radiographic contrast (by volume) is attached to the inflation port on the first catheter and the inflation device is used to inject the saline and contrast mixture through the first catheter lumen and into the central void of the balloon at a pressure of 2 atmospheres, resulting in full expansion of the balloon. An injection of radiographic contrast into the hub of the third catheter, through the lumen of the third catheter, and into the lumen of the LAA adjacent to the expanded detachable balloon confirms occlusion of the LAA by the expanded detachable balloon. Transesophageal ultrasound is used to confirm. The physician then removes a second medical device provided with the detachable balloon catheter as a kit, the second medical device comprising a 300 cm long first elongated body comprising a coiled platinum wire joined to a second elongated body comprising a pusher wire. The first elongated body has a 0.035" secondary diameter and comprises a single 6 mm tertiary loop at the distal end, with the remainder of the first elongated body having no tertiary shape, when related. The first elongated body is joined to the second elongated body (a pusher wire) by a mechanical attachment. The physician opens the valved rotating lock on the hub of the first catheter to enable movement of the second catheter and under fluoroscopic guidance, the second catheter is withdrawn until its tip is within the central void of the expanded detachable balloon and proximal to the proximal portion of the telescoping catheter segment bonded to the distal neck of the expanded detachable balloon, while the position of the expanded detachable balloon, first catheter, and the third catheter remain fixed and unchanged. The guidewire is removed from the lumen of the second catheter and the first elongated body is inserted into the lumen of the second catheter and advanced until the distal 6 mm loop is within the central void of the expanded detachable balloon. The physician advances the remaining portion of the first expandable body into the central void of the expanded detachable balloon, using the fluoroscopic marker bands on the second catheter for guidance. An injection of radiographic contrast into the hub of the third catheter, through the lumen of the third catheter, and into the lumen of the LAA adjacent to the expanded detachable balloon confirms occlusion of the LAA by the expanded detachable balloon, and appropriate placement of the expanded detachable balloon and the first elongated body. Transesophageal ultrasound is used to confirm. The physician places the proximal end of the second elongated body of the second medical device into a handle provided with the kit comprising the detachable balloon catheter and the second medical device, detaches the first elongated body from the second elongated body and removes the second elongated body from the patient. The physician then withdraws the tip of the second catheter until it is proximal to the coupling of the male and female tubular structures, which unlocks the coupling between the male and female structures. The physician then withdraws the first catheter and second catheter from the patient, using the marker bands on each catheter and the radiopaque female tubular structure bonded to proximal neck of the detachable balloon to confirm separation, leaving the expanded detached balloon and the first elongated body in the LAA. An injection of radiographic contrast into the hub of the third catheter, through the lumen of the third catheter, and into the lumen of the LAA adjacent to the expanded detachable balloon confirms occlusion of the LAA by the expanded detachable balloon, and appropriate placement of the expanded detachable balloon and the first elongated body. Transesophageal ultrasound is used to confirm. The physician removes the third catheter and the 8 Fr guide catheter, and then removes the introducer sheath in the right femoral vein and seals the hole in the right femoral vein by applying manual pressure, having successfully occluded the LAA. Over the next few months the elongated body within the central void of the balloon helps the balloon resist collapse, compression, or compaction. The thin outer layer of gold on the surface of the balloon induces a complete layer of new endothelium over the blood-contacting surfaces of the balloon which completely seals the neck of the LAA and holds the balloon in place.

Example 34: Treatment of an Aortic Valve Paravalvular Leak Using a Detachable Flexible Metalized Polymer Balloon Catheter and a Single Elongated Body A detachable balloon catheter (or first medical device) is provided, comprising a pleated and folded detachable flexible metalized polymer balloon and a catheter assembly comprising a first catheter and a second catheter.

The detachable balloon has a proximal neck and a distal neck. A female tubular structure is joined to proximal neck of the detachable flexible metalized polymer balloon. The distal portion of the female tubular structure projects into the central void of the balloon. A telescoping catheter segment with proximal and distal marker bands is joined to the distal neck of the detachable balloon. The proximal portion of the telescoping catheter segment projects into the central void of the detachable balloon. The diameter of the detachable balloon (measured in a plane parallel to the second axis) is 6 mm and the length is 16 mm (measured in a plane parallel to the first axis), excluding the length of the proximal and distal necks. The proximal and distal regions 110 & 120 of the detachable balloon 10 are rounded. The wall of the detachable balloon comprises an inner layer of PET with a single wall thickness of 14 microns made by blow molding, and an outer layer of gold with a single wall thickness of 1000 angstroms, made by sputter deposition on the external surface of the PET base layer.

The first catheter comprises a proximal end with a hub comprising a port for the injection of fluid and a distal end generally opposite the proximal end, wherein the distal end of the first catheter is joined to the proximal end of a male tubular structure with three arms and tabs. The distal end of the male tubular structure is operably coupled to the tubular female structure that is joined to the proximal neck of the detachable balloon. The distal end of the first catheter further comprises a fluoroscopic marker band. The hub of the first catheter also comprises a rotating, valved lock configured to secure the hub of the first catheter to the shaft of the second catheter. The second catheter comprises a proximal end with a hub comprising a port for accepting a 0.014" guidewire, and a distal end that is open. The second catheter further comprises two fluoroscopic marker bands to facilitate the placement and detachment of a first elongated body. The second catheter is longer than the first catheter. A proximal portion of the second catheter passes through the hub of the first catheter and is secured to the hub of the first catheter by a rotating valved lock. A middle portion of the second catheter passes through the lumen of the first catheter. A distal portion of the second catheter passes through the proximal neck opening, central void, distal neck opening, and telescoping catheter segment of the pleated and folded detachable balloon and extends distal to the distal end of the distal neck telescoping catheter segment of the detachable balloon. The internal surface of the first catheter and the external surface of the second catheter define a first lumen to allow for passage of a fluid medium from the proximal end of the first catheter to the distal end of the first catheter, and into the central void of the detachable balloon. The lumen of the second catheter defines the second lumen.

A physician advances a needle into the right femoral artery in a patient who had a transcatheter aortic valve replacement and now presents with a paravalvular leak. A 0.035" guidewire is advanced into the artery in a retrograde fashion. The needle is removed, and a 6 Fr introducer sheath is placed into the right femoral artery. A 6 Fr guide catheter with a Tuohy-Borst adaptor is inserted into the introducer sheath and advanced over the guidewire and advanced into the left ventricle. Standard digital subtraction angiography is performed, identifying the paravalvular leak path. The diameter of the paravalvular leak path is confirmed as 4 mm. The length of the paravalvular leak path is confirmed as 12 mm. The tip of the 6 Fr guide catheter is withdrawn into the aorta just distal to the paravalvular leak and a 5 Fr diagnostic catheter and a 300 cm 0.014" guidewire are used to catheterize the paravalvular leak path and place the guidewire into the left ventricle. The 5 Fr diagnostic catheter is removed. The physician removes residual air from the detachable balloon catheter and advances it over the guidewire until the distal end of the pleated and folded detachable balloon is positioned just inside the left ventricle and the proximal end of the pleated and folded detachable balloon is positioned just inside the aorta. An inflation device filled with an inflation port on the first catheter and the inflation device is used to inject the saline and contrast mixture through the first catheter lumen and into the central void of the balloon at a pressure of 2 atmospheres, resulting in full expansion of the balloon. Transesophageal ultrasound is used to confirm complete occlusion of the paravalvular leak. The physician then removes a second medical device provided with the detachable balloon catheter as a kit, the second medical device comprising a 80 cm long first elongated body comprising a coiled platinum wire joined to a second elongated body comprising a pusher wire. The first elongated body has a 0.014" secondary diameter and comprises a single 4 mm tertiary loop at the distal end, with the remainder of the first elongated body having no tertiary shape, when related. The first elongated body is joined to the second elongated body (a pusher wire) by a mechanical attachment. The physician opens the valved rotating lock on the hub of the first catheter to enable movement of the second catheter and under fluoroscopic guidance, the second catheter is withdrawn until its tip is within the central void of the expanded detachable balloon and proximal to the proximal portion of the telescoping catheter segment bonded to the distal neck of the expanded detachable balloon, while the position of the expanded detachable balloon and first catheter remain fixed and unchanged. The guidewire is removed from the lumen of the second catheter and the first elongated body is inserted into the lumen of the second catheter and advanced until the distal 4 mm loop is advanced into the central void of the balloon. The physician then advances the remaining portion of the first expandable body into the central void of the expanded detachable balloon, using the fluoroscopic marker bands on the second catheter for guidance. Transesophageal ultrasound is used to confirm complete occlusion of the paravalvular leak. Fluoroscopy is used to confirm appropriate placement of the expanded detachable balloon and the first elongated body. The physician places the proximal end of the second elongated body of the second medical device into a handle provided with the kit comprising the detachable balloon catheter and the second medical device, detaches the first elongated body from the second elongated body and removes the second elongated body from the patient. The physician then withdraws the tip of the second catheter until it is proximal to the coupling of the male and female tubular structures, which unlocks the coupling between the male and female structures. The physician then withdraws the first catheter and second catheter from the patient, using the marker bands on each catheter and the radiopaque female tubular structure bonded to proximal neck of the detachable balloon to confirm separation, leaving the expanded detached balloon and the first elongated body in the paravalvular leak path. The 6 Fr guide catheter is advanced into the left ventricle and an injection of radiographic contrast through the 6 Fr guide catheter using the side arm of the Tuohy-Borst adaptor confirms complete occlusion of the paravalvular leak, and appropriate placement of the expanded detachable balloon and the first elongated body. The physician then removes the 6 Fr guide catheter and introducer sheath in the right femoral artery and seals the hole in the right femoral artery with a closure device, having successfully occluded the aortic paravalvular leak. Over the next few months the elongated body within the central void of the balloon helps the balloon resist collapse, compression, or compaction. The thin outer layer of gold on the surface of the balloon induces a complete layer of new endothelium over the blood-contacting surfaces of the balloon and induces the formation of a capsule of tissue that seals the paravalvular leak path and holds the balloon in place.

Example 35: Treatment of a Basilar Tip Aneurysm Using a Detachable Flexible Metalized Polymer Balloon Catheter and a Single Elongated Body In this treatment example, a detachable balloon catheter comprising a flexible metalized polymer balloon with a diameter of 8 mm and a length of 5.3 mm, excluding the proximal and distal necks, is placed in a basilar tip aneurysm, as described in Example 1. Then a 100 cm first elongated body is placed, with the distal portion in the aneurysm sac distal to the expanded detachable balloon and the proximal portion in the central void of the expanded detachable balloon, also as described in Example 1. In this example, prior to detachment of either the first elongated body or the expanded detachable balloon, the physician determines the diameter of the expanded detachable balloon is too small and the length of the first elongated body is too short to provide an adequate treatment. The physician removes the first elongated body from the expanded detachable balloon and then from the patient by pulling on the second elongated body. The physician then pulls a negative pressure on the inflation port on the hub of the first catheter of the detachable balloon catheter using the inflation device, resulting in collapse of the expanded detachable balloon. The physician removes the detachable balloon from the aneurysm by pulling on the first catheter of the detachable balloon catheter and removes the detachable balloon catheter from the patient. The physician then successfully treats the aneurysm with a detachable balloon catheter with a larger balloon and a second medical device with a longer first elongated body, using the methods described in Example 1.

Example 36: Treatment of a Left Atrial Appendage Using a Detachable Flexible Metalized Polymer Balloon Catheter and a Single Elongated Body In this treatment example, a left atrial appendage (LAA) is treated with a detachable balloon catheter, as described in Example 7. After uncovering the retention feature and expanding the detachable balloon of the detachable balloon catheter, the physician determines that the expanded detachable balloon extends into the right atrium. The physician pulls a negative pressure on the inflation port on the hub of the first catheter of the detachable balloon catheter using the inflation device, resulting in collapse of the expanded detachable balloon. The physician opens the rotating, valved lock on the hub of the third catheter and advances the tip of the third catheter forward while the detachable balloon, first catheter, and second catheter remain fixed in place, until the balloon is covered by the third catheter and the retention structure is collapsed and covered by the third catheter. The physician advances the detachable balloon catheter farther into the LAA and completes a successful treatment of the LAA using the methods described in Example 7.

Example 37: Treatment of a Basilar Tip Aneurysm Using a Detachable Flexible Metalized Polymer Balloon Catheter and a Single Elongated Body A detachable balloon catheter (or first medical device) is provided, comprising a pleated and folded detachable flexible metalized polymer balloon and a catheter assembly comprising a first catheter and a second catheter, as described in Example 1, except i) the tubular male structure is replaced by a tubular structure sensitive to electrolysis or anode, wherein the proximal end of the anode 390 is joined to the distal end of the first catheter, the distal end of the anode 390 is joined to the female tubular structure of the proximal neck assembly of the detachable balloon; ii) the internal surface of a platinum cathode ring structure is joined to the outer surface of the middle portion of the first catheter; iii) the hub of the first catheter further comprises an electrical jack; iv) a conductive wire electrically connects the anode 390 to the electrical jack on the hub of the first catheter; and v) a conductive wire electrically connects the platinum cathode ring structure on the first catheter to the electrical jack on the hub of the first catheter.

The physician places the expanded detachable balloon and the first elongated body in the aneurysm, as described in Example 1, up to the detachment steps. An electrically conductive cable is used to make an electrical connection between an electrolytic detachment controller and the electrical jack on the hub of the first catheter. A 2 mA current is applied to the anode 390, resulting in corrosion and dissolution of a ring of exposed stainless steel. The current is applied until the anode 390 is severed. The remainder of the procedure then continues to a successful completion, as described in Example 1.

Example 38: Treatment of a Basilar Tip Aneurysm Using a Detachable Flexible Metalized Polymer Balloon Catheter and a Single Elongated Body A detachable balloon catheter (or first medical device) is provided, comprising a pleated and folded detachable flexible metalized polymer balloon and a catheter assembly comprising a first catheter and a second catheter, as described in Example 1, except i) the tubular male structure is replaced by a heat sensitive tubular structure, wherein the proximal end of the heat sensitive tubular structure is joined to the distal end of the first catheter, the distal end of the heat sensitive tubular structure is joined to the female tubular structure of the proximal neck assembly of the detachable balloon.

The physician places the expanded detachable balloon and the first elongated body in the aneurysm, as described in Example 1, up to the detachment steps. The first elongated body is detached from the second elongated body, as described in Example 1. The second elongated body is removed from the second catheter of the detachable balloon catheter and the second catheter is removed from the patient. A third device comprising a catheter with conductive wires and a resistive wire segment at the distal end is advanced into the lumen of the second catheter of the detachable balloon catheter until the resistive wire segment is located within the heat sensitive tubular structure. An electrically conductive cable is used to make an electrical connection between an electrothermal detachment controller and an electrical jack on the hub of the third medical device. An electrical current is applied to the resistive wire, resulting in heating of the resistive wire and melting of the heat sensitive tubular structure, severing the heat sensitive tubular structure. The first catheter of the detachable balloon catheter and the third medical device are removed from the patient and the remainder of the procedure then continues to a successful completion, as described in Example 1.

Example 39: Treatment of a Basilar Tip Aneurysm Using a Detachable Flexible Metalized Polymer Balloon Catheter and Two or More Elongated Bodies A detachable balloon catheter (or first medical device) is provided, comprising a pleated and folded detachable flexible metalized polymer balloon and a catheter assembly comprising a first catheter and a second catheter.

The detachable balloon has a proximal neck and a distal neck. A female tubular structure is joined to proximal neck of the detachable flexible metalized polymer balloon. The distal portion of the female tubular structure projects into the central void of the balloon. A telescoping catheter segment with proximal and distal marker bands is joined to the distal neck of the detachable balloon. The proximal portion of the telescoping catheter segment projects into the central void of the detachable balloon. The diameter of the detachable balloon (measured in a plane parallel to the second axis) is 8 mm and the length is 5.3 mm (measured in a plane parallel to the first axis), excluding the length of the proximal and distal necks. The proximal and distal regions 110 & 120 of the detachable balloon 10 are rounded. The wall of the detachable balloon comprises an inner layer of PET with a single wall thickness of 10 microns made by blow molding, and an outer layer of gold with a single wall thickness of 1000 angstroms, made by sputter deposition on the external surface of the PET base layer.

The first catheter comprises a proximal end with a hub comprising a port for the injection of fluid and a distal end generally opposite the proximal end, wherein the distal end of the first catheter is joined to the proximal end of a male tubular structure with three arms and tabs. The distal end of the male tubular structure is operably coupled to the tubular female structure that is joined to the proximal neck of the detachable balloon. The distal end of the first catheter further comprises a fluoroscopic marker band. The hub of the first catheter also comprises a rotating, valved lock configured to secure the hub of the first catheter to the shaft of the second catheter. The second catheter comprises a proximal end with a hub comprising a port for accepting a 0.014" guidewire, and a distal end that is open. The second catheter further comprises two fluoroscopic marker bands to facilitate the placement and detachment of a first elongated body. The second catheter is longer than the first catheter. A proximal portion of the second catheter passes through the hub of the first catheter and is secured to the hub of the first catheter by a rotating, valved lock. A middle portion of the second catheter passes through the lumen of the first catheter. A distal portion of the second catheter passes through the proximal neck opening, central void, distal neck opening, and telescoping catheter segment of the pleated and folded detachable balloon and extends distal to the distal end of the distal neck telescoping catheter segment of the detachable balloon. The internal surface of the first catheter and the external surface of the second catheter define a first lumen to allow for passage of a fluid medium from the proximal end of the first catheter to the distal end of the first catheter, and into the central void of the detachable balloon. The lumen of the second catheter defines the second lumen.

A physician advances a needle into the right femoral artery in a patient with a saccular terminal aneurysm of the basilar artery and advances a 0.035" guidewire into the artery in a retrograde fashion. The needle is removed, and a 6 Fr introducer sheath is placed into the right femoral artery. A 6 Fr guide catheter with a Tuohy-Borst adaptor is inserted into the introducer sheath and advanced over the guidewire to the origin of the right vertebral artery. Standard digital subtraction angiography is performed, and the aneurysm dimensions are confirmed. The neck of the aneurysm measures 6 mm in diameter, the width and depth of the aneurysm measure 9 mm and the height of the aneurysm measures 12 mm. The 0.035" guidewire is removed and a 2 Fr catheter is advanced over a 0.014" guidewire and advanced until its tip is in the sac of the aneurysm. A 12 mm×40 cm framing coil is placed into the sac of the aneurysm. The 2 Fr catheter is removed. The physician removes residual air from the detachable balloon catheter and advances it over a 0.014" guidewire until the pleated and folded detachable balloon is positioned in the center of the aneurysm sac and also in the center of the loops of the previously placed framing coil. An inflation device filled with a mixture of 50% saline and 50% radiographic contrast (by volume) is attached to the inflation port on the first catheter and the inflation device is used to inject the saline and contrast mixture through the first catheter lumen and into the central void of the balloon at a pressure of 2 atmospheres, resulting in full expansion of the balloon. The physician then pulls the expanded detachable balloon back by pulling on the assembly of the first and second catheters, until the proximal surface of the expanded detachable balloon makes contact with the loops of the previously placed framing coils that are present at aneurysm neck. The physician opens the valved, rotating lock on the hub of the first catheter to enable movement of the second catheter and advances the tip of the second catheter over the guidewire into the distal end of the aneurysm sac not filled by the expanded detachable balloon, while maintaining the position of the expanded detachable balloon and the first catheter. The physician then selects a second medical device comprising a 100 cm long first elongated body comprising a coiled platinum wire joined to a second elongated body comprising a pusher wire. The first elongated body has a 0.014" secondary diameter and comprises a single 4 mm tertiary loop at the distal end, with the remainder of the first elongated body having no tertiary shape, when related. The first elongated body is joined to the second elongated body (a pusher wire) by a mechanical attachment. The guidewire is removed from the lumen of the second catheter and the first elongated body is inserted into the lumen of the second catheter and advanced into the aneurysm sac under fluoroscopic guidance. The physician advances the distal 70 cm of the first expandable body into the aneurysm sac, using visual marks on the second elongated body of the second medical device for guidance. An injection of radiographic contrast through the 6 Fr guide catheter using the side arm of the Tuohy-Borst adaptor confirms continued occlusion of the neck of the aneurysm by the framing coils and the expanded detachable balloon, and appropriate placement of the expanded detachable balloon and the first elongated body. Under fluoroscopic guidance, the second catheter is withdrawn until its tip is within the central void of the expanded detachable balloon and proximal to the proximal portion of the telescoping catheter segment bonded to the distal neck of the expanded detachable balloon, while the position of the expanded detachable balloon and first catheter remain fixed and unchanged. The physician then advances the remaining 30 cm of the first expandable body into the central void of the expanded detachable balloon. An injection of radiographic contrast through the 6 Fr guide catheter using the side arm of the Tuohy-Borst adaptor confirms continued occlusion of the neck of the aneurysm by the framing coil and the expanded detachable balloon, and appropriate placement of the expanded detachable balloon and the first elongated body. The physician places the proximal end of the second elongated body of the second medical device into a handle provided with the second medical device, detaches the first elongated body from the second elongated body and removes the second elongated body from the patient. The physician then withdraws the tip of the second catheter until it is proximal to the coupling of the male and female tubular structures, which unlocks the coupling between the male and female structures. The physician then withdraws the first catheter and second catheter from the patient, using the marker bands on each catheter and the radiopaque female tubular structure bonded to proximal neck of the detachable balloon to confirm separation, leaving the expanded detached balloon and the first elongated body in the aneurysm sac. An injection of radiographic contrast through the 6 Fr guide catheter using the side arm of the Tuohy-Borst adaptor confirms complete occlusion of the neck and sac of the aneurysm by the framing coil and the expanded detachable balloon, and appropriate placement of the expanded detachable balloon and the first elongated body. The physician then removes the introducer sheath in the right femoral artery and seals the hole in the right femoral artery with a closure device, having successfully occluded the saccular aneurysm. Over the next few months the elongated body within the central void of the balloon helps the balloon resist collapse, compression, or compaction. The thin outer layer of gold on the surface of the balloon induces a complete layer of new endothelium over the blood-contacting surfaces of the balloon which completely seals the neck of the aneurysm and also induces the formation of a capsule of tissue that holds the balloon in place. In this example, the expanded detached balloon is used to fill the central portion of an aneurysm after placement of one or more framing coils, and is used in lieu of one, several, or many finishing coils.

Other Treatment Examples

One skilled in the art would understand that the foregoing Examples: 27, 28, 35, 37, and 38 can be used to treat other types of saccular aneurysms, including sidewall aneurysms and other types of bifurcation aneurysms. One skilled in the art would understand that the methods described in Examples 31-38 can be used to treat other blood-containing structures, biological conduits, and biological spaces.

Other Aspects and Embodiments of the Present Disclosure are Presented in the Following Clauses Aspects and embodiments related to methods of manufacturing the systems and devices as disclosed herein:

1. A system comprising one or more medical devices for the treatment of a human patient, the system comprising:
  a first medical device further comprising:
    a compressed, collapsed, or pleated and folded balloon configured for permanent implantation in a human patient, the balloon comprising, when expanded:
      a distal region, a proximal region generally opposite the distal region, an intermediate region transitioning from the distal region to the proximal region;
      a wall extending generally continuously from the proximal region through the intermediate region, to the distal region, with an exterior surface and an interior surface, the interior surface defining a central void or interior volume;
      an opening in the wall of the proximal region that allows for the passage of fluid from a first catheter into the central void or interior volume of the balloon and also allows for the passage of a portion of a second catheter through the central void or interior volume of the balloon;
      an opening in the wall of the distal region that allows for the passage of a portion of the second catheter out of the central void or interior volume of the balloon;
    a first catheter that partially defines a first lumen to allow for passage of fluid from the proximal end of the first catheter to the distal end of the first catheter, and into the central void or interior volume of the balloon; the first catheter comprising:
      a proximal end that is joined to a proximal hub; and
      a distal portion that is operably coupled or joined to the opening in the wall of the proximal region of the balloon;
    a second catheter that defines a second lumen configured to accept an elongated body, expandable body, or solidifying fluid, the second catheter comprising:
      a proximal end that is joined to a proximal hub;
      a proximal portion that passes through the proximal hub of the first catheter;
      a distal portion that passes through the opening in the wall of the proximal region of the balloon, the central void or interior volume of the balloon, and the opening in the wall of the distal region of the balloon, and extends beyond the opening in the wall of the distal region of the balloon; and
a distal tip having an open end;
wherein:
the passage of fluid through the first catheter into the central void or interior volume of the balloon can result in expansion of the balloon;
after expansion of the balloon, the second catheter can be moved forward or backward while the expanded balloon remain fixed in position;
after expansion of the balloon, one or more elongated bodies, expandable bodies, or solidifying fluids can be placed through the lumen of the second catheter and into a biological space adjacent to the balloon;
after expansion of the balloon, the second catheter can be pulled back until the distal tip of the second catheter is located in the central void or interior volume of the expanded balloon, and one or more elongated bodies, expandable bodies, or solidifying fluids can be passed through the lumen of the second catheter and into the central void or interior volume of the balloon; and
after expansion of the balloon and placement of elongated bodies, expandable bodies, or solidifying fluids, the first catheter can be separated from the expanded balloon and the first and second catheters can be removed from the patient while the balloon and the one or more elongated bodies, expandable bodies, or solidifying fluids remain in place in the patient; and
a second medical device comprising a first elongated or expandable body configured for permanent implantation in a human patient joined to a second elongated body configured to push the first elongated or expandable body into the lumen of second catheter and pull the first elongated or expandable body from the lumen of second catheter;
wherein:
the first elongated or expandable body is configured to pass through the lumen of the second catheter of the first medical device and into a human patient in an elongated, constrained, compressed, or collapsed form;
at least a portion of the first elongated or expandable body is configured for implantation into the central void or interior volume of the balloon of the first medical device;
the first elongated or expandable body can be separated from the second elongated body; and
the second elongated body can be removed from the lumen of the second catheter while the first elongated body remains in place in the patient.

2. The system of claim 1, wherein the balloon of the first medical device comprises polymer.

3. The system of claim 2, wherein the polymer comprises polyethylene terephthalate (PET), polyamide (nylon), or polyether block amide (Pebax).

4. The system of claims 1-3, wherein the proximal portion of the balloon comprises a proximal neck that projects away from the balloon and a radiopaque tubular segment that is conspicuous during fluoroscopy is joined to the proximal neck of the balloon.

5. The system of claims 1-3, wherein the distal portion of the balloon comprises a distal neck that projects away from the balloon and a radiopaque tubular segment that is conspicuous during fluoroscopy is joined to the distal neck of the balloon.

6. The system of claims 1-3, wherein the proximal portion of the balloon comprises a proximal neck that projects away from the balloon and a radiopaque tubular segment is joined to the proximal neck of the balloon; and wherein the distal portion of the balloon comprises a distal neck that projects away from the balloon and a radiopaque tubular segment is joined to the distal neck of the balloon.

7. The system of claims 1-6, wherein of the first catheter or the first medical device comprises a radiopaque marker that is conspicuous during fluoroscopy at or near the distal end of the first catheter.

8. The system of claim 1, wherein, after expansion of the balloon of the first medical device, the second catheter of the first medical device can be moved forward or backward while the first catheter of the first medical device remains fixed in position.

9. The system of claim 1, wherein the second catheter of the first medical device comprises two radiopaque markers that are conspicuous during fluoroscopy at or near the distal end of the catheter, and wherein the radiopaque markers are configured to assist in the passage of first elongated or expandable bodies through the lumen of the second catheter and to assist the detachment of first elongated or expandable bodies that are passed through the lumen of the second catheter.

10. The medical device of claim 9, wherein a first marker band is 0.3-1.5 mm from the distal end of the second catheter of the first medical device.

11. The medical device of claim 9 wherein a first marker band is 0.3, 0.4, 0.5, 0.6, 0.7, 0.8, 0.9, 1.0, 1.1, 1.2, 1.3, 1.4, or 1.5 mm proximal to the distal end of the second catheter.

12. The medical device of claim 9-11, wherein a second marker band is 2.0-4.0 mm proximal to the distal end of the second catheter of the first medical device.

13. The system of claims 4-7 and 9-12, wherein a radiopaque marker comprises platinum, iridium, gold, tungsten, or combinations thereof.

14. The system of claim 1, wherein the first elongated or expandable body of the second medical device comprises a coiled wire.

15. The system of claim 14, wherein the primary diameter of the coiled wire is 0.00175-0.003 inch in diameter.

16. The system of claims 14 and 15, wherein the first elongated or expandable body of the second medical device is a coiled wire and the secondary diameter of the coiled wire is 0.010-0.050 inch in diameter.

17. The system of claims 1-15, wherein the secondary diameter of the coiled wire of the first elongated or expandable body is 0.010, 0.011, 0.012, 0.013, 0.014, 0.015, 0.016, 0.017, 0.018, 0.019, 0.020, 0.021, 0.023, 0.024, 0.025, 0.026, 0.027, 0.028, 0.029, 0.030, 0.031, 0.032, 0.033, 0.034, 0.035, 0.036, or 0.037, 0.038, 0.039, 0.040, 0.041, 0.042, 0.043, 0.044, 0.045, 0.046, 0.047, 0.048, 0.049, or 0.050 inch.

18. The system of claims 14-17, wherein the first elongated or expandable body has a tertiary structure without pre-formed loops or shapes.

19. The system of claims 14-17, wherein the first elongated or expandable body is configured to form a straight or unformed tertiary shape when relaxed.

20. The medical device of claims 14-17, wherein the coiled wire is a straight vascular coil.

21. The system of claim 5, wherein at least a portion of the first elongated or expandable body has a helical, spherical, or complex tertiary structure.

22. The system of claims 14-17, wherein the first elongated or expandable body is a coiled wire and wherein at least a portion of the first elongated or expandable body is configured to form a coiled, helical, or complex tertiary shape when relaxed.

23. The medical device of claims 14-17, wherein the coiled wire is a vascular coil.

24. The system of claims 20-23, wherein the distal portion of the first elongated or expandable body comprises one loop of tertiary structure and the remainder of the first elongated or expandable body comprises a tertiary structure without pre-formed loops or shapes, when relaxed.

25. The system of claims 20-23, wherein the distal portion of the first elongated or expandable body comprises one loop of tertiary structure and the remainder of the first elongated or expandable body comprises a tertiary structure configured to form a straight or unformed tertiary shape, when relaxed.

26. The system of claims 20-23, wherein the distal portion of the first elongated or expandable body comprises two loops of tertiary structure and the remainder of the first elongated or expandable body comprises a tertiary structure without pre-formed loops or shapes, when relaxed.

27. The system of claims 20-23, wherein the distal portion of the first elongated or expandable body comprises two loops of tertiary structure and the remainder of the first elongated or expandable body comprises a tertiary structure configured to form a straight or unformed tertiary shape, when relaxed.

28. The system of claims 20-23, wherein the distal portion of the first elongated or expandable body comprises three loops of tertiary structure and the remainder of the first elongated or expandable body comprises a tertiary structure without pre-formed loops or shapes, when relaxed.

29. The system of claims 20-23, wherein the distal portion of the first elongated or expandable body comprises three loops of tertiary structure and the remainder of the first elongated or expandable body comprises a tertiary structure configured to form a straight or unformed tertiary shape, when relaxed.

30. The system of claims 20-23, wherein the distal portion of the first elongated or expandable body comprises four or more loops of tertiary structure, without pre-formed loops or shapes, when relaxed.

31. The system of claims 20-23, wherein the distal portion of the first elongated or expandable body comprises four loops of tertiary structure and the remainder of the first elongated or expandable body comprises a tertiary structure configured to form a straight or unformed tertiary shape, when relaxed.

32. The system of claims 21-30, wherein the tertiary diameter of the looped, coiled, or formed portion of the first elongated or expandable body is 2-100 mm.

33. The system of claims 21-30, wherein the tertiary diameter of the looped, coiled, or formed portion of the first elongated or expandable body is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm.

34. The system of claims 14-32, wherein the first elongated or expandable body comprises platinum, iridium, nickel, tungsten or combinations thereof.

35. The system of claim 1, wherein the first elongated or expandable body of the second medical device is a wire.

36. The system of claim 34, wherein the diameter of the wire is 0.005-0.050 inch.

37. The system of claim 34, wherein the diameter of the wire is 0.005, 0.006, 0.007, 0.009, 0.010, 0.011, 0.012, 0.013, 0.014, 0.015, 0.016, 0.017, 0.018, 0.019, 0.020, 0.021, 0.023, 0.024, 0.025, 0.026, 0.027, 0.028, 0.029, 0.030, 0.031, 0.032, 0.033, 0.034, 0.035, 0.036, or 0.037, 0.038, 0.039, 0.040, 0.041, 0.042, 0.043, 0.044, 0.045, 0.046, 0.047, 0.048, 0.049, or 0.050 inch.

38. The system of claims 35 and 36, wherein the wire diameter is a primary diameter.

39. The system of claims 34-37, wherein the wire does not have a secondary diameter.

40. The system of claims 34-37, wherein the first elongated or expandable body has a tertiary structure without pre-formed loops or shapes.

41. The system of claims 34-36, wherein the first elongated or expandable body is configured to form a straight or unformed tertiary shape when relaxed.

42. The medical device of claims 34-36, wherein the coiled wire is a straight vascular coil.

43. The system of claims 34-36, wherein at least a portion of the first elongated or expandable body has a helical, spherical, or complex tertiary structure.

44. The system of claims 34-36 wherein the distal portion of the first elongated or expandable body comprises one loop of tertiary structure and the remainder of the first elongated or expandable body comprises a tertiary structure without pre-formed loops or shapes, when relaxed.

45. The system of claims 34-36, wherein the distal portion of the first elongated or expandable body comprises one loop of tertiary structure and the remainder of the first elongated or expandable body comprises a tertiary structure configured to form a straight or unformed tertiary shape, when relaxed.

46. The system of claims 34-36, wherein the distal portion of the first elongated or expandable body comprises two loops of tertiary structure and the remainder of the first elongated or expandable body comprises a tertiary structure without pre-formed loops or shapes, when relaxed.

47. The system of claims 34-36, wherein the distal portion of the first elongated or expandable body comprises two loops of tertiary structure and the remainder of the first elongated or expandable body comprises a tertiary structure configured to form a straight or unformed tertiary shape, when relaxed.

48. The system of claims 34-36, wherein the distal portion of the first elongated or expandable body comprises three loops of tertiary structure and the remainder of the first elongated or expandable body comprises a tertiary structure without pre-formed loops or shapes, when relaxed.

49. The system of claims 34-36, wherein the distal portion of the first elongated or expandable body comprises three loops of tertiary structure and the remainder of the first elongated or expandable body comprises a tertiary structure configured to form a straight or unformed tertiary shape, when relaxed.

50. The system of claims 34-36, wherein the distal portion of the first elongated or expandable body comprises four or more loops of tertiary structure, when relaxed.

51. The system of claims 34-49, wherein the tertiary diameter of the looped, coiled, or formed portion of the first elongated or expandable body is 2-100 mm.

52. The system of claims 34-49, wherein the tertiary diameter of the looped, coiled, or formed portion of the first elongated or expandable body is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm.

53. The system of claims 34-51, wherein the wire comprises nitinol.

54. The system of claim 52, wherein the nitinol wire is plated or coated with platinum or gold.

55. The system of claims 52 and 53, wherein the nitinol wire further comprises one or more radiopaque markers that are visible during fluoroscopy.

56. The system of claim 54, wherein a radiopaque marker comprises platinum, iridium, gold, tungsten, or combinations thereof.

57. The system of claims 54 and 55, wherein the radiopaque marker is in the form of a ring or band around a portion of the wire.

58. The system of claims 34-56, wherein the second medical device further comprises a catheter, and wherein the first elongated or expandable body of the second medical device is configured to be carried through the lumen of the second catheter of the first medical device by the catheter of the second medical device.

59. The system of claim 57, wherein the distal portion of the catheter comprises a radiopaque marker that is visible during fluoroscopy.

60. The system of claim 58, wherein the radiopaque marker comprises platinum, iridium, gold, tungsten, or combinations thereof.

61. The system of claim 1, wherein the first elongated or expandable body of the second medical device comprises a wire assembly, coiled wire assembly, braided wire assembly, woven wire assembly, or other expandable body.

62. The system of claim 60, wherein the first elongated or expandable body of the second medical device is self-expanding.

63. The system of claims 60 and 61, wherein the wire assembly, coiled wire assembly, braided wire assembly, or woven wire assembly is configured to form into the general shape and size of the expanded balloon of the first medical device when not in a compressed, collapsed, constrained, or elongated form.

64. The system of claims 60-62, wherein the wire assembly, coiled wire assembly, braided wire assembly, or woven wire assembly is configured to form into the shape of a generally cylindrical form when not in a compressed, collapsed, constrained, or elongated form.

65. The system of claims 60-62, wherein the wire assembly, coiled wire assembly, braided wire assembly, or woven wire assembly is configured to form into the shape of a generally spherical shape when not in a compressed, collapsed, constrained, or elongated form.

66. The system of claim 60-64, wherein the first elongated or expandable body of the second medical device comprises nitinol.

67. The system of claim 65, wherein the nitinol wire is plated or coated with platinum or gold.

68. The system of claims 65 and 66, wherein the nitinol wire further comprises one or more radiopaque markers that are visible during fluoroscopy.

69. The system of claim 67, wherein a radiopaque marker comprises platinum, iridium, gold, tungsten, or combinations thereof.

70. The system of claim 1, wherein the first elongated or expandable body of the second medical device comprises a polymer strand.

71. The system of claim 69, wherein the polymer strand is plated or coated with platinum or gold.

72. The system of claims 69 and 70, wherein the polymer strand further comprises one or more radiopaque markers that are visible during fluoroscopy.

73. The system of claim 71, wherein a radiopaque marker comprises platinum, iridium, gold, tungsten, or combinations thereof.

74. The system of claims 71 and 72, wherein the radiopaque marker is in the form of a ring or band around a portion of the polymer strand.

75. The system of claims 1-73, wherein the first elongated or expandable body is 10-400 cm in length.

76. The system of claims 1-73, wherein the first elongated or expandable body is 10-70 cm in length.

77. The system of claims 1-73, wherein the first elongated or expandable body is 70-400 cm in length.

78. The system of claims 1-73, wherein the first elongated or expandable body has a length of 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 cm.

79. The system of claims 1-77, wherein the first elongated or expandable body comprises a lubricious layer or coating.

80. The system of claim 78, wherein the lubricous layer or coating is hydrophilic.

81. The system of claims 78 and 79, wherein the coating is a Serene™ coating sold by SurModics, Inc. or an Assist™ coating sold by BioInteractions Ltd.

82. The system of claims 78 and 79, wherein the lubricious layer is PTFE, polyimide, or a PTFE and polyimide composite.

83. The system of claims 1-81 wherein the second elongated body comprises a lubricious layer or coating.

84. The system of claim 82, wherein the lubricous layer or coating is hydrophilic.

85. The system of claims 82 and 83, wherein the coating is a Serene™ coating sold by SurModics, Inc. or an Assist™ coating sold by BioInteractions Ltd.

86. The system of claims 82 and 83, wherein the lubricious layer is PTFE, polyimide, or a PTFE and polyimide composite.

87. The system of claims 1-85, wherein the second elongated body of the second medical device comprises visual or tactile markings that enable a user to determine the length of the first elongated or expandable body that has been pushed distal to the distal tip of the second catheter.

88. The system of claims 1-86, wherein the first elongated or expandable body of the second medical device is joined to the second elongated body of the second medical device by a bond or joint that can be separated after placement of the first elongated or expandable body into an artery, vein, left atrial appendage, aneurysm, blood-containing space, biological conduit, or the central void or interior volume of the expanded balloon of the first medical device.

89. The system of claims 1-86, wherein the first elongated or expandable body of the second medical device is joined to the second elongated body of the second medical device and wherein, after expulsion of the first elongated or expandable body of the second medical device from the distal end of the second catheter of the first medical device, the second elongated body of the second medical device can be separated from the first elongated or expandable body of the second medical device and the second elongated body can be removed from the patient while the first elongated or expandable body remains in the patient.

90. The system of claims 87 and 88, wherein the first elongated or expandable body of the second medical device and the second elongated body of the second medical device are configured to separate by mechanical means.

91. The system of claims 87 and 88, wherein the first elongated or expandable body of the second medical device and the second elongated body of the second medical device are configured to separate by electrolysis or corrosion.

92. The system of claims 87, 88, and 90, wherein the region of separation between the first elongated or expandable body and second elongated body is sensitive to electrolysis or corrosion.

93. The system of claim 90 and 91, wherein the segment sensitive to electrolysis or corrosion comprises stainless steel.

94. The system of claims 90-92, wherein the second elongated body of the second medical device is configured to enable the passage of an electrical current from a proximal portion of the second elongated body to the region that is sensitive to electrolysis or corrosion.

95. The system of claim 93, wherein at least a portion of the second elongated body of the second medical device is configured to enable the passage of a direct electrical current.

96. The system of 90-94, wherein at least a portion of the second elongated body of the second medical device is covered with a substance that insulates it from electrical conduction.

97. The system of claims 90-95 wherein at least a portion of the segment sensitive to electrolysis or corrosion, or configured for dissolution by electrolysis, is not covered with a substance that insulates it from electrical conduction.

98. The system of claims 87 and 88, wherein the first elongated or expandable body of the second medical device and the second elongated body of the second medical device are configured to separate by an electrothermal process.

99. The system of claim 97, wherein the separation occurs in a region between the first elongated or expandable body and the second elongated body can melt with heating.

100. The system of claims 97 and 98, wherein the second medical device is configured to enable the passage of an electrical current from a proximal portion of the second elongated body to a resistive heating element on or near the region between the first elongated or expandable body and the second elongated body that can melt with heating.

101. The system of 97-99, wherein at least a portion of the second elongated body of the second medical device is covered with a substance that insulates it from electrical conduction.

102. The system of claims 1-86, wherein the first elongated or expandable body of the second medical device and the second elongated body of the second medical device are not joined and the second elongated body of the second medical device is configured to push the first elongated or expandable body of the second medical device through the lumen of the second catheter of the first medical device.

103. The system of claim 101, wherein the second elongated body of the second medical device is configured to expel the first elongated or expandable body of the second medical device from the distal end of the lumen of the second catheter of the first medical device.

104. The system of claims 101 and 102, wherein the second elongated body of the second medical device can be removed from the lumen of the second catheter of the first medical device after expulsion of the first elongated or expandable body of the second medical device from the distal end of the lumen of the second catheter of the first medical device.

105. The system of claims 1-103, comprising a carrier for the first elongated or expandable body and at least a portion of the second elongated body wherein the end of the carrier that holds the distal end of the first elongated or expandable body is configured for joining to the proximal hub of the second catheter.

106. The system of claim 104, wherein the carrier is configured into a coiled shape.

107. The system of claims 1-105, wherein a portion of the first or expandable elongated body of the second medical device is configured to contact the interior surface of the expanded balloon of the first medical device.

108. The system of claims 1-106, wherein the largest overall diameter or tertiary diameter of the first elongated or expandable body of the second medical device is in a range from 5% smaller than the largest diameter of the expanded balloon of the first medical device to 20% larger than the largest diameter of the expanded balloon of the first medical device.

109. The system of claims 1-107, wherein the largest overall or tertiary diameter of the first elongated or expandable body of the second medical device is 1, 2, 3, 4, 5, 6, 7, 8, 9, or 10 mm larger than the largest diameter of the expanded balloon of the first medical device.

110. The system of claims 1-108, wherein the volume of the one or more first elongated or expandable bodies of the second medical device would fill 5-75% of the volume of the central void of the expanded balloon.

111. The system of claims 1-108, wherein the volume of the one or more first elongated or expandable bodies of the second medical device would fill 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75% of the volume of the central void of the expanded balloon.

112. The system of claims 1-110, wherein a first elongated or expandable body is flexible, a second elongated body is flexible, or a first elongated and a second elongated body are flexible.

113. A method for using a system of any one of claims 1-111 in a human patient, wherein:
a first medical device is advanced over a guidewire into an artery, vein, left atrial appendage, other blood containing structure, biological conduit, or biological space;
the balloon of a first medical device is expanded;
the guidewire is removed from the lumen of the second catheter of the first medical device;
the second catheter of the first medical device is pulled back until the tip of the second catheter of the first medical device is located in the central void or interior lumen of the expanded balloon of the first medical device, while the expanded balloon of the first medical device remains fixed in position;
the first elongated or expandable body of a second medical device is passed through the lumen of a second catheter of the first medical device and placed in the central void or interior lumen of the expanded balloon of the first medical device;
the first elongated or expandable body of the second medical device is separated from the second elongated body of the second medical device;
the balloon of the first medical device is separated from the first catheter of the first medical device; and the first catheter of the first medical device, the second catheter of the first medical device, and the second elongated body of the second medical device are removed from the patient.

114. A method for using a system of any one of claims 1-111 to treat an artery, vein, other blood containing structure, biological conduit, or biological space of a human patient, wherein:
a first medical device is advanced over a guidewire into the lumen of the of an artery, vein, other blood containing structure, biological conduit, or biological space;
the balloon of the first medical device is expanded;
the guidewire is removed from the lumen of the second catheter of the first medical device;
the distal portion of the first elongated or expandable body of a second medical device is passed through the lumen of a second catheter of the first medical device and placed in the lumen of the artery, vein, other blood containing structure, biological conduit, or biological space distal to the expanded balloon;
the second catheter of the first medical device is pulled back until the tip of the second catheter of the first medical device is located in the central void or interior lumen of the expanded balloon of the first medical device, while the expanded balloon of the first medical device remains fixed in position;
the remainder of the first elongated or expandable body of the second medical device is passed through the lumen of the second catheter of the first medical device and placed in the central void or interior lumen of the expanded balloon of the first medical device;
the first elongated or expandable body of the second medical device is separated from the second elongated body of the second medical device;
the balloon of the first medical device is separated from the first catheter of the first medical device; and
the first catheter and second catheter of the first medical device and the second elongated body of the second medical device are removed from the patient.

115. A method for using a system of any one of claims 1-111 to treat a saccular aneurysm of a human patient, wherein:
a first medical device is advanced over a guidewire into the sac of an aneurysm;
the balloon of the first medical device is expanded in the aneurysm sac;
the expanded balloon of the first medical device is pulled back until a portion of the external surface of the expanded balloon makes contact with a portion of the neck of the aneurysm;
the guidewire is removed from the lumen of the second catheter of the first medical device;
optionally, the second catheter of the first medical device is advanced forward into the aneurysm sac distal to the expanded balloon, while the expanded balloon of the first medical device remains fixed in position;
the distal portion of the first elongated or expandable body of a second medical device is passed through the lumen of a second catheter of the first medical device and placed in the aneurysm sac distal to the expanded balloon;
the second catheter of the first medical device is pulled back until the tip of the second catheter of the first medical device is located in the central void or interior lumen of the expanded balloon of the first medical device, while the expanded balloon of the first medical device remains fixed in position;
the remainder of the first elongated or expandable body of the second medical device is passed through the lumen of a second catheter of the first medical device and placed in the central void or interior lumen of the expanded balloon of the first medical device;
the first elongated or expandable body of the second medical device is separated from the second elongated body of the second medical device;
the balloon of the first medical device is separated from the first catheter of the first medical device; and
the first catheter and second catheter of the first medical device and the second elongated body of the second medical device are removed from the patient.

116. The use of a system of claim 114, wherein the size of the first medical device and second medical are chosen so that, when the distal portion of the first elongated or expandable body of the second medical device is placed in an aneurysm or left atrial appendage and the proximal portion of the second elongated body of the second medical device is placed in the central void of the expanded detachable balloon, the volume of the portion of the first elongated or expandable body in the aneurysm or left atrial appendage fills 5-75% of the volume of the remaining unfilled aneurysm or left atrial appendage, and the volume of the portion of the first elongated or expandable body in the central void of the expanded balloon fills 5-75% of the volume of the central void of the expanded balloon.

117. The use of a system of claim 115, wherein 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75% of the volume of the aneurysm or left atrial appendage not filled by the expanded balloon is filled by the first elongated or expandable body.

118. The use of a system of claim 115, wherein 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75% of the volume of the central void of the expanded balloon is filled.

Aspects and embodiments related to elongated bodies and removal of elongated bodies and expanded detached balloon as disclosed herein:

1. A medical device comprising an elongated body, wherein the elongated body is a coiled wire and wherein at least a portion of the first elongated or expandable body is configured to form a coiled, helical, or complex tertiary shape when relaxed.

2. The medical device of claim 1, wherein the distal portion of the elongated body comprises one loop of tertiary structure, the middle portion of the elongated body comprises a tertiary structure without pre-formed loops or shapes when relaxed, and the proximal portion of the elongated body comprises one loop of tertiary structure.

3. The medical device of claim 1, wherein the distal portion of the elongated body comprises two loops of tertiary structure, the middle portion of the elongated body comprises a tertiary structure without pre-formed loops or shapes when relaxed, and the proximal portion of the elongated body comprises two loops of tertiary structure.

4. The medical device of claim 1, wherein the distal portion of the elongated body comprises three loops of tertiary structure, the middle portion of the elongated body comprises a tertiary structure without pre-formed loops or shapes when relaxed, and the proximal portion of the elongated body comprises three loops of tertiary structure.

5. The medical device of claim 1, wherein the distal portion of the elongated body comprises one loop of tertiary structure, the middle portion of the elongated body comprises a tertiary structure configured to form a straight or unformed tertiary shape when relaxed, and the proximal portion of the elongated body comprises one loop of tertiary structure.

6. The medical device of claim 1, wherein the distal portion of the elongated body comprises two loops of tertiary structure, the middle portion of the elongated body comprises a tertiary structure configured to form a straight or unformed tertiary shape when relaxed, and the proximal portion of the elongated body comprises two loops of tertiary structure.

7. The medical device of claim 1, wherein the distal portion of the elongated body comprises three loops of tertiary structure, the middle portion of the elongated body comprises a tertiary structure configured to form a straight or unformed tertiary shape when relaxed, and the proximal portion of the elongated body comprises three loops of tertiary structure.

8. The medical device of claim 1, wherein the distal portion of the elongated body comprises a tertiary structure without pre-formed loops or shapes when relaxed, and the proximal portion of the elongated body comprises one loop of tertiary structure.

9. The medical device of claim 1, wherein the distal portion of the elongated body comprises a tertiary structure without pre-formed loops or shapes when relaxed, and the proximal portion of the elongated body comprises two loops of tertiary structure.

10. The medical device of claim 1, wherein the distal portion of the elongated body comprises a tertiary structure without pre-formed loops or shapes when relaxed, and the proximal portion of the elongated body comprises three loops of tertiary structure.

11. The medical device of claim 1, wherein the distal portion of the elongated body comprises a tertiary structure configured to form a straight or unformed tertiary shape when relaxed, and the proximal portion of the elongated body comprises one loop of tertiary structure.

12. The medical device of claim 1, wherein the distal portion of the elongated body comprises a tertiary structure configured to form a straight or unformed tertiary shape when relaxed, and the proximal portion of the elongated body comprises two loops of tertiary structure.

13. The medical device of claim 1, wherein the distal portion of the elongated body comprises a tertiary structure configured to form a straight or unformed tertiary shape when relaxed, and the proximal portion of the elongated body comprises three loops of tertiary structure.

Aspects and embodiments related to kits incorporating the medical devices as disclosed herein:

1. A kit comprising medical devices for the treatment of a human patient, wherein the kit comprises:
  one of a first type of medical device, the first medical device comprising:
    a compressed, collapsed or pleated and folded balloon configured for permanent implantation in a human patient, the balloon comprising:
      a distal region, a proximal region generally opposite the distal region, an intermediate region transitioning from the distal region to the proximal region, a first axis extending proximal-distal between the proximal region and distal region, and a second axis perpendicular to the first axis;
      a wall extending generally continuously from the proximal region through the intermediate region, to the distal region, with an exterior surface and an interior surface, the interior surface defining a central void or interior volume;
      an opening in the wall of the proximal region that allows for the passage of fluid from a first catheter into the central void or interior volume of the balloon and also allows for the passage of a portion of the second catheter into the central void or interior volume of the balloon;
      an opening in the wall of the distal region that allows for the passage of a portion of the second catheter out of the central void or interior volume of the balloon;
    a first catheter that partially defines a first lumen to allow for passage of fluid from the proximal end of the first catheter to the distal end of the first catheter, and into the central void or interior volume of the balloon; the first catheter comprising:
      a proximal end that is coupled to a proximal hub; and
      a distal portion that is operably coupled or joined to the opening in the wall of the proximal region of the balloon;
    a second catheter that defines a second lumen configured to accept an elongated body, expandable body, or solidifying fluid, the second catheter comprising:
      a proximal end that is coupled to a proximal hub;
      a portion that passes through the proximal hub of the first catheter; and
      a distal portion that passes through the central void or interior volume of the balloon and exits the central void or interior volume of the balloon through an opening in the wall of the distal region of the balloon;
      a distal end that is open;
    wherein:
      the passage of fluid through the first catheter into the central void or interior volume of the balloon can result in expansion of the balloon;
      after expansion of the balloon, the second catheter can be moved forward or backward while the expanded balloon remains fixed in position;
      after expansion of the balloon, one or more coils, wire assemblies, or solidifying fluids, can be placed through the lumen of the second catheter into a biological space adjacent to the balloon;
      after expansion of the balloon, the second catheter can be pulled back until the distal tip of the second catheter is located in the central void or interior volume of the balloon, and one or more elongated bodies, expandable bodies, or solidifying fluids can be passed through the lumen of the second catheter and placed in the central void or interior volume of the balloon; and
      after expansion of the balloon and placement of one or more elongated bodies, expandable bodies, or solidifying fluids, the first catheter can be separated from the expanded balloon and the first and second catheters can be removed from the patient while the balloon and the one or more elongated bodies, expandable bodies, or solidifying fluids remain in place in the patient; and
  one or more of a second type of medical device, the second medical device comprising:

one or more elongated bodies or expandable bodies configured to pass through the second catheter of the first medical device in a compressed, collapsed, constrained, or elongated form; and a delivery system for the one or more elongated bodies or expandable bodies.

2. The kit of claim 1, wherein the wall of the balloon comprises a single layer of polymer.

3. The the kit of any one of claims 1 and 2 wherein the wall of the balloon comprises a single layer of polyethylene terephthalate (PET), polyamide (nylon), or polyether block amide (Pebax).

4. The the kit of any one of claims 2-3, wherein the balloon comprises a continuous layer of polymer.

5. The the kit of any one of claims 2-3, wherein the balloon comprises a discontinuous layer of polymer.

6. The the kit of any one of claims 2-5, wherein the balloon has a wall thickness of 5-300 microns.

7. The the kit of any one of claims 2-5, wherein the balloon has a wall thickness of 0.0002-0.012 inch.

8. The the kit of any one of claims 1-7, comprising a balloon with a proximal neck and a distal neck.

9. The the kit of claim 1, wherein at least a portion of the wall of the balloon comprises two or more polymer layers.

10. The the kit of claim 9, wherein the inner layer of the balloon comprises polyethylene terephthalate, polyamide, or polyether block amide.

11. The the kit of claim 10, wherein the inner layer of the balloon has a wall thickness of 5-300 microns.

12. The the kit of any one of claims 10 and 11, wherein the polyethylene terephthalate, polyamide, or polyether block amide layer comprises a continuous layer.

13. The the kit of any one of claims 10 and 11, wherein the polyethylene terephthalate, polyamide, or polyether block amide layer comprises a discontinuous layer.

14. The the kit of any one of claims 9-13, comprising one or more outer layers or coatings comprising polyurethane, silicone, or poly(p-xylylene) (Parylene).

15. The the kit of claim 14, wherein the outer layers or coatings of the balloon have a wall thickness of 0.1-100 microns.

16. The the kit of any one of claims 14 and 15, wherein the polyurethane, silicone, or poly(p-xylylene layer comprises a continuous layer.

17. The the kit of any one of claims 14 and 15, wherein the polyurethane, silicone, or poly(p-xylylene layer comprises a discontinuous layer.

18. The the kit of any one of claims 2-17 comprising one or more layers or coatings comprising a metal with a thickness of 0.001-1 microns.

19. The the kit of claim 18, wherein the metal comprises gold or alloys thereof.

20. The the kit of claim 18, wherein the metal comprises titanium or alloys thereof.

21. The the kit of claim 18, wherein the metal comprises gold, titanium or alloys or combinations thereof.

22. The the kit of any one of claims 18-21, wherein the metal layer or coating comprises an external layer.

23. The the kit of any one of claims 2-22, wherein the overall thickness of the wall of the balloon is 5-400 microns.

24. The the kit of any one of claims 2-22, wherein the overall thickness of the wall of the balloon is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, or 400 microns.

25. The the kit of any one of claims 2-22, wherein the overall thickness of the wall of the balloon is 0.0002-0.016 inch.

26. The the kit of claim 1, wherein the wall of the balloon comprises a single layer of metal.

27. The the kit of any one of claim 26, wherein the balloon comprises a continuous layer of metal.

28. The the kit of any one of claim 26, wherein the balloon comprises a discontinuous layer of metal.

29. The the kit of claim 26-28, wherein the wall of the balloon comprises gold, or alloys thereof.

30. The the kit of claim 26-28, wherein the wall of the balloon comprises platinum, or alloys thereof.

31. The the kit of any one of claims 26-30, wherein the balloon has a wall thickness of 5-300 microns.

32. The the kit of any one of claims 26-30, wherein the balloon has a wall thickness of 0.0002-0.012 inch.

33. The the kit of any one of claims 26-32, comprising one or more outer layers or coatings, one or more inner layers or coatings, or both one or more outer layers or coatings and one or more inner layers or coatings.

34. The the kit of claim 33, wherein the outer layers or coatings and the inner layers or coatings comprise one or more polymers.

35. The the kit of any one of claims 33 and 34, wherein the inner layer or coating and the outer layer or coating comprise a material that insulates the metal layer from passing an electrical current to the inner or outer surfaces of the balloon.

36. The the kit of claim 35 and 36, wherein the one or more polymers comprise polyurethane, silicone, or poly(p-xylylene).

37. The the kit of any one of claims 35-36, wherein each outer layers or coatings of the balloon have a wall thickness of 0.1-100 microns.

38. The the kit of any one of claims 34-37, wherein at least one of the inner layers or coatings or outer layers or coatings comprises a continuous layer.

39. The the kit of any one of claims 34-37, wherein at least one of the inner layers or coatings or outer layers or coatings comprises a discontinuous layer.

40. The the kit of any one of claims 26-32, comprising a middle layer comprising metal, and an inner and outer layer or coating comprising polymer.

41. The the kit of claim 40, wherein the inner layer or coating and outer layer or coating are a continuous layer.

42. The the kit of claim 40, wherein the inner layer or coating and outer layer or coating are a discontinuous layer.

43. The the kit of any one of claims 40-42, wherein the inner layer or coating and the outer layer or coating comprise a material that insulates the metal layer from passing an electrical current to the outer or inner surface of the balloon.

44. The the kit of any one of claims 40-43, wherein the outer layer or coating and the inner layer or coating comprises polyurethane, silicone, or poly(p-xylylene).

45. The the kit of any one of claims 40-44, wherein the inner layer or coating of the balloon has a wall thickness of 0.1-100 microns and the outer layer or coating of the balloon has a wall thickness of 0.1-100 microns.

46. The the kit of any one of claims 26-32, comprising an inner layer comprising metal, and an outer layer or coating comprising polymer.

47. The kit of claim 45, wherein the outer layer or coating comprises a continuous layer.

48. The the kit of claim 45, wherein the outer layer or coating comprises a discontinuous layer.

49. The the kit of any one of claims 46-48, wherein the outer layer or coating comprise a material that insulates the metal layer from passing an electrical current to the outer surface of the balloon.

50. The the kit of claim 49, wherein the outer layer or coating comprises polyurethane, silicone, or poly(p-xylylene).

51. The the kit of any one of claims 46-50, wherein the thickness of the outer layer or coating is 0.1-100 microns.

52. The the kit of any one of claims 26-38, wherein the overall thickness of the balloon wall is 5-400 microns.

53. The the kit of any one of claims 26-38, wherein the overall thickness of the balloon wall is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, or 400 microns.

54. The the kit of any one of claims 26-38, wherein the overall thickness of the balloon wall is 0.0002-0.016 inch.

55. The the kit of any one of claims 26-54, wherein at least a portion of the outer surface of the metal has a rounded, pebbled, or granular surface structure.

56. The the kit of any one of claims 26-54, wherein the outer layer comprises metal and the exterior surface of the metal comprises a rounded, pebbled, or granular surface structure.

57. The the kit of any one of claims 55 and 56, wherein the pebbles or granules have a surface height of 0.01-10 microns.

58. The the kit of any one of claims 26-57, wherein at least a portion of the wall of the balloon is formed by electroplating or electroforming.

59. The the kit of any one of claims 26-58, wherein at least a portion of the wall of the balloon has been annealed.

60. The the kit of any one of claims 26-59, wherein the balloon possesses sufficient strength to maintain itself in an expanded or partially expanded configuration in vivo after separation from the first and second member shafts.

61. The the kit of any one of claims 26-59, wherein the metal balloon possesses sufficient strength to maintain itself in an expanded or partially expanded configuration in vivo when no solid or semi-solid material, not derived from the patient, is present in the central void of the expanded metal balloon after separation from the first and second catheter.

62. The the kit of any one of claims 26-59, wherein the expanded metal balloon possesses sufficient strength to maintain itself in an expanded or partially expanded configuration in vivo after separation from the first and second catheter; and wherein no solid or semi-solid material or member, not derived from the patient, is required in the central void or interior volume of the expanded metal balloon to at least assist in causing the metal balloon to assume or maintain the expanded configuration after separation of the expanded metal balloon and the first and second catheter.

63. The the kit of any one of claims 26-59, wherein the expanded metal balloon alone possesses sufficient strength to maintain itself in an expanded or partially expanded configuration in vivo after separation from the first and second catheters.

64. The the kit of any one of claims 26-59, wherein, after separation of the metal balloon from the first and second catheters in vivo, the pressure in the central void or interior volume of the expanded metal balloon is the same or lower than a pressure outside the expanded metal balloon.

65. The the kit of any one of claims 26-59, wherein the polymer and metal balloon is implanted in vivo in an unsealed configuration.

66. The the kit of claim 1, wherein the wall of the balloon comprises a layer of polymer and a layer of metal, wherein the layer of metal has a thickness of 1-300 microns.

67. The the kit of claim 66, wherein the balloon comprises a continuous layer of polymer.

68. The the kit of claim 66, wherein the balloon comprises a discontinuous layer of polymer.

69. The the kit of any one of claims 66-68, wherein the polymer comprises polyethylene terephthalate, polyamide, or polyether block amide.

70. The the kit of claim 66, wherein the balloon comprises a continuous layer of metal.

71. The the kit of claim 66, wherein the balloon comprises a discontinuous layer of metal.

72. The the kit of any one of claims 66, 70, and 71, wherein the metal comprises gold, or alloys thereof.

73. The the kit of any one of claims 66, 70, and 71, wherein the metal comprises platinum, or alloys thereof.

74. The the kit of any one of claims 66-73, wherein the metal layer is internal to the polymer layer.

75. The the kit of any one of claims 66-73, wherein the metal layer is external to the polymer layer.

76. The the kit of any one of claims 74 and 75, wherein the metal is formed as a wire and configured in a spiral, coil, braid, woven, or straight configuration.

77. The the kit of any one of claims 75 and 76, wherein the metal is joined to the underlying polymer by a glue or adhesive.

78. The the kit of any one of claims 75 and 76, wherein the metal is bonded to the underlying polymer by a glue or adhesive.

79. The the kit of any one of claims 75 and 76, wherein the metal is bonded or joined to the balloon by adhesive or glue 80. The the kit of any one of claims 75-79, comprising one or more additional layers or coatings of polymer external to the metal layer and the first polymer layer and the metal layer.

81. The the kit of claim 79, wherein at least one of the additional polymer layers or coatings is continuous.

82. The the kit of claim 79, wherein at least one of the additional polymer layers or coatings is discontinuous.

83. The the kit of any one of claims 80-82, wherein the additional polymer layer or coating comprises polyurethane, silicone, or poly(p-xylylene).

84. The the kit of any one of claims 76-83, wherein the metal wire is present on at least a portion of the intermediate region of the polymer and metal balloon.

85. The the kit of claim 76-83, wherein the metal wire is present on at least a portion of the proximal region of the polymer and metal balloon.

86. The the kit of claim 76-83, wherein the metal wire is present on at least a portion of the distal region of the polymer and metal balloon.

87. The the kit of claim 76-83, wherein the metal wire is present on at least a portion of the proximal and intermediate regions of the polymer and metal balloon.

88. The the kit of claim 76-83, wherein the metal wire is present on at least a portion of the distal and intermediate regions of the polymer and metal balloon.

89. The the kit of claim 76-83, wherein the metal wire is present on at least a portion of the proximal, intermediate, and distal regions of the polymer and metal balloon.

90. The the kit of any one of claims 76-90, wherein the cross-section profile of the metal wire is circular, oval, square, or rectangular.

91. The the kit of any one of claims 76-90, wherein the metal wire has a diameter or width of 10-1000 microns.

92. The the kit of any one of claims 76-90, wherein the metal wire has a diameter or width of 10, 20, 30, 40, 50, 60, 70, 80, 90, 100, 110, 120, 130, 140, 150, 200, 250, 300, 350, 400, 450, 500, 550, 600, 650, 700, 750, 800, 850, 900, 950, or 1000 microns.

93. The the kit of any one of claims 66-92, wherein the overall thickness of at least a portion of the wall of the polymer and balloon, including any polymer, metal wire, adhesive, and coatings, is 5-1300 microns.

94. The the kit of any one of claims 66-92, wherein the total thickness of at least a portion of the wall of the polymer and balloon, including any polymer, metal wire, adhesive, and coatings, is 5, 10, 20, 30, 40, 50, 60, 70, 80, 90, 100, 110, 120, 130, 140, 150, 200, 250, 300, 350, 400, 450, 500, 550, 600, 650, 700, 750, 800, 850, 900, 950, 1000, 1050, 1100, 1150, 1200, 1250, or 1300 microns.

95. The the kit of any one of claims 66-94, wherein the polymer and metal balloon possesses sufficient strength to maintain itself in an expanded or partially expanded configuration in vivo after separation from the first and second member shafts.

96. The the kit of any one of claims 66-94, wherein the polymer and metal balloon possesses sufficient strength to maintain itself in an expanded or partially expanded configuration in vivo when no solid or semi-solid material, not derived from the patient, is present in the central void of the expanded polymer and metal balloon after separation from the first and second catheter.

97. The the kit of any one of claims 66-94, wherein the expanded polymer and metal balloon possesses sufficient strength to maintain itself in an expanded or partially expanded configuration in vivo after separation from the first and second catheter; and wherein no solid or semi-solid material or member, not derived from the patient, is required in the central void or interior volume of the expanded polymer and metal balloon to at least assist in causing the polymer and metal balloon to assume or maintain the expanded configuration after separation of the expanded polymer and metal balloon from the first and second catheter.

98. The the kit of any one of claims 66-94, wherein the expanded polymer and metal balloon alone possesses sufficient strength to maintain itself in an expanded or partially expanded configuration in vivo after separation from the first and second catheters.

99. The the kit of any one of claims 66-94, wherein, after separation of the expanded polymer and metal balloon from the first and second catheters in vivo, the pressure in the central void or interior volume of the expanded metal balloon is not greater than a pressure outside the expanded metal balloon.

100. The the kit of any one of claims 66-94, wherein the polymer and metal balloon is implanted in vivo in an unsealed configuration.

101. The the kit of any one of claims 1-100, comprising an expandable metal retention structure wherein, after expansion, the diameter of a portion of the metal structure is equal to or greater than the diameter of the expanded balloon.

102. The the kit of claim 101, wherein a portion of the expandable metal retention structure is configured to make contact with the wall of an artery, vein, left atrial appendage, aneurysm, biological conduit, or other blood containing space or biological space.

103. The the kit of any one of claims 101 and 102, wherein the expandable metal retention structure comprises a plurality of elongated ribs extending from a ring structure.

104. The the kit of any one of claim 103, wherein the free end of at least one elongated rib of the expandable metal retention structure comprises a hook or barb configured to engage a portion of the wall of an artery, vein, left atrial appendage, aneurysm, biological conduit, or other blood containing space or biological space.

105. The the kit of any one of claims 101 and 102, wherein the expandable metal retention structure comprises a plurality of elongated ribs extending from ring structures on both ends.

106. The the kit of claim 105, wherein at least one elongated rib comprises a hook or barb configured to engage a portion of the wall of an artery, vein, left atrial appendage, aneurysm, biological conduit, or other blood containing space or biological space.

107. The the kit of any one of claims 101-106, wherein the elongated ribs are biased outward.

108. The the kit of claim 101-106, wherein the expandable metal retention structure is self-expanding.

109. The the kit of any one of claims 101-106, wherein the retention structure comprises nitinol or stainless steel.

110. The the kit of any one of claims 101-106, wherein the external diameter of the ring structures when expanded, is 3-40 mm, as measured parallel to the second axis, and the diameter of the balloon, when expanded, is 3-40 mm, when measured parallel to the second axis.

111. The kit of any one of claims 101-106, wherein one end of the expandable metal retention structure is joined to a distal portion or distal neck of the balloon.

112. The kit of any one of claims 101-106, wherein one end of the expandable metal retention structure is joined to a proximal portion or proximal neck of the balloon.

113. The kit of any one of claims 1-112, further comprising one or more second medical devices comprising an elongated body, expandable body, or solidifying fluid, can be placed through the lumen of the second catheter into a biological space adjacent to the balloon;
  wherein, after expansion of the balloon, the second catheter can be pulled back until the distal tip of the second catheter is located in the central void or interior volume of the balloon, while the first catheter and the balloon remain fixed in position, and all, or a portion of, one or more second medical devices comprising an elongated body, expandable body, solidifying fluid or other balloon support material can be passed through the second lumen of the second catheter and placed into the central void or interior volume of the balloon; and, 114. wherein, after expansion of the balloon and placement of all or a portion of one or more second medical devices comprising an elongated body, expandable body, solidifying fluid, or other balloon support material, the first catheter can be separated from the expanded balloon and the first and second catheters can be removed from the patient while the balloon and all or a portion of one or more elongated bodies, expandable bodies, solidifying fluids or other balloon support materials remain in the patient. The kit of any one of claims 1-113, comprising a carrier for the first flexible elongated body and at least a portion of the second flexible elongated body wherein the end of the carrier that holds the distal end of the first flexible elongated body is configured for joining to the proximal hub of the second catheter.

115. The kit of claim 114, wherein the carrier is configured into a coiled shape.

116. The kit of claims 1-113, wherein a portion of the first flexible elongated body of the second medical device is configured to contact the interior surface of the expanded balloon of the first medical device.

117. The kit of claims 1-113, wherein the largest overall diameter or tertiary diameter of the first flexible elongated body of the second medical device is in a range from 5% smaller than the largest diameter of the expanded balloon of the first medical device to 20% larger than the largest diameter of the expanded balloon of the first medical device.

118. The kit of claim 1-113, wherein the largest overall or tertiary diameter of the first flexible elongated body of the second medical device is 1, 2, 3, 4, 5, 6, 7, 8, 9, or 10 mm larger than the largest diameter of the expanded balloon of the first medical device.

119. The kit of claims 1-113, wherein the volume of the first flexible elongated body of the second medical device would fill 5-75% of the volume of the central void of the expanded balloon.

120. The kit of claims 1-113, wherein the volume of the first flexible elongated body of the second medical device would fill 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75% of the volume of the central void of the expanded balloon.

121. The kit of claims 1-113, comprising a fourth medical device configured to cause separation of the expanded balloon of the first medical device and the first catheter of the first medical device.

122. The kit of claim 121, wherein the fourth medical device is configured to form an electrical connection with the first catheter of the first medical device.

123. The kit of claim 121, wherein the fourth medical device is configured to form an electrical connection with the catheter of the third medical device.

124. The kit of claims 1-113, comprising a fifth medical device configured to cause separation of the first elongated or expandable body of the second medical device from the second elongated body of the second medical device.

125. The kit of claim 124, wherein the fifth medical device is configured to form an electrical connection with the second elongated body of the second medical device.

126. The kit of claims 1-113, comprising a sixth medical device configured to cause separation of the expanded balloon of the first medical device and the first catheter of the first medical device and also configured to cause separation of the first elongated or expandable body of the second medical device from the second elongated body of the second medical device.

127. The kit of claim 126, wherein the sixth medical device is configured to form an electrical connection with the first catheter of the first medical device and also configured to form an electrical connection with the second elongated body of the second medical device.

128. The kit of claims 121-127, comprising a seventh medical device configured to provide an electrical connection between the fourth medical device and the first catheter of the first medical device, between the fourth medical device and the catheter of the third medical device, between the fifth medical device and the second elongated body of the second medical device, or an electrical connection between the sixth medical device and the first catheter of the first medical device and the second elongated body of the second medical device.

129. The kit of claim 128, wherein the seventh medical device comprises an electrical cable.

130. The kit of claim 129, wherein seventh medical device comprises one or more electrical jacks or connectors.

131. The kit of claims 129 and 230, wherein the seventh medical device is configured to pass an electrical current to the first medical device, the second medical device, or the third medical device.

132. The kit of claims 1-131, further comprising a guidewire.

133. The kit of claim 132, where the diameter of the guidewire is 0.010-0.038 inch.

134. The kit of claim 132, where the diameter of the guidewire is 0.010, 0.011, 0.012, 0.013, 0.014, 0.015, 0.016, 0.017, 0.018, 0.033, 0.034, 0.035, 0.036, 0.037, or 0.038 inch.

135. The kit of claim 132-134, wherein the length of the guidewire is at least two times the length of the second catheter of the first medical device.

136. The kit of claim 132-134, wherein the length of the guidewire is 50-500 cm.

137. The kit of claim 132-134, wherein the length of the guidewire is 200-400 cm.

138. The kit of claim 132-137, wherein the tip of the guidewire as formed is angled relative to the body of the guidewire.

139. The kit of claim 137-137, wherein the tip of the guidewire is formed is curved relative to the body of the guidewire.

140. The kit of claim 139, wherein the curved tip generally forms a J or C-shape.

Aspects and embodiments related to methods of manufacturing a detachable balloon and detachable devices as disclosed herein:

1. A method of manufacturing a medical device for the treatment of a human patient comprising:
 a balloon comprising an opening in the proximal portion of the balloon and an opening in the distal portion of the balloon;
 a first catheter comprising a proximal hub; and
 a second catheter comprising a proximal hub;
wherein:
 the balloon can be pleated and folded;
 a distal end of the first catheter can be joined or operably coupled to the opening of in the proximal portion of the balloon;
 the second catheter passes through the entire lumen of the first catheter;
 the distal portion the second catheter passes through the opening in the proximal portion of the balloon, through the central void or internal volume of the balloon, and through the opening in the distal portion of the balloon;
 injection of fluid into the proximal hub of the first catheter, through the lumen of the first catheter, and into the central void or interior volume of the balloon can result in expansion of the balloon; and
 after expansion of the balloon in a human patient, the expanded balloon can be separated from the first catheter, and the first catheter and second catheter can be removed from the patient while the expanded balloon remains in the patient;

the method comprising:
 manufacturing a first catheter;
 manufacturing a second catheter;
 manufacturing a polymer balloon with a proximal opening, thereby creating a first polymer layer of the polymer balloon;
 expanding the polymer balloon;
 adding a first layer of metal with a thickness in the range of 0.0005 to 1 micron to at least a portion of the external surface of the balloon through a sputter coating or vapor deposition process;
 forming the wall of the metalized balloon into a pleated and folded configuration;
  joining or operably coupling the metalized polymer balloon to the first catheter in a manner that allows for the separation of the metalized polymer balloon from the first catheter after expansion in a patient.

2. A method of manufacturing a medical device for the treatment of a human patient comprising:
 a balloon comprising an opening in the proximal portion of the balloon and an opening in the distal portion of the balloon;
 a first catheter comprising a proximal hub; and
 a second catheter comprising a proximal hub;
wherein:
 the balloon can be pleated and folded;
 the distal end of the first catheter can be joined or operably coupled to the opening of in the proximal portion of the balloon;
 the second catheter passes through the entire lumen of the first catheter;
 a distal portion the second catheter passes through the opening in the proximal portion of the balloon, through the central void or internal volume of the balloon, and through the opening in the distal portion of the balloon;
 injection of fluid into the proximal hub of the first catheter, through the lumen of the first catheter, and into the central void or interior volume of the balloon can result in expansion of the balloon; and
 after expansion of the balloon in a human patient, the expanded balloon can be separated from the first catheter, and the first catheter and second catheter can be removed from the patient while the expanded balloon remains in the patient;
the method comprising:
 manufacturing a first catheter;
 manufacturing a second catheter;
 manufacturing a polymer balloon with a proximal opening and a distal opening, thereby creating a first polymer layer of the polymer balloon;
 expanding the polymer balloon;
 adding a first layer of metal with a thickness in the range of 0.0005 to 1 micron to at least a portion of the external surface of the balloon through a sputter coating or vapor deposition process;
 adding a second layer of metal with a thickness of 1 to 50 microns to at least a portion of the external surface of the first metal layer; through an electroforming or electroplating process;
 forming the wall of the metalized balloon into a pleated and folded configuration;
 joining or operably coupling the metalized polymer balloon to the first catheter in a manner that allows for the separation of the metalized polymer balloon from the first catheter after expansion in a patient.

3. A method of manufacturing a medical device for the treatment of a human patient comprising:
 a balloon comprising an opening in the proximal portion of the balloon and an opening in the distal portion of the balloon; and
 a first catheter comprising a proximal hub;
 a second catheter comprising a proximal hub;
wherein:
 the balloon can be pleated and folded;
 the distal end of the first catheter can be joined or operably coupled to the opening of in the proximal portion of the balloon;
 the second catheter passes through the entire lumen of the first catheter;
 a distal portion the second catheter passes through the opening in the proximal portion of the balloon, through the central void or internal volume of the balloon, and through the opening in the distal portion of the balloon;
 injection of fluid into the proximal hub of the first catheter, through the lumen of the first catheter, and into the central void or interior volume of the balloon can result in expansion of the balloon; and
 after expansion of the balloon in a human patient, the expanded balloon can be separated from the first catheter, and the first catheter and second catheter can be removed from the patient while the expanded balloon remains in the patient;
the method comprising:
 manufacturing a first catheter;
 manufacturing a second catheter;
 manufacturing a polymer balloon with a proximal and distal opening, thereby creating a first polymer layer of the polymer balloon;
 expanding the polymer balloon;
 adding a first adhesive layer to at least a portion of the external surface of the balloon;
 applying metal wire with a thickness of 25-100 microns to the external, adhesive-coated surface of the expanded balloon in a spiral, coil, braid, woven, or straight pattern, thereby creating a first metal layer;
 adding a second adhesive layer to at least a portion of the external adhesive-coated surface and at least a portion of the external metal wire covered surface of the expanded balloon;
 drying, hardening, or curing the adhesive layers;
 forming the wall of the metalized balloon into a pleated and folded configuration;
 joining or operably coupling the metalized polymer balloon to the first catheter in a manner that allows for the separation of the metalized polymer balloon from the first catheter after expansion in a patient.

4. The method of claim 1, wherein the first metal layer is gold, titanium, or combinations thereof.

5. The method of claim 1, wherein the balloon comprises a first metal layer that is continuous.

6. The method of claim 1, wherein the balloon comprises a first metal layer that is discontinuous.

7. The method of claim 6, wherein a first metal layer is formed on the proximal region, the intermediate region, the distal region, the proximal and intermediate regions, the intermediate and distal regions, or the proximal, intermediate, and distal regions.

8. The method of claims 6 and 7, wherein one or more masks are applied to an outer surface of the polymer balloon prior to creating the first metal layer such that only a portion of the external surface of the polymer balloon is covered by a first metal layer.

9. The method of claim 2, wherein the first metal layer comprises gold, titanium, or combinations thereof.

10. The method of claim 2, wherein the balloon comprises a first metal layer that is continuous.

11. The method of claim 2, wherein the balloon comprises a first metal layer that is discontinuous.

12. The method of claim 11, wherein a first metal layer is formed on the proximal region, the intermediate region, the distal region, the proximal and intermediate regions, the intermediate and distal regions, or the proximal, intermediate, and distal regions.

13. The method of claims 11 and 12, wherein one or more masks are applied to an outer surface of the polymer balloon prior to creating the first metal layer such that only a portion of the external surface of the polymer balloon is covered by a first metal layer.

14. The method of claim 2, wherein the second metal layer comprises gold, platinum, or combinations thereof.

15. The method of claim 2, wherein the balloon comprises a second metal layer that is continuous.

16. The method of claim 2, wherein the balloon comprises a second metal layer that is discontinuous.

17. The method of claim 16, wherein a second metal layer is formed on the proximal region, the intermediate region, the distal region, the proximal and intermediate regions, the intermediate and distal regions, or the proximal, intermediate, and distal regions.

18. The method of claims 16 and 17, wherein one or more masks are applied to an outer surface of the metalized balloon prior to creating the second metal layer such that only a portion of the external surface of the metalized balloon is covered by a second metal layer.

19. The method of claim 3, wherein the first layer of adhesive comprises urethane.

20. The method of claims 3 and 19, wherein the balloon comprises a first adhesive layer that is continuous.

21. The method of claims 3 and 19, wherein the balloon comprises a first adhesive layer that is discontinuous.

22. The method of claim 21, wherein a first adhesive layer is formed on the proximal region, the intermediate region, the distal region, the proximal and intermediate regions, the intermediate and distal regions, or the proximal, intermediate, and distal regions.

23. The method of claims 3 and 21-22, wherein one or more masks are applied to an outer surface of the polymer balloon prior to applying the first layer of adhesive such that only a portion of the external surface of the polymer balloon is coated by a first adhesive layer.

24. The method of claims 3 and 21-23, wherein the first adhesive layer is formed by dipping the balloon in a solution comprising urethane in a solvent having a concentration of urethane in a range of 1-20%.

25. The method of claims 3 and 21-23, wherein the first adhesive layer is formed by spraying the balloon in a solution comprising urethane in a solvent having a concentration of urethane in a range of 1-20%.

26. The method of claims 3 and 21-25, wherein the first metal layer comprises gold, platinum, iridium, silver, or combinations thereof.

27. The method of claims 3 and 26, wherein the metal wire is wound onto the expanded balloon.

28. The method of claims 3 and 27, wherein the pitch and angle of the winding of the wire is uniform.

29. The method of claims 3 and 27, wherein the pitch and angle of the winding of the wire is non-uniform.

30. The method of claim 3, wherein the second layer of adhesive comprises urethane.

31. The method of claims 3 and 19, wherein the balloon comprises a second adhesive layer that is continuous.

32. The method of claims 3 and 19, wherein the balloon comprises a second adhesive layer that is discontinuous.

33. The method of claim 21, wherein a second adhesive layer is formed on the proximal region, the intermediate region, the distal region, the proximal and intermediate regions, the intermediate and distal regions, or the proximal, intermediate, and distal regions.

34. The method of claims 3 and 21-22, wherein one or more masks are applied to an outer surface of the metalized balloon prior to applying the second layer of adhesive such that only a portion of the external surface of the metalized balloon is coated by a second adhesive layer.

35. The method of claims 3 and 21-23, wherein the second adhesive layer is formed by dipping the balloon in a solution comprising urethane in a solvent having a concentration of urethane in a range of 1-20%.

36. The method of claims 3 and 21-23, wherein the second adhesive layer is formed by spraying the balloon in a solution comprising urethane in a solvent having a concentration of urethane in a range of 1-20%.

37. The method of claim 32, wherein a second adhesive layer is formed on the proximal region, the intermediate region, the distal region, the proximal and intermediate regions, the intermediate and distal regions, or the proximal, intermediate, and distal regions.

38. The method of claims 32 and 37, wherein one or more masks are applied to an outer surface of the metalized balloon prior to applying the second layer of adhesive such that only a portion of the external surface of the metalized balloon is coated by a second adhesive layer.

39. The method of claims 1-3, wherein the polymer balloon comprises polyethylene terephthalate (PET), polyamide (nylon), or polyether block amide (Pebax).

40. The method of claims 1-3, wherein the polymer balloon is manufactured by blow molding.

41. The method of claims 1-3, wherein the balloon is formed with a distal region, a proximal region generally opposite the distal region, and an intermediate region transitioning from the distal region to the proximal region.

42. The method of claims 1-3, wherein the polymer layer is continuous, except for the proximal and distal opening.

43. The method of claims 1-3, wherein the rated burst pressure of the polymer balloon is <30, <25, <20, <15, <10, <5, <4, <3, <2, or <1 atmospheres.

44. The method of claims 1-3, wherein the thickness of a single wall of the polymer balloon is <75, <50, <25, <20, <15, <10, or <5 microns.

45. The method of claims 1-3, wherein forming the metalized balloon generates an overall wall with a thickness in a range of 3-175 microns.

46. The method of claims 1-3, wherein the medical device is manufactured such that at least a portion of the external surface of the balloon comprises a textured surface.

47. The method of claim 46, wherein the distance between the highest portions of the external surface of the balloon and the lowest portions of the external surface of the balloon is 0.0001-1 microns.

48. The method of manufacturing of claims 1-47, wherein the wall of the metalized balloon is formed into a pleated and folded configuration before joining or operatively coupling the metalized balloon to the first catheter.

49. The method of manufacturing of claims 1-47, wherein the wall of the metalized balloon is formed into a pleated and folded configuration after joining or operatively coupling the metalized balloon to the first catheter.

Aspects and embodiments related to methods of treating an artery or vein as disclosed herein:

1. A method of reducing the flow of blood in a segment of an artery or vein of a human patient with two or more medical devices, the method comprising:
  a) determining a diameter and length of a segment of artery or vein to be treated and selecting a first medical device comprising a balloon with an expanded diameter equal to or greater than the diameter of the selected segment of artery or vein and an expanded length such that the balloon can occupy at least a portion of the lumen of the selected artery and vein segment when the balloon of the first medical device is expanded:
  b) placing the balloon of the first medical device into the lumen of the selected segment of artery or vein, such first medical device comprising:
    i) a pleated and folded balloon configured for permanent implantation in a human patient, the balloon comprising:
      a distal region, a proximal region generally opposite the distal region, an intermediate region transitioning from the distal region to the proximal region, a first axis extending proximal-distal between the proximal region and distal region, and a second axis perpendicular to the first axis;
      a wall extending generally continuously from the proximal region through the intermediate region, to the distal region, with an exterior surface and an interior surface, the interior surface defining a central void or interior volume;
      an opening in the wall of the proximal region that allows for the passage of fluid from a first catheter into the central void or interior volume of the balloon and also allows for the passage of a portion of the second catheter into the central void or interior volume of the balloon;
      an opening in the wall of the distal region that allows for the passage of a portion of the second catheter out of the central void or interior volume of the balloon;
      a proximal neck or neck assembly; and
      a distal neck or neck assembly;
    ii) a first catheter that partially defines a first lumen to allow for passage of fluid from the proximal end of the first catheter to the distal end of the first catheter, and into the central void or interior volume of the balloon; the first catheter comprising:
      a proximal end comprising a proximal hub; and
      a distal portion that is operably coupled or joined to the proximal neck or neck assembly of the balloon;
    iii) a second catheter that defines a second lumen configured to accept a guidewire, elongated body, expandable body, or solidifying fluid, the second catheter comprising:
      a proximal end comprising a proximal hub;
      a proximal portion that passes through the proximal hub of the first catheter;
      a middle portion that passes through the lumen of the first catheter;
      a distal portion that extends distal to the distal end of the first catheter;
      a distal portion that passes through the proximal neck or neck assembly of the balloon;
      a distal portion that passes through the central void or interior volume of the balloon;
      a distal portion that engages or passes through the distal neck or neck assembly in the balloon; and
      a distal end that is open;
    iv) wherein:
      the passage of fluid through the first catheter into the central void or interior volume of the balloon results in expansion of the balloon;
      after expansion of the balloon, the second catheter can be moved forward or backward while the expanded balloon remains fixed in position;
      after expansion of the balloon, one or more first elongated bodies, expandable bodies, solidifying fluids, solutions comprising drugs or therapeutic agents, or solutions or suspensions comprising embolic particles can be placed through the lumen of the second catheter into a biological space adjacent to the balloon, including before or after advancing the tip of the second catheter forward;
      after expansion of the balloon, the second catheter can be pulled back until the distal tip of the second catheter is located in the central void or interior volume of the balloon, and one or more one or more first elongated bodies, expandable bodies, or solidifying fluids can be passed through the lumen of the second catheter and placed in the central void or interior volume of the balloon;
      the first catheter can be separated from the expanded balloon; and
      the first and second catheters can be removed from the patient while the balloon and the one or more first elongated bodies, expandable bodies, and solidifying fluids remain in the patient;
  c) delivering a fluid medium into the central void or interior volume of the balloon of the first medical device through the first lumen to cause the balloon to assume an expanded configuration wherein the expanded balloon fills a portion of the lumen of the selected artery or vein segment and is in contact with at least a portion of the wall of the artery or vein segment;
  d) withdrawing the second catheter of the first medical device until the distal tip of the second catheter of the first medical device is within the central void or interior volume of the expanded balloon of the first medical device, while maintaining the position of the expanded balloon of the first medical device;
  e) delivering the first elongated body or expandable body of the second medical device from the proximal end of the second catheter of the first medical device, through the lumen of the second catheter of the first medical device, and into the central void or interior volume of the expanded balloon of the first medical device, the second medical device comprising:
    i) a distal portion comprising a first elongated body or expandable body;
    ii) a proximal portion comprising a second elongated body or delivery system;
    iii) wherein:
      after placement of the first elongated body or expandable body of the second medical device into the expanded balloon of the first medical device, at least a portion of the first elongated body or expandable body of the second medical device contacts at least a portion of the wall of the expanded balloon of the first medical device;
      after placement of the first elongated body or expandable body of the second medical device into the central void or internal volume of the expanded balloon of the first medical device, but prior to separation of the first elongated body or expandable body of the second medical device and the second elongated body of the second medical device, the second medical device can be removed from the patient;
the first elongated body or expandable body can be separated from the second elongated body; and
after separation of the first elongated body or expandable body from the second elongated body, the second elongated body can be removed from the patient while the first elongated body or expandable body remains in the patient;
f) causing the first elongated body or expandable body of the second medical device to separate from the second elongated body of the second medical device and removing the second elongated body from the patient while leaving the first elongated body or expandable body of the second medical device in the patient;
g) repeating steps e) and f) until the desired percent volume of the central void or interior volume of the expanded balloon of the first medical device is filled with first elongated bodies or first expandable bodies;
h) causing the expanded balloon of the first medical device to separate from the first catheter of the first medical device and removing the first and second catheters of the first medical device from the patient while leaving the expanded balloon of the first medical device and the one or more first elongated bodies or first expandable bodies of the second medical device in the patient.

2. A method of reducing the flow of blood in a segment of an artery or vein of a human patient with two or more medical devices, the method comprising:
a) determining a diameter and length of a segment of artery or vein to be treated and selecting a first medical device comprising a balloon with an expanded diameter equal to or greater than the diameter of the selected segment of artery or vein and an expanded length such that the balloon can occupy at least a portion of the lumen of the selected artery and vein segment when the balloon of the first medical device is expanded:
b) placing the balloon of the first medical device into the lumen of the selected segment of artery or vein, such first medical device comprising:
   i) a pleated and folded balloon configured for permanent implantation in a human patient, the balloon comprising:
      a distal region, a proximal region generally opposite the distal region, an intermediate region transitioning from the distal region to the proximal region, a first axis extending proximal-distal between the proximal region and distal region, and a second axis perpendicular to the first axis;
      a wall extending generally continuously from the proximal region through the intermediate region, to the distal region, with an exterior surface and an interior surface, the interior surface defining a central void or interior volume;
      an opening in the wall of the proximal region that allows for the passage of fluid from a first catheter into the central void or interior volume of the balloon and also allows for the passage of a portion of the second catheter into the central void or interior volume of the balloon;
      an opening in the wall of the distal region that allows for the passage of a portion of the second catheter out of the central void or interior volume of the balloon;
      a proximal neck or neck assembly; and
      a distal neck or neck assembly;
   ii) a first catheter that partially defines a first lumen to allow for passage of fluid from the proximal end of the first catheter to the distal end of the first catheter, and into the central void or interior volume of the balloon; the first catheter comprising:
      a proximal end comprising a proximal hub; and
      a distal portion that is operably coupled or joined to the proximal neck or neck assembly of the balloon;
   iii) a second catheter that defines a second lumen configured to accept a guidewire, elongated body, expandable body, or solidifying fluid, the second catheter comprising:
      a proximal end comprising a proximal hub;
      a proximal portion that passes through the proximal hub of the first catheter;
      a middle portion that passes through the lumen of the first catheter;
      a distal portion that extends distal to the distal end of the first catheter;
      a distal portion that passes through the proximal neck or neck assembly of the balloon;
      a distal portion that passes through the central void or interior volume of the balloon;
      a distal portion that engages or passes through the distal neck or neck assembly in the balloon; and
      a distal end that is open;
   iv) wherein:
      the passage of fluid through the first catheter into the central void or interior volume of the balloon results in expansion of the balloon;
      after expansion of the balloon, the second catheter can be moved forward or backward while the expanded balloon remains fixed in position;
      after expansion of the balloon, one or more first elongated bodies, expandable bodies, solidifying fluids, solutions comprising drugs or therapeutic agents, or solutions or suspensions comprising embolic particles can be placed through the lumen of the second catheter into a biological space adjacent to the balloon, including before or after advancing the tip of the second catheter forward;
      after expansion of the balloon, the second catheter can be pulled back until the distal tip of the second catheter is located in the central void or interior volume of the balloon, and one or more one or more first elongated bodies, expandable bodies, or solidifying fluids can be passed through the lumen of the second catheter and placed in the central void or interior volume of the balloon;
      the first catheter can be separated from the expanded balloon; and
      the first and second catheters can be removed from the patient while the balloon and the one or more first elongated bodies, expandable bodies, and solidifying fluids remain in the patient;
c) delivering a fluid medium into the central void or interior volume of the balloon of the first medical device through the first lumen to cause the balloon to assume an expanded configuration wherein the expanded balloon fills a portion of the lumen of the selected artery or vein segment and is in contact with at least a portion of the wall of the artery or vein segment;
d) delivering at least a distal portion of a first elongated body or expandable body of the second medical device from the proximal end of the second catheter of the first medical device, through the lumen of the second catheter of the first medical device, and into the lumen of the artery or vein adjacent to the expanded balloon of the first medical device, the second medical device comprising:
  i) a distal portion comprising a first elongated body or expandable body;
  ii) a proximal portion comprising a second elongated body or delivery system;
  iii) wherein:
    after placement of the first elongated body or expandable body of the second medical device into the lumen of the artery or vein adjacent to the expanded balloon of the first medical device, at least a portion of the first elongated body or expandable body of the second medical device contacts at least a portion of the wall of the artery or vein adjacent to the expanded balloon of the first medical device;
    after placement of the first elongated body or expandable body of the second medical device into the lumen of the artery or vein adjacent to the expanded balloon of the first medical device, but prior to separation of the first elongated body or expandable body of the second medical device and the second elongated body of the second medical device, the second medical device can be removed from the patient;
    the first elongated body or expandable body can be separated from the second elongated body; and
    after separation of the first elongated body or expandable body from the second elongated body, the second elongated body can be removed from the patient while the first elongated body or expandable body remains in the patient;
e) withdrawing the second catheter of the first medical device until the distal tip of the second catheter of the first medical device is within the central void or interior volume of the expanded balloon of the first medical device, while maintaining the position of the expanded balloon of the first medical device;
f) delivering the remainder of the first elongated body or expandable body of the second medical device into the central void or interior volume of the expanded balloon of the first medical device, wherein at least a portion of the first elongated body or expandable body contacts at least a portion of the wall of the expanded balloon of the first medical device;
i) causing the first elongated body or expandable body of the second medical device to separate from the and the second elongated body of the second medical device and removing the second elongated body from the patient while leaving first elongated body or expandable body of the second medical device in the central void or interior volume of the expanded balloon of the first medical device;
j) optionally, delivering the first elongated body or expandable body of a second medical device from the proximal end of the second catheter of the first medical device, through the lumen of the second catheter of the first medical device and into the central void or interior volume of the expanded balloon of the first medical device;
k) optionally, causing the first elongated body or expandable body of the second medical device to separate from the second elongated body of the second medical device and removing the second elongated body from the patient while leaving first elongated body or expandable body of the second medical device in the central void or interior volume of the expanded balloon of the first medical device;
l) optionally, repeating steps j) and k) until the desired percent volume of the unfilled portion of the central void or interior volume of the expanded balloon of the first medical device is filled with first elongated bodies or expandable bodies;
m) causing the expanded balloon of the first medical device to separate from the first catheter of the first medical device and removing the first and second catheters of the first medical device from the patient while leaving the expanded balloon of the first medical device and the one or more first elongated bodies or expandable bodies of the second medical device in the patient.

3. The method of claims 1 and 2, wherein, after expansion of the balloon of the first medical device and prior to withdrawing the second catheter of the first medical device into the central void or interior volume of the expanded balloon of the first medical device, a solution comprising a fluoroscopic contrast agent, drug or therapeutic agent, a solidifying fluid, a solution or suspension comprising embolic particles, or combinations thereof, is injected through the lumen of the second catheter of the first medical device and into the lumen of the artery or vein adjacent to the expanded balloon of the first medical device.

4. The method of claim 3, wherein a syringe or other appropriate delivery system, is used to inject the drug, therapeutic agent, solidifying fluid, solution or suspension comprising embolic particles, or combinations thereof, through the lumen of the shaft of the second catheter of the first medical device, and into the lumen of the artery or vein adjacent to the expanded balloon of the first medical device.

5. The method of claims 3 and 4, wherein, prior to injecting the drug, therapeutic agent, solidifying fluid, or solution or suspension comprising embolic particles through the lumen of the shaft of the second catheter of the first medical device and into the lumen of the artery or vein adjacent to the expanded balloon of the first medical device, the second catheter of the first medical device is advanced forward in the artery or vein while maintaining the position of the balloon of the first medical device.

6. The method of claims 1 and 2, wherein, prior to causing the expanded balloon of the first medical device to separate from the first catheter of the first medical device, a solidifying fluid is injected from the proximal end of the first catheter of the first medical device, through the lumen of the first catheter of the first medical device, and into the central void or interior volume of the expanded balloon of the first medical device.

7. The method of claims 1-6, wherein, after placement in the central void or interior volume of the expanded balloon, a first elongated body or expandable body of the second medical device exerts a force on the wall of the expanded balloon of the first medical device.

8. The method of claim 7, wherein the force on the wall of the expanded balloon of the first medical device is in an outward direction.

9. The method of claims 1-8, wherein the largest diameter or tertiary diameter of the second medical device is equal to the largest diameter of the expanded balloon.

10. The method of claims 1-8, wherein the largest diameter or tertiary diameter of the first elongated or expandable body of the second medical device is in a range from equal to the largest diameter of the expanded balloon of the first medical device to 50% larger than the largest diameter of the expanded balloon of the first medical device.

11. The method of claims 1-8, wherein the largest diameter or tertiary diameter of the first elongated or expandable body of the second medical device is 1, 2, 3, 4, 5, 6, 7, 8, 9, or 10 mm larger than the largest diameter of the expanded balloon of the first medical device.

12. The method of claims 1-11, wherein the volume of the one or more first elongated or expandable bodies of the second medical device would fill 5-75% of the volume of the central void of the expanded balloon.

13. The method of claims 1-11, wherein the volume of the first elongated or expandable body of the second medical device would fill 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75% of the volume of the central void of the expanded balloon.

14. The method of claims 1-13, wherein the expanded balloon is configured to contact at least 100%, 90%, 80%, 70%, 60%, 50%, 40%, 30%, 20%, 10%, or 5% of the area of the luminal surface of the selected segment of artery or vein.

15. The method of claims 1-14, wherein the expanded balloon is configured to fill at least 100%, 90%, 80%, 70%, 60%, 50%, 40%, 30%, 20%, 10%, or 5% of the volume of the lumen of the selected segment of the artery or vein.

16. The method of claims 1-15, wherein the distal portion of the second catheter of the first medical device comprises a radiopaque portion, ring or marker that is visible during fluoroscopy, and wherein fluoroscopy is used to monitor the position of the distal portion of the second catheter of the first medical device relative to the position of the distal portion of the balloon of the first medical device when the second catheter of the first medical device is moved.

17. The method of claims 1-16, wherein the distal portion of the balloon of the first medical device comprises a radiopaque portion, ring or marker that is visible during fluoroscopy, and wherein fluoroscopy is used to monitor the position of the distal portion of the second catheter of the first medical device relative to the position of the distal portion of the balloon of the first catheter when the second catheter of the first medical device is moved.

18. The method of claims 1-17, wherein at least a portion of the distal telescoping structure of the first medical device comprises a radiopaque portion, ring or marker that is visible during fluoroscopy, and wherein fluoroscopy is used to monitor the position of the distal portion of the second catheter of the first medical device relative to the position of the distal telescoping structure of the first medical device when the second catheter of the first medical device is moved.

19. The method of claims 1-18, wherein at least a portion of the first elongated or expanded body of the second medical device is made from a material that is radiopaque and visible during fluoroscopy and fluoroscopy is used to monitor the placement and position of the first elongated or expanded body of the second medical device.

20. The method of claims 1-19, wherein the second catheter of the first medical device comprises one, two, or more than two radiopaque portions, rings or markers, and fluoroscopy is used to monitor the position of the second catheter of the first medical device relative to the position of the first elongated or expanded body of the second medical device.

21. The method of claims 1-20, wherein the distal portion of the first catheter of the first medical device comprises a radiopaque marker that is visible during fluoroscopy, and wherein fluoroscopy is used to monitor the separation of the expanded balloon of the first medical device from the first catheter of the first medical device.

22. The method of claims 1-21, wherein the proximal portion of the balloon of the first medical device comprises a radiopaque marker that is visible during fluoroscopy, and wherein fluoroscopy is used to monitor the separation of the expanded balloon of the first medical device from the first catheter of the first medical device.

23. The method of claims 1-22, wherein the distal portion of the first catheter of the first medical device comprises a radiopaque marker that is visible during fluoroscopy, and wherein fluoroscopy is used to monitor the separation of the expanded balloon of the first medical device from the first catheter of the first medical device.

24. The method of claims 17-23, wherein the radiopaque portion, ring, or marker comprises platinum, iridium, gold, tungsten, or combinations thereof.

25. The method of claims 1-24, wherein the wall of artery or vein has been damaged or has ruptured.

26. The method of claims 1-24, wherein the wall of artery or vein has not been damaged or ruptured.

27. The method of claims 1-26, wherein the second catheter of the first medical device and the distal neck or distal neck assembly of the balloon of the first medical device are coupled by a friction fit, and wherein the second catheter of the first medical device and the expanded balloon of the first medical device are separated by applying an axial tensile force to the tubular segment.

28. The method of claim 27, wherein the second catheter of the first medical device and the distal neck or distal neck assembly of the balloon of the first medical device are coupled by an elastomer valve.

29. The method of claim 28, wherein the elastomer valve serves to reduce blood flow through the central void or interior volume of the expanded balloon of the first medical device following removal of the second catheter of the first medical device from the patient.

30. The method of claims 1-29, wherein the first catheter of the first medical device and the proximal neck or proximal neck assembly of the balloon of the first medical device are coupled by a friction fit, and wherein the first catheter of the first medical device and the expanded balloon of the first medical device are separated by applying an axial tensile force to an elastomer tubular segment.

31. The method of claim 30, wherein the first catheter of the first medical device and the proximal neck or proximal neck assembly of the balloon of the first medical device are coupled by the elastomer tubular segment.

32. The method of claims 1-29, wherein the first catheter of the first medical device and the balloon of the first medical device are coupled by a tubular structure, wherein a male portion of the tubular structure is joined to the distal end of the first catheter and a female portion of the tubular structure is joined to the proximal neck or proximal neck assembly of the balloon of the first medical device.

33. The method of claim 32, wherein the proximal neck of the balloon of the first medical device is the second portion of the mechanical latch.

34. The method of claims 32 and 33, wherein the two portions of the mechanical latch are engaged or operably coupled when the second catheter of the first medical device passes through the mechanical latch.

35. The method of claim 34, wherein the second catheter of the first medical device is removed from the mechanical latch and the mechanical latch and the two portions of the mechanical latch are disengaged or operably decoupled.

36. The method of claim 35, wherein the first catheter of the first medical device and the expanded balloon of the first medical device are pulled apart.

37. The method of claims 1-29, wherein the first catheter of the first medical device and the proximal neck or proximal neck assembly of the balloon of the first medical device are joined by an adhesive, glue, or solder, and wherein a tubular segment sensitive to electrolysis of the first medical device is corroded by electrolysis.

38. The method of claim 37, wherein the first catheter of the first medical device and the expanded balloon of the first medical device are pulled apart after corrosion of a portion of the proximal neck or proximal neck assembly of the balloon of the first medical device.

39. The method of claims 1-29, wherein the first catheter of the first medical device and the proximal neck or proximal neck assembly of the balloon of the first medical device are joined by an adhesive, glue, or solder, and wherein a distal portion of the first catheter of the first medical device, a portion of the proximal neck or proximal neck assembly of the balloon of the first medical device, or a portion of a bond between a distal portion of the first catheter of the first medical device and a heat sensitive first tubular segment is melted by heating.

40. The method of claim 39, wherein the first catheter of the first medical device and the expanded balloon of the first medical device are pulled apart after melting a distal portion of the first catheter of the first medical device, a portion of the proximal neck or proximal neck assembly of the balloon of the first medical device, or a portion of a bond between a distal portion of the first catheter of the first medical device and the proximal neck or proximal neck assembly of the balloon of the first medical device.

41. The method of claims 1-40, wherein the first elongated or expandable body of the second medical device is flexible, the second elongated body of the second medical device is flexible, or the first elongated body and the second elongated body of the second medical device are flexible.

42. The method of claims 1-41, wherein the first catheter of the first medical device is flexible, the second catheter of the first medical device is flexible, or the first catheter and second catheter of the first medical device are flexible.

43. The method of claims 1-42, wherein the balloon of the first medical device is detachable.

44. The method of claims 1-43, wherein the balloon of the first medical device s collapsed or compressed prior to expansion.

45. The method of claims 1-43, wherein the fluid used to expand the balloon of the first medical device is water, a saline solution, a fluoroscopic contrast agent, or combinations thereof.

46. The method of claims 1-45, wherein a solution comprising a fluoroscopic contrast agent is injected during fluoroscopy into the hub of the second catheter of the first medical device, through the second catheter of the first medical device, and into the lumen of the artery or vein adjacent to the distal tip of the second catheter of the first medical device prior to the expansion of the balloon of the first medical device.

47. The method of claims 1-46, wherein a solution comprising a fluoroscopic contrast agent is injected during fluoroscopy into the hub of the second catheter of the first medical device, through the second catheter of the first medical device, and into the lumen of the artery or vein adjacent to the distal tip of the second catheter of the first medical device after expansion of the balloon of the first medical device but prior to separation of the expanded balloon of the first medical device and the first catheter of the first medical device.

48. The method of claims 1-47, wherein a solution comprising a fluoroscopic contrast agent is injected during fluoroscopy into the hub of the second catheter of the first medical device, through the second catheter of the first medical device, and into the lumen of the artery or vein adjacent to the distal tip of the second catheter of the first medical device after separation of the expanded balloon of the first medical device and the first catheter of the first medical device.

49. The method of claims 1-48, comprising providing the first medical device and the one or more second medical devices.

Aspects and embodiments related to methods of treating an artery or vein with a retention structure as disclosed herein:

1. A method of reducing the flow of blood in a segment of an artery or vein of a human patient with two or more medical devices, the method comprising:
   a) determining a diameter and length of a segment of artery or vein to be treated and selecting a first medical device comprising a balloon with an expanded diameter equal to or greater than the diameter of the selected segment of artery or vein and an expanded length such that the balloon can occupy at least a portion of the lumen of the selected artery and vein segment when the balloon of the first medical device is expanded;
   b) placing the balloon of the first medical device into the lumen of the selected segment of artery or vein, such first medical device comprising:
      i) a pleated and folded balloon configured for permanent implantation in a human patient, the balloon comprising:
         a distal region, a proximal region generally opposite the distal region, an intermediate region transitioning from the distal region to the proximal region, a first axis extending proximal-distal between the proximal region and distal region, and a second axis perpendicular to the first axis;
         a wall extending generally continuously from the proximal region through the intermediate region, to the distal region, with an exterior surface and an interior surface, the interior surface defining a central void or interior volume;
         an opening in the wall of the proximal region that allows for the passage of fluid from a first catheter into the central void or interior volume of the balloon and also allows for the passage of a portion of the second catheter into the central void or interior volume of the balloon;
         an opening in the wall of the distal region that allows for the passage of a portion of the second catheter out of the central void or interior volume of the balloon;
         a proximal neck or neck assembly;
         a distal neck or neck assembly; and
         a self-expanding metal retention structure wherein, after expansion, the diameter of at least a portion of the self-expanding metal structure is equal to or greater than the diameter of the expanded balloon;
      ii) a first catheter that partially defines a first lumen to allow for passage of fluid from the proximal end of the first catheter to the distal end of the first catheter, and into the central void or interior volume of the balloon; the first catheter comprising:
a proximal end comprising a proximal hub;
a proximal portion that passes through the proximal hub of the third catheter;
a middle portion that passes through the lumen of the third catheter;
a distal portion that extends distal to the distal end of the third catheter; and
a distal portion that is operably coupled or joined to the proximal neck or neck assembly of the balloon;
iii) a second catheter that defines a second lumen configured to accept a guidewire, elongated body, expandable body, or solidifying fluid, the second catheter comprising:
a proximal end comprising a proximal hub;
a proximal portion that passes through the proximal hub of the first catheter;
a middle portion that passes through the lumen of the first catheter;
a distal portion that extends distal to the distal end of the third catheter and the distal end of the first catheter;
a distal portion that passes through the proximal neck or neck assembly of the balloon;
a distal portion that passes through the central void or interior volume of the balloon;
a distal portion that engages or passes through the distal neck or neck assembly of the balloon; and
a distal end that is open;
iv) a third catheter that partially defines a third lumen to allow for passage of fluid from the proximal end of the third catheter to the distal end of the third catheter and is configured to constrain the retention structure of the balloon of the first medical device; the second catheter comprising:
a proximal end comprising a proximal hub;
a distal end that is open;
v) wherein:
the third catheter of the first medical device can move forward or backward while the first catheter, the third catheter, and the balloon of the first medical device remain fixed in position;
the passage of fluid through the first catheter into the central void or interior volume of the balloon results in expansion of the balloon;
after expansion of the balloon, the second catheter can be moved forward or backward while the expanded balloon remains fixed in position;
after expansion of the balloon, one or more first elongated bodies, expandable bodies, solidifying fluids, solutions comprising drugs or therapeutic agents, or solutions or suspensions comprising embolic particles can be placed through the lumen of the second catheter into a biological space adjacent to the balloon, including before or after advancing the tip of the second catheter forward;
after expansion of the balloon, the second catheter can be pulled back until the distal tip of the second catheter is located in the central void or interior volume of the balloon, and one or more one or more first elongated bodies, expandable bodies, or solidifying fluids can be passed through the lumen of the second catheter and placed in the central void or interior volume of the balloon;
the first catheter can be separated from the expanded balloon; and
the first and second catheters can be removed from the patient while the balloon and the one or more first elongated bodies, expandable bodies, and solidifying fluids remain in the patient.
c) pulling back the third catheter of the first medical device while the first catheter and the balloon of the first medical device remain fixed in position, until the retention structure of the balloon of the first medical device expands and a portion of the retention structure makes contact with the wall of the artery or vein;
d) optionally, placing axial tensile force on the first catheter after expansion of the retention structure to confirm attachment of the retention structure to the wall of the artery or vein;
e) pulling back the third catheter of the first medical device until the balloon of the first medical device is uncovered;
f) delivering a fluid medium into the central void or interior volume of the balloon of the first medical device through the first lumen to cause the balloon to assume an expanded configuration wherein the expanded balloon fills a portion of the lumen of the selected artery or vein segment and is in contact with at least a portion of the wall of the artery or vein segment;
g) withdrawing the second catheter of the first medical device until the distal tip of the second catheter of the first medical device is within the central void or interior volume of the expanded balloon of the first medical device, while maintaining the position of the expanded balloon of the first medical device;
h) delivering the first elongated body or expandable body of the second medical device from the proximal end of the second catheter of the first medical device, through the lumen of the second catheter of the first medical device, and into the central void or interior volume of the expanded balloon of the first medical device, the second medical device comprising:
i) a distal portion comprising a first elongated body or expandable body;
ii) a proximal portion comprising a second elongated body or delivery system;
iii) wherein:
after placement of the first elongated body or expandable body of the second medical device into the expanded balloon of the first medical device, at least a portion of the first elongated body or expandable body of the second medical device contacts at least a portion of the wall of the expanded balloon of the first medical device;
after placement of the first elongated body or expandable body of the second medical device into the central void or internal volume of the expanded balloon of the first medical device, but prior to separation of the first elongated body or expandable body of the second medical device and the second elongated body of the second medical device, the second medical device can be removed from the patient;
the first elongated body or expandable body can be separated from the second elongated body; and
after separation of the first elongated body or expandable body from the second elongated body, the second elongated body can be removed from the patient while the first elongated body or expandable body remains in the patient;

i) causing the first elongated body or expandable body of the second medical device to separate from the second elongated body of the second medical device and removing the second elongated body from the patient while leaving first elongated body or expandable body of the second medical device in the central void or interior volume of the expanded balloon of the first medical device;

j) optionally, repeating steps h) and i) until the desired percent volume of the central void or interior volume of the expanded balloon of the first medical device is filled with first elongated bodies or expandable bodies;

k) causing the expanded balloon of the first medical device to separate from the first catheter of the first medical device and removing the first and second catheters of the first medical device from the patient while leaving the expanded balloon of the first medical device and the one or more first elongated bodies or expandable bodies of the second medical device in the patient.

2. A method of reducing the flow of blood in a segment of an artery or vein of a human patient with two or more medical devices, the method comprising:
   a) determining a diameter and length of a segment of artery or vein to be treated and selecting a first medical device comprising a balloon with an expanded diameter equal to or greater than the diameter of the selected segment of artery or vein and an expanded length such that the balloon can occupy at least a portion of the lumen of the selected artery and vein segment when the balloon of the first medical device is expanded:
   b) placing the balloon of the first medical device into the lumen of the selected segment of artery or vein, such first medical device comprising:
      i) a pleated and folded balloon configured for permanent implantation in a human patient, the balloon comprising:
         a distal region, a proximal region generally opposite the distal region, an intermediate region transitioning from the distal region to the proximal region, a first axis extending proximal-distal between the proximal region and distal region, and a second axis perpendicular to the first axis;
         a wall extending generally continuously from the proximal region through the intermediate region, to the distal region, with an exterior surface and an interior surface, the interior surface defining a central void or interior volume;
         an opening in the wall of the proximal region that allows for the passage of fluid from a first catheter into the central void or interior volume of the balloon and also allows for the passage of a portion of the second catheter into the central void or interior volume of the balloon;
         an opening in the wall of the distal region that allows for the passage of a portion of the second catheter out of the central void or interior volume of the balloon;
         a proximal neck or neck assembly;
         a distal neck or neck assembly; and
         a self-expanding metal retention structure wherein, after expansion, the diameter of at least a portion of the metal structure is equal to or greater than the diameter of the expanded balloon;
      ii) a first catheter that partially defines a first lumen to allow for passage of fluid from the proximal end of the first catheter to the distal end of the first catheter, and into the central void or interior volume of the balloon; the first catheter comprising:
         a proximal end comprising a proximal hub;
         a proximal portion that passes through the proximal hub of the third catheter;
         a middle portion that passes through the lumen of the third catheter;
         a distal portion that extends distal to the distal end of the third catheter; and
         a distal portion that is operably coupled or joined to the proximal neck or neck assembly of the balloon;
      iii) a second catheter that defines a second lumen configured to accept a guidewire, elongated body, expandable body, or solidifying fluid, the second catheter comprising:
         a proximal end comprising a proximal hub;
         a proximal portion that passes through the proximal hub of the first catheter;
         a middle portion that passes through the lumen of the first catheter;
         a distal portion that extends distal to the distal end of the third catheter and the distal end of the first catheter;
         a distal portion that passes through the proximal neck or neck assembly of the balloon;
         a distal portion that passes through the central void or interior volume of the balloon;
         a distal portion that engages or passes through the distal neck or neck assembly of the balloon; and
         a distal end that is open;
      iv) a third catheter that partially defines a third lumen to allow for passage of fluid from the proximal end of the third catheter to the distal end of the third catheter and is configured to constrain the retention structure of the balloon of the first medical device; the second catheter comprising:
         a proximal end comprising a proximal hub;
         a distal end that is open;
      v) wherein:
         the third catheter of the first medical device can move forward or backward while the first catheter, the third catheter, and the balloon of the first medical device remain fixed in position;
         the passage of fluid through the first catheter into the central void or interior volume of the balloon results in expansion of the balloon;
         after expansion of the balloon, the second catheter can be moved forward or backward while the expanded balloon remains fixed in position;
         after expansion of the balloon, one or more first elongated bodies, expandable bodies, solidifying fluids, solutions comprising drugs or therapeutic agents, or solutions or suspensions comprising embolic particles can be placed through the lumen of the second catheter into a biological space adjacent to the balloon, including before or after advancing the tip of the second catheter forward;
         after expansion of the balloon, the second catheter can be pulled back until the distal tip of the second catheter is located in the central void or interior volume of the balloon, and one or more one or more first elongated bodies, expandable bodies, or solidifying fluids can be passed through the lumen of the second catheter and placed in the central void or interior volume of the balloon;

the first catheter can be separated from the expanded balloon; and the first and second catheters can be removed from the patient while the balloon and the one or more first elongated bodies, expandable bodies, and solidifying fluids remain in the patient;

c) pulling back the third catheter of the first medical device while the first catheter and the balloon of the first medical device remain fixed in position, until the retention structure of the balloon of the first medical device expands and a portion of the retention structure makes contact with the wall of the artery or vein;

d) optionally, placing axial tensile force on the first catheter after expansion of the retention structure to confirm attachment of the retention structure to the wall of the artery or vein;

e) pulling back the third catheter of the first medical device until the balloon of the first medical device is uncovered;

f) delivering a fluid medium into the central void or interior volume of the balloon of the first medical device through the first lumen to cause the balloon to assume an expanded configuration wherein the expanded balloon fills a portion of the lumen of the selected artery or vein segment and is in contact with at least a portion of the wall of the artery or vein segment;

g) delivering at least a distal portion of a first elongated body or expandable body of the second medical device from the proximal end of the second catheter of the first medical device, through the lumen of the second catheter of the first medical device, and into the lumen of the artery or vein adjacent to the expanded balloon of the first medical device, the second medical device comprising:
  i) a distal portion comprising a first elongated body or expandable body;
  ii) a proximal portion comprising a second elongated body or delivery system;
  iii) wherein:
    after placement of the first elongated body or expandable body of the second medical device into the lumen of the artery or vein adjacent to the expanded balloon of the first medical device, at least a portion of the first elongated body or expandable body of the second medical device contacts at least a portion of the wall of the artery or vein adjacent to the expanded balloon of the first medical device;
    after placement of the first elongated body or expandable body of the second medical device into the lumen of the artery or vein adjacent to the expanded balloon of the first medical device, but prior to separation of the first elongated body or expandable body of the second medical device and the second elongated body of the second medical device, the second medical device can be removed from the patient;
    the first elongated body or expandable body can be separated from the second elongated body; and
    after separation of the first elongated body or expandable body from the second elongated body, the second elongated body can be removed from the patient while the first elongated body or expandable body remains in the patient;

h) withdrawing the second catheter of the first medical device until the distal tip of the second catheter of the first medical device is within the central void or interior volume of the expanded balloon of the first medical device, while maintaining the position of the expanded balloon of the first medical device;

i) delivering the remainder of the first elongated body or expandable body of the second medical device into the central void or interior volume of the expanded balloon of the first medical device, wherein at least a portion of the first elongated body or expandable body contacts at least a portion of the wall of the expanded balloon of the first medical device;

j) causing the first elongated body or expandable body of the second medical device to separate from the second elongated body of the second medical device and removing the second elongated body from the patient while leaving first elongated body or expandable body of the second medical device in the central void or interior volume of the expanded balloon of the first medical device;

k) optionally, delivering the first elongated body or expandable body of a second medical device from the proximal end of the second catheter of the first medical device, through the lumen of the second catheter of the first medical device and into the central void or interior volume of the expanded balloon of the first medical device;

l) optionally, causing the first elongated body or expandable body of the second medical device to separate from the second elongated body of the second medical device and removing the second elongated body from the patient while leaving first elongated body or expandable body of the second medical device in the central void or interior volume of the expanded balloon of the first medical device;

m) optionally, repeating steps k) and l) until the desired percent volume of the unfilled portion of the central void or interior volume of the expanded balloon of the first medical device is filled with first elongated bodies or expandable bodies;

n) causing the expanded balloon of the first medical device to separate from the first catheter of the first medical device and removing the first and second catheters of the first medical device from the patient while leaving the expanded balloon of the first medical device and the one or more first elongated bodies or expandable bodies of the second medical device in the patient.

3. The method of claims 1 and 2, wherein, after expansion of the balloon of the first medical device and prior to withdrawing the second catheter of the first medical device into the central void or interior volume of the expanded balloon of the first medical device, a solution comprising a fluoroscopic contrast agent, drug or therapeutic agent, a solidifying fluid, a solution or suspension comprising embolic particles, or combinations thereof, is injected through the lumen of the second catheter of the first medical device and into the lumen of the artery or vein adjacent to the expanded balloon of the first medical device.

4. The method of claim 3, wherein a syringe or other appropriate delivery system, is used to inject the fluoroscopic contrast agent, drug, therapeutic agent, solidifying fluid, solution or suspension comprising embolic particles, or combinations thereof, through the lumen of the shaft of the second catheter of the first medical device, and into the lumen of the artery or vein adjacent to the expanded balloon of the first medical device.

5. The method of claims 3 and 4, wherein, prior to injecting the fluoroscopic contrast agent, drug, therapeutic agent, solidifying fluid, or solution or suspension comprising embolic particles through the lumen of the shaft of the second catheter of the first medical device and into the lumen of the artery or vein adjacent to the expanded balloon of the first medical device, the second catheter of the first medical device is advanced forward in the artery or vein while maintaining the position of the balloon of the first medical device.

6. The method of claims 1 and 2, wherein, prior to causing the expanded balloon of the first medical device to separate from the first catheter of the first medical device, a solidifying fluid is injected from the proximal end of the first catheter of the first medical device, through the lumen of the first catheter of the first medical device, and into the central void or interior volume of the expanded balloon of the first medical device.

7. The method of claims 1-6, wherein, after placement in the central void or interior volume of the expanded balloon, a first elongated body or expandable body of the second medical device exerts a force on the wall of the expanded balloon of the first medical device.

8. The method of claim 7, wherein the force on the wall of the expanded balloon of the first medical device is in an outward direction.

9. The method of claims 1-8, wherein the largest diameter or tertiary diameter of the second medical device is equal to the largest diameter of the expanded balloon.

10. The method of claims 1-8, wherein the largest diameter or tertiary diameter of the first elongated or expandable body of the second medical device is in a range from equal to the largest diameter of the expanded balloon of the first medical device to 50% larger than the largest diameter of the expanded balloon of the first medical device.

11. The method of claims 1-8, wherein the largest diameter or tertiary diameter of the first elongated or expandable body of the second medical device is 1, 2, 3, 4, 5, 6, 7, 8, 9, or 10 mm larger than the largest diameter of the expanded balloon of the first medical device.

12. The method of claims 1-11, wherein the volume of the one or more first elongated or expandable bodies of the second medical device would fill 5-75% of the volume of the central void of the expanded balloon.

13. The method of claims 1-11, wherein the volume of the first elongated or expandable body of the second medical device would fill 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75% of the volume of the central void of the expanded balloon.

14. The method of claims 1-13, wherein the expanded balloon is configured to contact at least 100%, 90%, 80%, 70, 60%, 50%, 40%, 30%, 20%, 10%, or 5% of the area of the luminal surface of the selected segment of the artery or vein.

15. The method of claims 1-14, wherein the expanded balloon is configured to fill at least 100%, 90%, 80%, 70%, 60%, 50%, 40%, 30%, 20%, 10%, or 5% of the volume of the lumen of the selected segment of artery or vein.

16. The method of claims 1-15, wherein the distal portion of the second catheter of the first medical device comprises a radiopaque portion, ring or marker that is visible during fluoroscopy, and wherein fluoroscopy is used to monitor the position of the distal portion of the second catheter of the first medical device relative to the position of the distal portion of the balloon of the first medical device when the second catheter of the first medical device is moved.

17. The method of claims 1-16, wherein the distal portion of the balloon of the first medical device comprises a radiopaque portion, ring or marker that is visible during fluoroscopy, and wherein fluoroscopy is used to monitor the position of the distal portion of the second catheter of the first medical device relative to the position of the distal portion of the balloon of the first catheter when the second catheter of the first medical device is moved.

18. The method of claims 1-17, wherein at least a portion of the distal telescoping structure of the first medical device comprises a radiopaque portion, ring or marker that is visible during fluoroscopy, and wherein fluoroscopy is used to monitor the position of the distal portion of the second catheter of the first medical device relative to the position of the distal telescoping structure of the first medical device when the second catheter of the first medical device is moved.

19. The method of claims 1-18, wherein at least a portion of the first elongated or expanded body of the second medical device is made from a material that is radiopaque and visible during fluoroscopy and fluoroscopy is used to monitor the placement and position of the first elongated or expanded body of the second medical device.

20. The method of claims 1-19, wherein the second catheter of the first medical device comprises one, two, or more than two radiopaque portions, rings or markers, and fluoroscopy is used to monitor the position of the second catheter of the first medical device relative to the position of the first elongated or expanded body of the second medical device.

21. The method of claims 1-20, wherein the distal portion of the first catheter of the first medical device comprises a radiopaque marker that is visible during fluoroscopy, and wherein fluoroscopy is used to monitor the separation of the expanded balloon of the first medical device from the first catheter of the first medical device.

22. The method of claims 1-21, wherein the proximal portion of the balloon of the first medical device comprises a radiopaque marker that is visible during fluoroscopy, and wherein fluoroscopy is used to monitor the separation of the expanded balloon of the first medical device from the first catheter of the first medical device.

23. The method of claims 16-22, wherein the radiopaque portion, ring, or marker comprises platinum, iridium, gold, tungsten, or combinations thereof.

24. The method of claims 1-23, wherein the wall of artery or vein has been damaged or has ruptured.

25. The method of claims 1-23, wherein the wall of artery or vein has not been damaged or ruptured.

26. The method of claims 1-25, wherein the second catheter of the first medical device and the distal neck or distal neck assembly of the balloon of the first medical device are coupled by a friction fit, and wherein the second catheter of the first medical device and the expanded balloon of the first medical device are separated by applying an axial tensile force to the coupling.

27. The method of claim 26, wherein the second catheter of the first medical device and the distal neck or distal neck assembly of the balloon of the first medical device are coupled by an elastomer valve.

28. The method of claim 27, wherein the elastomer valve serves to reduce blood flow through the central void or interior volume of the expanded balloon of the first medical device following removal of the second catheter of the first medical device from the patient.

29. The method of claims 1-28, wherein the first catheter of the first medical device and the proximal neck or proximal neck assembly of the balloon of the first medical device are coupled by a friction fit, and wherein the first catheter of the first medical device and the expanded balloon of the first medical device are separated by applying an axial tensile force to a coupling or tubular segment.

30. The method of claim 29, wherein the first catheter of the first medical device and the proximal neck or proximal neck assembly of the balloon of the first medical device are coupled by an elastomer tubular segment.

31. The method of claims 1-28, wherein the first catheter of the first medical device and the balloon of the first medical device are coupled by a mechanical latch or tubular structure, wherein one portion of the mechanical latch is joined to the distal end of the first catheter and the second portion of the mechanical latch is joined to the proximal neck or proximal neck assembly of the balloon of the first medical device.

32. The method of claim 31, wherein the proximal neck of the balloon of the first medical device is the second portion of the mechanical latch.

33. The method of claims 31 and 32, wherein the two portions of the mechanical latch are engaged or operably coupled when the second catheter of the first medical device passes through the mechanical latch.

34. The method of claim 33, wherein the second catheter of the first medical device is removed from the mechanical latch and the mechanical latch and the two portions of the mechanical latch are disengaged or operably decoupled.

35. The method of claim 33, wherein the first catheter of the first medical device and the expanded balloon of the first medical device are pulled apart.

36. The method of claims 1-28, wherein the first catheter of the first medical device and the proximal neck or proximal neck assembly of the balloon of the first medical device are joined by an adhesive, glue, or solder, and wherein a portion of the proximal neck or proximal neck assembly of the balloon of the first medical device is corroded by electrolysis.

37. The method of claim 36, wherein the first catheter of the first medical device and the expanded balloon of the first medical device are pulled apart after corrosion of a portion of the proximal neck or proximal neck assembly of the balloon of the first medical device.

38. The method of claims 1-28, wherein the first catheter of the first medical device and the proximal neck or proximal neck assembly of the balloon of the first medical device are joined by an adhesive, glue, or solder, and wherein a distal portion of the first catheter of the first medical device, a portion of the proximal neck or proximal neck assembly of the balloon of the first medical device, or a portion of a bond between a distal portion of the first catheter of the first medical device and the proximal neck or proximal neck assembly of the balloon of the first medical device is melted by heating.

39. The method of claim 38, wherein the first catheter of the first medical device and the expanded balloon of the first medical device are pulled apart after melting a distal portion of the first catheter of the first medical device, a portion of the proximal neck or proximal neck assembly of the balloon of the first medical device, or a portion of a bond between a distal portion of the first catheter of the first medical device and the proximal neck or proximal neck assembly of the balloon of the first medical device.

40. The method of claims 1-39, wherein the self-expanding retention structure is joined to the distal neck of the balloon of the first medical device.

41. The method of claims 1-39, wherein the self-expanding retention structure is joined to the proximal neck of the balloon of the first medical device.

42. The method of claims 1-41, wherein the first elongated or expandable body of the second medical device is flexible, the second elongated body of the second medical device is flexible, or the first elongated body and the second elongated body of the second medical device are flexible.

43. The method of claims 1-42, wherein the first catheter of the first medical device is flexible, a second catheter of the first medical device is flexible, the third catheter of the first medical device is flexible, or the first catheter, second, catheter and third catheter of the first medical device are flexible.

44. The method of claims 1-43, wherein the balloon of the first medical device is detachable.

45. The method of claims 1-44, wherein the balloon of the first medical device is collapsed or compressed prior to expansion.

46. The method of claims 1-45, wherein the fluid used to expand the balloon of the first medical device is water, a saline solution, a fluoroscopic contrast agent, or combinations thereof.

47. The method of claims 1-46, wherein a solution comprising a fluoroscopic contrast agent is injected during fluoroscopy into the hub of the second catheter of the first medical device, through the second catheter of the first medical device, and into the lumen of the artery or vein adjacent to the distal tip of the second catheter of the first medical device prior to expansion of the retention structure.

48. The method of claims 1-47, wherein a solution comprising a fluoroscopic contrast agent is injected during fluoroscopy into the hub of the second catheter of the first medical device, through the second catheter of the first medical device, and into the lumen of the artery or vein adjacent to the distal tip of the second catheter of the first medical device after expansion of the retention structure of the balloon of the first medical device, but prior to the expansion of the balloon of the first medical device.

49. The method of claims 1-48, wherein a solution comprising a fluoroscopic contrast agent is injected during fluoroscopy into the hub of the second catheter of the first medical device, through the second catheter of the first medical device, and into the lumen of the artery or vein adjacent to the distal tip of the second catheter of the first medical device after expansion of the balloon of the first medical device but prior to separation of the expanded balloon of the first medical device and the first catheter of the first medical device.

50. The method of claims 1-49, wherein a solution comprising a fluoroscopic contrast agent is injected during fluoroscopy into the hub of the second catheter of the first medical device, through the second catheter of the first medical device, and into the lumen of the artery or vein adjacent to the distal tip of the second catheter of the first medical device after separation of the expanded balloon of the first medical device and the first catheter of the first medical device.

51. The method of claims 1-50, wherein a solution comprising a fluoroscopic contrast agent is injected during fluoroscopy into the hub of the third catheter of the first medical device, through the third catheter of the first medical device, and into the lumen of the artery or vein adjacent to the distal tip of the third catheter of the first medical device prior to expansion of the retention structure.

52. The method of claims 1-51, wherein a solution comprising a fluoroscopic contrast agent is injected during fluoroscopy into the hub of the third catheter of the first medical device, through the third catheter of the first medical device, and into the lumen of the artery or vein adjacent to the distal tip of the third catheter of the first medical device after expansion of the retention structure of the balloon of the first medical device, but prior to the expansion of the balloon of the first medical device.

53. The method of claims 1-52, wherein a solution comprising a fluoroscopic contrast agent is injected during fluoroscopy into the hub of the third catheter of the first medical device, through the third catheter of the first medical device, and into the lumen of the artery or vein adjacent to the distal tip of the third catheter of the first medical device after expansion of the balloon of the first medical device but prior to separation of the expanded balloon of the first medical device and the first catheter of the first medical device.

54. The method of claims 1-53, wherein a solution comprising a fluoroscopic contrast agent is injected during fluoroscopy into the hub of the third catheter of the first medical device, through the third catheter of the first medical device, and into the lumen of the artery or vein adjacent to the distal tip of the third catheter of the first medical device after separation of the expanded balloon of the first medical device and the first catheter of the first medical device.

55. The method of claims 1-54, comprising providing the first medical device and the one or more second medical devices.

Aspects and embodiments related to methods of treating an treating an aneurysm as disclosed herein:

1. A method for reducing the flow of blood into a saccular aneurysm of a human patient with two or more medical devices, the method comprising:
   a) determining the maximum aneurysm neck diameter, the minimum aneurysm width, the minimum aneurysm depth, and the minimum aneurysm height, and selecting a first medical device comprising a balloon wherein:
      the diameter of the expanded balloon is larger than the maximum diameter of the aneurysm neck;
      the diameter of the expanded balloon is smaller than the minimum width of the aneurysm;
      the diameter of the expanded balloon is smaller than the minimum depth of the aneurysm; and
      the length of the expanded balloon is smaller than the minimum height of the aneurysm;
   b) placing the balloon of the first medical device into the lumen of the aneurysm, such first medical device comprising:
      i) a pleated and folded balloon configured for permanent implantation in a human patient, the balloon comprising:
         a distal region, a proximal region generally opposite the distal region, an intermediate region transitioning from the distal region to the proximal region, a first axis extending proximal-distal between the proximal region and distal region, and a second axis perpendicular to the first axis;
         a wall extending generally continuously from the proximal region through the intermediate region, to the distal region, with an exterior surface and an interior surface, the interior surface defining a central void or interior volume;
         an opening in the wall of the proximal region that allows for the passage of fluid from a first catheter into the central void or interior volume of the balloon and also allows for the passage of a portion of the second catheter into the central void or interior volume of the balloon;
         an opening in the wall of the distal region that allows for the passage of a portion of the second catheter out of the central void or interior volume of the balloon;
         a proximal neck or neck assembly; and
         a distal neck or neck assembly;
      ii) a first catheter that partially defines a first lumen to allow for passage of fluid from the proximal end of the first catheter to the distal end of the first catheter, and into the central void or interior volume of the balloon; the first catheter comprising:
         a proximal end comprising a proximal hub; and
         a distal portion that is operably coupled or joined to the proximal neck or neck assembly of the balloon;
      iii) a second catheter that defines a second lumen configured to accept a guidewire, elongated body, expandable body, or solidifying fluid, the second catheter comprising:
         a proximal end comprising a proximal hub;
         a proximal portion that passes through the proximal hub of the first catheter;
         a middle portion that passes through the lumen of the first catheter;
         a distal portion that extends distal to the distal end of the first catheter;
         a distal portion that passes through the proximal neck or neck assembly of the balloon;
         a distal portion that passes through the central void or interior volume of the balloon;
         a distal portion that engages or passes through the distal neck or neck assembly of the balloon; and
         a distal end that is open;
      iv) wherein:
         the passage of fluid through the first catheter into the central void or interior volume of the balloon results in expansion of the balloon;
         after expansion of the balloon, the second catheter can be moved forward or backward while the expanded balloon remains fixed in position;
         after expansion of the balloon, one or more first elongated bodies, expandable bodies, solidifying fluids, or solutions comprising drugs or therapeutic agents, can be placed through the lumen of the second catheter into a biological space adjacent to the balloon, including before or after advancing the tip of the second catheter forward;
         after expansion of the balloon, the second catheter can be pulled back until the distal tip of the second catheter is located in the central void or interior volume of the balloon, and one or more one or more first elongated bodies, expandable bodies, or solidifying fluids can be passed through the lumen of the second catheter and placed in the central void or interior volume of the balloon;
         the first catheter can be separated from the expanded balloon; and
         the first and second catheters can be removed from the patient while the balloon and the one or more first elongated bodies, expandable bodies, and solidifying fluids remain in the patient.
   c) delivering a fluid medium into the interior volume of the balloon of the first medical device through the first lumen to cause the balloon to assume an expanded configuration wherein the expanded balloon fills a portion of the aneurysm lumen but leaves a portion of the aneurysm lumen unfilled;

d) optionally, pulling the expanded balloon of the first medical device back until at least a portion of the expanded balloon is in contact with at least a portion of the neck of the aneurysm or at least a portion of the wall of the aneurysm adjacent to the neck of the aneurysm;

e) optionally, advancing the second catheter of the first medical device forward into the aneurysm while maintaining the position of the expanded balloon of the first medical device;

f) delivering the first elongated body or expandable body of the second medical device from the proximal end of the second catheter of the first medical device, through the lumen of the second catheter of the first medical device, and into the unfilled portion of the aneurysm lumen adjacent to the expanded balloon of the first medical device, the second medical device comprising:
  i) a distal portion comprising a first elongated body or expandable body;
  ii) a proximal portion comprising a second elongated body or delivery system;
  iii) wherein:
    after placement of the first elongated body or expandable body of the second medical device into the unfilled portion of the aneurysm lumen adjacent to the expanded balloon of the first medical device, at least a portion of the first elongated body or expandable body of the second medical device contacts at least a portion of the wall of the aneurysm adjacent to the expanded balloon of the first medical device;
    after placement of the first elongated body or expandable body of the second medical device into the unfilled portion of the aneurysm lumen adjacent to the expanded balloon of the first medical device, but prior to separation of the first elongated body or expandable body of the second medical device and the second elongated body of the second medical device, the second medical device can be removed from the patient;
    the first elongated body or expandable body can be separated from the second elongated body; and
    after separation of the first elongated body or expandable body from the second elongated body, the second elongated body can be removed from the patient while the first elongated body or expandable body remains in the patient;

g) causing the first elongated body or expandable body of the second medical device to separate from the second elongated body of the second medical device and removing the second elongated body from the patient while leaving first elongated body or expandable body of the second medical device in the lumen of the aneurysm;

h) optionally, repeating steps e) and f) until the desired percent volume of the unfilled portion of the aneurysm lumen adjacent to the expanded balloon of the first medical device is filled with first elongated bodies or expandable bodies;

i) causing the expanded balloon of the first medical device to separate from the first catheter of the first medical device and removing the first and second catheters of the first medical device from the patient while leaving the expanded balloon of the first medical device and the one or more first elongated bodies or expandable bodies of the second medical device in the patient.

2. A method for reducing the flow of blood into a saccular aneurysm of a human patient with two or more medical devices, the method comprising:

a) determining the maximum aneurysm neck diameter, the minimum aneurysm width, the minimum aneurysm depth, and the minimum aneurysm height, and selecting a first medical device comprising a balloon wherein:
  the diameter of the expanded balloon is larger than the maximum diameter of the aneurysm neck;
  the diameter of the expanded balloon is smaller than the minimum width of the aneurysm;
  the diameter of the expanded balloon is smaller than the minimum depth of the aneurysm; and
  the length of the expanded balloon is smaller than the minimum height of the aneurysm;

b) placing the balloon of the first medical device into the lumen of the aneurysm, such first medical device comprising:
  i) a pleated and folded balloon configured for permanent implantation in a human patient, the balloon comprising:
    a distal region, a proximal region generally opposite the distal region, an intermediate region transitioning from the distal region to the proximal region, a first axis extending proximal-distal between the proximal region and distal region, and a second axis perpendicular to the first axis;
    a wall extending generally continuously from the proximal region through the intermediate region, to the distal region, with an exterior surface and an interior surface, the interior surface defining a central void or interior volume;
    an opening in the wall of the proximal region that allows for the passage of fluid from a first catheter into the central void or interior volume of the balloon and also allows for the passage of a portion of the second catheter into the central void or interior volume of the balloon;
    an opening in the wall of the distal region that allows for the passage of a portion of the second catheter out of the central void or interior volume of the balloon;
    a proximal neck or neck assembly; and
    a distal neck or neck assembly;
  ii) a first catheter that partially defines a first lumen to allow for passage of fluid from the proximal end of the first catheter to the distal end of the first catheter, and into the central void or interior volume of the balloon; the first catheter comprising:
    a proximal end comprising a proximal hub; and
    a distal portion that is operably coupled or joined to the proximal neck or neck assembly of the balloon;
  iii) a second catheter that defines a second lumen configured to accept a guidewire, elongated body, expandable body, or solidifying fluid, the second catheter comprising:
    a proximal end comprising a proximal hub;
    a proximal portion that passes through the proximal hub of the first catheter;
    a middle portion that passes through the lumen of the first catheter;
    a distal portion that extends distal to the distal end of the first catheter;
    a distal portion that passes through the proximal neck or neck assembly of the balloon;

a distal portion that passes through the central void or interior volume of the balloon;
a distal portion that engages or passes through the distal neck or neck assembly of the balloon; and
a distal end that is open;
iv) wherein:
the passage of fluid through the first catheter into the central void or interior volume of the balloon results in expansion of the balloon;
after expansion of the balloon, the second catheter can be moved forward or backward while the expanded balloon remains fixed in position;
after expansion of the balloon, one or more first elongated bodies, expandable bodies, solidifying fluids, or solutions comprising drugs or therapeutic agents, can be placed through the lumen of the second catheter into a biological space adjacent to the balloon, including before or after advancing the tip of the second catheter forward;
after expansion of the balloon, the second catheter can be pulled back until the distal tip of the second catheter is located in the central void or interior volume of the balloon, and one or more one or more first elongated bodies, expandable bodies, or solidifying fluids can be passed through the lumen of the second catheter and placed in the central void or interior volume of the balloon;
the first catheter can be separated from the expanded balloon; and
the first and second catheters can be removed from the patient while the balloon and the one or more first elongated bodies, expandable bodies, and solidifying fluids remain in the patient.
c) delivering a fluid medium into the interior volume of the balloon of the first medical device through the first lumen to cause the balloon to assume an expanded configuration wherein the expanded balloon fills a portion of the aneurysm lumen but leaves a portion of the aneurysm lumen unfilled;
d) optionally, pulling the expanded balloon of the first medical device back until at least a portion of the expanded balloon is in contact with at least a portion of the neck of the aneurysm or at least a portion of the wall of the aneurysm adjacent to the neck of the aneurysm;
e) optionally, advancing the second catheter of the first medical device forward into the aneurysm while maintaining the position of the expanded balloon of the first medical device;
f) delivering at least a distal portion of the first elongated body or expandable body of the second medical device from the proximal end of the second catheter of the first medical device, through the lumen of the second catheter of the first medical device, and into the unfilled portion of the aneurysm lumen adjacent to the expanded balloon of the first medical device, the second medical device comprising:
i) a distal portion comprising a first elongated body or expandable body;
ii) a proximal portion comprising a second elongated body or delivery system;
iii) wherein:
after placement of the first elongated body or expandable body of the second medical device into the unfilled portion of the aneurysm lumen adjacent to the expanded balloon of the first medical device, at least a portion of the first elongated body or expandable body of the second medical device contacts at least a portion of the wall of the aneurysm adjacent to the expanded balloon of the first medical device;
after placement of the first elongated body or expandable body of the second medical device into the unfilled portion of the aneurysm lumen adjacent to the expanded balloon of the first medical device, but prior to separation of the first elongated body or expandable body of the second medical device and the second elongated body of the second medical device, the second medical device can be removed from the patient;
the first elongated body or expandable body can be separated from the second elongated body; and
after separation of the first elongated body or expandable body from the second elongated body, the second elongated body can be removed from the patient while the first elongated body or expandable body remains in the patient;
g) withdrawing the second catheter of the first medical device until the distal tip of the second catheter of the first medical device is within the central void or interior volume of the expanded balloon of the first medical device, while maintaining the position of the expanded balloon of the first medical device;
h) delivering the remainder of the first elongated body or expandable body of the second medical device into the central void or interior volume of the expanded balloon of the first medical device, wherein at least a portion of the first elongated body or expandable body contacts at least a portion of the wall of the expanded balloon of the first medical device;
i) causing the first elongated body or expandable body of the second medical device to separate from the second elongated body of the second medical device and removing the second elongated body from the patient while leaving first elongated body or expandable body of the second medical device in the lumen of the aneurysm;
j) optionally, delivering the first elongated body or expandable body of a second medical device from the proximal end of the second catheter of the first medical device, through the lumen of the second catheter of the first medical device and into the central void or interior volume of the expanded balloon of the first medical device;
k) optionally, causing the first elongated body or expandable body of the second medical device to separate from the second elongated body of the second medical device and removing the second elongated body from the patient while leaving first elongated body or expandable body of the second medical device in the central void or interior volume of the expanded balloon of the first medical device;
l) optionally, repeating steps j) and k) until the desired percent volume of the unfilled portion of the central void or interior volume of the expanded balloon of the first medical device is filled with first elongated bodies or expandable bodies;
m) causing the expanded balloon of the first medical device to separate from the first catheter of the first medical device and removing the first and second catheters of the first medical device from the patient while leaving the expanded balloon of the first medical device and the one or more first elongated bodies or expandable bodies of the second medical device in the patient.

3. The method of claims 1 and 2, wherein, after expansion of the balloon of the first medical device and prior to withdrawing the second catheter of the first medical device into the central void or interior volume of the expanded balloon of the first medical device, a solution comprising a fluoroscopic contrast agent, drug or therapeutic agent, a solidifying fluid, or combinations thereof, are injected through the lumen of the second catheter of the first medical device and into the lumen of aneurysm adjacent to the expanded balloon of the first medical device.

4. The method of claim 3, wherein a syringe or other appropriate delivery system, is used to inject the fluoroscopic contrast agent, drug, therapeutic agent, solidifying fluid, or combinations thereof.

5. The method of claims 3 and 4, wherein, prior to injecting the fluoroscopic contrast agent, drug, therapeutic agent, solidifying fluid, or combinations thereof, through the lumen of the shaft of the second catheter of the first medical device and into the lumen of the aneurysm adjacent to the expanded balloon of the first medical device, the second catheter of the first medical device is advanced forward in the lumen of the aneurysm while maintaining the position of the balloon of the first medical device.

6. The method of claims 1 and 2, wherein, prior to causing the expanded balloon of the first medical device to separate from the first catheter of the first medical device, a solidifying fluid is injected from the proximal end of the first catheter of the first medical device, through the lumen of the first catheter of the first medical device, and into the central void or interior volume of the expanded balloon of the first medical device.

7. The method of claims 1-6, wherein the expanded balloon is configured to contact at least 100%, 90%, 80%, 70, 60%, 50%, 40%, 30%, 20%, 10%, or 5% of the area of the luminal surface of the aneurysm.

8. The method of claims 1-6, wherein the expanded balloon is configured to fill at least 100%, 90%, 80%, 70%, 60%, 50%, 40%, 30%, 20%, 10%, or 5% of the volume of the lumen of the aneurysm.

9. The method of claims 1-8, wherein the largest diameter or tertiary diameter of a second medical device is equal or greater than the largest diameter of the portion of the aneurysm not filled by the expanded balloon of the first medical device.

10. The method of claims 1-8, wherein the largest diameter or tertiary diameter of a first elongated or expandable body of the second medical device is in a range from equal to the largest diameter of the expanded balloon of the first medical device to 20% larger than the largest diameter of the portion of the aneurysm not filled by the expanded balloon of the first medical device.

11. The method of claims 1-10, wherein the largest diameter or tertiary diameter of a first elongated or expandable body of the second medical device is 1, 2, 3, 4, 5, 6, 7, 8, 9, or 10 mm larger than the largest diameter of the portion of the aneurysm not filled by the expanded balloon of the first medical device.

12. The method of claims 1-11, wherein, after placement in the aneurysm lumen, at least a portion of a first elongated body or expandable body of the second medical device exerts a force on the wall of the aneurysm and on the wall of expanded balloon of the first medical device.

13. The method of claim 12, wherein the force of the first elongated body or expandable body on the wall of the expanded balloon pushes the expanded balloon towards the aneurysm neck.

14. The method of claims 1-13, wherein the largest diameter or largest tertiary diameter of a first elongated body or expandable body of the second medical is equal or greater than the largest diameter of the expanded balloon.

15. The method of claims 1-14, wherein the largest diameter or largest tertiary diameter of a first elongated or expandable body of the second medical device is in a range from equal to the largest diameter of the expanded balloon of the first medical device to 50% larger than the largest diameter of the expanded balloon of the first medical device.

16. The method of claims 1-14, wherein the largest diameter or tertiary diameter of the first elongated or expandable body of the second medical device is 1, 2, 3, 4, 5, 6, 7, 8, 9, or 10 mm larger than the largest diameter of the expanded balloon of the first medical device.

17. The method of claims 9-11, wherein, after placement in the central void or interior volume of the expanded balloon, a first elongated body or expandable body of the second medical device exerts a force on the wall of the expanded balloon of the first medical device.

18. The method of claim 17, wherein the force on the wall of the expanded balloon of the first medical device is in an outward direction.

19. The method of claims 1-18, wherein the volume of the first elongated bodies or expandable bodies of the second medical device placed into the central void or internal volume of the expanded balloon fill 5-75% of the volume of the central void or internal volume of the expanded balloon.

20. The method of claims 1-18, wherein the volume of the first elongated bodies or expandable bodies of the second medical device placed into the central void or internal volume of the expanded balloon fill 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75% of the volume of the central void or internal volume of the expanded balloon.

21. The method of claims 1-20, wherein the volume of the first elongated bodies or expandable bodies of the second medical device placed into the lumen of the aneurysm fill 5-75% of the volume of the aneurysm not filled by the expanded balloon.

22. The method of claims 1-20, wherein the volume of the first elongated bodies or expandable bodies of the second medical device placed into the lumen of the aneurysm fill 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75% of the volume of the aneurysm not filled by the expanded balloon.

23. The method of claims 1-22, wherein the distal portion of the second catheter of the first medical device comprises a radiopaque portion, ring or marker that is visible during fluoroscopy, and wherein fluoroscopy is used to monitor the position of the distal portion of the second catheter of the first medical device relative to the position of the distal portion of the balloon of the first medical device when the second catheter of the first medical device is moved.

24. The method of claims 1-23, wherein the distal portion of the balloon of the first medical device comprises a radiopaque portion, ring or marker that is visible during fluoroscopy, and wherein fluoroscopy is used to monitor the position of the distal portion of the second catheter of the first medical device relative to the position of the distal portion of the balloon of the first catheter when the second catheter of the first medical device is moved.

25. The method of claims 1-24, wherein at least a portion of the distal telescoping structure of the first medical device comprises a radiopaque portion, ring or marker that is visible during fluoroscopy, and wherein fluoroscopy is used to monitor the position of the distal portion of the second catheter of the first medical device relative to the position of the distal telescoping structure of the first medical device when the second catheter of the first medical device is moved.

26. The method of claims 1-25, wherein at least a portion of the first elongated or expanded body of the second medical device is made from a material that is radiopaque and visible during fluoroscopy and fluoroscopy is used to monitor the placement and position of the first elongated or expanded body of the second medical device.

27. The method of claims 1-26, wherein the second catheter of the first medical device comprises one, two, or more than two radiopaque portions, rings or markers, and fluoroscopy is used to monitor the position of the second catheter of the first medical device relative to the position of the first elongated or expanded body of the second medical device.

28. The method of claims 1-27, wherein the distal portion of the first catheter of the first medical device comprises a radiopaque marker that is visible during fluoroscopy, and wherein fluoroscopy is used to monitor the separation of the expanded balloon of the first medical device from the first catheter of the first medical device.

29. The method of claims 1-28, wherein the proximal portion of the balloon of the first medical device comprises a radiopaque marker that is visible during fluoroscopy, and wherein fluoroscopy is used to monitor the separation of the expanded balloon of the first medical device from the first catheter of the first medical device.

30. The method of claims 23-29, wherein the radiopaque portion, ring, or marker comprises platinum, iridium, gold, tungsten, or combinations thereof.

31. The method of claims 1-30, wherein the wall of the aneurysm has been damaged or has ruptured.

32. The method of claims 1-30, wherein the wall of the aneurysm has not been damaged or ruptured.

33. The method of claims 1-32, wherein the second catheter of the first medical device and the distal neck or distal neck assembly of the balloon of the first medical device are coupled by a friction fit, and wherein the second catheter of the first medical device and the expanded balloon of the first medical device are separated by applying an axial tensile force to the coupling.

34. The method of claim 33, wherein the second catheter of the first medical device and the distal neck or distal neck assembly of the balloon of the first medical device are coupled by an elastomer valve.

35. The method of claim 34, wherein the elastomer valve serves to reduce blood flow through the central void or interior volume of the expanded balloon of the first medical device following removal of the second catheter of the first medical device from the patient.

36. The method of claims 1-35, wherein the first catheter of the first medical device and the proximal neck or proximal neck assembly of the balloon of the first medical device are coupled by a friction fit, and wherein the first catheter of the first medical device and the expanded balloon of the first medical device are separated by applying an axial tensile force to the coupling.

37. The method of claim 36, wherein the first catheter of the first medical device and the proximal neck or proximal neck assembly of the balloon of the first medical device are coupled by an elastomer tubular segment.

38. The method of claims 1-35, wherein the first catheter of the first medical device and the balloon of the first medical device are coupled by a mechanical latch, wherein one portion of the mechanical latch is joined to the distal end of the first catheter and the second portion of the mechanical latch is joined to the proximal neck or proximal neck assembly of the balloon of the first medical device.

39. The method of claim 38, wherein the proximal neck of the balloon of the first medical device is the second portion of the mechanical latch.

40. The method of claims 38 and 39, wherein the two portions of the mechanical latch are engaged or operably coupled when the second catheter of the first medical device passes through the mechanical latch.

41. The method of claim 40, wherein the second catheter of the first medical device is removed from the mechanical latch and the mechanical latch and the two portions of the mechanical latch are disengaged or operably decoupled.

42. The method of claim 41, wherein the first catheter of the first medical device and the expanded balloon of the first medical device are pulled apart.

43. The method of claims 1-42, wherein the first catheter of the first medical device and the proximal neck or proximal neck assembly of the balloon of the first medical device are joined by an adhesive, glue, or solder, and wherein a portion of the proximal neck or proximal neck assembly of the balloon of the first medical device is corroded by electrolysis.

44. The method of claim 43, wherein the first catheter of the first medical device and the expanded balloon of the first medical device are pulled apart after corrosion of a portion of the proximal neck or proximal neck assembly of the balloon of the first medical device.

45. The method of claims 1-35, wherein the first catheter of the first medical device and the proximal neck or proximal neck assembly of the balloon of the first medical device are joined by an adhesive, glue, or solder, and wherein a distal portion of the first catheter of the first medical device, a portion of the proximal neck or proximal neck assembly of the balloon of the first medical device, or a portion of a bond between a distal portion of the first catheter of the first medical device and the proximal neck or proximal neck assembly of the balloon of the first medical device is melted by heating.

46. The method of claim 45, wherein the first catheter of the first medical device and the expanded balloon of the first medical device are pulled apart after melting a distal portion of the first catheter of the first medical device, a portion of the proximal neck or proximal neck assembly of the balloon of the first medical device, or a portion of a bond between a distal portion of the first catheter of the first medical device and the proximal neck or proximal neck assembly of the balloon of the first medical device.

47. The method of claims 1-46, wherein the balloon is collapsed or compressed prior to placement into the aneurysm lumen.

48. The method of claims 1 and 2, wherein the expanded balloon of the first medical device occupies a portion of the lumen of the aneurysm and reduces the flow of blood from the parent vessel into the lumen of the aneurysm.

49. The method of claims 1 and 2, comprising pulling the expanded balloon of the first medical device towards the aneurysm neck to obstruct the neck of the aneurysm and reduce the flow of blood into the aneurysm.

50. The method of claim 49, comprising pulling the expanded balloon of the first medical device towards the neck of the aneurysm prior to placing a first elongated body or expandable body into the lumen of the aneurysm.

51. The method of claim 49, comprising pulling the expanded balloon of the first medical device towards the aneurysm neck after placing a first elongated body or expandable body into the lumen of the aneurysm and prior to separating the first catheter of the first medical device from the expanded balloon of the first medical device.

52. The method of claims 1-51, wherein the expanded balloon of the first medical device fills at least a portion of a lumen of an aneurysm and also a portion of a lumen of an adjacent artery.

53. The method of claims 1-52, wherein the first elongated or expandable body of the second medical device is flexible, the second elongated body of the second medical device is flexible, or the first elongated body and the second elongated body of the second medical device are flexible.

54. The method of claims 1-52, wherein the first catheter of the first medical device is flexible, the second catheter of the first medical device is flexible, or the first catheter of the first medical device and the second catheter of the first medical device are flexible.

55. The method of claims 1-54, wherein the balloon of the first medical device is detachable.

56. The method of claims 1-55, wherein the balloon of the first medical device is collapsed or compressed prior to expansion.

57. The method of claims 1-56, wherein the fluid used to expand the balloon of the first medical device is water, a saline solution, a fluoroscopic contrast agent, or combinations thereof.

58. The method of claims 1-57, wherein a solution comprising a fluoroscopic contrast agent is injected during fluoroscopy into the hub of the second catheter of the first medical device, through the second catheter of the first medical device, and into the lumen of the aneurysm adjacent to the distal tip of the second catheter of the first medical device prior to the expansion of the balloon of the first medical device.

59. The method of claims 1-58, wherein a solution comprising a fluoroscopic contrast agent is injected during fluoroscopy into the hub of the second catheter of the first medical device, through the second catheter of the first medical device, and into the lumen of the aneurysm adjacent to the distal tip of the second catheter of the first medical device after expansion of the balloon of the first medical device but prior to separation of the expanded balloon of the first medical device and the first catheter of the first medical device.

60. The method of claims 1-59, wherein a solution comprising a fluoroscopic contrast agent is injected during fluoroscopy into the hub of the second catheter of the first medical device, through the second catheter of the first medical device, and into the lumen of the aneurysm adjacent to the distal tip of the second catheter of the first medical device after separation of the expanded balloon of the first medical device and the first catheter of the first medical device.

61. The method of claims 1-60, comprising providing the first medical device and the one or more second medical devices.

Aspects and embodiments related to methods of treating an treating a left atrial appendage as disclosed herein:

1. A method for reducing the flow of blood into a left atrial appendage of a human patient with two or more medical devices, the method comprising:
   a) determining the maximum left atrial appendage neck diameter, the minimum left atrial appendage width, the left atrial appendage depth, and the minimum left atrial appendage height, and selecting a first medical device comprising a balloon wherein:
      the diameter of the expanded balloon is larger than the maximum diameter of the left atrial appendage neck;
      the diameter of the expanded balloon is smaller than the minimum width of the left atrial appendage;
      the diameter of the expanded balloon is smaller than the minimum depth of the left atrial appendage; and
      the length of the expanded balloon, including any retention feature, is smaller than the minimum height of the left atrial appendage;
   b) placing the balloon of the first medical device into the lumen of the left atrial appendage, such first medical device comprising:
      i) a pleated and folded balloon configured for permanent implantation in a human patient, the balloon comprising:
         a distal region, a proximal region generally opposite the distal region, an intermediate region transitioning from the distal region to the proximal region, a first axis extending proximal-distal between the proximal region and distal region, and a second axis perpendicular to the first axis;
         a wall extending generally continuously from the proximal region through the intermediate region, to the distal region, with an exterior surface and an interior surface, the interior surface defining a central void or interior volume;
         an opening in the wall of the proximal region that allows for the passage of fluid from a first catheter into the central void or interior volume of the balloon and also allows for the passage of a portion of the second catheter into the central void or interior volume of the balloon;
         an opening in the wall of the distal region that allows for the passage of a portion of the second catheter out of the central void or interior volume of the balloon;
         a proximal neck or neck assembly; and
         a distal neck or neck assembly;
         a self-expanding metal retention structure wherein, after expansion, the diameter of at least a portion of the metal structure is equal to or greater than the diameter of the expanded balloon;
      ii) a first catheter that partially defines a first lumen to allow for passage of fluid from the proximal end of the first catheter to the distal end of the first catheter, and into the central void or interior volume of the balloon; the first catheter comprising:
         a proximal end comprising a proximal hub;
         a proximal portion that passes through the proximal hub of the third catheter;
         a middle portion that passes through the lumen of the third catheter;
         a distal portion that extends distal to the distal end of the third catheter; and
         a distal portion that is operably coupled or joined to the proximal neck or neck assembly of the balloon;

iii) a second catheter that defines a second lumen configured to accept a guidewire, elongated body, expandable body, or solidifying fluid, the second catheter comprising:
   a proximal end comprising a proximal hub;
   a proximal portion that passes through the proximal hub of the first catheter;
   a middle portion that passes through the lumen of the first catheter;
   a distal portion that extends distal to the distal end of the first catheter;
   a distal portion that passes through the proximal neck or neck assembly of the balloon;
   a distal portion that passes through the central void or interior volume of the balloon;
   a distal portion that engages or passes through the distal neck or neck assembly of the balloon; and
   a distal end that is open;
iv) a third catheter that partially defines a third lumen to allow for passage of fluid from the proximal end of the third catheter to the distal end of the third catheter and is configured to constrain the retention structure of the balloon of the first medical device; the second catheter comprising:
   a proximal end comprising a proximal hub;
   a distal end that is open;
v) wherein:
   the third catheter of the first medical device can move forward or backward while the first catheter, the third catheter, and the balloon of the first medical device remain fixed in position;
   the passage of fluid through the first catheter into the central void or interior volume of the balloon results in expansion of the balloon;
   after expansion of the balloon, the second catheter can be moved forward or backward while the expanded balloon remains fixed in position;
   after expansion of the balloon, one or more first elongated bodies, expandable bodies, solidifying fluids, or solutions comprising drugs or therapeutic agents, can be placed through the lumen of the second catheter into a biological space adjacent to the balloon, including before or after advancing the tip of the second catheter forward;
   after expansion of the balloon, the second catheter can be pulled back until the distal tip of the second catheter is located in the central void or interior volume of the balloon, and one or more one or more first elongated bodies, expandable bodies, or solidifying fluids can be passed through the lumen of the second catheter and placed in the central void or interior volume of the balloon;
   the first catheter can be separated from the expanded balloon; and
   the first and second catheters can be removed from the patient while the balloon and the one or more first elongated bodies, expandable bodies, and solidifying fluids remain in the patient.
c) pulling back the third catheter of the first medical device while the first catheter and the balloon of the first medical device remain fixed in position, until the retention structure of the balloon of the first medical device expands and a portion of the retention structure makes contact with the wall of the left atrial appendage;
d) optionally, placing axial tensile force on the first catheter after expansion of the retention structure to confirm attachment of the retention structure to the wall of the left atrial appendage;
e) pulling back the third catheter of the first medical device while the first catheter and the balloon of the first medical device remain fixed in position, until the balloon of the first medical device is uncovered;
f) delivering a fluid medium into the interior volume of the balloon of the first medical device through the first lumen to cause the balloon to assume an expanded configuration wherein the expanded balloon fills a portion of the left atrial appendage lumen;
g) withdrawing the second catheter of the first medical device until the distal tip of the second catheter of the first medical device is within the central void or interior volume of the expanded balloon of the first medical device, while maintaining the position of the expanded balloon of the first medical device;
h) delivering a first elongated body or expandable body of the second medical device from the proximal end of the second catheter of the first medical device, through the lumen of the second catheter of the first medical device, and into the central void or interior volume of the expanded balloon of the first medical device, the second medical device comprising:
   i) a distal portion comprising a first elongated body or expandable body;
   ii) a proximal portion comprising a second elongated body or delivery system;
   iii) wherein:
      after placement of the first elongated body or expandable body of the second medical device into the central void or interior volume of the expanded balloon of the first medical device, at least a portion of the first elongated body or expandable body of the second medical device contacts at least a portion of the wall of the expanded balloon of the first medical device;
      after placement of the first elongated body or expandable body of the second medical device into the central void or interior volume of the expanded balloon of the first medical device, but prior to separation of the first elongated body or expandable body of the second medical device and the second elongated body of the second medical device, the second medical device can be removed from the patient;
      the first elongated body or expandable body can be separated from the second elongated body; and
      after separation of the first elongated body or expandable body from the second elongated body, the second elongated body can be removed from the patient while the first elongated body or expandable body remains in the patient;
i) causing the first elongated body or expandable body of the second medical device to separate from the second elongated body of the second medical device and removing the second elongated body from the patient while leaving first elongated body or expandable body of the second medical device in the lumen of the left atrial appendage;
j) optionally, repeating steps h) and i) until the desired percent volume of the unfilled portion of the central void or interior volume of the expanded balloon of the first medical device is filled with first elongated bodies or expandable bodies;
k) causing the expanded balloon of the first medical device to separate from the first catheter of the first medical device and removing the first and second catheters of the first medical device from the patient while leaving the expanded balloon of the first medical device and the one or more first elongated bodies or expandable bodies of the second medical device in the patient.

2. The method of claim 1, wherein, after expansion of the balloon of the first medical device and prior to withdrawing the second catheter of the first medical device into the central void or interior volume of the expanded balloon of the first medical device, a solution comprising a fluoroscopic contrast agent, drug or therapeutic agent, a solidifying fluid, or combinations thereof, are injected through the lumen of the second catheter of the first medical device and into the lumen of left atrial appendage adjacent to the expanded balloon of the first medical device.

3. The method of claim 2, wherein a syringe or other appropriate delivery system, is used to inject the fluoroscopic contrast agent, drug, therapeutic agent, solidifying fluid, or combinations thereof.

4. The method of claims 2 and 3, wherein, prior to injecting the fluoroscopic contrast agent, drug, therapeutic agent, solidifying fluid, or combinations thereof, through the lumen of the shaft of the second catheter of the first medical device and into the lumen of the left atrial appendage adjacent to the expanded balloon of the first medical device, the second catheter of the first medical device is advanced forward in the lumen of the left atrial appendage while maintaining the position of the balloon of the first medical device.

5. The method of claims 1 and 2, wherein, prior to causing the expanded balloon of the first medical device to separate from the first catheter of the first medical device, a solidifying fluid is injected from the proximal end of the second catheter of the first medical device, through the lumen of the second catheter of the first medical device, and into the central void or interior volume of the expanded balloon of the first medical device.

6. The method of claims 1-5, wherein the expanded balloon is configured to contact at least 100%, 90%, 80%, 70, 60%, 50%, 40%, 30%, 20%, 10%, or 5% of the area of the luminal surface of the left atrial appendage.

7. The method of claims 1-5, wherein the expanded balloon is configured to fill at least 100%, 90%, 80%, 70%, 60%, 50%, 40%, 30%, 20%, 10%, or 5% of the volume of the lumen of the left atrial appendage.

8. The method of claims 1-7, wherein the largest diameter or tertiary diameter of a first elongated or expandable body of a second medical device is equal or greater than the largest diameter of the expanded balloon of the first medical device.

9. The method of claims 1-7, wherein the largest diameter or tertiary diameter of a first elongated or expandable body of the second medical device is in a range from equal to the largest diameter of the expanded balloon of the first medical device to 50% larger than the largest diameter of the expanded balloon of the first medical device.

10. The method of claims 1-9, wherein the largest overall or tertiary diameter of a first elongated or expandable body of the second medical device is 1, 2, 3, 4, 5, 6, 7, 8, 9, or 10 mm larger than the largest diameter of the expanded balloon of the first medical device.

11. The method of claims 8-10, wherein, after placement in the central void or interior volume of the expanded balloon, a first elongated body or expandable body of the second medical device exerts a force on the wall of the expanded balloon of the first medical device.

12. The method of claim 11, wherein the force on the wall of the expanded balloon of the first medical device is in an outward direction.

13. The method of claims 1-12, wherein the volume of the first elongated bodies or expandable bodies of the second medical device placed into the central void or internal volume of the expanded balloon fill 5-75% of the volume of the central void or internal volume of the expanded balloon.

14. The method of claims 1-12, wherein the volume of the first elongated bodies or expandable bodies of the second medical device placed into the central void or internal volume of the expanded balloon fill 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75% of the volume of the central void or internal volume of the expanded balloon.

15. The method of claims 1-14, wherein the distal portion of the second catheter of the first medical device comprises a radiopaque portion, ring or marker that is visible during fluoroscopy, and wherein fluoroscopy is used to monitor the position of the distal portion of the second catheter of the first medical device relative to the position of the distal portion of the balloon of the first medical device when the second catheter of the first medical device is moved.

16. The method of claims 1-15, wherein the distal portion of the balloon of the first medical device comprises a radiopaque portion, ring or marker that is visible during fluoroscopy, and wherein fluoroscopy is used to monitor the position of the distal portion of the second catheter of the first medical device relative to the position of the distal portion of the balloon of the first catheter when the second catheter of the first medical device is moved.

17. The method of claims 1-16, wherein at least a portion of the distal telescoping structure of the first medical device comprises a radiopaque portion, ring or marker that is visible during fluoroscopy, and wherein fluoroscopy is used to monitor the position of the distal portion of the second catheter of the first medical device relative to the position of the distal telescoping structure of the first medical device when the second catheter of the first medical device is moved.

18. The method of claims 1-17, wherein at least a portion of the first elongated or expanded body of the second medical device is made from a material that is radiopaque and visible during fluoroscopy and fluoroscopy is used to monitor the placement and position of the first elongated or expanded body of the second medical device.

19. The method of claims 1-18, wherein the second catheter of the first medical device comprises one, two, or more than two radiopaque portions, rings or markers, and fluoroscopy is used to monitor the position of the second catheter of the first medical device relative to the position of the first elongated or expanded body of the second medical device.

20. The method of claims 1-19, wherein the distal portion of the first catheter of the first medical device comprises a radiopaque marker that is visible during fluoroscopy, and wherein fluoroscopy is used to monitor the separation of the expanded balloon of the first medical device from the first catheter of the first medical device.

21. The method of claims 1-20, wherein the proximal portion of the balloon of the first medical device comprises a radiopaque marker that is visible during fluoroscopy, and wherein fluoroscopy is used to monitor the separation of the expanded balloon of the first medical device from the first catheter of the first medical device.

22. The method of claims 15-21, wherein the radiopaque portion, ring, or marker comprises platinum, iridium, gold, tungsten, or combinations thereof.

23. The method of claims 1-22, wherein the second catheter of the first medical device and the distal neck or distal neck assembly of the balloon of the first medical device are coupled by a friction fit, and wherein the second catheter of the first medical device and the expanded balloon of the first medical device are separated by applying an axial tensile force to the coupling.

24. The method of claim 23, wherein the second catheter of the first medical device and the distal neck or distal neck assembly of the balloon of the first medical device are coupled by an elastomer valve.

25. The method of claim 24, wherein the elastomer valve serves to reduce blood flow through the central void or interior volume of the expanded balloon of the first medical device following removal of the second catheter of the first medical device from the patient.

26. The method of claims 1-25, wherein the first catheter of the first medical device and the proximal neck or proximal neck assembly of the balloon of the first medical device are coupled by a friction fit, and wherein the first catheter of the first medical device and the expanded balloon of the first medical device are separated by applying an axial tensile force to the coupling.

27. The method of claim 26, wherein the first catheter of the first medical device and the proximal neck or proximal neck assembly of the balloon of the first medical device are coupled by an elastomer tubular segment.

28. The method of claims 1-25, wherein the first catheter of the first medical device and the balloon of the first medical device are coupled by a mechanical latch, wherein one portion of the mechanical latch is joined to the distal end of the first catheter and the second portion of the mechanical latch is joined to the proximal neck or proximal neck assembly of the balloon of the first medical device.

29. The method of claim 28, wherein the proximal neck of the balloon of the first medical device is the second portion of the mechanical latch.

30. The method of claims 28 and 29, wherein the two portions of the mechanical latch are engaged or operably coupled when the second catheter of the first medical device passes through the mechanical latch.

31. The method of claim 30, wherein the second catheter of the first medical device is removed from the mechanical latch and the mechanical latch and the two portions of the mechanical latch are disengaged or operably decoupled.

32. The method of claim 31, wherein the first catheter of the first medical device and the expanded balloon of the first medical device are pulled apart.

33. The method of claims 1-32, wherein the first catheter of the first medical device and the proximal neck or proximal neck assembly of the balloon of the first medical device are joined by an adhesive, glue, or solder, and wherein a portion of the proximal neck or proximal neck assembly of the balloon of the first medical device is corroded by electrolysis.

34. The method of claim 33, wherein the first catheter of the first medical device and the expanded balloon of the first medical device are pulled apart after corrosion of a portion of the proximal neck or proximal neck assembly of the balloon of the first medical device.

35. The method of claims 1-25, wherein the first catheter of the first medical device and the proximal neck or proximal neck assembly of the balloon of the first medical device are joined by an adhesive, glue, or solder, and wherein a distal portion of the first catheter of the first medical device, a portion of the proximal neck or proximal neck assembly of the balloon of the first medical device, or a portion of a bond between a distal portion of the first catheter of the first medical device and the proximal neck or proximal neck assembly of the balloon of the first medical device is melted by heating.

36. The method of claim 35, wherein the first catheter of the first medical device and the expanded balloon of the first medical device are pulled apart after melting a distal portion of the first catheter of the first medical device, a portion of the proximal neck or proximal neck assembly of the balloon of the first medical device, or a portion of a bond between a distal portion of the first catheter of the first medical device and the proximal neck or proximal neck assembly of the balloon of the first medical device.

37. The method of claims 1-36, wherein the balloon is collapsed or compressed prior to placement in the lumen of a left atrial appendage.

38. The method of claim 1, wherein the expanded balloon of the first medical device occupies a portion of the lumen of the left atrial appendage and reduces the flow of blood from the right atrium into the lumen of the left atrial appendage.

39. The method of claims 1-38, wherein the expanded balloon of the first medical device fills at least a portion of a lumen of a left atrial appendage and also a portion of a lumen of an adjacent left atrium.

40. The method of claims 1-39, wherein the self-expanding retention structure is joined to the distal neck of the balloon of the first medical device.

41. The method of claims 1-40, wherein the first elongated or expandable body of the second medical device is flexible, the second elongated body of the second medical device is flexible, or the first elongated body and the second elongated body of the second medical device are flexible.

42. The method of claims 1-41, wherein the first catheter of the first medical device is flexible, the second catheter of the first medical device is flexible, the third catheter of the first medical device is flexible, or the first catheter, the second catheter, and the third catheter of the first medical device are flexible.

43. The method of claims 1-42, wherein the balloon of the first medical device is detachable.

44. The method of claims 1-43, wherein the balloon of the first medical device is collapsed or compressed prior to expansion.

45. The method of claims 1-44, wherein the fluid used to expand the balloon of the first medical device is water, a saline solution, a fluoroscopic contrast agent, or combinations thereof.

46. The method of claims 1-45, wherein a solution comprising a fluoroscopic contrast agent is injected during fluoroscopy into the hub of the second catheter of the first medical device, through the second catheter of the first medical device, and into the lumen of the left atrial appendage adjacent to the distal tip of the second catheter of the first medical device prior to expansion of the retention structure.

47. The method of claims 1-46, wherein a solution comprising a fluoroscopic contrast agent is injected during fluoroscopy into the hub of the second catheter of the first medical device, through the second catheter of the first medical device, and into the lumen of the left atrial appendage adjacent to the tip of the second catheter of the first medical device after expansion of the retention structure of the balloon of the first medical device, but prior to the expansion of the balloon of the first medical device.

48. The method of claims 1-47, wherein a solution comprising a fluoroscopic contrast agent is injected during fluoroscopy into the hub of the second catheter of the first medical device, through the second catheter of the first medical device, and into the lumen of the left atrial appendage adjacent to the distal tip of the second catheter of the first medical device after expansion of the balloon of the first medical device but prior to separation of the expanded balloon of the first medical device and the first catheter of the first medical device.

49. The method of claims 1-48, wherein a solution comprising a fluoroscopic contrast agent is injected during fluoroscopy into the hub of the second catheter of the first medical device, through the second catheter of the first medical device, and into the lumen of the left atrial appendage adjacent to the distal tip of the second catheter of the first medical device after separation of the expanded balloon of the first medical device and the first catheter of the first medical device.

50. The method of claims 1-49, wherein a solution comprising a fluoroscopic contrast agent is injected during fluoroscopy into the hub of the third catheter of the first medical device, through the third catheter of the first medical device, and into the lumen of the left atrial appendage adjacent to the distal tip of the third catheter of the first medical device prior to expansion of the retention structure.

51. The method of claims 1-50, wherein a solution comprising a fluoroscopic contrast agent is injected during fluoroscopy into the hub of the third catheter of the first medical device, through the third catheter of the first medical device, and into the lumen of the left atrial appendage adjacent to the distal tip of the third catheter of the first medical device after expansion of the retention structure of the balloon of the first medical device, but prior to the expansion of the balloon of the first medical device.

52. The method of claims 1-52, wherein a solution comprising a fluoroscopic contrast agent is injected during fluoroscopy into the hub of the third catheter of the first medical device, through the third catheter of the first medical device, and into the lumen of the left atrial appendage adjacent to the distal tip of the third catheter of the first medical device after expansion of the balloon of the first medical device but prior to separation of the expanded balloon of the first medical device and the first catheter of the first medical device.

53. The method of claims 1-53, wherein a solution comprising a fluoroscopic contrast agent is injected during fluoroscopy into the hub of the third catheter of the first medical device, through the third catheter of the first medical device, and into the lumen of the left atrial appendage adjacent to the distal tip of the third catheter of the first medical device after separation of the expanded balloon of the first medical device and the first catheter of the first medical device.

54. The method of claims 1-54, comprising providing the first medical device and the one or more second medical devices.

Aspects and embodiments related to methods of treating a paravalvular leak with a detachable balloon catheter as disclosed herein:

1. A method of reducing the flow of blood in a paravalvular leak path of a human patient with two or more medical devices, the method comprising:
   a) determining a diameter and length of a segment of a paravalvular leak path to be treated and selecting a first medical device comprising a balloon with an expanded diameter equal to or greater than the diameter of the selected segment of paravalvular leak path and an expanded length such that the balloon can occupy at least a portion of the lumen of the paravalvular leak path when the balloon of the first medical device is expanded:
   b) placing the balloon of the first medical device into the lumen of the paravalvular leak path, such first medical device comprising:
      i) a pleated and folded balloon configured for permanent implantation in a human patient, the balloon comprising:
         a distal region, a proximal region generally opposite the distal region, an intermediate region transitioning from the distal region to the proximal region, a first axis extending proximal-distal between the proximal region and distal region, and a second axis perpendicular to the first axis;
         a wall extending generally continuously from the proximal region through the intermediate region, to the distal region, with an exterior surface and an interior surface, the interior surface defining a central void or interior volume;
         an opening in the wall of the proximal region that allows for the passage of fluid from a first catheter into the central void or interior volume of the balloon and also allows for the passage of a portion of the second catheter into the central void or interior volume of the balloon;
         an opening in the wall of the distal region that allows for the passage of a portion of the second catheter out of the central void or interior volume of the balloon;
         a proximal neck or neck assembly; and
         a distal neck or neck assembly;
      ii) a first catheter that partially defines a first lumen to allow for passage of fluid from the proximal end of the first catheter to the distal end of the first catheter, and into the central void or interior volume of the balloon; the first catheter comprising:
         a proximal end comprising a proximal hub; and
         a distal portion that is operably coupled or joined to the proximal neck or neck assembly of the balloon;
      iii) a second catheter that defines a second lumen configured to accept a guidewire, elongated body, expandable body, or solidifying fluid, the second catheter comprising:
         a proximal end comprising a proximal hub;
         a proximal portion that passes through the proximal hub of the first catheter;
         a middle portion that passes through the lumen of the first catheter;
         a distal portion that extends distal to the distal end of the first catheter;
         a distal portion that passes through the proximal neck or neck assembly of the balloon;
         a distal portion that passes through the central void or interior volume of the balloon;
         a distal portion that engages or passes through the distal neck or neck assembly in the balloon; and
         a distal end that is open;
      iv) wherein:
         the passage of fluid through the first catheter into the central void or interior volume of the balloon results in expansion of the balloon;

after expansion of the balloon, the second catheter can be moved forward or backward while the expanded balloon remains fixed in position;

after expansion of the balloon, one or more first elongated bodies, expandable bodies, solidifying fluids, solutions comprising drugs or therapeutic agents, or solutions or suspensions comprising embolic particles can be placed through the lumen of the second catheter into a biological space adjacent to the balloon, including before or after advancing the tip of the second catheter forward;

after expansion of the balloon, the second catheter can be pulled back until the distal tip of the second catheter is located in the central void or interior volume of the balloon, and one or more one or more first elongated bodies, expandable bodies, or solidifying fluids can be passed through the lumen of the second catheter and placed in the central void or interior volume of the balloon;

the first catheter can be separated from the expanded balloon; and the first and second catheters can be removed from the patient while the balloon and the one or more first elongated bodies, expandable bodies, and solidifying fluids remain in the patient;

c) delivering a fluid medium into the central void or interior volume of the balloon of the first medical device through the first lumen to cause the balloon to assume an expanded configuration wherein the expanded balloon fills a portion of the lumen of the paravalvular leak path and is in contact with at least a portion of the wall of the paravalvular leak path;

d) withdrawing the second catheter of the first medical device until the distal tip of the second catheter of the first medical device is within the central void or interior volume of the expanded balloon of the first medical device, while maintaining the position of the expanded balloon of the first medical device;

e) delivering the first elongated body or expandable body of the second medical device from the proximal end of the second catheter of the first medical device, through the lumen of the second catheter of the first medical device, and into the central void or interior volume of the expanded balloon of the first medical device, the second medical device comprising:
  i) a distal portion comprising a first elongated body or expandable body;
  ii) a proximal portion comprising a second elongated body or delivery system;
  iii) wherein:
    after placement of the first elongated body or expandable body of the second medical device into the expanded balloon of the first medical device, at least a portion of the first elongated body or expandable body of the second medical device contacts at least a portion of the wall of the expanded balloon of the first medical device;
    after placement of the first elongated body or expandable body of the second medical device into the central void or internal volume of the expanded balloon of the first medical device, but prior to separation of the first elongated body or expandable body of the second medical device and the second elongated body of the second medical device, the second medical device can be removed from the patient;
    the first elongated body or expandable body can be separated from the second elongated body; and
    after separation of the first elongated body or expandable body from the second elongated body, the second elongated body can be removed from the patient while the first elongated body or expandable body remains in the patient;

f) causing the first elongated body or expandable body of the second medical device to separate from the second elongated body of the second medical device and removing the second elongated body from the patient while leaving the first elongated body or expandable body of the second medical device in the patient;

g) repeating steps e) and f) until the desired percent volume of the central void or interior volume of the expanded balloon of the first medical device is filled with first elongated bodies or first expandable bodies;

h) causing the expanded balloon of the first medical device to separate from the first catheter of the first medical device and removing the first and second catheters of the first medical device from the patient while leaving the expanded balloon of the first medical device and the one or more first elongated bodies or first expandable bodies of the second medical device in the patient.

2. The method of claim 1, wherein, prior to causing the expanded balloon of the first medical device to separate from the first catheter of the first medical device, a solidifying fluid is injected from the proximal end of the second catheter of the first medical device, through the lumen of the second catheter of the first medical device, and into the central void or interior volume of the expanded balloon of the first medical device.

3. The method of claims 1 and 2, wherein, after placement in the central void or interior volume of the expanded balloon, a first elongated body or expandable body of the second medical device exerts a force on the wall of the expanded balloon of the first medical device.

4. The method of claim 3, wherein the force on the wall of the expanded balloon of the first medical device is in an outward direction.

5. The method of claims 1-4, wherein the largest diameter or tertiary diameter of the second medical device is equal to the largest diameter of the expanded balloon.

6. The method of claims 1-4, wherein the largest diameter or tertiary diameter of the first elongated or expandable body of the second medical device is in a range from equal to the largest diameter of the expanded balloon of the first medical device to 50% larger than the largest diameter of the expanded balloon of the first medical device.

7. The method of claims 1-4, wherein the largest diameter or tertiary diameter of the first elongated or expandable body of the second medical device is 1, 2, 3, 4, 5, 6, 7, 8, 9, or 10 mm larger than the largest diameter of the expanded balloon of the first medical device.

8. The method of claims 1-7, wherein the volume of the one or more first elongated or expandable bodies of the second medical device would fill 5-75% of the volume of the central void of the expanded balloon.

9. The method of claims 1-7, wherein the volume of the first elongated or expandable body of the second medical device would fill 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75% of the volume of the central void of the expanded balloon.

10. The method of claims 1-9, wherein the distal portion of the second catheter of the first medical device comprises a radiopaque portion, ring or marker that is visible during fluoroscopy, and wherein fluoroscopy is used to monitor the position of the distal portion of the second catheter of the first medical device relative to the position of the distal portion of the balloon of the first medical device when the second catheter of the first medical device is moved.

11. The method of claims 1-10, wherein the distal portion of the balloon of the first medical device comprises a radiopaque portion, ring or marker that is visible during fluoroscopy, and wherein fluoroscopy is used to monitor the position of the distal portion of the second catheter of the first medical device relative to the position of the distal portion of the balloon of the first catheter when the second catheter of the first medical device is moved.

12. The method of claims 1-11, wherein at least a portion of the distal telescoping structure of the first medical device comprises a radiopaque portion, ring or marker that is visible during fluoroscopy, and wherein fluoroscopy is used to monitor the position of the distal portion of the second catheter of the first medical device relative to the position of the distal telescoping structure of the first medical device when the second catheter of the first medical device is moved.

13. The method of claims 1-12, wherein at least a portion of the first elongated or expanded body of the second medical device is made from a material that is radiopaque and visible during fluoroscopy and fluoroscopy is used to monitor the placement and position of the first elongated or expanded body of the second medical device.

14. The method of claims 1-13, wherein the second catheter of the first medical device comprises one, two, or more than two radiopaque portions, rings or markers, and fluoroscopy is used to monitor the position of the second catheter of the first medical device relative to the position of the first elongated or expanded body of the second medical device.

15. The method of claims 1-14, wherein the distal portion of the first catheter of the first medical device comprises a radiopaque marker that is visible during fluoroscopy, and wherein fluoroscopy is used to monitor the separation of the expanded balloon of the first medical device from the first catheter of the first medical device.

16. The method of claims 1-15, wherein the proximal portion of the balloon of the first medical device comprises a radiopaque marker that is visible during fluoroscopy, and wherein fluoroscopy is used to monitor the separation of the expanded balloon of the first medical device from the first catheter of the first medical device.

17. The method of claims 10-16, wherein the radiopaque portion, ring, or marker comprises platinum, iridium, gold, tungsten, or combinations thereof.

18. The method of claims 1-17, wherein the second catheter of the first medical device and the distal neck or distal neck assembly of the balloon of the first medical device are coupled by a friction fit, and wherein the second catheter of the first medical device and the expanded balloon of the first medical device are separated by applying an axial tensile force to the coupling.

19. The method of claim 18, wherein the second catheter of the first medical device and the distal neck or distal neck assembly of the balloon of the first medical device are coupled by an elastomer valve.

20. The method of claim 19, wherein the elastomer valve serves to reduce blood flow through the central void or interior volume of the expanded balloon of the first medical device following removal of the second catheter of the first medical device from the patient.

21. The method of claims 1-20, wherein the first catheter of the first medical device and the proximal neck or proximal neck assembly of the balloon of the first medical device are coupled by a friction fit, and wherein the first catheter of the first medical device and the expanded balloon of the first medical device are separated by applying an axial tensile force to the coupling.

22. The method of claim 21, wherein the first catheter of the first medical device and the proximal neck or proximal neck assembly of the balloon of the first medical device are coupled by an elastomer tubular segment.

23. The method of claims 1-20, wherein the first catheter of the first medical device and the balloon of the first medical device are coupled by a mechanical latch, wherein one portion of the mechanical latch is joined to the distal end of the first catheter and the second portion of the mechanical latch is joined to the proximal neck or proximal neck assembly of the balloon of the first medical device.

24. The method of claim 23, wherein the proximal neck of the balloon of the first medical device is the second portion of the mechanical latch.

25. The method of claims 23 and 24, wherein the two portions of the mechanical latch are engaged or operably coupled when the second catheter of the first medical device passes through the mechanical latch.

26. The method of claim 25, wherein the second catheter of the first medical device is removed from the mechanical latch and the mechanical latch and the two portions of the mechanical latch are disengaged or operably decoupled.

27. The method of claim 26, wherein the first catheter of the first medical device and the expanded balloon of the first medical device are pulled apart.

28. The method of claims 1-20, wherein the first catheter of the first medical device and the proximal neck or proximal neck assembly of the balloon of the first medical device are joined by an adhesive, glue, or solder, and wherein a portion of the proximal neck or proximal neck assembly of the balloon of the first medical device is corroded by electrolysis.

29. The method of claim 28, wherein the first catheter of the first medical device and the expanded balloon of the first medical device are pulled apart after corrosion of a portion of the proximal neck or proximal neck assembly of the balloon of the first medical device.

30. The method of claims 1-20, wherein the first catheter of the first medical device and the proximal neck or proximal neck assembly of the balloon of the first medical device are joined by an adhesive, glue, or solder, and wherein a distal portion of the first catheter of the first medical device, a portion of the proximal neck or proximal neck assembly of the balloon of the first medical device, or a portion of a bond between a distal portion of the first catheter of the first medical device and the proximal neck or proximal neck assembly of the balloon of the first medical device is melted by heating.

31. The method of claim 30, wherein the first catheter of the first medical device and the expanded balloon of the first medical device are pulled apart after melting a distal portion of the first catheter of the first medical device, a portion of the proximal neck or proximal neck assembly of the balloon of the first medical device, or a portion of a bond between a distal portion of the first catheter of the first medical device and the proximal neck or proximal neck assembly of the balloon of the first medical device.

32. The method of claims 1-31, wherein the first elongated or expandable body of the second medical device is flexible, the second elongated body of the second medical device is flexible, or the first elongated body and the second elongated body of the second medical device are flexible.

33. The method of claims 1-32, wherein the first catheter of the first medical device is flexible, the second catheter is flexible, or the first catheter and the second catheter of the first medical device are flexible.

34. The method of claims 1-33, wherein the balloon of the first medical device is detachable.

35. The method of claims 1-34, wherein the balloon of the first medical device is collapsed or compressed prior to expansion.

36. The method of claims 1-35, wherein the fluid used to expand the balloon of the first medical device is water, a saline solution, a fluoroscopic contrast agent, or combinations thereof.

37. The method of claims 1-36, wherein a solution comprising a fluoroscopic contrast agent is injected into the hub of the second catheter of the first medical device, through the second catheter of the first medical device, and into the lumen of the aorta or the cardiac chamber adjacent to the distal tip of the second catheter of the first medical device prior to the expansion of the balloon of the first medical device.

38. The method of claims 1-37, wherein a solution comprising a fluoroscopic contrast agent is injected into the hub of the second catheter of the first medical device, through the second catheter of the first medical device, and into the lumen of the aorta or the cardiac chamber adjacent to the distal tip of the second catheter of the first medical device after expansion of the balloon of the first medical device but prior to separation of the expanded balloon of the first medical device and the first catheter of the first medical device.

39. The method of claims 1-38, wherein a solution comprising a fluoroscopic contrast agent is injected into the hub of the second catheter of the first medical device, through the second catheter of the first medical device, and into the lumen of the aorta or the cardiac chamber adjacent to the distal tip of the second catheter of the first medical device after separation of the expanded balloon of the first medical device and the first catheter of the first medical device.

40. The method of claims 1-39, comprising providing the first medical device and the one or more second medical devices.

Aspects and embodiments related to methods of treating a biological conduit as disclosed herein:

1. A method of reducing the flow of a biological fluid in a biological conduit of a human patient with two or more medical devices, the method comprising:
   a) determining a diameter and length of a segment of a biological conduit to be treated and selecting a first medical device comprising a balloon with an expanded diameter≥the diameter of the selected segment of biological conduit and an expanded length such that the balloon can occupy at least a portion of the lumen of the biological conduit when the balloon of the first medical device is expanded:
   b) placing the balloon of the first medical device into the lumen of the biological conduit, such first medical device comprising:
      i) a pleated and folded balloon configured for permanent implantation in a human patient, the balloon comprising:
         a distal region, a proximal region generally opposite the distal region, an intermediate region transitioning from the distal region to the proximal region, a first axis extending proximal-distal between the proximal region and distal region, and a second axis perpendicular to the first axis;
         a wall extending generally continuously from the proximal region through the intermediate region, to the distal region, with an exterior surface and an interior surface, the interior surface defining a central void or interior volume;
         an opening in the wall of the proximal region that allows for the passage of fluid from a first catheter into the central void or interior volume of the balloon and also allows for the passage of a portion of the second catheter into the central void or interior volume of the balloon;
         an opening in the wall of the distal region that allows for the passage of a portion of the second catheter out of the central void or interior volume of the balloon;
         a proximal neck or neck assembly; and
         a distal neck or neck assembly;
      ii) a first catheter that partially defines a first lumen to allow for passage of fluid from the proximal end of the first catheter to the distal end of the first catheter, and into the central void or interior volume of the balloon; the first catheter comprising:
         a proximal end comprising a proximal hub; and
         a distal portion that is operably coupled or joined to the proximal neck or neck assembly of the balloon;
      iii) a second catheter that defines a second lumen configured to accept a guidewire, elongated body, expandable body, or solidifying fluid, the second catheter comprising:
         a proximal end comprising a proximal hub;
         a proximal portion that passes through the proximal hub of the first catheter;
         a middle portion that passes through the lumen of the first catheter;
         a distal portion that extends distal to the distal end of the first catheter;
         a distal portion that passes through the proximal neck or neck assembly of the balloon;
         a distal portion that passes through the central void or interior volume of the balloon;
         a distal portion that engages or passes through the distal neck or neck assembly in the balloon; and
         a distal end that is open;
      iv) wherein:
         the passage of fluid through the first catheter into the central void or interior volume of the balloon results in expansion of the balloon;
         after expansion of the balloon, the second catheter can be moved forward or backward while the expanded balloon remains fixed in position;
         after expansion of the balloon, one or more first elongated bodies, expandable bodies, solidifying fluids, solutions comprising drugs or therapeutic agents, or solutions or suspensions comprising embolic particles can be placed through the lumen of the second catheter into a biological space adjacent to the balloon, including before or after advancing the tip of the second catheter forward;
         after expansion of the balloon, the second catheter can be pulled back until the distal tip of the second catheter is located in the central void or interior volume of the balloon, and one or more one or more first elongated bodies, expandable bodies, or solidifying fluids can be passed through the lumen of the second catheter and placed in the central void or interior volume of the balloon;

the first catheter can be separated from the expanded balloon; and the first and second catheters can be removed from the patient while the balloon and the one or more first elongated bodies, expandable bodies, and solidifying fluids remain in the patient;

c) delivering a fluid medium into the central void or interior volume of the balloon of the first medical device through the first lumen to cause the balloon to assume an expanded configuration wherein the expanded balloon fills a portion of the lumen of the biological conduit and is in contact with at least a portion of the wall of the biological conduit;

d) withdrawing the second catheter of the first medical device until the distal tip of the second catheter of the first medical device is within the central void or interior volume of the expanded balloon of the first medical device, while maintaining the position of the expanded balloon of the first medical device;

e) delivering the first elongated body or expandable body of the second medical device from the proximal end of the second catheter of the first medical device, through the lumen of the second catheter of the first medical device, and into the central void or interior volume of the expanded balloon of the first medical device, the second medical device comprising:

i) a distal portion comprising a first elongated body or expandable body;

ii) a proximal portion comprising a second elongated body or delivery system;

iii) wherein:

after placement of the first elongated body or expandable body of the second medical device into the expanded balloon of the first medical device, at least a portion of the first elongated body or expandable body of the second medical device contacts at least a portion of the wall of the expanded balloon of the first medical device;

after placement of the first elongated body or expandable body of the second medical device into the central void or internal volume of the expanded balloon of the first medical device, but prior to separation of the first elongated body or expandable body of the second medical device and the second elongated body of the second medical device, the second medical device can be removed from the patient;

the first elongated body or expandable body can be separated from the second elongated body; and after separation of the first elongated body or expandable body from the second elongated body, the second elongated body can be removed from the patient while the first elongated body or expandable body remains in the patient;

f) causing the first elongated body or expandable body of the second medical device to separate from the second elongated body of the second medical device and removing the second elongated body from the patient while leaving the first elongated body or expandable body of the second medical device in the patient;

g) repeating steps e) and f) until the desired percent volume of the central void or interior volume of the expanded balloon of the first medical device is filled with first elongated bodies or first expandable bodies;

h) causing the expanded balloon of the first medical device to separate from the first catheter of the first medical device and removing the first and second catheters of the first medical device from the patient while leaving the expanded balloon of the first medical device and the one or more first elongated bodies or first expandable bodies of the second medical device in the patient.

2. The method of claim 1, wherein, after expansion of the balloon of the first medical device and prior to withdrawing the second catheter of the first medical device into the central void or interior volume of the expanded balloon of the first medical device, a solution comprising a fluoroscopic contrast agent, drug or therapeutic agent, a solidifying fluid, or combinations thereof are injected through the lumen of the second catheter of the first medical device and into the biological conduit adjacent to the expanded balloon of the first medical device.

3. The method of claim 3, wherein a syringe or other appropriate delivery system, is used to inject the fluoroscopic contrast agent, drug, therapeutic agent, solidifying fluid, or combinations thereof, through the lumen of the shaft of the second catheter of the first medical device, and into the lumen of the biological conduit adjacent to the expanded balloon of the first medical device.

4. The method of claims 2 and 3, wherein, prior to injecting the fluoroscopic contrast agent, drug, therapeutic agent, solidifying fluid, or combinations thereof through the lumen of the shaft of the second catheter of the first medical device and into the lumen of the biological conduit adjacent to the expanded balloon of the first medical device, the second catheter of the first medical device is advanced forward in the biological conduit while maintaining the position of the balloon of the first medical device.

5. The method of claims 1 and 2, wherein, prior to causing the expanded balloon of the first medical device to separate from the first catheter of the first medical device, a solidifying fluid is injected from the proximal end of the second catheter of the first medical device, through the lumen of the second catheter of the first medical device, and into the central void or interior volume of the expanded balloon of the first medical device.

6. The method of claims 1-5, wherein, after placement in the central void or interior volume of the expanded balloon, a first elongated body or expandable body of the second medical device exerts a force on the wall of the expanded balloon of the first medical device.

7. The method of claim 6, wherein the force on the wall of the expanded balloon of the first medical device is in an outward direction.

8. The method of claims 1-7, wherein the largest diameter or tertiary diameter of the second medical device is equal to the largest diameter of the expanded balloon.

9. The method of claims 1-7, wherein the largest diameter or tertiary diameter of the first elongated or expandable body of the second medical device is in a range from equal to the largest diameter of the expanded balloon of the first medical device to 50% larger than the largest diameter of the expanded balloon of the first medical device.

10. The method of claims 1-7, wherein the largest diameter or tertiary diameter of the first elongated or expandable body of the second medical device is 1, 2, 3, 4, 5, 6, 7, 8, 9, or 10 mm larger than the largest diameter of the expanded balloon of the first medical device.

11. The method of claims 1-10, wherein the volume of the one or more first elongated or expandable bodies of the second medical device would fill 5-75% of the volume of the central void of the expanded balloon.

12. The method of claims 1-10, wherein the volume of the first elongated or expandable body of the second medical device would fill 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75% of the volume of the central void of the expanded balloon.

13. The method of claims 1-12, wherein the expanded balloon is configured to contact at least 100%, 90%, 80%, 70%, 60%, 50%, 40%, 30%, 20%, 10%, or 5% of the area of the selected biological conduit's luminal surface.

14. The method of claims 1-12, wherein the expanded balloon is configured to fill at least 100%, 90%, 80%, 70%, 60%, 50%, 40%, 30%, 20%, 10%, or 5% of the volume of the lumen of the selected segment of the biological conduit.

15. The method of claims 1-14, wherein the distal portion of the second catheter of the first medical device comprises a radiopaque portion, ring or marker that is visible during fluoroscopy, and wherein fluoroscopy is used to monitor the position of the distal portion of the second catheter of the first medical device relative to the position of the distal portion of the balloon of the first medical device when the second catheter of the first medical device is moved.

16. The method of claims 1-15, wherein the distal portion of the balloon of the first medical device comprises a radiopaque portion, ring or marker that is visible during fluoroscopy, and wherein fluoroscopy is used to monitor the position of the distal portion of the second catheter of the first medical device relative to the position of the distal portion of the balloon of the first catheter when the second catheter of the first medical device is moved.

17. The method of claims 1-16, wherein at least a portion of the distal telescoping structure of the first medical device comprises a radiopaque portion, ring or marker that is visible during fluoroscopy, and wherein fluoroscopy is used to monitor the position of the distal portion of the second catheter of the first medical device relative to the position of the distal telescoping structure of the first medical device when the second catheter of the first medical device is moved.

18. The method of claims 1-17, wherein at least a portion of the first elongated or expanded body of the second medical device is made from a material that is radiopaque and visible during fluoroscopy and fluoroscopy is used to monitor the placement and position of the first elongated or expanded body of the second medical device.

19. The method of claims 1-18, wherein the second catheter of the first medical device comprises one, two, or more than two radiopaque portions, rings or markers, and fluoroscopy is used to monitor the position of the second catheter of the first medical device relative to the position of the first elongated or expanded body of the second medical device.

20. The method of claims 1-19, wherein the distal portion of the first catheter of the first medical device comprises a radiopaque marker that is visible during fluoroscopy, and wherein fluoroscopy is used to monitor the separation of the expanded balloon of the first medical device from the first catheter of the first medical device.

21. The method of claims 1-20, wherein the proximal portion of the balloon of the first medical device comprises a radiopaque marker that is visible during fluoroscopy, and wherein fluoroscopy is used to monitor the separation of the expanded balloon of the first medical device from the first catheter of the first medical device.

22. The method of claims 15-21, wherein the radiopaque portion, ring, or marker comprises platinum, iridium, gold, tungsten, or combinations thereof.

23. The method of claims 1-22, wherein the second catheter of the first medical device and the distal neck or distal neck assembly of the balloon of the first medical device are coupled by a friction fit, and wherein the second catheter of the first medical device and the expanded balloon of the first medical device are separated by applying an axial tensile force to the coupling.

24. The method of claim 23, wherein the second catheter of the first medical device and the distal neck or distal neck assembly of the balloon of the first medical device are coupled by an elastomer valve.

25. The method of claim 24, wherein the elastomer valve serves to reduce the flow of biological fluid through the central void or interior volume of the expanded balloon of the first medical device following removal of the second catheter of the first medical device from the patient.

26. The method of claims 1-25, wherein the first catheter of the first medical device and the proximal neck or proximal neck assembly of the balloon of the first medical device are coupled by a friction fit, and wherein the first catheter of the first medical device and the expanded balloon of the first medical device are separated by applying an axial tensile force to the coupling.

27. The method of claim 26, wherein the first catheter of the first medical device and the proximal neck or proximal neck assembly of the balloon of the first medical device are coupled by an elastomer tubular segment.

28. The method of claims 1-25, wherein the first catheter of the first medical device and the balloon of the first medical device are coupled by a mechanical latch, wherein one portion of the mechanical latch is joined to the distal end of the first catheter and the second portion of the mechanical latch is joined to the proximal neck or proximal neck assembly of the balloon of the first medical device.

29. The method of claim 28, wherein the proximal neck of the balloon of the first medical device is the second portion of the mechanical latch.

30. The method of claims 28 and 29, wherein the two portions of the mechanical latch are engaged or operably coupled when the second catheter of the first medical device passes through the mechanical latch.

31. The method of claim 30, wherein the second catheter of the first medical device is removed from the mechanical latch and the mechanical latch and the two portions of the mechanical latch are disengaged or operably decoupled.

32. The method of claim 31, wherein the first catheter of the first medical device and the expanded balloon of the first medical device are pulled apart.

33. The method of claims 1-25, wherein the first catheter of the first medical device and the proximal neck or proximal neck assembly of the balloon of the first medical device are joined by an adhesive, glue, or solder, and wherein a portion of the proximal neck or proximal neck assembly of the balloon of the first medical device is corroded by electrolysis.

34. The method of claim 33, wherein the first catheter of the first medical device and the expanded balloon of the first medical device are pulled apart after corrosion of a portion of the proximal neck or proximal neck assembly of the balloon of the first medical device.

35. The method of claims 1-25, wherein the first catheter of the first medical device and the proximal neck or proximal neck assembly of the balloon of the first medical device are joined by an adhesive, glue, or solder, and wherein a distal portion of the first catheter of the first medical device, a portion of the proximal neck or proximal neck assembly of the balloon of the first medical device, or a portion of a bond between a distal portion of the first catheter of the first medical device and the proximal neck or proximal neck assembly of the balloon of the first medical device is melted by heating.

36. The method of claim 35, wherein the first catheter of the first medical device and the expanded balloon of the first medical device are pulled apart after melting a distal portion of the first catheter of the first medical device, a portion of the proximal neck or proximal neck assembly of the balloon of the first medical device, or a portion of a bond between a distal portion of the first catheter of the first medical device and the proximal neck or proximal neck assembly of the balloon of the first medical device.

37. The method of claims 1-36, wherein the first elongated or expandable body of the second medical device is flexible, the second elongated body of the second medical device is flexible, or the first elongated body and the second elongated body of the second medical device are flexible.

38. The method of claims 1-37, wherein the first catheter of the first medical device is flexible, the second catheter of the first medical device is flexible, or the first catheter and the second catheter of the first medical device are flexible.

39. The method of claims 1-38, wherein the balloon of the first medical device is detachable.

40. The method of claims 1-39, wherein the balloon of the first medical device is collapsed or compressed prior to expansion.

41. The method of claims 1-40, wherein the fluid used to expand the balloon of the first medical device is water, a saline solution, a fluoroscopic contrast agent, or combinations thereof.

42. The method of claims 1-41, wherein a solution comprising a fluoroscopic contrast agent is injected during fluoroscopy into the hub of the second catheter of the first medical device, through the second catheter of the first medical device, and into the lumen of the biological conduit adjacent to the distal tip of the second catheter of the first medical device prior to the expansion of the balloon of the first medical device.

43. The method of claims 1-42, wherein a solution comprising a fluoroscopic contrast agent is injected during fluoroscopy into the hub of the second catheter of the first medical device, through the second catheter of the first medical device, and into the lumen of the biological conduit adjacent to the distal tip of the second catheter of the first medical device after expansion of the balloon of the first medical device but prior to separation of the expanded balloon of the first medical device and the first catheter of the first medical device.

44. The method of claims 1-43, wherein a solution comprising a fluoroscopic contrast agent is injected during fluoroscopy into the hub of the second catheter of the first medical device, through the second catheter of the first medical device, and into the lumen of the biological conduit adjacent to the distal tip of the second catheter of the first medical device after separation of the expanded balloon of the first medical device and the first catheter of the first medical device.

45. The method of claims 1-44, comprising providing the first medical device and the one or more second medical devices.

Aspects and embodiments related to methods of treating a biological space as disclosed herein:

1. A method of reducing the flow of a biological fluid in a biological space of a human patient with two or more medical devices, the method comprising:
   a) determining a diameter and length of a biological space to be treated and selecting a first medical device comprising a balloon with an expanded diameter≥the diameter of the selected biological space and an expanded length such that the balloon can occupy at least a portion of the biological space when the balloon of the first medical device is expanded:
   b) placing the balloon of the first medical device into the biological space, such first medical device comprising:
      i) a pleated and folded balloon configured for permanent implantation in a human patient, the balloon comprising:
         a distal region, a proximal region generally opposite the distal region, an intermediate region transitioning from the distal region to the proximal region, a first axis extending proximal-distal between the proximal region and distal region, and a second axis perpendicular to the first axis;
         a wall extending generally continuously from the proximal region through the intermediate region, to the distal region, with an exterior surface and an interior surface, the interior surface defining a central void or interior volume;
         an opening in the wall of the proximal region that allows for the passage of fluid from a first catheter into the central void or interior volume of the balloon and also allows for the passage of a portion of the second catheter into the central void or interior volume of the balloon;
         an opening in the wall of the distal region that allows for the passage of a portion of the second catheter out of the central void or interior volume of the balloon;
         a proximal neck or neck assembly; and
         a distal neck or neck assembly;
      ii) a first catheter that partially defines a first lumen to allow for passage of fluid from the proximal end of the first catheter to the distal end of the first catheter, and into the central void or interior volume of the balloon; the first catheter comprising:
         a proximal end comprising a proximal hub; and
         a distal portion that is operably coupled or joined to the proximal neck or neck assembly of the balloon;
      iii) a second catheter that defines a second lumen configured to accept a guidewire, elongated body, expandable body, or solidifying fluid, the second catheter comprising:
         a proximal end comprising a proximal hub;
         a proximal portion that passes through the proximal hub of the first catheter;
         a middle portion that passes through the lumen of the first catheter;
         a distal portion that extends distal to the distal end of the first catheter;
         a distal portion that passes through the proximal neck or neck assembly of the balloon;
         a distal portion that passes through the central void or interior volume of the balloon;

a distal portion that engages or passes through the distal neck or neck assembly in the balloon; and
a distal end that is open;
iv) wherein:
the passage of fluid through the first catheter into the central void or interior volume of the balloon results in expansion of the balloon;
after expansion of the balloon, the second catheter can be moved forward or backward while the expanded balloon remains fixed in position;
after expansion of the balloon, one or more first elongated bodies, expandable bodies, solidifying fluids, solutions comprising drugs or therapeutic agents, or solutions or suspensions comprising embolic particles can be placed through the lumen of the second catheter into a biological space adjacent to the balloon, including before or after advancing the tip of the second catheter forward;
after expansion of the balloon, the second catheter can be pulled back until the distal tip of the second catheter is located in the central void or interior volume of the balloon, and one or more one or more first elongated bodies, expandable bodies, or solidifying fluids can be passed through the lumen of the second catheter and placed in the central void or interior volume of the balloon;
the first catheter can be separated from the expanded balloon; and
the first and second catheters can be removed from the patient while the balloon and the one or more first elongated bodies, expandable bodies, and solidifying fluids remain in the patient;
c) delivering a fluid medium into the central void or interior volume of the balloon of the first medical device through the first lumen to cause the balloon to assume an expanded configuration wherein the expanded balloon fills a portion of the biological space and is in contact with at least a portion of the wall of the biological space;
d) withdrawing the second catheter of the first medical device until the distal tip of the second catheter of the first medical device is within the central void or interior volume of the expanded balloon of the first medical device, while maintaining the position of the expanded balloon of the first medical device;
e) delivering the first elongated body or expandable body of the second medical device from the proximal end of the second catheter of the first medical device, through the lumen of the second catheter of the first medical device, and into the central void or interior volume of the expanded balloon of the first medical device, the second medical device comprising:
i) a distal portion comprising a first elongated body or expandable body;
ii) a proximal portion comprising a second elongated body or delivery system;
iii) wherein:
after placement of the first elongated body or expandable body of the second medical device into the expanded balloon of the first medical device, at least a portion of the first elongated body or expandable body of the second medical device contacts at least a portion of the wall of the expanded balloon of the first medical device;
after placement of the first elongated body or expandable body of the second medical device into the central void or internal volume of the expanded balloon of the first medical device, but prior to separation of the first elongated body or expandable body of the second medical device and the second elongated body of the second medical device, the second medical device can be removed from the patient;
the first elongated body or expandable body can be separated from the second elongated body; and
after separation of the first elongated body or expandable body from the second elongated body, the second elongated body can be removed from the patient while the first elongated body or expandable body remains in the patient;
f) causing the first elongated body or expandable body of the second medical device to separate from the second elongated body of the second medical device and removing the second elongated body from the patient while leaving the first elongated body or expandable body of the second medical device in the patient;
g) repeating steps e) and f) until the desired percent volume of the central void or interior volume of the expanded balloon of the first medical device is filled with first elongated bodies or first expandable bodies;
h) causing the expanded balloon of the first medical device to separate from the first catheter of the first medical device and removing the first and second catheters of the first medical device from the patient while leaving the expanded balloon of the first medical device and the one or more first elongated bodies or first expandable bodies of the second medical device in the patient.

2. The method of claim 1, wherein, after expansion of the balloon of the first medical device and prior to withdrawing the second catheter of the first medical device into the central void or interior volume of the expanded balloon of the first medical device, a solution comprising a fluoroscopic contrast agent, drug or therapeutic agent, a solidifying fluid, or combinations thereof are injected through the lumen of the second catheter of the first medical device and into the biological space adjacent to the expanded balloon of the first medical device.

3. The method of claim 3, wherein a syringe or other appropriate delivery system, is used to inject the fluoroscopic contrast agent, drug, therapeutic agent, solidifying fluid, or combinations thereof, through the lumen of the shaft of the second catheter of the first medical device, and into the biological space adjacent to the expanded balloon of the first medical device.

4. The method of claims 2 and 3, wherein, prior to injecting the fluoroscopic contrast agent, drug, therapeutic agent, solidifying fluid, or combinations thereof through the lumen of the shaft of the second catheter of the first medical device and into the biological space adjacent to the expanded balloon of the first medical device, the second catheter of the first medical device is advanced forward in the biological space while maintaining the position of the balloon of the first medical device.

5. The method of claims 1 and 2, wherein, prior to causing the expanded balloon of the first medical device to separate from the first catheter of the first medical device, a solidifying fluid is injected from the proximal end of the second catheter of the first medical device, through the lumen of the second catheter of the first medical device, and into the central void or interior volume of the expanded balloon of the first medical device.

6. The method of claims 1-5, wherein, after placement in the central void or interior volume of the expanded balloon, a first elongated body or expandable body of the second medical device exerts a force on the wall of the expanded balloon of the first medical device.

7. The method of claim 6, wherein the force on the wall of the expanded balloon of the first medical device is in an outward direction.

8. The method of claims 1-7, wherein the largest diameter or tertiary diameter of the second medical device is equal to the largest diameter of the expanded balloon.

9. The method of claims 1-7, wherein the largest diameter or tertiary diameter of the first elongated or expandable body of the second medical device is in a range from equal to the largest diameter of the expanded balloon of the first medical device to 50% larger than the largest diameter of the expanded balloon of the first medical device.

10. The method of claims 1-7, wherein the largest diameter or tertiary diameter of the first elongated or expandable body of the second medical device is 1, 2, 3, 4, 5, 6, 7, 8, 9, or 10 mm larger than the largest diameter of the expanded balloon of the first medical device.

11. The method of claims 1-10, wherein the volume of the one or more first elongated or expandable bodies of the second medical device would fill 5-75% of the volume of the central void of the expanded balloon.

12. The method of claims 1-10, wherein the volume of the first elongated or expandable body of the second medical device would fill 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75% of the volume of the central void of the expanded balloon.

13. The method of claims 1-12, wherein the expanded balloon is configured to contact at least 100%, 90%, 80%, 70, 60%, 50%, 40%, 30%, 20%, 10%, or 5% of the area of the selected biological space surface.

14. The method of claims 1-12, wherein the expanded balloon is configured to fill at least 100%, 90%, 80%, 70%, 60%, 50%, 40%, 30%, 20%, 10%, or 5% of the volume of the biological space.

15. The method of claims 1-14, wherein the distal portion of the second catheter of the first medical device comprises a radiopaque portion, ring or marker that is visible during fluoroscopy, and wherein fluoroscopy is used to monitor the position of the distal portion of the second catheter of the first medical device relative to the position of the distal portion of the balloon of the first medical device when the second catheter of the first medical device is moved.

16. The method of claims 1-15, wherein the distal portion of the balloon of the first medical device comprises a radiopaque portion, ring or marker that is visible during fluoroscopy, and wherein fluoroscopy is used to monitor the position of the distal portion of the second catheter of the first medical device relative to the position of the distal portion of the balloon of the first catheter when the second catheter of the first medical device is moved.

17. The method of claims 1-16, wherein at least a portion of the distal telescoping structure of the first medical device comprises a radiopaque portion, ring or marker that is visible during fluoroscopy, and wherein fluoroscopy is used to monitor the position of the distal portion of the second catheter of the first medical device relative to the position of the distal telescoping structure of the first medical device when the second catheter of the first medical device is moved.

18. The method of claims 1-17, wherein at least a portion of the first elongated or expanded body of the second medical device is made from a material that is radiopaque and visible during fluoroscopy and fluoroscopy is used to monitor the placement and position of the first elongated or expanded body of the second medical device.

19. The method of claims 1-18, wherein the second catheter of the first medical device comprises one, two, or more than two radiopaque portions, rings or markers, and fluoroscopy is used to monitor the position of the second catheter of the first medical device relative to the position of the first elongated or expanded body of the second medical device.

20. The method of claims 1-19, wherein the distal portion of the first catheter of the first medical device comprises a radiopaque marker that is visible during fluoroscopy, and wherein fluoroscopy is used to monitor the separation of the expanded balloon of the first medical device from the first catheter of the first medical device.

21. The method of claims 1-20, wherein the proximal portion of the balloon of the first medical device comprises a radiopaque marker that is visible during fluoroscopy, and wherein fluoroscopy is used to monitor the separation of the expanded balloon of the first medical device from the first catheter of the first medical device.

22. The method of claims 15-21, wherein the radiopaque portion, ring, or marker comprises platinum, iridium, gold, tungsten, or combinations thereof.

23. The method of claims 1-22, wherein the second catheter of the first medical device and the distal neck or distal neck assembly of the balloon of the first medical device are coupled by a friction fit, and wherein the second catheter of the first medical device and the expanded balloon of the first medical device are separated by applying an axial tensile force to the coupling.

24. The method of claim 23, wherein the second catheter of the first medical device and the distal neck or distal neck assembly of the balloon of the first medical device are coupled by an elastomer valve.

25. The method of claim 24, wherein the elastomer valve serves to reduce the flow of biological fluid through the central void or interior volume of the expanded balloon of the first medical device following removal of the second catheter of the first medical device from the patient.

26. The method of claims 1-25, wherein the first catheter of the first medical device and the proximal neck or proximal neck assembly of the balloon of the first medical device are coupled by a friction fit, and wherein the first catheter of the first medical device and the expanded balloon of the first medical device are separated by applying an axial tensile force to the coupling.

27. The method of claim 26, wherein the first catheter of the first medical device and the proximal neck or proximal neck assembly of the balloon of the first medical device are coupled by an elastomer tubular segment.

28. The method of claims 1-25, wherein the first catheter of the first medical device and the balloon of the first medical device are coupled by a mechanical latch, wherein one portion of the mechanical latch is joined to the distal end of the first catheter and the second portion of the mechanical latch is joined to the proximal neck or proximal neck assembly of the balloon of the first medical device.

29. The method of claim 28, wherein the proximal neck of the balloon of the first medical device is the second portion of the mechanical latch.

30. The method of claims 28 and 29, wherein the two portions of the mechanical latch are engaged or operably coupled when the second catheter of the first medical device passes through the mechanical latch.

31. The method of claim 30, wherein the second catheter of the first medical device is removed from the mechanical latch and the mechanical latch and the two portions of the mechanical latch are disengaged or operably decoupled.

32. The method of claim 31, wherein the first catheter of the first medical device and the expanded balloon of the first medical device are pulled apart.

33. The method of claims 1-25, wherein the first catheter of the first medical device and the proximal neck or proximal neck assembly of the balloon of the first medical device are joined by an adhesive, glue, or solder, and wherein a portion of the proximal neck or proximal neck assembly of the balloon of the first medical device is corroded by electrolysis.

34. The method of claim 33, wherein the first catheter of the first medical device and the expanded balloon of the first medical device are pulled apart after corrosion of a portion of the proximal neck or proximal neck assembly of the balloon of the first medical device.

35. The method of claims 1-25, wherein the first catheter of the first medical device and the proximal neck or proximal neck assembly of the balloon of the first medical device are joined by an adhesive, glue, or solder, and wherein a distal portion of the first catheter of the first medical device, a portion of the proximal neck or proximal neck assembly of the balloon of the first medical device, or a portion of a bond between a distal portion of the first catheter of the first medical device and the proximal neck or proximal neck assembly of the balloon of the first medical device is melted by heating.

36. The method of claim 35, wherein the first catheter of the first medical device and the expanded balloon of the first medical device are pulled apart after melting a distal portion of the first catheter of the first medical device, a portion of the proximal neck or proximal neck assembly of the balloon of the first medical device, or a portion of a bond between a distal portion of the first catheter of the first medical device and the proximal neck or proximal neck assembly of the balloon of the first medical device.

37. The method of claims 1-36, wherein the first elongated or expandable body of the second medical device is flexible, the second elongated body of the second medical device is flexible, or the first elongated body and the second elongated body of the second medical device are flexible.

38. The method of claims 1-37, wherein the first catheter of the first medical device is flexible, the second catheter of the first medical device is flexible, or the first catheter and the second catheter of the first medical device are flexible.

39. The method of claims 1-38, wherein the balloon of the first medical device is detachable.

40. The method of claims 1-39, wherein the balloon of the first medical device is collapsed or compressed prior to expansion.

41. The method of claims 1-40, wherein the fluid used to expand the balloon of the first medical device is water, a saline solution, a fluoroscopic contrast agent, or combinations thereof.

42. The method of claims 1-41, wherein a solution comprising a fluoroscopic contrast agent is injected during fluoroscopy into the hub of the second catheter of the first medical device, through the second catheter of the first medical device, and into the biological space adjacent to the distal tip of the second catheter of the first medical device prior to the expansion of the balloon of the first medical device.

43. The method of claims 1-42, wherein a solution comprising a fluoroscopic contrast agent is injected during fluoroscopy into the hub of the second catheter of the first medical device, through the second catheter of the first medical device, and into the biological space adjacent to the distal tip of the second catheter of the first medical device after expansion of the balloon of the first medical device but prior to separation of the expanded balloon of the first medical device and the first catheter of the first medical device.

44. The method of claims 1-43, wherein a solution comprising a fluoroscopic contrast agent is injected during fluoroscopy into the hub of the second catheter of the first medical device, through the second catheter of the first medical device, and into the biological space adjacent to the distal tip of the second catheter of the first medical device after separation of the expanded balloon of the first medical device and the first catheter of the first medical device.

45. The method of claims 1-44, comprising providing the first medical device and the one or more second medical devices.

It will be appreciated that the devices and methods of the present disclosure are capable of being incorporated in the form of a variety of embodiments, only a few of which have been illustrated and described above. The disclosures herein may be embodied in other specific forms without departing from its spirit or essential characteristics. The described embodiments are to be considered in all respects only as illustrative and not restrictive and the scope of the present invention is, therefore indicated by the appended claims rather than by the foregoing description. All changes that come within the meaning and range of equivalency of the claims are to be embraced within their scope.

The invention claimed is:

1. A medical device for placement in a biological space, the medical device comprising:
   a compressed balloon configured for permanent implantation in the biological space, the balloon comprising:
      a distal region, a proximal region generally opposite the distal region, an intermediate region transitioning from the distal region to the proximal region, a first axis extending proximally and distally between the proximal region and distal region, and a second axis perpendicular to the first axis;
   a wall extending generally continuously from the proximal region through the intermediate region, to the distal region, with an exterior surface and an interior surface, the interior surface defining a central void or interior volume;
   an opening in the wall at the proximal region that allows for a passage of fluid from a first catheter into the central void or interior volume of the balloon and also allows for passage of a portion of a second catheter into the central void or interior volume of the balloon;
   an opening in the wall of the distal region that allows for the passage of the portion of the second catheter out of the central void or interior volume of the balloon;
   the first catheter which, along with the second catheter, defines a first lumen to allow for passage of fluid from a proximal end of the first catheter to a distal end of the first catheter, and into the central void or interior volume of the balloon;
   the first catheter comprising: the proximal end that is coupled to a first proximal hub; and a distal portion that is operably coupled or joined to the opening in the wall of the proximal region of the balloon;
   the second catheter defines a second lumen configured to accept at least one of a guidewire, an elongated body, an expandable body, or a solidifying fluid, the second catheter comprising: a second proximal end that is coupled to a second proximal hub;
a proximal portion that passes through the first proximal hub of the first catheter;
a first distal portion that passes through the proximal opening of the balloon; a second distal portion that passes through the central void or interior volume of the balloon; a third distal portion that engages or passes through a distal opening in the balloon; and a distal end that is open; and;
a detachable assembly for joining the balloon to the first catheter;
the detachable assembly comprising:
a tubular male structure bonded to the distal end of the first catheter, the tubular male structure defining a first detachable assembly lumen extending from a male proximal end to a male distal end, wherein the male distal end comprises at least one movable arm having a distal tab projecting radially outward from an exterior surface, a tubular female structure bonded to a proximal neck or proximal neck assembly of the balloon that defines a second detachable assembly lumen extending from a female proximal end to a female distal end; and
the second catheter of a first medical device comprising a shaft portion wherein, in a first configuration, the tubular male structure can be fixed to the tubular female structure and the proximal neck or proximal neck assembly of the balloon, and wherein, in a second configuration, the tubular male structure is free to move relative to the second detachable assembly lumen of the tubular female structure and the proximal neck or proximal neck assembly of the balloon;
wherein: when the tubular male structure is received within the second detachable assembly lumen of the tubular female structure and a portion of the shaft of the second catheter is received within the first detachable assembly lumen of the tubular male structure, the first catheter exerts a radially outward force on the at least one movable arm of the tubular male structure resulting in an engaged configuration wherein the tubular male structure is joined to the tubular female structure; and when the tubular male structure is received within the second detachable assembly lumen of the tubular female structure and the shaft of the second catheter is withdrawn from within the first detachable assembly lumen of the tubular male structure, the detachable assembly changes from the engaged configuration to a disengaged configuration and the first catheter and the tubular male structure can be separated from the tubular female structure and the proximal neck or proximal neck assembly of the balloon, and the first catheter and the balloon can be pulled apart; and
wherein, when the detachable assembly is in the engaged configuration, at least a portion of at least one distal tab of the at least one movable arm of the tubular male structure extends distally beyond at least a portion of the female distal end of the tubular female structure, and at least a portion of the at least one distal tab of at the least one movable arm of the tubular male structure extends radially beyond at least a portion of an outer surface of the tubular female structure, thereby retaining the tubular male structure within the tubular female structure; and wherein:
the passage of fluid through the first catheter into the central void or interior volume of the balloon can result in expansion of the balloon;
after expansion of the balloon, the second catheter can be moved forward or backward while the expanded balloon remains fixed in position;
after expansion of the balloon, all, or a portion of, the one or more second medical devices comprising the elongated body, expandable body, or solidifying fluid, can be placed through the second lumen of the second catheter into the biological space adjacent to the balloon;
after expansion of the balloon, the second catheter can be pulled back until a distal tip of the second catheter is located in the central void or interior volume of the balloon, while the first catheter and the balloon remain fixed in position, and all, or a portion of, the one or more second medical devices comprising the elongated body, expandable body, solidifying fluid or other balloon support material can be passed through the second lumen of the second catheter and placed into the central void or interior volume of the balloon; and after expansion of the balloon and placement of all, or a portion of, the one or more second medical devices comprising the elongated body, expandable body, solidifying fluid, or other balloon support material, the first catheter can be separated from the expanded balloon and the first and second catheters can be removed from a patient while the balloon and all or a portion of the one or more second medical devices remain in the patient.

2. The medical device of claim 1, wherein the wall of the balloon comprises a single layer of polymer.

3. The medical device of claim 2, wherein the balloon comprises a continuous layer of polymer.

4. The medical device of claim 2, wherein the balloon comprises a discontinuous layer of polymer.

5. The medical device of claim 2, comprising one or more other layers or coatings comprising a metal with a thickness of 0.001-1 microns.

6. The medical device of claim 5, wherein the metal comprises gold or alloys thereof.

7. The medical device of claim 5, wherein the metal comprises titanium or alloys thereof.

8. The medical device of claim 5, wherein the metal comprises gold, titanium or alloys or combinations thereof.

9. The medical device of claim 1 wherein the wall of the balloon comprises a single layer of polyethylene terephthalate (PET), polyamide (nylon), or polyether block amide (Pebax).

10. The medical device of claim 1, comprising the balloon having the proximal neck or proximal neck assembly and a distal neck.

11. The medical device of claim 1, wherein at least a portion of the wall of the balloon comprises two or more polymer layers.

12. The medical device of claim 11, wherein an inner layer of the balloon comprises polyethylene terephthalate, polyamide, or polyether block amide.

13. The medical device of claim 12, wherein the polyethylene terephthalate, polyamide, or polyether block amide layer comprises a continuous layer.

14. The medical device of claim 12, wherein the polyethylene terephthalate, polyamide, or polyether block amide layer comprises a discontinuous layer.

15. The medical device of claim 12, comprising one or more outer layers or coatings comprising polyurethane, silicone, or poly(p-xylylene) (Parylene).

16. The medical device of claim 15, wherein the one or more outer layers or coatings of the balloon have a wall thickness of 0.1-100 microns.

17. The medical device of claim 15, wherein the polyurethane, silicone, or poly(p-xylylene) layer comprises a continuous layer.

18. The medical device of claim 15, wherein the polyurethane, silicone, or poly(p-xylylene) layer comprises a discontinuous layer.

19. The medical device of claim 1, wherein the wall of the balloon comprises a single layer of metal.

20. The medical device of claim 1, wherein the wall of the balloon comprises a layer of polymer and a layer of metal, wherein the layer of metal has a thickness of 1-300 microns.

21. The medical device of claim 20, wherein the polymer and metal balloon possesses sufficient strength to maintain itself in an expanded or partially expanded configuration in vivo when no solid or semi-solid material, not derived from the patient, is present in the central void or interior volume of the expanded polymer and metal balloon after separation from the first and second catheters.

22. The medical device of claim 1, further comprising an expandable metal retention structure wherein, after expansion, a diameter of a portion of the metal structure is equal to or greater than a diameter of the expanded balloon.

23. The medical device of claim 22, comprising a third catheter, wherein an inner surface of the third catheter and an outer surface the first catheter defines a third lumen configured to accept at least a portion of the first catheter, the second catheter, and the expandable retention structure, the third catheter comprising:
 a proximal portion that is coupled to a third proximal hub; and
 a distal portion that passes over at least a portion of the expandable retention structure and retains the expandable retention structure in a compressed configuration until the third catheter is withdrawn; and,
 wherein withdrawal of the third catheter can result in expansion of the compressed retention structure.

24. The medical device of claim 23, wherein the third catheter can be moved backward while the first catheter and balloon remain fixed in position, resulting in expansion of the expandable retention structure.

25. The medical device of claim 24, wherein the third catheter can be moved before expansion of the balloon.

26. The medical device of claim 1, comprising a third catheter, the third catheter comprising:
 a proximal end that is coupled to a proximal hub;
 a distal end that is open; and
 wherein:
  the proximal hub of the first catheter and the proximal hub of the second catheter are proximal to the proximal hub of the third catheter;
  first portions of the first and second catheters pass through the proximal hub of the third catheter;
  second portions of the first and second catheters pass through a lumen of the third catheter; and
  third portions of the first and second catheters are distal to the distal end of the third catheter.

27. The medical device of claim 26, wherein an inner surface of the third catheter and the outer surface of the first catheter define a fluid lumen to allow for passage of fluid from the proximal hub of the third catheter to the distal end of the third catheter and into the biological space adjacent to the distal end of the third catheter.

28. The medical device of claim 1, wherein the opening in the wall of the proximal region of the balloon is the proximal neck or proximal neck assembly that extends away from the proximal region of the balloon.

29. The medical device of claim 1, wherein the opening in the wall of the proximal region of the balloon is the proximal neck or proximal neck assembly that extends into the central void or interior volume of the balloon.

30. The medical device of claim 1, wherein the proximal neck of the balloon comprises a ring structure, tubular structure, telescoping structure, catheter segment, or telescoping catheter segment, or that is joined to the proximal neck of the balloon, thereby forming the proximal neck assembly of the balloon.

31. The medical device of claim 30, wherein the ring structure, tubular structure, telescoping structure, catheter segment or telescoping catheter segment that is joined to the proximal neck of the balloon is rigid.

32. The medical device of claim 31, wherein a portion of the ring structure, tubular structure, telescoping structure, catheter segment or telescoping catheter segment joined to the proximal neck of the balloon projects into the central void or interior volume of the balloon, and no portion of the ring structure, tubular structure, telescoping structure, catheter segment or telescoping catheter segment joined to the proximal neck of the balloon projects proximal to the proximal neck of the balloon.

33. A medical device for placement in a biological space, the medical device comprising:
 a compressed balloon configured for permanent implantation in the biological space, the balloon comprising: a distal region, a proximal region generally opposite the distal region, and an intermediate region transitioning from the distal region to the proximal region;
 a wall extending generally continuously from the proximal region through the intermediate region, to the distal region, with an exterior surface and an interior surface, the interior surface defining an interior volume;
 an opening in the wall at the proximal region that allows for a passage of fluid from a first catheter into the interior volume of the balloon and also allows for a passage of a portion of a second catheter into the interior volume of the balloon;
 an opening in the wall of the distal region that allows for the passage of the portion of the second catheter out of the interior volume of the balloon;
 the first catheter which, along with the second catheter, defines a first lumen to allow for the passage of fluid into the interior volume of the balloon; the first catheter comprising: a proximal end that is coupled to a first proximal hub; and
 a distal portion that is operably engaged to the opening in the wall of the proximal region of the balloon;
 the second catheter defines a second lumen configured to accept at least one of a guidewire, an elongated body, an expandable body, or a solidifying fluid, the second catheter comprising: a second proximal end that is coupled to a second proximal hub;
 a proximal portion that passes through the first proximal hub of the first catheter;
 a distal portion configured to pass through at least one of a proximal opening of the balloon, the interior volume of the balloon, or a distal opening in the balloon; and;
 a detachable assembly for joining the balloon to the first catheter; the detachable assembly comprising:
 a tubular male structure bonded to a distal end of the first catheter, the tubular male structure defining a first detachable assembly lumen, wherein the tubular male structure comprises at least one movable arm having a distal tab projecting radially outward from an exterior surface of the tubular male structure, a tubular female structure bonded to a proximal neck assembly of the balloon that defines a second detachable assembly lumen extending from a female proximal end to a female distal end; and the second catheter of a first medical device comprising a shaft portion wherein, in a first configuration the tubular male structure can be fixed to the tubular female structure and the proximal neck assembly of the balloon, and wherein, in a second configuration, the tubular male structure is free to move relative to the tubular female structure and the proximal neck assembly of the balloon;

wherein:

when the tubular male structure is received within the second detachable assembly lumen of the tubular female structure and a portion of a shaft of the second catheter is received within the first detachable assembly lumen of the tubular male structure, the first catheter exerts a radially outward force on the at least one movable arm of the tubular male structure resulting in an engaged configuration wherein the tubular male structure is joined to the tubular female structure; and when the tubular male structure is received within the second detachable assembly lumen of the tubular female structure and the shaft of the second catheter is withdrawn from within the first detachable assembly lumen of the tubular male structure, the detachable assembly changes from the engaged configuration to a disengaged configuration and the first catheter and the tubular male structure can be separated from the tubular female structure and the proximal neck of the balloon, and the first catheter and the balloon can be pulled apart; and wherein, when the detachable assembly is in the engaged configuration, at least a portion of the at least one distal tab of the at least one movable arm of the tubular male structure extends distally beyond at least a portion of the distal end of the female tubular structure, and at least a portion of the at least one distal tab of the at least one movable arm of the tubular male structure extends radially beyond at least a portion of an outer surface of the tubular female structure, thereby retaining the tubular male structure within the tubular female structure.

34. The medical device of claim 33 wherein:

the passage of fluid through the first catheter into the interior volume of the balloon can result in expansion of the balloon;

after expansion of the balloon, the second catheter can be moved forward or backward while the expanded balloon remains fixed in position;

after expansion of the balloon, all, or a portion of, one or more second medical devices comprising an elongated body, expandable body, or solidifying fluid, can be placed through the second lumen of the second catheter into the biological space adjacent to the balloon;

after expansion of the balloon, the second catheter can be pulled back until a distal tip of the second catheter is located in the interior volume of the balloon, while the first catheter and the balloon remain fixed in position, and all, or a portion of, the one or more second medical devices comprising the elongated body, expandable body, solidifying fluid or other balloon support material can be passed through the second lumen of the second catheter and placed into the interior volume of the balloon; and after expansion of the balloon and placement of all or a portion of the one or more second medical devices, the first catheter can be separated from the expanded balloon and the first and second catheters can be removed from a patient while the balloon and all, or a portion of, the one or more of the second medical devices remain in the patient.

* * * * *